US011655282B2

(12) United States Patent
Corey

(10) Patent No.: US 11,655,282 B2
(45) Date of Patent: May 23, 2023

(54) CHIMERIC ENGULFMENT RECEPTOR MOLECULES

(71) Applicant: CERO THERAPEUTICS, INC., South San Francisco, CA (US)

(72) Inventor: Daniel Mark Corey, Menlo Park, CA (US)

(73) Assignee: CERO THERAPEUTICS, INC., South San Francisco, CA (US)

( * ) Notice: Subject to any disclaimer, the term of this patent is extended or adjusted under 35 U.S.C. 154(b) by 0 days.

(21) Appl. No.: 17/400,082

(22) Filed: Aug. 11, 2021

(65) Prior Publication Data

US 2022/0098273 A1 Mar. 31, 2022

Related U.S. Application Data

(63) Continuation of application No. 16/334,224, filed as application No. PCT/US2017/053553 on Sep. 26, 2017.

(60) Provisional application No. 62/445,235, filed on Jan. 11, 2017, provisional application No. 62/400,578, filed on Sep. 27, 2016.

(51) Int. Cl.
| | |
|---|---|
| *C07K 14/705* | (2006.01) |
| *C07K 14/47* | (2006.01) |
| *C07K 14/735* | (2006.01) |
| *C07K 16/28* | (2006.01) |
| *C07K 16/30* | (2006.01) |
| *C12N 9/12* | (2006.01) |
| *A61K 38/00* | (2006.01) |
| *A61K 39/00* | (2006.01) |
| *A61P 35/00* | (2006.01) |
| *A61K 35/17* | (2015.01) |
| *C07K 14/535* | (2006.01) |

(52) U.S. Cl.
CPC ........ *C07K 14/70521* (2013.01); *A61K 35/17* (2013.01); *A61P 35/00* (2018.01); *C07K 14/4748* (2013.01); *C07K 14/535* (2013.01); *C07K 14/70503* (2013.01); *C07K 14/70535* (2013.01); *C07K 14/70546* (2013.01); *C07K 14/70578* (2013.01); *C07K 16/2803* (2013.01); *C07K 16/30* (2013.01); *C12N 9/12* (2013.01); *A61K 38/00* (2013.01); *A61K 2039/505* (2013.01); *A61K 2039/5156* (2013.01); *C07K 2317/24* (2013.01); *C07K 2317/53* (2013.01); *C07K 2317/622* (2013.01); *C07K 2317/73* (2013.01); *C07K 2319/02* (2013.01); *C07K 2319/03* (2013.01); *C07K 2319/30* (2013.01); *C07K 2319/33* (2013.01); *C12Y 207/10* (2013.01)

(58) Field of Classification Search
CPC .............................. C07K 14/705; C07K 16/18
See application file for complete search history.

(56) References Cited

U.S. PATENT DOCUMENTS

| | | | |
|---|---|---|---|
| 5,019,368 A | 5/1991 | Epstein et al. | |
| 5,283,173 A | 2/1994 | Fields et al. | |
| 5,468,614 A | 11/1995 | Fields et al. | |
| 5,641,863 A | 6/1997 | Schreiber et al. | |
| 5,641,875 A | 6/1997 | Schreiber et al. | |
| 5,747,498 A | 5/1998 | Schnur et al. | |
| 5,776,910 A | 7/1998 | Schreiber et al. | |
| 5,821,071 A | 10/1998 | Schreiber et al. | |
| 6,068,983 A | 5/2000 | Schreiber et al. | |
| 6,475,997 B1 | 11/2002 | Schreiber et al. | |
| 6,630,313 B2 | 10/2003 | Fadok et al. | |
| 7,195,761 B2 | 3/2007 | Holtzman et al. | |
| 7,247,303 B2 | 7/2007 | Thorpe et al. | |
| 7,892,544 B2 | 2/2011 | Pfeifer et al. | |
| 7,910,333 B2 | 3/2011 | Chilcote et al. | |
| 8,025,878 B2 | 9/2011 | Gellerfors et al. | |
| 8,119,772 B2 | 2/2012 | Yang et al. | |
| 8,496,938 B2 | 7/2013 | Smith et al. | |
| 8,940,276 B2 | 1/2015 | Weihofen et al. | |
| 8,956,616 B2 | 2/2015 | Thorpe et al. | |
| 10,980,836 B1 | 4/2021 | Getts et al. | |
| 2003/0072743 A1 | 4/2003 | Albert et al. | |
| 2003/0095962 A1 | 5/2003 | Ueda et al. | |
| 2003/0124114 A1 | 7/2003 | McIntire et al. | |
| 2003/0130218 A1 | 7/2003 | Schreiber et al. | |
| 2006/0002940 A1 | 1/2006 | Stevenson | |
| 2006/0257359 A1 | 11/2006 | Francois et al. | |
| 2007/0258897 A1 | 11/2007 | Devitt et al. | |
| 2008/0213216 A1 | 9/2008 | Schreiber et al. | |
| 2011/0165649 A1 | 7/2011 | Tyler et al. | |
| 2013/0071414 A1 | 3/2013 | Dotti et al. | |
| 2014/0162290 A1 | 6/2014 | Watanabe et al. | |
| 2015/0023986 A1 | 1/2015 | Jones et al. | |
| 2017/0058024 A1 | 3/2017 | West et al. | |
| 2017/0166622 A1 | 6/2017 | Baeuerle et al. | |
| 2018/0186855 A1 | 7/2018 | Rosenthal | |
| 2018/0186878 A1 | 7/2018 | Rosenthal | |

(Continued)

FOREIGN PATENT DOCUMENTS

| | | |
|---|---|---|
| EP | 0520722 B1 | 12/1996 |
| EP | 0787722 A1 | 8/1997 |

(Continued)

OTHER PUBLICATIONS

Aderem, "Phagocytosis and the Inflammatory Response," *JID 187*(Suppl 2):S340-S345, 2003.

(Continued)

*Primary Examiner* — Elly-Gerald Stoica
(74) *Attorney, Agent, or Firm* — Seed Intellectual Property Law Group LLP

(57) ABSTRACT

The present disclosure relates to chimeric engulfment receptor molecules, host cells modified to include the phagocytic engulfment molecules, and methods of making and using such receptor molecules and modified cells.

12 Claims, 161 Drawing Sheets

Specification includes a Sequence Listing.

(56) References Cited

U.S. PATENT DOCUMENTS

| | | |
|---|---|---|
| 2018/0291089 A1 | 10/2018 | Epstein et al. |
| 2018/0319862 A1 | 11/2018 | Thompson et al. |
| 2020/0055917 A1 | 2/2020 | Corey |
| 2020/0308305 A1 | 10/2020 | Corey |
| 2021/0015865 A1 | 1/2021 | Corey |
| 2021/0023135 A1 | 1/2021 | Corey |
| 2021/0024607 A1 | 1/2021 | Corey et al. |
| 2021/0087251 A1 | 3/2021 | Corey |
| 2021/0253696 A1 | 8/2021 | Corey et al. |

FOREIGN PATENT DOCUMENTS

| | | |
|---|---|---|
| EP | 0564409 B1 | 1/2000 |
| WO | WO 9633980 A1 | 10/1996 |
| WO | WO 9702266 A1 | 1/1997 |
| WO | WO 9709433 A1 | 3/1997 |
| WO | WO 9730034 A1 | 8/1997 |
| WO | WO 9738983 A1 | 10/1997 |
| WO | WO 9749688 A1 | 12/1997 |
| WO | WO 9903854 A1 | 1/1999 |
| WO | 01/68709 A1 | 9/2001 |
| WO | 01/85207 A2 | 11/2001 |
| WO | WO 02066470 A1 | 8/2002 |
| WO | WO 03064383 A2 | 8/2003 |
| WO | 2005/019429 A2 | 3/2005 |
| WO | 2005/090573 A2 | 9/2005 |
| WO | 2005/097211 A2 | 10/2005 |
| WO | WO 2006122806 A2 | 11/2006 |
| WO | WO 2007084786 A1 | 7/2007 |
| WO | WO 2009036082 A2 | 3/2009 |
| WO | WO 2009055730 A1 | 4/2009 |
| WO | 2013/074916 A1 | 5/2013 |
| WO | 2013/192294 A1 | 12/2013 |
| WO | 2014/031687 A1 | 2/2014 |
| WO | WO 2014059173 A2 | 4/2014 |
| WO | WO 2015066262 A1 | 5/2015 |
| WO | 2015/123642 A1 | 8/2015 |
| WO | 2015/184228 A1 | 12/2015 |
| WO | 2016/019300 A1 | 2/2016 |
| WO | 2016/044605 A1 | 3/2016 |
| WO | 2017/019848 A1 | 2/2017 |
| WO | 2017/025944 A2 | 2/2017 |
| WO | 2017/083700 A1 | 5/2017 |
| WO | 2018/031419 A1 | 2/2018 |
| WO | WO 2018064076 A1 | 4/2018 |
| WO | 2018/132695 A1 | 7/2018 |
| WO | 2018/212770 A1 | 11/2018 |
| WO | 2018/220224 A1 | 12/2018 |
| WO | 2019/067328 A1 | 4/2019 |
| WO | WO 2019079529 A1 | 4/2019 |
| WO | 2019/086571 A1 | 5/2019 |
| WO | WO 2019157440 A1 | 8/2019 |
| WO | 2019/191332 A1 | 10/2019 |
| WO | 2019/191334 A1 | 10/2019 |
| WO | 2019/191339 A1 | 10/2019 |
| WO | 2019/191340 A1 | 10/2019 |
| WO | WO 2021067875 A1 | 4/2021 |
| WO | WO 2022036265 A1 | 2/2022 |
| WO | WO 2022036285 A1 | 2/2022 |
| WO | WO 2022036287 A1 | 2/2022 |

OTHER PUBLICATIONS

Albert et al., "$\alpha_v\beta_5$ integrin recruits the CrkII-Dock180-Rac1 complex for phagocytosis of apoptotic cells," *Nat. Cell Biol.* 2(12):899-905, 2000.

Belzile et al., "Antibody targeting of phosphatidylserine for the detection and immunotherapy of cancer," *ImmunoTargets and Therapy* 7:1-14, 2018.

Castellano et al., "Membrane recruitment of Rac1 triggers phagocytosis," *Journal of Cell Science* 113:2955-2961, 2000.

Duclos et al., "Rab5 regulates the kiss and run fusion between phagosomes and endosomes and the acquisition of phagosome leishmanicidal properties in RAW 264.7 macrophages," *Journal of Cell Science* 113:3531-3541, 2000.

Fesnak et al., "Engineered T cells: the promise and challenges of cancer immunotherapy," *Nature Reviews Cancer* 16:566-581, 2016.

Gerber et al., "Tumor-specific targeting by Bavituximab, a phosphatidylserine-targeting monoclonal antibody with vascular targeting and immune modulating properties, in lung cancer xenografts," *Am. J. Nucl. Med. Mol. Imaging* 5(5):493-503, 2015.

Greenberg et al., "Clustered syk tyrosine kinase domains trigger phagocytosis," *Proc. Natl. Acad. Sci. USA* 93:1103-1107, 1996.

Hochreiter-Hufford et al., "Clearing the Dead: Apoptotic Cell Sensing, Recognition, Engulftnent, and Digestion," *Cold Spring Harb Perspect Biol* 5:a008748, 2013. (21 pages).

Hull et al., "The Monocuclear Phagocyte System in Homeostasis and Disease: A Role for Heme Oxygenase-1," *Antioxidants and Redox Signaling* 20(11): 1770-1788, 2014.

International Search Report and Written Opinion, dated Aug. 19, 2019, for International Application No. PCT/US2019/024441, 13 pages.

International Search Report and Written Opinion, dated Feb. 6, 2018, for International Application No. PCT/US17/53553, 13 pages.

International Search Report and Written Opinion, dated Jun. 28, 2019, for International Application No. PCT/US2019/024442, 12 pages.

International Search Report and Written Opinion, dated Jun. 7, 2019, for International Application No. PCT/US2019/024433, 13 pages.

International Search Report and Written Opinion, dated Mar. 25, 2019, for International Application No. PCT/US2018/052297, 10 pages.

International Search Report and Written Opinion, dated May 29, 2019, for International Application No. PCT/US2019/024435, 12 pages.

Khogeer et al., "Antiphosphatidylserine antibodies as diagnostic indicators of antiphospholipid syndrome," *Lupus* 24(2):186-190, 2015.

Kochenderfer et al., "Construction and preclinical evaluation of an anti-CD19 chimeric antigen receptor," *J Immunother.* 32(7):689-702, 2009. (26 pages).

Kruskal et al., "Phagocytic Chimeric Receptors Require Both Transmembrane and Cytoplasmic Domains from the Mannose Receptor," *J. Exp. Med.* 776:1673-1680, 1992.

Misyurin, "Structure and Functions of Main Apoptosis Receptors and Ligands," Russian Journal of Biotherapy 14(2):23-30, 2015.

Miyanishi et al., "Identification of Tim4 as a phosphatidylserine receptor," *Nature* 450:435-439, 2007.

Morrissey et al., "Chimeric antigen receptors that trigger phagocytosis," *eLife* 7:e36688, 2018. (21 pages).

Nishi et al., "Tim4- and MerTK-Mediated Engulfment of Apoptotic Cells by Mouse Resident Peritoneal Macrophages," *Molecular and Cellular Biology* 34(8):1512-1520, 2014.

Penberthy et al., "Apoptotic cell recognition receptors and scavenger receptors," *Immunological Reviews* 269:44-59, 2016.

Ravichandran, "Find-me and eat-me signals in apoptotic cell clearance: progress and conundrums," *J. Exp. Med.* 207(9):1807-1817, 2010.

Sato et al., "Enhancement of Fcγ Receptor-Mediated Phagocytosis by Transforming Mutants of Cb1[1]," *The Journal of Immunology* 163(11):6123-6131, 1999.

Schutters et al., "Phosphatidylserine targeting for diagnosis and treatment of human diseases," *Apoptosis* 15:1072-1082, 2010.

Wang et al., "A transgene-encoded cell surface polypeptide for selection, in vivo tracking, and ablation of engineered cells," *Blood* 118(5):1255-1263, 2011.

Williamson et al., "Cellular reconstitution of apoptotic cell clearance reveals a multi-step phosphorylation mechanism for Draper receptor triggering," *bioRxiv* :1-48, 2017. (58 pages).

Williamson et al., "Abstract A165: Engineering approaches to uncover the mechanism of apoptotic cell clearance by a conserved signaling system," *CRI-CIMT-EATI-AACR Inaugural International Cancer Immunotherapy Conference: Translating Science into Survival*, New York, New York, Sep. 16-19, 2015, (6 pages).

(56) References Cited

OTHER PUBLICATIONS

Williamson et al., "Abstract PR15: Engineering phagocytic signaling," *CRI-CIMT-EATI-AACR International Cancer Immunotherapy Conference: Translating Science into Survival*, New York, New York, Sep. 25-28, 2016. (4 pages).

Williamson et al., "Spatial control of Draper receptor signaling initiates apoptotic cell engulfment,"*J. Cell. Biol.* 217(11):3977-3992, 2018.

Delgado Tascón et al., "The granulocyte orphan receptor CEACAM4 is able to trigger phagocytosis of bacteria," *Journal of Leukocyte Biology* 97:521-531, Mar. 2015.

U.S. Appl. No. 16/646,530, filed Mar. 11, 2020, Chimeric Engulfment Receptor Molecules and Methods of Use.

U.S. Appl. No. 17/040,317, filed Sep. 22, 2020, Chimeric TIM4 Receptors and Uses Thereof.

U.S. Appl. No. 17/040,341, filed Sep. 22, 2020, Chimeric Engulfment Receptors and Uses Thereof for Neurodegenerative Diseases.

U.S. Appl. No. 17/040,464, filed Sep. 22, 2020, Expression Vectors for Chimeric Engulfment Receptors, Genetically Modified Host Cells, and Uses Thereof.

U.S. Appl. No. 17/040,472, filed Sep. 22, 2020, Cellular Immunotherapy Compositions and Uses Thereof.

PCT/US2020/054153, Oct. 2, 2020, Chimeric TIM4 Receptors and Uses Thereof.

U.S. Appl. No. 17/154,959, filed Jan. 21, 2021, Bivalent Chimeric Engulfment Receptors and Uses Thereof.

Agaugue et al., "224. Development of Safer & Optimized CAR-T Cells Using Lentiviral Vectors," *Mol. Ther.* 23(Suppl. 1):S88, May 2015.

Aggen et al., "Single-chain V(alpha)V(beta) T-cell receptors function without mispairing with endogenous TCR chains," *Gene Therapy* 19:365-374, 2012.

Alder et al., "Antibody responses of variable lymphocyte receptors in the lamprey," *Nature Immunology* 9(3):319-327, Mar. 2008.

Altman et al., "Phenotypic Analysis of Antigen-Specific T Lymphocytes," *Science* 274:94-96, 1996.

Arandjelovic et al., "Phagocytosis of apoptotic cells in homeostasis," *Nat. Immunol.* 16(9):907-917, Sep. 2015.

Baral et al., "Experimental therapy of African trypanosomiasis with a nanobody-conjugated human trypanolytic factor," *Nature Medicine* 12(5):580-584, May 2006.

Barthelemy et al., "Comprehensive Analysis of the Factors Contributing to the Stability and Solubility of Autonomous Human VH Domains*," *J. Biol. Chem.* 283(6):3639-3654, Feb. 8, 2008.

Blackburn et al., "Coregulation of CD8+ T cell exhaustion by multiple inhibitory receptors during chronic viral infection," *Nature Immunology* 10(1):29-37, Jan. 2009.

Burns et al., "A high molecular weight-melanoma associated antigen-specific chimeric antigen receptor redirects lymphocytes to target human melanomas," *Cancer Res.* 70(8):3027-3033, Apr. 15, 2010.

Chen et al., "Fusion Protein Linkers: Property, Design and Functionality," *Adv. Drug Deliv. Rev.* 65(10):1357-1369, Oct. 15, 2013.

Clackson et al., "Making antibody fragments using phage display libraries," *Nature* 352:624-628, Aug. 1991.

Colman, "Effects of amino acid sequence changes on antibody-antigen interactions," *Research in Immunology* 145(1):33-36, 1994.

Cordoba et al., "The large ectodomains of CD45 and CD148 regulate their segregation from and inhibition of ligated T-cell receptor," *Blood* 121(21):4295-4302, 2013.

Cortez-Retamozo et al., "Efficient Cancer Therapy with a Nanobody-Based Conjugate," *Cancer Research* 64:2853-2857, Apr. 2004.

Dillon et al., "Annexin V Binds to Viable B Cells and Colocalizes with a Marker of Lipid Rafts upon B Cell Receptor Activation," *The Journal of Immunology* 164:1322-1332, 2000.

Dolezal et al., "ScFv multimers of the anti-neuraminidase antibody NC10: shortening of the linker in single-chain Fv fragment assembled in V(L) to V(H) orientation drives the formation of dimers, trimers, tetramers and higher molecular mass multimers," *Protein Engineering* 13(8):565-574, 2000.

Engels et al., "Retroviral Vectors for High-Level Transgene Expression in T Lymphocytes," *Human Gene Therapy* 14:1155-1168, Aug. 2003.

Feng et al., "Interleukin-6 increases prostate cancer cells resistance to bicalutamide via TIF2," *Mol. Cancer Ther.* 8(3):665-671, Mar. 2009.

Frecha et al., "Advances in the Field of Lentivector-based Transduction of T and B Lymphocytes for Gene Therapy," *Molecular Therapy* 18(10):1748-1757, Oct. 2010.

Ghahroudi et al., "Selection and identification of single domain antibody fragments from camel heavy-chain antibodies," *FEBS Letters* 474:521-526, 1997.

Green et al., "Mitochondria and Apoptosis," *Science* 281(5381):1309-1312, Aug. 1998.

Greenberg, "Programmed cell death: A way of life for plants," *Proc. Natl. Acad. Sci. USA* 93:12094-12097, Oct. 1996.

Guest et al., "The Role of Extracellular Spacer Regions in the Optimal Design of Chimeric Immune Receptors: Evaluation of Four Different scFvs and Antigens," *Journal of Immunotherapy* 28(3):203-211, May/Jun. 2005.

Hamers-Casterman et al., "Naturally occurring antibodies devoid of light chains," *Nature* 363:446-448, Jun. 1993.

Hanayama et al., "Identification of a factor that links apoptotic cells to phagocytes," *Nature* 417:182-187, May 2002.

Hartt Meyers et al., "TIM-4 is the ligand for TIM-1, and the TIM-1—TIM-4 interaction regulates T cell proliferation," *Nat. Immunol.* 6(5):455-464, May 2005.

Herrin et al., "Structure and specificity of lamprey monoclonal antibodies," *PNAS* 105(6):2040-2045, Feb. 2008.

Hudecek et al., "Receptor Affinity and Extracellular Domain Modifications Affect Tumor Recognition by ROR1-Specific Chimeric Antigen Receptor T Cells," *Clin. Cancer Res.* 19(12):3153-31564, 2013.

Hudecek et al., "The Nonsignaling Extracellular Spacer Domain of Chimeric Antigen Receptors Is Decisive for In Vivo Antitumor Activity," *Cancer Immunol. Res.* 3(2):125-135, Feb. 2015.

Jespers et al., "Aggregation-resistant domain antibodies selected on phage by heat denaturation," *Nature Biotechnology* 22(9):1161-1165, Sep. 2004.

Jolly, "9: Emerging Viral Vectors," *Cold Spring Harbor Monograph Archive* 36:209-240, 1999.

Jones et al., "Lentiviral Vector Design for Optimal T Cell Receptor Gene Expression in the Transduction of Peripheral Blood Lymphocytes and Tumor-Infiltrating Lymphocytes," *Human Gene Therapy* 20:630-640, Jun. 2009.

June, "Adoptive T cell therapy for cancer in the clinic," *The Journal of Clinical Investigation* 117(6):1466-1476, Jun. 2007.

Kitchen et al., "Engineering Antigen-Specific T Cells from Genetically Modified Human Hematopoietic Stem Cells in Immunodeficient Mice," *PLoS One* 4(12):e8208, Dec. 2009.

Kobayashi et al., "TIM-1 and TIM-4 Glycoproteins Bind Phosphatidylserine and Mediate Uptake of Apoptotic Cells," *Immunity* 27:927-940, Dec. 2007.

Krisky et al., "Development of herpes simplex virus replication-defective multigene vectors for combination gene therapy applications," *Gene Therapy* 5:1517-1530, 1998.

Luo et al., "Development of genetically engineered CD4+ and CD8+ T cells expressing TCRs specific for a M. tuberculosis 38-kDa antigen," *Journal of Molecular Medicine* 89:903-913, 2011.

Maeda et al., "Engineering of Functional Chimeric Protein G-Vargula Luciferase," *Analytical Biochemistry* 249:147-152, 1997.

Miksa et al., "A novel method to determine the engulfment of apoptotic cells by macrophages using pHrodo succinimidyl ester," *J Immunol Methods* 342:71-77, 2009.

Morgan et al., "Cancer Regression in Patients After Transfer of Genetically Engineered Lymphocytes," *Science* 314(5796):126-129, Oct. 2006.

Muller et al., "Spliceosomal Peptide P140 for Immunotherapy of Systemic Lupus Erythematosus: Results of an Early Phase II Clinical Trial," *Arthritis & Rheumatism* 58(12):3873-3883, Dec. 2008.

Nguyen et al., "Heavy-chain antibodies in *Camelidae*; a case of evolutionary innovation," *Immunogenetics* 54:39-41, 2002.

(56) References Cited

OTHER PUBLICATIONS

Nguyen et al., "The Specific Variable Domain of Camel Heavy-chain Antibodies is Encoded in the Germline," *J. Mol. Biol.* 275:413-418, 1998.

Nishi et al., "Systematic characterization of deubiquitylating enzymes for roles in maintaining genome integrity," *Nat Cell Biol.* 16(10):1016-8, Oct. 2014, (27 pages).

Pfeifer et al., "Gene Therapy: Promises and Problems," *Annu. Rev. Genomics Hum. Genet.* 2:111-211, 2001.

Portolano et al., "Lack of Promiscuity in Autoantigen-Specific H and L Chain Combinations as Revealed by Human H and L Chain "Roulette"," *J. Immunol.* 150(3):880-887, Feb. 1993.

Rossi et al., "Genetic therapies against HIV," *Nat. Biotechnol.* 25(12):1444-1454, Dec. 2007.

Roux et al., "Structural analysis of the nurse shark (new) antigen receptor (NAR): Molecular convergence of NAR and unusual mammalian immunoglobulins," *PNAS* 95:11804-11809, Sep. 1998.

Safdari et al., "Antibody humanization methods—a review and update," *Biotechnology and Genetic Engineering Reviews* 29(2):175-186, 2013.

Sandberg et al., "Human T-cell lines with well-defined T-cell receptor gene rearrangements as controls for the BIOMED-2 multiplex polymerase chain reaction tubes," *Leukemia* 21:230-231, 2007.

Scatchard et al., "The Attractions of Proteins for Small Molecules and Ions," *Ann. N.Y. Acad. Sci.* 51:660-672, 1949.

Schmitt et al., "T Cell Receptor Gene Therapy for Cancer," *Human Gene Therapy* 20:1240-1248, Nov. 2009.

Scholten et al., "Codon modification of T cell receptors allows enhanced functional expression in transgenic human T cells," *Clin. Immunol.* 119:135-145, 2006.

Srivastava et al., "Engineering CAR-T Cells: Design Concepts," *Trends Immunol.* 36(8):494-502, 2015.

Stone et al., "A novel T cell receptor single-chain signaling complex mediates antigen-specific T cell activity and tumor control," *Cancer Immunol. Immunother.* 63(11):1163-1176, Nov. 2014.

Teplyakov et al., "Antibody modeling assessment II. Structures and models," *Proteins* 82(8):1563-1582, 2014. (20 pages).

Vallabhapurapu et al., "Variation in human cancer cell external phosphatidylserine is regulated by flippase activity and intracellular calcium," *Oncotarget* 6(33):34375-34388, 2015.

Verhoeyen et al., "Chapter 8: Lentiviral Vector Gene Transfer into Human T Cells," *Methods Mol. Biol.* 506:97-114, 2009.

Vincke et al., "General Strategy to Humanize a Camelid Single-domain Antibody and Identification of a Universal Humanized Nanobody Scaffold," *J. Biol. Chem.* 284(5):3273-3284, Jan. 2009.

Walseng et al., "A TCR-based Chimeric Antigen Receptor," *Scientific Reports* 7:10713, 2017, (10 pages).

Wilson, "Analyzing Biomolecular Interactions," *Science* 295(5562):2103-2105, 2002.

Wolff et al., "Monoclonal Antibody Homodimers: Enhanced Antitumor Activity in Nude Mice," *Cancer Res.* 53:2560-2565, Jun. 1993.

Wälchli et al., "A Practical Approach to T-Cell Receptor Cloning and Expression," *PLoS One* 6(11):e27930, 2011, (11 pages).

Zaritskaya et al., "New flow cytometric assays for monitoring cell-mediated cytotoxicity," *Expert Review of Vaccines* 9(6):601-616, Jun. 2010, (26 pages).

Zhang et al., "Transduction of Human T Cells with a Novel T-Cell Receptor Confers Anti-HCV Reactivity," *PLoS Pathogens* 6(7):e1001018, Jul. 2010, (13 pages).

Zhao et al., "Primary Human Lymphocytes Transduced with NY-ESO-1 Antigen-Specific TCR Genes Recognize and Kill Diverse Human Tumor Cell Lines," *J. Immunol.* 174:(7):4415-4423, Apr. 2005, (25 pages).

Moller-Tank et al., "Characterizing Functional Domains for TIM-Mediated Enveloped Virus Entry", J. Virology, Jun. 2014, 88(12): 6702-6713).

Nakaya,"Research on Molecular Mechanisms of Engulfrnent of Apoptotic Cells", *The Pharmaceutical Society of Japan* 135(8):949-954, 2015.

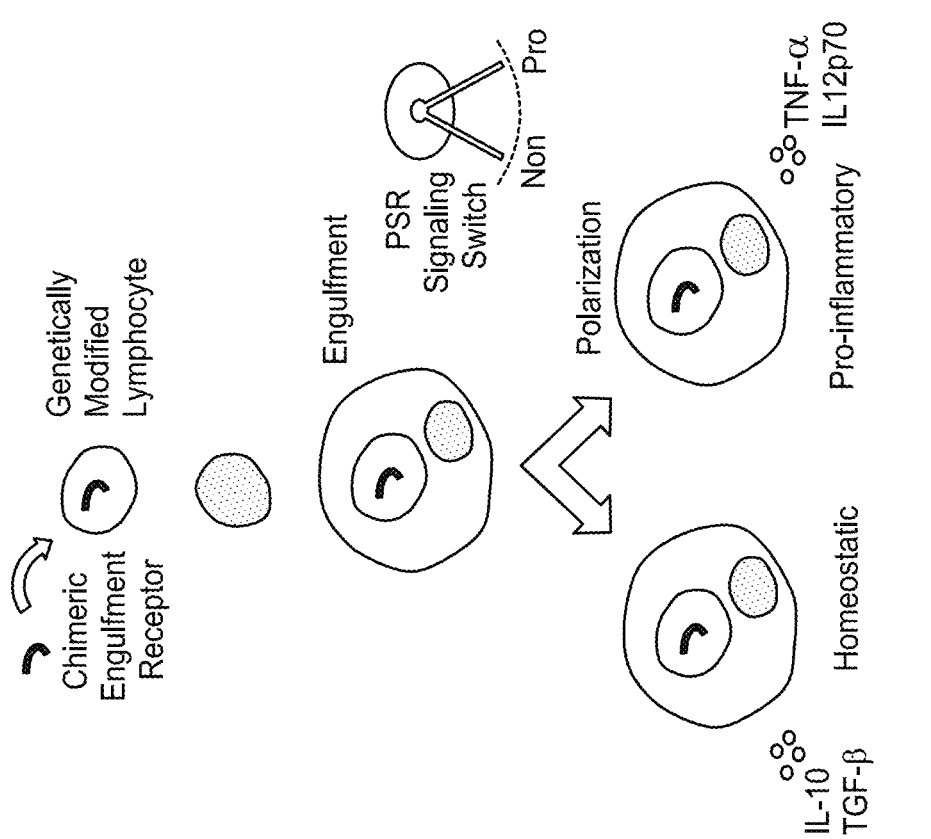
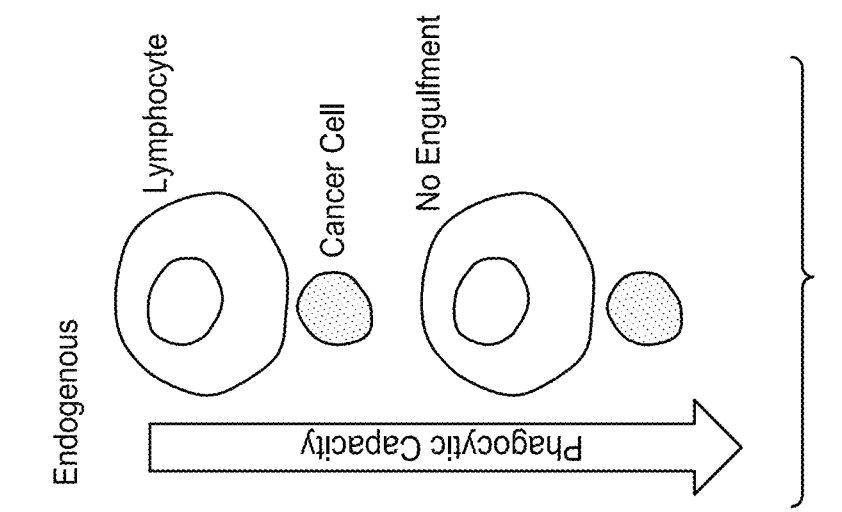
FIG. 3B
FIG. 3A

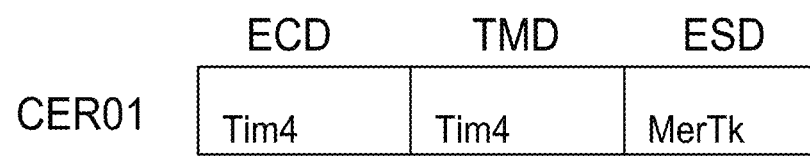
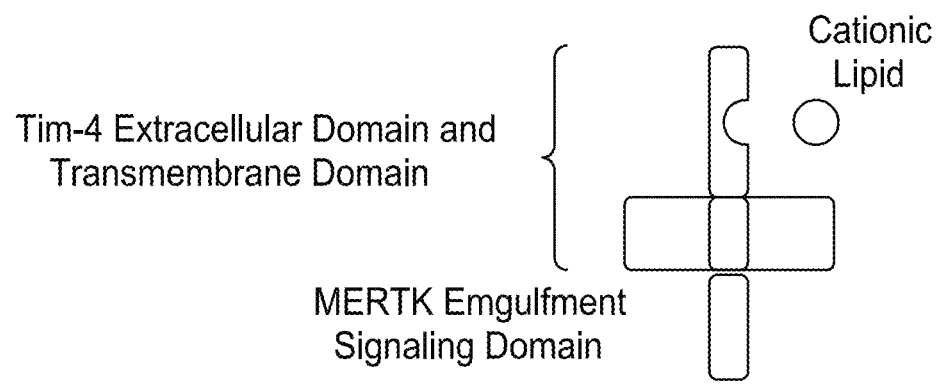
FIG. 6A

| Extracellular Domain | Transmembrane Domain | Enfulfment Signaling Domain |
|---|---|---|
| Tim4 | Tim4 | Syk |
| Tim4 | Tim4 | MyD88 |
| Tim4 | Tim4 | Zap70 |
| Tim4 | Tim4 | FcGR1 |
| Tim4 | Tim4 | FcGR2a |
| Tim4 | Tim4 | FcGR3a |
| FA58C2 | Tim4 | Syk |
| Fcr | Fcr | Syk |
| Fcr | Fcr | MyD88 |
| Fcr | Fcr | Zap70 |
| ScFv | CD8a | Syk |
| ScFv | CD8a | MyD88 |
| ScFv | CD8a | Zap70 |
| ScFv | CD8a | FcGR1 |
| ScFv | CD8a | FcGR2a |
| ScFv | CD8a | FcGR3a |

| Extracellular Domain | Transmembrane Domain | Primary Engulfment Signaling Domain | Secondary Engulfment Signaling Domain |
|---|---|---|---|
| FcR | FcR | MerTk | Syk |
| FcR | FcR | MerTk | MyD88 |
| FcR | FcR | MerTk | Zap70 |
| ScFv | CD8a | MerTk | Syk |
| ScFv | CD8a | MerTk | MyD88 |
| ScFv | CD8a | MerTk | Zap70 |
| ScFv | CD8a | Axl | Syk |
| Tim4 | Tim4 | MerTk | Syk |
| Tim4 | Tim4 | MerTk | MyD88 |
| Tim4 | Tim4 | MerTk | Zap70 |
| Tim4 | Tim4 | Axl | Syk |

FIG. 14

| Extracellular Domain | Transmembrane Domain | Primary Engulfment Signaling Domain | Secondary Engulfment Signaling Domain |
|---|---|---|---|
| Tim4 | Tim4 | MerTk | ItgB5 |
| Tim4 | Tim4 | MerTk | Syk |
| Tim4 | Tim4 | MerTk | MyD88 |
| Tim4 | Tim4 | MerTk | Zap70 |
| Tim4 | Tim4 | Axl | ItgB5 |
| Tim4 | Tim4 | Axl | Syk |
| Tim4 | Tim4 | Syk | |
| Tim4 | Tim4 | MyD88 | |
| Tim4 | Tim4 | Zap70 | |
| Tim4 | Tim4 | FcGR1 | |
| Tim4 | Tim4 | FcGR2a | |
| Tim4 | Tim4 | FcGR3a | |
| FA58C2 | Tm4 | MerTk | |
| FA58C2 | Tm4 | Axl | |
| FA58C2 | Tm4 | Syk | |
| FcR | FcR | MerTk | ItgB5 |
| FcR | FcR | MerTk | Syk |
| FcR | FcR | MerTk | MyD88 |
| FcR | FcR | MerTk | Zap70 |
| FcR | FcR | Axl | ItgB5 |
| FcR | FcR | Syk | |
| FcR | FcR | MyD88 | |
| FcR | FcR | Zap70 | |
| ScFv | CD8a | MerTk | ItgB5 |
| ScFv | CD8a | MerTk | Syk |
| ScFv | CD8a | MerTk | MyD88 |
| ScFv | CD8a | MerTk | Zap70 |
| ScFv | CD8a | Axl | ItgB5 |
| ScFv | CD8a | Axl | Syk |
| ScFv | CD8a | Syk | |
| ScFv | CD8a | MyD88 | |
| ScFv | CD8a | Zap70 | |
| ScFv | CD8a | FcGR1 | |
| ScFv | CD8a | FcGR2a | |
| ScFv | CD8a | FcGR3a | |

FIG. 15

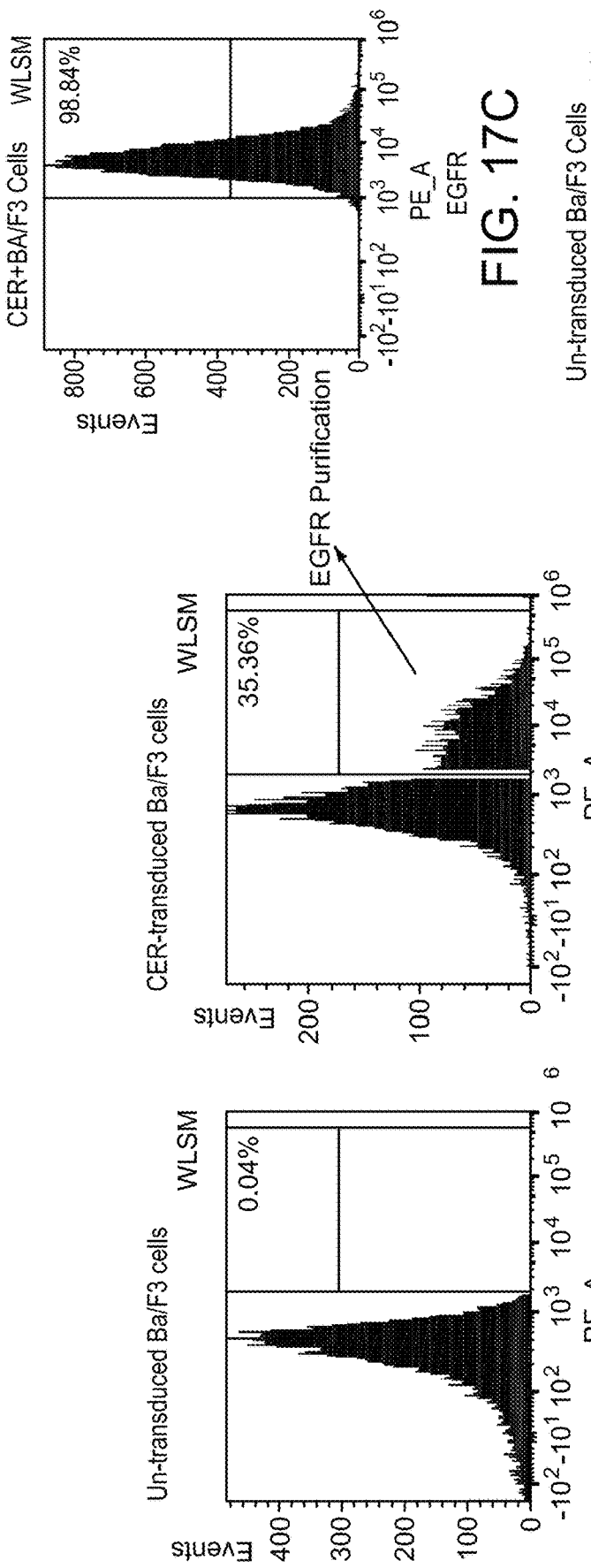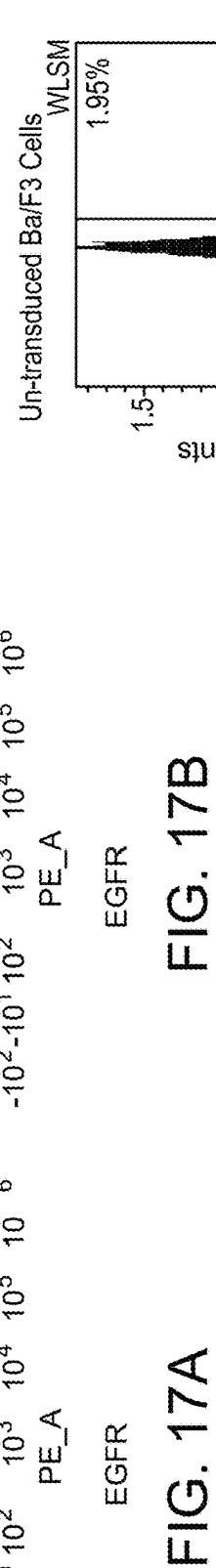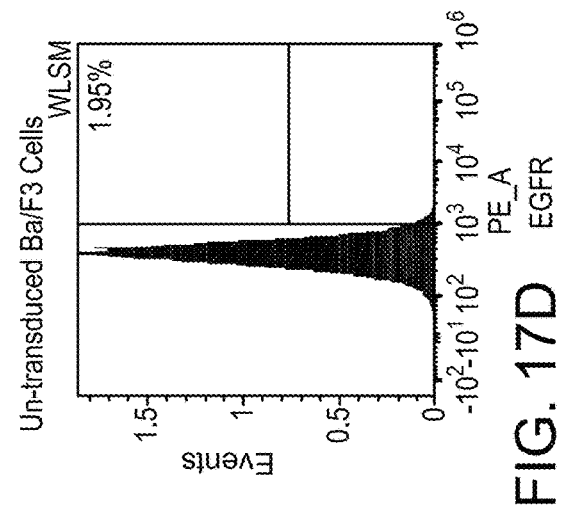

| | EGFRt | CER01 |
|---|---|---|
| Number of values | 2 | 2 |
| Minimum | 16.3 | 25.4 |
| 25% Percentile | 16.3 | 25.4 |
| Median | 17.45 | 25.8 |
| 75% Percentile | 18.6 | 26.2 |
| Maximum | 18.6 | 26.2 |
| Mean | 17.45 | 25.8 |
| Std. Deviation | 1.626 | 0.5657 |
| Std. Error of Mean | 1.15 | 0.4 |
| Lower 95% CI of mean | 2.838 | 20.72 |
| Upper 95% CI of mean | 32.06 | 30.88 |
| Sum | 34.9 | 51.6 |
| Hybrid Capture | 4.2 | 11.6 |
| Phagocytic Index | 73.29 | 229.28 |
| ttest | | 0.05 |

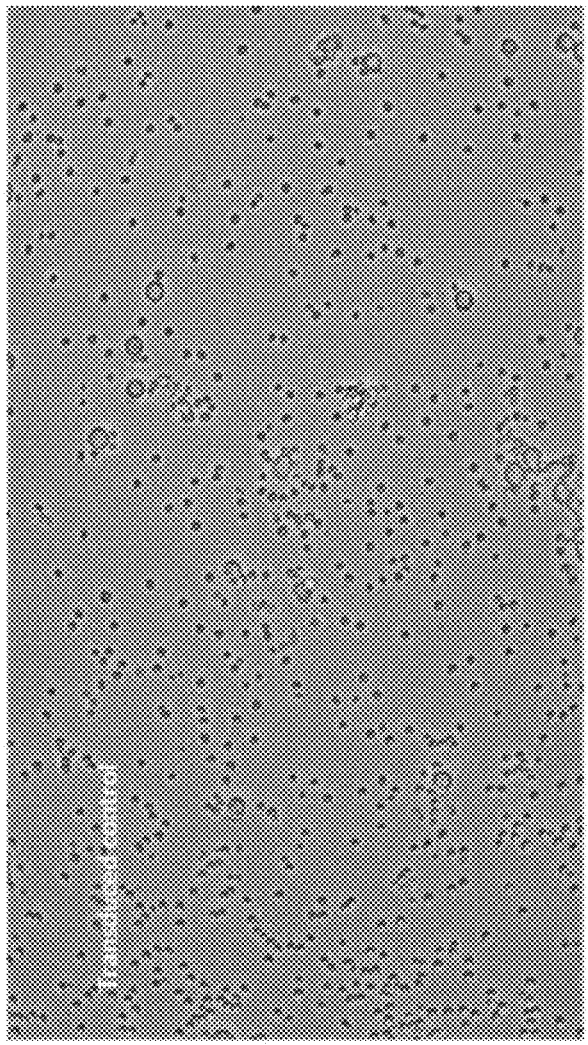
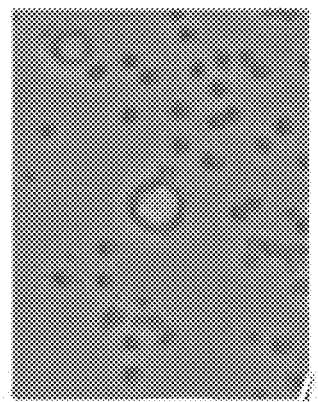
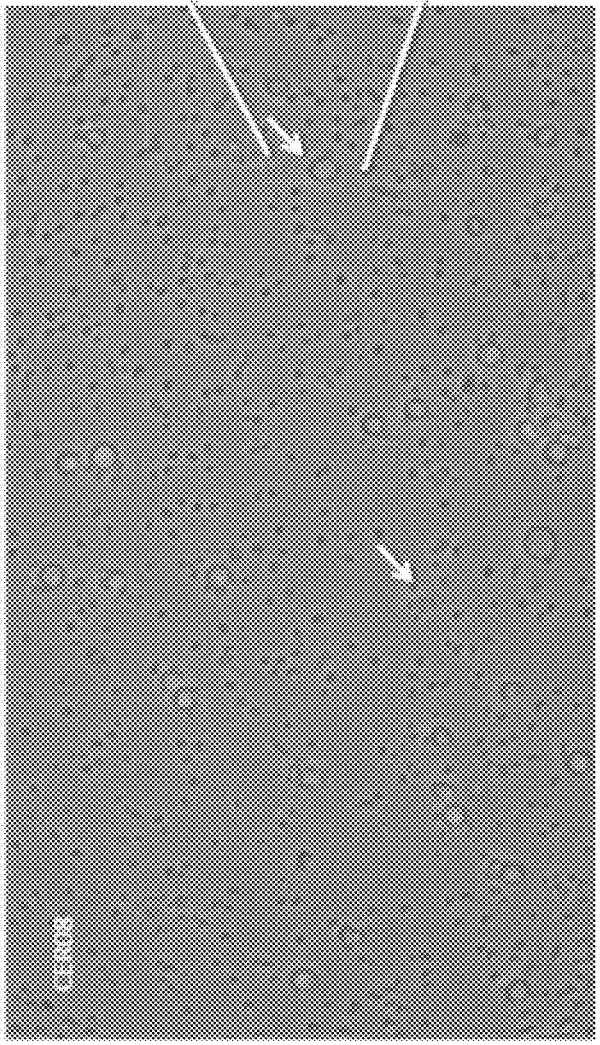
FIG. 38A
FIG. 38B

| | EGFRt | CER08 |
|---|---|---|
| Number of values | 2 | 2 |
| Minimum | 16.3 | 13.1 |
| 25% Percentile | 16.3 | 13.1 |
| Median | 17.45 | 17.25 |
| 75% Percentile | 18.6 | 21.4 |
| Maximum | 18.6 | 21.4 |
| Mean | 17.45 | 17.25 |
| Std. Deviation | 1.626 | 5.869 |
| Std. Error of Mean | 1.15 | 4.15 |
| Lower 95% CI of mean | 2.838 | -35.48 |
| Upper 95% CI of mean | 32.06 | 69.98 |
| Sum | 34.9 | 34.5 |
| Hybrid Capture | 4.2 | 13 |
| Phagocytic Index | 73.29 | 224.25 |
| ttest | | 0.95 |

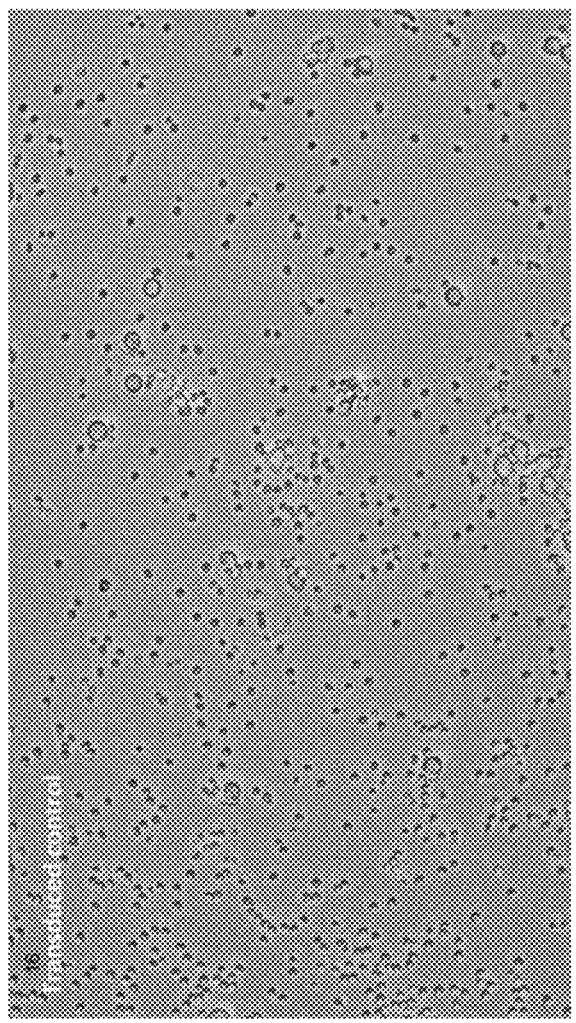
FIG. 42A
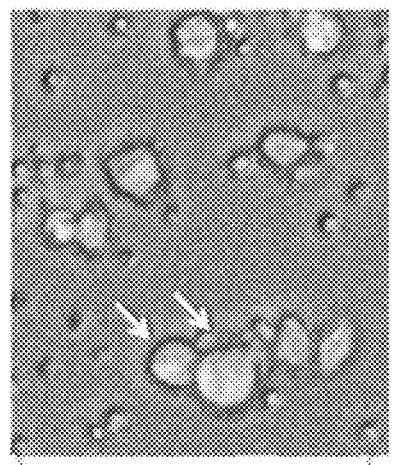
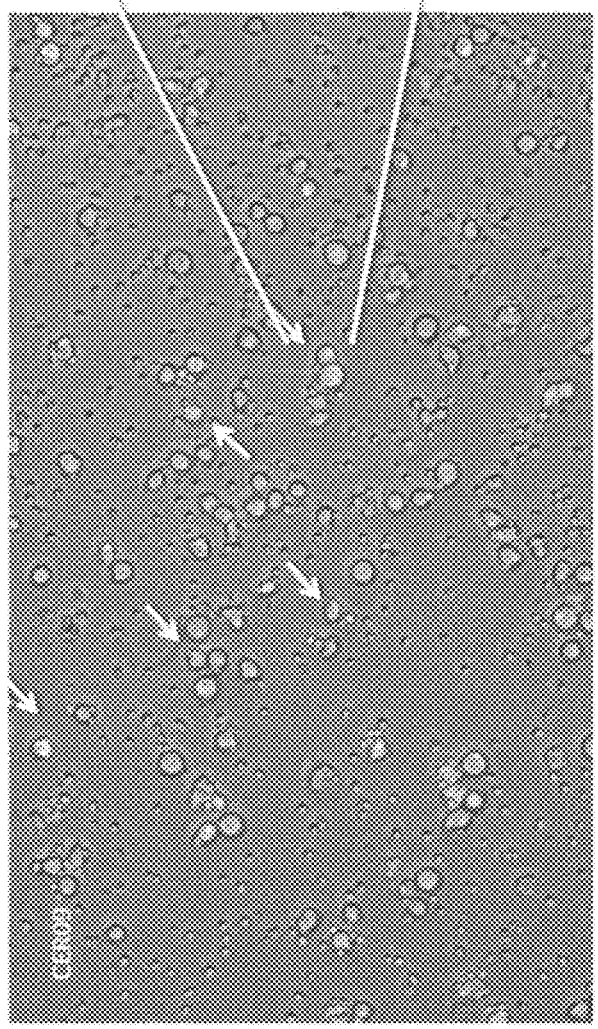
FIG. 42B

| | EGFRt | CER09 |
|---|---|---|
| Number of values | 2 | 2 |
| Minimum | 16.3 | 26.5 |
| 25% Percentile | 16.3 | 26.5 |
| Median | 17.45 | 28.35 |
| 75% Percentile | 18.6 | 30.2 |
| Maximum | 18.6 | 30.2 |
| Mean | 17.45 | 28.35 |
| Std. Deviation | 1.626 | 2.616 |
| Std. Error of Mean | 1.15 | 1.85 |
| Lower 95% CI of mean | 2.838 | 4.844 |
| Upper 95% CI of mean | 32.06 | 51.86 |
| Sum | 34.9 | 56.7 |
| Hybrid Capture | 4.2 | 15 |
| Phagocytic Index | 73.29 | 425.25 |
| ttest | | 0.17 |

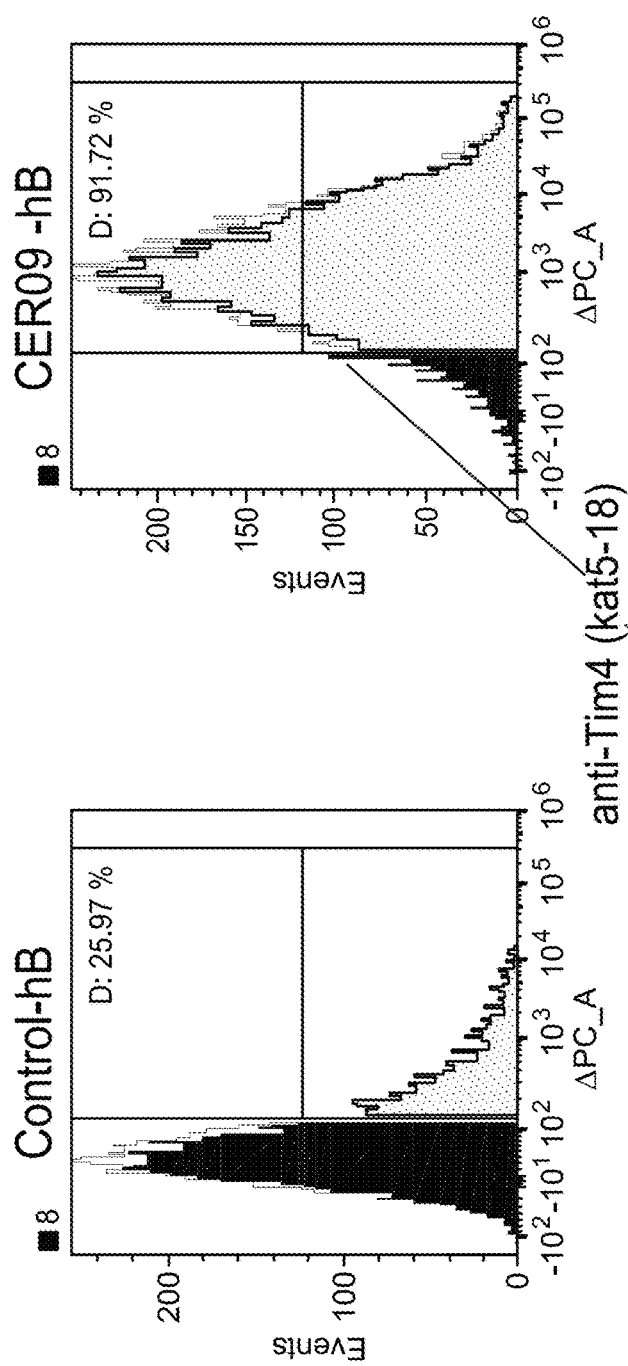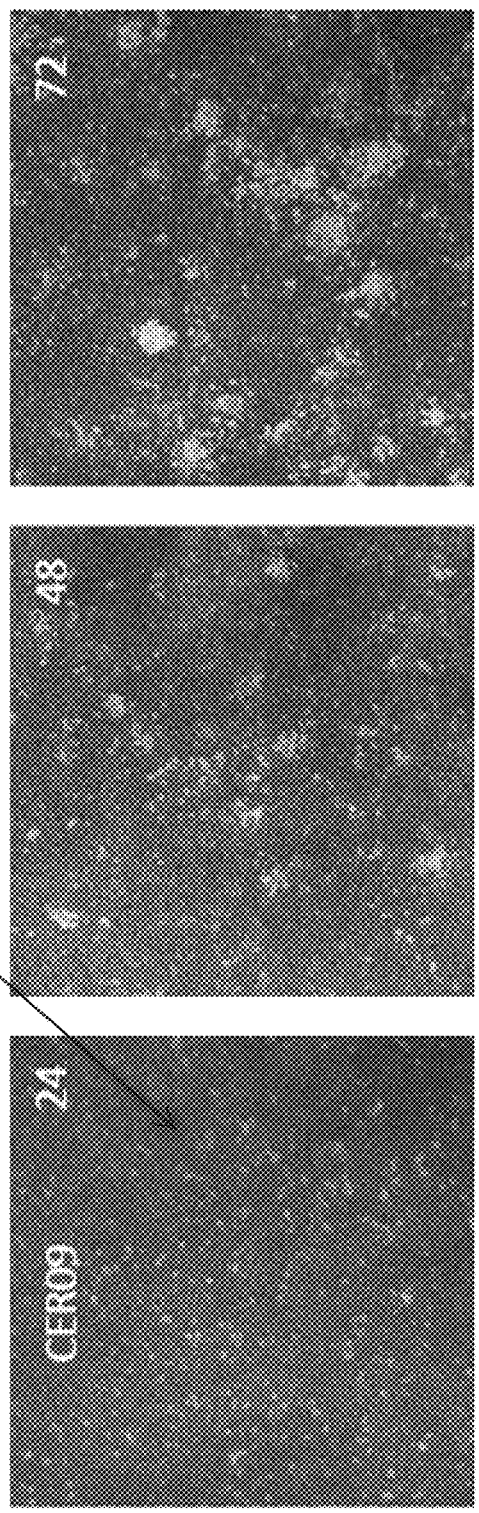
FIG. 49A
FIG. 49B

| | EGFRt | CER10 |
|---|---|---|
| Number of values | 2 | 2 |
| Minimum | 16.3 | 20.2 |
| 25% Percentile | 16.3 | 20.2 |
| Median | 17.45 | 22.45 |
| 75% Percentile | 18.6 | 24.7 |
| Maximum | 18.6 | 24.7 |
| Mean | 17.45 | 22.45 |
| Std. Deviation | 1.626 | 3.182 |
| Std. Error of Mean | 1.15 | 2.25 |
| Lower 95% CI of mean | 2.838 | 6.139 |
| Upper 95% CI of mean | 32.06 | 51.04 |
| Sum | 34.9 | 44.9 |
| Hybrid Capture | 4.2 | 7 |
| Phagocytic Index | 73.29 | 157.15 |
| ttest | | 0.13 |

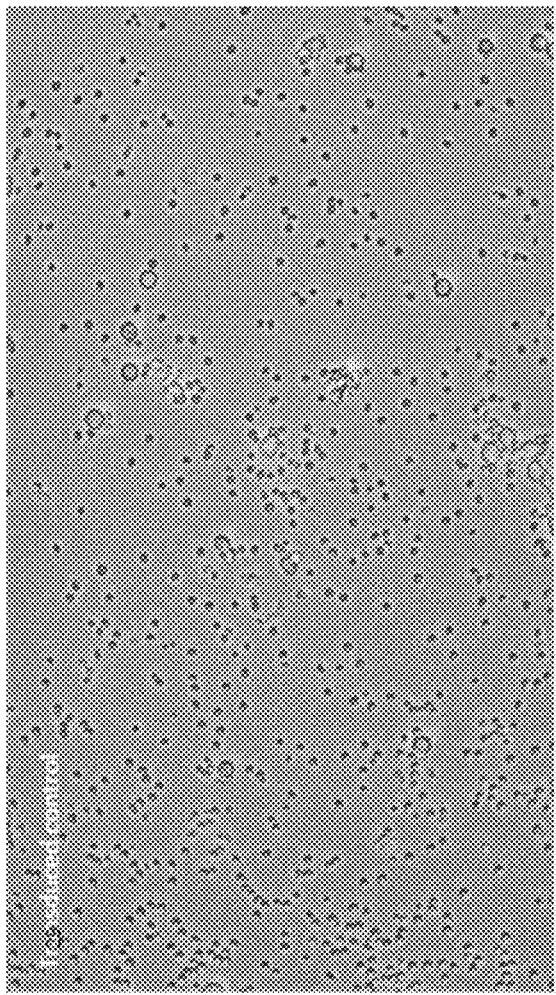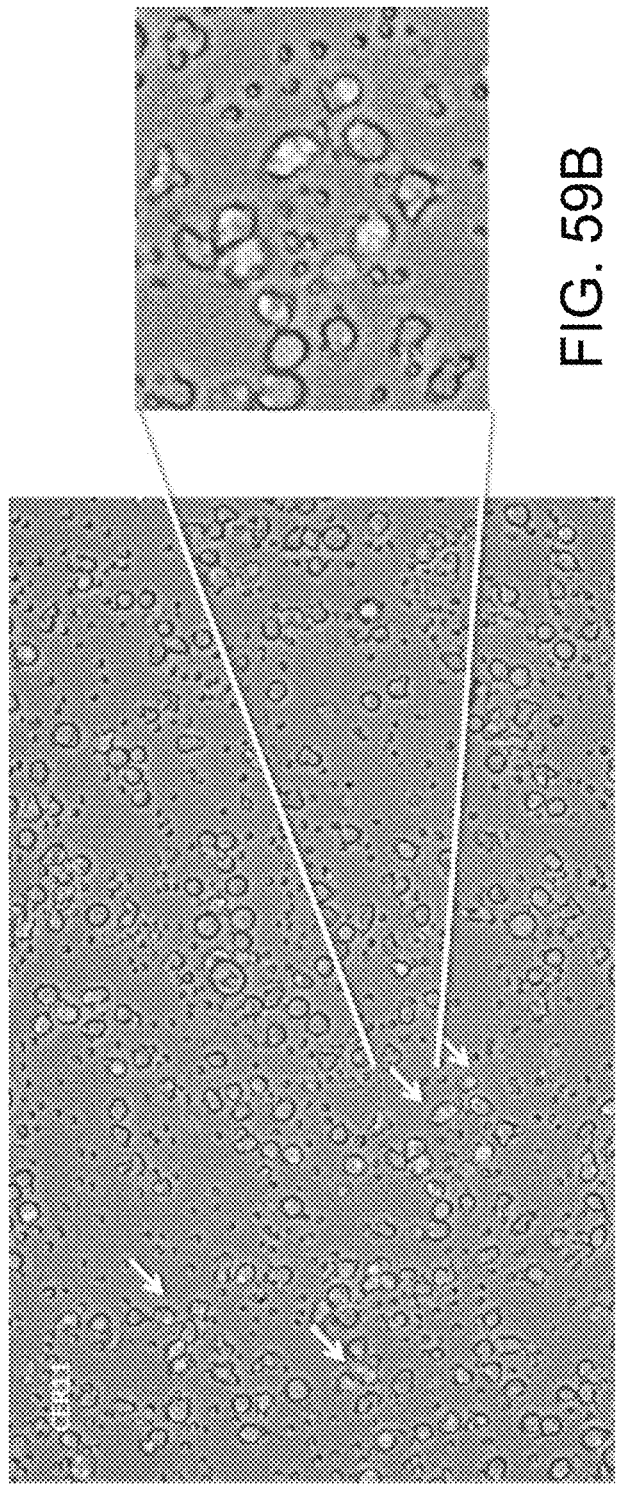

| | EGFRt | CER11 |
|---|---|---|
| Number of values | 2 | 2 |
| Minimum | 16.3 | 30.6 |
| 25% Percentile | 16.3 | 30.6 |
| Median | 17.45 | 30.95 |
| 75% Percentile | 18.6 | 31.3 |
| Maximum | 18.6 | 31.3 |
| Mean | 17.45 | 30.95 |
| Std. Deviation | 1.626 | 0.495 |
| Std. Error of Mean | 1.15 | 0.35 |
| Lower 95% CI of mean | 2.838 | 26.5 |
| Upper 95% CI of mean | 32.06 | 35.4 |
| Sum | 34.9 | 61.9 |
| Hybrid Capture | 4.2 | 12 |
| Phagocytic Index | 73.29 | 371.4 |
| ttest | | 0.03 |

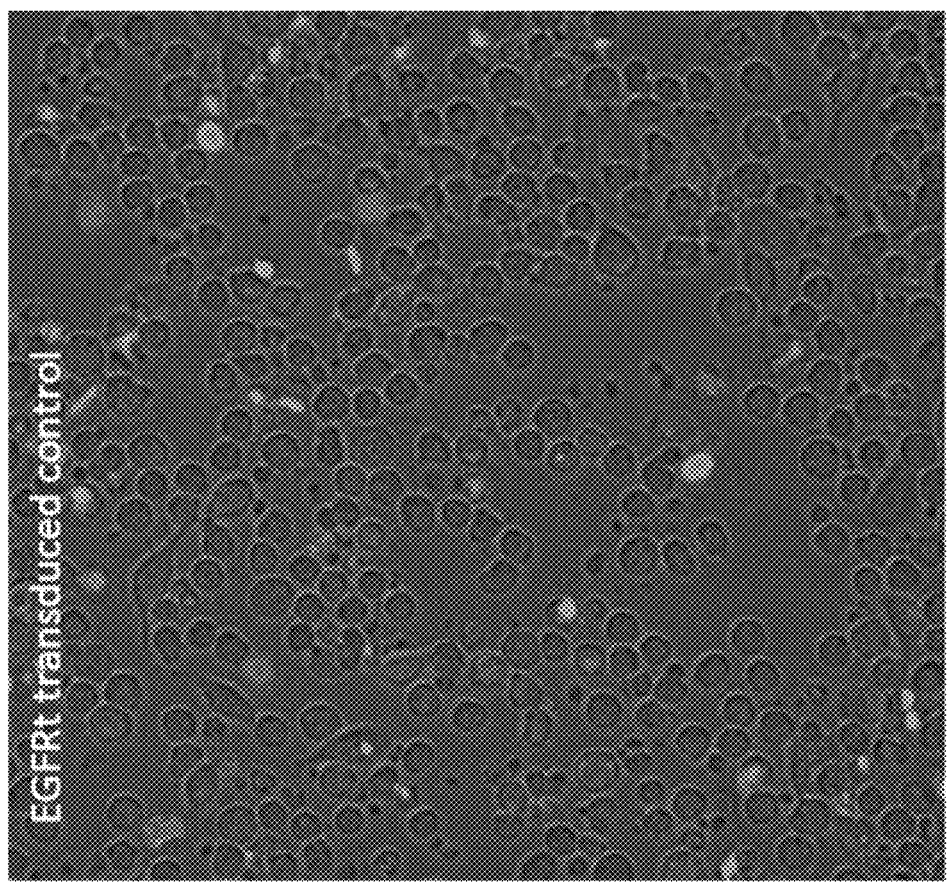
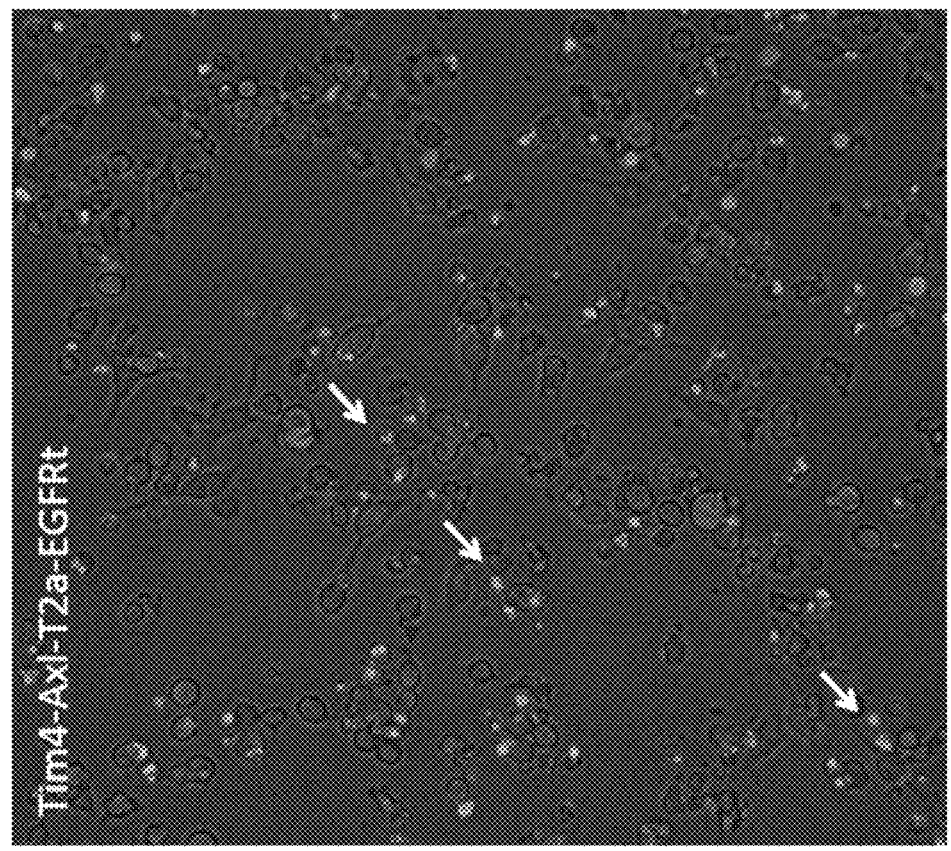
FIG. 61B
FIG. 61A

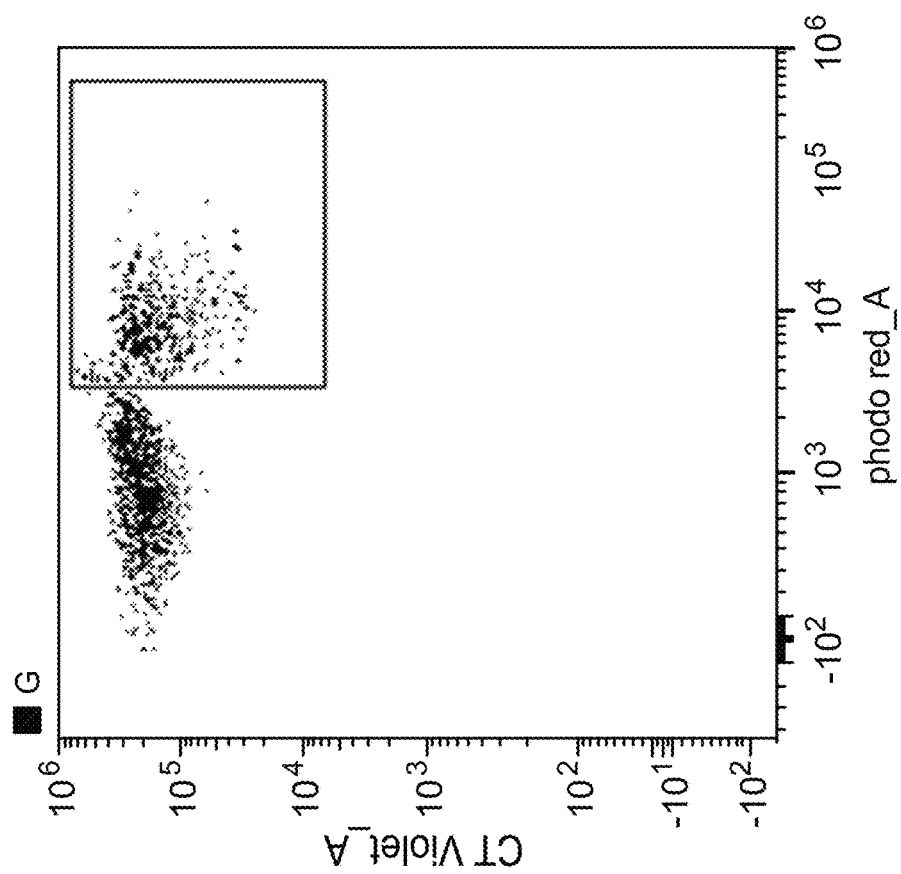
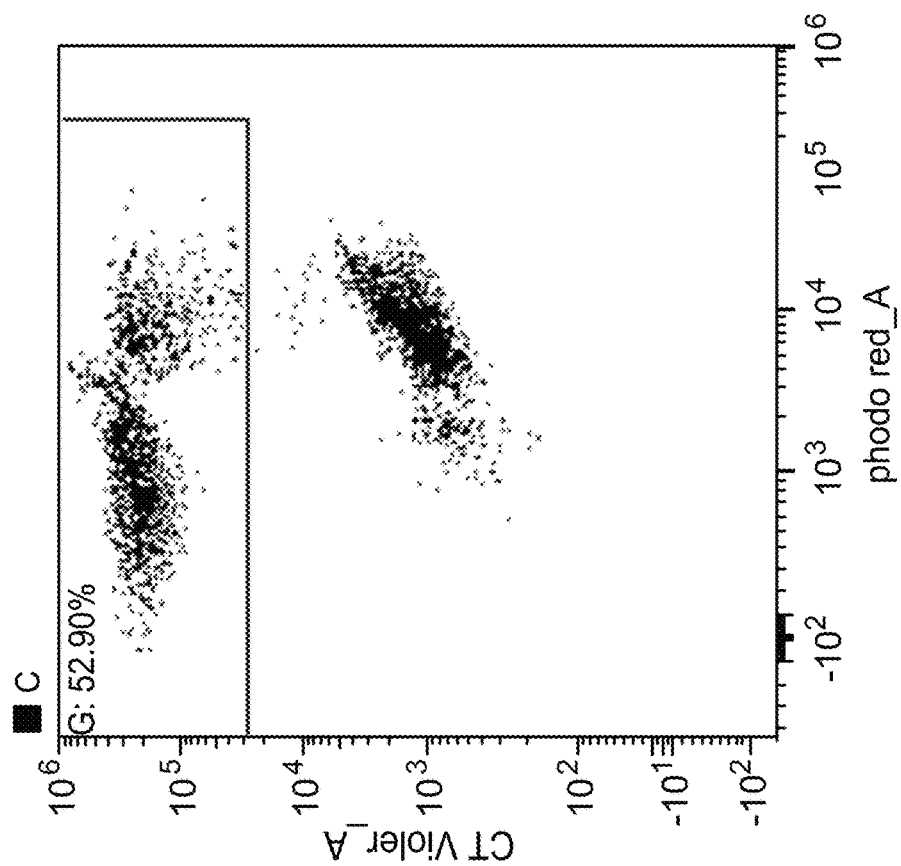
FIG. 64B
FIG. 64A

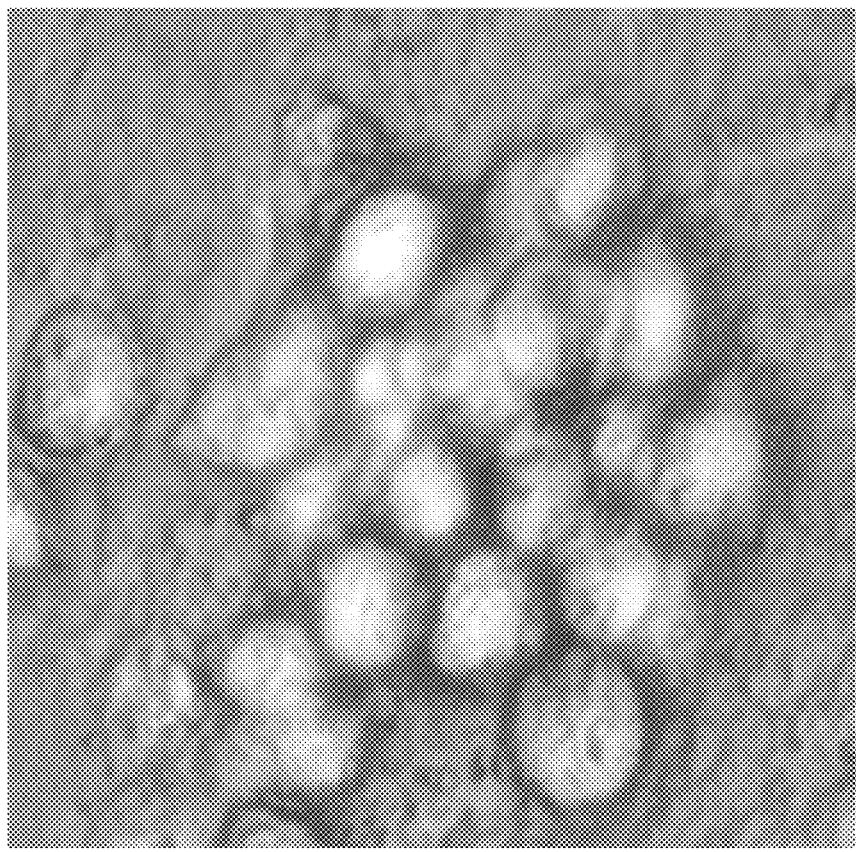
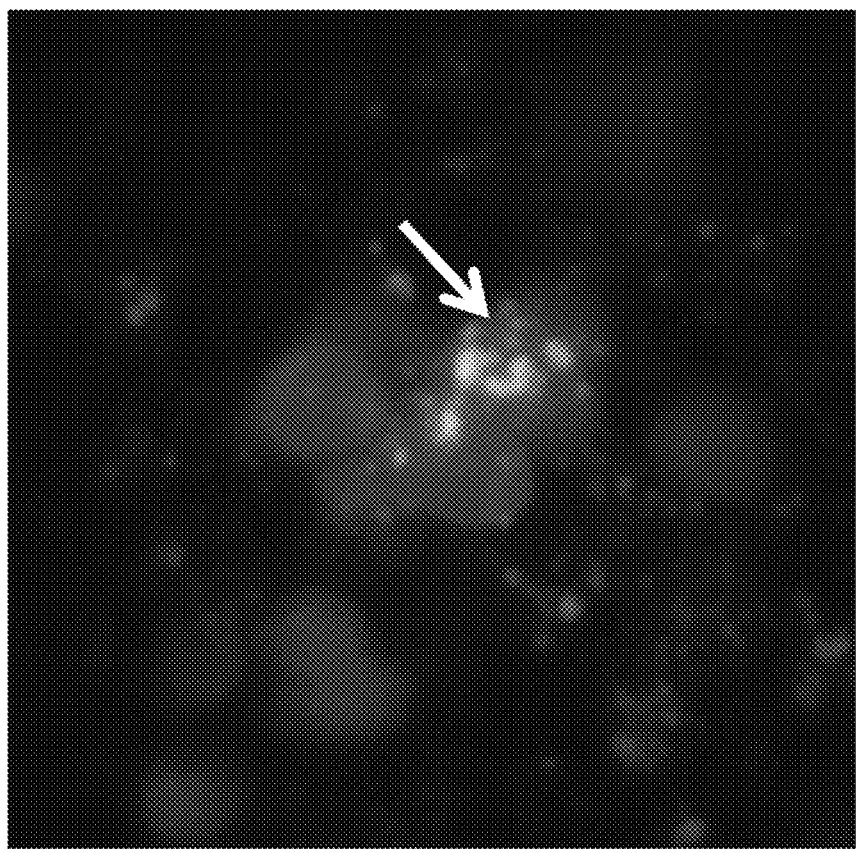
FIG. 69

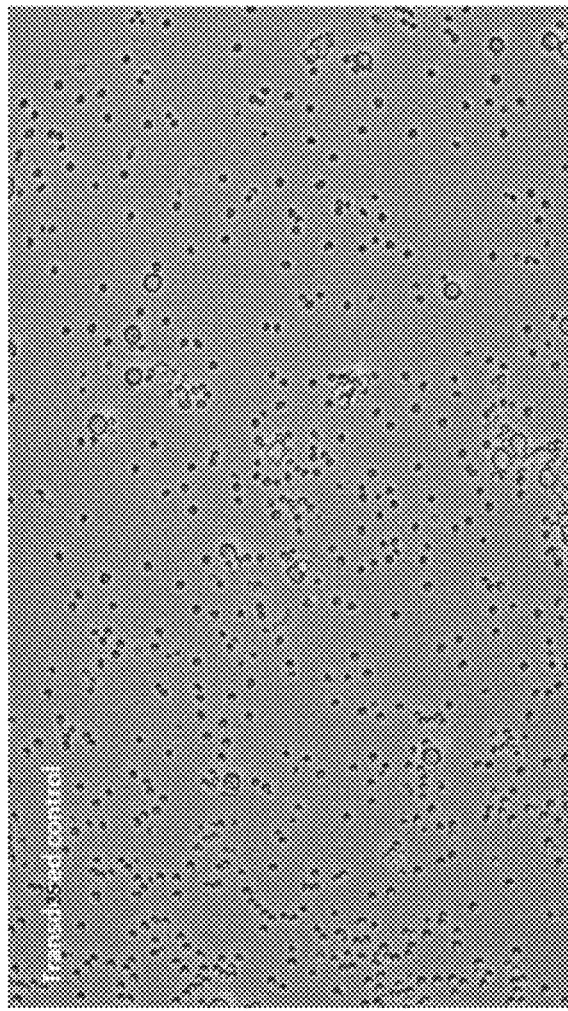
FIG. 73A
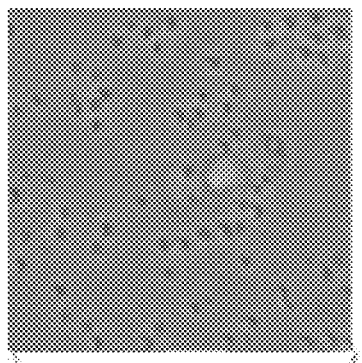
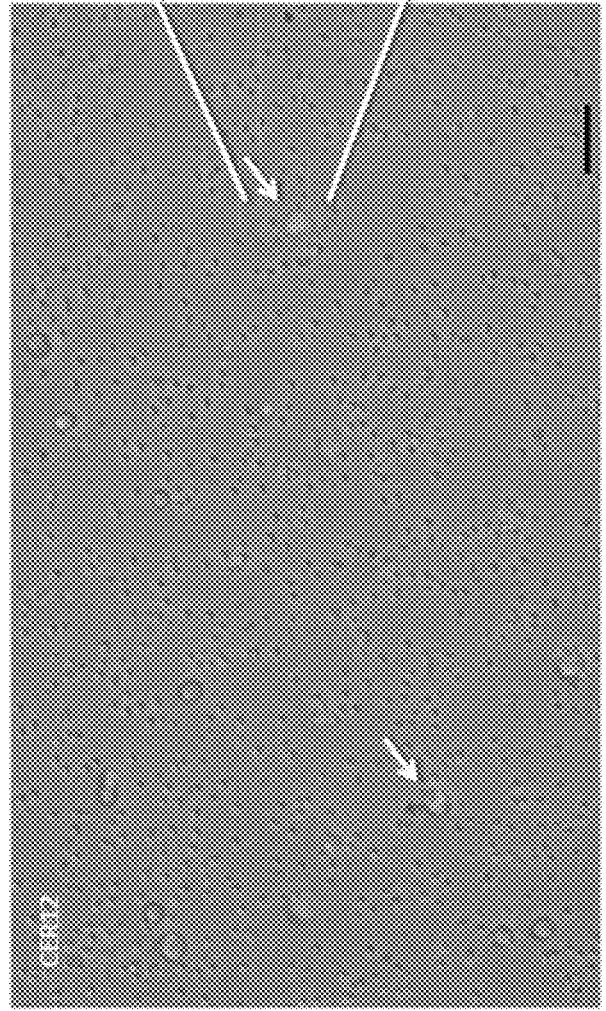
FIG. 73B

|  | EGFRt | CER12 |
|---|---|---|
| Number of values | 2 | 2 |
| Minimum | 16.3 | 16.3 |
| 25% Percentile | 16.3 | 16.3 |
| Median | 17.45 | 20.25 |
| 75% Percentile | 18.6 | 24.2 |
| Maximum | 18.6 | 24.2 |
| Mean | 17.45 | 20.25 |
| Std. Deviation | 1.626 | 5.586 |
| Std. Error of Mean | 1.15 | 3.95 |
| Lower 95% CI of mean | 2.838 | -29.94 |
| Upper 95% CI of mean | 32.06 | 70.44 |
| Sum | 34.9 | 40.5 |
| Hybrid Capture | 4.2 | 12.4 |
| Phagocytic Index | 73.29 | 251.1 |
| ttest |  | 0.68 |

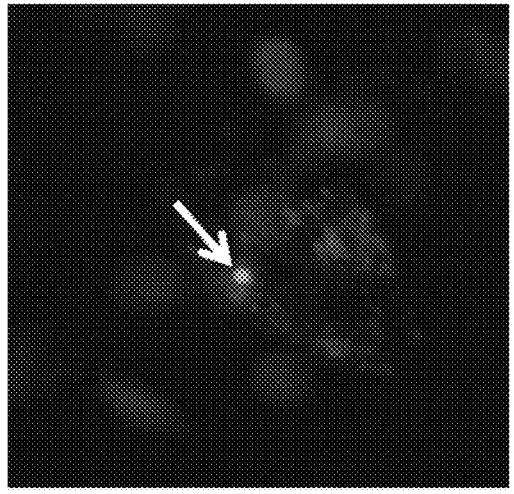
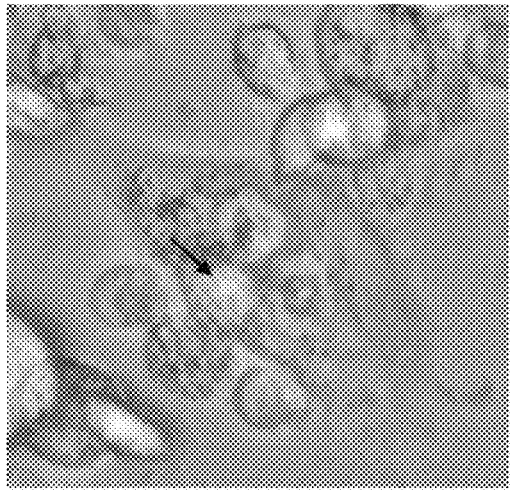
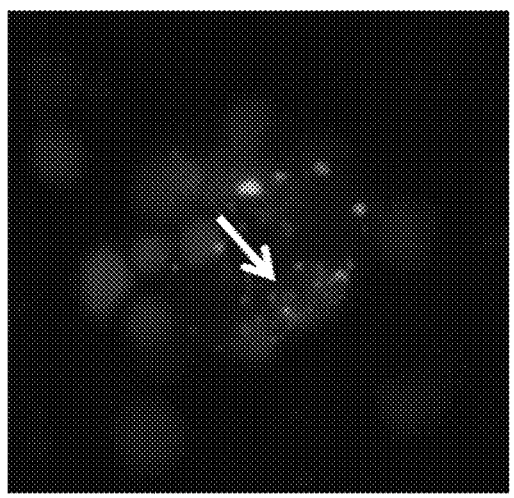
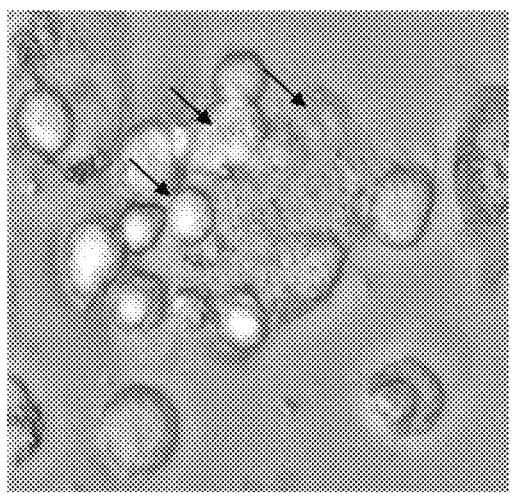
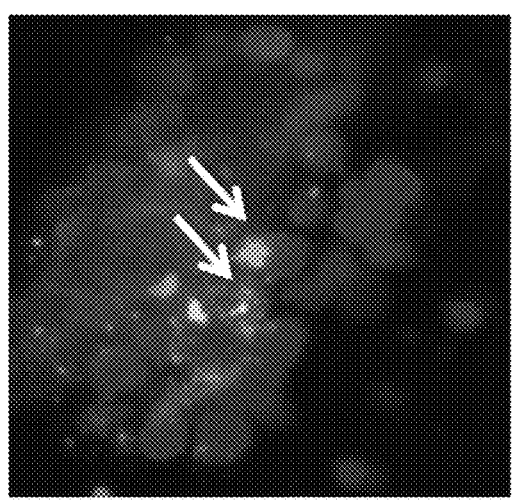
FIG. 81

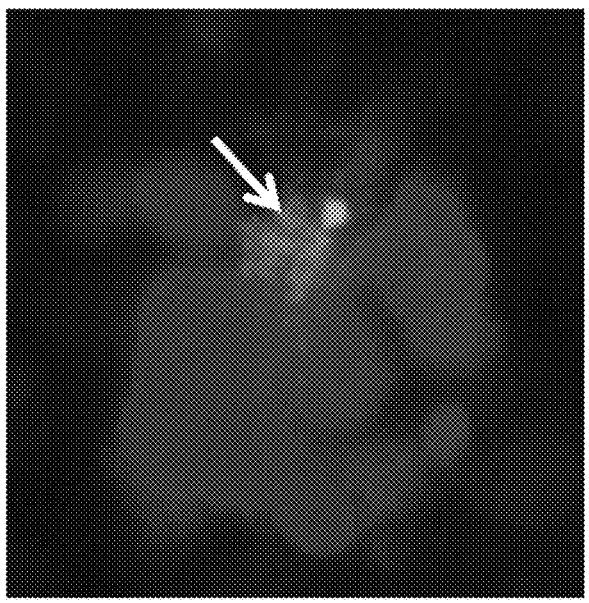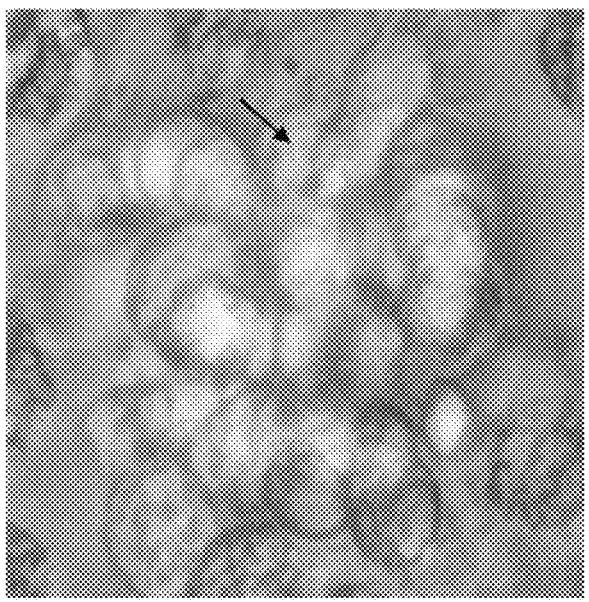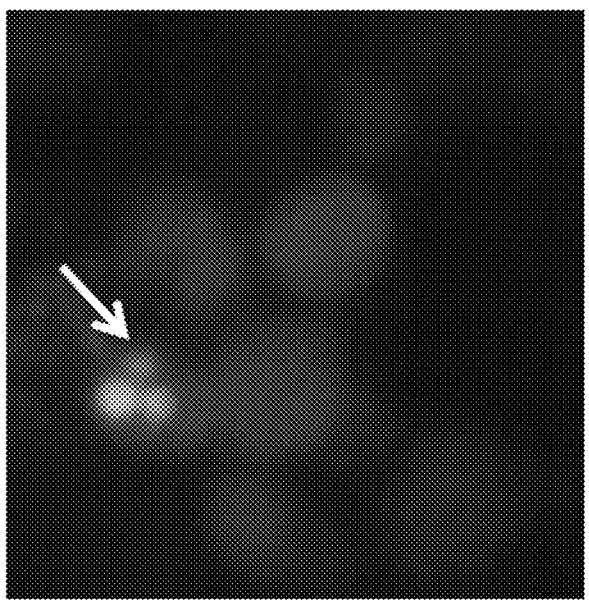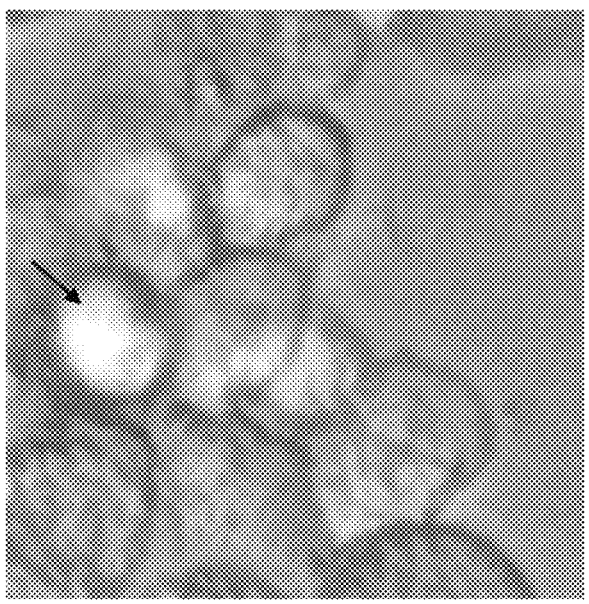
FIG. 82

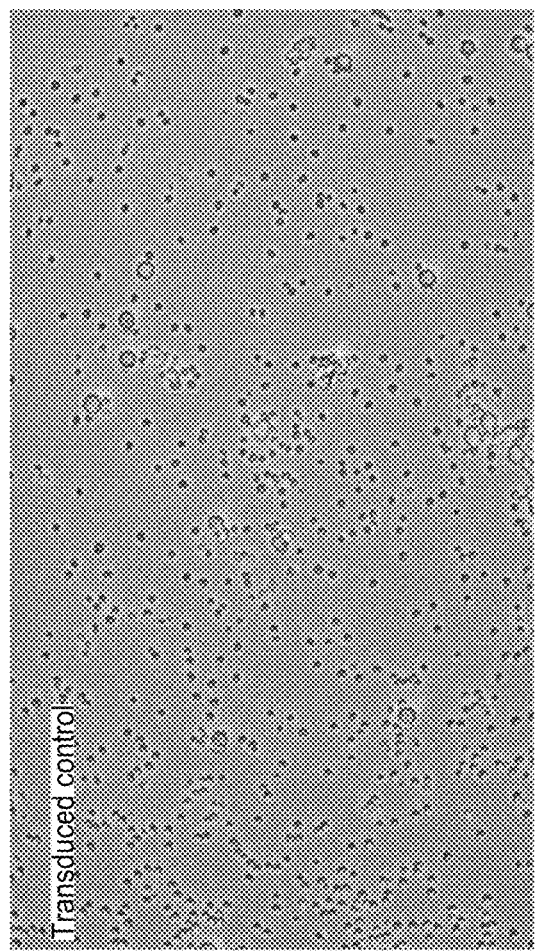
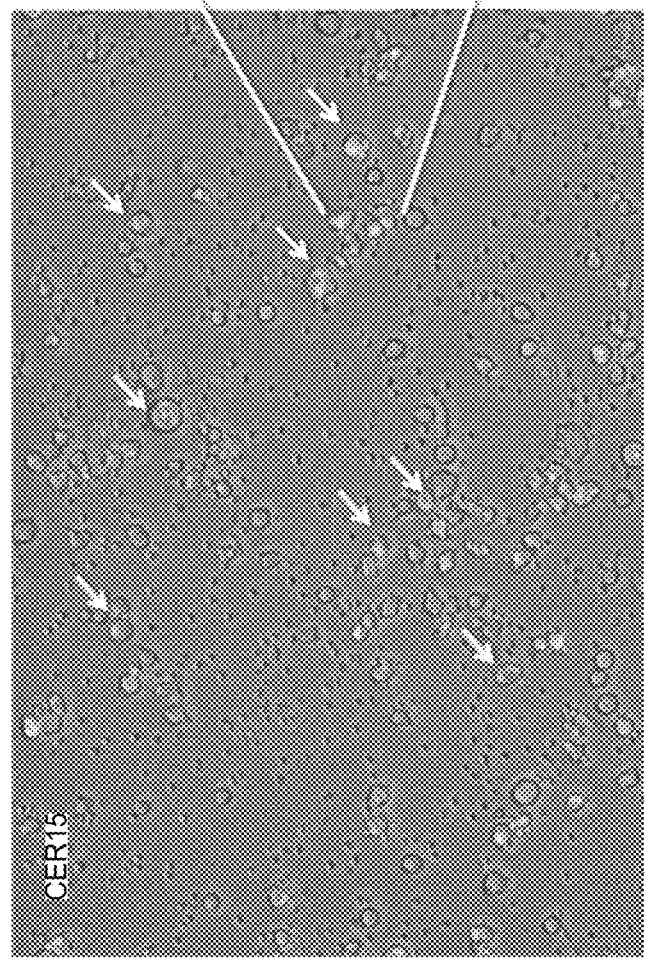
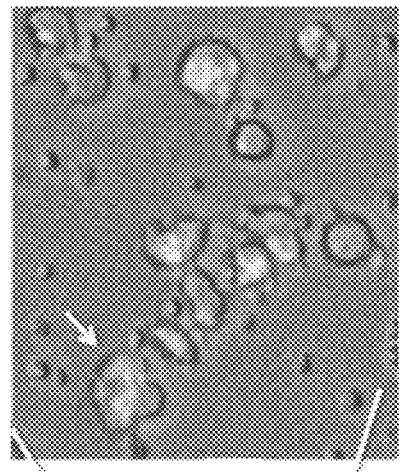
FIG. 85A
FIG. 85B

|  | EGFRt | CER15 |
|---|---|---|
| Number of values | 2 | 2 |
| Minimum | 16.3 | 47.9 |
| 25% Percentile | 16.3 | 47.9 |
| Median | 17.45 | 49.75 |
| 75% Percentile | 18.6 | 51.6 |
| Maximum | 18.6 | 51.6 |
| Mean | 17.45 | 49.75 |
| Std. Deviation | 1.626 | 2.616 |
| Std. Error of Mean | 1.15 | 1.85 |
| Lower 95% CI of mean | 2.838 | 26.24 |
| Upper 95% CI of mean | 32.06 | 73.26 |
| Sum | 34.9 | 99.5 |
| Hybrid Capture | 4.2 | 24 |
| Phagocytic Index | 73.29 | 1194 |
| ttest |  | 0.05 |

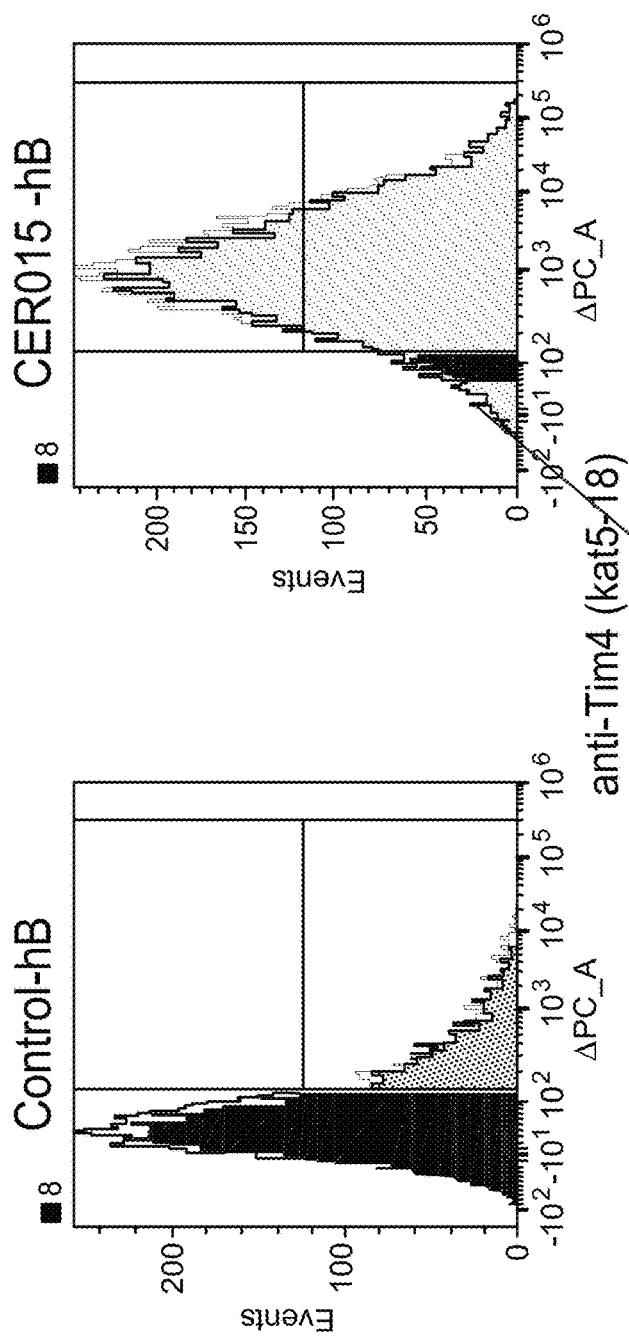
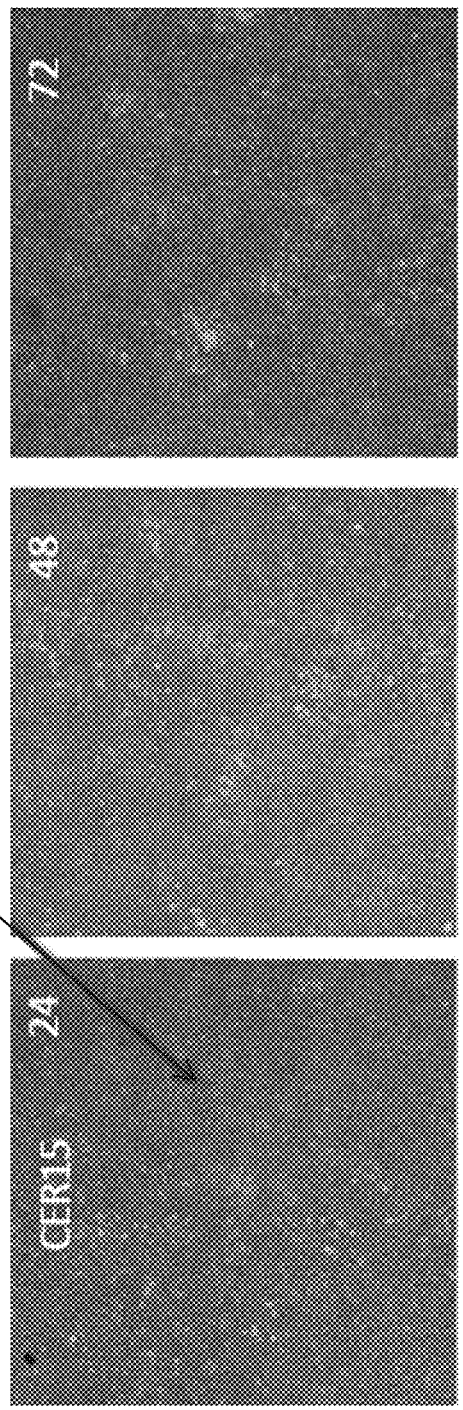
FIG. 90A
FIG. 90B

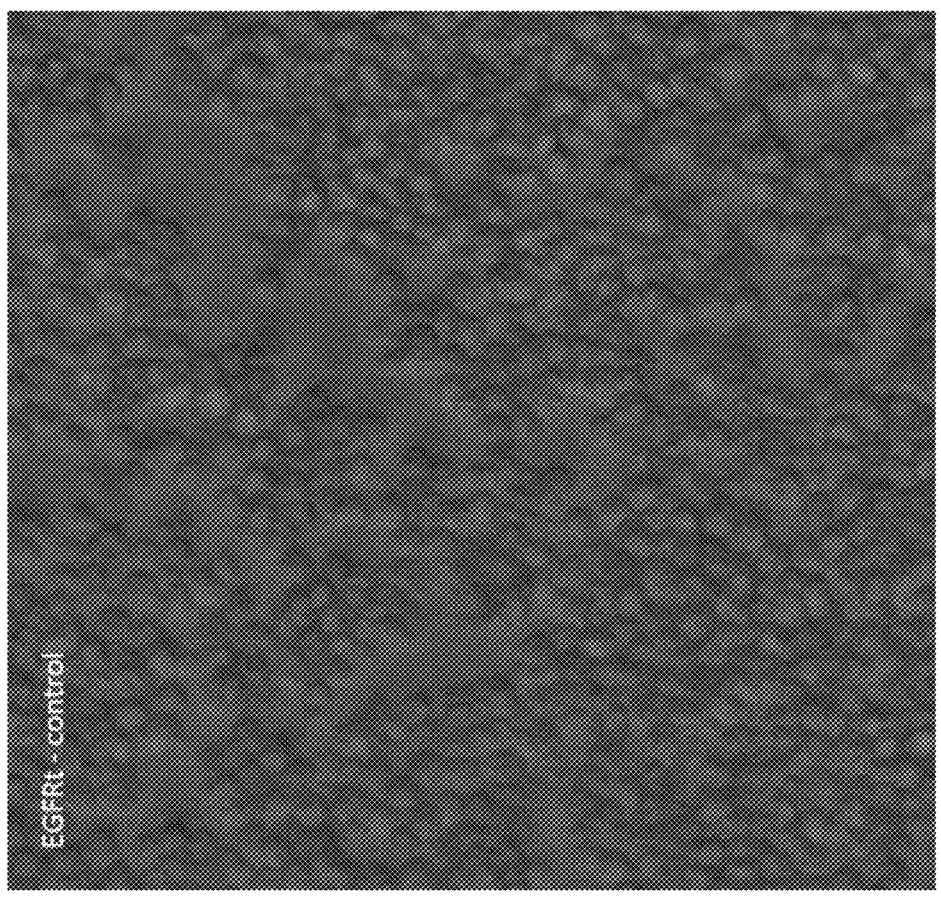
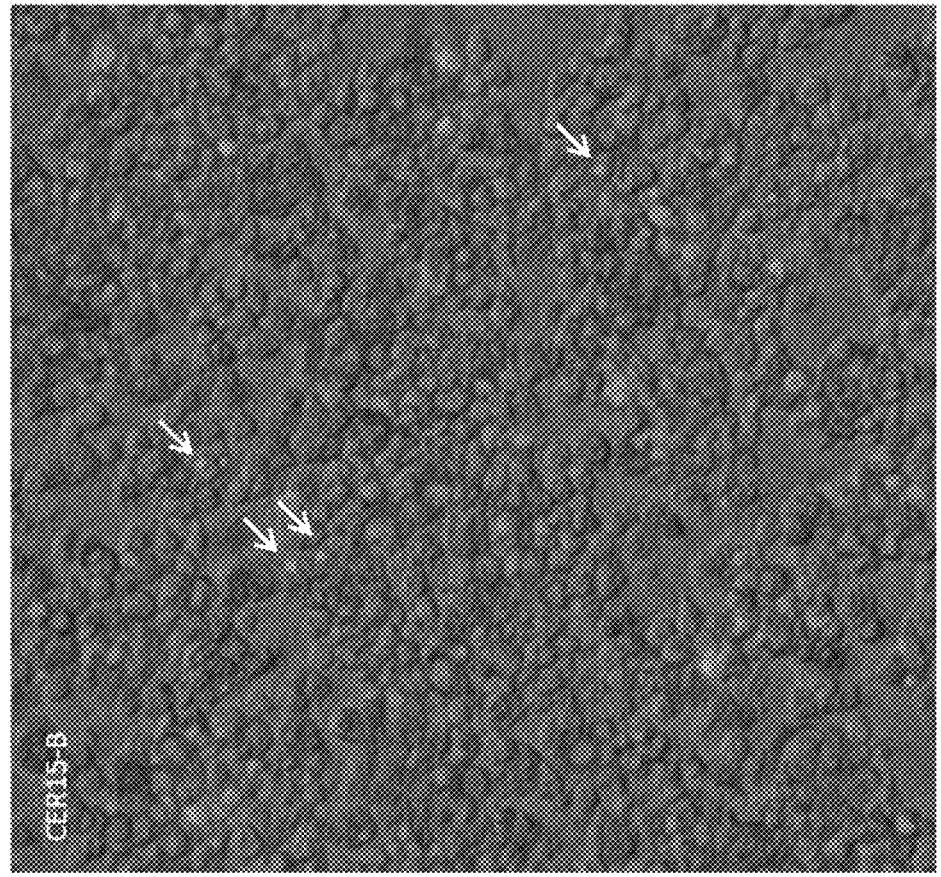

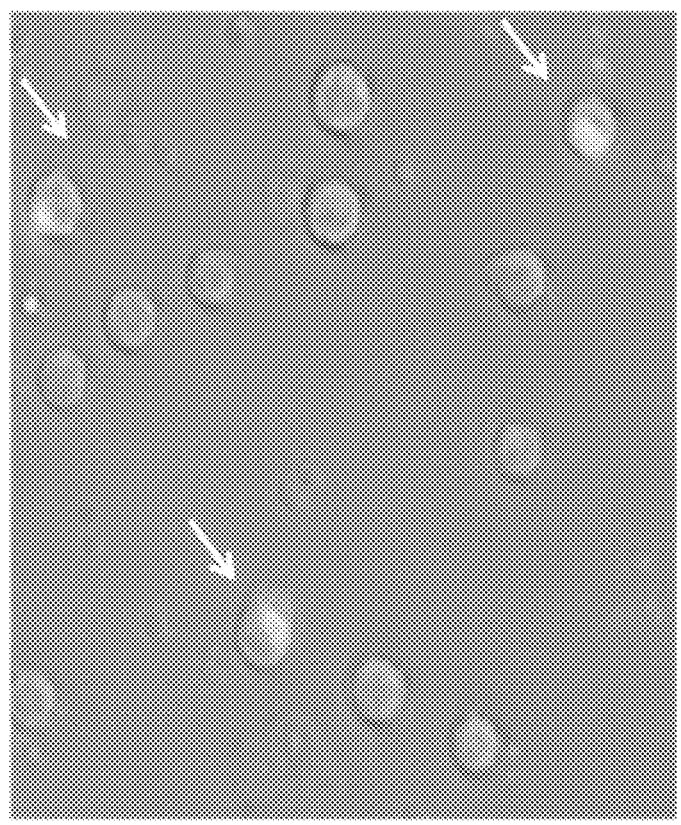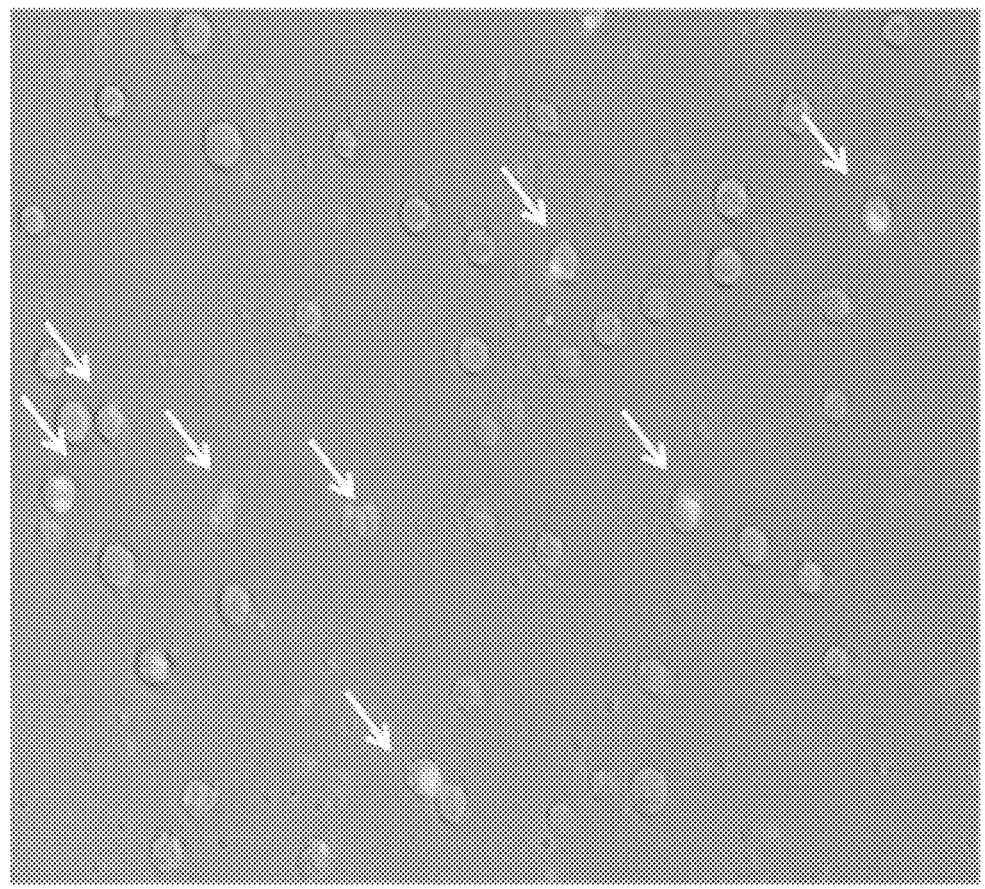
FIG. 98

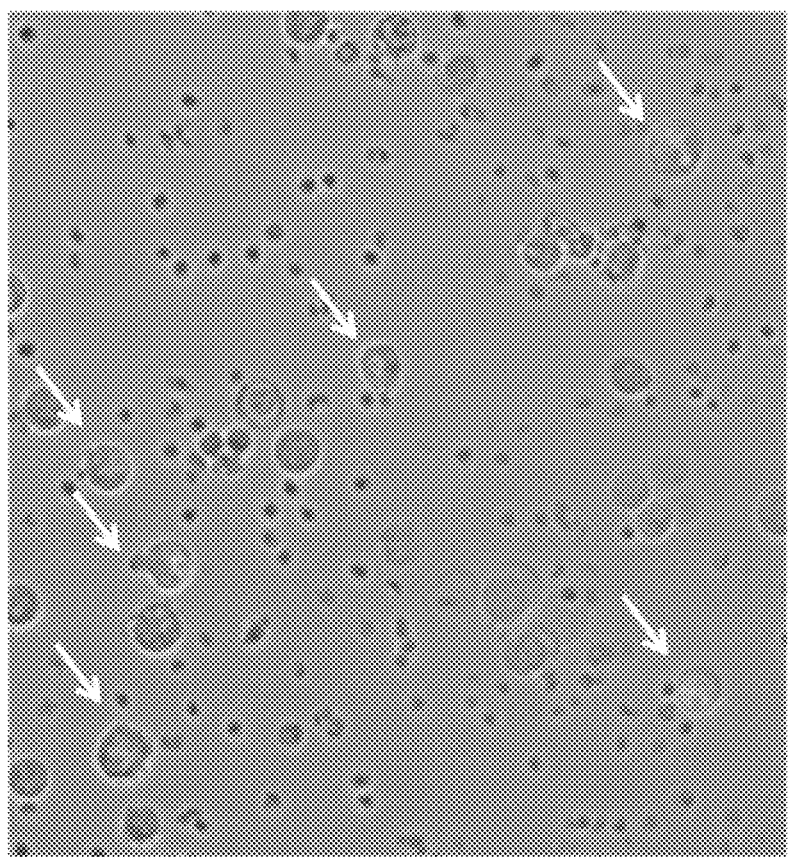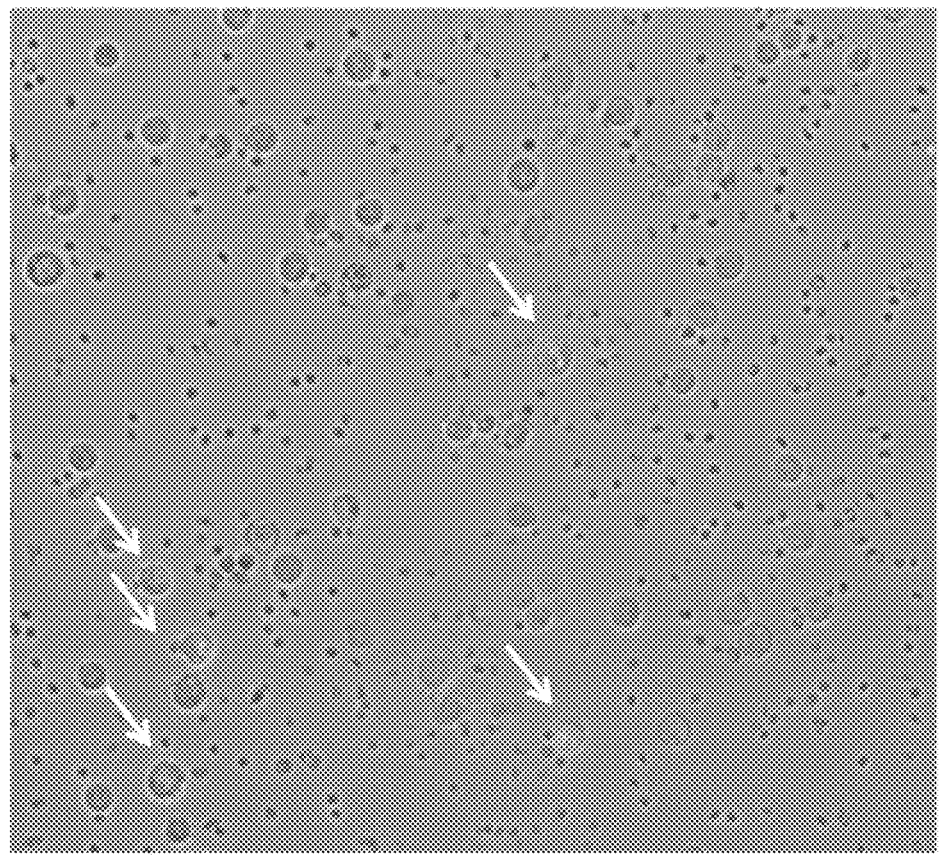
FIG. 118

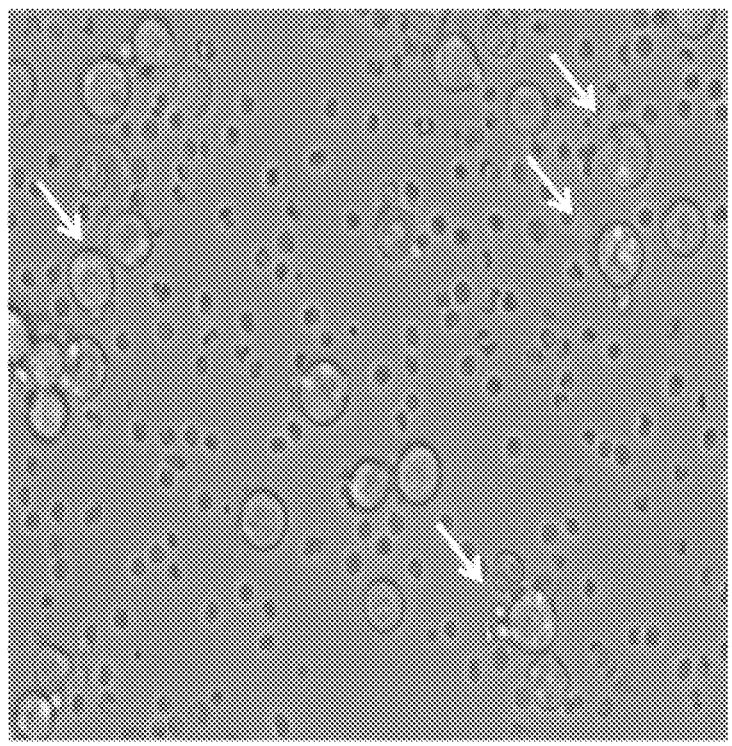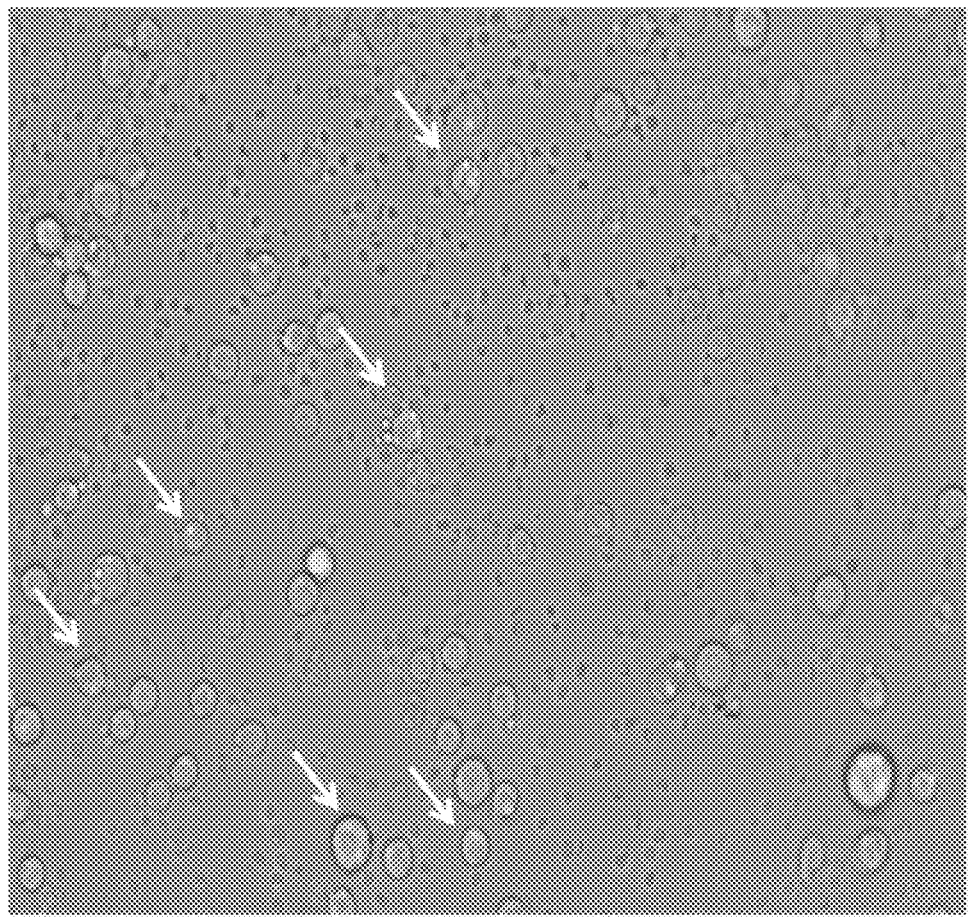
FIG. 122

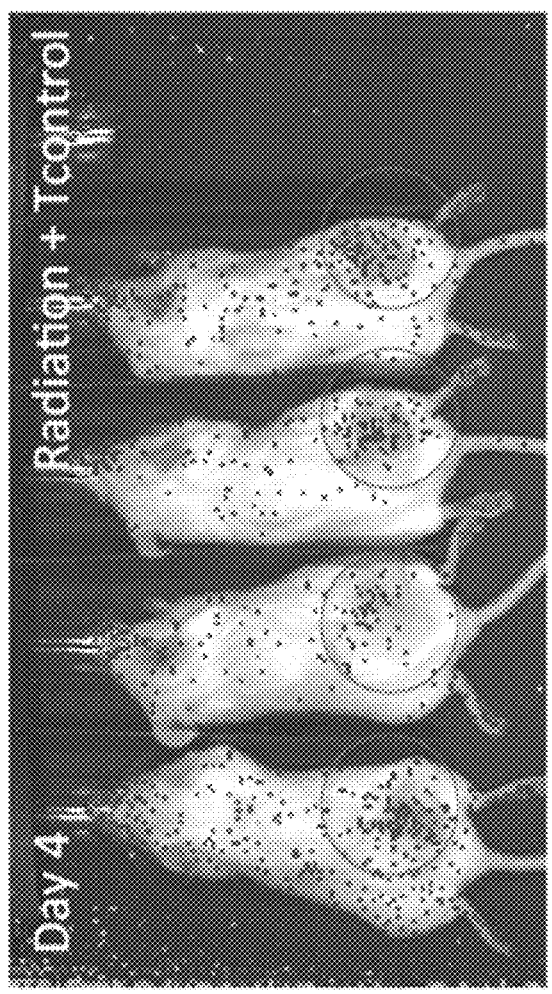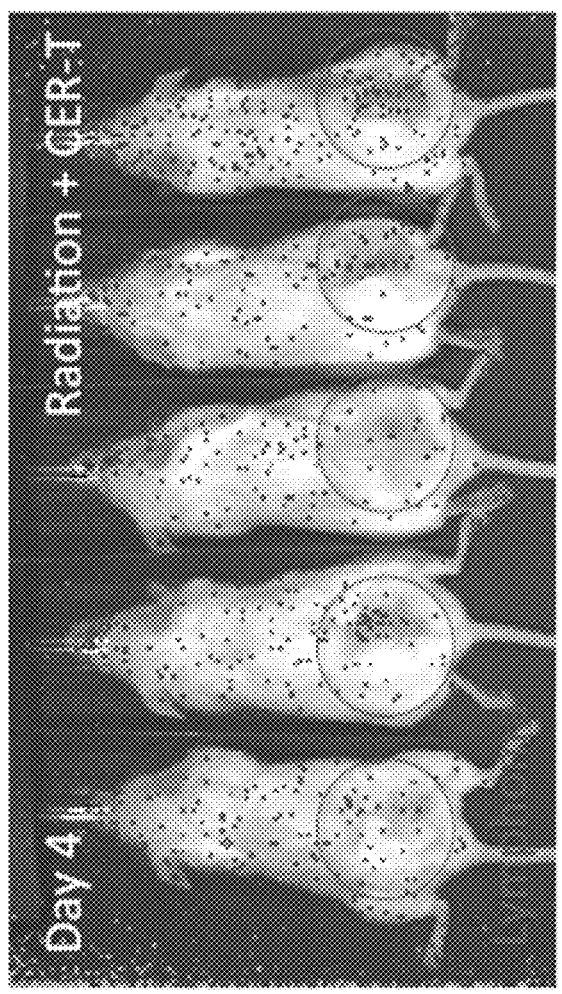
FIG. 132C

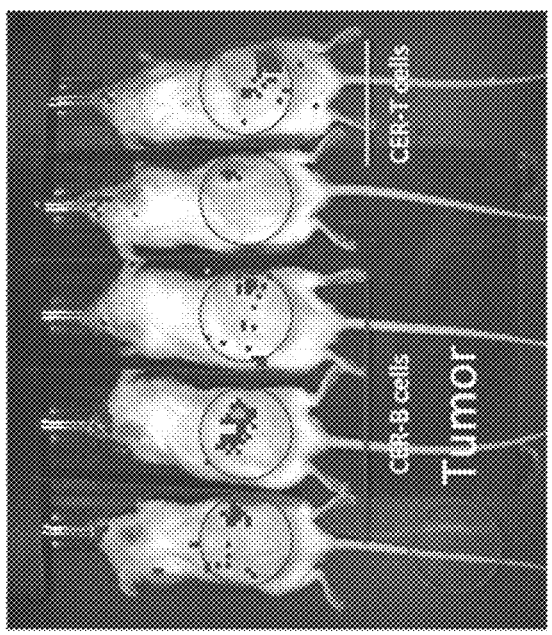
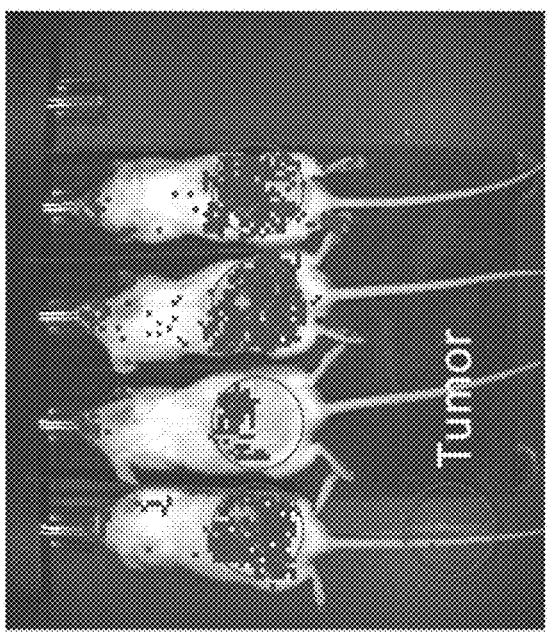
FIG. 133B

SEQUENCE LISTING

```
<160> NUMBER OF SEQ ID NOS: 153

<210> SEQ ID NO 1
<211> LENGTH: 870
<212> TYPE: DNA
<213> ORGANISM: Homo sapiens
<220> FEATURE:
<223> OTHER INFORMATION: Tim1 binding domain

<400> SEQUENCE: 1 atgcacccc  aggttgttat  actttcattg  atcctgcatt  tggccgactc  cgtggcgggt      60
tccgtaaaag ttggagggga agctggacca agcgtcacct tgccttgcca ctactctgga     120
gccgtgacga gtatgtgctg gaatcgagga tcctgtagtc ttttcacatg ccaaaatggc     180
atagtttgga ccaatgggac gcacgtcacc taccgaaaag acactagata caaactcctg     240
ggtgacctca gcaggagaga tgtgtctctg actattgaaa acactgctgt ttctgactct     300
ggagtctact gttgccgggt cgagcaccga ggatggttca atgacatgaa gatcacggtc     360
agcttggaaa tcgtcccgcc caaggtaacc actacaccaa tagttactac ggttcccacg     420
gtaaccacgg ttcgaaccag caccacagta cccacaacta cgaccgttcc aaccactaca     480
gtccccacaa ccatgagtat ccctacgaca actacggtcc tgacaaccat gaccgtcagc     540
actaccacga gtgtgcctac gactactagc ataccgacga ctacttcagt tccagtcacc     600
accacggtga gtacattcgt gcctccaatg ccattgccga ggcaaaacca cgaacccgtg     660
```

| | |
|---|---|
| gcgacatctc cgtctagtcc gcaaccagca gagacccatc ccaccacgct tcagggggca | 720 |
| atcaggagag aacctacaag ttcacccctc tacagctata caaccgatgg aaacgacaca | 780 |
| gttacagaaa gtagtgacgg tttgtggaat aacaaccaaa cacaattgtt cctggagcac | 840 |
| agtctgttga cagccaacac tacaaaggga | 870 |

<210> SEQ ID NO 2
<211> LENGTH: 942
<212> TYPE: DNA
<213> ORGANISM: Homo sapiens
<220> FEATURE:
<223> OTHER INFORMATION: Tim4 binding domain

<400> SEQUENCE: 2

| | |
|---|---|
| atgagtaaag agccgcttat cctgtggctt atgatagagt tttggtggtt gtatttgacc | 60 |
| ccggtcacga gcgaaacggt agtgactgaa gtattgggtc atcgggtaac cttgccttgc | 120 |
| ttgtatagct cctggtctca taatagtaat agcatgtgct ggggcaagga ccaatgcccc | 180 |
| tatagcggat gcaaggaggc gctcattcgc acagacggaa tgcgggtgac atcaaggaag | 240 |
| agtgctaagt accggcttca gggcacaatc ccacgcggcg acgtgtcact gactatcctt | 300 |
| aatccatccg agagcgactc tggtgtctat tgttgcagga tcgaggttcc gggatggttc | 360 |
| aatgatgtaa agatcaatgt aagactcaat ctgcaacggg catctacaac cacgcatcgg | 420 |
| acagccacta ctaccacaag gagaacaact actacgtcac ccacgactac tcgacagatg | 480 |
| accactacac ctgcggccct gccaactacg gttgtaacta ctccggatct gacaaccggg | 540 |
| acaccgttgc aaatgacaac cattgcagta tttaccacgg caaacacgtg tctctctctg | 600 |
| accccatcta ctcttccgga ggaggccacc gggctcctta caccggagcc gtctaaggaa | 660 |
| ggcccaatct tgaccgcaga gagtgagacc gtacttccga gcgattcatg gtccagtgtc | 720 |
| gagagcacat ccgctgacac cgtccttctt acgtccaaag aaagtaaagt ttgggacctc | 780 |
| ccgtccacga gccacgtttc tatgtggaag acctcagata gcgttagctc cccacagcca | 840 |
| ggagcaagcg acaccgcagt accggagcaa acaagacga ctaagactgg ccagatggat | 900 |
| ggtatcccaa tgtcaatgaa aaatgagatg cccatatcac aa | 942 |

<210> SEQ ID NO 3
<211> LENGTH: 483
<212> TYPE: DNA
<213> ORGANISM: Homo sapiens
<220> FEATURE:
<223> OTHER INFORMATION: FA58C2 binding domain

<400> SEQUENCE: 3

| | |
|---|---|
| ctcaacgggt gtgctaatcc ccttggcctg aagaataaca gcatacctga caagcaaata | 60 |
| acagcgtcaa gttcttataa aacttggggg ctgcatctgt tctcctggaa ccccagttac | 120 |
| gctagactcg acaaacaagg caattttaac gcatgggtgg caggctctta cgggaacgat | 180 |
| cagtggctgc aagtagactt gggaagtagt aaggaggtga ctgggatcat tacccagggg | 240 |
| gcacgaaatt tcggttccgt tcagttcgtt gcatcttata aggtagcgta ttcaaatgac | 300 |
| tccgcgaatt ggaccgaata tcaggacccg cgaaccggat caagcaagat ttttccgggg | 360 |
| aattgggaca ccactctca caaaaaaat ttgtttgaaa cacctatact ggcgcggtac | 420 |
| gttagaatcc tcccagttgc ctggcacaac cggatagcgc ttagactgga attgttgggg | 480 |
| tgc | 483 |

```
<210> SEQ ID NO 4
<211> LENGTH: 876
<212> TYPE: DNA
<213> ORGANISM: Homo sapiens
<220> FEATURE:
<223> OTHER INFORMATION: FcgammaRI binding domain

<400> SEQUENCE: 4
atgtggttcc tgactacgtt gttgctgtgg gtccctgtag acggccaagt agacacaacg      60
aaagcagtga tcacgctcca accgccttgg gtgtctgtgt tccaagaaga aacagttaca     120
ctgcactgtg aggtcctcca cctgcctggt tcttcatcta ctcaatggtt tctcaacgga     180
acagcaacac aaacaagtac cccttcctac agaattacga gtgcatctgt taacgattca     240
ggagagtata ggtgccagcg agggctttca ggccggtccg accccattca actcgaaatt     300
caccgcggtt ggcttctgct gcaagtatcc tctcgggtct tcacggaagg tgaaccactt     360
gccttgcgct gtcacgcatg aaagataag ctcgtctaca cgttttgta ttatcggaat      420 ggaaaggcat ttaagttttt tcattggaac tcaaacctta cgatcctcaa accaatatc     480 agtcataacg gtacgtacca ctgctcaggc atgggcaagc atcgctatac gtccgcaggg     540
attagcgtga cagttaagga gctcttcccc gcgcctgtgc tgaatgcgag cgtaacttca     600 cccttctgg agggcaactt ggtgaccctc tcttgtgaga cgaaacttct ccttcagagg      660
ccgggcctgc aactctattt cagcttttat atgggttcta aaactcttcg aggcagaaac     720
acgagcagcg aatatcagat actgactgcc ggcggggaag acagtggcct ttattggtgc     780
gaggctgcaa cagaagatgg caatgtcctt aaaaggtctc ccgaattgga gctccaagtg     840
cttggcttgc aactccctac accgtatgg ttccac                                876

<210> SEQ ID NO 5
<211> LENGTH: 282
<212> TYPE: DNA
<213> ORGANISM: Homo sapiens
<220> FEATURE:
<223> OTHER INFORMATION: GAS6 binding domain

<400> SEQUENCE: 5
atggctccct ctttgtcacc aggacctgcg gctcttaggc gagccccgca gctgctgctt      60
ctcctgctcg ctgcagaatg cgctctcgct gcactcttgc ccgcgaggga ggcgactcag     120
ttcttgcgcc cccggcagag acgagcattc caagtctttg aggaagcgaa acaaggtcat     180
ctcgagcgag aatgcgtgga ggagctgtgt tctagggagg aagcacgcga agtctttgag     240
aatgacccgg aaacggacta cttttacccc cggtatcttg at                        282

<210> SEQ ID NO 6
<211> LENGTH: 261
<212> TYPE: DNA
<213> ORGANISM: Homo sapiens
<220> FEATURE:
<223> OTHER INFORMATION: Protein S binding domain

<400> SEQUENCE: 6
atgcgcgtgt tgggggggtcg ctgtggtgcg ctccttgctt gtctcctttt ggttcttccc     60
gtctccgagg ctaatttcct gtcaaaacaa caggctagtc aagtcttggt gcgcaagagg     120
agagctaaca gccttctgga agagaccaag caaggtaatc tggagagaga gtgtatcgag     180
gaactttgta acaaagagga agcacgcgaa gtatttgaaa atgacccgga aaccgattat     240
ttttacccaa aatatctcgt a                                               261
```

<210> SEQ ID NO 7
<211> LENGTH: 606
<212> TYPE: DNA
<213> ORGANISM: Homo sapiens
<220> FEATURE:
<223> OTHER INFORMATION: Tim3 binding domain

<400> SEQUENCE: 7

```
atgtttagcc atctccctttt tgattgcgtc ttgttgcttc ttcttctcct tctgacgaga    60
tcatctgaag ttgaatatcg cgcggaagtc ggccaaaacg catatctgcc gtgttttac    120 accccggctg caccggggaa cttggttccc gtttgttggg gtaagggggc gtgtcccgtt    180
tttgagtgcg gtaacgtagt gctccgaact gatgaaagag atgtaaatta ctggacgagc    240
cggtactggt tgaatgggga ttttaggaag ggcgacgttt cccttaccat agaaaacgta    300
actcttgcgg attctgggat ttattgttgc aggatacaaa tccccggaat aatgaacgat    360
gagaaattca atttgaagct cgtaataaaa ccggcaaaag taactccagc tcccaccagg    420
cagcgagatt ttacggcagc atttcccagg atgctcacta ctcgcggtca tggccctgcc    480
gagactcaga ccctcggtag tcttcctgat atcaatctca cgcaaattag tacattggcg    540
aatgaattga gggattcaag actcgccaat gatctgcgcg acagtggagc gactattagg    600
ataggg                                                             606
```

<210> SEQ ID NO 8
<211> LENGTH: 63
<212> TYPE: DNA
<213> ORGANISM: Homo sapiens
<220> FEATURE:
<223> OTHER INFORMATION: Tim1 transmembrane domain

<400> SEQUENCE: 8

```
atatacgctg gagtctgtat aagtgtcctt gtactgttgg cgttgctggg ggtcattatt    60
gcc                                                                63
```

<210> SEQ ID NO 9
<211> LENGTH: 63
<212> TYPE: DNA
<213> ORGANISM: Homo sapiens
<220> FEATURE:
<223> OTHER INFORMATION: Tim4 transmembrane domain

<400> SEQUENCE: 9

```
ttgcttatga ttattgcgcc aagccttgga tttgtgctgt tcgcactctt cgtagcttt    60 ctc                                                                63
```

<210> SEQ ID NO 10
<211> LENGTH: 63
<212> TYPE: DNA
<213> ORGANISM: Homo sapiens
<220> FEATURE:
<223> OTHER INFORMATION: FcgammaRI transmembrane domain

<400> SEQUENCE: 10

```
gtactgtttt atctcgccgt agggataatg ttcctcgtga acaccgtact gtgggtaaca    60
ata                                                                63
```

<210> SEQ ID NO 11
<211> LENGTH: 63
<212> TYPE: DNA
<213> ORGANISM: Homo sapiens

```
<220> FEATURE:
<223> OTHER INFORMATION: CD8a transmembrane domain

<400> SEQUENCE: 11
atatacattt gggcaccgct ggctggaact tgcggcgttc tcttgttgag tctggtgatt    60
act                                                                  63

<210> SEQ ID NO 12
<211> LENGTH: 63
<212> TYPE: DNA
<213> ORGANISM: Homo sapiens
<220> FEATURE:
<223> OTHER INFORMATION: MERTK transmembrane domain

<400> SEQUENCE: 12
tttggctgtt tctgtggatt tattctgatt ggtcttatcc tctatatttc cttggcgatc    60
aga                                                                  63

<210> SEQ ID NO 13
<211> LENGTH: 63
<212> TYPE: DNA
<213> ORGANISM: Homo sapiens
<220> FEATURE:
<223> OTHER INFORMATION: Axl transmembrane domain

<400> SEQUENCE: 13
tatgtcttgc ttggtgccgt cgttgctgcc gcctgtgtgt tgatactcgc acttttcttg    60
gtg                                                                  63

<210> SEQ ID NO 14
<211> LENGTH: 63
<212> TYPE: DNA
<213> ORGANISM: Homo sapiens
<220> FEATURE:
<223> OTHER INFORMATION: Tyro3 transmembrane domain

<400> SEQUENCE: 14
gtacccgtcg ttttgggggt cctgaccgcg ctcgttactg cggcagcact cgcactgata    60
ctt                                                                  63

<210> SEQ ID NO 15
<211> LENGTH: 66
<212> TYPE: DNA
<213> ORGANISM: Homo sapiens
<220> FEATURE:
<223> OTHER INFORMATION: CD4 transmembrane domain

<400> SEQUENCE: 15
atggctctga tcgtactggg cggagtggca ggattgctgc tctttattgg actgggcatt    60
ttcttc                                                               66

<210> SEQ ID NO 16
<211> LENGTH: 1428
<212> TYPE: DNA
<213> ORGANISM: Mus musculus
<220> FEATURE:
<223> OTHER INFORMATION: MERTK signaling domain

<400> SEQUENCE: 16
gcgctgcggc gaagggtaca ggagacgaaa ttcggggag cctttagtga agaagacagc     60
cagttggtgg taaattacag agcgaaaaaa tctttctgcc gacgcgctat tgagcttact   120
```

| | |
|---|---|
| cttcaaagcc tcggtgtaag tgaggagttg cagaataaat tggaggacgt agtcatcgac | 180 |
| cgcaaccttc tggtcctcgg aaaagtcctc ggagaaggtg aattcggctc agtaatggaa | 240 |
| ggcaatctca aacaagaaga cggaacttct cagaaggtag cagtaaaaac catgaaactc | 300 |
| gacaacttca gccagcggga aatcgaagaa ttcctgtccg aagccgcctg tatgaaagac | 360 |
| ttcaatcacc caaacgtgat aagacttctc ggcgtatgta tagagttgtc ttcccagggc | 420 |
| atccccaaac caatggtgat actcccattt atgaagtacg ggacttgca cacattcctg | 480 |
| ttgtattcca gacttaatac aggacccaag tatatacatt tgcagaccct gctcaaattt | 540 |
| atgatggaca tcgcgcaggg gatggagtat ctcagcaaca ggatttttt gcatcgcgac | 600 |
| cttgctgcca ggaactgtat gttgagggac gacatgacgg tgtgtgtagc cgacttcggt | 660 |
| cttagcaaga gatctattc tggagactat acaggcaag gcagaatagc taagatgccg | 720 |
| gtcaagtgga tcgctattga gagcctcgca gaccgggtct atacttcaaa gtcagacgtt | 780 |
| tgggcttttg gggtaaccat gtgggagatc actacgaggg gatgacgcc ctatcccggg | 840 |
| gtccaaaatc acgagatgta tgattatctc ttgcatggcc accggctgaa acagcctgag | 900 |
| gactgtctgg acgagctcta cgatattatg tattcttgtt ggtccgcgga ccccctcgat | 960 |
| agaccaacct tttctgttct tcgactgcag ctcgaaaagc tttccgaatc tttgcctgat | 1020 |
| gcacaggaca agaaagcat catttatata aatacacagc tcctggaatc ttgcgaagga | 1080 |
| attgctaatg gacctagtct gactggattg acatgaata ttgacccgga cagcataatt | 1140 |
| gcatcttgca cacctggtgc agcggtatca gtcgtgacgg ccgaggtcca tgaaaacaat | 1200 |
| ctgcgggagg agcggtacat tttgaacggc ggaaacgaag agtgggagga cgtcagctca | 1260 |
| acccccttg cagccgtgac gccagagaaa gacggggtac ttcctgagga ccgccttacc | 1320 |
| aagaacgggg tatcctggtc tcaccacagc accctcccac ttgggagtcc atctcccgac | 1380 |
| gagcttctct tcgtagatga ttcacttgaa gattcagagg tgctcatg | 1428 |

<210> SEQ ID NO 17
<211> LENGTH: 1266
<212> TYPE: DNA
<213> ORGANISM: Homo sapiens
<220> FEATURE:
<223> OTHER INFORMATION: Axl signaling domain

<400> SEQUENCE: 17

| | |
|---|---|
| caccggagaa aaaagagac ccgctacgga gaggtctttg agcctacggt cgagagaggt | 60 |
| gagcttgttg tccggtacag agtgaggaag agctattcac ggaggactac tgaagccacc | 120 |
| ctgaattcac tcggcatcag cgaagagctg aaagagaaac ttcgggacgt aatggtcgat | 180 |
| cggcacaagg tagccctcgg gaagacgttg ggagagggcg aatttggggc cgtcatggag | 240 |
| ggtcagttga accaagatga ctcaatactt aaagtagcag tcaaaacgat gaaaatcgca | 300 |
| atttgtactc gctcagagct cgaagacttt ctctctgagg cggtatgcat gaaggaattc | 360 |
| gaccacccaa atgtaatgcg attgatcggt gtctgcttcc aaggttccga aagagagtca | 420 |
| tttcctgcac ccgttgtcat tttgccattt atgaagcatg gggacctcca ctcatttctc | 480 |
| ctctattcta gattgggtga ccaaccggtt tacctcccga cccaaatgct cgttaagttc | 540 |
| atggccgaca ttgcttccgg gatggagtac ctgagtacca agcggtttat acatcgggat | 600 |
| ctcgcagcac gaaactgcat gttgaatgag aacatgtctg tctgtgtggc tgactttgga | 660 |
| ctctccaaaa aaatttacaa cggtgattat taccgccagg gaagaatcgc taagatgccc | 720 |
| gtgaagtgga tagctattga gtcactcgct gatcgcgtat acactagtaa gtccgacgta | 780 |

```
tggtcctttg gtgtcacaat gtgggagatt gcgaccaggg ggcagacacc atatcccggc    840
gtggagaact ccgagattta tgattatctg cgacagggta acagacttaa gcaacctgcc    900
gattgcttgg atgggctcta cgctctgatg tctagatgct gggaattgaa tcctcaagat    960
cggccaagct tcactgaact gagagaagac ctggaaaata ccctgaaagc gctcccgccg   1020
gcgcaagaac cagatgaaat cttgtacgtc aatatggacg aaggggagg ctaccctgaa   1080 cccctgggg cggccggtgg ggcggacccc ccgacacaac cagatccgaa agactcctgt    1140
tcttgtctta ccgctgctga ggtacatccg gcaggaagat atgttttgtg tccctctacg   1200
acaccctctc ccgcacagcc cgcggatcgc gggtcacccg cggctccagg acaagaagat   1260
ggggca                                                              1266

<210> SEQ ID NO 18
<211> LENGTH: 1320
<212> TYPE: DNA
<213> ORGANISM: Homo sapiens
<220> FEATURE:
<223> OTHER INFORMATION: Tyro3 signaling domain

<400> SEQUENCE: 18
ttgcggaagc ggcgaaagga aaccagattc ggtcaagctt tcgacagcgt aatggcccgg     60
ggtgagccag ccgtccactt tagagccgct cggagcttca atagggaacg accgagagaa    120
atcgaggcta ctctcgattc tctcggaata tctgacgagt tgaaagaaaa actggaggat    180
gtcctcatcc cagaacaaca atttaccctc ggccgaatgc ttggaaaggg tgagtttggg    240
tcagttcgcg aggcgcagct taaacaggaa gacggtagtt ttgttaaagt cgcagtaaaa    300
atgttgaagg cggacataat cgcatccagc gatattgagg aatttcttcg cgaagcggca    360
tgtatgaaag agttcgacca cccgcacgtt gccaagctcg tgggcgtgtc tcttcgaagc    420
cgagctaagg gtagactccc tatcccaatg gtaatacttc cttttatgaa acatggggac    480
ttgcacgctt ttctgctcgc ttccaggata ggagaaaatc cgtttaattt gccgctccaa    540
acgcttatca ggtttatggt tgatattgcg tgtgggatgg aatacttgag ttcacgcaat    600
ttcatccatc gagacctggc cgcgcgaaat tgtatgctcg cagaggatat gaccgtatgt    660
gtagctgatt tcggcttgtc acgcaagata tatagcggcg attattatag acagggttgt    720
gcctctaagc tccctgtaaa gtggttggca ttggaatcac tggcggataa cctctatact    780
gtccagtcag atgtgtgggc atttggtgtc actatgtggg agattatgac acggggtcag    840
acaccctacg caggaatcga gaacgcggag atatataact acctgatagg tggcaaccga    900
ctgaaacaac ctccggaatg catggaggac gtgtatgacc tcatgtacca gtgttggagt    960
gccgatccga acaaagacc tagtttcact tgcctgagaa tggagttgga gaatattttg   1020
ggtcagttgt ccgtactgag cgccagccaa gatccgttgt atataaatat agagcgggcg   1080
gaggagccca cggccggcgg gtccctgaaa cttcctggac gagaccaacc gtactcaggg   1140
gccggagatg gaagtggaat gggggctgtt ggggggcacac cgtccgactg ccgatacata   1200
ctcactccgg gcggtctcgc agaacaaccg ggtcaagcag aacatcaacc agaaagtcca   1260
ctcaatgaga cacagcgact gttgttgttg caacagggct tgctgcctca ctcatcctgt   1320

<210> SEQ ID NO 19
<211> LENGTH: 783
<212> TYPE: DNA
<213> ORGANISM: Homo sapiens
<220> FEATURE:
```

-continued

<223> OTHER INFORMATION: Syk signaling domain

<400> SEQUENCE: 19

| | | | | | |
|---|---|---|---|---|---|
| acattggaag | acaaagaact | ggggtctggg | aacttcggga | cagtcaaaaa | ggggtactac | 60 |
| cagatgaaaa | aagttgtcaa | aactgtggcg | gtaaaaatct | tgaaaaatga | agctaatgac | 120 |
| cctgcactca | aggatgagct | tctggcagaa | gctaacgtga | tgcagcagct | tgataatcct | 180 |
| tatattgttc | gcatgatagg | tatatgtgag | gcggaaagct | ggatgctcgt | aatgaaatg | 240 |
| gcagaactgg | gaccattgaa | taaatatctg | caacaaaata | gacatgtgaa | ggataaaaac | 300 |
| atcatagagc | tcgtacacca | agtctctatg | gggatgaagt | acttggagga | gagcaacttc | 360 |
| gtgcataggg | acttggccgc | ccgaaacgta | ctgctcgtaa | ctcaacatta | cgcgaaaatc | 420 |
| tcagacttcg | gtttgtctaa | agcactccgg | gcagacgaga | actactacaa | agcccaaact | 480 |
| cacggcaagt | ggccagtcaa | gtggtacgcg | ccggaatgca | taaactatta | caagtttagt | 540 |
| tctaagtctg | atgtgtggag | cttcggggtt | ctgatgtggg | aagcctttag | ttatggacag | 600 |
| aagccctacc | ggggatgaa | aggaagcgag | gtaacagcta | tgctgaaaaa | aggggagcgg | 660 |
| atgggctgtc | cagcggggtg | tcctcgagaa | atgtatgatc | tcatgaacct | gtgttggacc | 720 |
| tacgatgtcg | agaatcgccc | gggctttgct | gcggtggaac | ttagactgag | gaattattac | 780 |
| tac | | | | | | 783 |

<210> SEQ ID NO 20
<211> LENGTH: 789
<212> TYPE: DNA
<213> ORGANISM: Homo sapiens
<220> FEATURE:
<223> OTHER INFORMATION: Zap70 signaling domain

<400> SEQUENCE: 20

| | | | | | |
|---|---|---|---|---|---|
| ctcattgccg | acatcgaact | tggttgcggc | aacttcggat | ctgtgagaca | aggcgtctac | 60 |
| cggatgagaa | agaagcagat | tgacgttgca | atcaaagtcc | tgaagcaggg | cacggaaaag | 120 |
| gcggacaccg | aggagatgat | gcgcgaggct | cagattatgc | accagctcga | caatccgtac | 180 |
| atcgttagac | ttatcggagt | ttgccaggca | gaagcgttga | tgctcgtgat | ggagatggca | 240 |
| ggcggtggtc | ctctgcataa | attttttggta | ggcaagcgag | aagagatccc | cgtcagcaat | 300 |
| gtagcagaat | tgttgcatca | agtgagcatg | gggatgaagt | accttgagga | aaaaaatttc | 360 |
| gtacatcgcg | acctcgctgc | gagaaatgtg | cttttggtaa | atcgccatta | cgctaaaatt | 420 |
| agtgactttg | gactcagtaa | ggcattgggt | gctgacgact | catattacac | ggcaagaagc | 480 |
| gcaggtaagt | ggcctctgaa | gtggtatgct | cccgagtgca | tcaacttccg | caagttttct | 540 |
| tccaggtctg | acgtttggag | ctacggtgtc | acgatgtggg | aagccctgag | ctatggtcag | 600 |
| aaaccttaca | agaaaatgaa | gggacctgaa | gtcatggcct | ttatagagca | gggaaagaga | 660 |
| atggagtgtc | cccagaatg | cccacccgag | ctctatgcac | tgatgagtga | ctgctggatt | 720 |
| tacaaatggg | aggatcggcc | tgactttctt | acggttgagc | aaaggatgag | ggcgtgctat | 780 |
| tattctctg | | | | | | 789 |

<210> SEQ ID NO 21
<211> LENGTH: 183
<212> TYPE: DNA
<213> ORGANISM: Homo sapiens
<220> FEATURE:
<223> OTHER INFORMATION: FcgammaRI signaling domain

<400> SEQUENCE: 21

-continued

```
agaaaggaac tcaagcgcaa gaagaagtgg gacctggaga tttctctcga ctccggtcac    60 gaaagaagg tcatcagtag cttgcaagag gaccgacact tggaagaaga acttaaatgc    120
caggaacaga aagaggagca gctccaggag ggagtccacc ggaaagaacc acagggagca    180
act                                                                  183

<210> SEQ ID NO 22
<211> LENGTH: 231
<212> TYPE: DNA
<213> ORGANISM: Homo sapiens
<220> FEATURE:
<223> OTHER INFORMATION: FcgammaR2A signaling domain

<400> SEQUENCE: 22
tgtcgaaaga agcggatttc agccaatagt acagacccag tgaaagccgc tcaatttgag    60
ccacccggtc gacagatgat cgcaattagg aaacgccaac tggaggaaac gaataatgat    120
tacgaaacgg cagatggggg ctacatgacg ctcaatccta gagctccgac cgacgacgac    180
aagaatatat atctgactct ccctcccaac gaccacgtaa acagtaataa c             231

<210> SEQ ID NO 23
<211> LENGTH: 231
<212> TYPE: DNA
<213> ORGANISM: Homo sapiens
<220> FEATURE:
<223> OTHER INFORMATION: FcgammaR2C signaling domain

<400> SEQUENCE: 23
tgcagaaaga agcggataag tgcaaatagt actgatcccg ttaaagcagc acaatttgag    60
ccgccaggac ggcaaatgat tgcaatcaga aaacgacaac ccgaggaaac caataatgac    120
tacgagaccg ctgacggagg gtatatgacg ttgaatcccc gcgcaccaac ggatgacgat    180
aagaacattt atcttacgct gccccctaac gatcatgtga atagcaataa c             231

<210> SEQ ID NO 24
<211> LENGTH: 75
<212> TYPE: DNA
<213> ORGANISM: Homo sapiens
<220> FEATURE:
<223> OTHER INFORMATION: FcgammaR3A signaling domain

<400> SEQUENCE: 24
aaaacaaata tccggtcctc tacgagggac tggaaagatc ataaattcaa gtggagaaaa    60
gatcctcagg ataaa                                                     75

<210> SEQ ID NO 25
<211> LENGTH: 168
<212> TYPE: DNA
<213> ORGANISM: Mus musculus
<220> FEATURE:
<223> OTHER INFORMATION: ItgB5 signaling domain

<400> SEQUENCE: 25
aagttgcttg taacaataca cgaccgccgg gagttcgcta agttccaatc agaaaggtct    60
agagcgcggt atgaaatggc atctaacccc ttgtaccgga aacctatctc tacgcacacg    120
gtggatttcg catttaataa gttcaataag agttacaacg gctcagtc                 168

<210> SEQ ID NO 26
<211> LENGTH: 888
<212> TYPE: DNA
```

<213> ORGANISM: Homo sapiens
<220> FEATURE:
<223> OTHER INFORMATION: MyD88 signaling domain

<400> SEQUENCE: 26

```
atggccgcgg gtggacccgg tgcagggtct gccgcaccgg tgtctagcac cagctcactg      60
ccgctggcag cgttgaacat gagggtaaga agacggctta gtcttttctt gaatgtgcga     120
acgcaggtgg ccgctgactg gacggccctc gctgaggaaa tggacttcga gtacctggag     180
atccggcaac tcgagactca agccgaccct actggaagat tgctcgatgc ctggcaggga     240
aggcccggcg catcagttgg taggttgttg gaactcctca ccaaactcgg gcagatgatg     300
gttcttttgg aacttggccc tagtattgag gaggactgtc aaaaatatat tctgaaacaa     360
caacaggaag aagcggagaa accgttgcaa gtggccgcag tcgattcttc agtgccgcgc     420
acagccgaac tggctggaat tactaccctg gatgatcccc tcggacacat gccggagcgg     480
ttcgacgcct tcatttgcta ttgtccctcc gacatccagt ttgtgcagga atgattagg     540
caactcgaac aaaccaacta taggcttaaa ctgtgtgtgt ccgatcgaga tgttttgcct     600
ggtacttgcg tatggtctat tgccagcgaa ctcatagaga aacgctgtcg ccgcatggta     660
gtggtcgtat ccgacgacta ccttcagtcc aaagagtgtg acttccagac gaaatttgca     720
ctgtcactga gtcctggagc acaccaaaaa aggctgattc cgatcaagta taggcgatg      780
aagaaggaat ttccttccat cctgaggttc ataactgtat gcgattacac aaatccgtgt     840
actaaatcct ggttctggac tcgacttgcc aaggcactgt ccctccca                  888
```

<210> SEQ ID NO 27
<211> LENGTH: 1566
<212> TYPE: DNA
<213> ORGANISM: Homo sapiens
<220> FEATURE:
<223> OTHER INFORMATION: Traf6 signaling domain

<400> SEQUENCE: 27

```
atgtcactcc ttaactgcga aaacagttgt gggagttcac aatccgaaag tgattgttgc      60
gtggcgatgg cgtcttcatg ctctgcggtt accaaggatg actctgtggg aggcaccgca     120
tctaccggaa atctgagctc ttcttttatg gaggaaattc agggctacga cgttgagttt     180
gatcctcctc tcgaatctaa gtatgagtgc cccatatgtc tcatggcgtt gagagaagca     240
gtgcagactc cgtgcggaca tcgcttctgc aaggcgtgta ttataaagag tatacgcgat     300
gcgggtcaca atgtccagt ggacaacgag atactgcttg aaaatcaact tttccccgac      360
aattttgcaa agagagagat actgtctttg atggttaagt gtccaaacga gggctgcttg     420
cacaaaatgg aactccgaca ccttgaagac caccaggcac actgcgagtt cgcccctcatg    480
gattgcccac aatgccagcg cccgttccaa agtttcaca taaacatcca catactgaag      540
gactgtccta ggagacaagt aagctgtgac aattgcgcag cgtcaatggc gttcgaggac     600
aaggagatac acgatcaaaa ctgtcctctg gcgaatgtga tctgcgaata ttgcaatacg     660
atcttgatcc gcgaacagat gcctaatcat tacgacctcg attgtccgac cgcgccaatt     720
ccttgtactt tttctacctt cggatgtcat gagaaaatgc aacgaaatca cctggctcgc     780
catcttcagg agaatactca gagccacatg cgcatgttgg ctcaagccgt acatagcctt     840
agcgtaaatac cggactcagg ttatatatcc gaagtacgga attttcaaga aaccatacat     900
caacttgaag gaaggttggt acgacaggat catcagatac gcgaattgac ggccaagatg     960
gaaacccaga gcatgtatgt cagtgagctt aagcgcacta tccgaaccct ggaggataaa    1020
```

-continued

```
gttgccgaaa tcgaagctca acaatgcaac gggatataca tttggaaaat aggtaacttc    1080
ggaatgcacc tgaagtgtca agaagaagaa aaacctgtcg ttattcattc ccccggcttt    1140
tatacaggga agcctgggta taagctttgc atgaggctcc acctccaatt gccgacggcg    1200
caaaggtgcg caaattacat ttctctgttt gtccatacta tgcagggtga gtacgatagt    1260
cacttgccgt ggcccttcca gggtaccata cgattgacca tcctggatca gagcgaggcc    1320
cccgtgcgac agaatcatga agaaataatg gatgctaagc cggaactgct cgctttccag    1380
agacctacaa ttccgcgaaa tcctaagggt tttggctatg ttacgttcat gcatctggaa    1440 gcactcgac aaagaacatt cattaaagat gacaccttgc ttgtgcggtg tgaggtgtca    1500
accaggttcg acatgggatc tctcagacgg gagggttcc aaccgcgctc tacagacgct    1560
ggagtg                                                                1566
```

<210> SEQ ID NO 28
<211> LENGTH: 290
<212> TYPE: PRT
<213> ORGANISM: Homo sapiens
<220> FEATURE:
<223> OTHER INFORMATION: Tim1 binding domain
<220> FEATURE:
<221> NAME/KEY: SIGNAL
<222> LOCATION: (1)...(20)

<400> SEQUENCE: 28

```
Met His Pro Gln Val Val Ile Leu Ser Leu Ile Leu His Leu Ala Asp
1               5                   10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Asn
        35                  40                  45

Arg Gly Ser Cys Ser Leu Phe Thr Cys Gln Asn Gly Ile Val Trp Thr
    50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
        115                 120                 125

Val Thr Thr Thr Pro Ile Val Thr Thr Val Pro Thr Val Thr Thr Val
    130                 135                 140

Arg Thr Ser Thr Thr Val Pro Thr Thr Thr Val Pro Thr Thr
145                 150                 155                 160

Val Pro Thr Thr Met Ser Ile Pro Thr Thr Thr Val Leu Thr Thr
                165                 170                 175

Met Thr Val Ser Thr Thr Thr Ser Val Pro Thr Thr Thr Ser Ile Pro
            180                 185                 190

Thr Thr Thr Ser Val Pro Val Thr Thr Thr Val Ser Thr Phe Val Pro
        195                 200                 205

Pro Met Pro Leu Pro Arg Gln Asn His Glu Pro Val Ala Thr Ser Pro
    210                 215                 220

Ser Ser Pro Gln Pro Ala Glu Thr His Pro Thr Thr Leu Gln Gly Ala
225                 230                 235                 240
```

```
Ile Arg Arg Glu Pro Thr Ser Ser Pro Leu Tyr Ser Tyr Thr Thr Asp
                245                 250                 255

Gly Asn Asp Thr Val Thr Glu Ser Ser Asp Gly Leu Trp Asn Asn Asn
            260                 265                 270

Gln Thr Gln Leu Phe Leu Glu His Ser Leu Leu Thr Ala Asn Thr Thr
        275                 280                 285

Lys Gly
    290

<210> SEQ ID NO 29
<211> LENGTH: 314
<212> TYPE: PRT
<213> ORGANISM: Homo sapiens
<220> FEATURE:
<223> OTHER INFORMATION: Tim4 binding domain
<220> FEATURE:
<221> NAME/KEY: SIGNAL
<222> LOCATION: (1)...(24)

<400> SEQUENCE: 29

Met Ser Lys Glu Pro Leu Ile Leu Trp Leu Met Ile Glu Phe Trp Trp
1               5                   10                  15

Leu Tyr Leu Thr Pro Val Thr Ser Glu Thr Val Val Thr Glu Val Leu
            20                  25                  30

Gly His Arg Val Thr Leu Pro Cys Leu Tyr Ser Ser Trp Ser His Asn
        35                  40                  45

Ser Asn Ser Met Cys Trp Gly Lys Asp Gln Cys Pro Tyr Ser Gly Cys
    50                  55                  60

Lys Glu Ala Leu Ile Arg Thr Asp Gly Met Arg Val Thr Ser Arg Lys
65                  70                  75                  80

Ser Ala Lys Tyr Arg Leu Gln Gly Thr Ile Pro Arg Gly Asp Val Ser
                85                  90                  95

Leu Thr Ile Leu Asn Pro Ser Glu Ser Asp Ser Gly Val Tyr Cys Cys
            100                 105                 110

Arg Ile Glu Val Pro Gly Trp Phe Asn Asp Val Lys Ile Asn Val Arg
        115                 120                 125

Leu Asn Leu Gln Arg Ala Ser Thr Thr Thr His Arg Thr Ala Thr Thr
    130                 135                 140

Thr Thr Arg Arg Thr Thr Thr Thr Ser Pro Thr Thr Thr Arg Gln Met
145                 150                 155                 160

Thr Thr Thr Pro Ala Ala Leu Pro Thr Thr Val Val Thr Thr Pro Asp
                165                 170                 175

Leu Thr Thr Gly Thr Pro Leu Gln Met Thr Thr Ile Ala Val Phe Thr
            180                 185                 190

Thr Ala Asn Thr Cys Leu Ser Leu Thr Pro Ser Thr Leu Pro Glu Glu
        195                 200                 205

Ala Thr Gly Leu Leu Thr Pro Glu Pro Ser Lys Glu Gly Pro Ile Leu
    210                 215                 220

Thr Ala Glu Ser Glu Thr Val Leu Pro Ser Asp Ser Trp Ser Ser Val
225                 230                 235                 240

Glu Ser Thr Ser Ala Asp Thr Val Leu Leu Thr Ser Lys Glu Ser Lys
                245                 250                 255

Val Trp Asp Leu Pro Ser Thr Ser His Val Ser Met Trp Lys Thr Ser
            260                 265                 270

Asp Ser Val Ser Ser Pro Gln Pro Gly Ala Ser Asp Thr Ala Val Pro
        275                 280                 285
```

```
Glu Gln Asn Lys Thr Thr Lys Thr Gly Gln Met Asp Gly Ile Pro Met
        290                 295                 300
Ser Met Lys Asn Glu Met Pro Ile Ser Gln
305                 310

<210> SEQ ID NO 30
<211> LENGTH: 161
<212> TYPE: PRT
<213> ORGANISM: Homo sapiens
<220> FEATURE:
<223> OTHER INFORMATION: FA58C2 binding domain

<400> SEQUENCE: 30

Leu Asn Gly Cys Ala Asn Pro Leu Gly Leu Lys Asn Asn Ser Ile Pro
1               5                   10                  15
Asp Lys Gln Ile Thr Ala Ser Ser Tyr Lys Thr Trp Gly Leu His
                20                  25                  30
Leu Phe Ser Trp Asn Pro Ser Tyr Ala Arg Leu Asp Lys Gln Gly Asn
            35                  40                  45
Phe Asn Ala Trp Val Ala Gly Ser Tyr Gly Asn Asp Gln Trp Leu Gln
50                  55                  60
Val Asp Leu Gly Ser Ser Lys Glu Val Thr Gly Ile Ile Thr Gln Gly
65                  70                  75                  80
Ala Arg Asn Phe Gly Ser Val Gln Phe Val Ala Ser Tyr Lys Val Ala
                85                  90                  95
Tyr Ser Asn Asp Ser Ala Asn Trp Thr Glu Tyr Gln Asp Pro Arg Thr
                100                 105                 110
Gly Ser Ser Lys Ile Phe Pro Gly Asn Trp Asp Asn His Ser His Lys
            115                 120                 125
Lys Asn Leu Phe Glu Thr Pro Ile Leu Ala Arg Tyr Val Arg Ile Leu
130                 135                 140
Pro Val Ala Trp His Asn Arg Ile Ala Leu Arg Leu Glu Leu Leu Gly
145                 150                 155                 160
Cys

<210> SEQ ID NO 31
<211> LENGTH: 292
<212> TYPE: PRT
<213> ORGANISM: Homo sapiens
<220> FEATURE:
<223> OTHER INFORMATION: FcgammaRI binding domain
<220> FEATURE:
<221> NAME/KEY: SIGNAL
<222> LOCATION: (1)...(15)

<400> SEQUENCE: 31

Met Trp Phe Leu Thr Thr Leu Leu Leu Trp Val Pro Val Asp Gly Gln
1               5                   10                  15
Val Asp Thr Thr Lys Ala Val Ile Thr Leu Gln Pro Pro Trp Val Ser
                20                  25                  30
Val Phe Gln Glu Glu Thr Val Thr Leu His Cys Glu Val Leu His Leu
            35                  40                  45
Pro Gly Ser Ser Ser Thr Gln Trp Phe Leu Asn Gly Thr Ala Thr Gln
50                  55                  60
Thr Ser Thr Pro Ser Tyr Arg Ile Thr Ser Ala Ser Val Asn Asp Ser
65                  70                  75                  80
Gly Glu Tyr Arg Cys Gln Arg Gly Leu Ser Gly Arg Ser Asp Pro Ile
                85                  90                  95
```

```
Gln Leu Glu Ile His Arg Gly Trp Leu Leu Gln Val Ser Ser Arg
            100                 105                 110

Val Phe Thr Glu Gly Glu Pro Leu Ala Leu Arg Cys His Ala Trp Lys
    115                 120                 125

Asp Lys Leu Val Tyr Asn Val Leu Tyr Tyr Arg Asn Gly Lys Ala Phe
130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His
    290

<210> SEQ ID NO 32
<211> LENGTH: 94
<212> TYPE: PRT
<213> ORGANISM: Homo sapiens
<220> FEATURE:
<223> OTHER INFORMATION: Gas6 binding domain
<220> FEATURE:
<221> NAME/KEY: SIGNAL
<222> LOCATION: (1)...(30)

<400> SEQUENCE: 32

Met Ala Pro Ser Leu Ser Pro Gly Pro Ala Ala Leu Arg Arg Ala Pro
1               5                   10                  15

Gln Leu Leu Leu Leu Leu Leu Ala Ala Glu Cys Ala Leu Ala Ala Leu
                20                  25                  30

Leu Pro Ala Arg Glu Ala Thr Gln Phe Leu Arg Pro Arg Gln Arg Arg
            35                  40                  45

Ala Phe Gln Val Phe Glu Glu Ala Lys Gln Gly His Leu Glu Arg Glu
        50                  55                  60

Cys Val Glu Glu Leu Cys Ser Arg Glu Glu Ala Arg Glu Val Phe Glu
65                  70                  75                  80

Asn Asp Pro Glu Thr Asp Tyr Phe Tyr Pro Arg Tyr Leu Asp
                85                  90

<210> SEQ ID NO 33
<211> LENGTH: 87
<212> TYPE: PRT
<213> ORGANISM: Homo sapiens
<220> FEATURE:
<223> OTHER INFORMATION: Protein S binding domain
<220> FEATURE:
<221> NAME/KEY: SIGNAL
```

<222> LOCATION: (1)...(24)

<400> SEQUENCE: 33

Met Arg Val Leu Gly Arg Cys Gly Ala Leu Leu Ala Cys Leu Leu
1               5                   10                  15

Leu Val Leu Pro Val Ser Glu Ala Asn Phe Leu Ser Lys Gln Gln Ala
                20                  25                  30

Ser Gln Val Leu Val Arg Lys Arg Ala Asn Ser Leu Leu Glu Glu
            35                  40                  45

Thr Lys Gln Gly Asn Leu Glu Arg Glu Cys Ile Glu Glu Leu Cys Asn
    50                  55                  60

Lys Glu Glu Ala Arg Glu Val Phe Glu Asn Asp Pro Thr Asp Tyr
65                  70                  75                  80

Phe Tyr Pro Lys Tyr Leu Val
                85

<210> SEQ ID NO 34
<211> LENGTH: 202
<212> TYPE: PRT
<213> ORGANISM: Homo sapiens
<220> FEATURE:
<223> OTHER INFORMATION: Tim3 binding domain
<220> FEATURE:
<221> NAME/KEY: SIGNAL
<222> LOCATION: (1)...(21)

<400> SEQUENCE: 34

Met Phe Ser His Leu Pro Phe Asp Cys Val Leu Leu Leu Leu Leu
1               5                   10                  15

Leu Leu Thr Arg Ser Ser Glu Val Glu Tyr Arg Ala Glu Val Gly Gln
                20                  25                  30

Asn Ala Tyr Leu Pro Cys Phe Tyr Thr Pro Ala Ala Pro Gly Asn Leu
            35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
                100                 105                 110

Gln Ile Pro Gly Ile Met Asn Asp Glu Lys Phe Asn Leu Lys Leu Val
            115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly
        195                 200

<210> SEQ ID NO 35
<211> LENGTH: 21
<212> TYPE: PRT
<213> ORGANISM: Homo sapiens

```
<220> FEATURE:
<223> OTHER INFORMATION: Tim1 transmembrane domain

<400> SEQUENCE: 35

Ile Tyr Ala Gly Val Cys Ile Ser Val Leu Val Leu Leu Ala Leu Leu
1               5                   10                  15

Gly Val Ile Ile Ala
            20

<210> SEQ ID NO 36
<211> LENGTH: 21
<212> TYPE: PRT
<213> ORGANISM: Homo sapiens
<220> FEATURE:
<223> OTHER INFORMATION: Tim4 transmembrane domain

<400> SEQUENCE: 36

Leu Leu Met Ile Ile Ala Pro Ser Leu Gly Phe Val Leu Phe Ala Leu
1               5                   10                  15

Phe Val Ala Phe Leu
            20

<210> SEQ ID NO 37
<211> LENGTH: 21
<212> TYPE: PRT
<213> ORGANISM: Homo sapiens
<220> FEATURE:
<223> OTHER INFORMATION: FcgammaRI transmembrane domain

<400> SEQUENCE: 37

Val Leu Phe Tyr Leu Ala Val Gly Ile Met Phe Leu Val Asn Thr Val
1               5                   10                  15

Leu Trp Val Thr Ile
            20

<210> SEQ ID NO 38
<211> LENGTH: 21
<212> TYPE: PRT
<213> ORGANISM: Homo sapiens
<220> FEATURE:
<223> OTHER INFORMATION: CD8a transmembrane domain

<400> SEQUENCE: 38

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 39
<211> LENGTH: 21
<212> TYPE: PRT
<213> ORGANISM: Homo sapiens
<220> FEATURE:
<223> OTHER INFORMATION: MERTK transmembrane domain

<400> SEQUENCE: 39

Phe Gly Cys Phe Cys Gly Phe Ile Leu Ile Gly Leu Ile Leu Tyr Ile
1               5                   10                  15

Ser Leu Ala Ile Arg
            20

<210> SEQ ID NO 40
<211> LENGTH: 21
<212> TYPE: PRT
```

<213> ORGANISM: Homo sapiens
<220> FEATURE:
<223> OTHER INFORMATION: Axl transmembrane domain

<400> SEQUENCE: 40

Tyr Val Leu Leu Gly Ala Val Val Ala Ala Cys Val Leu Ile Leu
1               5                   10                  15

Ala Leu Phe Leu Val
            20

<210> SEQ ID NO 41
<211> LENGTH: 21
<212> TYPE: PRT
<213> ORGANISM: Homo sapiens
<220> FEATURE:
<223> OTHER INFORMATION: Tyro3 transmembrane domain

<400> SEQUENCE: 41

Val Pro Val Val Leu Gly Val Leu Thr Ala Leu Val Thr Ala Ala
1               5                   10                  15

Leu Ala Leu Ile Leu
            20

<210> SEQ ID NO 42
<211> LENGTH: 22
<212> TYPE: PRT
<213> ORGANISM: Homo sapiens
<220> FEATURE:
<223> OTHER INFORMATION: CD4 transmembrane domain

<400> SEQUENCE: 42

Met Ala Leu Ile Val Leu Gly Gly Val Ala Gly Leu Leu Leu Phe Ile
1               5                   10                  15

Gly Leu Gly Ile Phe Phe
            20

<210> SEQ ID NO 43
<211> LENGTH: 476
<212> TYPE: PRT
<213> ORGANISM: Mus musculus
<220> FEATURE:
<223> OTHER INFORMATION: MERTK signaling domain

<400> SEQUENCE: 43

Ala Leu Arg Arg Arg Val Gln Glu Thr Lys Phe Gly Ala Phe Ser
1               5                   10                  15

Glu Glu Asp Ser Gln Leu Val Val Asn Tyr Arg Ala Lys Lys Ser Phe
                20                  25                  30

Cys Arg Arg Ala Ile Glu Leu Thr Leu Gln Ser Leu Gly Val Ser Glu
            35                  40                  45

Glu Leu Gln Asn Lys Leu Glu Asp Val Val Ile Asp Arg Asn Leu Leu
        50                  55                  60

Val Leu Gly Lys Val Leu Gly Glu Gly Glu Phe Gly Ser Val Met Glu
65                  70                  75                  80

Gly Asn Leu Lys Gln Glu Asp Gly Thr Ser Gln Lys Val Ala Val Lys
                85                  90                  95

Thr Met Lys Leu Asp Asn Phe Ser Gln Arg Glu Ile Glu Glu Phe Leu
            100                 105                 110

Ser Glu Ala Ala Cys Met Lys Asp Phe Asn His Pro Asn Val Ile Arg
        115                 120                 125

Leu Leu Gly Val Cys Ile Glu Leu Ser Ser Gln Gly Ile Pro Lys Pro

```
            130                 135                 140
Met Val Ile Leu Pro Phe Met Lys Tyr Gly Asp Leu His Thr Phe Leu
145                 150                 155                 160

Leu Tyr Ser Arg Leu Asn Thr Gly Pro Lys Tyr Ile His Leu Gln Thr
                165                 170                 175

Leu Leu Lys Phe Met Met Asp Ile Ala Gln Gly Met Glu Tyr Leu Ser
            180                 185                 190

Asn Arg Asn Phe Leu His Arg Asp Leu Ala Ala Arg Asn Cys Met Leu
        195                 200                 205

Arg Asp Asp Met Thr Val Cys Val Ala Asp Phe Gly Leu Ser Lys Lys
    210                 215                 220

Ile Tyr Ser Gly Asp Tyr Tyr Arg Gln Gly Arg Ile Ala Lys Met Pro
225                 230                 235                 240

Val Lys Trp Ile Ala Ile Glu Ser Leu Ala Asp Arg Val Tyr Thr Ser
                245                 250                 255

Lys Ser Asp Val Trp Ala Phe Gly Val Thr Met Trp Glu Ile Thr Thr
            260                 265                 270

Arg Gly Met Thr Pro Tyr Pro Gly Val Gln Asn His Glu Met Tyr Asp
        275                 280                 285

Tyr Leu Leu His Gly His Arg Leu Lys Gln Pro Glu Asp Cys Leu Asp
    290                 295                 300

Glu Leu Tyr Asp Ile Met Tyr Ser Cys Trp Ser Ala Asp Pro Leu Asp
305                 310                 315                 320

Arg Pro Thr Phe Ser Val Leu Arg Leu Gln Leu Glu Lys Leu Ser Glu
                325                 330                 335

Ser Leu Pro Asp Ala Gln Asp Lys Glu Ser Ile Ile Tyr Ile Asn Thr
            340                 345                 350

Gln Leu Leu Glu Ser Cys Glu Gly Ile Ala Asn Gly Pro Ser Leu Thr
        355                 360                 365

Gly Leu Asp Met Asn Ile Asp Pro Asp Ser Ile Ile Ala Ser Cys Thr
    370                 375                 380

Pro Gly Ala Ala Val Ser Val Val Thr Ala Glu Val His Glu Asn Asn
385                 390                 395                 400

Leu Arg Glu Glu Arg Tyr Ile Leu Asn Gly Gly Asn Glu Glu Trp Glu
                405                 410                 415

Asp Val Ser Ser Thr Pro Phe Ala Ala Val Thr Pro Glu Lys Asp Gly
            420                 425                 430

Val Leu Pro Glu Asp Arg Leu Thr Lys Asn Gly Val Ser Trp Ser His
        435                 440                 445

His Ser Thr Leu Pro Leu Gly Ser Pro Ser Pro Asp Glu Leu Leu Phe
    450                 455                 460

Val Asp Asp Ser Leu Glu Asp Ser Glu Val Leu Met
465                 470                 475

<210> SEQ ID NO 44
<211> LENGTH: 422
<212> TYPE: PRT
<213> ORGANISM: Homo sapiens
<220> FEATURE:
<223> OTHER INFORMATION: Axl signaling domain

<400> SEQUENCE: 44

His Arg Arg Lys Lys Glu Thr Arg Tyr Gly Glu Val Phe Glu Pro Thr
1               5                   10                  15

Val Glu Arg Gly Glu Leu Val Val Arg Tyr Arg Val Arg Lys Ser Tyr
```

```
            20                  25                  30
Ser Arg Arg Thr Thr Glu Ala Thr Leu Asn Ser Leu Gly Ile Ser Glu
             35                  40                  45

Glu Leu Lys Glu Lys Leu Arg Asp Val Met Val Asp Arg His Lys Val
 50                  55                  60

Ala Leu Gly Lys Thr Leu Gly Glu Gly Glu Phe Gly Ala Val Met Glu
 65                  70                  75                  80

Gly Gln Leu Asn Gln Asp Asp Ser Ile Leu Lys Val Ala Val Lys Thr
             85                  90                  95

Met Lys Ile Ala Ile Cys Thr Arg Ser Glu Leu Glu Asp Phe Leu Ser
            100                 105                 110

Glu Ala Val Cys Met Lys Glu Phe Asp His Pro Asn Val Met Arg Leu
            115                 120                 125

Ile Gly Val Cys Phe Gln Gly Ser Glu Arg Glu Ser Phe Pro Ala Pro
            130                 135                 140

Val Val Ile Leu Pro Phe Met Lys His Gly Asp Leu His Ser Phe Leu
145                 150                 155                 160

Leu Tyr Ser Arg Leu Gly Asp Gln Pro Val Tyr Leu Pro Thr Gln Met
                165                 170                 175

Leu Val Lys Phe Met Ala Asp Ile Ala Ser Gly Met Glu Tyr Leu Ser
                180                 185                 190

Thr Lys Arg Phe Ile His Arg Asp Leu Ala Ala Arg Asn Cys Met Leu
                195                 200                 205

Asn Glu Asn Met Ser Val Cys Val Ala Asp Phe Gly Leu Ser Lys Lys
            210                 215                 220

Ile Tyr Asn Gly Asp Tyr Tyr Arg Gln Gly Arg Ile Ala Lys Met Pro
225                 230                 235                 240

Val Lys Trp Ile Ala Ile Glu Ser Leu Ala Asp Arg Val Tyr Thr Ser
                245                 250                 255

Lys Ser Asp Val Trp Ser Phe Gly Val Thr Met Trp Glu Ile Ala Thr
                260                 265                 270

Arg Gly Gln Thr Pro Tyr Pro Gly Val Glu Asn Ser Glu Ile Tyr Asp
                275                 280                 285

Tyr Leu Arg Gln Gly Asn Arg Leu Lys Gln Pro Ala Asp Cys Leu Asp
            290                 295                 300

Gly Leu Tyr Ala Leu Met Ser Arg Cys Trp Glu Leu Asn Pro Gln Asp
305                 310                 315                 320

Arg Pro Ser Phe Thr Glu Leu Arg Glu Asp Leu Glu Asn Thr Leu Lys
                325                 330                 335

Ala Leu Pro Pro Ala Gln Glu Pro Asp Glu Ile Leu Tyr Val Asn Met
                340                 345                 350

Asp Glu Gly Gly Gly Tyr Pro Glu Pro Gly Ala Ala Gly Gly Ala
            355                 360                 365

Asp Pro Pro Thr Gln Pro Asp Pro Lys Asp Ser Cys Ser Cys Leu Thr
            370                 375                 380

Ala Ala Glu Val His Pro Ala Gly Arg Tyr Val Leu Cys Pro Ser Thr
385                 390                 395                 400

Thr Pro Ser Pro Ala Gln Pro Ala Asp Arg Gly Ser Pro Ala Ala Pro
                405                 410                 415

Gly Gln Glu Asp Gly Ala
            420

<210> SEQ ID NO 45
```

```
<211> LENGTH: 440
<212> TYPE: PRT
<213> ORGANISM: Homo sapiens
<220> FEATURE:
<223> OTHER INFORMATION: Tyro3 signaling domain

<400> SEQUENCE: 45
```

| Leu | Arg | Lys | Arg | Arg | Lys | Glu | Thr | Arg | Phe | Gly | Gln | Ala | Phe | Asp | Ser |
|---|---|---|---|---|---|---|---|---|---|---|---|---|---|---|---|
| 1 | | | | 5 | | | | | 10 | | | | | 15 | |

| Val | Met | Ala | Arg | Gly | Glu | Pro | Ala | Val | His | Phe | Arg | Ala | Ala | Arg | Ser |
|---|---|---|---|---|---|---|---|---|---|---|---|---|---|---|---|
| | | | 20 | | | | | 25 | | | | | 30 | | |

| Phe | Asn | Arg | Glu | Arg | Pro | Glu | Arg | Ile | Glu | Ala | Thr | Leu | Asp | Ser | Leu |
|---|---|---|---|---|---|---|---|---|---|---|---|---|---|---|---|
| | | 35 | | | | | 40 | | | | | 45 | | | |

| Gly | Ile | Ser | Asp | Glu | Leu | Lys | Glu | Lys | Leu | Glu | Asp | Val | Leu | Ile | Pro |
|---|---|---|---|---|---|---|---|---|---|---|---|---|---|---|---|
| | 50 | | | | | 55 | | | | | 60 | | | | |

| Glu | Gln | Gln | Phe | Thr | Leu | Gly | Arg | Met | Leu | Gly | Lys | Gly | Glu | Phe | Gly |
|---|---|---|---|---|---|---|---|---|---|---|---|---|---|---|---|
| 65 | | | | | 70 | | | | | 75 | | | | | 80 |

| Ser | Val | Arg | Glu | Ala | Gln | Leu | Lys | Gln | Glu | Asp | Gly | Ser | Phe | Val | Lys |
|---|---|---|---|---|---|---|---|---|---|---|---|---|---|---|---|
| | | | | 85 | | | | | 90 | | | | | 95 | |

| Val | Ala | Val | Lys | Met | Leu | Lys | Ala | Asp | Ile | Ile | Ala | Ser | Ser | Asp | Ile |
|---|---|---|---|---|---|---|---|---|---|---|---|---|---|---|---|
| | | | 100 | | | | | 105 | | | | | 110 | | |

| Glu | Glu | Phe | Leu | Arg | Glu | Ala | Ala | Cys | Met | Lys | Glu | Phe | Asp | His | Pro |
|---|---|---|---|---|---|---|---|---|---|---|---|---|---|---|---|
| | | | 115 | | | | | 120 | | | | | 125 | | |

| His | Val | Ala | Lys | Leu | Val | Gly | Val | Ser | Leu | Arg | Ser | Arg | Ala | Lys | Gly |
|---|---|---|---|---|---|---|---|---|---|---|---|---|---|---|---|
| | 130 | | | | | 135 | | | | | 140 | | | | |

| Arg | Leu | Pro | Ile | Pro | Met | Val | Ile | Leu | Pro | Phe | Met | Lys | His | Gly | Asp |
|---|---|---|---|---|---|---|---|---|---|---|---|---|---|---|---|
| 145 | | | | | 150 | | | | | 155 | | | | | 160 |

| Leu | His | Ala | Phe | Leu | Leu | Ala | Ser | Arg | Ile | Gly | Glu | Asn | Pro | Phe | Asn |
|---|---|---|---|---|---|---|---|---|---|---|---|---|---|---|---|
| | | | | 165 | | | | | 170 | | | | | 175 | |

| Leu | Pro | Leu | Gln | Thr | Leu | Ile | Arg | Phe | Met | Val | Asp | Ile | Ala | Cys | Gly |
|---|---|---|---|---|---|---|---|---|---|---|---|---|---|---|---|
| | | | 180 | | | | | 185 | | | | | 190 | | |

| Met | Glu | Tyr | Leu | Ser | Ser | Arg | Asn | Phe | Ile | His | Arg | Asp | Leu | Ala | Ala |
|---|---|---|---|---|---|---|---|---|---|---|---|---|---|---|---|
| | | | 195 | | | | | 200 | | | | | 205 | | |

| Arg | Asn | Cys | Met | Leu | Ala | Glu | Asp | Met | Thr | Val | Cys | Val | Ala | Asp | Phe |
|---|---|---|---|---|---|---|---|---|---|---|---|---|---|---|---|
| | 210 | | | | | 215 | | | | | 220 | | | | |

| Gly | Leu | Ser | Arg | Lys | Ile | Tyr | Ser | Gly | Asp | Tyr | Tyr | Arg | Gln | Gly | Cys |
|---|---|---|---|---|---|---|---|---|---|---|---|---|---|---|---|
| 225 | | | | | 230 | | | | | 235 | | | | | 240 |

| Ala | Ser | Lys | Leu | Pro | Val | Lys | Trp | Leu | Ala | Leu | Glu | Ser | Leu | Ala | Asp |
|---|---|---|---|---|---|---|---|---|---|---|---|---|---|---|---|
| | | | | 245 | | | | | 250 | | | | | 255 | |

| Asn | Leu | Tyr | Thr | Val | Gln | Ser | Asp | Val | Trp | Ala | Phe | Gly | Val | Thr | Met |
|---|---|---|---|---|---|---|---|---|---|---|---|---|---|---|---|
| | | | 260 | | | | | 265 | | | | | 270 | | |

| Trp | Glu | Ile | Met | Thr | Arg | Gly | Gln | Thr | Pro | Tyr | Ala | Gly | Ile | Glu | Asn |
|---|---|---|---|---|---|---|---|---|---|---|---|---|---|---|---|
| | | 275 | | | | | 280 | | | | | 285 | | | |

| Ala | Glu | Ile | Tyr | Asn | Tyr | Leu | Ile | Gly | Gly | Asn | Arg | Leu | Lys | Gln | Pro |
|---|---|---|---|---|---|---|---|---|---|---|---|---|---|---|---|
| | 290 | | | | | 295 | | | | | 300 | | | | |

| Pro | Glu | Cys | Met | Glu | Asp | Val | Tyr | Asp | Leu | Met | Tyr | Gln | Cys | Trp | Ser |
|---|---|---|---|---|---|---|---|---|---|---|---|---|---|---|---|
| 305 | | | | | 310 | | | | | 315 | | | | | 320 |

| Ala | Asp | Pro | Lys | Gln | Arg | Pro | Ser | Phe | Thr | Cys | Leu | Arg | Met | Glu | Leu |
|---|---|---|---|---|---|---|---|---|---|---|---|---|---|---|---|
| | | | | 325 | | | | | 330 | | | | | 335 | |

| Glu | Asn | Ile | Leu | Gly | Gln | Leu | Ser | Val | Leu | Ser | Ala | Ser | Gln | Asp | Pro |
|---|---|---|---|---|---|---|---|---|---|---|---|---|---|---|---|
| | | | 340 | | | | | 345 | | | | | 350 | | |

| Leu | Tyr | Ile | Asn | Ile | Glu | Arg | Ala | Glu | Glu | Pro | Thr | Ala | Gly | Gly | Ser |
|---|---|---|---|---|---|---|---|---|---|---|---|---|---|---|---|
| | | 355 | | | | | 360 | | | | | 365 | | | |

| Leu | Glu | Leu | Pro | Gly | Arg | Asp | Gln | Pro | Tyr | Ser | Gly | Ala | Gly | Asp | Gly |
|---|---|---|---|---|---|---|---|---|---|---|---|---|---|---|---|
| | 370 | | | | | 375 | | | | | 380 | | | | |

```
Ser Gly Met Gly Ala Val Gly Thr Pro Ser Asp Cys Arg Tyr Ile
385                 390                 395                 400

Leu Thr Pro Gly Gly Leu Ala Glu Gln Pro Gly Gln Ala Glu His Gln
                405                 410                 415

Pro Glu Ser Pro Leu Asn Glu Thr Gln Arg Leu Leu Leu Leu Gln Gln
            420                 425                 430

Gly Leu Leu Pro His Ser Ser Cys
        435                 440

<210> SEQ ID NO 46
<211> LENGTH: 261
<212> TYPE: PRT
<213> ORGANISM: Homo sapiens
<220> FEATURE:
<223> OTHER INFORMATION: Syk signaling domain

<400> SEQUENCE: 46

Thr Leu Glu Asp Lys Glu Leu Gly Ser Gly Asn Phe Gly Thr Val Lys
1               5                   10                  15

Lys Gly Tyr Tyr Gln Met Lys Lys Val Val Lys Thr Val Ala Val Lys
            20                  25                  30

Ile Leu Lys Asn Glu Ala Asn Asp Pro Ala Leu Lys Asp Glu Leu Leu
        35                  40                  45

Ala Glu Ala Asn Val Met Gln Gln Leu Asp Asn Pro Tyr Ile Val Arg
    50                  55                  60

Met Ile Gly Ile Cys Glu Ala Glu Ser Trp Met Leu Val Met Glu Met
65                  70                  75                  80

Ala Glu Leu Gly Pro Leu Asn Lys Tyr Leu Gln Gln Asn Arg His Val
                85                  90                  95

Lys Asp Lys Asn Ile Ile Glu Leu Val His Gln Val Ser Met Gly Met
            100                 105                 110

Lys Tyr Leu Glu Glu Ser Asn Phe Val His Arg Asp Leu Ala Ala Arg
        115                 120                 125

Asn Val Leu Leu Val Thr Gln His Tyr Ala Lys Ile Ser Asp Phe Gly
    130                 135                 140

Leu Ser Lys Ala Leu Arg Ala Asp Glu Asn Tyr Tyr Lys Ala Gln Thr
145                 150                 155                 160

His Gly Lys Trp Pro Val Lys Trp Tyr Ala Pro Glu Cys Ile Asn Tyr
                165                 170                 175

Tyr Lys Phe Ser Ser Lys Ser Asp Val Trp Ser Phe Gly Val Leu Met
            180                 185                 190

Trp Glu Ala Phe Ser Tyr Gly Gln Lys Pro Tyr Arg Gly Met Lys Gly
        195                 200                 205

Ser Glu Val Thr Ala Met Leu Glu Lys Gly Glu Arg Met Gly Cys Pro
    210                 215                 220

Ala Gly Cys Pro Arg Glu Met Tyr Asp Leu Met Asn Leu Cys Trp Thr
225                 230                 235                 240

Tyr Asp Val Glu Asn Arg Pro Gly Phe Ala Ala Val Glu Leu Arg Leu
                245                 250                 255

Arg Asn Tyr Tyr Tyr
            260

<210> SEQ ID NO 47
<211> LENGTH: 263
<212> TYPE: PRT
<213> ORGANISM: Homo sapiens
```

```
<220> FEATURE:
<223> OTHER INFORMATION: Zap70 signaling domain

<400> SEQUENCE: 47

Leu Ile Ala Asp Ile Glu Leu Gly Cys Gly Asn Phe Gly Ser Val Arg
1               5                   10                  15

Gln Gly Val Tyr Arg Met Arg Lys Lys Gln Ile Asp Val Ala Ile Lys
            20                  25                  30

Val Leu Lys Gln Gly Thr Glu Lys Ala Asp Thr Glu Glu Met Met Arg
        35                  40                  45

Glu Ala Gln Ile Met His Gln Leu Asp Asn Pro Tyr Ile Val Arg Leu
    50                  55                  60

Ile Gly Val Cys Gln Ala Glu Ala Leu Met Leu Val Met Glu Met Ala
65                  70                  75                  80

Gly Gly Gly Pro Leu His Lys Phe Leu Val Gly Lys Arg Glu Glu Ile
                85                  90                  95

Pro Val Ser Asn Val Ala Glu Leu Leu His Gln Val Ser Met Gly Met
            100                 105                 110

Lys Tyr Leu Glu Glu Lys Asn Phe Val His Arg Asp Leu Ala Ala Arg
        115                 120                 125

Asn Val Leu Leu Val Asn Arg His Tyr Ala Lys Ile Ser Asp Phe Gly
    130                 135                 140

Leu Ser Lys Ala Leu Gly Ala Asp Asp Ser Tyr Tyr Thr Ala Arg Ser
145                 150                 155                 160

Ala Gly Lys Trp Pro Leu Lys Trp Tyr Ala Pro Glu Cys Ile Asn Phe
                165                 170                 175

Arg Lys Phe Ser Ser Arg Ser Asp Val Trp Ser Tyr Gly Val Thr Met
            180                 185                 190

Trp Glu Ala Leu Ser Tyr Gly Gln Lys Pro Tyr Lys Lys Met Lys Gly
        195                 200                 205

Pro Glu Val Met Ala Phe Ile Glu Gln Gly Lys Arg Met Glu Cys Pro
    210                 215                 220

Pro Glu Cys Pro Pro Glu Leu Tyr Ala Leu Met Ser Asp Cys Trp Ile
225                 230                 235                 240

Tyr Lys Trp Glu Asp Arg Pro Asp Phe Leu Thr Val Glu Gln Arg Met
                245                 250                 255

Arg Ala Cys Tyr Tyr Ser Leu
            260

<210> SEQ ID NO 48
<211> LENGTH: 61
<212> TYPE: PRT
<213> ORGANISM: Homo sapiens
<220> FEATURE:
<223> OTHER INFORMATION: FcgammaRI signaling domain

<400> SEQUENCE: 48

Arg Lys Glu Leu Lys Arg Lys Lys Lys Trp Asp Leu Glu Ile Ser Leu
1               5                   10                  15

Asp Ser Gly His Glu Lys Lys Val Ile Ser Ser Leu Gln Glu Asp Arg
            20                  25                  30

His Leu Glu Glu Glu Leu Lys Cys Gln Glu Gln Lys Glu Glu Gln Leu
        35                  40                  45

Gln Glu Gly Val His Arg Lys Glu Pro Gln Gly Ala Thr
    50                  55                  60
```

```
<210> SEQ ID NO 49
<211> LENGTH: 77
<212> TYPE: PRT
<213> ORGANISM: Homo sapiens
<220> FEATURE:
<223> OTHER INFORMATION: FcgammaR2A signaling domain

<400> SEQUENCE: 49

Cys Arg Lys Lys Arg Ile Ser Ala Asn Ser Thr Asp Pro Val Lys Ala
1               5                   10                  15

Ala Gln Phe Glu Pro Pro Gly Arg Gln Met Ile Ala Ile Arg Lys Arg
            20                  25                  30

Gln Leu Glu Glu Thr Asn Asn Asp Tyr Glu Thr Ala Asp Gly Gly Tyr
        35                  40                  45

Met Thr Leu Asn Pro Arg Ala Pro Thr Asp Asp Lys Asn Ile Tyr
    50                  55                  60

Leu Thr Leu Pro Pro Asn Asp His Val Asn Ser Asn Asn
65                  70                  75

<210> SEQ ID NO 50
<211> LENGTH: 77
<212> TYPE: PRT
<213> ORGANISM: Homo sapiens
<220> FEATURE:
<223> OTHER INFORMATION: FcgammaR2C signaling domain

<400> SEQUENCE: 50

Cys Arg Lys Lys Arg Ile Ser Ala Asn Ser Thr Asp Pro Val Lys Ala
1               5                   10                  15

Ala Gln Phe Glu Pro Pro Gly Arg Gln Met Ile Ala Ile Arg Lys Arg
            20                  25                  30

Gln Pro Glu Glu Thr Asn Asn Asp Tyr Glu Thr Ala Asp Gly Gly Tyr
        35                  40                  45

Met Thr Leu Asn Pro Arg Ala Pro Thr Asp Asp Lys Asn Ile Tyr
    50                  55                  60

Leu Thr Leu Pro Pro Asn Asp His Val Asn Ser Asn Asn
65                  70                  75

<210> SEQ ID NO 51
<211> LENGTH: 25
<212> TYPE: PRT
<213> ORGANISM: Homo sapiens
<220> FEATURE:
<223> OTHER INFORMATION: FcgammaR3A signaling domain

<400> SEQUENCE: 51

Lys Thr Asn Ile Arg Ser Ser Thr Arg Asp Trp Lys Asp His Lys Phe
1               5                   10                  15

Lys Trp Arg Lys Asp Pro Gln Asp Lys
            20                  25

<210> SEQ ID NO 52
<211> LENGTH: 56
<212> TYPE: PRT
<213> ORGANISM: Mus musculus
<220> FEATURE:
<223> OTHER INFORMATION: ItgB5 signaling domain

<400> SEQUENCE: 52

Lys Leu Leu Val Thr Ile His Asp Arg Arg Glu Phe Ala Lys Phe Gln
1               5                   10                  15

Ser Glu Arg Ser Arg Ala Arg Tyr Glu Met Ala Ser Asn Pro Leu Tyr
```

-continued

```
                    20                  25                  30
Arg Lys Pro Ile Ser Thr His Thr Val Asp Phe Ala Phe Asn Lys Phe
             35                  40                  45

Asn Lys Ser Tyr Asn Gly Ser Val
         50                  55

<210> SEQ ID NO 53
<211> LENGTH: 296
<212> TYPE: PRT
<213> ORGANISM: Homo sapiens
<220> FEATURE:
<223> OTHER INFORMATION: MyD88 signaling domain

<400> SEQUENCE: 53

Met Ala Ala Gly Gly Pro Gly Ala Gly Ser Ala Ala Pro Val Ser Ser
1               5                  10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
         35                  40                  45

Ala Leu Ala Glu Glu Met Asp Phe Glu Tyr Leu Glu Ile Arg Gln Leu
     50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Leu Thr Lys Leu
                 85                  90                  95

Gly Arg Asp Asp Val Leu Leu Glu Leu Gly Pro Ser Ile Glu Glu Asp
            100                 105                 110

Cys Gln Lys Tyr Ile Leu Lys Gln Gln Gln Glu Glu Ala Glu Lys Pro
         115                 120                 125

Leu Gln Val Ala Ala Val Asp Ser Ser Val Pro Arg Thr Ala Glu Leu
     130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile Gln Phe Val Gln
                165                 170                 175

Glu Met Ile Arg Gln Leu Glu Gln Thr Asn Tyr Arg Leu Lys Leu Cys
            180                 185                 190

Val Ser Asp Arg Asp Val Leu Pro Gly Thr Cys Val Trp Ser Ile Ala
         195                 200                 205

Ser Glu Leu Ile Glu Lys Arg Cys Arg Arg Met Val Val Val Val Ser
     210                 215                 220

Asp Asp Tyr Leu Gln Ser Lys Glu Cys Asp Phe Gln Thr Lys Phe Ala
225                 230                 235                 240

Leu Ser Leu Ser Pro Gly Ala His Gln Lys Arg Leu Ile Pro Ile Lys
                245                 250                 255

Tyr Lys Ala Met Lys Lys Glu Phe Pro Ser Ile Leu Arg Phe Ile Thr
            260                 265                 270

Val Cys Asp Tyr Thr Asn Pro Cys Thr Lys Ser Trp Phe Trp Thr Arg
         275                 280                 285

Leu Ala Lys Ala Leu Ser Leu Pro
     290                 295

<210> SEQ ID NO 54
<211> LENGTH: 522
<212> TYPE: PRT
```

<213> ORGANISM: Homo sapiens
<220> FEATURE:
<223> OTHER INFORMATION: Traf6 signaling domain

<400> SEQUENCE: 54

```
Met Ser Leu Leu Asn Cys Glu Asn Ser Cys Gly Ser Ser Gln Ser Glu
1               5                   10                  15

Ser Asp Cys Cys Val Ala Met Ala Ser Ser Cys Ser Ala Val Thr Lys
            20                  25                  30

Asp Asp Ser Val Gly Gly Thr Ala Ser Thr Gly Asn Leu Ser Ser Ser
        35                  40                  45

Phe Met Glu Glu Ile Gln Gly Tyr Asp Val Glu Phe Asp Pro Pro Leu
    50                  55                  60

Glu Ser Lys Tyr Glu Cys Pro Ile Cys Leu Met Ala Leu Arg Glu Ala
65              70                  75                  80

Val Gln Thr Pro Cys Gly His Arg Phe Cys Lys Ala Cys Ile Ile Lys
                85                  90                  95

Ser Ile Arg Asp Ala Gly His Lys Cys Pro Val Asp Asn Glu Ile Leu
            100                 105                 110

Leu Glu Asn Gln Leu Phe Pro Asp Asn Phe Ala Lys Arg Glu Ile Leu
        115                 120                 125

Ser Leu Met Val Lys Cys Pro Asn Glu Gly Cys Leu His Lys Met Glu
    130                 135                 140

Leu Arg His Leu Glu Asp His Gln Ala His Cys Glu Phe Ala Leu Met
145                 150                 155                 160

Asp Cys Pro Gln Cys Gln Arg Pro Phe Gln Lys Phe His Ile Asn Ile
                165                 170                 175

His Ile Leu Lys Asp Cys Pro Arg Arg Gln Val Ser Cys Asp Asn Cys
            180                 185                 190

Ala Ala Ser Met Ala Phe Glu Asp Lys Glu Ile His Asp Gln Asn Cys
        195                 200                 205

Pro Leu Ala Asn Val Ile Cys Glu Tyr Cys Asn Thr Ile Leu Ile Arg
    210                 215                 220

Glu Gln Met Pro Asn His Tyr Asp Leu Asp Cys Pro Thr Ala Pro Ile
225                 230                 235                 240

Pro Cys Thr Phe Ser Thr Phe Gly Cys His Glu Lys Met Gln Arg Asn
                245                 250                 255

His Leu Ala Arg His Leu Gln Glu Asn Thr Gln Ser His Met Arg Met
            260                 265                 270

Leu Ala Gln Ala Val His Ser Leu Ser Val Ile Pro Asp Ser Gly Tyr
        275                 280                 285

Ile Ser Glu Val Arg Asn Phe Gln Glu Thr Ile His Gln Leu Glu Gly
    290                 295                 300

Arg Leu Val Arg Gln Asp His Gln Ile Arg Glu Leu Thr Ala Lys Met
305                 310                 315                 320

Glu Thr Gln Ser Met Tyr Val Ser Glu Leu Lys Arg Thr Ile Arg Thr
                325                 330                 335

Leu Glu Asp Lys Val Ala Glu Ile Glu Ala Gln Gln Cys Asn Gly Ile
            340                 345                 350

Tyr Ile Trp Lys Ile Gly Asn Phe Gly Met His Leu Lys Cys Gln Glu
        355                 360                 365

Glu Glu Lys Pro Val Val Ile His Ser Pro Gly Phe Tyr Thr Gly Lys
    370                 375                 380

Pro Gly Tyr Lys Leu Cys Met Arg Leu His Leu Gln Leu Pro Thr Ala
```

```
                385                 390                 395                 400
        Gln Arg Cys Ala Asn Tyr Ile Ser Leu Phe Val His Thr Met Gln Gly
                        405                 410                 415
        Glu Tyr Asp Ser His Leu Pro Trp Pro Phe Gln Gly Thr Ile Arg Leu
                    420                 425                 430
        Thr Ile Leu Asp Gln Ser Glu Ala Pro Val Arg Gln Asn His Glu Glu
                435                 440                 445
        Ile Met Asp Ala Lys Pro Glu Leu Leu Ala Phe Gln Arg Pro Thr Ile
            450                 455                 460
        Pro Arg Asn Pro Lys Gly Phe Gly Tyr Val Thr Phe Met His Leu Glu
        465                 470                 475                 480
        Ala Leu Arg Gln Arg Thr Phe Ile Lys Asp Asp Thr Leu Leu Val Arg
                        485                 490                 495
        Cys Glu Val Ser Thr Arg Phe Asp Met Gly Ser Leu Arg Arg Glu Gly
                    500                 505                 510
        Phe Gln Pro Arg Ser Thr Asp Ala Gly Val
                    515                 520

<210> SEQ ID NO 55
<211> LENGTH: 138
<212> TYPE: DNA
<213> ORGANISM: Homo sapiens
<220> FEATURE:
<223> OTHER INFORMATION: MRC1 signaling domain

<400> SEQUENCE: 55
tataagaaac ggcgcgttca tcttcctcag gagggggcat tgaaaatac gttgtacttc      60 aacagccaga gcagtccagg tacgtctgat atgaaggatt tggtggggaa cattgaacag     120
aacgagcata gcgttata                                                   138

<210> SEQ ID NO 56
<211> LENGTH: 46
<212> TYPE: PRT
<213> ORGANISM: Homo sapiens
<220> FEATURE:
<223> OTHER INFORMATION: MRC1 signaling domain

<400> SEQUENCE: 56

Tyr Lys Lys Arg Arg Val His Leu Pro Gln Glu Gly Ala Phe Glu Asn
1               5                   10                  15
Thr Leu Tyr Phe Asn Ser Gln Ser Ser Pro Gly Thr Ser Asp Met Lys
            20                  25                  30
Asp Leu Val Gly Asn Ile Glu Gln Asn Glu His Ser Val Ile
        35                  40                  45

<210> SEQ ID NO 57
<211> LENGTH: 1080
<212> TYPE: DNA
<213> ORGANISM: Mus musculus
<220> FEATURE:
<223> OTHER INFORMATION: TIM4 extracellular and transmembrane domains

<400> SEQUENCE: 57
ttctctaggc gccggaattc gccaccatgt ctaaaggtct tcttctgctg tggctggtta      60
ctgaactgtg gtggttgtat ctcactcctg cagcaagtga ggataccatc attggtttct     120
tggggcagcc cgtcaccctc ccttgtcact accttagctg gagccagagc agaaatagta     180
tgtgttgggg taagggctcc tgtcctaata gcaaatgtaa tgcagagctc ttgcgaacag     240
```

```
acgggacacg gatcatcagt agaaagtcta ctaagtatac cttgcttggg aaggtacaat      300
ttggggaagt gtccctcact attagtaata caaatagagg tgacagcgga gtctattgct      360
gtagaataga agtaccaggt tggtttaacg atgtcaaaaa aaatgtacgg ctcgaattga      420
ggagggctac cactaccaag aaaccaacta caaccacccg ccccactaca accccttacg      480
tcaccacaac aacccctgaa ctgctgccca caactgtgat gaccaccagt gttcttccca      540
ctaccactcc tccccagacc ctggctacta ccgctttctc aacagccgta actacttgtc      600
cctcaactac ccctgggtca ttcagtcagg aaactacaaa ggggtccgct ttcactactg      660
agtcagaaac cctccctgct tctaatcact ctcaacgcag catgatgaca atatcaactg      720
acatcgctgt tctgagacca actggaagca atcccggtat cttgccctcc acatctcagc      780
tgacaacaca aaaaactacc ctgaccacat cagaatccct tcagaagaca actaagtccc      840
accaaatcaa ttcccgacag actattctta taatagcctg ttgtgtgggg tttgtgctga      900
tggttttgtt gttcctggct ttttttgcttc gcggcaaggt gactggtgcc aactgtctcc      960
aaaggcacaa aaggccagac aatacggaag attctgattc cgtgcttaac gatatgagcc     1020
acgggcggga cgatgaggat ggtatattca ccttgtgagc ggccgcccct ctccctcccc     1080
```

<210> SEQ ID NO 58
<211> LENGTH: 1428
<212> TYPE: DNA
<213> ORGANISM: Mus musculus
<220> FEATURE:
<223> OTHER INFORMATION: MERTK signaling domain

<400> SEQUENCE: 58

```
gctcttagga ggagggtgca ggagacaaag tttggtgggg ctttctcaga ggaggatagc       60
cagctcgttg taaactaccg ggccaagaaa tccttttgca gaagagcaat tgaacttaca      120
ttgcaaagcc tcggagtgtc tgaggagctt cagaataaac ttgaggacgt ggtcatcgat      180
cgcaaccttc ttgtgctggg gaaggtcttg ggagagggag agttcgggtc cgtgatggaa      240
ggtaacctta aacaagagga tggaactagc caaaaagtcg ccgtaaagac tatgaagctg      300
gataatttta gtcagcggga aattgaggaa tttcttttcag aggccgcttg catgaaggat      360
ttcaaccatc ccaatgttat caggctcctt ggtgtctgta tcgagcttag ttcccagggc      420
atacctaaac ctatggttat actgcctttc atgaagtatg gtgatctgca cacctttctt      480
ctctactccc ggcttaatac cgggccaaag tatatccacc tccaaaccct cttgaagttc      540
atgatggaca tagcacaggg gatggagtac ctttctaata ggaatttttct tcacagggat      600 ttggccgccc gaaattgtat gctcagagat gatatgactg tttgcgtcgc agattttgga      660
cttagcaaga aaatctacag tggtgattac tacagacagg gacgcattgc aaagatgcct      720
gtgaagtgga tagccatcga atcactggcc gatagggttt atacttccaa atccgatgtt      780
tgggcctttg gtgtgactat gtgggaaata acaacacggg ggatgactcc ttatcccggt     840
gttcaaaatc atgagatgta cgattatctc ctccacgggc accgacttaa acagcccgag      900
gactgcctgg acgaactgta tgacattatg tactcttgtt ggagcgctga tccattggac     960
cggcccactt tttccgtgct gcgacttcag ctggagaagc tgagtgagtc tctgcctgac     1020
gctcaggata aagagtcaat tatatacatc aacactcagc tccttgaatc ctgtgagggg    1080
atcgcaaacg gaccttcact cactggcttg acatgaata ttgatcccga ctccattatt     1140
gcttcctgta cacctggagc agctgtgagt gtggtaaccg ctgaggttca tgaaaataac    1200
ttgcgcgaag aaaggtatat actgaatggg ggaaacgagg aatgggaaga cgtatccagt    1260
```

```
acccccatttg ctgctgtgac ccccgagaag gatggggttc tgccagaaga tagactcacc    1320
aaaaatggtg tttcctggag tcaccattcc acacttcccc ttggcagtcc aagccctgac    1380
gaactccttt tgtagatga cagccttgag gacagcgaag tgctgatg                  1428
```

<210> SEQ ID NO 59
<211> LENGTH: 2100
<212> TYPE: DNA
<213> ORGANISM: Artificial Sequence
<220> FEATURE:
<223> OTHER INFORMATION: FA58C2-IgG4-CD28-MERTK CER03 chimeric engulfment receptor

<400> SEQUENCE: 59

```
atgttgctgc tcgttacgtc tctgctcctg tgcgaactgc cgcaccccgc cttcctcctg     60
attccgctga acggctgcgc taatccgctc ggtctgaaaa acaattctat acctgataaa    120
caaatcaccg cctcatcctc ttacaagacg tggggactcc atctcttttc ttggaaccca    180
tcttatgctc gactggacaa acaaggcaat ttcaatgcat gggtcgccgg gagttacggt    240
aacgaccaat ggctccaggt agaccttggt agtagtaagg aggtcacggg tatcatcaca    300 caggggggccc ggaatttcgg ttcagtgcag ttcgttgctt cctacaaggt cgcttattca    360
aacgatagtg ctaattggac agagtaccaa gaccctcgca cgggaagtag taagattttc    420
ccaggcaact gggataacca cagtcacaaa aaaaacttgt tcgagacgcc gatattggcg    480
agatatgtcc ggatacttcc ggtcgcgtgg cataacagaa ttgccctgag gctggaattg    540
ctgggatgcg aaagtaaata tggaccgcca tgccccccat gccccatgtt tgggtgttg    600 gtcgtagtgg gtggagtcct cgcttgctac tcattgctcg taacggttgc ttttattata    660
ttctgggttg ctcttaggag gagggtgcag agacaaagt tggtggggc tttctcagag    720 gaggatagcc agctcgttgt aaactaccgg gccaagaaat cctttttgcag aagagcaatt    780 gaacttacat tgcaaagcct cggagtgtct gaggagcttc agaataaact tgaggacgtg    840
gtcatcgatc gcaaccttct tgtgctgggg aaggtcttgg gagagggaga gttcgggtcc    900
gtgatggaag gtaaccttaa caagaggat ggaactagcc aaaaagtcgc cgtaaagact    960
atgaagctgg ataattttag tcagcgggaa attgaggaat tctttttcaga ggccgcttgc   1020 atgaaggatt caaccatcc caatgttatc aggctccttg gtgtctgtat cgagcttagt   1080
tcccagggca tacctaaacc tatggttata ctgcctttca tgaagtatgg tgatctgcac   1140
acctttcttc tctactcccg gcttaatacc gggccaaagt atatccacct ccaaaccctc   1200
ttgaagttca tgatggacat agcacagggg atggagtacc tttctaatag gaattttctt   1260
cacagggatt tggccgcccg aaattgtatg ctcagagatg atatgactgt tgcgtcgca   1320 gattttggac ttagcaagaa aatctacagt ggtgattact acagacaggg acgcattgca   1380
aagatgcctg tgaagtggat agccatcgaa tcactggccg atagggttta tacttccaaa   1440
tccgatgttt gggccttttgg tgtgactatg tgggaaataa caacacgggg gatgactcct   1500
tatcccggtg ttcaaaatca tgagatgtac gattatctcc tccacgggca ccgacttaaa   1560
cagcccgagg actgcctgga cgaactgtat gacattatgt actcttgttg gagcgctgat   1620
ccattggacc ggcccacttt ttccgtgctg cgacttcagc tggagaagct gagtgagtct   1680
ctgcctgacg ctcaggataa agagtcaatt atatacatca acactcagct ccttgaatcc   1740
tgtgagggga tcgcaaacgg accttcactc actggcttgg acatgaatat tgatcccgac   1800
tccattattg cttcctgtac acctggagca gctgtgagtg tggtaaccgc tgaggttcat   1860
```

```
gaaaataact tgcgcgaaga aaggtatata ctgaatgggg gaaacgagga atgggaagac   1920
gtatccagta ccccatttgc tgctgtgacc cccgagaagg atggggttct gccagaagat   1980
agactcacca aaaatggtgt ttcctggagt caccattcca cacttcccct tggcagtcca   2040
agccctgacg aactccttt tgtagatgac agccttgagg cagcgaagt gctgatgtga    2100
```

<210> SEQ ID NO 60
<211> LENGTH: 576
<212> TYPE: DNA
<213> ORGANISM: Homo sapiens
<220> FEATURE:
<223> OTHER INFORMATION: Rac1

<400> SEQUENCE: 60

```
atgcaagcca ttaagtgcgt agtagttggt gatggagccg tcggcaaaac atgcctgctg     60
atctcttata ccacaaacgc attcccgggc gagtacattc ccactgtatt tgacaactac    120
agtgctaacg tcatggtaga tggtaagccg gttaacctcg gactctggga taccgccggc    180
caggaagact atgatagact tagaccgctc agctatccgc aaaccgatgt gttcctgatt    240
tgctttagcc tggtctcccc cgcttcattt gagaatgtga gagcgaagtg gtatccagag    300
gtgcgccatc actgtccgaa cacacccatt atactcgtgg ggactaaact cgacctgagg    360
gatgacaagg acaccatcga aaactgaaa gaaagaaac ttacaccaat aacgtaccct     420
cagggtctgg ctatggcaaa agaaattggc gcggtgaaat acctggaatg cagtgcgctc    480
acccagcggg gcttgaagac ggtgttcgat gaggctatac gcgccgtgct gtgtcccca    540 ccagtgaaga aacgaaaacg aaagtgtctt ctccctt                             576
```

<210> SEQ ID NO 61
<211> LENGTH: 645
<212> TYPE: DNA
<213> ORGANISM: Homo sapiens
<220> FEATURE:
<223> OTHER INFORMATION: Rab5

<400> SEQUENCE: 61

```
atggcgtctc gcggagccac tcgcccaaac ggcccaaaca ctggcaataa atttgccaa     60 ttcaagttgg tacttctcgg ggaaagtgct gtgggtaagt catctctcgt acttcgcttc    120
gtgaaagggc agtttcacga gttccaagag tctactatcg gagcggcatt cttgacgcag    180
acagtatgtc tggacgacac tactgtaaaa tttgaaatat gggatacagc ggggcaagag    240
aggtatcact ctcttgctcc gatgtattat agaggcgcgc aagcggccat agtcgtatat    300
gatattacca atgaggaatc atttgcacgg gcgaaaaatt gggtaaaaga actgcagcgc    360
caggcgtcac ccaatatagt aattgctttg tctggaaata aggcagattt ggctaacaag    420
cgcgcggtag actttcaaga ggctcaaagc tacgcagacg acaatagttt gctgttcatg    480
gaaacatcag cgaaaactag tatgaatgta acgaaatct tcatggcaat cgctaagaaa    540
ctcccaaaaa acgagccgca gaaccctggg gccaacagcg caggggaag aggcgttgac    600 ttgactgagc cgactcaacc aaccagaaac caatgctgtt ccaac                    645
```

<210> SEQ ID NO 62
<211> LENGTH: 1281
<212> TYPE: DNA
<213> ORGANISM: Artificial Sequence
<220> FEATURE:
<223> OTHER INFORMATION: Rac1-P2A-Rab5a construct

<400> SEQUENCE: 62

```
atgcaagcca ttaagtgcgt agtagttggt gatggagccg tcggcaaaac atgcctgctg      60
atctcttata ccacaaacgc attcccgggc gagtacattc ccactgtatt tgacaactac     120
agtgctaacg tcatggtaga tggtaagccg gttaacctcg gactctggga taccgccggc     180
caggaagact atgatagact tagaccgctc agctatccgc aaaccgatgt gttcctgatt     240
tgctttagcc tggtctcccc cgcttcattt gagaatgtga gagcgaagtg gtatccagag     300
gtgcgccatc actgtccgaa cacacccatt atactcgtgg ggactaaact cgacctgagg     360
gatgacaagg acaccatcga aaaactgaaa gaaaagaaac ttacaccaat aacgtaccct     420
cagggtctgg ctatggcaaa agaaattggc gcggtgaaat acctggaatg cagtgcgctc     480
acccagcggg gcttgaagac ggtgttcgat gaggctatac gcgccgtgct gtgtccccca     540
ccagtgaaga aacgaaaacg aaagtgtctt ctccttgcca ccaacttcag cctgctgaag     600
caggccggcg acgtggagga gaaccccggc cccatggcgt ctcgcggagc cactcgccca     660
aacggcccaa acactggcaa taaaatttgc caattcaagt tggtacttct cggggaaagt     720
gctgtgggta agtcatctct cgtacttcgc ttcgtgaaag gcagtttca cgagttccaa      780
gagtctacta tcggagcggc attcttgacg cagacagtat gtctggacga cactactgta     840
aaatttgaaa tatgggatac agcggggcaa gagaggtatc actctcttgc tccgatgtat     900
tatagaggcg cgcaagcggc catagtcgta tatgatatta ccaatgagga atcatttgca     960
cgggcgaaaa attgggtaaa agaactgcag cgccaggcgt cacccaatat agtaattgct    1020
ttgtctggaa ataaggcaga tttggctaac aagcgcgcgg tagactttca agaggctcaa    1080
agctacgcag acgacaatag tttgctgttc atggaaacat cagcgaaaac tagtatgaat    1140
gtaaacgaaa tcttcatggc aatcgctaag aaactcccaa aaaacgagcc gcagaaccct    1200
ggggccaaca gcgcaagggg aagaggcgtt gacttgactg agccgactca accaaccaga    1260
aaccaatgct gttccaactg a                                               1281
```

<210> SEQ ID NO 63
<211> LENGTH: 1455
<212> TYPE: DNA
<213> ORGANISM: Artificial Sequence
<220> FEATURE:
<223> OTHER INFORMATION: FA58C2-IgG4-CD28-Syk CER04 chimeric engulfment receptor

<400> SEQUENCE: 63

```
atgttgctgc tcgttacgtc tctgctcctg tgcgaactgc cgcaccccgc cttcctcctg      60
attccgctga acggctgcgc taatccgctc ggtctgaaaa acaattctat acctgataaa     120
caatcaccg cctcatcctc ttacaagacg tggggactcc atctcttttc ttggaaccca     180
tcttatgctc gactggacaa acaaggcaat tcaatgcat gggtcgccgg gagttacggt     240
aacgaccaat ggctccaggt agaccttggt agtagtaagg aggtcacggg tatcatcaca     300
caggggggccc ggaatttcgg ttcagtgcag ttcgttgctt cctacaaggt cgcttattca     360
aacgatagtg ctaattggac agagtaccaa gaccctcgca cgggaagtag taagattttc     420
ccaggcaact gggataacca cagtcacaaa aaaaacttgt cgagacgcc gatattggcg     480
agatatgtcc ggatacttcc ggtcgcgtgg cataacagaa ttgccctgag ctggaattg     540
ctgggatgcg aaagtaaata tggaccgcca tgccccccat gccccatgtt tgggtgttg     600
gtcgtagtgg gtggagtcct cgcttgctac tcattgctcg taacggttgc ttttattata    660
```

```
ttctgggtta cactcgagga taaagagctc ggatctggta atttcggcac agttaagaaa    720
gggtactacc aaatgaagaa agttgttaag actgtagccg tcaagatact caaaaacgaa    780
gcgaatgatc cggcgctgaa agacgaattg ctcgcggaag cgaacgtgat gcaacagctg    840
gataatccct acattgtcag gatgatagga atatgtgagg ctgaaagctg gatgcttgtt    900
atggagatgg cggagcttgg acccctgaac aaatacctcc agcagaatcg gcatgtgaag    960
gataagaata tcatagaatt ggtccaccag gtttcaatgg gtatgaagta tctggaagaa    1020
agtaacttcg ttcatcggga cttggccgcg cgcaatgtct tgcttgtcac gcaacactac    1080
gccaaaatat ccgacttcgg attgagtaag gccctgcgag cagacgaaaa ttattataag    1140
gctcagacac atggaaaatg gcctgtaaag tggtacgcgc ctgagtgcat caactactac    1200
aagttttcaa gtaaatctga tgtatggagc tttggtgtgc tgatgtggga agctttttct    1260
tatggccaaa aaccgtatag aggaatgaag ggatcagaag tcaccgcaat gctcgaaaaa    1320
ggtgaaagga tggggtgccc cgcgggatgc cctcgagaga tgtatgacct gatgaacctt    1380
tgctggactt atgatgtaga gaatagacct gggttcgcag ccgttgagtt gcgcctcagg    1440
aattactact attga                                                    1455
```

<210> SEQ ID NO 64
<211> LENGTH: 783
<212> TYPE: PRT
<213> ORGANISM: Artificial Sequence
<220> FEATURE:
<223> OTHER INFORMATION: GMCSF-FMC63-IgG4-CD28-MERTK CER40 chimeric
      engulfment receptor
<220> FEATURE:
<221> NAME/KEY: SIGNAL
<222> LOCATION: (1)...(22)
<223> OTHER INFORMATION: GM-CSF signal peptide

<400> SEQUENCE: 64

```
Met Leu Leu Leu Val Thr Ser Leu Leu Cys Glu Leu Pro His Pro
        -20             -15                 -10

Ala Phe Leu Leu Ile Pro Asp Ile Gln Met Thr Gln Thr Thr Ser Ser
    -5               1               5                   10

Leu Ser Ala Ser Leu Gly Asp Arg Val Thr Ile Ser Cys Arg Ala Ser
                15                  20                  25

Gln Asp Ile Ser Lys Tyr Leu Asn Trp Tyr Gln Gln Lys Pro Asp Gly
            30                  35                  40

Thr Val Lys Leu Leu Ile Tyr His Thr Ser Arg Leu His Ser Gly Val
            45                  50                  55

Pro Ser Arg Phe Ser Gly Ser Gly Ser Gly Thr Asp Tyr Ser Leu Thr
60                  65                  70

Ile Ser Asn Leu Glu Gln Glu Asp Ile Ala Thr Tyr Phe Cys Gln Gln
75                  80                  85                  90

Gly Asn Thr Leu Pro Tyr Thr Phe Gly Gly Gly Thr Lys Leu Glu Ile
                95                  100                 105

Thr Gly Ser Thr Ser Gly Ser Gly Lys Pro Gly Ser Gly Glu Gly Ser
            110                 115                 120

Thr Lys Gly Glu Val Lys Leu Gln Glu Ser Gly Pro Gly Leu Val Ala
            125                 130                 135

Pro Ser Gln Ser Leu Ser Val Thr Cys Thr Val Ser Gly Val Ser Leu
            140                 145                 150

Pro Asp Tyr Gly Val Ser Trp Ile Arg Gln Pro Pro Arg Lys Gly Leu
155                 160                 165                 170
```

```
Glu Trp Leu Gly Val Ile Trp Gly Ser Glu Thr Thr Tyr Tyr Asn Ser
                    175                 180                 185
Ala Leu Lys Ser Arg Leu Thr Ile Ile Lys Asp Asn Ser Lys Ser Gln
            190                 195                 200
Val Phe Leu Lys Met Asn Ser Leu Gln Thr Asp Asp Thr Ala Ile Tyr
        205                 210                 215
Tyr Cys Ala Lys His Tyr Tyr Gly Gly Ser Tyr Ala Met Asp Tyr
    220                 225                 230
Trp Gly Gln Gly Thr Ser Val Thr Val Ser Ser Glu Ser Lys Tyr Gly
235                 240                 245                 250
Pro Pro Cys Pro Pro Cys Pro Met Phe Trp Val Leu Val Val Val Gly
                255                 260                 265
Gly Val Leu Ala Cys Tyr Ser Leu Leu Val Thr Val Ala Phe Ile Ile
            270                 275                 280
Phe Trp Val Ala Leu Arg Arg Val Gln Glu Thr Lys Phe Gly Gly
        285                 290                 295
Ala Phe Ser Glu Glu Asp Ser Gln Leu Val Val Asn Tyr Arg Ala Lys
    300                 305                 310
Lys Ser Phe Cys Arg Arg Ala Ile Glu Leu Thr Leu Gln Ser Leu Gly
315                 320                 325                 330
Val Ser Glu Glu Leu Gln Asn Lys Leu Glu Asp Val Val Ile Asp Arg
                335                 340                 345
Asn Leu Leu Val Leu Gly Lys Val Leu Gly Glu Gly Glu Phe Gly Ser
            350                 355                 360
Val Met Glu Gly Asn Leu Lys Gln Glu Asp Gly Thr Ser Gln Lys Val
        365                 370                 375
Ala Val Lys Thr Met Lys Leu Asp Asn Phe Ser Gln Arg Glu Ile Glu
    380                 385                 390
Glu Phe Leu Ser Glu Ala Ala Cys Met Lys Asp Phe Asn His Pro Asn
395                 400                 405                 410
Val Ile Arg Leu Leu Gly Val Cys Ile Glu Leu Ser Ser Gln Gly Ile
                415                 420                 425
Pro Lys Pro Met Val Ile Leu Pro Phe Met Lys Tyr Gly Asp Leu His
            430                 435                 440
Thr Phe Leu Leu Tyr Ser Arg Leu Asn Thr Gly Pro Lys Tyr Ile His
        445                 450                 455
Leu Gln Thr Leu Leu Lys Phe Met Met Asp Ile Ala Gln Gly Met Glu
    460                 465                 470
Tyr Leu Ser Asn Arg Asn Phe Leu His Arg Asp Leu Ala Ala Arg Asn
475                 480                 485                 490
Cys Met Leu Arg Asp Asp Met Thr Val Cys Val Ala Asp Phe Gly Leu
                495                 500                 505
Ser Lys Lys Ile Tyr Ser Gly Asp Tyr Tyr Arg Gln Gly Arg Ile Ala
            510                 515                 520
Lys Met Pro Val Lys Trp Ile Ala Ile Glu Ser Leu Ala Asp Arg Val
        525                 530                 535
Tyr Thr Ser Lys Ser Asp Val Trp Ala Phe Gly Val Thr Met Trp Glu
    540                 545                 550
Ile Thr Thr Arg Gly Met Thr Pro Tyr Pro Gly Val Gln Asn His Glu
555                 560                 565                 570
Met Tyr Asp Tyr Leu Leu His Gly His Arg Leu Lys Gln Pro Glu Asp
                575                 580                 585
Cys Leu Asp Glu Leu Tyr Asp Ile Met Tyr Ser Cys Trp Ser Ala Asp
```

```
                    590                 595                 600
Pro Leu Asp Arg Pro Thr Phe Ser Val Leu Arg Leu Gln Leu Glu Lys
                605                 610                 615

Leu Ser Glu Ser Leu Pro Asp Ala Gln Asp Lys Glu Ser Ile Ile Tyr
            620                 625                 630

Ile Asn Thr Gln Leu Leu Glu Ser Cys Glu Gly Ile Ala Asn Gly Pro
635                 640                 645                 650

Ser Leu Thr Gly Leu Asp Met Asn Ile Asp Pro Asp Ser Ile Ile Ala
                655                 660                 665

Ser Cys Thr Pro Gly Ala Ala Val Ser Val Val Thr Ala Glu Val His
            670                 675                 680

Glu Asn Asn Leu Arg Glu Arg Tyr Ile Leu Asn Gly Gly Asn Glu
                685                 690                 695

Glu Trp Glu Asp Val Ser Ser Thr Pro Phe Ala Ala Val Thr Pro Glu
            700                 705                 710

Lys Asp Gly Val Leu Pro Glu Asp Arg Leu Thr Lys Asn Gly Val Ser
715                 720                 725                 730

Trp Ser His His Ser Thr Leu Pro Leu Gly Ser Pro Ser Pro Asp Glu
                735                 740                 745

Leu Leu Phe Val Asp Asp Ser Leu Glu Asp Ser Glu Val Leu Met
            750                 755                 760

<210> SEQ ID NO 65
<211> LENGTH: 22
<212> TYPE: PRT
<213> ORGANISM: Homo sapiens
<220> FEATURE:
<223> OTHER INFORMATION: GM-CSF signal peptide

<400> SEQUENCE: 65

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 66
<211> LENGTH: 245
<212> TYPE: PRT
<213> ORGANISM: Artificial Sequence
<220> FEATURE:
<223> OTHER INFORMATION: anti-CD19 FMC63 scFv

<400> SEQUENCE: 66

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110
```

```
Ser Gly Lys Pro Gly Ser Gly Glu Gly Ser Thr Lys Gly Glu Val Lys
            115                 120                 125

Leu Gln Glu Ser Gly Pro Gly Leu Val Ala Pro Ser Gln Ser Leu Ser
        130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser
                245

<210> SEQ ID NO 67
<211> LENGTH: 12
<212> TYPE: PRT
<213> ORGANISM: Artificial Sequence
<220> FEATURE:
<223> OTHER INFORMATION: modified IgG4 hinge region

<400> SEQUENCE: 67

Glu Ser Lys Tyr Gly Pro Pro Cys Pro Pro Cys Pro
1               5                   10

<210> SEQ ID NO 68
<211> LENGTH: 27
<212> TYPE: PRT
<213> ORGANISM: Homo sapiens
<220> FEATURE:
<223> OTHER INFORMATION: CD28 transmembrane domain

<400> SEQUENCE: 68

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 69
<211> LENGTH: 473
<212> TYPE: PRT
<213> ORGANISM: Homo sapiens
<220> FEATURE:
<223> OTHER INFORMATION: MERTK signaling domain

<400> SEQUENCE: 69

Lys Arg Val Gln Glu Thr Lys Phe Gly Asn Ala Phe Thr Glu Glu Asp
1               5                   10                  15

Ser Glu Leu Val Val Asn Tyr Ile Ala Lys Lys Ser Phe Cys Arg Arg
            20                  25                  30

Ala Ile Glu Leu Thr Leu His Ser Leu Gly Val Ser Glu Glu Leu Gln
        35                  40                  45

Asn Lys Leu Glu Asp Val Val Ile Asp Arg Asn Leu Leu Ile Leu Gly
    50                  55                  60

Lys Ile Leu Gly Glu Gly Glu Phe Gly Ser Val Met Glu Gly Asn Leu
```

```
            65                  70                  75                  80
Lys Gln Glu Asp Gly Thr Ser Leu Lys Val Ala Val Lys Thr Met Lys
                    85                  90                  95

Leu Asp Asn Ser Ser Gln Arg Glu Ile Glu Phe Leu Ser Glu Ala
            100                 105                 110

Ala Cys Met Lys Asp Phe Ser His Pro Asn Val Ile Arg Leu Leu Gly
            115                 120                 125

Val Cys Ile Glu Met Ser Ser Gln Gly Ile Pro Lys Pro Met Val Ile
        130                 135                 140

Leu Pro Phe Met Lys Tyr Gly Asp Leu His Thr Tyr Leu Leu Tyr Ser
145                 150                 155                 160

Arg Leu Glu Thr Gly Pro Lys His Ile Pro Leu Gln Thr Leu Leu Lys
                165                 170                 175

Phe Met Val Asp Ile Ala Leu Gly Met Glu Tyr Leu Ser Asn Arg Asn
            180                 185                 190

Phe Leu His Arg Asp Leu Ala Ala Arg Asn Cys Met Leu Arg Asp Asp
            195                 200                 205

Met Thr Val Cys Val Ala Asp Phe Gly Leu Ser Lys Lys Ile Tyr Ser
        210                 215                 220

Gly Asp Tyr Tyr Arg Gln Gly Arg Ile Ala Lys Met Pro Val Lys Trp
225                 230                 235                 240

Ile Ala Ile Glu Ser Leu Ala Asp Arg Val Tyr Thr Ser Lys Ser Asp
                245                 250                 255

Val Trp Ala Phe Gly Val Thr Met Trp Glu Ile Ala Thr Arg Gly Met
            260                 265                 270

Thr Pro Tyr Pro Gly Val Gln Asn His Glu Met Tyr Asp Tyr Leu Leu
        275                 280                 285

His Gly His Arg Leu Lys Gln Pro Glu Asp Cys Leu Asp Glu Leu Tyr
        290                 295                 300

Glu Ile Met Tyr Ser Cys Trp Arg Thr Asp Pro Leu Asp Arg Pro Thr
305                 310                 315                 320

Phe Ser Val Leu Arg Leu Gln Leu Glu Lys Leu Leu Glu Ser Leu Pro
                325                 330                 335

Asp Val Arg Asn Gln Ala Asp Val Ile Tyr Val Asn Thr Gln Leu Leu
            340                 345                 350

Glu Ser Ser Glu Gly Leu Ala Gln Gly Ser Thr Leu Ala Pro Leu Asp
        355                 360                 365

Leu Asn Ile Asp Pro Asp Ser Ile Ile Ala Ser Cys Thr Pro Arg Ala
370                 375                 380

Ala Ile Ser Val Val Thr Ala Glu Val His Asp Ser Lys Pro His Glu
385                 390                 395                 400

Gly Arg Tyr Ile Leu Asn Gly Gly Ser Glu Glu Trp Glu Asp Leu Thr
                405                 410                 415

Ser Ala Pro Ser Ala Ala Val Thr Ala Glu Lys Asn Ser Val Leu Pro
            420                 425                 430

Gly Glu Arg Leu Val Arg Asn Gly Val Ser Trp Ser His Ser Ser Met
        435                 440                 445

Leu Pro Leu Gly Ser Ser Leu Pro Asp Glu Leu Leu Phe Ala Asp Asp
        450                 455                 460

Ser Ser Glu Gly Ser Glu Val Leu Met
465                 470

<210> SEQ ID NO 70
```

<211> LENGTH: 484
<212> TYPE: PRT
<213> ORGANISM: Artificial Sequence
<220> FEATURE:
<223> OTHER INFORMATION: GMCSF-FA58C2-IgG4-CD28-SYK CER04 chimeric engulfment receptor
<220> FEATURE:
<221> NAME/KEY: SIGNAL
<222> LOCATION: (1)...(22)
<223> OTHER INFORMATION: GM-CSF signal peptide

<400> SEQUENCE: 70

```
Met Leu Leu Leu Val Thr Ser Leu Leu Leu Cys Glu Leu Pro His Pro
        -20             -15             -10

Ala Phe Leu Leu Ile Pro Leu Asn Gly Cys Ala Asn Pro Leu Gly Leu
 -5               1               5                       10

Lys Asn Asn Ser Ile Pro Asp Lys Gln Ile Thr Ala Ser Ser Ser Tyr
                15              20              25

Lys Thr Trp Gly Leu His Leu Phe Ser Trp Asn Pro Ser Tyr Ala Arg
            30              35              40

Leu Asp Lys Gln Gly Asn Phe Asn Ala Trp Val Ala Gly Ser Tyr Gly
        45              50              55

Asn Asp Gln Trp Leu Gln Val Asp Leu Gly Ser Ser Lys Glu Val Thr
 60              65              70

Gly Ile Ile Thr Gln Gly Ala Arg Asn Phe Gly Ser Val Gln Phe Val
 75              80              85              90

Ala Ser Tyr Lys Val Ala Tyr Ser Asn Asp Ser Ala Asn Trp Thr Glu
                95              100             105

Tyr Gln Asp Pro Arg Thr Gly Ser Ser Lys Ile Phe Pro Gly Asn Trp
            110             115             120

Asp Asn His Ser His Lys Lys Asn Leu Phe Glu Thr Pro Ile Leu Ala
            125             130             135

Arg Tyr Val Arg Ile Leu Pro Val Ala Trp His Asn Arg Ile Ala Leu
        140             145             150

Arg Leu Glu Leu Leu Gly Cys Glu Ser Lys Tyr Gly Pro Pro Cys Pro
155             160             165             170

Pro Cys Pro Met Phe Trp Val Leu Val Val Gly Gly Val Leu Ala
            175             180             185

Cys Tyr Ser Leu Leu Val Thr Val Ala Phe Ile Ile Phe Trp Val Thr
            190             195             200

Leu Glu Asp Lys Glu Leu Gly Ser Gly Asn Phe Gly Thr Val Lys Lys
            205             210             215

Gly Tyr Tyr Gln Met Lys Lys Val Val Lys Thr Val Ala Val Lys Ile
            220             225             230

Leu Lys Asn Glu Ala Asn Asp Pro Ala Leu Lys Asp Glu Leu Leu Ala
235             240             245             250

Glu Ala Asn Val Met Gln Gln Leu Asp Asn Pro Tyr Ile Val Arg Met
                255             260             265

Ile Gly Ile Cys Glu Ala Glu Ser Trp Met Leu Val Met Glu Met Ala
            270             275             280

Glu Leu Gly Pro Leu Asn Lys Tyr Leu Gln Gln Asn Arg His Val Lys
            285             290             295

Asp Lys Asn Ile Ile Glu Leu Val His Gln Val Ser Met Gly Met Lys
            300             305             310

Tyr Leu Glu Glu Ser Asn Phe Val His Arg Asp Leu Ala Ala Arg Asn
            315             320             325             330
```

-continued

```
Val Leu Leu Val Thr Gln His Tyr Ala Lys Ile Ser Asp Phe Gly Leu
            335                 340                 345

Ser Lys Ala Leu Arg Ala Asp Glu Asn Tyr Tyr Lys Ala Gln Thr His
        350                 355                 360

Gly Lys Trp Pro Val Lys Trp Tyr Ala Pro Glu Cys Ile Asn Tyr Tyr
    365                 370                 375

Lys Phe Ser Ser Lys Ser Asp Val Trp Ser Phe Gly Val Leu Met Trp
380                 385                 390

Glu Ala Phe Ser Tyr Gly Gln Lys Pro Tyr Arg Gly Met Lys Gly Ser
395                 400                 405                 410

Glu Val Thr Ala Met Leu Glu Lys Gly Glu Arg Met Gly Cys Pro Ala
            415                 420                 425

Gly Cys Pro Arg Glu Met Tyr Asp Leu Met Asn Leu Cys Trp Thr Tyr
        430                 435                 440

Asp Val Glu Asn Arg Pro Gly Phe Ala Ala Val Glu Leu Arg Leu Arg
            445                 450                 455

Asn Tyr Tyr Tyr
    460

<210> SEQ ID NO 71
<211> LENGTH: 776
<212> TYPE: PRT
<213> ORGANISM: Artificial Sequence
<220> FEATURE:
<223> OTHER INFORMATION: Tim4-Tim4-MERTK CER01 mouse chimeric engulfment
      receptor
<220> FEATURE:
<221> NAME/KEY: SIGNAL
<222> LOCATION: (1)...(22)

<400> SEQUENCE: 71

Met Ser Lys Gly Leu Leu Leu Trp Leu Val Thr Glu Leu Trp Trp
        -20                 -15                 -10

Leu Tyr Leu Thr Pro Ala Ala Ser Glu Asp Thr Ile Ile Gly Phe Leu
        -5                  1                   5                   10

Gly Gln Pro Val Thr Leu Pro Cys His Tyr Leu Ser Trp Ser Gln Ser
            15                  20                  25

Arg Asn Ser Met Cys Trp Gly Lys Gly Ser Cys Pro Asn Ser Lys Cys
            30                  35                  40

Asn Ala Glu Leu Leu Arg Thr Asp Gly Thr Arg Ile Ile Ser Arg Lys
        45                  50                  55

Ser Thr Lys Tyr Thr Leu Leu Gly Lys Val Gln Phe Gly Glu Val Ser
    60                  65                  70

Leu Thr Ile Ser Asn Thr Asn Arg Gly Asp Ser Gly Val Tyr Cys Cys
75                  80                  85                  90

Arg Ile Glu Val Pro Gly Trp Phe Asn Asp Val Lys Lys Asn Val Arg
                95                  100                 105

Leu Glu Leu Arg Arg Ala Thr Thr Thr Lys Lys Pro Thr Thr Thr Thr
                110                 115                 120

Arg Pro Thr Thr Thr Pro Tyr Val Thr Thr Thr Pro Glu Leu Leu
            125                 130                 135

Pro Thr Thr Val Met Thr Thr Ser Val Leu Pro Thr Thr Thr Pro Pro
            140                 145                 150

Gln Thr Leu Ala Thr Thr Ala Phe Ser Thr Ala Val Thr Thr Cys Pro
155                 160                 165                 170

Ser Thr Thr Pro Gly Ser Phe Ser Gln Glu Thr Thr Lys Gly Ser Ala
                175                 180                 185
```

-continued

Phe Thr Thr Glu Ser Glu Thr Leu Pro Ala Ser Asn His Ser Gln Arg
          190                 195                 200

Ser Met Met Thr Ile Ser Thr Asp Ile Ala Val Leu Arg Pro Thr Gly
          205                 210                 215

Ser Asn Pro Gly Ile Leu Pro Ser Thr Ser Gln Leu Thr Thr Gln Lys
          220                 225                 230

Thr Thr Leu Thr Thr Ser Glu Ser Leu Gln Lys Thr Thr Lys Ser His
235                 240                 245                 250

Gln Ile Asn Ser Arg Gln Thr Ile Leu Ile Ala Cys Cys Val Gly
              255                 260                 265

Phe Val Leu Met Val Leu Leu Phe Leu Ala Phe Leu Ala Leu Arg Arg
          270                 275                 280

Arg Val Gln Glu Thr Lys Phe Gly Gly Ala Phe Ser Glu Glu Asp Ser
          285                 290                 295

Gln Leu Val Val Asn Tyr Arg Ala Lys Lys Ser Phe Cys Arg Arg Ala
          300                 305                 310

Ile Glu Leu Thr Leu Gln Ser Leu Gly Val Ser Glu Glu Leu Gln Asn
315                 320                 325                 330

Lys Leu Glu Asp Val Ile Asp Arg Asn Leu Leu Val Leu Gly Lys
              335                 340                 345

Val Leu Gly Glu Gly Glu Phe Gly Ser Val Met Glu Gly Asn Leu Lys
          350                 355                 360

Gln Glu Asp Gly Thr Ser Gln Lys Val Ala Val Lys Thr Met Lys Leu
          365                 370                 375

Asp Asn Phe Ser Gln Arg Glu Ile Glu Glu Phe Leu Ser Glu Ala Ala
380                 385                 390

Cys Met Lys Asp Phe Asn His Pro Asn Val Ile Arg Leu Leu Gly Val
395                 400                 405                 410

Cys Ile Glu Leu Ser Ser Gln Gly Ile Pro Lys Pro Met Val Ile Leu
              415                 420                 425

Pro Phe Met Lys Tyr Gly Asp Leu His Thr Phe Leu Leu Tyr Ser Arg
              430                 435                 440

Leu Asn Thr Gly Pro Lys Tyr Ile His Leu Gln Thr Leu Leu Lys Phe
              445                 450                 455

Met Met Asp Ile Ala Gln Gly Met Glu Tyr Leu Ser Asn Arg Asn Phe
460                 465                 470

Leu His Arg Asp Leu Ala Ala Arg Asn Cys Met Leu Arg Asp Asp Met
475                 480                 485                 490

Thr Val Cys Val Ala Asp Phe Gly Leu Ser Lys Lys Ile Tyr Ser Gly
              495                 500                 505

Asp Tyr Tyr Arg Gln Gly Arg Ile Ala Lys Met Pro Val Lys Trp Ile
              510                 515                 520

Ala Ile Glu Ser Leu Ala Asp Arg Val Tyr Thr Ser Lys Ser Asp Val
          525                 530                 535

Trp Ala Phe Gly Val Thr Met Trp Glu Ile Thr Thr Arg Gly Met Thr
          540                 545                 550

Pro Tyr Pro Gly Val Gln Asn His Glu Met Tyr Asp Tyr Leu Leu His
555                 560                 565                 570

Gly His Arg Leu Lys Gln Pro Glu Asp Cys Leu Asp Glu Leu Tyr Asp
              575                 580                 585

Ile Met Tyr Ser Cys Trp Ser Ala Asp Pro Leu Asp Arg Pro Thr Phe
              590                 595                 600

-continued

```
Ser Val Leu Arg Leu Gln Leu Glu Lys Leu Ser Glu Ser Leu Pro Asp
            605                 610                 615

Ala Gln Asp Lys Glu Ser Ile Ile Tyr Ile Asn Thr Gln Leu Leu Glu
        620                 625                 630

Ser Cys Glu Gly Ile Ala Asn Gly Pro Ser Leu Thr Gly Leu Asp Met
635                 640                 645                 650

Asn Ile Asp Pro Asp Ser Ile Ile Ala Ser Cys Thr Pro Gly Ala Ala
                655                 660                 665

Val Ser Val Val Thr Ala Glu Val His Glu Asn Asn Leu Arg Glu Glu
            670                 675                 680

Arg Tyr Ile Leu Asn Gly Gly Asn Glu Glu Trp Glu Asp Val Ser Ser
        685                 690                 695

Thr Pro Phe Ala Ala Val Thr Pro Glu Lys Asp Gly Val Leu Pro Glu
700                 705                 710

Asp Arg Leu Thr Lys Asn Gly Val Ser Trp Ser His His Ser Thr Leu
715                 720                 725                 730

Pro Leu Gly Ser Pro Ser Pro Asp Glu Leu Leu Phe Val Asp Asp Ser
                735                 740                 745

Leu Glu Asp Ser Glu Val Leu Met
            750

<210> SEQ ID NO 72
<211> LENGTH: 22
<212> TYPE: PRT
<213> ORGANISM: Mus musculus
<220> FEATURE:
<223> OTHER INFORMATION: Tim4 signal peptide

<400> SEQUENCE: 72

Met Ser Lys Gly Leu Leu Leu Trp Leu Val Thr Glu Leu Trp Trp
1               5                   10                  15

Leu Tyr Leu Thr Pro Ala
            20

<210> SEQ ID NO 73
<211> LENGTH: 257
<212> TYPE: PRT
<213> ORGANISM: Mus musculus
<220> FEATURE:
<223> OTHER INFORMATION: Tim4 binding domain without signal peptide

<400> SEQUENCE: 73

Ala Ser Glu Asp Thr Ile Ile Gly Phe Leu Gly Gln Pro Val Thr Leu
1               5                   10                  15

Pro Cys His Tyr Leu Ser Trp Ser Gln Ser Arg Asn Ser Met Cys Trp
            20                  25                  30

Gly Lys Gly Ser Cys Pro Asn Ser Lys Cys Asn Ala Glu Leu Leu Arg
        35                  40                  45

Thr Asp Gly Thr Arg Ile Ile Ser Arg Lys Ser Thr Lys Tyr Thr Leu
    50                  55                  60

Leu Gly Lys Val Gln Phe Gly Glu Val Ser Leu Thr Ile Ser Asn Thr
65                  70                  75                  80

Asn Arg Gly Asp Ser Gly Val Tyr Cys Cys Arg Ile Glu Val Pro Gly
                85                  90                  95

Trp Phe Asn Asp Val Lys Lys Asn Val Arg Leu Glu Leu Arg Arg Ala
            100                 105                 110

Thr Thr Thr Lys Lys Pro Thr Thr Thr Arg Pro Thr Thr Thr Pro
        115                 120                 125
```

```
Tyr Val Thr Thr Thr Thr Pro Glu Leu Leu Pro Thr Thr Val Met Thr
        130                 135                 140

Thr Ser Val Leu Pro Thr Thr Thr Pro Pro Gln Thr Leu Ala Thr Thr
145                 150                 155                 160

Ala Phe Ser Thr Ala Val Thr Thr Cys Pro Ser Thr Thr Pro Gly Ser
                165                 170                 175

Phe Ser Gln Glu Thr Thr Lys Gly Ser Ala Phe Thr Thr Glu Ser Glu
                180                 185                 190

Thr Leu Pro Ala Ser Asn His Ser Gln Arg Ser Met Met Thr Ile Ser
            195                 200                 205

Thr Asp Ile Ala Val Leu Arg Pro Thr Gly Ser Asn Pro Gly Ile Leu
        210                 215                 220

Pro Ser Thr Ser Gln Leu Thr Thr Gln Lys Thr Thr Leu Thr Thr Ser
225                 230                 235                 240

Glu Ser Leu Gln Lys Thr Thr Lys Ser His Gln Ile Asn Ser Arg Gln
                245                 250                 255

Thr

<210> SEQ ID NO 74
<211> LENGTH: 21
<212> TYPE: PRT
<213> ORGANISM: Mus musculus
<220> FEATURE:
<223> OTHER INFORMATION: Tim4 transmembrane domain

<400> SEQUENCE: 74

Ile Leu Ile Ile Ala Cys Cys Val Gly Phe Val Leu Met Val Leu Leu
1               5                   10                  15

Phe Leu Ala Phe Leu
            20

<210> SEQ ID NO 75
<211> LENGTH: 699
<212> TYPE: PRT
<213> ORGANISM: Artificial Sequence
<220> FEATURE:
<223> OTHER INFORMATION: GMCSF-FA58C2-IgG4-CD28-MERTK CER03 chimeric
      engulfment receptor
<220> FEATURE:
<221> NAME/KEY: SIGNAL
<222> LOCATION: (1)...(22)

<400> SEQUENCE: 75

Met Leu Leu Leu Val Thr Ser Leu Leu Leu Cys Glu Leu Pro His Pro
        -20                 -15                 -10

Ala Phe Leu Leu Ile Pro Leu Asn Gly Cys Ala Asn Pro Leu Gly Leu
        -5                  1                   5                   10

Lys Asn Asn Ser Ile Pro Asp Lys Gln Ile Thr Ala Ser Ser Tyr
                15                  20                  25

Lys Thr Trp Gly Leu His Leu Phe Ser Trp Asn Pro Tyr Ala Arg
            30                  35                  40

Leu Asp Lys Gln Gly Asn Phe Asn Ala Trp Val Ala Gly Ser Tyr Gly
            45                  50                  55

Asn Asp Gln Trp Leu Gln Val Asp Leu Gly Ser Ser Lys Glu Val Thr
        60                  65                  70

Gly Ile Ile Thr Gln Gly Ala Arg Asn Phe Gly Ser Val Gln Phe Val
75                  80                  85                  90

Ala Ser Tyr Lys Val Ala Tyr Ser Asn Asp Ser Ala Asn Trp Thr Glu
```

-continued

```
                95                  100                 105
Tyr Gln Asp Pro Arg Thr Gly Ser Ser Lys Ile Phe Pro Gly Asn Trp
            110                 115                 120
Asp Asn His Ser His Lys Lys Asn Leu Phe Glu Thr Pro Ile Leu Ala
            125                 130                 135
Arg Tyr Val Arg Ile Leu Pro Val Ala Trp His Asn Arg Ile Ala Leu
        140                 145                 150
Arg Leu Glu Leu Leu Gly Cys Glu Ser Lys Tyr Gly Pro Pro Cys Pro
155                 160                 165                 170
Pro Cys Pro Met Phe Trp Val Leu Val Val Gly Gly Val Leu Ala
                175                 180                 185
Cys Tyr Ser Leu Leu Val Thr Val Ala Phe Ile Ile Phe Trp Val Ala
                190                 195                 200
Leu Arg Arg Arg Val Gln Glu Thr Lys Phe Gly Gly Ala Phe Ser Glu
                205                 210                 215
Glu Asp Ser Gln Leu Val Val Asn Tyr Arg Ala Lys Lys Ser Phe Cys
220                 225                 230
Arg Arg Ala Ile Glu Leu Thr Leu Gln Ser Leu Gly Val Ser Glu Glu
235                 240                 245                 250
Leu Gln Asn Lys Leu Glu Asp Val Val Ile Asp Arg Asn Leu Leu Val
                255                 260                 265
Leu Gly Lys Val Leu Gly Glu Gly Glu Phe Gly Ser Val Met Glu Gly
                270                 275                 280
Asn Leu Lys Gln Glu Asp Gly Thr Ser Gln Lys Val Ala Val Lys Thr
                285                 290                 295
Met Lys Leu Asp Asn Phe Ser Gln Arg Glu Ile Glu Glu Phe Leu Ser
        300                 305                 310
Glu Ala Ala Cys Met Lys Asp Phe Asn His Pro Asn Val Ile Arg Leu
315                 320                 325                 330
Leu Gly Val Cys Ile Glu Leu Ser Ser Gln Gly Ile Pro Lys Pro Met
                335                 340                 345
Val Ile Leu Pro Phe Met Lys Tyr Gly Asp Leu His Thr Phe Leu Leu
                350                 355                 360
Tyr Ser Arg Leu Asn Thr Gly Pro Lys Tyr Ile His Leu Gln Thr Leu
                365                 370                 375
Leu Lys Phe Met Met Asp Ile Ala Gln Gly Met Glu Tyr Leu Ser Asn
            380                 385                 390
Arg Asn Phe Leu His Arg Asp Leu Ala Ala Arg Asn Cys Met Leu Arg
395                 400                 405                 410
Asp Asp Met Thr Val Cys Val Ala Asp Phe Gly Leu Ser Lys Lys Ile
                415                 420                 425
Tyr Ser Gly Asp Tyr Tyr Arg Gln Gly Arg Ile Ala Lys Met Pro Val
                430                 435                 440
Lys Trp Ile Ala Ile Glu Ser Leu Ala Asp Arg Val Tyr Thr Ser Lys
                445                 450                 455
Ser Asp Val Trp Ala Phe Gly Val Thr Met Trp Glu Ile Thr Thr Arg
460                 465                 470
Gly Met Thr Pro Tyr Pro Gly Val Gln Asn His Glu Met Tyr Asp Tyr
475                 480                 485                 490
Leu Leu His Gly His Arg Leu Lys Gln Pro Glu Asp Cys Leu Asp Glu
                495                 500                 505
Leu Tyr Asp Ile Met Tyr Ser Cys Trp Ser Ala Asp Pro Leu Asp Arg
                510                 515                 520
```

```
Pro Thr Phe Ser Val Leu Arg Leu Gln Leu Glu Lys Leu Ser Glu Ser
        525                 530                 535
Leu Pro Asp Ala Gln Asp Lys Glu Ser Ile Ile Tyr Ile Asn Thr Gln
540                 545                 550
Leu Leu Glu Ser Cys Glu Gly Ile Ala Asn Gly Pro Ser Leu Thr Gly
555                 560                 565                 570
Leu Asp Met Asn Ile Asp Pro Asp Ser Ile Ile Ala Ser Cys Thr Pro
                575                 580                 585
Gly Ala Ala Val Ser Val Val Thr Ala Glu Val His Glu Asn Asn Leu
                590                 595                 600
Arg Glu Glu Arg Tyr Ile Leu Asn Gly Gly Asn Glu Glu Trp Glu Asp
                605                 610                 615
Val Ser Ser Thr Pro Phe Ala Ala Val Thr Pro Glu Lys Asp Gly Val
        620                 625                 630
Leu Pro Glu Asp Arg Leu Thr Lys Asn Gly Val Ser Trp Ser His His
635                 640                 645                 650
Ser Thr Leu Pro Leu Gly Ser Pro Pro Asp Glu Leu Leu Phe Val
                655                 660                 665
Asp Asp Ser Leu Glu Asp Ser Glu Val Leu Met
                670                 675
```

<210> SEQ ID NO 76
<211> LENGTH: 192
<212> TYPE: PRT
<213> ORGANISM: Homo sapiens
<220> FEATURE:
<223> OTHER INFORMATION: Rac1

<400> SEQUENCE: 76

```
Met Gln Ala Ile Lys Cys Val Val Val Gly Asp Gly Ala Val Gly Lys
1               5                   10                  15
Thr Cys Leu Leu Ile Ser Tyr Thr Thr Asn Ala Phe Pro Gly Glu Tyr
            20                  25                  30
Ile Pro Thr Val Phe Asp Asn Tyr Ser Ala Asn Val Met Val Asp Gly
        35                  40                  45
Lys Pro Val Asn Leu Gly Leu Trp Asp Thr Ala Gly Gln Glu Asp Tyr
    50                  55                  60
Asp Arg Leu Arg Pro Leu Ser Tyr Pro Gln Thr Asp Val Phe Leu Ile
65                  70                  75                  80
Cys Phe Ser Leu Val Ser Pro Ala Ser Phe Glu Asn Val Arg Ala Lys
                85                  90                  95
Trp Tyr Pro Glu Val Arg His His Cys Pro Asn Thr Pro Ile Ile Leu
            100                 105                 110
Val Gly Thr Lys Leu Asp Leu Arg Asp Asp Lys Asp Thr Ile Glu Lys
        115                 120                 125
Leu Lys Glu Lys Lys Leu Thr Pro Ile Thr Tyr Pro Gln Gly Leu Ala
    130                 135                 140
Met Ala Lys Glu Ile Gly Ala Val Lys Tyr Leu Glu Cys Ser Ala Leu
145                 150                 155                 160
Thr Gln Arg Gly Leu Lys Thr Val Phe Asp Glu Ala Ile Arg Ala Val
                165                 170                 175
Leu Cys Pro Pro Pro Val Lys Lys Arg Lys Arg Lys Cys Leu Leu Leu
            180                 185                 190
```

<210> SEQ ID NO 77

<211> LENGTH: 215
<212> TYPE: PRT
<213> ORGANISM: Homo sapiens
<220> FEATURE:
<223> OTHER INFORMATION: Rab5

<400> SEQUENCE: 77

Met Ala Ser Arg Gly Ala Thr Arg Pro Asn Gly Pro Asn Thr Gly Asn
1               5                   10                  15

Lys Ile Cys Gln Phe Lys Leu Val Leu Leu Gly Glu Ser Ala Val Gly
            20                  25                  30

Lys Ser Ser Leu Val Leu Arg Phe Val Lys Gly Gln Phe His Glu Phe
        35                  40                  45

Gln Glu Ser Thr Ile Gly Ala Ala Phe Leu Thr Gln Thr Val Cys Leu
    50                  55                  60

Asp Asp Thr Thr Val Lys Phe Glu Ile Trp Asp Thr Ala Gly Gln Glu
65                  70                  75                  80

Arg Tyr His Ser Leu Ala Pro Met Tyr Tyr Arg Gly Ala Gln Ala Ala
                85                  90                  95

Ile Val Val Tyr Asp Ile Thr Asn Glu Glu Ser Phe Ala Arg Ala Lys
            100                 105                 110

Asn Trp Val Lys Glu Leu Gln Arg Gln Ala Ser Pro Asn Ile Val Ile
        115                 120                 125

Ala Leu Ser Gly Asn Lys Ala Asp Leu Ala Asn Lys Arg Ala Val Asp
    130                 135                 140

Phe Gln Glu Ala Gln Ser Tyr Ala Asp Asp Asn Ser Leu Leu Phe Met
145                 150                 155                 160

Glu Thr Ser Ala Lys Thr Ser Met Asn Val Asn Glu Ile Phe Met Ala
                165                 170                 175

Ile Ala Lys Lys Leu Pro Lys Asn Glu Pro Gln Asn Pro Gly Ala Asn
            180                 185                 190

Ser Ala Arg Gly Arg Gly Val Asp Leu Thr Glu Pro Thr Gln Pro Thr
        195                 200                 205

Arg Asn Gln Cys Cys Ser Asn
    210                 215

<210> SEQ ID NO 78
<211> LENGTH: 155
<212> TYPE: PRT
<213> ORGANISM: Homo sapiens
<220> FEATURE:
<223> OTHER INFORMATION: truncated MyD88 without TIR domain

<400> SEQUENCE: 78

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Leu Thr Lys Leu
                85                  90                  95

Gly Arg Asp Asp Val Leu Leu Glu Leu Gly Pro Ser Ile Glu Glu Asp

```
              100                 105                 110
Cys Gln Lys Tyr Ile Leu Lys Gln Gln Gln Glu Glu Ala Glu Lys Pro
            115                 120                 125

Leu Gln Val Ala Ala Val Asp Ser Ser Val Pro Arg Thr Ala Glu Leu
        130                 135                 140

Ala Gly Ile Thr Thr Leu Asp Asp Pro Leu Gly
145                 150                 155

<210> SEQ ID NO 79
<211> LENGTH: 455
<212> TYPE: PRT
<213> ORGANISM: Artificial Sequence
<220> FEATURE:
<223> OTHER INFORMATION: Tim4-Tim4 TM-tMyD88 CER15 chimeric engulfment
      receptor
<220> FEATURE:
<221> NAME/KEY: SIGNAL
<222> LOCATION: (1)...(22)

<400> SEQUENCE: 79

Met Ser Lys Gly Leu Leu Leu Trp Leu Val Thr Glu Leu Trp Trp
            -20                 -15                 -10

Leu Tyr Leu Thr Pro Ala Ala Ser Glu Asp Thr Ile Ile Gly Phe Leu
         -5                   1                   5                  10

Gly Gln Pro Val Thr Leu Pro Cys His Tyr Leu Ser Trp Ser Gln Ser
             15                  20                  25

Arg Asn Ser Met Cys Trp Gly Lys Gly Ser Cys Pro Asn Ser Lys Cys
             30                  35                  40

Asn Ala Glu Leu Leu Arg Thr Asp Gly Thr Arg Ile Ile Ser Arg Lys
             45                  50                  55

Ser Thr Lys Tyr Thr Leu Leu Gly Lys Val Gln Phe Gly Glu Val Ser
         60                  65                  70

Leu Thr Ile Ser Asn Thr Asn Arg Gly Asp Ser Gly Val Tyr Cys Cys
 75                  80                  85                  90

Arg Ile Glu Val Pro Gly Trp Phe Asn Asp Val Lys Lys Asn Val Arg
                 95                 100                 105

Leu Glu Leu Arg Arg Ala Thr Thr Thr Lys Lys Pro Thr Thr Thr Thr
            110                 115                 120

Arg Pro Thr Thr Thr Pro Tyr Val Thr Thr Thr Thr Pro Glu Leu Leu
            125                 130                 135

Pro Thr Thr Val Met Thr Thr Ser Val Leu Pro Thr Thr Thr Pro Pro
        140                 145                 150

Gln Thr Leu Ala Thr Ala Phe Ser Thr Ala Val Thr Thr Cys Pro
155                 160                 165                 170

Ser Thr Thr Pro Gly Ser Phe Ser Gln Glu Thr Thr Lys Gly Ser Ala
            175                 180                 185

Phe Thr Thr Glu Ser Glu Thr Leu Pro Ala Ser Asn His Ser Gln Arg
            190                 195                 200

Ser Met Met Thr Ile Ser Thr Asp Ile Ala Val Leu Arg Pro Thr Gly
            205                 210                 215

Ser Asn Pro Gly Ile Leu Pro Ser Thr Ser Gln Leu Thr Thr Gln Lys
            220                 225                 230

Thr Thr Leu Thr Thr Ser Glu Ser Leu Gln Lys Thr Thr Lys Ser His
235                 240                 245                 250

Gln Ile Asn Ser Arg Gln Thr Ile Leu Ile Ala Cys Cys Val Gly
            255                 260                 265
```

```
Phe Val Leu Met Val Leu Leu Phe Leu Ala Phe Leu Met Ala Ala Gly
                270                 275                 280

Gly Pro Gly Ala Gly Ser Ala Ala Pro Val Ser Ser Thr Ser Ser Leu
            285                 290                 295

Pro Leu Ala Ala Leu Asn Met Arg Val Arg Arg Arg Leu Ser Leu Phe
        300                 305                 310

Leu Asn Val Arg Thr Gln Val Ala Ala Asp Trp Thr Ala Leu Ala Glu
315                 320                 325                 330

Glu Met Asp Phe Glu Tyr Leu Glu Ile Arg Gln Leu Glu Thr Gln Ala
                335                 340                 345

Asp Pro Thr Gly Arg Leu Leu Asp Ala Trp Gln Gly Arg Pro Gly Ala
            350                 355                 360

Ser Val Gly Arg Leu Leu Glu Leu Leu Thr Lys Leu Gly Arg Asp Asp
            365                 370                 375

Val Leu Leu Glu Leu Gly Pro Ser Ile Glu Glu Asp Cys Gln Lys Tyr
380                 385                 390

Ile Leu Lys Gln Gln Gln Glu Glu Ala Glu Lys Pro Leu Gln Val Ala
395                 400                 405                 410

Ala Val Asp Ser Ser Val Pro Arg Thr Ala Glu Leu Ala Gly Ile Thr
            415                 420                 425

Thr Leu Asp Asp Pro Leu Gly
            430

<210> SEQ ID NO 80
<211> LENGTH: 596
<212> TYPE: PRT
<213> ORGANISM: Artificial Sequence
<220> FEATURE:
<223> OTHER INFORMATION: Tim4-Tim4 TM-MyD88 CER16 chimeric engulfment
      receptor
<220> FEATURE:
<221> NAME/KEY: SIGNAL
<222> LOCATION: (1)...(22)

<400> SEQUENCE: 80

Met Ser Lys Gly Leu Leu Leu Leu Trp Leu Val Thr Glu Leu Trp Trp
        -20                 -15                 -10

Leu Tyr Leu Thr Pro Ala Ala Ser Glu Asp Thr Ile Ile Gly Phe Leu
    -5                   1                   5                  10

Gly Gln Pro Val Thr Leu Pro Cys His Tyr Leu Ser Trp Ser Gln Ser
                15                  20                  25

Arg Asn Ser Met Cys Trp Gly Lys Gly Ser Cys Pro Asn Ser Lys Cys
            30                  35                  40

Asn Ala Glu Leu Leu Arg Thr Asp Gly Thr Arg Ile Ile Ser Arg Lys
        45                  50                  55

Ser Thr Lys Tyr Thr Leu Leu Gly Lys Val Gln Phe Gly Glu Val Ser
60                  65                  70

Leu Thr Ile Ser Asn Thr Asn Arg Gly Asp Ser Gly Val Tyr Cys Cys
75                  80                  85                  90

Arg Ile Glu Val Pro Gly Trp Phe Asn Asp Val Lys Lys Asn Val Arg
                95                  100                 105

Leu Glu Leu Arg Arg Ala Thr Thr Thr Lys Lys Pro Thr Thr Thr Thr
            110                 115                 120

Arg Pro Thr Thr Thr Pro Tyr Val Thr Thr Thr Thr Pro Glu Leu Leu
        125                 130                 135

Pro Thr Thr Val Met Thr Thr Ser Val Leu Pro Thr Thr Thr Pro Pro
    140                 145                 150
```

-continued

```
Gln Thr Leu Ala Thr Thr Ala Phe Ser Thr Ala Val Thr Thr Cys Pro
155                 160                 165                 170

Ser Thr Thr Pro Gly Ser Phe Ser Gln Glu Thr Thr Lys Gly Ser Ala
                175                 180                 185

Phe Thr Thr Glu Ser Glu Thr Leu Pro Ala Ser Asn His Ser Gln Arg
            190                 195                 200

Ser Met Met Thr Ile Ser Thr Asp Ile Ala Val Leu Arg Pro Thr Gly
        205                 210                 215

Ser Asn Pro Gly Ile Leu Pro Ser Thr Ser Gln Leu Thr Thr Gln Lys
    220                 225                 230

Thr Thr Leu Thr Thr Ser Glu Ser Leu Gln Lys Thr Thr Lys Ser His
235                 240                 245                 250

Gln Ile Asn Ser Arg Gln Thr Ile Leu Ile Ala Cys Cys Val Gly
                255                 260                 265

Phe Val Leu Met Val Leu Leu Phe Leu Ala Phe Leu Met Ala Ala Gly
            270                 275                 280

Gly Pro Gly Ala Gly Ser Ala Ala Pro Val Ser Ser Thr Ser Ser Leu
        285                 290                 295

Pro Leu Ala Ala Leu Asn Met Arg Val Arg Arg Leu Ser Leu Phe
300                 305                 310

Leu Asn Val Arg Thr Gln Val Ala Ala Asp Trp Thr Ala Leu Ala Glu
315                 320                 325                 330

Glu Met Asp Phe Glu Tyr Leu Glu Ile Arg Gln Leu Glu Thr Gln Ala
                335                 340                 345

Asp Pro Thr Gly Arg Leu Leu Asp Ala Trp Gln Gly Arg Pro Gly Ala
            350                 355                 360

Ser Val Gly Arg Leu Leu Glu Leu Leu Thr Lys Leu Gly Arg Asp Asp
        365                 370                 375

Val Leu Leu Glu Leu Gly Pro Ser Ile Glu Glu Asp Cys Gln Lys Tyr
    380                 385                 390

Ile Leu Lys Gln Gln Gln Glu Glu Ala Glu Lys Pro Leu Gln Val Ala
395                 400                 405                 410

Ala Val Asp Ser Ser Val Pro Arg Thr Ala Glu Leu Ala Gly Ile Thr
                415                 420                 425

Thr Leu Asp Asp Pro Leu Gly His Met Pro Glu Arg Phe Asp Ala Phe
            430                 435                 440

Ile Cys Tyr Cys Pro Ser Asp Ile Gln Phe Val Gln Glu Met Ile Arg
        445                 450                 455

Gln Leu Glu Gln Thr Asn Tyr Arg Leu Lys Leu Cys Val Ser Asp Arg
    460                 465                 470

Asp Val Leu Pro Gly Thr Cys Val Trp Ser Ile Ala Ser Glu Leu Ile
475                 480                 485                 490

Glu Lys Arg Cys Arg Arg Met Val Val Val Ser Asp Asp Tyr Leu
                495                 500                 505

Gln Ser Lys Glu Cys Asp Phe Gln Thr Lys Phe Ala Leu Ser Leu Ser
            510                 515                 520

Pro Gly Ala His Gln Lys Arg Leu Ile Pro Ile Lys Tyr Lys Ala Met
        525                 530                 535

Lys Lys Glu Phe Pro Ser Ile Leu Arg Phe Ile Thr Val Cys Asp Tyr
    540                 545                 550

Thr Asn Pro Cys Thr Lys Ser Trp Phe Trp Thr Arg Leu Ala Lys Ala
555                 560                 565                 570
```

Leu Ser Leu Pro

<210> SEQ ID NO 81
<211> LENGTH: 21
<212> TYPE: PRT
<213> ORGANISM: Homo sapiens
<220> FEATURE:
<221> NAME/KEY: PEPTIDE
<222> LOCATION: (0)...(0)
<223> OTHER INFORMATION: DAP12 transmembrane domain

<400> SEQUENCE: 81

Gly Val Leu Ala Gly Ile Val Met Gly Asp Leu Val Leu Thr Val Leu
1               5                   10                  15

Ile Ala Leu Ala Val
            20

<210> SEQ ID NO 82
<211> LENGTH: 52
<212> TYPE: PRT
<213> ORGANISM: Homo sapiens
<220> FEATURE:
<223> OTHER INFORMATION: DAP12 signaling domain

<400> SEQUENCE: 82

Tyr Phe Leu Gly Arg Leu Val Pro Arg Gly Arg Gly Ala Ala Glu Ala
1               5                   10                  15

Ala Thr Arg Lys Gln Arg Ile Thr Glu Thr Glu Ser Pro Tyr Gln Glu
            20                  25                  30

Leu Gln Gly Gln Arg Ser Asp Val Tyr Ser Asp Leu Asn Thr Gln Arg
        35                  40                  45

Pro Tyr Tyr Lys
    50

<210> SEQ ID NO 83
<211> LENGTH: 740
<212> TYPE: PRT
<213> ORGANISM: Artificial Sequence
<220> FEATURE:
<223> OTHER INFORMATION: Tim4-Tim4 TM-Tyro3 CER08 chimeric engulfment
      receptor
<220> FEATURE:
<221> NAME/KEY: SIGNAL
<222> LOCATION: (1)...(22)
<223> OTHER INFORMATION: Tim4 signal peptide

<400> SEQUENCE: 83

Met Ser Lys Gly Leu Leu Leu Trp Leu Val Thr Glu Leu Trp Trp
        -20                 -15                 -10

Leu Tyr Leu Thr Pro Ala Ala Ser Glu Asp Thr Ile Ile Gly Phe Leu
    -5                   1                   5                  10

Gly Gln Pro Val Thr Leu Pro Cys His Tyr Leu Ser Trp Ser Gln Ser
                15                  20                  25

Arg Asn Ser Met Cys Trp Gly Lys Gly Ser Cys Pro Asn Ser Lys Cys
            30                  35                  40

Asn Ala Glu Leu Leu Arg Thr Asp Gly Thr Arg Ile Ile Ser Arg Lys
        45                  50                  55

Ser Thr Lys Tyr Thr Leu Leu Gly Lys Val Gln Phe Gly Glu Val Ser
    60                  65                  70

Leu Thr Ile Ser Asn Thr Asn Arg Gly Asp Ser Gly Val Tyr Cys Cys
75                  80                  85                  90

Arg Ile Glu Val Pro Gly Trp Phe Asn Asp Val Lys Lys Asn Val Arg

-continued

```
                95                  100                 105
Leu Glu Leu Arg Arg Ala Thr Thr Thr Lys Lys Pro Thr Thr Thr Thr
                110                 115                 120

Arg Pro Thr Thr Thr Pro Tyr Val Thr Thr Thr Pro Glu Leu Leu
            125                 130                 135

Pro Thr Thr Val Met Thr Thr Ser Val Leu Pro Thr Thr Pro Pro
        140                 145                 150

Gln Thr Leu Ala Thr Thr Ala Phe Ser Thr Ala Val Thr Thr Cys Pro
155                 160                 165                 170

Ser Thr Thr Pro Gly Ser Phe Ser Gln Glu Thr Thr Lys Gly Ser Ala
                175                 180                 185

Phe Thr Thr Glu Ser Glu Thr Leu Pro Ala Ser Asn His Ser Gln Arg
                190                 195                 200

Ser Met Met Thr Ile Ser Thr Asp Ile Ala Val Leu Arg Pro Thr Gly
                205                 210                 215

Ser Asn Pro Gly Ile Leu Pro Ser Thr Ser Gln Leu Thr Thr Gln Lys
            220                 225                 230

Thr Thr Leu Thr Thr Ser Glu Ser Leu Gln Lys Thr Thr Lys Ser His
235                 240                 245                 250

Gln Ile Asn Ser Arg Gln Thr Ile Leu Ile Ile Ala Cys Cys Val Gly
                255                 260                 265

Phe Val Leu Met Val Leu Leu Phe Leu Ala Phe Leu Leu Arg Lys Arg
                270                 275                 280

Arg Lys Glu Thr Arg Phe Gly Gln Ala Phe Asp Ser Val Met Ala Arg
            285                 290                 295

Gly Glu Pro Ala Val His Phe Arg Ala Ala Arg Ser Phe Asn Arg Glu
        300                 305                 310

Arg Pro Glu Arg Ile Glu Ala Thr Leu Asp Ser Leu Gly Ile Ser Asp
315                 320                 325                 330

Glu Leu Lys Glu Lys Leu Glu Asp Val Leu Ile Pro Glu Gln Gln Phe
                335                 340                 345

Thr Leu Gly Arg Met Leu Gly Lys Gly Glu Phe Gly Ser Val Arg Glu
            350                 355                 360

Ala Gln Leu Lys Gln Glu Asp Gly Ser Phe Val Lys Val Ala Val Lys
        365                 370                 375

Met Leu Lys Ala Asp Ile Ile Ala Ser Ser Asp Ile Glu Glu Phe Leu
        380                 385                 390

Arg Glu Ala Ala Cys Met Lys Glu Phe Asp His Pro His Val Ala Lys
395                 400                 405                 410

Leu Val Gly Val Ser Leu Arg Ser Arg Ala Lys Gly Arg Leu Pro Ile
                415                 420                 425

Pro Met Val Ile Leu Pro Phe Met Lys His Gly Asp Leu His Ala Phe
            430                 435                 440

Leu Leu Ala Ser Arg Ile Gly Glu Asn Pro Phe Asn Leu Pro Leu Gln
            445                 450                 455

Thr Leu Ile Arg Phe Met Val Asp Ile Ala Cys Gly Met Glu Tyr Leu
    460                 465                 470

Ser Ser Arg Asn Phe Ile His Arg Asp Leu Ala Ala Arg Asn Cys Met
475                 480                 485                 490

Leu Ala Glu Asp Met Thr Val Cys Val Ala Asp Phe Gly Leu Ser Arg
                495                 500                 505

Lys Ile Tyr Ser Gly Asp Tyr Tyr Arg Gln Gly Cys Ala Ser Lys Leu
            510                 515                 520
```

```
Pro Val Lys Trp Leu Ala Leu Glu Ser Leu Ala Asp Asn Leu Tyr Thr
        525                 530                 535

Val Gln Ser Asp Val Trp Ala Phe Gly Val Thr Met Trp Glu Ile Met
    540                 545                 550

Thr Arg Gly Gln Thr Pro Tyr Ala Gly Ile Glu Asn Ala Glu Ile Tyr
555                 560                 565                 570

Asn Tyr Leu Ile Gly Gly Asn Arg Leu Lys Gln Pro Pro Glu Cys Met
                575                 580                 585

Glu Asp Val Tyr Asp Leu Met Tyr Gln Cys Trp Ser Ala Asp Pro Lys
            590                 595                 600

Gln Arg Pro Ser Phe Thr Cys Leu Arg Met Glu Leu Glu Asn Ile Leu
        605                 610                 615

Gly Gln Leu Ser Val Leu Ser Ala Ser Gln Asp Pro Leu Tyr Ile Asn
    620                 625                 630

Ile Glu Arg Ala Glu Glu Pro Thr Ala Gly Gly Ser Leu Glu Leu Pro
635                 640                 645                 650

Gly Arg Asp Gln Pro Tyr Ser Gly Ala Gly Asp Gly Ser Gly Met Gly
                655                 660                 665

Ala Val Gly Gly Thr Pro Ser Asp Cys Arg Tyr Ile Leu Thr Pro Gly
            670                 675                 680

Gly Leu Ala Glu Gln Pro Gly Gln Ala Glu His Gln Pro Glu Ser Pro
        685                 690                 695

Leu Asn Glu Thr Gln Arg Leu Leu Leu Gln Gln Gly Leu Leu Pro
    700                 705                 710

His Ser Ser Cys
715

<210> SEQ ID NO 84
<211> LENGTH: 352
<212> TYPE: PRT
<213> ORGANISM: Artificial Sequence
<220> FEATURE:
<223> OTHER INFORMATION: Tim4-Tim4 TM-DAP12 CER09 chimeric engulfment
      receptor
<220> FEATURE:
<221> NAME/KEY: SIGNAL
<222> LOCATION: (1)...(22)
<223> OTHER INFORMATION: Tim4 signal peptide

<400> SEQUENCE: 84

Met Ser Lys Gly Leu Leu Leu Trp Leu Val Thr Glu Leu Trp Trp
        -20                 -15                 -10

Leu Tyr Leu Thr Pro Ala Ala Ser Glu Asp Thr Ile Ile Gly Phe Leu
    -5                  1                   5                   10

Gly Gln Pro Val Thr Leu Pro Cys His Tyr Leu Ser Trp Ser Gln Ser
                15                  20                  25

Arg Asn Ser Met Cys Trp Gly Lys Gly Ser Cys Pro Asn Ser Lys Cys
            30                  35                  40

Asn Ala Glu Leu Leu Arg Thr Asp Gly Thr Arg Ile Ile Ser Arg Lys
        45                  50                  55

Ser Thr Lys Tyr Thr Leu Leu Gly Lys Val Gln Phe Gly Glu Val Ser
    60                  65                  70

Leu Thr Ile Ser Asn Thr Asn Arg Gly Asp Ser Gly Val Tyr Cys Cys
75                  80                  85                  90

Arg Ile Glu Val Pro Gly Trp Phe Asn Asp Val Lys Lys Asn Val Arg
                95                  100                 105
```

```
Leu Glu Leu Arg Arg Ala Thr Thr Thr Lys Lys Pro Thr Thr Thr
        110                 115                 120

Arg Pro Thr Thr Thr Pro Tyr Val Thr Thr Thr Pro Glu Leu Leu
    125                 130                 135

Pro Thr Thr Val Met Thr Thr Ser Val Leu Pro Thr Thr Thr Pro Pro
140                 145                 150

Gln Thr Leu Ala Thr Thr Ala Phe Ser Thr Ala Val Thr Thr Cys Pro
155                 160                 165                 170

Ser Thr Thr Pro Gly Ser Phe Ser Gln Glu Thr Thr Lys Gly Ser Ala
            175                 180                 185

Phe Thr Thr Glu Ser Glu Thr Leu Pro Ala Ser Asn His Ser Gln Arg
        190                 195                 200

Ser Met Met Thr Ile Ser Thr Asp Ile Ala Val Leu Arg Pro Thr Gly
        205                 210                 215

Ser Asn Pro Gly Ile Leu Pro Ser Thr Ser Gln Leu Thr Thr Gln Lys
        220                 225                 230

Thr Thr Leu Thr Thr Ser Glu Ser Leu Gln Lys Thr Thr Lys Ser His
235                 240                 245                 250

Gln Ile Asn Ser Arg Gln Thr Ile Leu Ile Ile Ala Cys Cys Val Gly
            255                 260                 265

Phe Val Leu Met Val Leu Leu Phe Leu Ala Phe Leu Tyr Phe Leu Gly
        270                 275                 280

Arg Leu Val Pro Arg Gly Arg Gly Ala Ala Glu Ala Ala Thr Arg Lys
            285                 290                 295

Gln Arg Ile Thr Glu Thr Glu Ser Pro Tyr Gln Glu Leu Gln Gly Gln
300                 305                 310

Arg Ser Asp Val Tyr Ser Asp Leu Asn Thr Gln Arg Pro Tyr Tyr Lys
315                 320                 325                 330

<210> SEQ ID NO 85
<211> LENGTH: 63
<212> TYPE: DNA
<213> ORGANISM: Homo sapiens
<220> FEATURE:
<223> OTHER INFORMATION: FcepsilonRIgamma transmembrane domain

<400> SEQUENCE: 85
ctttgttaca ttctcgacgc gatattgttc ctttatggaa tagttttgac gctcctttat    60
tgc                                                                  63

<210> SEQ ID NO 86
<211> LENGTH: 352
<212> TYPE: PRT
<213> ORGANISM: Artificial Sequence
<220> FEATURE:
<223> OTHER INFORMATION: Tim4-DAP12-DAP12 CER10 chimeric engulfment
      receptor
<220> FEATURE:
<221> NAME/KEY: SIGNAL
<222> LOCATION: (1)...(22)
<223> OTHER INFORMATION: Tim4 signal peptide

<400> SEQUENCE: 86

Met Ser Lys Gly Leu Leu Leu Leu Trp Leu Val Thr Glu Leu Trp Trp
        -20                 -15                 -10

Leu Tyr Leu Thr Pro Ala Ala Ser Glu Asp Thr Ile Ile Gly Phe Leu
        -5                   1               5                  10

Gly Gln Pro Val Thr Leu Pro Cys His Tyr Leu Ser Trp Ser Gln Ser
                15                  20                  25
```

```
Arg Asn Ser Met Cys Trp Gly Lys Gly Ser Cys Pro Asn Ser Lys Cys
             30                  35                  40

Asn Ala Glu Leu Leu Arg Thr Asp Gly Thr Arg Ile Ile Ser Arg Lys
             45                  50                  55

Ser Thr Lys Tyr Thr Leu Leu Gly Lys Val Gln Phe Gly Glu Val Ser
 60                  65                  70

Leu Thr Ile Ser Asn Thr Asn Arg Gly Asp Ser Gly Val Tyr Cys Cys
 75                  80                  85                  90

Arg Ile Glu Val Pro Gly Trp Phe Asn Asp Val Lys Lys Asn Val Arg
                 95                 100                 105

Leu Glu Leu Arg Arg Ala Thr Thr Thr Lys Lys Pro Thr Thr Thr Thr
            110                 115                 120

Arg Pro Thr Thr Thr Pro Tyr Val Thr Thr Thr Pro Glu Leu Leu
            125                 130                 135

Pro Thr Thr Val Met Thr Thr Ser Val Leu Pro Thr Thr Pro Pro
140                 145                 150

Gln Thr Leu Ala Thr Thr Ala Phe Ser Thr Ala Val Thr Thr Cys Pro
155                 160                 165                 170

Ser Thr Thr Pro Gly Ser Phe Ser Gln Glu Thr Thr Lys Gly Ser Ala
                175                 180                 185

Phe Thr Thr Glu Ser Glu Thr Leu Pro Ala Ser Asn His Ser Gln Arg
            190                 195                 200

Ser Met Met Thr Ile Ser Thr Asp Ile Ala Val Leu Arg Pro Thr Gly
            205                 210                 215

Ser Asn Pro Gly Ile Leu Pro Ser Thr Ser Gln Leu Thr Thr Gln Lys
220                 225                 230

Thr Thr Leu Thr Thr Ser Glu Ser Leu Gln Lys Thr Thr Lys Ser His
235                 240                 245                 250

Gln Ile Asn Ser Arg Gln Thr Gly Val Leu Ala Gly Ile Val Met Gly
                255                 260                 265

Asp Leu Val Leu Thr Val Leu Ile Ala Leu Ala Val Tyr Phe Leu Gly
                270                 275                 280

Arg Leu Val Pro Arg Gly Arg Gly Ala Ala Glu Ala Ala Thr Arg Lys
                285                 290                 295

Gln Arg Ile Thr Glu Thr Glu Ser Pro Tyr Gln Glu Leu Gln Gly Gln
300                 305                 310

Arg Ser Asp Val Tyr Ser Asp Leu Asn Thr Gln Arg Pro Tyr Tyr Lys
315                 320                 325                 330

<210> SEQ ID NO 87
<211> LENGTH: 722
<212> TYPE: PRT
<213> ORGANISM: Artificial Sequence
<220> FEATURE:
<223> OTHER INFORMATION: Tim4-Tim4-Axl CER11 chimeric engulfment
      receptor
<220> FEATURE:
<221> NAME/KEY: SIGNAL
<222> LOCATION: (1)...(22)
<223> OTHER INFORMATION: Tim4 signal peptide

<400> SEQUENCE: 87

Met Ser Lys Gly Leu Leu Leu Trp Leu Val Thr Glu Leu Trp Trp
            -20                 -15                 -10

Leu Tyr Leu Thr Pro Ala Ala Ser Glu Asp Thr Ile Ile Gly Phe Leu
         -5                   1                   5                  10
```

Gly Gln Pro Val Thr Leu Pro Cys His Tyr Leu Ser Trp Ser Gln Ser
            15                  20                  25

Arg Asn Ser Met Cys Trp Gly Lys Gly Ser Cys Pro Asn Ser Lys Cys
            30                  35                  40

Asn Ala Glu Leu Leu Arg Thr Asp Gly Thr Arg Ile Ile Ser Arg Lys
            45                  50                  55

Ser Thr Lys Tyr Thr Leu Leu Gly Lys Val Gln Phe Gly Glu Val Ser
60                  65                  70

Leu Thr Ile Ser Asn Thr Asn Arg Gly Asp Ser Gly Val Tyr Cys Cys
75                  80                  85                  90

Arg Ile Glu Val Pro Gly Trp Phe Asn Asp Val Lys Lys Asn Val Arg
            95                  100                 105

Leu Glu Leu Arg Arg Ala Thr Thr Lys Lys Pro Thr Thr Thr Thr
            110                 115                 120

Arg Pro Thr Thr Thr Pro Tyr Val Thr Thr Thr Pro Glu Leu Leu
            125                 130                 135

Pro Thr Thr Val Met Thr Thr Ser Val Leu Pro Thr Thr Thr Pro Pro
            140                 145                 150

Gln Thr Leu Ala Thr Ala Phe Ser Thr Ala Val Thr Thr Cys Pro
155                 160                 165                 170

Ser Thr Thr Pro Gly Ser Phe Ser Gln Glu Thr Thr Lys Gly Ser Ala
            175                 180                 185

Phe Thr Thr Glu Ser Glu Thr Leu Pro Ala Ser Asn His Ser Gln Arg
            190                 195                 200

Ser Met Met Thr Ile Ser Thr Asp Ile Ala Val Leu Arg Pro Thr Gly
            205                 210                 215

Ser Asn Pro Gly Ile Leu Pro Ser Thr Ser Gln Leu Thr Thr Gln Lys
            220                 225                 230

Thr Thr Leu Thr Thr Ser Glu Ser Leu Gln Lys Thr Thr Lys Ser His
235                 240                 245                 250

Gln Ile Asn Ser Arg Gln Thr Ile Leu Ile Ile Ala Cys Cys Val Gly
            255                 260                 265

Phe Val Leu Met Val Leu Leu Phe Leu Ala Phe Leu His Arg Arg Lys
            270                 275                 280

Lys Glu Thr Arg Tyr Gly Glu Val Phe Glu Pro Thr Val Glu Arg Gly
            285                 290                 295

Glu Leu Val Val Arg Tyr Arg Val Arg Lys Ser Tyr Ser Arg Arg Thr
            300                 305                 310

Thr Glu Ala Thr Leu Asn Ser Leu Gly Ile Ser Glu Glu Leu Lys Glu
315                 320                 325                 330

Lys Leu Arg Asp Val Met Val Asp Arg His Lys Val Ala Leu Gly Lys
            335                 340                 345

Thr Leu Gly Glu Gly Glu Phe Gly Ala Val Met Glu Gly Gln Leu Asn
            350                 355                 360

Gln Asp Asp Ser Ile Leu Lys Val Ala Val Lys Thr Met Lys Ile Ala
            365                 370                 375

Ile Cys Thr Arg Ser Glu Leu Glu Asp Phe Leu Ser Glu Ala Val Cys
            380                 385                 390

Met Lys Glu Phe Asp His Pro Asn Val Met Arg Leu Ile Gly Val Cys
395                 400                 405                 410

Phe Gln Gly Ser Glu Arg Glu Ser Phe Pro Ala Pro Val Val Ile Leu
            415                 420                 425

Pro Phe Met Lys His Gly Asp Leu His Ser Phe Leu Leu Tyr Ser Arg

```
            430                 435                 440
Leu Gly Asp Gln Pro Val Tyr Leu Pro Thr Gln Met Leu Val Lys Phe
                445                 450                 455
Met Ala Asp Ile Ala Ser Gly Met Glu Tyr Leu Ser Thr Lys Arg Phe
        460                 465                 470
Ile His Arg Asp Leu Ala Ala Arg Asn Cys Met Leu Asn Glu Asn Met
475                 480                 485                 490
Ser Val Cys Val Ala Asp Phe Gly Leu Ser Lys Lys Ile Tyr Asn Gly
                495                 500                 505
Asp Tyr Tyr Arg Gln Gly Arg Ile Ala Lys Met Pro Val Lys Trp Ile
            510                 515                 520
Ala Ile Glu Ser Leu Ala Asp Arg Val Tyr Thr Ser Lys Ser Asp Val
        525                 530                 535
Trp Ser Phe Gly Val Thr Met Trp Glu Ile Ala Thr Arg Gly Gln Thr
    540                 545                 550
Pro Tyr Pro Gly Val Glu Asn Ser Glu Ile Tyr Asp Tyr Leu Arg Gln
555                 560                 565                 570
Gly Asn Arg Leu Lys Gln Pro Ala Asp Cys Leu Asp Gly Leu Tyr Ala
                575                 580                 585
Leu Met Ser Arg Cys Trp Glu Leu Asn Pro Gln Asp Arg Pro Ser Phe
            590                 595                 600
Thr Glu Leu Arg Glu Asp Leu Glu Asn Thr Leu Lys Ala Leu Pro Pro
        605                 610                 615
Ala Gln Glu Pro Asp Glu Ile Leu Tyr Val Asn Met Asp Glu Gly Gly
    620                 625                 630
Gly Tyr Pro Glu Pro Pro Gly Ala Ala Gly Gly Ala Asp Pro Pro Thr
635                 640                 645                 650
Gln Pro Asp Pro Lys Asp Ser Cys Ser Cys Leu Thr Ala Ala Glu Val
                655                 660                 665
His Pro Ala Gly Arg Tyr Val Leu Cys Pro Ser Thr Thr Pro Ser Pro
            670                 675                 680
Ala Gln Pro Ala Asp Arg Gly Ser Pro Ala Ala Pro Gly Gln Glu Asp
        685                 690                 695
Gly Ala
    700

<210> SEQ ID NO 88
<211> LENGTH: 42
<212> TYPE: PRT
<213> ORGANISM: Homo sapiens
<220> FEATURE:
<223> OTHER INFORMATION: FcepsilonRIgamma signaling domain

<400> SEQUENCE: 88

Arg Leu Lys Ile Gln Val Arg Lys Ala Ala Ile Thr Ser Tyr Glu Lys
1               5                   10                  15
Ser Asp Gly Val Tyr Thr Gly Leu Ser Thr Arg Asn Gln Glu Thr Tyr
            20                  25                  30
Glu Thr Leu Lys His Glu Lys Pro Pro Gln
        35                  40

<210> SEQ ID NO 89
<211> LENGTH: 21
<212> TYPE: PRT
<213> ORGANISM: Homo sapiens
<220> FEATURE:
<223> OTHER INFORMATION: FcepsilonRIgamma transmembrane domain
```

<400> SEQUENCE: 89

Leu Cys Tyr Ile Leu Asp Ala Ile Leu Phe Leu Tyr Gly Ile Val Leu
1               5                   10                  15

Thr Leu Leu Tyr Cys
            20

<210> SEQ ID NO 90
<211> LENGTH: 342
<212> TYPE: PRT
<213> ORGANISM: Artificial Sequence
<220> FEATURE:
<223> OTHER INFORMATION: Tim4-Tim4- FcepsilonRIgamma CER12 chimeric
      engulfment receptor
<220> FEATURE:
<221> NAME/KEY: SIGNAL
<222> LOCATION: (1)...(22)

<400> SEQUENCE: 90

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
        50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
        275                 280                 285

Phe Val Leu Met Val Leu Leu Phe Leu Ala Phe Leu Arg Leu Lys Ile
        290                 295                 300

```
Gln Val Arg Lys Ala Ala Ile Thr Ser Tyr Glu Lys Ser Asp Gly Val
305                 310                 315                 320

Tyr Thr Gly Leu Ser Thr Arg Asn Gln Glu Thr Tyr Glu Thr Leu Lys
                325                 330                 335

His Glu Lys Pro Pro Gln
            340

<210> SEQ ID NO 91
<211> LENGTH: 342
<212> TYPE: PRT
<213> ORGANISM: Artificial Sequence
<220> FEATURE:
<223> OTHER INFORMATION: Tim4- Fc(epsilon)RI(gamma)-Fc(epsilon)RI(gamma)
      CER13 chimeric engulfment receptor
<220> FEATURE:
<221> NAME/KEY: SIGNAL
<222> LOCATION: (1)...(22)

<400> SEQUENCE: 91

Met Ser Lys Gly Leu Leu Leu Trp Leu Val Thr Glu Leu Trp Trp
        -20                 -15                 -10

Leu Tyr Leu Thr Pro Ala Ala Ser Glu Asp Thr Ile Ile Gly Phe Leu
        -5                  1                   5                   10

Gly Gln Pro Val Thr Leu Pro Cys His Tyr Leu Ser Trp Ser Gln Ser
                15                  20                  25

Arg Asn Ser Met Cys Trp Gly Lys Gly Ser Cys Pro Asn Ser Lys Cys
                30                  35                  40

Asn Ala Glu Leu Leu Arg Thr Asp Gly Thr Arg Ile Ile Ser Arg Lys
                45                  50                  55

Ser Thr Lys Tyr Thr Leu Leu Gly Lys Val Gln Phe Gly Glu Val Ser
        60                  65                  70

Leu Thr Ile Ser Asn Thr Asn Arg Gly Asp Ser Gly Val Tyr Cys Cys
75                  80                  85                  90

Arg Ile Glu Val Pro Gly Trp Phe Asn Asp Val Lys Lys Asn Val Arg
                95                  100                 105

Leu Glu Leu Arg Arg Ala Thr Thr Thr Lys Lys Pro Thr Thr Thr Thr
                110                 115                 120

Arg Pro Thr Thr Thr Pro Tyr Val Thr Thr Thr Thr Pro Glu Leu Leu
                125                 130                 135

Pro Thr Thr Val Met Thr Thr Ser Val Leu Pro Thr Thr Thr Pro Pro
                140                 145                 150

Gln Thr Leu Ala Thr Thr Ala Phe Ser Thr Ala Val Thr Thr Cys Pro
155                 160                 165                 170

Ser Thr Thr Pro Gly Ser Phe Ser Gln Glu Thr Thr Lys Gly Ser Ala
                175                 180                 185

Phe Thr Thr Glu Ser Glu Thr Leu Pro Ala Ser Asn His Ser Gln Arg
                190                 195                 200

Ser Met Met Thr Ile Ser Thr Asp Ile Ala Val Leu Arg Pro Thr Gly
                205                 210                 215

Ser Asn Pro Gly Ile Leu Pro Ser Thr Ser Gln Leu Thr Thr Gln Lys
                220                 225                 230

Thr Thr Leu Thr Thr Ser Glu Ser Leu Gln Lys Thr Thr Lys Ser His
235                 240                 245                 250

Gln Ile Asn Ser Arg Gln Thr Leu Cys Tyr Ile Leu Asp Ala Ile Leu
                255                 260                 265

Phe Leu Tyr Gly Ile Val Leu Thr Leu Leu Tyr Cys Arg Leu Lys Ile
```

```
                    270                 275                 280
Gln Val Arg Lys Ala Ala Ile Thr Ser Tyr Glu Lys Ser Asp Gly Val
            285                 290                 295

Tyr Thr Gly Leu Ser Thr Arg Asn Gln Glu Thr Tyr Glu Thr Leu Lys
300                 305                 310

His Glu Lys Pro Pro Gln
315                 320

<210> SEQ ID NO 92
<211> LENGTH: 86
<212> TYPE: PRT
<213> ORGANISM: Homo sapiens
<220> FEATURE:
<223> OTHER INFORMATION: NFAM1 signaling domain

<400> SEQUENCE: 92

Leu Trp Asn Lys Lys Arg Met Arg Gly Pro Gly Lys Asp Pro Thr Arg
1               5                   10                  15

Lys Cys Pro Asp Pro Arg Ser Ala Ser Ser Pro Lys Gln His Pro Ser
            20                  25                  30

Glu Ser Val Tyr Thr Ala Leu Gln Arg Arg Glu Thr Glu Val Tyr Ala
        35                  40                  45

Cys Ile Glu Asn Glu Asp Gly Ser Ser Pro Thr Ala Lys Gln Ser Pro
    50                  55                  60

Leu Ser Gln Glu Arg Pro His Arg Phe Glu Asp Gly Glu Leu Asn
65                  70                  75                  80

Leu Val Tyr Glu Asn Leu
                85

<210> SEQ ID NO 93
<211> LENGTH: 386
<212> TYPE: PRT
<213> ORGANISM: Artificial Sequence
<220> FEATURE:
<223> OTHER INFORMATION: Tim4-Tim4-NFAM1 CER25 chimeric engulfment
      receptor
<220> FEATURE:
<221> NAME/KEY: SIGNAL
<222> LOCATION: (1)...(22)

<400> SEQUENCE: 93

Met Ser Lys Gly Leu Leu Leu Leu Trp Leu Val Thr Glu Leu Trp Trp
        -20                 -15                 -10

Leu Tyr Leu Thr Pro Ala Ala Ser Glu Asp Thr Ile Ile Gly Phe Leu
    -5                   1                   5                  10

Gly Gln Pro Val Thr Leu Pro Cys His Tyr Leu Ser Trp Ser Gln Ser
                15                  20                  25

Arg Asn Ser Met Cys Trp Gly Lys Gly Ser Cys Pro Asn Ser Lys Cys
            30                  35                  40

Asn Ala Glu Leu Leu Arg Thr Asp Gly Thr Arg Ile Ile Ser Arg Lys
        45                  50                  55

Ser Thr Lys Tyr Thr Leu Leu Gly Lys Val Gln Phe Gly Glu Val Ser
    60                  65                  70

Leu Thr Ile Ser Asn Thr Asn Arg Gly Asp Ser Gly Val Tyr Cys Cys
75                  80                  85                  90

Arg Ile Glu Val Pro Gly Trp Phe Asn Asp Val Lys Lys Asn Val Arg
                95                  100                 105

Leu Glu Leu Arg Arg Ala Thr Thr Thr Lys Lys Pro Thr Thr Thr
            110                 115                 120
```

Arg Pro Thr Thr Thr Pro Tyr Val Thr Thr Thr Thr Pro Glu Leu Leu
            125                 130                 135

Pro Thr Thr Val Met Thr Thr Ser Val Leu Pro Thr Thr Thr Pro Pro
        140                 145                 150

Gln Thr Leu Ala Thr Thr Ala Phe Ser Thr Ala Val Thr Thr Cys Pro
155                 160                 165                 170

Ser Thr Thr Pro Gly Ser Phe Ser Gln Glu Thr Thr Lys Gly Ser Ala
                175                 180                 185

Phe Thr Thr Glu Ser Glu Thr Leu Pro Ala Ser Asn His Ser Gln Arg
            190                 195                 200

Ser Met Met Thr Ile Ser Thr Asp Ile Ala Val Leu Arg Pro Thr Gly
        205                 210                 215

Ser Asn Pro Gly Ile Leu Pro Ser Thr Ser Gln Leu Thr Thr Gln Lys
220                 225                 230

Thr Thr Leu Thr Thr Ser Glu Ser Leu Gln Lys Thr Thr Lys Ser His
235                 240                 245                 250

Gln Ile Asn Ser Arg Gln Thr Ile Leu Ile Ile Ala Cys Cys Val Gly
                255                 260                 265

Phe Val Leu Met Val Leu Leu Phe Leu Ala Phe Leu Leu Trp Asn Lys
            270                 275                 280

Lys Arg Met Arg Gly Pro Gly Lys Asp Pro Thr Arg Lys Cys Pro Asp
        285                 290                 295

Pro Arg Ser Ala Ser Ser Pro Lys Gln His Pro Ser Glu Ser Val Tyr
300                 305                 310

Thr Ala Leu Gln Arg Arg Glu Thr Glu Val Tyr Ala Cys Ile Glu Asn
315                 320                 325                 330

Glu Asp Gly Ser Ser Pro Thr Ala Lys Gln Ser Pro Leu Ser Gln Glu
                335                 340                 345

Arg Pro His Arg Phe Glu Asp Asp Gly Glu Leu Asn Leu Val Tyr Glu
            350                 355                 360

Asn Leu

<210> SEQ ID NO 94
<211> LENGTH: 85
<212> TYPE: PRT
<213> ORGANISM: Homo sapiens
<220> FEATURE:
<223> OTHER INFORMATION: BaFFR signaling domain

<400> SEQUENCE: 94

Ser Trp Arg Arg Arg Gln Arg Arg Leu Arg Gly Ala Ser Ser Ala Glu
1               5                   10                  15

Ala Pro Asp Gly Asp Lys Asp Ala Pro Glu Pro Leu Asp Lys Val Ile
            20                  25                  30

Ile Leu Ser Pro Gly Ile Ser Asp Ala Thr Ala Pro Ala Trp Pro Pro
        35                  40                  45

Pro Gly Glu Asp Pro Gly Thr Thr Pro Pro Gly His Ser Val Pro Val
    50                  55                  60

Pro Ala Thr Glu Leu Gly Ser Thr Glu Leu Val Thr Thr Lys Thr Ala
65                  70                  75                  80

Gly Pro Glu Gln Gln
                85

<210> SEQ ID NO 95
<211> LENGTH: 540

<212> TYPE: PRT
<213> ORGANISM: Artificial Sequence
<220> FEATURE:
<223> OTHER INFORMATION: Tim4-tMyD88-BaFFR CER85 chimeric engulfment
      receptor
<220> FEATURE:
<221> NAME/KEY: SIGNAL
<222> LOCATION: (1)...(22)

<400> SEQUENCE: 95

```
Met Ser Lys Gly Leu Leu Leu Trp Leu Val Thr Glu Leu Trp Trp
        -20              -15                 -10

Leu Tyr Leu Thr Pro Ala Ala Ser Glu Asp Thr Ile Ile Gly Phe Leu
        -5                   1               5                   10

Gly Gln Pro Val Thr Leu Pro Cys His Tyr Leu Ser Trp Ser Gln Ser
                15                  20                  25

Arg Asn Ser Met Cys Trp Gly Lys Gly Ser Cys Pro Asn Ser Lys Cys
                30                  35                  40

Asn Ala Glu Leu Leu Arg Thr Asp Gly Thr Arg Ile Ile Ser Arg Lys
                45                  50                  55

Ser Thr Lys Tyr Thr Leu Leu Gly Lys Val Gln Phe Gly Glu Val Ser
        60                  65                  70

Leu Thr Ile Ser Asn Thr Asn Arg Gly Asp Ser Gly Val Tyr Cys Cys
75                  80                  85                  90

Arg Ile Glu Val Pro Gly Trp Phe Asn Asp Val Lys Lys Asn Val Arg
                    95                  100                 105

Leu Glu Leu Arg Arg Ala Thr Thr Thr Lys Lys Pro Thr Thr Thr Thr
                110                 115                 120

Arg Pro Thr Thr Thr Pro Tyr Val Thr Thr Thr Thr Pro Glu Leu Leu
        125                 130                 135

Pro Thr Thr Val Met Thr Thr Ser Val Leu Pro Thr Thr Thr Pro Pro
        140                 145                 150

Gln Thr Leu Ala Thr Thr Ala Phe Ser Thr Ala Val Thr Thr Cys Pro
155                 160                 165                 170

Ser Thr Thr Pro Gly Ser Phe Ser Gln Glu Thr Thr Lys Gly Ser Ala
                    175                 180                 185

Phe Thr Thr Glu Ser Glu Thr Leu Pro Ala Ser Asn His Ser Gln Arg
                190                 195                 200

Ser Met Met Thr Ile Ser Thr Asp Ile Ala Val Leu Arg Pro Thr Gly
                205                 210                 215

Ser Asn Pro Gly Ile Leu Pro Ser Thr Ser Gln Leu Thr Thr Gln Lys
        220                 225                 230

Thr Thr Leu Thr Thr Ser Glu Ser Leu Gln Lys Thr Thr Lys Ser His
235                 240                 245                 250

Gln Ile Asn Ser Arg Gln Thr Ile Leu Ile Ala Cys Cys Val Gly
                    255                 260                 265

Phe Val Leu Met Val Leu Leu Phe Leu Ala Phe Leu Met Ala Ala Gly
                270                 275                 280

Gly Pro Gly Ala Gly Ser Ala Ala Pro Val Ser Ser Thr Ser Ser Leu
            285                 290                 295

Pro Leu Ala Ala Leu Asn Met Arg Val Arg Arg Leu Ser Leu Phe
        300                 305                 310

Leu Asn Val Arg Thr Gln Val Ala Ala Asp Trp Thr Ala Leu Ala Glu
315                 320                 325                 330

Glu Met Asp Phe Glu Tyr Leu Glu Ile Arg Gln Leu Glu Thr Gln Ala
                335                 340                 345
```

```
Asp Pro Thr Gly Arg Leu Leu Asp Ala Trp Gln Gly Arg Pro Gly Ala
            350                 355                 360

Ser Val Gly Arg Leu Leu Glu Leu Thr Lys Leu Gly Arg Asp Asp
        365                 370                 375

Val Leu Leu Glu Leu Gly Pro Ser Ile Glu Asp Cys Gln Lys Tyr
380                 385                 390

Ile Leu Lys Gln Gln Gln Glu Ala Glu Lys Pro Leu Gln Val Ala
395                 400                 405                 410

Ala Val Asp Ser Ser Val Pro Arg Thr Ala Glu Leu Ala Gly Ile Thr
                415                 420                 425

Thr Leu Asp Pro Leu Gly Ser Trp Arg Arg Arg Gln Arg Arg Leu
            430                 435                 440

Arg Gly Ala Ser Ser Ala Glu Ala Pro Asp Gly Asp Lys Asp Ala Pro
            445                 450                 455

Glu Pro Leu Asp Lys Val Ile Ile Leu Ser Pro Gly Ile Ser Asp Ala
            460                 465                 470

Thr Ala Pro Ala Trp Pro Pro Gly Glu Asp Pro Gly Thr Thr Pro
475                 480                 485                 490

Pro Gly His Ser Val Pro Val Pro Ala Thr Glu Leu Gly Ser Thr Glu
                495                 500                 505

Leu Val Thr Thr Lys Thr Ala Gly Pro Glu Gln Gln
            510                 515

<210> SEQ ID NO 96
<211> LENGTH: 507
<212> TYPE: PRT
<213> ORGANISM: Artificial Sequence
<220> FEATURE:
<223> OTHER INFORMATION: Tim4-tMyD88-Dap12 CER86 chimeric engulfment
      receptor
<220> FEATURE:
<221> NAME/KEY: SIGNAL
<222> LOCATION: (1)...(22)

<400> SEQUENCE: 96

Met Ser Lys Gly Leu Leu Leu Trp Leu Val Thr Glu Leu Trp Trp
        -20                 -15                 -10

Leu Tyr Leu Thr Pro Ala Ala Ser Glu Asp Thr Ile Ile Gly Phe Leu
        -5                  1                   5                   10

Gly Gln Pro Val Thr Leu Pro Cys His Tyr Leu Ser Trp Ser Gln Ser
                15                  20                  25

Arg Asn Ser Met Cys Trp Gly Lys Gly Ser Cys Pro Asn Ser Lys Cys
            30                  35                  40

Asn Ala Glu Leu Leu Arg Thr Asp Gly Thr Arg Ile Ile Ser Arg Lys
            45                  50                  55

Ser Thr Lys Tyr Thr Leu Leu Gly Lys Val Gln Phe Gly Glu Val Ser
        60                  65                  70

Leu Thr Ile Ser Asn Thr Asn Arg Gly Asp Ser Gly Val Tyr Cys Cys
75                  80                  85                  90

Arg Ile Glu Val Pro Gly Trp Phe Asn Asp Val Lys Lys Asn Val Arg
                95                  100                 105

Leu Glu Leu Arg Arg Ala Thr Thr Thr Lys Lys Pro Thr Thr Thr
            110                 115                 120

Arg Pro Thr Thr Thr Pro Tyr Val Thr Thr Thr Pro Glu Leu Leu
        125                 130                 135

Pro Thr Thr Val Met Thr Thr Ser Val Leu Pro Thr Thr Thr Pro Pro
```

```
                140             145                 150
Gln Thr Leu Ala Thr Thr Ala Phe Ser Thr Ala Val Thr Thr Cys Pro
155                 160                 165                 170

Ser Thr Thr Pro Gly Ser Phe Ser Gln Glu Thr Thr Lys Gly Ser Ala
                175                 180                 185

Phe Thr Thr Glu Ser Glu Thr Leu Pro Ala Ser Asn His Ser Gln Arg
                190                 195                 200

Ser Met Met Thr Ile Ser Thr Asp Ile Ala Val Leu Arg Pro Thr Gly
                205                 210                 215

Ser Asn Pro Gly Ile Leu Pro Ser Thr Ser Gln Leu Thr Thr Gln Lys
                220                 225                 230

Thr Thr Leu Thr Thr Ser Glu Ser Leu Gln Lys Thr Thr Lys Ser His
235                 240                 245                 250

Gln Ile Asn Ser Arg Gln Thr Ile Leu Ile Ala Cys Cys Val Gly
                255                 260                 265

Phe Val Leu Met Val Leu Leu Phe Leu Ala Phe Leu Met Ala Ala Gly
                270                 275                 280

Gly Pro Gly Ala Gly Ser Ala Ala Pro Val Ser Ser Thr Ser Ser Leu
                285                 290                 295

Pro Leu Ala Ala Leu Asn Met Arg Val Arg Arg Leu Ser Leu Phe
300                 305                 310

Leu Asn Val Arg Thr Gln Val Ala Ala Asp Trp Thr Ala Leu Ala Glu
315                 320                 325                 330

Glu Met Asp Phe Glu Tyr Leu Glu Ile Arg Gln Leu Glu Thr Gln Ala
                335                 340                 345

Asp Pro Thr Gly Arg Leu Leu Asp Ala Trp Gln Gly Arg Pro Gly Ala
                350                 355                 360

Ser Val Gly Arg Leu Leu Glu Leu Leu Thr Lys Leu Gly Arg Asp Asp
                365                 370                 375

Val Leu Leu Glu Leu Gly Pro Ser Ile Glu Glu Asp Cys Gln Lys Tyr
380                 385                 390

Ile Leu Lys Gln Gln Gln Glu Glu Ala Glu Lys Pro Leu Gln Val Ala
395                 400                 405                 410

Ala Val Asp Ser Ser Val Pro Arg Thr Ala Glu Leu Ala Gly Ile Thr
                415                 420                 425

Thr Leu Asp Asp Pro Leu Gly Tyr Phe Leu Gly Arg Leu Val Pro Arg
                430                 435                 440

Gly Arg Gly Ala Ala Glu Ala Ala Thr Arg Lys Gln Arg Ile Thr Glu
                445                 450                 455

Thr Glu Ser Pro Tyr Gln Glu Leu Gln Gly Gln Arg Ser Asp Val Tyr
460                 465                 470

Ser Asp Leu Asn Thr Gln Arg Pro Tyr Tyr Lys
475                 480                 485

<210> SEQ ID NO 97
<211> LENGTH: 29
<212> TYPE: PRT
<213> ORGANISM: Homo sapiens
<220> FEATURE:
<223> OTHER INFORMATION: CD79b signaling domain

<400> SEQUENCE: 97

Asp Ser Lys Ala Gly Met Glu Glu Asp His Thr Tyr Glu Gly Leu Asp
1               5                   10                  15

Ile Asp Gln Thr Ala Thr Tyr Glu Asp Ile Val Thr Leu
```

```
                 20                  25

<210> SEQ ID NO 98
<211> LENGTH: 484
<212> TYPE: PRT
<213> ORGANISM: Artificial Sequence
<220> FEATURE:
<223> OTHER INFORMATION: Tim4-tMyD88-CD79b CER89 chimeric engulfment
      receptor
<220> FEATURE:
<221> NAME/KEY: SIGNAL
<222> LOCATION: (1)...(22)

<400> SEQUENCE: 98

Met Ser Lys Gly Leu Leu Leu Trp Leu Val Thr Glu Leu Trp Trp
        -20                 -15                 -10

Leu Tyr Leu Thr Pro Ala Ala Ser Glu Asp Thr Ile Ile Gly Phe Leu
    -5                   1               5                  10

Gly Gln Pro Val Thr Leu Pro Cys His Tyr Leu Ser Trp Ser Gln Ser
                 15                  20                  25

Arg Asn Ser Met Cys Trp Gly Lys Gly Ser Cys Pro Asn Ser Lys Cys
             30                  35                  40

Asn Ala Glu Leu Leu Arg Thr Asp Gly Thr Arg Ile Ile Ser Arg Lys
         45                  50                  55

Ser Thr Lys Tyr Thr Leu Leu Gly Lys Val Gln Phe Gly Glu Val Ser
 60                  65                  70

Leu Thr Ile Ser Asn Thr Asn Arg Gly Asp Ser Gly Val Tyr Cys Cys
 75                  80                  85                  90

Arg Ile Glu Val Pro Gly Trp Phe Asn Asp Val Lys Lys Asn Val Arg
                 95                 100                 105

Leu Glu Leu Arg Arg Ala Thr Thr Thr Lys Lys Pro Thr Thr Thr Thr
             110                 115                 120

Arg Pro Thr Thr Thr Pro Tyr Val Thr Thr Thr Thr Pro Glu Leu Leu
         125                 130                 135

Pro Thr Thr Val Met Thr Thr Ser Val Leu Pro Thr Thr Thr Pro Pro
 140                 145                 150

Gln Thr Leu Ala Thr Thr Ala Phe Ser Thr Ala Val Thr Thr Cys Pro
155                 160                 165                 170

Ser Thr Thr Pro Gly Ser Phe Ser Gln Glu Thr Thr Lys Gly Ser Ala
                 175                 180                 185

Phe Thr Thr Glu Ser Glu Thr Leu Pro Ala Ser Asn His Ser Gln Arg
             190                 195                 200

Ser Met Met Thr Ile Ser Thr Asp Ile Ala Val Leu Arg Pro Thr Gly
         205                 210                 215

Ser Asn Pro Gly Ile Leu Pro Ser Thr Ser Gln Leu Thr Thr Gln Lys
 220                 225                 230

Thr Thr Leu Thr Thr Ser Glu Ser Leu Gln Lys Thr Thr Lys Ser His
235                 240                 245                 250

Gln Ile Asn Ser Arg Gln Thr Ile Leu Ile Ile Ala Cys Cys Val Gly
                 255                 260                 265

Phe Val Leu Met Val Leu Leu Phe Leu Ala Phe Leu Met Ala Ala Gly
             270                 275                 280

Gly Pro Gly Ala Gly Ser Ala Ala Pro Val Ser Ser Thr Ser Ser Leu
         285                 290                 295

Pro Leu Ala Ala Leu Asn Met Arg Val Arg Arg Arg Leu Ser Leu Phe
 300                 305                 310
```

```
Leu Asn Val Arg Thr Gln Val Ala Ala Asp Trp Thr Ala Leu Ala Glu
315                 320                 325                 330

Glu Met Asp Phe Glu Tyr Leu Glu Ile Arg Gln Leu Glu Thr Gln Ala
                335                 340                 345

Asp Pro Thr Gly Arg Leu Leu Asp Ala Trp Gln Gly Arg Pro Gly Ala
            350                 355                 360

Ser Val Gly Arg Leu Leu Glu Leu Leu Thr Lys Leu Gly Arg Asp Asp
        365                 370                 375

Val Leu Leu Glu Leu Gly Pro Ser Ile Glu Glu Asp Cys Gln Lys Tyr
380                 385                 390

Ile Leu Lys Gln Gln Gln Glu Glu Ala Glu Lys Pro Leu Gln Val Ala
395                 400                 405                 410

Ala Val Asp Ser Ser Val Pro Arg Thr Ala Glu Leu Ala Gly Ile Thr
            415                 420                 425

Thr Leu Asp Asp Pro Leu Gly Asp Ser Lys Ala Gly Met Glu Glu Asp
            430                 435                 440

His Thr Tyr Glu Gly Leu Asp Ile Asp Gln Thr Ala Thr Tyr Glu Asp
            445                 450                 455

Ile Val Thr Leu
        460

<210> SEQ ID NO 99
<211> LENGTH: 465
<212> TYPE: DNA
<213> ORGANISM: Homo sapiens
<220> FEATURE:
<223> OTHER INFORMATION: truncated MyD88 signaling domain

<400> SEQUENCE: 99
atggctgcag gaggtcccgg cgcggggtct gcggccccgg tctcctccac atcctccctt    60
cccctggctg ctctcaacat gcgagtgcgg cgccgcctgt ctctgttctt gaacgtgcgg   120
acacaggtgg cggccgactg gaccgcgctg gcggaggaga tggactttga gtacttggag   180
atccggcaac tggagacaca gcggacccc actggcaggc tgctggacgc ctggcaggga   240
cgccctggcg cctctgtagg ccgactgctc gagctgctta ccaagctggg ccgcgacgac   300
gtgctgctgg agctgggacc cagcattgag gaggattgcc aaaagtatat cttgaagcag   360
cagcaggagg aggctgagaa gcctttacag gtggccgctg tagacagcag tgtcccacgg   420
acagcagagc tggcgggcat caccacactt gatgaccccc tgggg                   465

<210> SEQ ID NO 100
<211> LENGTH: 541
<212> TYPE: PRT
<213> ORGANISM: Artificial Sequence
<220> FEATURE:
<223> OTHER INFORMATION: Tim4-tMyD88-NFAM1 CER90 chimeric engulfment
      receptor
<220> FEATURE:
<221> NAME/KEY: SIGNAL
<222> LOCATION: (1)...(22)

<400> SEQUENCE: 100

Met Ser Lys Gly Leu Leu Leu Leu Trp Leu Val Thr Glu Leu Trp Trp
        -20                 -15                 -10

Leu Tyr Leu Thr Pro Ala Ala Ser Glu Asp Thr Ile Ile Gly Phe Leu
    -5                   1               5                  10

Gly Gln Pro Val Thr Leu Pro Cys His Tyr Leu Ser Trp Ser Gln Ser
                15                  20                  25
```

```
Arg Asn Ser Met Cys Trp Gly Lys Gly Ser Cys Pro Asn Ser Lys Cys
             30                  35                  40

Asn Ala Glu Leu Leu Arg Thr Asp Gly Thr Arg Ile Ile Ser Arg Lys
             45                  50                  55

Ser Thr Lys Tyr Thr Leu Leu Gly Lys Val Gln Phe Gly Glu Val Ser
             60                  65                  70

Leu Thr Ile Ser Asn Thr Asn Arg Gly Asp Ser Gly Val Tyr Cys Cys
 75                  80                  85                  90

Arg Ile Glu Val Pro Gly Trp Phe Asn Asp Val Lys Lys Asn Val Arg
                 95                 100                 105

Leu Glu Leu Arg Arg Ala Thr Thr Thr Lys Lys Pro Thr Thr Thr Thr
            110                 115                 120

Arg Pro Thr Thr Thr Pro Tyr Val Thr Thr Thr Thr Pro Glu Leu Leu
            125                 130                 135

Pro Thr Thr Val Met Thr Thr Ser Val Leu Pro Thr Thr Thr Pro Pro
            140                 145                 150

Gln Thr Leu Ala Thr Thr Ala Phe Ser Thr Ala Val Thr Thr Cys Pro
155                 160                 165                 170

Ser Thr Thr Pro Gly Ser Phe Ser Gln Glu Thr Thr Lys Gly Ser Ala
                175                 180                 185

Phe Thr Thr Glu Ser Glu Thr Leu Pro Ala Ser Asn His Ser Gln Arg
            190                 195                 200

Ser Met Met Thr Ile Ser Thr Asp Ile Ala Val Leu Arg Pro Thr Gly
            205                 210                 215

Ser Asn Pro Gly Ile Leu Pro Ser Thr Ser Gln Leu Thr Thr Gln Lys
            220                 225                 230

Thr Thr Leu Thr Thr Ser Glu Ser Leu Gln Lys Thr Thr Lys Ser His
235                 240                 245                 250

Gln Ile Asn Ser Arg Gln Thr Ile Leu Ile Ile Ala Cys Cys Val Gly
                255                 260                 265

Phe Val Leu Met Val Leu Leu Phe Leu Ala Phe Leu Met Ala Ala Gly
            270                 275                 280

Gly Pro Gly Ala Gly Ser Ala Ala Pro Val Ser Ser Thr Ser Ser Leu
            285                 290                 295

Pro Leu Ala Ala Leu Asn Met Arg Val Arg Arg Arg Leu Ser Leu Phe
300                 305                 310

Leu Asn Val Arg Thr Gln Val Ala Ala Asp Trp Thr Ala Leu Ala Glu
315                 320                 325                 330

Glu Met Asp Phe Glu Tyr Leu Glu Ile Arg Gln Leu Glu Thr Gln Ala
                335                 340                 345

Asp Pro Thr Gly Arg Leu Leu Asp Ala Trp Gln Gly Arg Pro Gly Ala
            350                 355                 360

Ser Val Gly Arg Leu Leu Glu Leu Leu Thr Lys Leu Gly Arg Asp Asp
            365                 370                 375

Val Leu Leu Glu Leu Gly Pro Ser Ile Glu Glu Asp Cys Gln Lys Tyr
            380                 385                 390

Ile Leu Lys Gln Gln Gln Glu Glu Ala Glu Lys Pro Leu Gln Val Ala
395                 400                 405                 410

Ala Val Asp Ser Ser Val Pro Arg Thr Ala Glu Leu Ala Gly Ile Thr
                415                 420                 425

Thr Leu Asp Asp Pro Leu Gly Leu Trp Asn Lys Lys Arg Met Arg Gly
            430                 435                 440

Pro Gly Lys Asp Pro Thr Arg Lys Cys Pro Asp Pro Arg Ser Ala Ser
```

```
                    445                 450                 455

Ser Pro Lys Gln His Pro Ser Glu Ser Val Tyr Thr Ala Leu Gln Arg
        460                 465                 470

Arg Glu Thr Glu Val Tyr Ala Cys Ile Glu Asn Glu Asp Gly Ser Ser
475                 480                 485                 490

Pro Thr Ala Lys Gln Ser Pro Leu Ser Gln Glu Arg Pro His Arg Phe
                495                 500                 505

Glu Asp Asp Gly Glu Leu Asn Leu Val Tyr Glu Asn Leu
                510                 515

<210> SEQ ID NO 101
<211> LENGTH: 805
<212> TYPE: PRT
<213> ORGANISM: Artificial Sequence
<220> FEATURE:
<223> OTHER INFORMATION: Tim4-MerTk-CD79b CER95 chimeric engulfment
      receptor
<220> FEATURE:
<221> NAME/KEY: SIGNAL
<222> LOCATION: (1)...(22)

<400> SEQUENCE: 101

Met Ser Lys Gly Leu Leu Leu Trp Leu Val Thr Glu Leu Trp Trp
        -20                 -15                 -10

Leu Tyr Leu Thr Pro Ala Ala Ser Glu Asp Thr Ile Ile Gly Phe Leu
        -5                   1                   5                  10

Gly Gln Pro Val Thr Leu Pro Cys His Tyr Leu Ser Trp Ser Gln Ser
                15                  20                  25

Arg Asn Ser Met Cys Trp Gly Lys Gly Ser Cys Pro Asn Ser Lys Cys
                30                  35                  40

Asn Ala Glu Leu Leu Arg Thr Asp Gly Thr Arg Ile Ile Ser Arg Lys
                45                  50                  55

Ser Thr Lys Tyr Thr Leu Leu Gly Lys Val Gln Phe Gly Glu Val Ser
        60                  65                  70

Leu Thr Ile Ser Asn Thr Asn Arg Gly Asp Ser Gly Val Tyr Cys Cys
75                  80                  85                  90

Arg Ile Glu Val Pro Gly Trp Phe Asn Asp Val Lys Lys Asn Val Arg
                95                  100                 105

Leu Glu Leu Arg Arg Ala Thr Thr Thr Lys Lys Pro Thr Thr Thr Thr
                110                 115                 120

Arg Pro Thr Thr Thr Pro Tyr Val Thr Thr Thr Thr Pro Glu Leu Leu
                125                 130                 135

Pro Thr Thr Val Met Thr Thr Ser Val Leu Pro Thr Thr Thr Pro Pro
        140                 145                 150

Gln Thr Leu Ala Thr Thr Ala Phe Ser Thr Ala Val Thr Thr Cys Pro
155                 160                 165                 170

Ser Thr Thr Pro Gly Ser Phe Ser Gln Glu Thr Thr Lys Gly Ser Ala
                175                 180                 185

Phe Thr Thr Glu Ser Glu Thr Leu Pro Ala Ser Asn His Ser Gln Arg
                190                 195                 200

Ser Met Met Thr Ile Ser Thr Asp Ile Ala Val Leu Arg Pro Thr Gly
                205                 210                 215

Ser Asn Pro Gly Ile Leu Pro Ser Thr Ser Gln Leu Thr Thr Gln Lys
                220                 225                 230

Thr Thr Leu Thr Thr Ser Glu Ser Leu Gln Lys Thr Thr Lys Ser His
235                 240                 245                 250
```

-continued

```
Gln Ile Asn Ser Arg Gln Thr Ile Leu Ile Ile Ala Cys Cys Val Gly
            255                 260                 265

Phe Val Leu Met Val Leu Leu Phe Leu Ala Phe Leu Ala Leu Arg Arg
            270                 275                 280

Arg Val Gln Glu Thr Lys Phe Gly Gly Ala Phe Ser Glu Glu Asp Ser
            285                 290                 295

Gln Leu Val Val Asn Tyr Arg Ala Lys Lys Ser Phe Cys Arg Arg Ala
            300                 305                 310

Ile Glu Leu Thr Leu Gln Ser Leu Gly Val Ser Glu Glu Leu Gln Asn
315                 320                 325                 330

Lys Leu Glu Asp Val Val Ile Asp Arg Asn Leu Leu Val Leu Gly Lys
                335                 340                 345

Val Leu Gly Glu Gly Glu Phe Gly Ser Val Met Glu Gly Asn Leu Lys
            350                 355                 360

Gln Glu Asp Gly Thr Ser Gln Lys Val Ala Val Lys Thr Met Lys Leu
            365                 370                 375

Asp Asn Phe Ser Gln Arg Glu Ile Glu Glu Phe Leu Ser Glu Ala Ala
            380                 385                 390

Cys Met Lys Asp Phe Asn His Pro Asn Val Ile Arg Leu Leu Gly Val
395                 400                 405                 410

Cys Ile Glu Leu Ser Ser Gln Gly Ile Pro Lys Pro Met Val Ile Leu
                415                 420                 425

Pro Phe Met Lys Tyr Gly Asp Leu His Thr Phe Leu Leu Tyr Ser Arg
            430                 435                 440

Leu Asn Thr Gly Pro Lys Tyr Ile His Leu Gln Thr Leu Leu Lys Phe
            445                 450                 455

Met Met Asp Ile Ala Gln Gly Met Glu Tyr Leu Ser Asn Arg Asn Phe
460                 465                 470

Leu His Arg Asp Leu Ala Arg Asn Cys Met Leu Arg Asp Asp Met
475                 480                 485                 490

Thr Val Cys Val Ala Asp Phe Gly Leu Ser Lys Lys Ile Tyr Ser Gly
                495                 500                 505

Asp Tyr Tyr Arg Gln Gly Arg Ile Ala Lys Met Pro Val Lys Trp Ile
            510                 515                 520

Ala Ile Glu Ser Leu Ala Asp Arg Val Tyr Thr Ser Lys Ser Asp Val
            525                 530                 535

Trp Ala Phe Gly Val Thr Met Trp Glu Ile Thr Thr Arg Gly Met Thr
            540                 545                 550

Pro Tyr Pro Gly Val Gln Asn His Glu Met Tyr Asp Tyr Leu Leu His
555                 560                 565                 570

Gly His Arg Leu Lys Gln Pro Glu Asp Cys Leu Asp Glu Leu Tyr Asp
                575                 580                 585

Ile Met Tyr Ser Cys Trp Ser Ala Asp Pro Leu Asp Arg Pro Thr Phe
            590                 595                 600

Ser Val Leu Arg Leu Gln Leu Glu Lys Leu Ser Glu Ser Leu Pro Asp
            605                 610                 615

Ala Gln Asp Lys Glu Ser Ile Ile Tyr Ile Asn Thr Gln Leu Leu Glu
            620                 625                 630

Ser Cys Glu Gly Ile Ala Asn Gly Pro Ser Leu Thr Gly Leu Asp Met
635                 640                 645                 650

Asn Ile Asp Pro Asp Ser Ile Ile Ala Ser Cys Thr Pro Gly Ala Ala
                655                 660                 665

Val Ser Val Val Thr Ala Glu Val His Glu Asn Asn Leu Arg Glu Glu
```

```
                            670                 675                 680
Arg Tyr Ile Leu Asn Gly Gly Asn Glu Glu Trp Glu Asp Val Ser Ser
            685                 690                 695

Thr Pro Phe Ala Ala Val Thr Pro Glu Lys Asp Gly Val Leu Pro Glu
        700                 705                 710

Asp Arg Leu Thr Lys Asn Gly Val Ser Trp Ser His His Ser Thr Leu
715                 720                 725                 730

Pro Leu Gly Ser Pro Ser Pro Asp Glu Leu Leu Phe Val Asp Asp Ser
                735                 740                 745

Leu Glu Asp Ser Glu Val Leu Met Asp Ser Lys Ala Gly Met Glu Glu
            750                 755                 760

Asp His Thr Tyr Glu Gly Leu Asp Ile Asp Gln Thr Ala Thr Tyr Glu
        765                 770                 775

Asp Ile Val Thr Leu
    780

<210> SEQ ID NO 102
<211> LENGTH: 862
<212> TYPE: PRT
<213> ORGANISM: Artificial Sequence
<220> FEATURE:
<223> OTHER INFORMATION: Tim4-MerTk-NFAM1 CER96 chimeric engulfment
      receptor
<220> FEATURE:
<221> NAME/KEY: SIGNAL
<222> LOCATION: (1)...(22)

<400> SEQUENCE: 102

Met Ser Lys Gly Leu Leu Leu Trp Leu Val Thr Glu Leu Trp Trp
         -20                 -15                 -10

Leu Tyr Leu Thr Pro Ala Ala Ser Glu Asp Thr Ile Ile Gly Phe Leu
     -5                   1                   5                  10

Gly Gln Pro Val Thr Leu Pro Cys His Tyr Leu Ser Trp Ser Gln Ser
                 15                  20                  25

Arg Asn Ser Met Cys Trp Gly Lys Gly Ser Cys Pro Asn Ser Lys Cys
             30                  35                  40

Asn Ala Glu Leu Leu Arg Thr Asp Gly Thr Arg Ile Ile Ser Arg Lys
         45                  50                  55

Ser Thr Lys Tyr Thr Leu Leu Gly Lys Val Gln Phe Gly Glu Val Ser
     60                  65                  70

Leu Thr Ile Ser Asn Thr Asn Arg Gly Asp Ser Gly Val Tyr Cys Cys
75                  80                  85                  90

Arg Ile Glu Val Pro Gly Trp Phe Asn Asp Val Lys Lys Asn Val Arg
                 95                 100                 105

Leu Glu Leu Arg Arg Ala Thr Thr Thr Lys Lys Pro Thr Thr Thr Thr
             110                 115                 120

Arg Pro Thr Thr Thr Pro Tyr Val Thr Thr Thr Pro Glu Leu Leu
         125                 130                 135

Pro Thr Thr Val Met Thr Thr Ser Val Leu Pro Thr Thr Pro Pro
     140                 145                 150

Gln Thr Leu Ala Thr Thr Ala Phe Ser Thr Ala Val Thr Thr Cys Pro
155                 160                 165                 170

Ser Thr Thr Pro Gly Ser Phe Ser Gln Glu Thr Thr Lys Gly Ser Ala
                 175                 180                 185

Phe Thr Thr Glu Ser Glu Thr Leu Pro Ala Ser Asn His Ser Gln Arg
             190                 195                 200
```

-continued

```
Ser Met Met Thr Ile Ser Thr Asp Ile Ala Val Leu Arg Pro Thr Gly
            205                 210                 215

Ser Asn Pro Gly Ile Leu Pro Ser Thr Ser Gln Leu Thr Thr Gln Lys
    220                 225                 230

Thr Thr Leu Thr Thr Ser Glu Ser Leu Gln Lys Thr Thr Lys Ser His
235                 240                 245                 250

Gln Ile Asn Ser Arg Gln Thr Ile Leu Ile Ala Cys Cys Val Gly
                255                 260                 265

Phe Val Leu Met Val Leu Leu Phe Leu Ala Phe Leu Ala Leu Arg Arg
            270                 275                 280

Arg Val Gln Glu Thr Lys Phe Gly Gly Ala Phe Ser Glu Glu Asp Ser
        285                 290                 295

Gln Leu Val Val Asn Tyr Arg Ala Lys Lys Ser Phe Cys Arg Arg Ala
    300                 305                 310

Ile Glu Leu Thr Leu Gln Ser Leu Gly Val Ser Glu Glu Leu Gln Asn
315                 320                 325                 330

Lys Leu Glu Asp Val Val Ile Asp Arg Asn Leu Leu Val Leu Gly Lys
                335                 340                 345

Val Leu Gly Glu Gly Glu Phe Gly Ser Val Met Glu Gly Asn Leu Lys
            350                 355                 360

Gln Glu Asp Gly Thr Ser Gln Lys Val Ala Val Lys Thr Met Lys Leu
        365                 370                 375

Asp Asn Phe Ser Gln Arg Glu Ile Glu Glu Phe Leu Ser Glu Ala Ala
    380                 385                 390

Cys Met Lys Asp Phe Asn His Pro Asn Val Ile Arg Leu Leu Gly Val
395                 400                 405                 410

Cys Ile Glu Leu Ser Ser Gln Gly Ile Pro Lys Pro Met Val Ile Leu
                415                 420                 425

Pro Phe Met Lys Tyr Gly Asp Leu His Thr Phe Leu Leu Tyr Ser Arg
            430                 435                 440

Leu Asn Thr Gly Pro Lys Tyr Ile His Leu Gln Thr Leu Leu Lys Phe
        445                 450                 455

Met Met Asp Ile Ala Gln Gly Met Glu Tyr Leu Ser Asn Arg Asn Phe
    460                 465                 470

Leu His Arg Asp Leu Ala Ala Arg Asn Cys Met Leu Arg Asp Asp Met
475                 480                 485                 490

Thr Val Cys Val Ala Asp Phe Gly Leu Ser Lys Lys Ile Tyr Ser Gly
                495                 500                 505

Asp Tyr Tyr Arg Gln Gly Arg Ile Ala Lys Met Pro Val Lys Trp Ile
            510                 515                 520

Ala Ile Glu Ser Leu Ala Asp Arg Val Tyr Thr Ser Lys Ser Asp Val
        525                 530                 535

Trp Ala Phe Gly Val Thr Met Trp Glu Ile Thr Thr Arg Gly Met Thr
    540                 545                 550

Pro Tyr Pro Gly Val Gln Asn His Glu Met Tyr Asp Tyr Leu Leu His
555                 560                 565                 570

Gly His Arg Leu Lys Gln Pro Glu Asp Cys Leu Asp Glu Leu Tyr Asp
                575                 580                 585

Ile Met Tyr Ser Cys Trp Ser Ala Asp Pro Leu Asp Arg Pro Thr Phe
            590                 595                 600

Ser Val Leu Arg Leu Gln Leu Glu Lys Leu Ser Glu Ser Leu Pro Asp
        605                 610                 615

Ala Gln Asp Lys Glu Ser Ile Ile Tyr Ile Asn Thr Gln Leu Leu Glu
```

-continued

```
                620                 625                 630
Ser Cys Glu Gly Ile Ala Asn Gly Pro Ser Leu Thr Gly Leu Asp Met
635                 640                 645                 650

Asn Ile Asp Pro Asp Ser Ile Ile Ala Ser Cys Thr Pro Gly Ala Ala
                655                 660                 665

Val Ser Val Val Thr Ala Glu Val His Glu Asn Asn Leu Arg Glu Glu
                670                 675                 680

Arg Tyr Ile Leu Asn Gly Gly Asn Glu Glu Trp Glu Asp Val Ser Ser
                685                 690                 695

Thr Pro Phe Ala Ala Val Thr Pro Glu Lys Asp Gly Val Leu Pro Glu
700                 705                 710

Asp Arg Leu Thr Lys Asn Gly Val Ser Trp Ser His His Ser Thr Leu
715                 720                 725                 730

Pro Leu Gly Ser Pro Ser Pro Asp Glu Leu Leu Phe Val Asp Asp Ser
                735                 740                 745

Leu Glu Asp Ser Glu Val Leu Met Leu Trp Asn Lys Lys Arg Met Arg
                750                 755                 760

Gly Pro Gly Lys Asp Pro Thr Arg Lys Cys Pro Asp Pro Arg Ser Ala
                765                 770                 775

Ser Ser Pro Lys Gln His Pro Ser Glu Ser Val Tyr Thr Ala Leu Gln
780                 785                 790

Arg Arg Glu Thr Glu Val Tyr Ala Cys Ile Glu Asn Glu Asp Gly Ser
795                 800                 805                 810

Ser Pro Thr Ala Lys Gln Ser Pro Leu Ser Gln Glu Arg Pro His Arg
                815                 820                 825

Phe Glu Asp Asp Gly Glu Leu Asn Leu Val Tyr Glu Asn Leu
                830                 835                 840

<210> SEQ ID NO 103
<211> LENGTH: 861
<212> TYPE: PRT
<213> ORGANISM: Artificial Sequence
<220> FEATURE:
<223> OTHER INFORMATION: Tim4-MERTK-BAFFR CER93 chimeric engulfment
      receptor
<220> FEATURE:
<221> NAME/KEY: SIGNAL
<222> LOCATION: (1)...(22)

<400> SEQUENCE: 103

Met Ser Lys Gly Leu Leu Leu Leu Trp Leu Val Thr Glu Leu Trp Trp
        -20                 -15                 -10

Leu Tyr Leu Thr Pro Ala Ala Ser Glu Asp Thr Ile Ile Gly Phe Leu
   -5                   1                   5                  10

Gly Gln Pro Val Thr Leu Pro Cys His Tyr Leu Ser Trp Ser Gln Ser
                 15                  20                  25

Arg Asn Ser Met Cys Trp Gly Lys Gly Ser Cys Pro Asn Ser Lys Cys
                 30                  35                  40

Asn Ala Glu Leu Leu Arg Thr Asp Gly Thr Arg Ile Ile Ser Arg Lys
             45                  50                  55

Ser Thr Lys Tyr Thr Leu Leu Gly Lys Val Gln Phe Gly Glu Val Ser
         60                  65                  70

Leu Thr Ile Ser Asn Thr Asn Arg Gly Asp Ser Gly Val Tyr Cys Cys
75                  80                  85                  90

Arg Ile Glu Val Pro Gly Trp Phe Asn Asp Val Lys Lys Asn Val Arg
                 95                 100                 105
```

-continued

```
Leu Glu Leu Arg Arg Ala Thr Thr Thr Lys Lys Pro Thr Thr Thr Thr
            110                 115                 120

Arg Pro Thr Thr Thr Pro Tyr Val Thr Thr Thr Pro Glu Leu Leu
    125                 130                 135

Pro Thr Thr Val Met Thr Thr Ser Val Leu Pro Thr Thr Thr Pro Pro
140                 145                 150

Gln Thr Leu Ala Thr Thr Ala Phe Ser Thr Ala Val Thr Thr Cys Pro
155                 160                 165                 170

Ser Thr Thr Pro Gly Ser Phe Ser Gln Glu Thr Thr Lys Gly Ser Ala
            175                 180                 185

Phe Thr Thr Glu Ser Glu Thr Leu Pro Ala Ser Asn His Ser Gln Arg
            190                 195                 200

Ser Met Met Thr Ile Ser Thr Asp Ile Ala Val Leu Arg Pro Thr Gly
            205                 210                 215

Ser Asn Pro Gly Ile Leu Pro Ser Thr Ser Gln Leu Thr Thr Gln Lys
220                 225                 230

Thr Thr Leu Thr Thr Ser Glu Ser Leu Gln Lys Thr Thr Lys Ser His
235                 240                 245                 250

Gln Ile Asn Ser Arg Gln Thr Ile Leu Ile Ile Ala Cys Cys Val Gly
            255                 260                 265

Phe Val Leu Met Val Leu Leu Phe Leu Ala Phe Leu Ala Leu Arg Arg
            270                 275                 280

Arg Val Gln Glu Thr Lys Phe Gly Gly Ala Phe Ser Glu Glu Asp Ser
            285                 290                 295

Gln Leu Val Val Asn Tyr Arg Ala Lys Lys Ser Phe Cys Arg Arg Ala
300                 305                 310

Ile Glu Leu Thr Leu Gln Ser Leu Gly Val Ser Glu Glu Leu Gln Asn
315                 320                 325                 330

Lys Leu Glu Asp Val Val Ile Asp Arg Asn Leu Leu Val Leu Gly Lys
            335                 340                 345

Val Leu Gly Glu Gly Glu Phe Gly Ser Val Met Glu Gly Asn Leu Lys
            350                 355                 360

Gln Glu Asp Gly Thr Ser Gln Lys Val Ala Val Lys Thr Met Lys Leu
            365                 370                 375

Asp Asn Phe Ser Gln Arg Glu Ile Glu Glu Phe Leu Ser Glu Ala Ala
380                 385                 390

Cys Met Lys Asp Phe Asn His Pro Asn Val Ile Arg Leu Leu Gly Val
395                 400                 405                 410

Cys Ile Glu Leu Ser Ser Gln Gly Ile Pro Lys Pro Met Val Ile Leu
            415                 420                 425

Pro Phe Met Lys Tyr Gly Asp Leu His Thr Phe Leu Leu Tyr Ser Arg
            430                 435                 440

Leu Asn Thr Gly Pro Lys Tyr Ile His Leu Gln Thr Leu Leu Lys Phe
            445                 450                 455

Met Met Asp Ile Ala Gln Gly Met Glu Tyr Leu Ser Asn Arg Asn Phe
460                 465                 470

Leu His Arg Asp Leu Ala Ala Arg Asn Cys Met Leu Arg Asp Asp Met
475                 480                 485                 490

Thr Val Cys Val Ala Asp Phe Gly Leu Ser Lys Lys Ile Tyr Ser Gly
            495                 500                 505

Asp Tyr Tyr Arg Gln Gly Arg Ile Ala Lys Met Pro Val Lys Trp Ile
            510                 515                 520

Ala Ile Glu Ser Leu Ala Asp Arg Val Tyr Thr Ser Lys Ser Asp Val
```

```
                525                 530                 535
Trp Ala Phe Gly Val Thr Met Trp Glu Ile Thr Thr Arg Gly Met Thr
    540                 545                 550

Pro Tyr Pro Gly Val Gln Asn His Glu Met Tyr Asp Tyr Leu Leu His
555                 560                 565                 570

Gly His Arg Leu Lys Gln Pro Glu Asp Cys Leu Asp Glu Leu Tyr Asp
                575                 580                 585

Ile Met Tyr Ser Cys Trp Ser Ala Asp Pro Leu Asp Arg Pro Thr Phe
            590                 595                 600

Ser Val Leu Arg Leu Gln Leu Glu Lys Leu Ser Glu Ser Leu Pro Asp
        605                 610                 615

Ala Gln Asp Lys Glu Ser Ile Ile Tyr Ile Asn Thr Gln Leu Leu Glu
    620                 625                 630

Ser Cys Glu Gly Ile Ala Asn Gly Pro Ser Leu Thr Gly Leu Asp Met
635                 640                 645                 650

Asn Ile Asp Pro Asp Ser Ile Ile Ala Ser Cys Thr Pro Gly Ala Ala
                655                 660                 665

Val Ser Val Val Thr Ala Glu Val His Glu Asn Asn Leu Arg Glu Glu
            670                 675                 680

Arg Tyr Ile Leu Asn Gly Gly Asn Glu Glu Trp Glu Asp Val Ser Ser
        685                 690                 695

Thr Pro Phe Ala Ala Val Thr Pro Glu Lys Asp Gly Val Leu Pro Glu
    700                 705                 710

Asp Arg Leu Thr Lys Asn Gly Val Ser Trp Ser His Ser Thr Leu
715                 720                 725                 730

Pro Leu Gly Ser Pro Ser Pro Asp Glu Leu Leu Phe Val Asp Asp Ser
                735                 740                 745

Leu Glu Asp Ser Glu Val Leu Met Ser Trp Arg Arg Gln Arg Arg
            750                 755                 760

Leu Arg Gly Ala Ser Ser Ala Glu Ala Pro Asp Gly Asp Lys Asp Ala
        765                 770                 775

Pro Glu Pro Leu Asp Lys Val Ile Ile Leu Ser Pro Gly Ile Ser Asp
    780                 785                 790

Ala Thr Ala Pro Ala Trp Pro Pro Gly Glu Asp Pro Gly Thr Thr
795                 800                 805                 810

Pro Pro Gly His Ser Val Pro Val Pro Ala Thr Glu Leu Gly Ser Thr
                815                 820                 825

Glu Leu Val Thr Thr Lys Thr Ala Gly Pro Glu Gln Gln
            830                 835

<210> SEQ ID NO 104
<211> LENGTH: 19
<212> TYPE: PRT
<213> ORGANISM: Artificial Sequence
<220> FEATURE:
<223> OTHER INFORMATION: P2A self-cleaving peptide

<400> SEQUENCE: 104

Ala Thr Asn Phe Ser Leu Leu Lys Gln Ala Gly Asp Val Glu Glu Asn
1               5                   10                  15

Pro Gly Pro

<210> SEQ ID NO 105
<211> LENGTH: 692
<212> TYPE: PRT
<213> ORGANISM: Artificial Sequence
```

<220> FEATURE:
<223> OTHER INFORMATION: Tim4-tMyD88-P2A-Rab5a CER91 chimeric engulfment receptor
<220> FEATURE:
<221> NAME/KEY: SIGNAL
<222> LOCATION: (1)...(22)

<400> SEQUENCE: 105

```
Met Ser Lys Gly Leu Leu Leu Trp Leu Val Thr Glu Leu Trp Trp
        -20              -15              -10

Leu Tyr Leu Thr Pro Ala Ala Ser Glu Asp Thr Ile Ile Gly Phe Leu
         -5               1               5                   10

Gly Gln Pro Val Thr Leu Pro Cys His Tyr Leu Ser Trp Ser Gln Ser
                 15              20                  25

Arg Asn Ser Met Cys Trp Gly Lys Gly Ser Cys Pro Asn Ser Lys Cys
             30              35                  40

Asn Ala Glu Leu Leu Arg Thr Asp Gly Thr Arg Ile Ile Ser Arg Lys
             45              50                  55

Ser Thr Lys Tyr Thr Leu Leu Gly Lys Val Gln Phe Gly Glu Val Ser
         60              65                  70

Leu Thr Ile Ser Asn Thr Asn Arg Gly Asp Ser Gly Val Tyr Cys Cys
75               80                  85                       90

Arg Ile Glu Val Pro Gly Trp Phe Asn Asp Val Lys Lys Asn Val Arg
                 95              100                 105

Leu Glu Leu Arg Arg Ala Thr Thr Thr Lys Lys Pro Thr Thr Thr Thr
             110                 115                 120

Arg Pro Thr Thr Thr Pro Tyr Val Thr Thr Thr Thr Pro Glu Leu Leu
         125                 130                 135

Pro Thr Thr Val Met Thr Thr Ser Val Leu Pro Thr Thr Thr Pro Pro
         140                 145                 150

Gln Thr Leu Ala Thr Thr Ala Phe Ser Thr Ala Val Thr Thr Cys Pro
155                 160                 165                 170

Ser Thr Thr Pro Gly Ser Phe Ser Gln Glu Thr Thr Lys Gly Ser Ala
             175                 180                 185

Phe Thr Thr Glu Ser Glu Thr Leu Pro Ala Ser Asn His Ser Gln Arg
             190                 195                 200

Ser Met Met Thr Ile Ser Thr Asp Ile Ala Val Leu Arg Pro Thr Gly
             205                 210                 215

Ser Asn Pro Gly Ile Leu Pro Ser Thr Ser Gln Leu Thr Thr Gln Lys
         220                 225                 230

Thr Thr Leu Thr Thr Ser Glu Ser Leu Gln Lys Thr Thr Lys Ser His
235                 240                 245                 250

Gln Ile Asn Ser Arg Gln Thr Ile Leu Ile Ala Cys Cys Val Gly
             255                 260                 265

Phe Val Leu Met Val Leu Leu Phe Leu Ala Phe Leu Met Ala Ala Gly
             270                 275                 280

Gly Pro Gly Ala Gly Ser Ala Ala Pro Val Ser Ser Thr Ser Ser Leu
         285                 290                 295

Pro Leu Ala Ala Leu Asn Met Arg Val Arg Arg Leu Ser Leu Phe
         300                 305                 310

Leu Asn Val Arg Thr Gln Val Ala Ala Asp Trp Thr Ala Leu Ala Glu
315                 320                 325                 330

Glu Met Asp Phe Glu Tyr Leu Glu Ile Arg Gln Leu Glu Thr Gln Ala
                 335                 340                 345

Asp Pro Thr Gly Arg Leu Leu Asp Ala Trp Gln Gly Arg Pro Gly Ala
```

```
              350                 355                 360
Ser Val Gly Arg Leu Leu Glu Leu Leu Thr Lys Leu Gly Arg Asp Asp
            365                 370                 375
Val Leu Leu Glu Leu Gly Pro Ser Ile Glu Glu Asp Cys Gln Lys Tyr
        380                 385                 390
Ile Leu Lys Gln Gln Gln Glu Glu Ala Glu Lys Pro Leu Gln Val Ala
395                 400                 405                 410
Ala Val Asp Ser Ser Val Pro Arg Thr Ala Glu Leu Ala Gly Ile Thr
                415                 420                 425
Thr Leu Asp Asp Pro Leu Gly Gly Ser Gly Ala Thr Asn Phe Ser Leu
            430                 435                 440
Leu Lys Gln Ala Gly Asp Val Glu Glu Asn Pro Gly Pro Met Ala Ser
        445                 450                 455
Arg Gly Ala Thr Arg Pro Asn Gly Pro Asn Thr Gly Asn Lys Ile Cys
    460                 465                 470
Gln Phe Lys Leu Val Leu Leu Gly Glu Ser Ala Val Gly Lys Ser Ser
475                 480                 485                 490
Leu Val Leu Arg Phe Val Lys Gly Gln Phe His Glu Phe Gln Glu Ser
                495                 500                 505
Thr Ile Gly Ala Ala Phe Leu Thr Gln Thr Val Cys Leu Asp Asp Thr
            510                 515                 520
Thr Val Lys Phe Glu Ile Trp Asp Thr Ala Gly Gln Glu Arg Tyr His
        525                 530                 535
Ser Leu Ala Pro Met Tyr Tyr Arg Gly Ala Gln Ala Ala Ile Val Val
    540                 545                 550
Tyr Asp Ile Thr Asn Glu Glu Ser Phe Ala Arg Ala Lys Asn Trp Val
555                 560                 565                 570
Lys Glu Leu Gln Arg Gln Ala Ser Pro Asn Ile Val Ile Ala Leu Ser
                575                 580                 585
Gly Asn Lys Ala Asp Leu Ala Asn Lys Arg Ala Val Asp Phe Gln Glu
            590                 595                 600
Ala Gln Ser Tyr Ala Asp Asp Asn Ser Leu Leu Phe Met Glu Thr Ser
        605                 610                 615
Ala Lys Thr Ser Met Asn Val Asn Glu Ile Phe Met Ala Ile Ala Lys
    620                 625                 630
Lys Leu Pro Lys Asn Glu Pro Gln Asn Pro Gly Ala Asn Ser Ala Arg
635                 640                 645                 650
Gly Arg Gly Val Asp Leu Thr Glu Pro Thr Gln Pro Thr Arg Asn Gln
                655                 660                 665
Cys Cys Ser Asn
            670

<210> SEQ ID NO 106
<211> LENGTH: 264
<212> TYPE: PRT
<213> ORGANISM: Artificial Sequence
<220> FEATURE:
<223> OTHER INFORMATION: mesothelin specific scFv derived from M912
      antibody
<220> FEATURE:
<221> NAME/KEY: SIGNAL
<222> LOCATION: (1)...(22)

<400> SEQUENCE: 106

Met Leu Leu Leu Val Thr Ser Leu Leu Leu Cys Glu Leu Pro His Pro
        -20                 -15                 -10
```

```
Ala Phe Leu Leu Ile Pro Asp Ile Gln Met Thr Gln Ser Pro Ser Ser
        -5              1               5                  10

Leu Ser Ala Ser Val Gly Asp Arg Val Thr Ile Thr Cys Arg Ala Ser
                15                  20              25

Gln Ser Ile Ser Ser Tyr Leu Asn Trp Tyr Gln Gln Lys Pro Gly Lys
            30                  35              40

Ala Pro Lys Leu Leu Ile Tyr Ala Ala Ser Ser Leu Gln Ser Gly Val
        45              50              55

Pro Ser Gly Phe Ser Gly Ser Gly Ser Gly Thr Asp Phe Thr Leu Thr
    60              65              70

Ile Ser Ser Leu Gln Pro Glu Asp Phe Ala Thr Tyr Tyr Cys Gln Gln
75              80              85                  90

Ser Tyr Ser Thr Pro Leu Thr Phe Gly Gly Gly Thr Lys Val Glu Ile
                95              100             105

Lys Arg Gly Gly Gly Gly Ser Gly Gly Gly Gly Ser Gly Gly Gly Gly
            110             115             120

Ser Gln Val Gln Leu Gln Glu Ser Gly Pro Gly Leu Val Lys Pro Ser
        125             130             135

Glu Thr Leu Ser Leu Thr Cys Thr Val Ser Gly Gly Ser Val Ser Ser
140             145             150

Gly Ser Tyr Tyr Trp Ser Trp Ile Arg Gln Pro Pro Gly Lys Gly Leu
155             160             165             170

Glu Trp Ile Gly Tyr Ile Tyr Tyr Ser Gly Ser Thr Asn Tyr Asn Pro
                175             180             185

Ser Leu Lys Ser Arg Val Thr Ile Ser Val Asp Thr Ser Lys Asn Gln
            190             195             200

Phe Ser Leu Lys Leu Ser Ser Val Thr Ala Ala Asp Thr Ala Val Tyr
        205             210             215

Tyr Cys Ala Arg Glu Gly Lys Asn Gly Ala Phe Asp Ile Trp Gly Gln
    220             225             230

Gly Thr Met Val Thr Val Ser Ser
235             240
```

<210> SEQ ID NO 107
<211> LENGTH: 452
<212> TYPE: PRT
<213> ORGANISM: Artificial Sequence
<220> FEATURE:
<223> OTHER INFORMATION: M912 scFv-IgG4 spacer-Tim4 TM-tMyD88 CER50
      chimeric engulfment receptor
<220> FEATURE:
<221> NAME/KEY: SIGNAL
<222> LOCATION: (1)...(22)

<400> SEQUENCE: 107

```
Met Leu Leu Leu Val Thr Ser Leu Leu Leu Cys Glu Leu Pro His Pro
        -20             -15                 -10

Ala Phe Leu Leu Ile Pro Asp Ile Gln Met Thr Gln Ser Pro Ser Ser
        -5              1               5                   10

Leu Ser Ala Ser Val Gly Asp Arg Val Thr Ile Thr Cys Arg Ala Ser
                15                  20              25

Gln Ser Ile Ser Ser Tyr Leu Asn Trp Tyr Gln Gln Lys Pro Gly Lys
            30                  35              40

Ala Pro Lys Leu Leu Ile Tyr Ala Ala Ser Ser Leu Gln Ser Gly Val
        45              50              55

Pro Ser Gly Phe Ser Gly Ser Gly Ser Gly Thr Asp Phe Thr Leu Thr
    60              65              70
```

Ile Ser Ser Leu Gln Pro Glu Asp Phe Ala Thr Tyr Tyr Cys Gln Gln
 75                  80                  85                  90

Ser Tyr Ser Thr Pro Leu Thr Phe Gly Gly Gly Thr Lys Val Glu Ile
                 95                 100                 105

Lys Arg Gly Gly Gly Gly Ser Gly Gly Gly Gly Ser Gly Gly Gly Gly
            110                 115                 120

Ser Gln Val Gln Leu Gln Glu Ser Gly Pro Gly Leu Val Lys Pro Ser
            125                 130                 135

Glu Thr Leu Ser Leu Thr Cys Thr Val Ser Gly Gly Ser Val Ser Ser
            140                 145                 150

Gly Ser Tyr Tyr Trp Ser Trp Ile Arg Gln Pro Pro Gly Lys Gly Leu
155                 160                 165                 170

Glu Trp Ile Gly Tyr Ile Tyr Tyr Ser Gly Ser Thr Asn Tyr Asn Pro
                175                 180                 185

Ser Leu Lys Ser Arg Val Thr Ile Ser Val Asp Thr Ser Lys Asn Gln
            190                 195                 200

Phe Ser Leu Lys Leu Ser Ser Val Thr Ala Ala Asp Thr Ala Val Tyr
            205                 210                 215

Tyr Cys Ala Arg Glu Gly Lys Asn Gly Ala Phe Asp Ile Trp Gly Gln
220                 225                 230

Gly Thr Met Val Thr Val Ser Ser Glu Ser Lys Tyr Gly Pro Pro Cys
235                 240                 245                 250

Pro Pro Cys Pro Ile Leu Ile Ile Ala Cys Cys Val Gly Phe Val Leu
                255                 260                 265

Met Val Leu Leu Phe Leu Ala Phe Leu Met Ala Ala Gly Gly Pro Gly
            270                 275                 280

Ala Gly Ser Ala Ala Pro Val Ser Ser Thr Ser Ser Leu Pro Leu Ala
            285                 290                 295

Ala Leu Asn Met Arg Val Arg Arg Arg Leu Ser Leu Phe Leu Asn Val
300                 305                 310

Arg Thr Gln Val Ala Ala Asp Trp Thr Ala Leu Ala Glu Glu Met Asp
315                 320                 325                 330

Phe Glu Tyr Leu Glu Ile Arg Gln Leu Glu Thr Gln Ala Asp Pro Thr
                335                 340                 345

Gly Arg Leu Leu Asp Ala Trp Gln Gly Arg Pro Gly Ala Ser Val Gly
            350                 355                 360

Arg Leu Leu Glu Leu Leu Thr Lys Leu Gly Arg Asp Asp Val Leu Leu
            365                 370                 375

Glu Leu Gly Pro Ser Ile Glu Glu Asp Cys Gln Lys Tyr Ile Leu Lys
            380                 385                 390

Gln Gln Gln Glu Glu Ala Glu Lys Pro Leu Gln Val Ala Ala Val Asp
395                 400                 405                 410

Ser Ser Val Pro Arg Thr Ala Glu Leu Ala Gly Ile Thr Thr Leu Asp
                415                 420                 425

Asp Pro Leu Gly
            430

<210> SEQ ID NO 108

<400> SEQUENCE: 108

000

<210> SEQ ID NO 109

```
<400> SEQUENCE: 109

000

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114
<211> LENGTH: 57
<212> TYPE: PRT
<213> ORGANISM: Homo sapiens
<220> FEATURE:
<223> OTHER INFORMATION: ItgB5 signaling domain

<400> SEQUENCE: 114

Lys Leu Leu Val Thr Ile His Asp Arg Arg Glu Phe Ala Lys Phe Gln
1               5                   10                  15

Ser Glu Arg Ser Arg Ala Arg Tyr Glu Met Ala Ser Asn Pro Leu Tyr
                20                  25                  30

Arg Lys Pro Ile Ser Thr His Thr Val Asp Phe Thr Phe Asn Lys Phe
            35                  40                  45

Asn Lys Ser Tyr Asn Gly Thr Val Asp
        50                  55

<210> SEQ ID NO 115
<211> LENGTH: 279
<212> TYPE: PRT
<213> ORGANISM: Mus musculus
<220> FEATURE:
<223> OTHER INFORMATION: Tim4 binding domain
<220> FEATURE:
<221> NAME/KEY: SIGNAL
<222> LOCATION: (1)...(22)

<400> SEQUENCE: 115

Met Ser Lys Gly Leu Leu Leu Trp Leu Val Thr Glu Leu Trp Trp
        -20                 -15                 -10

Leu Tyr Leu Thr Pro Ala Ala Ser Glu Asp Thr Ile Ile Gly Phe Leu
        -5                  1                   5                   10

Gly Gln Pro Val Thr Leu Pro Cys His Tyr Leu Ser Trp Ser Gln Ser
                15                  20                  25

Arg Asn Ser Met Cys Trp Gly Lys Gly Ser Cys Pro Asn Ser Lys Cys
            30                  35                  40
```

```
Asn Ala Glu Leu Leu Arg Thr Asp Gly Thr Arg Ile Ile Ser Arg Lys
            45                  50                  55

Ser Thr Lys Tyr Thr Leu Leu Gly Lys Val Gln Phe Gly Glu Val Ser
    60                  65                  70

Leu Thr Ile Ser Asn Thr Asn Arg Gly Asp Ser Gly Val Tyr Cys Cys
 75              80                  85                      90

Arg Ile Glu Val Pro Gly Trp Phe Asn Asp Val Lys Lys Asn Val Arg
                95                 100                 105

Leu Glu Leu Arg Arg Ala Thr Thr Lys Lys Pro Thr Thr Thr
                110                 115                 120

Arg Pro Thr Thr Thr Pro Tyr Val Thr Thr Thr Pro Glu Leu Leu
                125                 130                 135

Pro Thr Thr Val Met Thr Thr Ser Val Leu Pro Thr Thr Thr Pro Pro
    140                 145                 150

Gln Thr Leu Ala Thr Thr Ala Phe Ser Thr Ala Val Thr Thr Cys Pro
155                 160                 165                 170

Ser Thr Thr Pro Gly Ser Phe Ser Gln Glu Thr Thr Lys Gly Ser Ala
                175                 180                 185

Phe Thr Thr Glu Ser Glu Thr Leu Pro Ala Ser Asn His Ser Gln Arg
                190                 195                 200

Ser Met Met Thr Ile Ser Thr Asp Ile Ala Val Leu Arg Pro Thr Gly
                205                 210                 215

Ser Asn Pro Gly Ile Leu Pro Ser Thr Ser Gln Leu Thr Thr Gln Lys
                220                 225                 230

Thr Thr Leu Thr Thr Ser Glu Ser Leu Gln Lys Thr Thr Lys Ser His
235                 240                 245                 250

Gln Ile Asn Ser Arg Gln Thr
                255

<210> SEQ ID NO 116
<211> LENGTH: 829
<212> TYPE: PRT
<213> ORGANISM: Artificial Sequence
<220> FEATURE:
<223> OTHER INFORMATION: CER96 with truncated NFAM1 chimeric engulfment
      receptor
<220> FEATURE:
<221> NAME/KEY: SIGNAL
<222> LOCATION: (1)...(22)

<400> SEQUENCE: 116

Met Ser Lys Gly Leu Leu Leu Leu Trp Leu Val Thr Glu Leu Trp Trp
        -20                 -15                 -10

Leu Tyr Leu Thr Pro Ala Ala Ser Glu Asp Thr Ile Ile Gly Phe Leu
        -5                   1                   5              10

Gly Gln Pro Val Thr Leu Pro Cys His Tyr Leu Ser Trp Ser Gln Ser
                15                  20                  25

Arg Asn Ser Met Cys Trp Gly Lys Gly Ser Cys Pro Asn Ser Lys Cys
                30                  35                  40

Asn Ala Glu Leu Leu Arg Thr Asp Gly Thr Arg Ile Ile Ser Arg Lys
            45                  50                  55

Ser Thr Lys Tyr Thr Leu Leu Gly Lys Val Gln Phe Gly Glu Val Ser
    60                  65                  70

Leu Thr Ile Ser Asn Thr Asn Arg Gly Asp Ser Gly Val Tyr Cys Cys
 75              80                  85                      90

Arg Ile Glu Val Pro Gly Trp Phe Asn Asp Val Lys Lys Asn Val Arg
```

```
                    95                  100                 105
Leu Glu Leu Arg Arg Ala Thr Thr Thr Lys Lys Pro Thr Thr Thr Thr
                110                 115                 120

Arg Pro Thr Thr Thr Pro Tyr Val Thr Thr Thr Pro Glu Leu Leu
                125                 130                 135

Pro Thr Thr Val Met Thr Thr Ser Val Leu Pro Thr Thr Pro Pro
        140                 145                 150

Gln Thr Leu Ala Thr Thr Ala Phe Ser Thr Ala Val Thr Thr Cys Pro
155                 160                 165                 170

Ser Thr Thr Pro Gly Ser Phe Ser Gln Glu Thr Thr Lys Gly Ser Ala
                175                 180                 185

Phe Thr Thr Glu Ser Glu Thr Leu Pro Ala Ser Asn His Ser Gln Arg
                190                 195                 200

Ser Met Met Thr Ile Ser Thr Asp Ile Ala Val Leu Arg Pro Thr Gly
                205                 210                 215

Ser Asn Pro Gly Ile Leu Pro Ser Thr Ser Gln Leu Thr Thr Gln Lys
        220                 225                 230

Thr Thr Leu Thr Thr Ser Glu Ser Leu Gln Lys Thr Thr Lys Ser His
235                 240                 245                 250

Gln Ile Asn Ser Arg Gln Thr Ile Leu Ile Ile Ala Cys Cys Val Gly
                255                 260                 265

Phe Val Leu Met Val Leu Leu Phe Leu Ala Phe Leu Ala Leu Arg Arg
                270                 275                 280

Arg Val Gln Glu Thr Lys Phe Gly Gly Ala Phe Ser Glu Glu Asp Ser
                285                 290                 295

Gln Leu Val Val Asn Tyr Arg Ala Lys Lys Ser Phe Cys Arg Arg Ala
300                 305                 310

Ile Glu Leu Thr Leu Gln Ser Leu Gly Val Ser Glu Glu Leu Gln Asn
315                 320                 325                 330

Lys Leu Glu Asp Val Val Ile Asp Arg Asn Leu Leu Val Leu Gly Lys
                335                 340                 345

Val Leu Gly Glu Gly Glu Phe Gly Ser Val Met Glu Gly Asn Leu Lys
                350                 355                 360

Gln Glu Asp Gly Thr Ser Gln Lys Val Ala Val Lys Thr Met Lys Leu
                365                 370                 375

Asp Asn Phe Ser Gln Arg Glu Ile Glu Glu Phe Leu Ser Glu Ala Ala
                380                 385                 390

Cys Met Lys Asp Phe Asn His Pro Asn Val Ile Arg Leu Leu Gly Val
395                 400                 405                 410

Cys Ile Glu Leu Ser Ser Gln Gly Ile Pro Lys Pro Met Val Ile Leu
                415                 420                 425

Pro Phe Met Lys Tyr Gly Asp Leu His Thr Phe Leu Leu Tyr Ser Arg
                430                 435                 440

Leu Asn Thr Gly Pro Lys Tyr Ile His Leu Gln Thr Leu Leu Lys Phe
                445                 450                 455

Met Met Asp Ile Ala Gln Gly Met Glu Tyr Leu Ser Asn Arg Asn Phe
        460                 465                 470

Leu His Arg Asp Leu Ala Ala Arg Asn Cys Met Leu Arg Asp Asp Met
475                 480                 485                 490

Thr Val Cys Val Ala Asp Phe Gly Leu Ser Lys Lys Ile Tyr Ser Gly
                495                 500                 505

Asp Tyr Tyr Arg Gln Gly Arg Ile Ala Lys Met Pro Val Lys Trp Ile
                510                 515                 520
```

-continued

Ala Ile Glu Ser Leu Ala Asp Arg Val Tyr Thr Ser Lys Ser Asp Val
            525                 530                 535

Trp Ala Phe Gly Val Thr Met Trp Glu Ile Thr Thr Arg Gly Met Thr
    540                 545                 550

Pro Tyr Pro Gly Val Gln Asn His Glu Met Tyr Asp Tyr Leu Leu His
555                 560                 565                 570

Gly His Arg Leu Lys Gln Pro Glu Asp Cys Leu Asp Glu Leu Tyr Asp
                575                 580                 585

Ile Met Tyr Ser Cys Trp Ser Ala Asp Pro Leu Asp Arg Pro Thr Phe
            590                 595                 600

Ser Val Leu Arg Leu Gln Leu Glu Lys Leu Ser Glu Ser Leu Pro Asp
            605                 610                 615

Ala Gln Asp Lys Glu Ser Ile Ile Tyr Ile Asn Thr Gln Leu Leu Glu
        620                 625                 630

Ser Cys Glu Gly Ile Ala Asn Gly Pro Ser Leu Thr Gly Leu Asp Met
635                 640                 645                 650

Asn Ile Asp Pro Asp Ser Ile Ile Ala Ser Cys Thr Pro Gly Ala Ala
                655                 660                 665

Val Ser Val Val Thr Ala Glu Val His Glu Asn Asn Leu Arg Glu Glu
            670                 675                 680

Arg Tyr Ile Leu Asn Gly Gly Asn Glu Glu Trp Glu Asp Val Ser Ser
        685                 690                 695

Thr Pro Phe Ala Ala Val Thr Pro Glu Lys Asp Gly Val Leu Pro Glu
    700                 705                 710

Asp Arg Leu Thr Lys Asn Gly Val Ser Trp Ser His His Ser Thr Leu
715                 720                 725                 730

Pro Leu Gly Ser Pro Ser Pro Asp Glu Leu Leu Phe Val Asp Asp Ser
                735                 740                 745

Leu Glu Asp Ser Glu Val Leu Met Leu Trp Asn Lys Lys Arg Met Arg
            750                 755                 760

Gly Pro Gly Lys Asp Pro Thr Arg Lys Cys Pro Asp Pro Arg Ser Ala
        765                 770                 775

Ser Ser Pro Lys Gln His Pro Ser Glu Ser Val Tyr Thr Ala Leu Gln
    780                 785                 790

Arg Arg Glu Thr Glu Val Tyr Ala Cys Ile Glu Asn Glu
795                 800                 805

<210> SEQ ID NO 117
<211> LENGTH: 918
<212> TYPE: PRT
<213> ORGANISM: Homo sapiens
<220> FEATURE:
<223> OTHER INFORMATION: BAI1 binding domain

<400> SEQUENCE: 117

Ala Ala Gly Ala Asp Ala Gly Pro Gly Pro Glu Pro Cys Ala Thr Leu
1               5                   10                  15

Val Gln Gly Lys Phe Phe Gly Tyr Phe Ser Ala Ala Ala Val Phe Pro
            20                  25                  30

Ala Asn Ala Ser Arg Cys Ser Trp Thr Leu Arg Asn Pro Asp Pro Arg
        35                  40                  45

Arg Tyr Thr Leu Tyr Met Lys Val Ala Lys Ala Pro Val Pro Cys Ser
    50                  55                  60

Gly Pro Gly Arg Val Arg Thr Tyr Gln Phe Asp Ser Phe Leu Glu Ser
65                  70                  75                  80

```
Thr Arg Thr Tyr Leu Gly Val Glu Ser Phe Asp Val Leu Arg Leu
                85                  90                  95

Cys Asp Pro Ser Ala Pro Leu Ala Phe Leu Gln Ala Ser Lys Gln Phe
            100                 105                 110

Leu Gln Met Arg Arg Gln Gln Pro Pro Gln His Asp Gly Leu Arg Pro
        115                 120                 125

Arg Ala Gly Pro Pro Gly Pro Thr Asp Asp Phe Ser Val Glu Tyr Leu
    130                 135                 140

Val Val Gly Asn Arg Asn Pro Ser Arg Ala Ala Cys Gln Met Leu Cys
145                 150                 155                 160

Arg Trp Leu Asp Ala Cys Leu Ala Gly Ser Arg Ser His Pro Cys
                165                 170                 175

Gly Ile Met Gln Thr Pro Cys Ala Cys Leu Gly Gly Glu Ala Gly Gly
                180                 185                 190

Pro Ala Ala Gly Pro Leu Ala Pro Arg Gly Asp Val Cys Leu Arg Asp
            195                 200                 205

Ala Val Ala Gly Gly Pro Glu Asn Cys Leu Thr Ser Leu Thr Gln Asp
        210                 215                 220

Arg Gly Gly His Gly Ala Thr Gly Gly Trp Lys Leu Trp Ser Leu Trp
225                 230                 235                 240

Gly Glu Cys Thr Arg Asp Cys Gly Gly Gly Leu Gln Thr Arg Thr Arg
                245                 250                 255

Thr Cys Leu Pro Ala Pro Gly Val Glu Gly Gly Cys Glu Gly Val
                260                 265                 270

Leu Glu Glu Gly Arg Gln Cys Asn Arg Glu Ala Cys Gly Pro Ala Gly
            275                 280                 285

Arg Thr Ser Ser Arg Ser Gln Ser Leu Arg Ser Thr Asp Ala Arg Arg
        290                 295                 300

Arg Glu Glu Leu Gly Asp Glu Leu Gln Gln Phe Gly Phe Pro Ala Pro
305                 310                 315                 320

Gln Thr Gly Asp Pro Ala Ala Glu Glu Trp Ser Pro Trp Ser Val Cys
                325                 330                 335

Ser Ser Thr Cys Gly Glu Gly Trp Gln Thr Arg Thr Arg Phe Cys Val
                340                 345                 350

Ser Ser Ser Tyr Ser Thr Gln Cys Ser Gly Pro Leu Arg Glu Gln Arg
            355                 360                 365

Leu Cys Asn Asn Ser Ala Val Cys Pro Val His Gly Ala Trp Asp Glu
    370                 375                 380

Trp Ser Pro Trp Ser Leu Cys Ser Ser Thr Cys Gly Arg Gly Phe Arg
385                 390                 395                 400

Asp Arg Thr Arg Thr Cys Arg Pro Pro Gln Phe Gly Gly Asn Pro Cys
                405                 410                 415

Glu Gly Pro Glu Lys Gln Thr Lys Phe Cys Asn Ile Ala Leu Cys Pro
                420                 425                 430

Gly Arg Ala Val Asp Gly Asn Trp Asn Glu Trp Ser Ser Trp Ser Ala
        435                 440                 445

Cys Ser Ala Ser Cys Ser Gln Gly Arg Gln Arg Thr Arg Glu Cys
    450                 455                 460

Asn Gly Pro Ser Tyr Gly Gly Ala Glu Cys Gln Gly His Trp Val Glu
465                 470                 475                 480

Thr Arg Asp Cys Phe Leu Gln Gln Cys Pro Val Asp Gly Lys Trp Gln
                485                 490                 495
```

```
Ala Trp Ala Ser Trp Gly Ser Cys Ser Val Thr Cys Gly Ala Gly Ser
            500                 505                 510

Gln Arg Arg Glu Arg Val Cys Ser Gly Pro Phe Phe Gly Gly Ala Ala
        515                 520                 525

Cys Gln Gly Pro Gln Asp Glu Tyr Arg Gln Cys Gly Thr Gln Arg Cys
    530                 535                 540

Pro Glu Pro His Glu Ile Cys Asp Glu Asp Asn Phe Gly Ala Val Ile
545                 550                 555                 560

Trp Lys Glu Thr Pro Ala Gly Glu Val Ala Ala Val Arg Cys Pro Arg
                565                 570                 575

Asn Ala Thr Gly Leu Ile Leu Arg Arg Cys Glu Leu Asp Glu Glu Gly
            580                 585                 590

Ile Ala Tyr Trp Glu Pro Pro Thr Tyr Ile Arg Cys Val Ser Ile Asp
        595                 600                 605

Tyr Arg Asn Ile Gln Met Met Thr Arg Glu His Leu Ala Lys Ala Gln
    610                 615                 620

Arg Gly Leu Pro Gly Glu Gly Val Ser Glu Val Ile Gln Thr Leu Val
625                 630                 635                 640

Glu Ile Ser Gln Asp Gly Thr Ser Tyr Ser Gly Asp Leu Leu Ser Thr
                645                 650                 655

Ile Asp Val Leu Arg Asn Met Thr Glu Ile Phe Arg Arg Ala Tyr Tyr
            660                 665                 670

Ser Pro Thr Pro Gly Asp Val Gln Asn Phe Val Gln Ile Leu Ser Asn
        675                 680                 685

Leu Leu Ala Glu Glu Asn Arg Asp Lys Trp Glu Glu Ala Gln Leu Ala
690                 695                 700

Gly Pro Asn Ala Lys Glu Leu Phe Arg Leu Val Glu Asp Phe Val Asp
705                 710                 715                 720

Val Ile Gly Phe Arg Met Lys Asp Leu Arg Asp Ala Tyr Gln Val Thr
                725                 730                 735

Asp Asn Leu Val Leu Ser Ile His Lys Leu Pro Ala Ser Gly Ala Thr
            740                 745                 750

Asp Ile Ser Phe Pro Met Lys Gly Trp Arg Ala Thr Gly Asp Trp Ala
        755                 760                 765

Lys Val Pro Glu Asp Arg Val Thr Val Ser Lys Ser Val Phe Ser Thr
    770                 775                 780

Gly Leu Thr Glu Ala Asp Glu Ala Ser Val Phe Val Val Gly Thr Val
785                 790                 795                 800

Leu Tyr Arg Asn Leu Gly Ser Phe Leu Ala Leu Gln Arg Asn Thr Thr
                805                 810                 815

Val Leu Asn Ser Lys Val Ile Ser Val Thr Val Lys Pro Pro Pro Arg
            820                 825                 830

Ser Leu Arg Thr Pro Leu Glu Ile Glu Phe Ala His Met Tyr Asn Gly
        835                 840                 845

Thr Thr Asn Gln Thr Cys Ile Leu Trp Asp Glu Thr Asp Val Pro Ser
    850                 855                 860

Ser Ser Ala Pro Pro Gln Leu Gly Pro Trp Ser Trp Arg Gly Cys Arg
865                 870                 875                 880

Thr Val Pro Leu Asp Ala Leu Arg Thr Arg Cys Leu Cys Asp Arg Leu
                885                 890                 895

Ser Thr Phe Ala Ile Leu Ala Gln Leu Ser Ala Asp Ala Asn Met Glu
            900                 905                 910

Lys Ala Thr Leu Pro Ser
```

```
                915

<210> SEQ ID NO 118
<211> LENGTH: 21
<212> TYPE: PRT
<213> ORGANISM: Homo sapiens
<220> FEATURE:
<223> OTHER INFORMATION: MRC1 transmembrane domain

<400> SEQUENCE: 118

Gly Val Val Ile Ile Val Ile Leu Leu Ile Leu Thr Gly Ala Gly Leu
1               5                   10                  15

Ala Ala Tyr Phe Phe
            20

<210> SEQ ID NO 119
<211> LENGTH: 46
<212> TYPE: PRT
<213> ORGANISM: Homo sapiens
<220> FEATURE:
<223> OTHER INFORMATION: MRC1 signaling domain

<400> SEQUENCE: 119

Tyr Lys Lys Arg Arg Val His Leu Pro Gln Glu Gly Ala Phe Glu Asn
1               5                   10                  15

Thr Leu Tyr Phe Asn Ser Gln Ser Ser Pro Gly Thr Ser Asp Met Lys
            20                  25                  30

Asp Leu Val Gly Asn Ile Glu Gln Asn Glu His Ser Val Ile
        35                  40                  45

<210> SEQ ID NO 120
<211> LENGTH: 727
<212> TYPE: PRT
<213> ORGANISM: Homo sapiens
<220> FEATURE:
<223> OTHER INFORMATION: ELMO

<400> SEQUENCE: 120

Met Pro Pro Pro Ala Asp Ile Val Lys Val Ala Ile Glu Trp Pro Gly
1               5                   10                  15

Ala Tyr Pro Lys Leu Met Glu Ile Asp Gln Lys Lys Pro Leu Ser Ala
            20                  25                  30

Ile Ile Lys Glu Val Cys Asp Gly Trp Ser Leu Ala Asn His Glu Tyr
        35                  40                  45

Phe Ala Leu Gln His Ala Asp Ser Ser Asn Phe Tyr Ile Thr Glu Lys
    50                  55                  60

Asn Arg Asn Glu Ile Lys Asn Gly Thr Ile Leu Arg Leu Thr Thr Ser
65                  70                  75                  80

Pro Ala Gln Asn Ala Gln Gln Leu His Glu Arg Ile Gln Ser Ser Ser
                85                  90                  95

Met Asp Ala Lys Leu Glu Ala Leu Lys Asp Leu Ala Ser Leu Ser Arg
            100                 105                 110

Asp Val Thr Phe Ala Gln Glu Phe Ile Asn Leu Asp Gly Ile Ser Leu
        115                 120                 125

Leu Thr Gln Met Val Glu Ser Gly Thr Glu Arg Tyr Gln Lys Leu Gln
    130                 135                 140

Lys Ile Met Lys Pro Cys Phe Gly Asp Met Leu Ser Phe Thr Leu Thr
145                 150                 155                 160

Ala Phe Val Glu Leu Met Asp His Gly Ile Val Ser Trp Asp Thr Phe
                165                 170                 175
```

```
Ser Val Ala Phe Ile Lys Lys Ile Ala Ser Phe Val Asn Lys Ser Ala
            180                 185                 190
Ile Asp Ile Ser Ile Leu Gln Arg Ser Leu Ala Ile Leu Glu Ser Met
            195                 200                 205
Val Leu Asn Ser His Asp Leu Tyr Gln Lys Val Ala Gln Glu Ile Thr
210                 215                 220
Ile Gly Gln Leu Ile Pro His Leu Gln Gly Ser Asp Gln Glu Ile Gln
225                 230                 235                 240
Thr Tyr Thr Ile Ala Val Ile Asn Ala Leu Phe Leu Lys Ala Pro Asp
                245                 250                 255
Glu Arg Arg Gln Glu Met Ala Asn Ile Leu Ala Gln Lys Gln Leu Arg
            260                 265                 270
Ser Ile Ile Leu Thr His Val Ile Arg Ala Gln Arg Ala Ile Asn Asn
            275                 280                 285
Glu Met Ala His Gln Leu Tyr Val Leu Gln Val Leu Thr Phe Asn Leu
            290                 295                 300
Leu Glu Asp Arg Met Met Thr Lys Met Asp Pro Gln Asp Gln Ala Gln
305                 310                 315                 320
Arg Asp Ile Ile Phe Glu Leu Arg Ile Ala Phe Ala Glu Ser
                325                 330                 335
Glu Pro Asn Asn Ser Ser Gly Ser Met Glu Lys Arg Lys Ser Met Tyr
            340                 345                 350
Thr Arg Asp Tyr Lys Lys Leu Gly Phe Ile Asn His Val Asn Pro Ala
            355                 360                 365
Met Asp Phe Thr Gln Thr Pro Pro Gly Met Leu Ala Leu Asp Asn Met
370                 375                 380
Leu Tyr Phe Ala Lys His His Gln Asp Ala Tyr Ile Arg Ile Val Leu
385                 390                 395                 400
Glu Asn Ser Ser Arg Glu Asp Lys His Glu Cys Pro Phe Gly Arg Ser
                405                 410                 415
Ser Ile Glu Leu Thr Lys Met Leu Cys Glu Ile Leu Lys Val Gly Glu
            420                 425                 430
Leu Pro Ser Glu Thr Cys Asn Asp Phe His Pro Met Phe Phe Thr His
            435                 440                 445
Asp Arg Ser Phe Glu Glu Phe Phe Cys Ile Cys Ile Gln Leu Leu Asn
450                 455                 460
Lys Thr Trp Lys Glu Met Arg Ala Thr Ser Glu Asp Phe Asn Lys Val
465                 470                 475                 480
Met Gln Val Val Lys Glu Gln Val Met Arg Ala Leu Thr Thr Lys Pro
                485                 490                 495
Ser Ser Leu Asp Gln Phe Lys Ser Lys Leu Gln Asn Leu Ser Tyr Thr
            500                 505                 510
Glu Ile Leu Lys Ile Arg Gln Ser Glu Arg Met Asn Gln Glu Asp Phe
            515                 520                 525
Gln Ser Arg Pro Ile Leu Glu Leu Leu Glu Lys Ile Gln Pro Glu Ile
530                 535                 540
Leu Glu Leu Ile Lys Gln Gln Arg Leu Asn Arg Leu Val Glu Gly Thr
545                 550                 555                 560
Cys Phe Arg Lys Leu Asn Ala Arg Arg Arg Gln Asp Lys Phe Trp Tyr
                565                 570                 575
Cys Arg Leu Ser Pro Asn His Lys Val Leu His Tyr Gly Asp Leu Glu
            580                 585                 590
```

```
Glu Ser Pro Gln Gly Glu Val Pro His Asp Ser Leu Gln Asp Lys Leu
            595                 600                 605

Pro Val Ala Asp Ile Lys Ala Val Val Thr Gly Lys Asp Cys Pro His
610                 615                 620

Met Lys Glu Lys Gly Ala Leu Lys Gln Asn Lys Glu Val Leu Glu Leu
625                 630                 635                 640

Ala Phe Ser Ile Leu Tyr Asp Ser Asn Cys Gln Leu Asn Phe Ile Ala
                645                 650                 655

Pro Asp Lys His Glu Tyr Cys Ile Trp Thr Asp Gly Leu Asn Ala Leu
            660                 665                 670

Leu Gly Lys Asp Met Met Ser Asp Leu Thr Arg Asn Asp Leu Asp Thr
            675                 680                 685

Leu Leu Ser Met Glu Ile Lys Leu Arg Leu Leu Asp Leu Glu Asn Ile
            690                 695                 700

Gln Ile Pro Asp Ala Pro Pro Ile Pro Lys Glu Pro Ser Asn Tyr
705                 710                 715                 720

Asp Phe Val Tyr Asp Cys Asn
                725

<210> SEQ ID NO 121
<211> LENGTH: 285
<212> TYPE: PRT
<213> ORGANISM: Homo sapiens
<220> FEATURE:
<223> OTHER INFORMATION: truncated EGFR

<400> SEQUENCE: 121

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220
```

```
Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
            245                 250                 255

His Cys Val Lys Thr Cys Pro Ala Gly Val Met Gly Glu Asn Asn Thr
        260                 265                 270

Leu Val Trp Lys Tyr Ala Asp Ala Gly His Val Cys His
    275                 280                 285

<210> SEQ ID NO 122
<211> LENGTH: 207
<212> TYPE: PRT
<213> ORGANISM: Homo sapiens
<220> FEATURE:
<223> OTHER INFORMATION: Rab7

<400> SEQUENCE: 122

Met Thr Ser Arg Lys Lys Val Leu Leu Lys Val Ile Ile Leu Gly Asp
1               5                   10                  15

Ser Gly Val Gly Lys Thr Ser Leu Met Asn Gln Tyr Val Asn Lys Lys
            20                  25                  30

Phe Ser Asn Gln Tyr Lys Ala Thr Ile Gly Ala Asp Phe Leu Thr Lys
        35                  40                  45

Glu Val Met Val Asp Asp Arg Leu Val Thr Met Gln Ile Trp Asp Thr
50                  55                  60

Ala Gly Gln Glu Arg Phe Gln Ser Leu Gly Val Ala Phe Tyr Arg Gly
65                  70                  75                  80

Ala Asp Cys Cys Val Leu Val Phe Asp Val Thr Ala Pro Asn Thr Phe
                85                  90                  95

Lys Thr Leu Asp Ser Trp Arg Asp Glu Phe Leu Ile Gln Ala Ser Pro
            100                 105                 110

Arg Asp Pro Glu Asn Phe Pro Phe Val Val Leu Gly Asn Lys Ile Asp
        115                 120                 125

Leu Glu Asn Arg Gln Val Ala Thr Lys Arg Ala Gln Ala Trp Cys Tyr
130                 135                 140

Ser Lys Asn Asn Ile Pro Tyr Phe Glu Thr Ser Ala Lys Glu Ala Ile
145                 150                 155                 160

Asn Val Glu Gln Ala Phe Gln Thr Ile Ala Arg Asn Ala Leu Lys Gln
                165                 170                 175

Glu Thr Glu Val Glu Leu Tyr Asn Glu Phe Pro Glu Pro Ile Lys Leu
            180                 185                 190

Asp Lys Asn Asp Arg Ala Lys Ala Ser Ala Glu Ser Cys Ser Cys
        195                 200                 205

<210> SEQ ID NO 123
<211> LENGTH: 184
<212> TYPE: PRT
<213> ORGANISM: Homo sapiens
<220> FEATURE:
<223> OTHER INFORMATION: Rap1A

<400> SEQUENCE: 123

Met Arg Glu Tyr Lys Leu Val Val Leu Gly Ser Gly Gly Val Gly Lys
1               5                   10                  15

Ser Ala Leu Thr Val Gln Phe Val Gln Gly Ile Phe Val Glu Lys Tyr
            20                  25                  30

Asp Pro Thr Ile Glu Asp Ser Tyr Arg Lys Gln Val Glu Val Asp Cys
        35                  40                  45
```

```
Gln Gln Cys Met Leu Glu Ile Leu Asp Thr Ala Gly Thr Glu Gln Phe
         50                  55                  60

Thr Ala Met Arg Asp Leu Tyr Met Lys Asn Gly Gln Gly Phe Ala Leu
 65                  70                  75                  80

Val Tyr Ser Ile Thr Ala Gln Ser Thr Phe Asn Asp Leu Gln Asp Leu
                 85                  90                  95

Arg Glu Gln Ile Leu Arg Val Lys Asp Thr Glu Asp Val Pro Met Ile
            100                 105                 110

Leu Val Gly Asn Lys Cys Asp Leu Glu Asp Glu Arg Val Val Gly Lys
            115                 120                 125

Glu Gln Gly Gln Asn Leu Ala Arg Gln Trp Cys Asn Cys Ala Phe Leu
130                 135                 140

Glu Ser Ser Ala Lys Ser Lys Ile Asn Val Asn Glu Ile Phe Tyr Asp
145                 150                 155                 160

Leu Val Arg Gln Ile Asn Arg Lys Thr Pro Val Glu Lys Lys Lys Pro
                165                 170                 175

Lys Lys Lys Ser Cys Leu Leu Leu
                180
```

<210> SEQ ID NO 124
<211> LENGTH: 193
<212> TYPE: PRT
<213> ORGANISM: Homo sapiens
<220> FEATURE:
<223> OTHER INFORMATION: RhoA

<400> SEQUENCE: 124

```
Met Ala Ala Ile Arg Lys Lys Leu Val Ile Val Gly Asp Gly Ala Cys
 1               5                  10                  15

Gly Lys Thr Cys Leu Leu Ile Val Phe Ser Lys Asp Gln Phe Pro Glu
                 20                  25                  30

Val Tyr Val Pro Thr Val Phe Glu Asn Tyr Val Ala Asp Ile Glu Val
             35                  40                  45

Asp Gly Lys Gln Val Glu Leu Ala Leu Trp Asp Thr Ala Gly Gln Glu
 50                  55                  60

Asp Tyr Asp Arg Leu Arg Pro Leu Ser Tyr Pro Asp Thr Asp Val Ile
 65                  70                  75                  80

Leu Met Cys Phe Ser Ile Asp Ser Pro Asp Ser Leu Glu Asn Ile Pro
                 85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Glu His Thr Arg
            115                 120                 125

Arg Glu Leu Ala Lys Met Lys Gln Glu Pro Val Lys Pro Glu Glu Gly
130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Lys Ser Gly Cys Leu Val
            180                 185                 190

Leu
```

<210> SEQ ID NO 125
<211> LENGTH: 191

<212> TYPE: PRT
<213> ORGANISM: Homo sapiens
<220> FEATURE:
<223> OTHER INFORMATION: CDC42

<400> SEQUENCE: 125

Met Gln Thr Ile Lys Cys Val Val Val Gly Asp Gly Ala Val Gly Lys
1               5                   10                  15

Thr Cys Leu Leu Ile Ser Tyr Thr Thr Asn Lys Phe Pro Ser Glu Tyr
            20                  25                  30

Val Pro Thr Val Phe Asp Asn Tyr Ala Val Thr Val Met Ile Gly Gly
        35                  40                  45

Glu Pro Tyr Thr Leu Gly Leu Phe Asp Thr Ala Gly Gln Glu Asp Tyr
    50                  55                  60

Asp Arg Leu Arg Pro Leu Ser Tyr Pro Gln Thr Asp Val Phe Leu Val
65                  70                  75                  80

Cys Phe Ser Val Val Ser Pro Ser Ser Phe Glu Asn Val Lys Glu Lys
                85                  90                  95

Trp Val Pro Glu Ile Thr His His Cys Pro Lys Thr Pro Phe Leu Leu
            100                 105                 110

Val Gly Thr Gln Ile Asp Leu Arg Asp Asp Pro Ser Thr Ile Glu Lys
        115                 120                 125

Leu Ala Lys Asn Lys Gln Lys Pro Ile Thr Pro Glu Thr Ala Glu Lys
    130                 135                 140

Leu Ala Arg Asp Leu Lys Ala Val Lys Tyr Val Glu Cys Ser Ala Leu
145                 150                 155                 160

Thr Gln Lys Gly Leu Lys Asn Val Phe Asp Glu Ala Ile Leu Ala Ala
                165                 170                 175

Leu Glu Pro Pro Glu Pro Lys Lys Ser Arg Arg Cys Val Leu Leu
            180                 185                 190

<210> SEQ ID NO 126
<211> LENGTH: 255
<212> TYPE: DNA
<213> ORGANISM: Homo sapiens
<220> FEATURE:
<223> OTHER INFORMATION: BAFFR signaling domain

<400> SEQUENCE: 126
tcctggagac ggcgacaaag gcgcttgcgc ggcgcatcat ccgcagaggc gcccgacggc      60
gataaggacg cgcccgaacc ccttgataaa gttattatct tgtcaccggg aatttctgac     120
gctacggcac ccgcgtggcc tcctccgggc gaagatcctg gtacgacacc ccctggacac     180
agtgttcccg tgcccgcgac agagctcggt agcacagaac tggtgaccac aaagacggcg     240
ggaccggaac agcaa                                                      255

<210> SEQ ID NO 127
<211> LENGTH: 156
<212> TYPE: DNA
<213> ORGANISM: Homo sapiens
<220> FEATURE:
<223> OTHER INFORMATION: DAP12 signaling domain

<400> SEQUENCE: 127
tattttctgg gaaggctcgt tcctagaggt agaggtgctg ccgaagcagc gacgcgcaaa      60
cagaggatta ctgaaacgga gtctccctac caagagctgc aaggccagag gtcagatgtc     120
tattcagact tgaacacaca aggccatac tacaaa                                156

<210> SEQ ID NO 128
<211> LENGTH: 135
<212> TYPE: DNA
<213> ORGANISM: Homo sapiens
<220> FEATURE:
<223> OTHER INFORMATION: CD79b signaling domain

<400> SEQUENCE: 128

```
gacagtaaag ccgggatgga agaggaccac acatacgagg ggcttgacat agatcaaaca    60
gcgacatacg aagacatcgt aaccttgcgg actggagagg ttaaatggtc agtcggagaa   120
caccccggcc aagaa                                                   135
```

<210> SEQ ID NO 129
<211> LENGTH: 258
<212> TYPE: DNA
<213> ORGANISM: Homo sapiens
<220> FEATURE:
<223> OTHER INFORMATION: NFAM1 signaling domain

<400> SEQUENCE: 129

```
ctctggaata aaaagaggat gcgcggcccg ggaaaagacc caacgagaaa gtgtcccgat    60
ccccgcagtg cgtcaagccc caagcagcat ccttccgaaa gcgtatatac ggcacttcaa   120
cgccgggaaa cggaggtata tgcgtgtatt gagaacgagg acgggtcatc cccgaccgcc   180
aaacagtccc ctctcagcca agagcgacct cacaggtttg aggacgatgg tgaactcaat   240
ctggtctacg aaaacctg                                                 258
```

<210> SEQ ID NO 130
<211> LENGTH: 540
<212> TYPE: PRT
<213> ORGANISM: Artificial Sequence
<220> FEATURE:
<223> OTHER INFORMATION: Tim4-BAFFR-tMyD88 CER87 chimeric engulfment
      receptor
<220> FEATURE:
<221> NAME/KEY: SIGNAL
<222> LOCATION: (1)...(22)

<400> SEQUENCE: 130

```
Met Ser Lys Gly Leu Leu Leu Trp Leu Val Thr Glu Leu Trp Trp
        -20             -15                 -10

Leu Tyr Leu Thr Pro Ala Ala Ser Glu Asp Thr Ile Ile Gly Phe Leu
    -5                   1               5                  10

Gly Gln Pro Val Thr Leu Pro Cys His Tyr Leu Ser Trp Ser Gln Ser
                 15                  20                  25

Arg Asn Ser Met Cys Trp Gly Lys Gly Ser Cys Pro Asn Ser Lys Cys
             30                  35                  40

Asn Ala Glu Leu Leu Arg Thr Asp Gly Thr Arg Ile Ile Ser Arg Lys
         45                  50                  55

Ser Thr Lys Tyr Thr Leu Leu Gly Lys Val Gln Phe Gly Glu Val Ser
     60                  65                  70

Leu Thr Ile Ser Asn Thr Asn Arg Gly Asp Ser Gly Val Tyr Cys Cys
 75                  80                  85                  90

Arg Ile Glu Val Pro Gly Trp Phe Asn Asp Val Lys Lys Asn Val Arg
                 95                 100                 105

Leu Glu Leu Arg Arg Ala Thr Thr Thr Lys Lys Pro Thr Thr Thr
                110                 115                 120

Arg Pro Thr Thr Thr Pro Tyr Val Thr Thr Thr Pro Glu Leu Leu
                125                 130                 135
```

```
Pro Thr Thr Val Met Thr Thr Ser Val Leu Pro Thr Thr Pro Pro
    140                 145                 150

Gln Thr Leu Ala Thr Thr Ala Phe Ser Thr Ala Val Thr Cys Pro
155                 160                 165                 170

Ser Thr Thr Pro Gly Ser Phe Ser Gln Glu Thr Thr Lys Gly Ser Ala
                175                 180                 185

Phe Thr Thr Glu Ser Glu Thr Leu Pro Ala Ser Asn His Ser Gln Arg
                190                 195                 200

Ser Met Met Thr Ile Ser Thr Asp Ile Ala Val Leu Arg Pro Thr Gly
                205                 210                 215

Ser Asn Pro Gly Ile Leu Pro Ser Thr Ser Gln Leu Thr Thr Gln Lys
    220                 225                 230

Thr Thr Leu Thr Thr Ser Glu Ser Leu Gln Lys Thr Thr Lys Ser His
235                 240                 245                 250

Gln Ile Asn Ser Arg Gln Thr Ile Leu Ile Ile Ala Cys Cys Val Gly
                255                 260                 265

Phe Val Leu Met Val Leu Leu Phe Leu Ala Phe Leu Ser Trp Arg Arg
                270                 275                 280

Arg Gln Arg Arg Leu Arg Gly Ala Ser Ser Ala Glu Ala Pro Asp Gly
    285                 290                 295

Asp Lys Asp Ala Pro Glu Pro Leu Asp Lys Val Ile Ile Leu Ser Pro
300                 305                 310

Gly Ile Ser Asp Ala Thr Ala Pro Ala Trp Pro Pro Pro Gly Glu Asp
315                 320                 325                 330

Pro Gly Thr Thr Pro Pro Gly His Ser Val Pro Val Pro Ala Thr Glu
                335                 340                 345

Leu Gly Ser Thr Glu Leu Val Thr Thr Lys Thr Ala Gly Pro Glu Gln
                350                 355                 360

Gln Met Ala Ala Gly Gly Pro Gly Ala Gly Ser Ala Ala Pro Val Ser
                365                 370                 375

Ser Thr Ser Ser Leu Pro Leu Ala Ala Leu Asn Met Arg Val Arg Arg
    380                 385                 390

Arg Leu Ser Leu Phe Leu Asn Val Arg Thr Gln Val Ala Ala Asp Trp
395                 400                 405                 410

Thr Ala Leu Ala Glu Glu Met Asp Phe Glu Tyr Leu Glu Ile Arg Gln
                415                 420                 425

Leu Glu Thr Gln Ala Asp Pro Thr Gly Arg Leu Leu Asp Ala Trp Gln
                430                 435                 440

Gly Arg Pro Gly Ala Ser Val Gly Arg Leu Leu Glu Leu Leu Thr Lys
                445                 450                 455

Leu Gly Arg Asp Asp Val Leu Leu Glu Leu Gly Pro Ser Ile Glu Glu
460                 465                 470

Asp Cys Gln Lys Tyr Ile Leu Lys Gln Gln Glu Glu Ala Glu Lys
475                 480                 485                 490

Pro Leu Gln Val Ala Ala Val Asp Ser Ser Val Pro Arg Thr Ala Glu
                495                 500                 505

Leu Ala Gly Ile Thr Thr Leu Asp Asp Pro Leu Gly
                510                 515
```

<210> SEQ ID NO 131
<211> LENGTH: 507
<212> TYPE: PRT
<213> ORGANISM: Artificial Sequence
<220> FEATURE:

<223> OTHER INFORMATION: Tim4-DAP12-tMyD88 CER88 chimeric engulfment
      receptor
<220> FEATURE:
<221> NAME/KEY: SIGNAL
<222> LOCATION: (1)...(22)

<400> SEQUENCE: 131

Met Ser Lys Gly Leu Leu Leu Trp Leu Val Thr Glu Leu Trp Trp
        -20              -15              -10

Leu Tyr Leu Thr Pro Ala Ala Ser Glu Asp Thr Ile Ile Gly Phe Leu
        -5               1               5                    10

Gly Gln Pro Val Thr Leu Pro Cys His Tyr Leu Ser Trp Ser Gln Ser
                15              20              25

Arg Asn Ser Met Cys Trp Gly Lys Gly Ser Cys Pro Asn Ser Lys Cys
                30              35              40

Asn Ala Glu Leu Leu Arg Thr Asp Gly Thr Arg Ile Ile Ser Arg Lys
            45              50              55

Ser Thr Lys Tyr Thr Leu Leu Gly Lys Val Gln Phe Gly Glu Val Ser
    60              65              70

Leu Thr Ile Ser Asn Thr Asn Arg Gly Asp Ser Gly Val Tyr Cys Cys
75              80              85              90

Arg Ile Glu Val Pro Gly Trp Phe Asn Asp Val Lys Lys Asn Val Arg
                95              100             105

Leu Glu Leu Arg Arg Ala Thr Thr Thr Lys Lys Pro Thr Thr Thr Thr
            110             115             120

Arg Pro Thr Thr Thr Pro Tyr Val Thr Thr Thr Pro Glu Leu Leu
        125             130             135

Pro Thr Thr Val Met Thr Thr Ser Val Leu Pro Thr Thr Thr Pro Pro
    140             145             150

Gln Thr Leu Ala Thr Thr Ala Phe Ser Thr Ala Val Thr Thr Cys Pro
155             160             165             170

Ser Thr Thr Pro Gly Ser Phe Ser Gln Glu Thr Thr Lys Gly Ser Ala
                175             180             185

Phe Thr Thr Glu Ser Glu Thr Leu Pro Ala Ser Asn His Ser Gln Arg
            190             195             200

Ser Met Met Thr Ile Ser Thr Asp Ile Ala Val Leu Arg Pro Thr Gly
        205             210             215

Ser Asn Pro Gly Ile Leu Pro Ser Thr Ser Gln Leu Thr Thr Gln Lys
        220             225             230

Thr Thr Leu Thr Thr Ser Glu Ser Leu Gln Lys Thr Thr Lys Ser His
235             240             245             250

Gln Ile Asn Ser Arg Gln Thr Ile Leu Ile Ile Ala Cys Cys Val Gly
                255             260             265

Phe Val Leu Met Val Leu Leu Phe Leu Ala Phe Leu Tyr Phe Leu Gly
                270             275             280

Arg Leu Val Pro Arg Gly Arg Gly Ala Ala Glu Ala Ala Thr Arg Lys
            285             290             295

Gln Arg Ile Thr Glu Thr Glu Ser Pro Tyr Gln Glu Leu Gln Gly Gln
        300             305             310

Arg Ser Asp Val Tyr Ser Asp Leu Asn Thr Gln Arg Pro Tyr Tyr Lys
315             320             325             330

Met Ala Ala Gly Gly Pro Gly Ala Gly Ser Ala Ala Pro Val Ser Ser
                335             340             345

Thr Ser Ser Leu Pro Leu Ala Ala Leu Asn Met Arg Val Arg Arg Arg
            350             355             360

```
Leu Ser Leu Phe Leu Asn Val Arg Thr Gln Val Ala Ala Asp Trp Thr
        365                 370                 375

Ala Leu Ala Glu Glu Met Asp Phe Glu Tyr Leu Glu Ile Arg Gln Leu
        380                 385                 390

Glu Thr Gln Ala Asp Pro Thr Gly Arg Leu Leu Asp Ala Trp Gln Gly
395                 400                 405                 410

Arg Pro Gly Ala Ser Val Gly Arg Leu Leu Glu Leu Leu Thr Lys Leu
                415                 420                 425

Gly Arg Asp Asp Val Leu Leu Glu Leu Gly Pro Ser Ile Glu Glu Asp
                430                 435                 440

Cys Gln Lys Tyr Ile Leu Lys Gln Gln Gln Glu Ala Glu Lys Pro
                445                 450                 455

Leu Gln Val Ala Ala Val Asp Ser Ser Val Pro Arg Thr Ala Glu Leu
        460                 465                 470

Ala Gly Ile Thr Thr Leu Asp Asp Pro Leu Gly
475                 480                 485

<210> SEQ ID NO 132
<211> LENGTH: 53
<212> TYPE: PRT
<213> ORGANISM: Homo sapiens
<220> FEATURE:
<223> OTHER INFORMATION: truncated NFAM1 signaling domain

<400> SEQUENCE: 132

Leu Trp Asn Lys Lys Arg Met Arg Gly Pro Gly Lys Asp Pro Thr Arg
1               5                   10                  15

Lys Cys Pro Asp Pro Arg Ser Ala Ser Ser Pro Lys Gln His Pro Ser
            20                  25                  30

Glu Ser Val Tyr Thr Ala Leu Gln Arg Arg Glu Thr Glu Val Tyr Ala
        35                  40                  45

Cys Ile Glu Asn Glu
    50

<210> SEQ ID NO 133
<211> LENGTH: 931
<212> TYPE: PRT
<213> ORGANISM: Artificial Sequence
<220> FEATURE:
<223> OTHER INFORMATION: TIM4-MERTK-tMYD88 CER92 chimeric engulfment
      receptor
<220> FEATURE:
<221> NAME/KEY: SIGNAL
<222> LOCATION: (1)...(22)

<400> SEQUENCE: 133

Met Ser Lys Gly Leu Leu Leu Leu Trp Leu Val Thr Glu Leu Trp Trp
        -20                 -15                 -10

Leu Tyr Leu Thr Pro Ala Ala Ser Glu Asp Thr Ile Ile Gly Phe Leu
    -5                  1                   5                   10

Gly Gln Pro Val Thr Leu Pro Cys His Tyr Leu Ser Trp Ser Gln Ser
                15                  20                  25

Arg Asn Ser Met Cys Trp Gly Lys Gly Ser Cys Pro Asn Ser Lys Cys
            30                  35                  40

Asn Ala Glu Leu Leu Arg Thr Asp Gly Thr Arg Ile Ile Ser Arg Lys
        45                  50                  55

Ser Thr Lys Tyr Thr Leu Leu Gly Lys Val Gln Phe Gly Glu Val Ser
    60                  65                  70
```

-continued

```
Leu Thr Ile Ser Asn Thr Asn Arg Gly Asp Ser Gly Val Tyr Cys Cys
 75                  80                  85                  90

Arg Ile Glu Val Pro Gly Trp Phe Asn Asp Val Lys Lys Asn Val Arg
                 95                 100                 105

Leu Glu Leu Arg Arg Ala Thr Thr Thr Lys Lys Pro Thr Thr Thr Thr
            110                 115                 120

Arg Pro Thr Thr Thr Pro Tyr Val Thr Thr Thr Thr Pro Glu Leu Leu
        125                 130                 135

Pro Thr Thr Val Met Thr Thr Ser Val Leu Pro Thr Thr Thr Pro Pro
    140                 145                 150

Gln Thr Leu Ala Thr Thr Ala Phe Ser Thr Ala Val Thr Thr Cys Pro
155                 160                 165                 170

Ser Thr Thr Pro Gly Ser Phe Ser Gln Glu Thr Thr Lys Gly Ser Ala
                175                 180                 185

Phe Thr Thr Glu Ser Glu Thr Leu Pro Ala Ser Asn His Ser Gln Arg
            190                 195                 200

Ser Met Met Thr Ile Ser Thr Asp Ile Ala Val Leu Arg Pro Thr Gly
        205                 210                 215

Ser Asn Pro Gly Ile Leu Pro Ser Thr Ser Gln Leu Thr Thr Gln Lys
    220                 225                 230

Thr Thr Leu Thr Thr Ser Glu Ser Leu Gln Lys Thr Thr Lys Ser His
235                 240                 245                 250

Gln Ile Asn Ser Arg Gln Thr Ile Leu Ile Ile Ala Cys Cys Val Gly
                255                 260                 265

Phe Val Leu Met Val Leu Leu Phe Leu Ala Phe Leu Ala Leu Arg Arg
            270                 275                 280

Arg Val Gln Glu Thr Lys Phe Gly Gly Ala Phe Ser Glu Glu Asp Ser
        285                 290                 295

Gln Leu Val Val Asn Tyr Arg Ala Lys Lys Ser Phe Cys Arg Arg Ala
    300                 305                 310

Ile Glu Leu Thr Leu Gln Ser Leu Gly Val Ser Glu Glu Leu Gln Asn
315                 320                 325                 330

Lys Leu Glu Asp Val Val Ile Asp Arg Asn Leu Leu Val Leu Gly Lys
                335                 340                 345

Val Leu Gly Glu Gly Glu Phe Gly Ser Val Met Glu Gly Asn Leu Lys
            350                 355                 360

Gln Glu Asp Gly Thr Ser Gln Lys Val Ala Val Lys Thr Met Lys Leu
        365                 370                 375

Asp Asn Phe Ser Gln Arg Glu Ile Glu Glu Phe Leu Ser Glu Ala Ala
    380                 385                 390

Cys Met Lys Asp Phe Asn His Pro Asn Val Ile Arg Leu Leu Gly Val
395                 400                 405                 410

Cys Ile Glu Leu Ser Ser Gln Gly Ile Pro Lys Pro Met Val Ile Leu
                415                 420                 425

Pro Phe Met Lys Tyr Gly Asp Leu His Thr Phe Leu Leu Tyr Ser Arg
            430                 435                 440

Leu Asn Thr Gly Pro Lys Tyr Ile His Leu Gln Thr Leu Leu Lys Phe
        445                 450                 455

Met Met Asp Ile Ala Gln Gly Met Glu Tyr Leu Ser Asn Arg Asn Phe
    460                 465                 470

Leu His Arg Asp Leu Ala Ala Arg Asn Cys Met Leu Arg Asp Asp Met
475                 480                 485                 490

Thr Val Cys Val Ala Asp Phe Gly Leu Ser Lys Lys Ile Tyr Ser Gly
```

-continued

```
               495                 500                 505
Asp Tyr Tyr Arg Gln Gly Arg Ile Ala Lys Met Pro Val Lys Trp Ile
            510                 515                 520

Ala Ile Glu Ser Leu Ala Asp Arg Val Tyr Thr Ser Lys Ser Asp Val
            525                 530                 535

Trp Ala Phe Gly Val Thr Met Trp Glu Ile Thr Thr Arg Gly Met Thr
540                 545                 550

Pro Tyr Pro Gly Val Gln Asn His Glu Met Tyr Asp Tyr Leu Leu His
555                 560                 565                 570

Gly His Arg Leu Lys Gln Pro Glu Asp Cys Leu Asp Glu Leu Tyr Asp
                575                 580                 585

Ile Met Tyr Ser Cys Trp Ser Ala Asp Pro Leu Asp Arg Pro Thr Phe
                590                 595                 600

Ser Val Leu Arg Leu Gln Leu Glu Lys Leu Ser Glu Ser Leu Pro Asp
                605                 610                 615

Ala Gln Asp Lys Glu Ser Ile Ile Tyr Ile Asn Thr Gln Leu Leu Glu
                620                 625                 630

Ser Cys Glu Gly Ile Ala Asn Gly Pro Ser Leu Thr Gly Leu Asp Met
635                 640                 645                 650

Asn Ile Asp Pro Asp Ser Ile Ile Ala Ser Cys Thr Pro Gly Ala Ala
                    655                 660                 665

Val Ser Val Val Thr Ala Glu Val His Glu Asn Asn Leu Arg Glu Glu
                670                 675                 680

Arg Tyr Ile Leu Asn Gly Gly Asn Glu Glu Trp Glu Asp Val Ser Ser
                685                 690                 695

Thr Pro Phe Ala Ala Val Thr Pro Glu Lys Asp Gly Val Leu Pro Glu
700                 705                 710

Asp Arg Leu Thr Lys Asn Gly Val Ser Trp Ser His His Ser Thr Leu
715                 720                 725                 730

Pro Leu Gly Ser Pro Ser Pro Asp Glu Leu Leu Phe Val Asp Asp Ser
                735                 740                 745

Leu Glu Asp Ser Glu Val Leu Met Met Ala Ala Gly Gly Pro Gly Ala
                750                 755                 760

Gly Ser Ala Ala Pro Val Ser Ser Thr Ser Ser Leu Pro Leu Ala Ala
                765                 770                 775

Leu Asn Met Arg Val Arg Arg Arg Leu Ser Leu Phe Leu Asn Val Arg
                780                 785                 790

Thr Gln Val Ala Ala Asp Trp Thr Ala Leu Ala Glu Glu Met Asp Phe
795                 800                 805                 810

Glu Tyr Leu Glu Ile Arg Gln Leu Glu Thr Gln Ala Asp Pro Thr Gly
                815                 820                 825

Arg Leu Leu Asp Ala Trp Gln Gly Arg Pro Gly Ala Ser Val Gly Arg
                830                 835                 840

Leu Leu Glu Leu Leu Thr Lys Leu Gly Arg Asp Asp Val Leu Leu Glu
                845                 850                 855

Leu Gly Pro Ser Ile Glu Glu Asp Cys Gln Lys Tyr Ile Leu Lys Gln
                860                 865                 870

Gln Gln Glu Glu Ala Glu Lys Pro Leu Gln Val Ala Ala Val Asp Ser
875                 880                 885                 890

Ser Val Pro Arg Thr Ala Glu Leu Ala Gly Ile Thr Thr Leu Asp Asp
                895                 900                 905

Pro Leu Gly
```

<210> SEQ ID NO 134
<211> LENGTH: 828
<212> TYPE: PRT
<213> ORGANISM: Artificial Sequence
<220> FEATURE:
<223> OTHER INFORMATION: TIM4-MERTK-DAP12 CER94 chimeric engulfment receptor
<220> FEATURE:
<221> NAME/KEY: SIGNAL
<222> LOCATION: (1)...(22)

<400> SEQUENCE: 134

```
Met Ser Lys Gly Leu Leu Leu Trp Leu Val Thr Glu Leu Trp Trp
        -20              -15                 -10

Leu Tyr Leu Thr Pro Ala Ala Ser Glu Asp Thr Ile Ile Gly Phe Leu
        -5                1              5                    10

Gly Gln Pro Val Thr Leu Pro Cys His Tyr Leu Ser Trp Ser Gln Ser
                15                  20                  25

Arg Asn Ser Met Cys Trp Gly Lys Gly Ser Cys Pro Asn Ser Lys Cys
                30                  35                  40

Asn Ala Glu Leu Leu Arg Thr Asp Gly Thr Arg Ile Ile Ser Arg Lys
            45                  50                  55

Ser Thr Lys Tyr Thr Leu Leu Gly Lys Val Gln Phe Gly Glu Val Ser
    60                  65                  70

Leu Thr Ile Ser Asn Thr Asn Arg Gly Asp Ser Gly Val Tyr Cys Cys
75                  80                  85                  90

Arg Ile Glu Val Pro Gly Trp Phe Asn Asp Val Lys Lys Asn Val Arg
                95                  100                 105

Leu Glu Leu Arg Arg Ala Thr Thr Thr Lys Lys Pro Thr Thr Thr Thr
            110                 115                 120

Arg Pro Thr Thr Thr Pro Tyr Val Thr Thr Thr Pro Glu Leu Leu
                125                 130                 135

Pro Thr Thr Val Met Thr Thr Ser Val Leu Pro Thr Thr Thr Pro Pro
        140                 145                 150

Gln Thr Leu Ala Thr Thr Ala Phe Ser Thr Ala Val Thr Thr Cys Pro
155                 160                 165                 170

Ser Thr Thr Pro Gly Ser Phe Ser Gln Glu Thr Thr Lys Gly Ser Ala
                175                 180                 185

Phe Thr Thr Glu Ser Glu Thr Leu Pro Ala Ser Asn His Ser Gln Arg
                190                 195                 200

Ser Met Met Thr Ile Ser Thr Asp Ile Ala Val Leu Arg Pro Thr Gly
                205                 210                 215

Ser Asn Pro Gly Ile Leu Pro Ser Thr Ser Gln Leu Thr Thr Gln Lys
            220                 225                 230

Thr Thr Leu Thr Thr Ser Glu Ser Leu Gln Lys Thr Thr Lys Ser His
235                 240                 245                 250

Gln Ile Asn Ser Arg Gln Thr Ile Leu Ile Ala Cys Cys Val Gly
                255                 260                 265

Phe Val Leu Met Val Leu Leu Phe Leu Ala Phe Leu Ala Leu Arg Arg
                270                 275                 280

Arg Val Gln Glu Thr Lys Phe Gly Gly Ala Phe Ser Glu Glu Asp Ser
                285                 290                 295

Gln Leu Val Val Asn Tyr Arg Ala Lys Lys Ser Phe Cys Arg Arg Ala
            300                 305                 310

Ile Glu Leu Thr Leu Gln Ser Leu Gly Val Ser Glu Glu Leu Gln Asn
315                 320                 325                 330
```

```
Lys Leu Glu Asp Val Val Ile Asp Arg Asn Leu Val Leu Gly Lys
                335             340             345

Val Leu Gly Glu Gly Glu Phe Gly Ser Val Met Glu Gly Asn Leu Lys
            350             355             360

Gln Glu Asp Gly Thr Ser Gln Lys Val Ala Val Lys Thr Met Lys Leu
        365             370             375

Asp Asn Phe Ser Gln Arg Glu Ile Glu Glu Phe Leu Ser Glu Ala Ala
    380             385             390

Cys Met Lys Asp Phe Asn His Pro Asn Val Ile Arg Leu Leu Gly Val
395             400             405             410

Cys Ile Glu Leu Ser Ser Gln Gly Ile Pro Lys Pro Met Val Ile Leu
            415             420             425

Pro Phe Met Lys Tyr Gly Asp Leu His Thr Phe Leu Leu Tyr Ser Arg
        430             435             440

Leu Asn Thr Gly Pro Lys Tyr Ile His Leu Gln Thr Leu Leu Lys Phe
            445             450             455

Met Met Asp Ile Ala Gln Gly Met Glu Tyr Leu Ser Asn Arg Asn Phe
        460             465             470

Leu His Arg Asp Leu Ala Ala Arg Asn Cys Met Leu Arg Asp Asp Met
475             480             485             490

Thr Val Cys Val Ala Asp Phe Gly Leu Ser Lys Lys Ile Tyr Ser Gly
            495             500             505

Asp Tyr Tyr Arg Gln Gly Arg Ile Ala Lys Met Pro Val Lys Trp Ile
            510             515             520

Ala Ile Glu Ser Leu Ala Asp Arg Val Tyr Thr Ser Lys Ser Asp Val
        525             530             535

Trp Ala Phe Gly Val Thr Met Trp Glu Ile Thr Thr Arg Gly Met Thr
        540             545             550

Pro Tyr Pro Gly Val Gln Asn His Glu Met Tyr Asp Tyr Leu Leu His
555             560             565             570

Gly His Arg Leu Lys Gln Pro Glu Asp Cys Leu Asp Glu Leu Tyr Asp
            575             580             585

Ile Met Tyr Ser Cys Trp Ser Ala Asp Pro Leu Asp Arg Pro Thr Phe
            590             595             600

Ser Val Leu Arg Leu Gln Leu Glu Lys Leu Ser Glu Ser Leu Pro Asp
        605             610             615

Ala Gln Asp Lys Glu Ser Ile Ile Tyr Ile Asn Thr Gln Leu Leu Glu
        620             625             630

Ser Cys Glu Gly Ile Ala Asn Gly Pro Ser Leu Thr Gly Leu Asp Met
635             640             645             650

Asn Ile Asp Pro Asp Ser Ile Ile Ala Ser Cys Thr Pro Gly Ala Ala
            655             660             665

Val Ser Val Val Thr Ala Glu Val His Glu Asn Asn Leu Arg Glu Glu
            670             675             680

Arg Tyr Ile Leu Asn Gly Gly Asn Glu Glu Trp Glu Asp Val Ser Ser
            685             690             695

Thr Pro Phe Ala Ala Val Thr Pro Glu Lys Asp Gly Val Leu Pro Glu
    700             705             710

Asp Arg Leu Thr Lys Asn Gly Val Ser Trp Ser His Ser Thr Leu
715             720             725             730

Pro Leu Gly Ser Pro Ser Pro Asp Glu Leu Leu Phe Val Asp Asp Ser
            735             740             745
```

| Leu | Glu | Asp | Ser | Glu | Val | Leu | Met | Tyr | Phe | Leu | Gly | Arg | Leu | Val | Pro |
| | | | 750 | | | | | 755 | | | | | 760 | | |

| Arg | Gly | Arg | Gly | Ala | Ala | Glu | Ala | Ala | Thr | Arg | Lys | Gln | Arg | Ile | Thr |
| | | | 765 | | | | | 770 | | | | | 775 | | |

| Glu | Thr | Glu | Ser | Pro | Tyr | Gln | Glu | Leu | Gln | Gly | Gln | Arg | Ser | Asp | Val |
| | | | 780 | | | | | 785 | | | | | 790 | | |

| Tyr | Ser | Asp | Leu | Asn | Thr | Gln | Arg | Pro | Tyr | Tyr | Lys |
| 795 | | | | | 800 | | | | | 805 | |

<210> SEQ ID NO 135
<211> LENGTH: 2754
<212> TYPE: DNA
<213> ORGANISM: Homo sapiens
<220> FEATURE:
<223> OTHER INFORMATION: BAI1 binding domain

<400> SEQUENCE: 135

```
gccgccggag cagacgcggg gcccgggccc gagccgtgcg ccacgctggt gcagggaaag      60
ttcttcggct acttctccgc ggccgccgtg ttcccggcca acgcctcgcg ctgctcctgg     120
acgctacgca acccggaccc gcggcgctac actctctaca tgaaggtggc caaggcgccc     180
gtgccctgca gcggccccgg ccgcgtgcgc acctaccagt tcgactcctt cctcgagtcc     240
acgcgcacct acctgggcgt ggagagcttc gacgaggtgc tgcggctctg cgaccccgcc     300
gcacccctgg cctcctgca ggccagcaag cagttcctgc agatgcgcg ccagcagccg      360
ccccagcacg acgggctccg gccccgggcc gggccgccgg ccccaccga cgacttctcc     420
gtggagtacc tggtggtggg gaaccgcaac cccagccgtg ccgcctgcca gatgctgtgc     480
cgctggctgg acgcgtgtct ggccggtagt cgcagctcgc accctgcgg gatcatgcag     540
accccctgcg cctgcctggg cggcgaggcg ggcggccctg ccgcgggacc cctggccccc     600
cgcggggatg tctgcttgag agatgcggtg gctggtggcc ctgaaaactg cctcaccagc     660
ctgacccagg accggggcgg gcacggcgcc acaggcggct ggaagctgtg gtccctgtgg     720
ggcgaatgca cgcgggactg cgggggaggc ctccagacgc ggacgcgcac ctgcctgccc     780
gcgccggggcg tggagggcgg cggctgcgag ggggtgctgg aggagggtcg ccagtgcaac     840
cgcgaggcct gcggccccgc tgggcgcacc agctcccgga gccagtccct gcggtccaca     900
gatgcccggc ggcgcgagga gctggggggac gagctgcagc agtttgggtt cccagccccc     960
cagaccggtg acccagcagc cgaggagtgg tccccgtgga gcgtgtgctc cagcacctgc    1020
ggcgagggct ggcagacccg cacgcgcttc tgcgtgtcct cctcctacag cacgcagtgc    1080
agcggacccc tgcgcgagca gcggctgtgc aacaactctg ccgtgtgccc agtgcatggt    1140
gcctgggatg agtggtcgcc ctggagcctc tgctccagca cctgtggccg tggcttcgg    1200
gatcgcacgc gcacctgcag gccccccag tttgggggca accctgtga gggccctgag    1260
aagcaaacca agttctgcaa cattgccctg tgccctggcc gggcagtgga tggaaactgg    1320
aatgagtggt cgagctggag cgcctgctcc gccagctgct cccagggccg acagcagcgc    1380
acgcgtgaat gcaacgggcc ttcctacggg ggtgcggagt gccagggcca ctgggtggag    1440
acccgagact gcttcctgca gcagtgccca gtggatggca gtggcaggc ctgggcgtca    1500
tggggcagtt gcagcgtcac gtgtggggct ggcagccagc gacgggagcg tgtctgctct    1560
gggccctct tcggggagc agcctgccag ggccccagg atgagtaccg gcagtgcggc    1620
acccagcggg tcccgagcc ccatgagatc tgtgatgagg acaactttgg tgctgtgatc    1680
tggaaggaga ccccagcggg agaggtggct gctgtccggt gtccccgcaa cgccacagga    1740
```

```
ctcatcctgc gacggtgtga gctggacgag gaaggcatcg cctactggga gccccccacc   1800
tacatccgct gtgtttccat tgactacaga aacatccaga tgatgacccg ggagcacctg   1860
gccaaggctc agcgagggct gcctggggag ggggtctcgg aggtcatcca gacactggtg   1920
gagatctctc aggacgggac cagctacagt ggggacctgc tgtccaccat cgatgtcctg   1980
aggaacatga cagagatttt ccggagagcg tactacagcc ccacccctgg ggacgtacag   2040
aactttgtcc agatccttag caacctgttg gcagaggaga atcgggacaa gtgggaggag   2100
gcccagctgg cgggccccaa cgccaaggag ctgttccggc tggtggagga ctttgtggac   2160
gtcatcggct ccgcatgaa ggacctgagg gatgcatacc aggtgacaga caacctggtt   2220
ctcagcatcc ataagctccc agccagcgga gccactgaca tcagcttccc catgaagggc   2280
tggcgggcca cgggtgactg ggccaaggtg ccagaggaca gggtcactgt gtccaagagt   2340
gtcttctcca cggggctgac agaggccgat gaagcatccg tgtttgtggt gggcaccgtg   2400
ctctacagga acctgggcag cttcctggcc ctgcagagga acacgaccgt cctgaattct   2460
aaggtgatct ccgtgactgt gaaaccccg cctcgctccc tgcgcacacc cttggagatc   2520
gagtttgccc acatgtataa tggcaccacc aaccagacct gtatcctgtg ggatgagacg   2580 gatgtacct cctcctccgc cccccgcag ctcgggccct ggtcgtggcg cggctgccgc   2640
acggtgcccc tcgacgccct ccggacgcgc tgcctctgtg accggctctc caccttcgcc   2700
atcttagccc agctcagcgc cgacgcgaac atggagaagg cgactctgcc gtcg           2754
```

<210> SEQ ID NO 136
<211> LENGTH: 397
<212> TYPE: PRT
<213> ORGANISM: Homo sapiens
<220> FEATURE:
<223> OTHER INFORMATION: BAI1 signaling domain

<400> SEQUENCE: 136

```
Arg Arg Glu Val Gln Asp Ala Val Lys Cys Arg Val Val Asp Arg Gln
1               5                   10                  15

Glu Glu Gly Asn Gly Asp Ser Gly Gly Ser Phe Gln Asn Gly His Ala
            20                  25                  30

Gln Leu Met Thr Asp Phe Glu Lys Asp Val Asp Leu Ala Cys Arg Ser
        35                  40                  45

Val Leu Asn Lys Asp Ile Ala Ala Cys Arg Thr Ala Thr Ile Thr Gly
    50                  55                  60

Thr Leu Lys Arg Pro Ser Leu Pro Glu Glu Lys Leu Lys Leu Ala
65                  70                  75                  80

His Ala Lys Gly Pro Pro Thr Asn Phe Asn Ser Leu Pro Ala Asn Val
                85                  90                  95

Ser Lys Leu His Leu His Gly Ser Pro Arg Tyr Pro Gly Gly Pro Leu
            100                 105                 110

Pro Asp Phe Pro Asn His Ser Leu Thr Leu Lys Arg Asp Lys Ala Pro
        115                 120                 125

Lys Ser Ser Phe Val Gly Asp Gly Asp Ile Phe Lys Lys Leu Asp Ser
    130                 135                 140

Glu Leu Ser Arg Ala Gln Glu Lys Ala Leu Asp Thr Ser Tyr Val Ile
145                 150                 155                 160

Leu Pro Thr Ala Thr Ala Thr Leu Arg Pro Lys Pro Lys Glu Glu Pro
                165                 170                 175

Lys Tyr Ser Ile His Ile Asp Gln Met Pro Gln Thr Arg Leu Ile His
```

180                 185                 190
Leu Ser Thr Ala Pro Glu Ala Ser Leu Pro Ala Arg Ser Pro Pro Ser
                195                 200                 205
Arg Gln Pro Pro Ser Gly Gly Pro Glu Ala Pro Pro Ala Gln Pro
            210                 215                 220
Pro Pro Pro Pro Pro Pro Pro Pro Pro Gln Gln Pro Leu Pro
225                 230                 235                 240
Pro Pro Pro Asn Leu Glu Pro Ala Pro Ser Leu Gly Asp Pro Gly
                245                 250                 255
Glu Pro Ala Ala His Pro Gly Pro Ser Thr Gly Pro Ser Thr Lys Asn
                260                 265                 270
Glu Asn Val Ala Thr Leu Ser Val Ser Ser Leu Glu Arg Arg Lys Ser
                275                 280                 285
Arg Tyr Ala Glu Leu Asp Phe Glu Lys Ile Met His Thr Arg Lys Arg
                290                 295                 300
His Gln Asp Met Phe Gln Asp Leu Asn Arg Lys Leu Gln His Ala Ala
305                 310                 315                 320
Glu Lys Asp Lys Glu Val Leu Gly Pro Asp Ser Lys Pro Glu Lys Gln
                325                 330                 335
Gln Thr Pro Asn Lys Arg Pro Trp Glu Ser Leu Arg Lys Ala His Gly
                340                 345                 350
Thr Pro Thr Trp Val Lys Lys Glu Leu Glu Pro Leu Gln Pro Ser Pro
                355                 360                 365
Leu Glu Leu Arg Ser Val Glu Trp Gly Arg Ser Gly Ala Thr Ile Pro
                370                 375                 380
Leu Val Gly Gln Asp Ile Ile Asp Leu Gln Thr Glu Val
385                 390                 395

<210> SEQ ID NO 137
<211> LENGTH: 171
<212> TYPE: DNA
<213> ORGANISM: Homo sapiens
<220> FEATURE:
<223> OTHER INFORMATION: ItgB5 signaling domain

<400> SEQUENCE: 137
aagctgcttg tcaccatcca cgaccggagg gagtttgcaa agtttcagag cgagcgatcc      60
agggcccgct atgaaatggc ttcaaatcca ttatacagaa agcctatctc cacgcacact     120
gtggacttca ccttcaacaa gttcaacaaa tcctacaatg gcactgtgga c              171

<210> SEQ ID NO 138
<211> LENGTH: 1419
<212> TYPE: DNA
<213> ORGANISM: Homo sapiens
<220> FEATURE:
<223> OTHER INFORMATION: MERTK signaling domain

<400> SEQUENCE: 138
aaaagagtcc aggagacaaa gtttgggaat gcattcacag aggaggattc tgaattagtg      60
gtgaattata tagcaaagaa atccttctgt cggcgagcca ttgaacttac cttacatagc     120
ttgggagtca gtgaggaact acaaaataaa ctagaagatg ttgtgattga caggaatctt     180
ctaattcttg gaaaaattct gggtgaagga gagtttgggt ctgtaatgga aggaaatctt     240
aagcaggaag atgggacctc tctgaaagtg gcagtgaaga ccatgaagtt ggacaactct     300
tcacagcggg agatcgagga gtttctcagt gaggcagcgt gcatgaaaga cttcagccac     360

```
ccaaatgtca ttcgacttct aggtgtgtgt atagaaatga gctctcaagg catcccaaag    420
cccatggtaa ttttacccctt catgaaatac ggggacctgc atacttactt actttattcc    480
cgattggaga caggaccaaa gcatattcct ctgcagacac tattgaagtt catggtggat    540
attgccctgg gaatggagta tctgagcaac aggaattttc ttcatcgaga tttagctgct    600
cgaaactgca tgttgcgaga tgacatgact gtctgtgttg cggacttcgg cctctctaag    660
aagatttaca gtggcgatta ttaccgccaa ggccgcattg ctaagatgcc tgttaaatgg    720
atcgccatag aaagtcttgc agaccgagtc tacacaagta aaagtgatgt gtgggcattt    780
ggcgtgacca tgtgggaaat agctacgcgg ggaatgactc cctatcctgg ggtccagaac    840
catgagatgt atgactatct tctccatggc cacaggttga agcagcccga agactgcctg    900
gatgaactgt atgaaataat gtactcttgc tggagaaccg atcccttaga ccgcccacc    960 ttttcagtat tgaggctgca gctagaaaaa ctcttagaaa gtttgcctga cgttcggaac   1020
caagcagacg ttatttacgt caatacacag ttgctggaga gctctgaggg cctggcccag   1080
ggctccaccc ttgctccact ggacttgaac atcgaccctg actctataat tgcctcctgc   1140
actccccgcg ctgccatcag tgtggtcaca gcagaagttc atgacagcaa acctcatgaa   1200
ggacggtaca tcctgaatgg gggcagtgag gaatgggaag atctgacttc tgcccctct   1260 gctgcagtca cagctgaaaa gaacagtgtt ttaccggggg agagacttgt taggaatggg   1320
gtctcctggt cccattcgag catgctgccc ttgggaagct cattgcccga tgaactttg    1380 tttgctgacg actcctcaga aggctcagaa gtcctgatg                           1419

<210> SEQ ID NO 139
<211> LENGTH: 1191
<212> TYPE: DNA
<213> ORGANISM: Homo sapiens
<220> FEATURE:
<223> OTHER INFORMATION: BAI1 signaling domain

<400> SEQUENCE: 139
cgtagagagg tccaggacgc tgtgaaatgc cgtgtggttg accggcagga ggagggcaac     60
ggggactcag ggggctcctt ccagaacggc acgcccagc tcatgaccga cttcgagaag    120
gacgtggatc tggcctgtag atcagtgctg aacaaggaca tcgcggcctg ccgcactgcc    180
accatcacgg gcacactgaa gcggccgtct ctgcccgagg aggagaagct gaagctggcc    240
catgccaagg ggccgcccac caatttcaac agcctgccgg ccaacgtgtc caagctgcac    300
ctgcacggct caccccgcta tcccggcggg ccctgcccg acttccccaa ccactcactg    360
accctcaaga gggacaaggc gcccaagtcc tccttcgtcg gtgacgggga catcttcaag    420
aagctggact cggagctgag ccgggcccag gagaaggctc tggacacgag ctacgtgatc    480
ctgcccacgg ccacggccac gctgcggccc aagcccaagg aggagcccaa gtacagcatc    540
cacattgacc agatgccgca gaccgcctc atccacctca gcacggcccc cgaggccagc    600
ctccccgccc gcagcccgcc ctcccgccag cccccagcg cgggcccccc cgaggcaccc    660
cctgcccagc ccccaccgcc tccgcccca ccgccaccac ctcccagca gccctgccc    720 ccaccgccca atctggagcc ggcaccccc agctggggg atcccgggga gcctgccgcc    780
catccgggac ccagcacggg gccagcacc aagaacgaga atgtcgccac cttgtctgtg    840
agctccctgg agcggcggaa gtcgcggtat gcagaactgg actttgagaa gatcatgcac    900
acccggaagc ggcaccaaga catgttccag gacctgaacc ggaagctgca gcacgcagcg    960
gagaaggaca aggaggtgct ggggccggac agcaagccgg aaaagcagca gacgcccaac   1020
```

```
aagaggccct gggagagcct ccggaaagcc cacgggacgc ccacgtgggt gaagaaggag    1080
ctggagccgc tgcagccgtc gccgctggag cttcgcagcg tggagtggga gaggtcgggc    1140
gccacgatcc cgctggtggg ccaggacatc atcgacctcc agaccgaggt c             1191
```

<210> SEQ ID NO 140
<211> LENGTH: 1191
<212> TYPE: DNA
<213> ORGANISM: Homo sapiens
<220> FEATURE:
<223> OTHER INFORMATION: ELMO

<400> SEQUENCE: 140

```
cgtagagagg tccaggacgc tgtgaaatgc cgtgtggttg accggcagga ggagggcaac      60
ggggactcag ggggctcctt ccagaacggc acgcccagc tcatgaccga cttcgagaag     120
gacgtggatc tggcctgtag atcagtgctg aacaaggaca tcgcggcctg ccgcactgcc    180
accatcacgg gcacactgaa gcggccgtct ctgcccgagg aggagaagct gaagctggcc    240
catgccaagg ggccgcccac caatttcaac agcctgccgg ccaacgtgtc caagctgcac    300
ctgcacggct caccccgcta tcccggcggg ccctgcccg acttccccaa ccactcactg     360
accctcaaga gggacaaggc gcccaagtcc tccttcgtcg gtgacgggga catcttcaag    420
aagctggact cggagctgag ccgggcccag gagaaggctc tggacacgag ctacgtgatc    480
ctgcccacgg ccacggccac gctgcggccc aagcccaagg aggagcccaa gtacagcatc    540
cacattgacc agatgccgca gacccgcctc atccacctca gcacggcccc cgaggccagc    600
ctccccgccc gcagcccgcc ctcccgccag cccccagcg gcgggcccc cgaggcaccc      660 cctgcccagc ccccaccgcc tccgccccca ccgccaccac ctcccagca gcccctgccc     720 ccaccgccca atctggagcc ggcacccccc agcctggggg atcccgggga gcctgccgcc    780
catccgggac ccagcacggg gcccagcacc aagaacgaga atgtcgccac cttgtctgtg    840
agctccctgg agcggcggaa gtcgcggtat gcagaactgg actttgagaa gatcatgcac    900
acccggaagc ggcaccaaga catgttccag gacctgaacc ggaagctgca gcacgcagcg    960
gagaaggaca aggaggtgct ggggccggac agcaagccgg aaaagcagca gacgcccaac   1020
aagaggccct gggagagcct ccggaaagcc cacgggacgc ccacgtgggt gaagaaggag   1080
ctggagccgc tgcagccgtc gccgctggag cttcgcagcg tggagtggga gaggtcgggc   1140
gccacgatcc cgctggtggg ccaggacatc atcgacctcc agaccgaggt c             1191
```

<210> SEQ ID NO 141
<211> LENGTH: 126
<212> TYPE: DNA
<213> ORGANISM: Homo sapiens
<220> FEATURE:
<223> OTHER INFORMATION: Fc(epsilon) RI(gamma) signaling domain

<400> SEQUENCE: 141

```
cgactgaaga tccaagtgcg aaaggcagct ataaccagct atgagaaatc agatggtgtt     60
tacacgggcc tgagcaccag gaaccaggag acttacgaga ctctgaagca tgagaaacca    120
ccacag                                                                126
```

<210> SEQ ID NO 142
<211> LENGTH: 21
<212> TYPE: PRT
<213> ORGANISM: Homo sapiens
<220> FEATURE:

<223> OTHER INFORMATION: BAI1 transmembrane domain

<400> SEQUENCE: 142

Val Thr Leu Ile Val Gly Cys Gly Val Ser Ser Leu Thr Leu Leu Met
1               5                   10                  15

Leu Val Ile Ile Tyr
            20

<210> SEQ ID NO 143
<211> LENGTH: 63
<212> TYPE: DNA
<213> ORGANISM: Homo sapiens
<220> FEATURE:
<223> OTHER INFORMATION: BAI1 transmembrane domain

<400> SEQUENCE: 143
gtgacgctca tcgtgggctg tggcgtgtcc tctctcaccc tgctcatgct ggtcatcatc    60
tac                                                                  63

<210> SEQ ID NO 144
<211> LENGTH: 81
<212> TYPE: DNA
<213> ORGANISM: Homo sapiens
<220> FEATURE:
<223> OTHER INFORMATION: CD28 transmembrane domain

<400> SEQUENCE: 144
ttttgggtgc tggtggtggt tggtggagtc ctggcttgct atagcttgct agtaacagtg    60
gcctttatta ttttctgggt g                                              81

<210> SEQ ID NO 145
<211> LENGTH: 63
<212> TYPE: DNA
<213> ORGANISM: Homo sapiens
<220> FEATURE:
<223> OTHER INFORMATION: DAP12 transmembrane domain

<400> SEQUENCE: 145
ggcgtgctgg cagggatcgt gatgggagac ctggtgctga cagtgctcat tgccctggcc    60
gtg                                                                  63

<210> SEQ ID NO 146

<400> SEQUENCE: 146

000

<210> SEQ ID NO 147
<211> LENGTH: 18
<212> TYPE: PRT
<213> ORGANISM: Artificial Sequence
<220> FEATURE:
<223> OTHER INFORMATION: T2A self-cleaving peptide

<400> SEQUENCE: 147

Glu Gly Arg Gly Ser Leu Leu Thr Cys Gly Asp Val Glu Glu Asn Pro
1               5                   10                  15

Gly Pro

<210> SEQ ID NO 148
<211> LENGTH: 20
<212> TYPE: PRT
<213> ORGANISM: Artificial Sequence -continued

```
<220> FEATURE:
<223> OTHER INFORMATION: E2A self-cleaving peptide

<400> SEQUENCE: 148

Gln Cys Thr Asn Tyr Ala Leu Leu Lys Leu Ala Gly Asp Val Glu Ser
1               5                   10                  15

Asn Pro Gly Pro
            20

<210> SEQ ID NO 149
<211> LENGTH: 22
<212> TYPE: PRT
<213> ORGANISM: Artificial Sequence
<220> FEATURE:
<223> OTHER INFORMATION: F2A self-cleaving peptide

<400> SEQUENCE: 149

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 150

<400> SEQUENCE: 150

000

<210> SEQ ID NO 151

<400> SEQUENCE: 151

000

<210> SEQ ID NO 152
<211> LENGTH: 774
<212> TYPE: PRT
<213> ORGANISM: Artificial Sequence
<220> FEATURE:
<223> OTHER INFORMATION: CER97 chimeric engulfment receptor
<220> FEATURE:
<221> NAME/KEY: SIGNAL
<222> LOCATION: (1)...(22)

<400> SEQUENCE: 152

Met Ser Lys Gly Leu Leu Leu Trp Leu Val Thr Glu Leu Trp Trp
        -20                 -15                 -10

Leu Tyr Leu Thr Pro Ala Ala Ser Glu Asp Thr Ile Ile Gly Phe Leu
        -5                  1                   5                   10

Gly Gln Pro Val Thr Leu Pro Cys His Tyr Leu Ser Trp Ser Gln Ser
                15                  20                  25

Arg Asn Ser Met Cys Trp Gly Lys Gly Ser Cys Pro Asn Ser Lys Cys
                30                  35                  40

Asn Ala Glu Leu Leu Arg Thr Asp Gly Thr Arg Ile Ile Ser Arg Lys
            45                  50                  55

Ser Thr Lys Tyr Thr Leu Leu Gly Lys Val Gln Phe Gly Glu Val Ser
        60                  65                  70

Leu Thr Ile Ser Asn Thr Asn Arg Gly Asp Ser Gly Val Tyr Cys Cys
75                  80                  85                  90

Arg Ile Glu Val Pro Gly Trp Phe Asn Asp Val Lys Lys Asn Val Arg
                95                  100                 105

Leu Glu Leu Arg Arg Ala Thr Thr Thr Lys Lys Pro Thr Thr Thr Thr
```

```
                110                 115                 120
Arg Pro Thr Thr Thr Pro Tyr Val Thr Thr Thr Thr Pro Glu Leu Leu
            125                 130                 135
Pro Thr Thr Val Met Thr Thr Ser Val Leu Pro Thr Thr Thr Pro Pro
        140                 145                 150
Gln Thr Leu Ala Thr Thr Ala Phe Ser Thr Ala Val Thr Thr Cys Pro
155                 160                 165                 170
Ser Thr Thr Pro Gly Ser Phe Ser Gln Glu Thr Thr Lys Gly Ser Ala
            175                 180                 185
Phe Thr Thr Glu Ser Glu Thr Leu Pro Ala Ser Asn His Ser Gln Arg
        190                 195                 200
Ser Met Met Thr Ile Ser Thr Asp Ile Ala Val Leu Arg Pro Thr Gly
        205                 210                 215
Ser Asn Pro Gly Ile Leu Pro Ser Thr Ser Gln Leu Thr Thr Gln Lys
        220                 225                 230
Thr Thr Leu Thr Thr Ser Glu Ser Leu Gln Lys Thr Thr Lys Ser His
235                 240                 245                 250
Gln Ile Asn Ser Arg Gln Thr Ile Leu Ile Ile Ala Cys Cys Val Gly
            255                 260                 265
Phe Val Leu Met Val Leu Leu Phe Leu Ala Phe Leu His Arg Arg Lys
            270                 275                 280
Lys Glu Thr Arg Tyr Gly Glu Val Phe Glu Pro Thr Val Glu Arg Gly
        285                 290                 295
Glu Leu Val Val Arg Tyr Arg Val Arg Lys Ser Tyr Ser Arg Arg Thr
        300                 305                 310
Thr Glu Ala Thr Leu Asn Ser Leu Gly Ile Ser Glu Glu Leu Lys Glu
315                 320                 325                 330
Lys Leu Arg Asp Val Met Val Asp Arg His Lys Val Ala Leu Gly Lys
            335                 340                 345
Thr Leu Gly Glu Gly Glu Phe Gly Ala Val Met Glu Gly Gln Leu Asn
        350                 355                 360
Gln Asp Asp Ser Ile Leu Lys Val Ala Val Lys Thr Met Lys Ile Ala
        365                 370                 375
Ile Cys Thr Arg Ser Glu Leu Glu Asp Phe Leu Ser Glu Ala Val Cys
        380                 385                 390
Met Lys Glu Phe Asp His Pro Asn Val Met Arg Leu Ile Gly Val Cys
395                 400                 405                 410
Phe Gln Gly Ser Glu Arg Glu Ser Phe Pro Ala Pro Val Val Ile Leu
            415                 420                 425
Pro Phe Met Lys His Gly Asp Leu His Ser Phe Leu Leu Tyr Ser Arg
            430                 435                 440
Leu Gly Asp Gln Pro Val Tyr Leu Pro Thr Gln Met Leu Val Lys Phe
        445                 450                 455
Met Ala Asp Ile Ala Ser Gly Met Glu Tyr Leu Ser Thr Lys Arg Phe
        460                 465                 470
Ile His Arg Asp Leu Ala Ala Arg Asn Cys Met Leu Asn Glu Asn Met
475                 480                 485                 490
Ser Val Cys Val Ala Asp Phe Gly Leu Ser Lys Lys Ile Tyr Asn Gly
            495                 500                 505
Asp Tyr Tyr Arg Gln Gly Arg Ile Ala Lys Met Pro Val Lys Trp Ile
            510                 515                 520
Ala Ile Glu Ser Leu Ala Asp Arg Val Tyr Thr Ser Lys Ser Asp Val
        525                 530                 535
```

```
Trp Ser Phe Gly Val Thr Met Trp Glu Ile Ala Thr Arg Gly Gln Thr
        540                 545                 550

Pro Tyr Pro Gly Val Glu Asn Ser Glu Ile Tyr Asp Tyr Leu Arg Gln
555                 560                 565                 570

Gly Asn Arg Leu Lys Gln Pro Ala Asp Cys Leu Asp Gly Leu Tyr Ala
                575                 580                 585

Leu Met Ser Arg Cys Trp Glu Leu Asn Pro Gln Asp Arg Pro Ser Phe
                590                 595                 600

Thr Glu Leu Arg Glu Asp Leu Glu Asn Thr Leu Lys Ala Leu Pro Pro
            605                 610                 615

Ala Gln Glu Pro Asp Glu Ile Leu Tyr Val Asn Met Asp Glu Gly Gly
        620                 625                 630

Gly Tyr Pro Glu Pro Pro Gly Ala Ala Gly Gly Ala Asp Pro Pro Thr
635                 640                 645                 650

Gln Pro Asp Pro Lys Asp Ser Cys Ser Cys Leu Thr Ala Ala Glu Val
                655                 660                 665

His Pro Ala Gly Arg Tyr Val Leu Cys Pro Ser Thr Thr Pro Ser Pro
                670                 675                 680

Ala Gln Pro Ala Asp Arg Gly Ser Pro Ala Ala Pro Gly Gln Glu Asp
            685                 690                 695

Gly Ala Tyr Phe Leu Gly Arg Leu Val Pro Arg Gly Arg Gly Ala Ala
        700                 705                 710

Glu Ala Ala Thr Arg Lys Gln Arg Ile Thr Glu Thr Glu Ser Pro Tyr
715                 720                 725                 730

Gln Glu Leu Gln Gly Gln Arg Ser Asp Val Tyr Ser Asp Leu Asn Thr
                735                 740                 745

Gln Arg Pro Tyr Tyr Lys
            750

<210> SEQ ID NO 153
<211> LENGTH: 767
<212> TYPE: PRT
<213> ORGANISM: Artificial Sequence
<220> FEATURE:
<223> OTHER INFORMATION: CER98 chimeric engulfment receptor
<220> FEATURE:
<221> NAME/KEY: SIGNAL
<222> LOCATION: (1)...(22)

<400> SEQUENCE: 153

Met Ser Lys Gly Leu Leu Leu Trp Leu Val Thr Glu Leu Trp Trp
        -20                 -15                 -10

Leu Tyr Leu Thr Pro Ala Ala Ser Glu Asp Thr Ile Ile Gly Phe Leu
        -5                  1                   5                   10

Gly Gln Pro Val Thr Leu Pro Cys His Tyr Leu Ser Trp Ser Gln Ser
                15                  20                  25

Arg Asn Ser Met Cys Trp Gly Lys Gly Ser Cys Pro Asn Ser Lys Cys
                30                  35                  40

Asn Ala Glu Leu Leu Arg Thr Asp Gly Thr Arg Ile Ile Ser Arg Lys
            45                  50                  55

Ser Thr Lys Tyr Thr Leu Leu Gly Lys Val Gln Phe Gly Glu Val Ser
        60                  65                  70

Leu Thr Ile Ser Asn Thr Asn Arg Gly Asp Ser Gly Val Tyr Cys Cys
75                  80                  85                  90

Arg Ile Glu Val Pro Gly Trp Phe Asn Asp Val Lys Lys Asn Val Arg
                95                  100                 105
```

```
Leu Glu Leu Arg Arg Ala Thr Thr Thr Lys Lys Pro Thr Thr Thr Thr
                110                 115                 120

Arg Pro Thr Thr Thr Pro Tyr Val Thr Thr Thr Thr Pro Glu Leu Leu
        125                 130                 135

Pro Thr Thr Val Met Thr Thr Ser Val Leu Pro Thr Thr Thr Pro Pro
140                 145                 150

Gln Thr Leu Ala Thr Thr Ala Phe Ser Thr Ala Val Thr Thr Cys Pro
155                 160                 165                 170

Ser Thr Thr Pro Gly Ser Phe Ser Gln Glu Thr Thr Lys Gly Ser Ala
                175                 180                 185

Phe Thr Thr Glu Ser Glu Thr Leu Pro Ala Ser Asn His Ser Gln Arg
                190                 195                 200

Ser Met Met Thr Ile Ser Thr Asp Ile Ala Val Leu Arg Pro Thr Gly
                205                 210                 215

Ser Asn Pro Gly Ile Leu Pro Ser Thr Ser Gln Leu Thr Thr Gln Lys
        220                 225                 230

Thr Thr Leu Thr Thr Ser Glu Ser Leu Gln Lys Thr Thr Lys Ser His
235                 240                 245                 250

Gln Ile Asn Ser Arg Gln Thr Ile Leu Ile Ala Cys Cys Val Gly
                255                 260                 265

Phe Val Leu Met Val Leu Leu Phe Leu Ala Phe Leu His Arg Arg Lys
                270                 275                 280

Lys Glu Thr Arg Tyr Gly Glu Val Phe Glu Pro Thr Val Glu Arg Gly
                285                 290                 295

Glu Leu Val Val Arg Tyr Arg Val Arg Lys Ser Tyr Ser Arg Arg Thr
300                 305                 310

Thr Glu Ala Thr Leu Asn Ser Leu Gly Ile Ser Glu Glu Leu Lys Glu
315                 320                 325                 330

Lys Leu Arg Asp Val Met Val Asp Arg His Lys Val Ala Leu Gly Lys
                335                 340                 345

Thr Leu Gly Glu Gly Glu Phe Gly Ala Val Met Glu Gly Gln Leu Asn
                350                 355                 360

Gln Asp Asp Ser Ile Leu Lys Val Ala Val Lys Thr Met Lys Ile Ala
                365                 370                 375

Ile Cys Thr Arg Ser Glu Leu Glu Asp Phe Leu Ser Glu Ala Val Cys
                380                 385                 390

Met Lys Glu Phe Asp His Pro Asn Val Met Arg Leu Ile Gly Val Cys
395                 400                 405                 410

Phe Gln Gly Ser Glu Arg Glu Ser Phe Pro Ala Pro Val Val Ile Leu
                415                 420                 425

Pro Phe Met Lys His Gly Asp Leu His Ser Phe Leu Leu Tyr Ser Arg
                430                 435                 440

Leu Gly Asp Gln Pro Val Tyr Leu Pro Thr Gln Met Leu Val Lys Phe
                445                 450                 455

Met Ala Asp Ile Ala Ser Gly Met Glu Tyr Leu Ser Thr Lys Arg Phe
                460                 465                 470

Ile His Arg Asp Leu Ala Ala Arg Asn Cys Met Leu Asn Glu Asn Met
475                 480                 485                 490

Ser Val Cys Val Ala Asp Phe Gly Leu Ser Lys Lys Ile Tyr Asn Gly
                495                 500                 505

Asp Tyr Tyr Arg Gln Gly Arg Ile Ala Lys Met Pro Val Lys Trp Ile
                510                 515                 520
```

```
-continued

Ala Ile Glu Ser Leu Ala Asp Arg Val Tyr Thr Ser Lys Ser Asp Val
        525                 530                 535

Trp Ser Phe Gly Val Thr Met Trp Glu Ile Ala Thr Arg Gly Gln Thr
    540                 545                 550

Pro Tyr Pro Gly Val Glu Asn Ser Glu Ile Tyr Asp Tyr Leu Arg Gln
555                 560                 565                 570

Gly Asn Arg Leu Lys Gln Pro Ala Asp Cys Leu Asp Gly Leu Tyr Ala
            575                 580                 585

Leu Met Ser Arg Cys Trp Glu Leu Asn Pro Gln Asp Arg Pro Ser Phe
            590                 595                 600

Thr Glu Leu Arg Glu Asp Leu Glu Asn Thr Leu Lys Ala Leu Pro Pro
        605                 610                 615

Ala Gln Glu Pro Asp Glu Ile Leu Tyr Val Asn Met Asp Glu Gly Gly
        620                 625                 630

Gly Tyr Pro Glu Pro Pro Gly Ala Ala Gly Gly Ala Asp Pro Pro Thr
635                 640                 645                 650

Gln Pro Asp Pro Lys Asp Ser Cys Ser Cys Leu Thr Ala Ala Glu Val
            655                 660                 665

His Pro Ala Gly Arg Tyr Val Leu Cys Pro Ser Thr Thr Pro Ser Pro
            670                 675                 680

Ala Gln Pro Ala Asp Arg Gly Ser Pro Ala Ala Pro Gly Gln Glu Asp
        685                 690                 695

Gly Ala Asp Ser Lys Ala Gly Met Glu Glu Asp His Thr Tyr Glu Gly
        700                 705                 710

Leu Asp Ile Asp Gln Thr Ala Thr Tyr Glu Asp Ile Val Thr Leu Arg
715                 720                 725                 730

Thr Gly Glu Val Lys Trp Ser Val Gly Glu His Pro Gly Gln Glu
            735                 740                 745
```

CHIMERIC ENGULFMENT RECEPTOR MOLECULES

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200265_401C1_SEQ-Listing_08-09-2021.txt. The text file is 275 KB, was created on Aug. 9, 2021, and is being submitted electronically via EFS-Web.

BACKGROUND

There are two principle types of phagocytosis, which are influenced by the target, cell-type and surrounding milieu. Anti-microbe phagocytosis clears and degrades disease-causing microbes, induces pro-inflammatory signaling through cytokine and chemokine secretion, and recruits immune cells to mount an effective inflammatory response. This type of phagocytosis is often referred to as "inflammatory phagocytosis" (or "immunogenic phagocytosis"). However, in some instances, such as with certain persistent infections, anti-inflammatory responses may follow microbial uptake. Anti-microbe phagocytosis is commonly performed by professional phagocytes of the myeloid lineage, such as immature dendritic cells (DCs) and macrophages and by tissue-resident immune cells.

Phagocytosis of damaged, self-derived apoptotic cells or cell debris (e.g., efferocytosis), in contrast, is typically a non-inflammatory (also referred to as a "non-immunogenic") process. Billions of damaged, dying, and unwanted cells undergo apoptosis each day. Unwanted cells include, for example, excess cells generated during development, senescent cells, infected cells (intracellular bacteria or viruses), transformed or malignant cells, and cells irreversibly damaged by cytotoxic agents. Phagocytes execute specific, swift removal of apoptotic cells without causing damage to the surrounding tissues or inducing a pro-inflammatory immune response. Steps for apoptotic cell clearance include: (1) release of "find me" signals from apoptotic cells to recruit phagocytes to the location of apoptotic cells; (2) "eat me" signals exposed on the surface of apoptotic cells are bound by phagocytes via specific receptors; (3) cytoskeletal rearrangement to engulf the apoptotic cell; and (4) the ingested apoptotic cell is digested and specific phagocytic responses are elicited (e.g., secretion of anti-inflammatory cytokines).

There is an ongoing need for new compositions and methods of treating infections, inflammatory diseases, immune diseases, and various cancers. The methods and compositions disclosed herein meets such needs by enhancing the removal of infected, transformed, malignant, apoptotic, damaged or necrotic cells or particles from the body in treatment of various cancers, acute and chronic infections, inflammatory, immune and selected neurological diseases.

BRIEF SUMMARY

Chimeric, engulfment receptors are described herein. In certain embodiments, the chimeric engulfment receptors ("CER" in the singular and "CERs" in the plural) include an extracellular domain, a transmembrane domain, and an intracellular engulfment signaling domain. The transmembrane domain is positioned between and connects the extracellular domain and the engulfment signaling domain. The extracellular domain comprises a binding domain and an optional extracellular spacer domain positioned between and connecting the binding domain and transmembrane domain. In certain embodiments, the chimeric engulfment receptors described herein are chimeric proteins having (a) and extracellular domain that targets a pro-engulfment marker or a target antigen associated with a disease, disorder, condition, or infection, (b) a transmembrane domain, and (c) an engulfment signaling domain. In certain embodiments, the engulfment signaling domain comprises at least one of a homeostatic engulfment domain and a pro-inflammatory engulfment domain. In some embodiments, the engulfment signaling domain comprises a primary engulfment signaling domain and a secondary engulfment signaling domain. In particular embodiments, the chimeric engulfment receptors are single chain chimeric proteins. Chimeric engulfment receptors may be designed to generate an inflammatory response to a target cell/organ/tissue/area. While apoptotic cell clearance is typically a non-inflammatory process, inflammation can be beneficial to the host in certain contexts, such as, for example, in the context clearance of apoptotic tumor cells to induce an immune response to residual tumor cells.

In some embodiments, the extracellular domain of the CER includes a binding domain specific to a pro-engulfment marker. In certain such embodiments, the extracellular domain includes a phosphatidylserine (PtdSer) binding domain. In embodiments of the CERs described herein, a PtdSer binding domain can include all or a portion of the extracellular domain of T cell immunoglobulin and mucin domain 1 (Tim1), T cell immunoglobulin and mucin domain 4 (Tim4), or T cell immunoglobulin and mucin domain 3 (Tim3). In other embodiments a PtdSer binding domain can include all or a portion of a binding domain derived from FA58C2, GAS6, protein S, Factor VII, Factor IX, Factor X, or prothrombin PS.

In further embodiments, the extracellular domain binds to a target antigen. In certain such embodiments, the extracellular domain includes all or part of the extracellular domain of an Fc receptor (FcR), such as, for example, FcGR1, FcGR2A, FcGR2B2, FcGR2C, FcGR3A, FcεR1, and FcαR1. In still other embodiments where the extracellular domain binds a target antigen, the extracellular domain can include an antibody or an antigen-binding domain thereof. For example, the extracellular domain can include an antibody or an antigen-binding domain selected from intrabodies, peptibodies, nanobodies, single domain antibodies, SMIPs, and multispecific antibodies. In certain such embodiments, the extracellular domain includes a Fab binding domain. In yet other such embodiments, the extracellular domain includes a scFv.

Upon binding of the extracellular domain of the CER to the pro-engulfment marker or targeted antigen, the engulfment signaling domain of the CER stimulates engulfment signaling activity. Thus, upon activation, the engulfment signaling domain included in the CER transduces effector functional signals that direct the host cell to engulf. In certain embodiments, the engulfment signaling domain of the CER includes a homeostatic engulfment signaling domain. Examples of homeostatic engulfment signaling domains include MRC1, ItgB5, MERTK, Tyro3, and Axl signaling domains. In other embodiments, the engulfment signaling domain includes a pro-inflammatory engulfment signaling domain. Examples of pro-inflammatory engulfment signaling domains include Traf6, Syk, MyD88, Zap70, FcγR1, FcγR2A, FcγR2B2, FcγR2C, FcγR3A, FcεR1, FcαR1, BAFF-R, NFAM1, DAP12, and CD79b signaling domains. In still other embodiments, the engulfment signaling domain includes a primary engulfment signaling domain and a secondary engulfment signaling domain. In such embodiments, the primary engulfment signaling domain and the secondary engulfment signaling domain can be independently selected from homeostatic and pro-inflammatory engulfment signaling domains, including those described herein.

In further aspects, the present disclosure is directed to cells genetically modified to express a CER. In specific embodiments, the CER confers and engulfment phenotype not exhibited by a single, naturally-occurring receptor protein. In other embodiments, CER according to the present description confers an engulfment phenotype to a cell that does not naturally exhibit engulfment activity. In certain embodiments, cells are genetically modified to express a CER that targets a pro-engulfment marker associated with dead, dying, damaged, infected, or necrotic cells. In other embodiments, cells are genetically modified to express a CER that targets a marker, such as an antibody, associated with an infectious microbe or molecule induced by an infectious particle. In such embodiments, the genetically modified cells promote clearance or degradation of the targeted cells or microbes upon binding by the CER of the marker associated with the targeted infectious microbe or the targeted molecule induced by an infectious particle. In other specific embodiments, cells are genetically modified to express a CER that targets an antigenic marker that does not normally trigger engulfment. For example, in such embodiments, the extracellular domain of the CER can include an antibody or antigen-binding portion of an antibody, such as a Fab binding domain or a scFv specific to an antigenic marker. In certain such embodiments, the antigenic marker can be a surface protein, glycoprotein, or glycolipid characteristic of aberrant cells associated with a disease, disorder, or other undesirable condition. In such embodiments, the genetically modified cells promote clearance or degradation of the aberrant cells upon binding of the antigenic marker by the CER.

In further embodiments, a CER-modified cell may be further modified to co-express a small GTPase. A small GTPase may be introduced into a CER-modified cell using a vector encoding bot the CER and the small GTPase. Alternatively, a small GTPase may be introduced into a cell that is or will be a CER-modified cell using a vector different than the vector used to introduce the CER.

In yet further aspects, the present disclosure is directed to a method treating a subject suffering from a disease, disorder or undesired condition. Embodiments of these methods include administering to a subject a therapeutically effective amount of a pharmaceutical composition including one or more CERs or a population of cells genetically modified to express one or more CERs according to the present description.

In other aspects, the present disclosure provides methods for altering the engulfment phenotype of a host cell. In certain embodiments, such methods include one or more of the following: methods for producing a population of cells exhibiting an engulfment phenotype by introducing into and expressing a CER in host cells that do not naturally exhibit an engulfment phenotype; methods for altering the engulfment phenotype of a population of cells by introducing into and expressing a CER in the host cells, wherein the CER confers an engulfment phenotype specific to a pro-engulfment marker or antigenic marker that is not naturally targeted by the host cells; and methods for enhancing the engulfment phenotype of a population of cells by introducing into and expressing a CER in the host cells, where the CER is specific to a pro-engulfment marker or antigenic marker naturally targeted by the host cells and expression of the CER by the host cells enhances the engulfment by the host cells of cells, microbes, or particles exhibiting the targeted pro-engulfment or antigenic marker.

BRIEF DESCRIPTION OF THE SEVERAL VIEWS OF THE DRAWINGS

FIG. 1A shows two illustrative CERs having extracellular domains specific for phosphatidylserine (Tim4 and scFv) and table include a single engulfment signaling domain. FIG. 1B shows two illustrative CERs having binding domains specific for phosphatidylserine (Tim4 and scFv) and include an engulfment signaling domain that includes a primary engulfment signaling domain and a secondary engulfment signaling domain. Integration of an accessory or secondary engulfment signaling domain into a CER may enhance engulfment responses even in the absence of expressed ligands for accessory receptors. FIG. 1C shows two illustrative CERs having extracellular domains comprising a Fab or FcR and include a single engulfment signaling domain. FIG. 1D shows two illustrative CERs having comprising a Fab or FcR and include an engulfment signaling domain that includes a primary engulfment signaling domain and a secondary engulfment signaling domain. "TMD"=transmembrane domain.

FIGS. 3A-3B show a comparison of a natural lymphocyte and a lymphocyte modified with a CER of the present disclosure. FIG. 3A shows an endogenous lymphocyte. FIG. 3B shows a lymphocyte modified with a CER of the present disclosure.

FIG. 5A shows a treatment scheme for therapy with cells modified with a CER. FIG. 5B shows a treatment scheme for CER-modified cells used in combination with non-phagocytic T cellular immune therapies. FIG. 5C shows a treatment scheme for CER-modified cells used in combination with monoclonal antibodies, conventional chemotherapy, or radiation therapy.

FIGS. 6A-6F show Tim4-MERTK chimeric engulfment receptor (CER) mediated in vitro engulfment of apoptotic target cells. FIG. 6A shows an illustrative schematic of Tim4-MERTK CER. ECD=extracellular domain; TMD=transmembrane domain; ESD=engulfment signaling domain. FIG. 6B shows a fluorescence-activated cell sorting (FACs) plot of murine Ba/F3 B-cells transduced with pMSCV retroviral vector comprising a nucleotide sequence encoding the Tim4-MERTK CER of FIG. 6A and a nucleotide sequence encoding green fluorescent protein (GFP). Positive Ba/F3 B-cell transductants were sorted by staining for green fluorescent protein marker and Tim4 using flow cytometry, demonstrating the presence of the Tim4-MERTK CER on the cellular membrane of Ba/F3 B-cells. FIG. 6C shows a bar graph of phagocytosis of apoptotic primary thymocytes by Tim4-MERTK chimeric engulfment receptor-expressing Ba/F3 B-cells at 2 hours and 24 hours post-incubation as quantified by FACs. BA/F3 B-cells transduced with pMSCV comprising nucleotide sequence encoding Tim4 and GFP were used as a negative control. FIG. 6D shows a line graph illustrating the correlation between quantity of Tim4-MERTK CER surface expression, as well as duration of target cell incubation, with phagocytosis of apoptotic primary thymocytes. FIG. 6E shows an image from fluorescence microscopy, showing that Tim4-MERTK CER-expressing cells engulf pHrodo Red dye-stained apoptotic primary thymocytes. Yellow triangles indicate apoptotic primary thymocytes inside phagolysosomes; white squares indicate low intensity staining of un-engulfed apoptotic primary thymocytes. FIG. 6F shows FACs and histogram plots of Ba/F3 cells that are double positive for pHrodo Red and Tim4-MERTK CER expression, demonstrating in vitro phagocytosis.

FIG. 7A shows time-lapse images of Tim4-MERTK CER-mediated clearance of target apoptotic thymocytes at 12 hours and 48 hours incubation time. Greater than 95% of target cells had been eliminated within four days. Sheets of apoptotic thymocytes persist in the presence of control Ba/F3 cells expressing Tim4 (bottom panel) (white arrows point to thymocytes). FIG. 7B shows a line graph quantifying the number of thymocytes present per high power microscopic field in control (Tim4 expressing Ba/F3 cells) and Tim4-MERTK CER-expressing Ba/F3 cells samples. FIG. 7B demonstrates essentially complete elimination of the apoptotic thymocytes by the lymphocytes expressing the Tim4-MERTK CER.

FIG. 8A shows a FACs plot of Ba/F3 cells that are double positive for pHrodo Red and Tim4-MERTK CER expression, demonstrating in vitro phagocytosis, and FIG. 8B shows a bar graph of phagocytosis of Raji Burkitt's lymphoma cells by Tim4-MERTK CER-expressing Ba/F3 B-cells as compared to control Ba/F3 B-cells expressing Tim4. FIG. 8C shows a fluorescence micrograph of Tim4-MERTK CER-mediated clearance of Raji Burkitt's lymphoma cells.

FIG. 9A shows an illustrative schematic of FA58C2-MERTK CER. FIG. 9B shows a bar graph of phagocytosis of apoptotic primary thymocytes by FA58C2-MERTK CER-expressing Ba/F3 B-cells at 2 hours and 24 hours post-incubation as quantified by FACs. BA/F3 B-cells transduced with pMSCV comprising a nucleotide sequence encoding Tim4 and GFP were used as a negative control. FIG. 9C shows a line graph illustrating the correlation between quantity of FA58C2-MERTK CER surface expression, as well as duration of target cell incubation, with phagocytosis of apoptotic primary thymocytes. FIG. 9D shows an image from fluorescence microscopy, showing that FA58C3-MERTK CER-expressing cells engulf pHrodo Red dye-stained apoptotic primary thymocytes. Yellow triangles indicate apoptotic primary thymocytes inside phagolysosomes. FIG. 9E shows a FACs plot and FIG. 9F shows a histogram plot of Ba/F3 cells that are double positive for pHrodo Red and FA58C2-MERTK CER expression, demonstrating in vitro phagocytosis.

FIG. 10A shows an illustrative schematic of a bi-cistronic retroviral expression cassette for FA58C2-MERTK CER and Rac1 or Rab5 separated by P2A sequence (top panel) and a resulting co-expressed FA58C2-MERTK CER and GTPase (Rac1) (bottom panel). FIG. 10B shows a line graph illustrating the correlation between quantity of FA58C2-MERTK CER surface expression with phagocytosis of apoptotic primary thymocytes at 24 hours incubation in Ba/F3 B-cells expressing FA58C2-MERTK CER or FA58C2-MERTK CER+Rac1. FIG. 10C shows an image from fluorescence microscopy, showing that FA58C3-MERTK CER+Rac1-expressing cells engulf pHrodo Red dye-stained apoptotic primary thymocytes. FIG. 10D shows a FACs plot and FIG. 10E shows a histogram plot of Ba/F3 cells that are double positive for pHrodo Red and FA58C2-MERTK CER+Rac1 expression, demonstrating in vitro phagocytosis.

FIG. 11A shows an illustrative schematic of a retroviral expression cassette for FA58C2-Syk CER and a bi-cistronic retroviral expression cassette for FA58C2-Syk CER and small GTPase Rac1 separated by P2A sequence (top panel) and a resulting co-expressed FA58C2-Syk CER and Rac1 (bottom panel). FIG. 11B shows a bar graph of phagocytosis of apoptotic primary thymocytes by FA58C2-Syk CER– or FA58C2-Syk CER+Rac1-expressing Ba/F3 B-cells at 2 hours and 24 hours post-incubation as quantified by FACs. BA/F3 B-cells transduced with pMSCV comprising a nucleotide sequence encoding Tim4 and green fluorescent protein were used as a negative control. FIG. 11C shows a line graph illustrating the correlation between quantity of FA58C2-Syk CER surface expression with phagocytosis of apoptotic primary thymocytes at 24 hours incubation in Ba/F3 B-cells expressing FA58C2-Syk CER or FA58C2-Syk CER+Rac1. The addition of small GTPase Rac1 enhances phagocytosis. FIG. 11D shows an image from fluorescence microscopy, showing that FA58C3-Syk CER+Rac1-expressing cells engulf pHrodo Red dye-stained apoptotic primary thymocytes. Yellow triangles indicate apoptotic primary thymocytes inside phagolysosomes. FIG. 11E shows a FACs plot of Ba/F3 cells that are double positive for pHrodo Red and FA58C2-Syk CER+Rac1 expression, demonstrating in vitro phagocytosis.

FIG. 12A shows an illustrative schematic of a bi-cistronic retroviral expression cassette for FA58C2-Syk CER and small GTPase Rab5 separated by P2A sequence (top panel) and a resulting co-expressed FA58C2-Syk CER and Rab5 (bottom panel). FIG. 12B shows a bar graph of phagocytosis of apoptotic primary thymocytes by FA58C2-Syk CER– or FA58C2-Syk CER+Rab5-expressing Ba/F3 B-cells at 2 hours post-incubation as quantified by FACs. BA/F3 B-cells transduced with pMSCV comprising a nucleotide sequence encoding Tim4 and GFP were used as a negative control. FIG. 12C shows an image from fluorescence microscopy, showing that FA58C3-Syk CER+Rab5-expressing cells engulf pHrodo Red dye-stained apoptotic primary thymocytes. FIG. 12D shows FACs plots of Ba/F3 cells that are double positive for pHrodo Red and FA58C2-Syk CER (left plot), FA58C2-Syk CER+Rab5 expression (middle plot), or Tim4 control, demonstrating in vitro phagocytosis for FA58C2-Syk CER expressing cells (9%) and increased phagocytosis with the addition of Rab5 (12.5%).

FIG. 13A shows an illustrative schematic of a retroviral expression cassette for CD19-MERTK CER (top panel) and the resulting co-expressed CD19-MERTK CER (bottom panel). FIG. 13B shows an illustrative schematic of a retroviral expression cassette for a bi-cistronic retroviral expression cassette for CD19-MERTK CER and small GTPase Rac1 separated by P2A sequence (top panel) and the resulting co-expressed CD19-MERTK CER and Rac1 (bottom panel). FIG. 13C shows a bar graph of phagocytosis of Raji Burkitt's lymphoma cells by CD19-MERTK CER− or CD19-MERTK CER+Rac1-expressing Ba/F3 B-cells at 2 hours and 24 hours post-incubation as quantified by FACs. Ba/F3 B-cells transduced with pMSCV comprising a nucleotide sequence encoding Tim4 and GFP were used as a negative control. FIG. 13D shows a line graph illustrating the correlation between quantity of CD19-MERTK CER surface expression with phagocytosis of Raji Burkitt's lymphoma cells at 24 hours incubation in Ba/F3 B-cells expressing CD19-MERTK CER. FIG. 13E shows an image from fluorescence microscopy, showing that CD19-MERTK CER+Rac1-expressing cells engulf pHrodo Red dye-stained Raji Burkitt's lymphoma cells. Yellow triangles indicate Raji Burkitt's lymphoma cells inside phagolysosomes. FIG. 13F shows a FACs plot of Ba/F3 cells that are double positive for pHrodo Red and CD19-MERTK CER expression, demonstrating in vitro phagocytosis at 2 hours incubation with Raji Burkitt's lymphoma target cells or at 24 hours incubation with Raji Burkitt's lymphoma target cells (FIG. 13G). FIG. 13H shows a fluorescent microscope image of CD19-MERTK CER expressing cells that engulfed pHrodo Red dye stained Raji Burkitt's lymphoma cells. White arrows indicate engulfment events.

FIG. 14 shows examples of CERs according the present disclosure.

FIG. 15 shows examples of CERs according the present disclosure.

FIGS. 17A-17D show FACS purification of Ba/F3 murine cells transduced with CER01. Biotin-labeled cetuximab (anti-EGFR antibody) followed by streptavidin conjugated with R-phycoerythrin (SA-PE) were used to detect EGFR expression by FACS in untransduced Ba/F3 cells (FIG. 17A) and Ba/F3 murine B cells transduced with the CER01-T2A-EGFRt containing lentivirus (FIG. 17B) at 48 hours post-transduction. CER+EGFRt+ expressing cells (FIG. 17C) were selected by FACs and expanded for downstream assays. FIG. 17D shows untransduced Ba/F3 control cells following EGFRt purification.

FIG. 18A shows fluorescent microscope images of Ba/F3 cells transduced with EGFRt+ control co-cultured with dexamethasone-treated thymocytes; FIG. 18B shows fluorescent microscope images of Ba/F3 cells transduced with CER01 co-cultured with dexamethasone-treated thymocytes (white arrows indicate engulfment events). A high magnification image of a portion of FIG. 18B is shown to the right.

FIG. 20A shows a table of values for percentage of phagocytosing cells and hybrid capture values of CER01+ cells or EGFRt+ control Ba/F3 cells co-cultured with dexamethansone-treated thymocytes. FIG. 20B shows a graph of phagocytic index for CER01+ cells or EGFRt+ control Ba/F3 cells.

FIG. 22A shows a histogram plot of hybrid cell counts extracting CT26 target cell area from CER01+ Ba/F3 cells, and FIG. 22B shows hybrid cell counts for EGFRt+ control Ba/F3 cells. The area ratio represents the overlay area of CT26 cells within Ba/F3 cells.

FIG. 26A shows a histogram plot of hybrid cell counts extracting A20 target cell area from CER01+ Ba/F3 cells, and FIG. 26B shows hybrid cell counts for EGFRt+ control Ba/F3 cells. The area ratio represents the overlay area of A20 cells within Ba/F3 cells.

FIG. 31A shows FACS analysis of human primary B cells transduced with CER01 (right histogram) and control B cells (left histogram) using an anti-EGFR antibody and then an anti-Tim4 Katy-18 antibody. FIG. 31B shows purified CER01+ B cells that were expanded at 24 hours, 48 hours and 72 hours.

FIGS. 38A-38B show fluorescent microscope images of phagocytosis of dexamethasone treated thymocytes by CER08+ Ba/F3 cells (FIG. 38B) as compared to EGFRt+ Ba/Fe control cells (FIG. 38A). White arrows indicate phagocytosis events. High magnification of an engulfment event is shown on the right.

FIG. 39A shows a table of values for percentage of phagocytosing cells and hybrid capture values of CER08+ cells or EGFRt+ control Ba/F3 cells co-cultured with dexamethansone-treated thymocytes. FIG. 39B shows a graph of phagocytic index for CER08+ cells or EGFRt+ control Ba/F3 cells.

FIGS. 42A-42B show fluorescent microscope images of phagocytosis of dexamethasone treated thymocytes by CER09+ Ba/F3 cells (FIG. 42B) as compared to EGFRt+ Ba/Fe control cells (FIG. 42A). White arrows indicate phagocytosis events. High magnification of an engulfment event is shown on the right.

FIG. 43A shows a table of values for percentage of phagocytosing cells and hybrid capture values of CER09+ cells or EGFRt+ control Ba/F3 cells co-cultured with dexamethansone-treated thymocytes. FIG. 43B shows a graph of phagocytic index for CER09+ cells or EGFRt+ control Ba/F3 cells.

FIGS. 49A-49B show transduction and expansion of CER09+ human primary B cells. FIG. 49A shows FACS analysis of human primary B cells transduced with CER09 (right histogram) and control B cell (left histogram) using an anti-EGFR antibody and then an anti-Tim4 Kat5-18 antibody. FIG. 49B shows purified CER09+ B cells that were expanded at 24 hours, 48 hours and 72 hours.

FIG. 56A shows a table of values for percentage of phagocytosing cells and hybrid capture values of CER10+ cells or EGFRt+ control Ba/F3 cells co-cultured with dexamethansone-treated thymocytes. FIG. 56B shows a graph of phagocytic index for CER10+ cells or EGFRt+ control Ba/F3 cells.

FIGS. 59A-59B show fluorescent microscope images of in vitro phagocytosis of dexamethasone treated thymocytes by CER11+ Ba/F3 cells (FIG. 59B) or control EGFRt+ Ba/F3 cells (FIG. 59A). White arrows indicate phagocytosis events. High magnification of an engulfment event is shown on the right.

FIG. 60A shows a table of values for percentage of phagocytosing cells and hybrid capture values of CER11+ cells or EGFRt+ control Ba/F3 cells co-cultured with dexamethansone-treated thymocytes. FIG. 60B shows a graph of phagocytic index for CER11+ cells or EGFRt+ control Ba/F3 cells.

FIGS. 61A-61B show fluorescent microscope images of in vitro phagocytosis of staurosporine treated CT26 colon carcinoma cells by CER11+ Ba/F3 cells (left photo) or control EGFRt+ Ba/F3 cells (right photo). White arrows indicate phagocytosis events.

FIGS. 64A-64B show FACS analysis of CER11+ Ba/F3 effector cells (FIG. 64A) and quantification of engulfment of WR19L lymphoma cells by CER11+ Ba/F3 murine B cells by measuring the cell population that stained double positive for pHrodo Red and CELLTRACE Violet (FIG. 64B).

FIG. 69 shows fluorescent microscope images of in vitro phagocytosis of paclitaxel or paclitaxel treated A204 rhabdomyosarcoma cells by CER11+ human primary B cells. Arrows indicate phagocytosis events.

FIGS. 73A-73B show fluorescent microscope images of in vitro phagocytosis of dexamethasone treated thymocytes by CER12+ Ba/F3 cells (FIG. 73B) or control EGFRt+ Ba/F3 cells (FIG. 73A). White arrows indicate phagocytosis events. High magnification of an engulfment event is shown on the right.

FIG. 74A shows a table of values for percentage of phagocytosing cells and hybrid capture values of CER12+ cells or EGFRt+ control Ba/F3 cells co-cultured with dexamethansone-treated thymocytes. FIG. 74B shows a graph of phagocytic index for CER12+ cells or EGFRt+ control Ba/F3 cells.

FIG. 81 shows fluorescent microscope images of in vitro phagocytosis of paclitaxel treated A204 rhabdomyosarcoma cells by CER13+ human primary B cells. Arrows indicate phagocytosis events.

FIG. 82 shows fluorescent microscope images of in vitro phagocytosis of paclitaxel and gemcitabine treated Colo320 HSR colon cancer cells by CER13+ human primary B cells. Arrows indicate phagocytosis events.

FIGS. 85A-85B show fluorescent microscope images of in vitro phagocytosis of dexamethasone treated thymocytes by CER15+ Ba/F3 cells (FIG. 85B) or control EGFRt+ Ba/F3 cells (FIG. 85A). White arrows indicate phagocytosis events. High magnification of an engulfment event is shown on the right.

FIG. 86A shows a table of values for percentage of phagocytosing cells and hybrid capture values of CER15+ cells or EGFRt+ control Ba/F3 cells co-cultured with dexamethansone-treated thymocytes. FIG. 86B shows a graph of phagocytic index for CER15+ cells or EGFRt+ control Ba/F3 cells.

FIGS. 90A-90B show transduction and expansion of CER15+ human primary B cells. FIG. 90A shows FACS analysis of human primary B cells transduced with CER15 (right histogram) and control B cell (left histogram) using an anti-EGFR antibody and then an anti-Tim4 Kat5-18 antibody. FIG. 49B shows purified CER15+ B cells that were expanded at 24 hours, 48 hours and 72 hours.

FIGS. 93A-93B show fluorescent microscope images of in vitro phagocytosis of staurosporine treated Jurkat cells by CER15+ human primary B cells (FIG. 93A) compared to control human primary B cells transduced with truncated EGFR (FIG. 93B). White arrows indicate phagocytosis events.

FIG. 98 shows fluorescent microscope images of in vitro phagocytosis by CER25+ Ba/F3 cells co-cultured with dexamethasone treated thymocytes. High magnification of an engulfment event is shown to the right. White arrows indicate phagocytosis events.

The lentiviral vector also comprises a sequence encoding truncated EGFR (SEQ ID NO:121), which is separated from the CER86 sequence by a viral T2A sequence.

Figure 105:
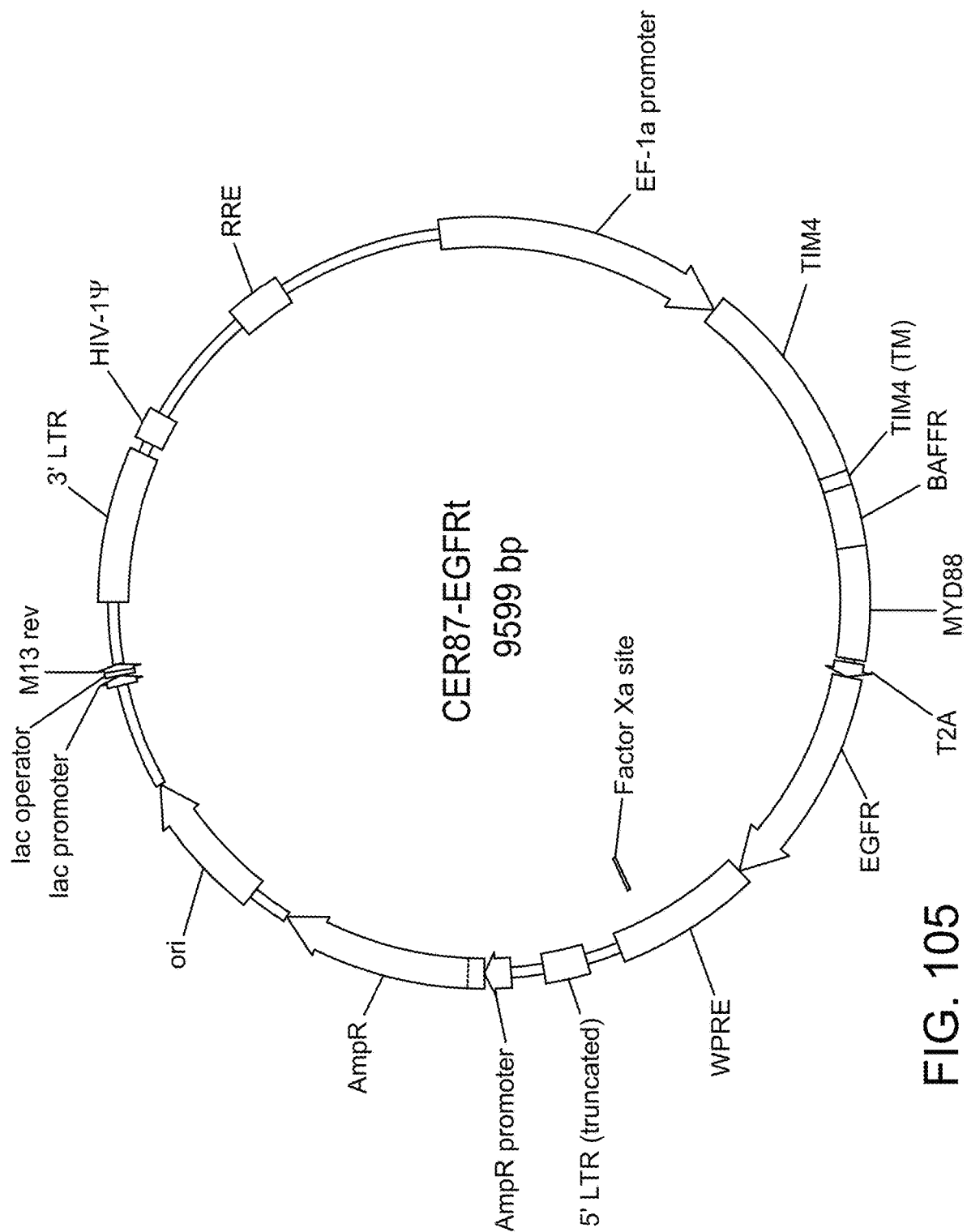

FIG. 105 shows a vector map for a lentiviral vector comprising "CER87" chimeric engulfment receptor having an amino acid sequence of SEQ ID NO:130. CER87 comprises a Tim4 binding domain, a Tim4 transmembrane domain, a primary engulfment signaling domain that is a BAFFR signaling domain, and a secondary engulfment signaling domain that is a truncated MyD88 signaling domain. The lentiviral vector also comprises a sequence encoding truncated EGFR (SEQ ID NO:121), which is separated from the CER87 sequence by a viral T2A sequence.

Figure 106B:
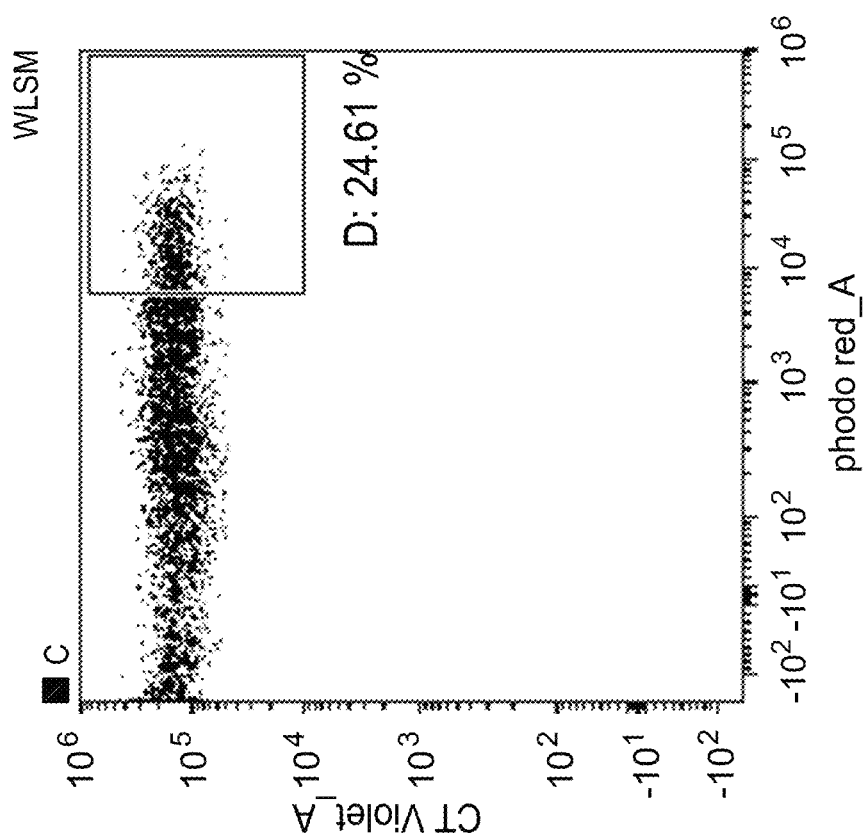
Figure 106A:
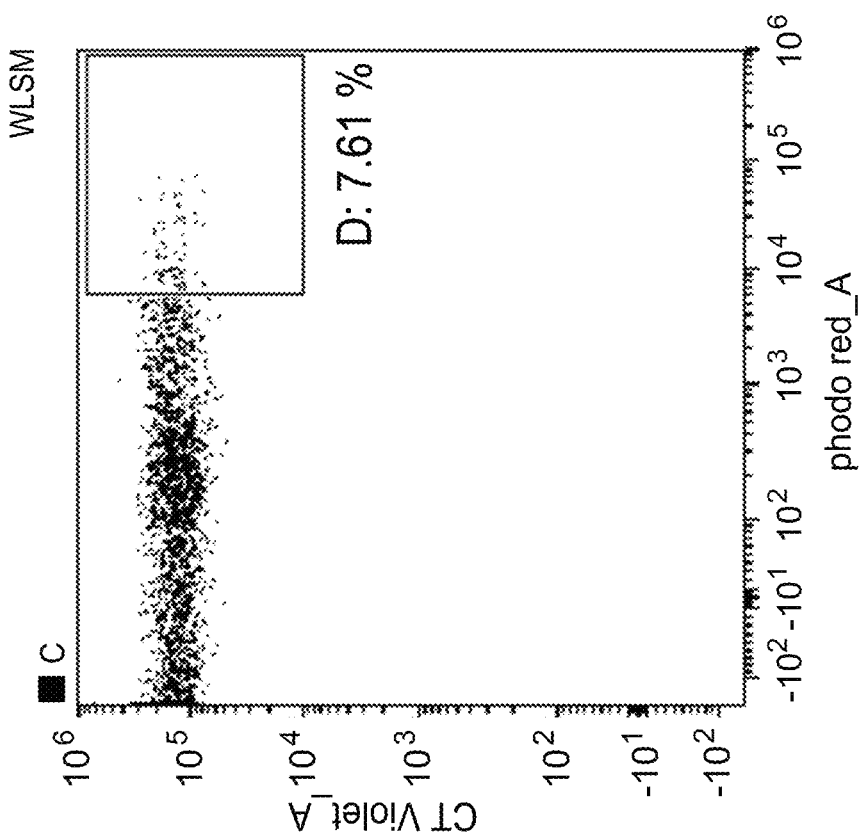

FIGS. 106A-106B show FACS quantification of engulfment of dexamethasone treated thymocytes by CER87+ Ba/F3 murine B cells by measuring the cell population that stained double positive for pHrodo Red and CELLTRACE Violet (FIG. 106A) compared to control Ba/F3 cells transduced with truncated EGFR (FIG. 106B).

Figure 107:
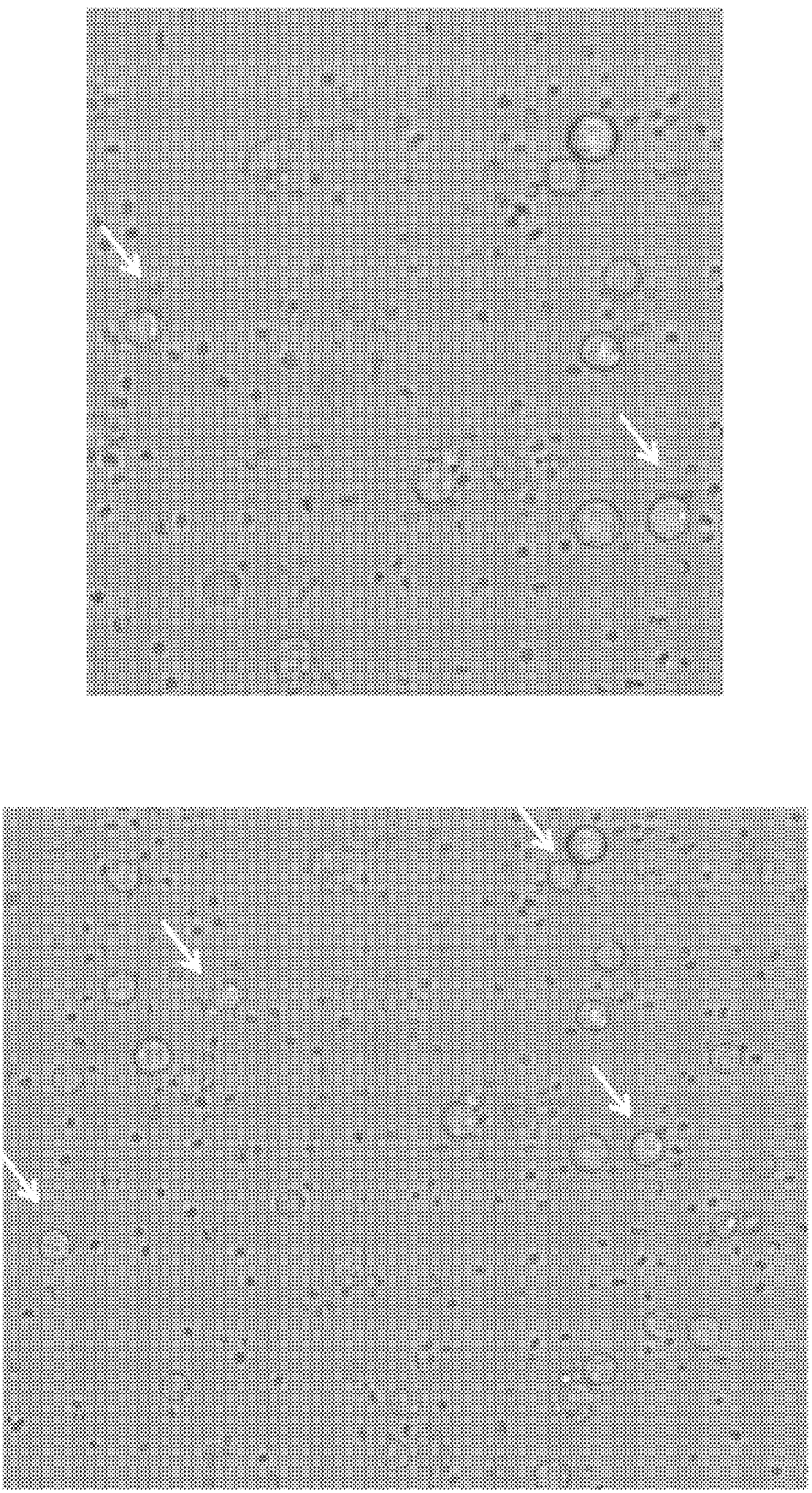

FIG. 107 shows fluorescent microscope images of in vitro phagocytosis by CER87+ Ba/F3 cells co-cultured with dexamethasone treated thymocytes. High magnification of an engulfment event is shown to the right. White arrows indicate phagocytosis events.

Figure 108:
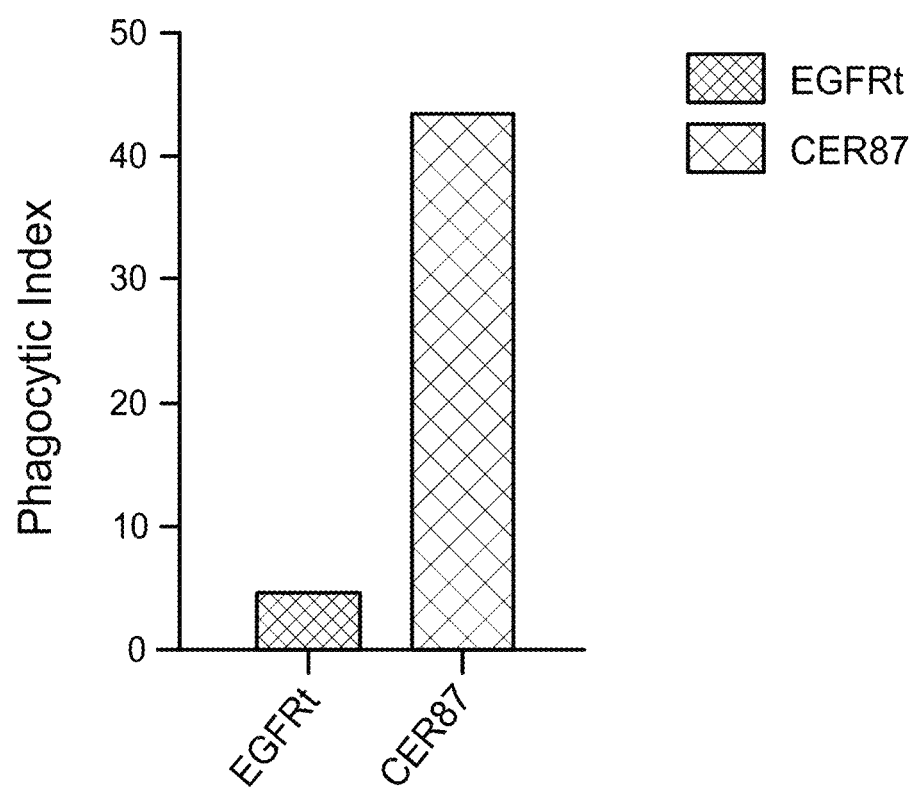

FIG. 108 shows a graph of phagocytic index of CER87+ Ba/F3 cells co-cultured with dexamethasone treated thymocytes compared to control Ba/F3 cells transduced with truncated EGFR.

Figure 109:
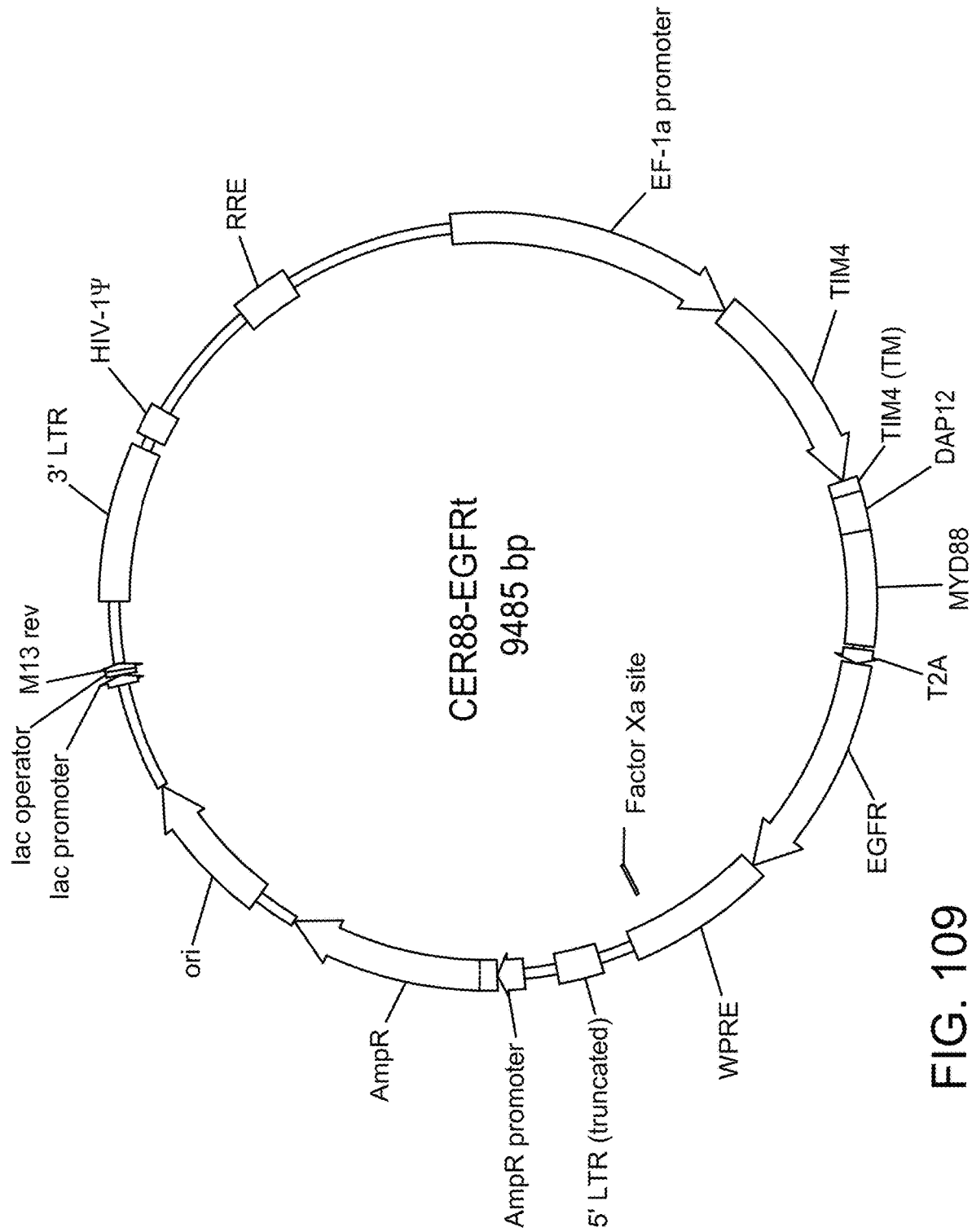

FIG. 109 shows a vector map for a lentiviral vector comprising "CER88" chimeric engulfment receptor having an amino acid sequence of SEQ ID NO:131. CER88 comprises a Tim4 binding domain, a Tim4 transmembrane domain, a primary engulfment signaling domain that is a DAP12 signaling domain, and a secondary engulfment signaling domain that is a truncated MyD88 signaling domain. The lentiviral vector also comprises a sequence encoding truncated EGFR (SEQ ID NO:121), which is separated from the CER88 sequence by a viral T2A sequence.

Figure 110:
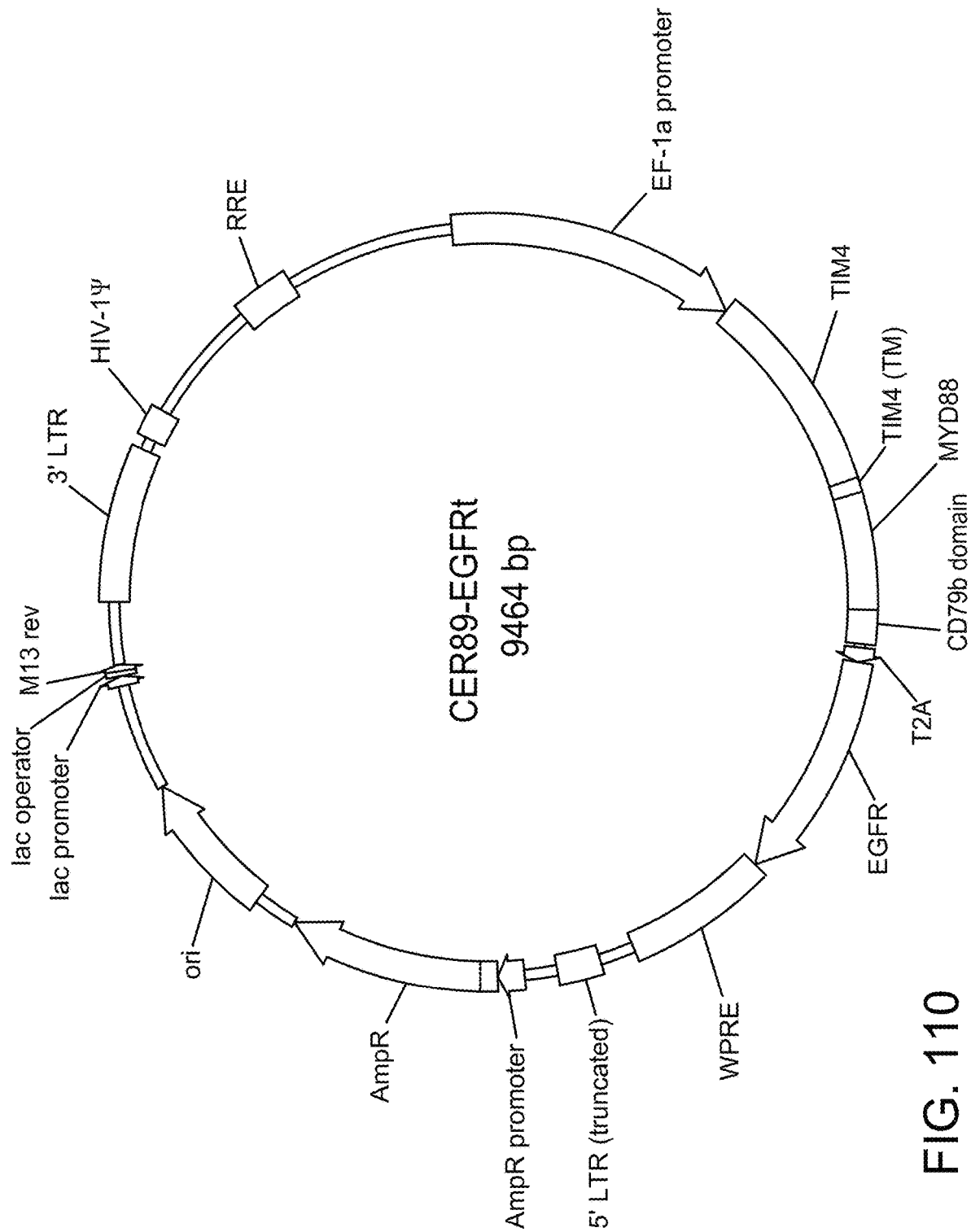

FIG. 110 shows a vector map for a lentiviral vector comprising "CER89" chimeric engulfment receptor having an amino acid sequence of SEQ ID NO:98. CER89 comprises a Tim4 binding domain, a Tim4 transmembrane domain, a primary engulfment signaling domain that is a truncated MyD88 signaling domain, and a secondary engulfment signaling domain that is a CD79b signaling domain. The lentiviral vector also comprises a sequence encoding truncated EGFR (SEQ ID NO:121), which is separated from the CER89 sequence by a viral T2A sequence.

Figure 111:
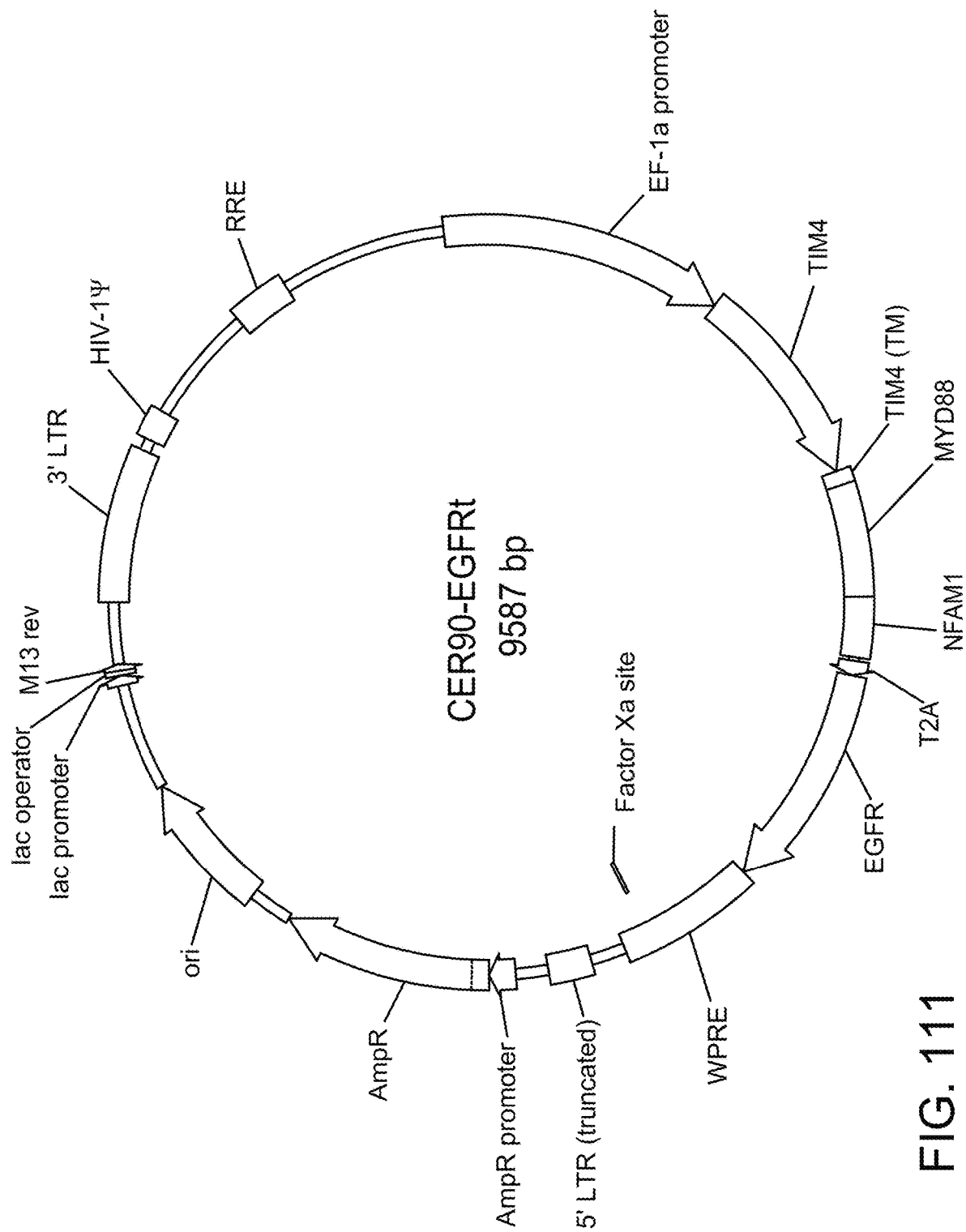

FIG. 111 shows a vector map for a lentiviral vector comprising "CER90" chimeric engulfment receptor having an amino acid sequence of SEQ ID NO:100. CER90 comprises a Tim4 binding domain, a Tim4 transmembrane domain, a primary engulfment signaling domain that is a truncated MyD88 signaling domain, and a secondary engulfment signaling domain that is a NFAM1 signaling domain. The lentiviral vector also comprises a sequence encoding truncated EGFR (SEQ ID NO:121), which is separated from the CER90 sequence by a viral T2A sequence.

Figure 112:
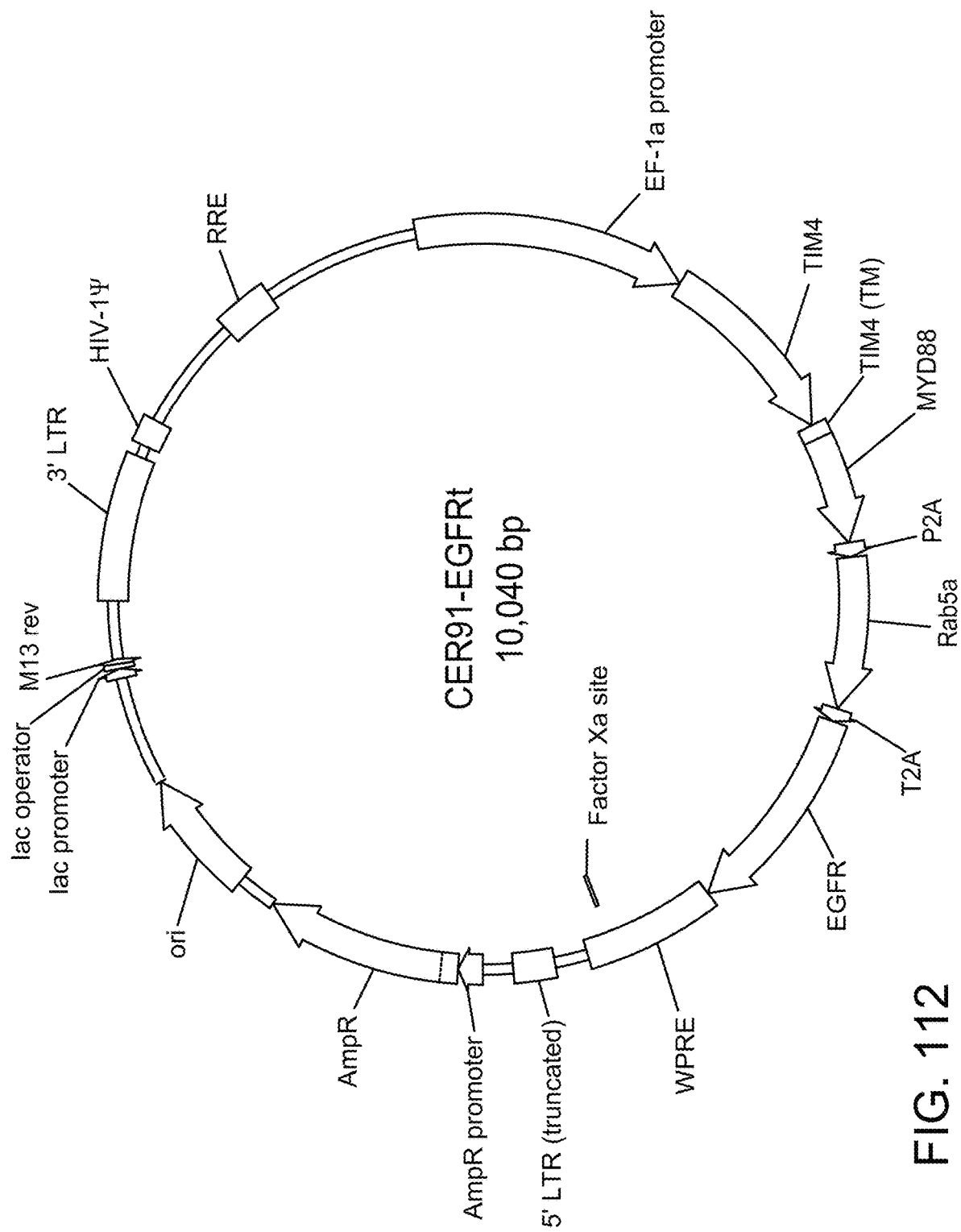

FIG. 112 shows a vector map for a lentiviral vector comprising "CER91" chimeric engulfment receptor having an amino acid sequence of SEQ ID NO:105. CER91 comprises a Tim4 binding domain, a Tim4 transmembrane domain, a primary engulfment signaling domain that is a truncated MyD88 signaling domain, a sequence encoding Rab5a, which is separated from the CER sequence by a viral P2A sequence, and a sequence encoding truncated EGFR (SEQ ID NO:121), which is separated from the Rab5a sequence by a viral T2A sequence.

Figure 113B:
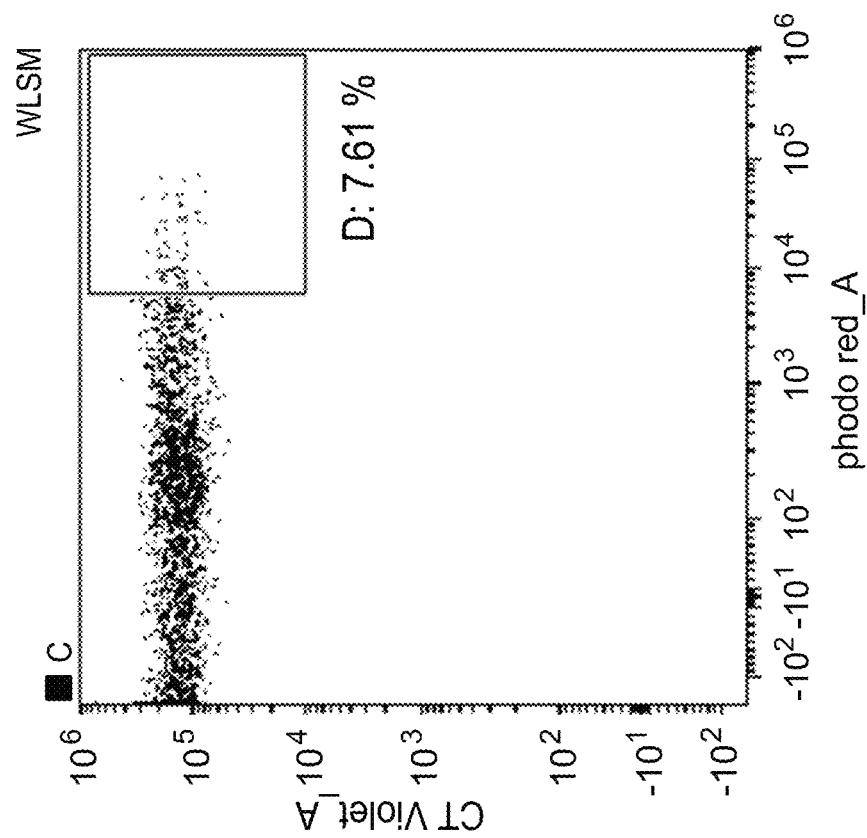
Figure 113A:
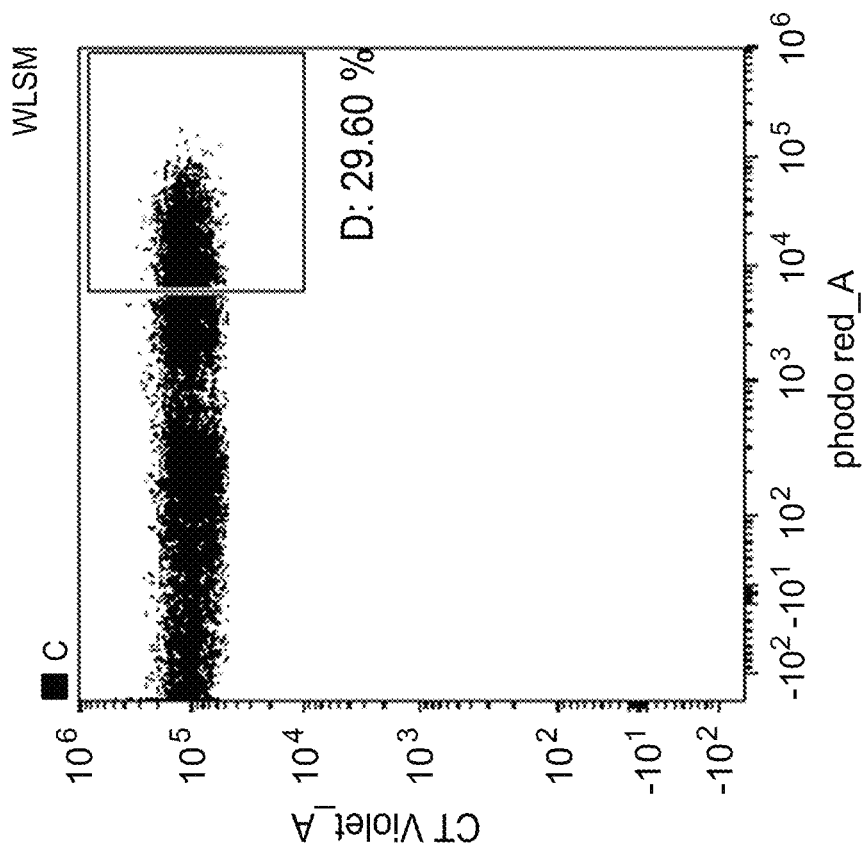

FIGS. 113A-113B show FACS quantification of engulfment of dexamethasone treated thymocytes by CER91+ Ba/F3 murine B cells by measuring the cell population that stained double positive for pHrodo Red and CELLTRACE Violet (FIG. 113A) compared to control Ba/F3 cells transduced with truncated EGFR (FIG. 113B).

Figure 114:
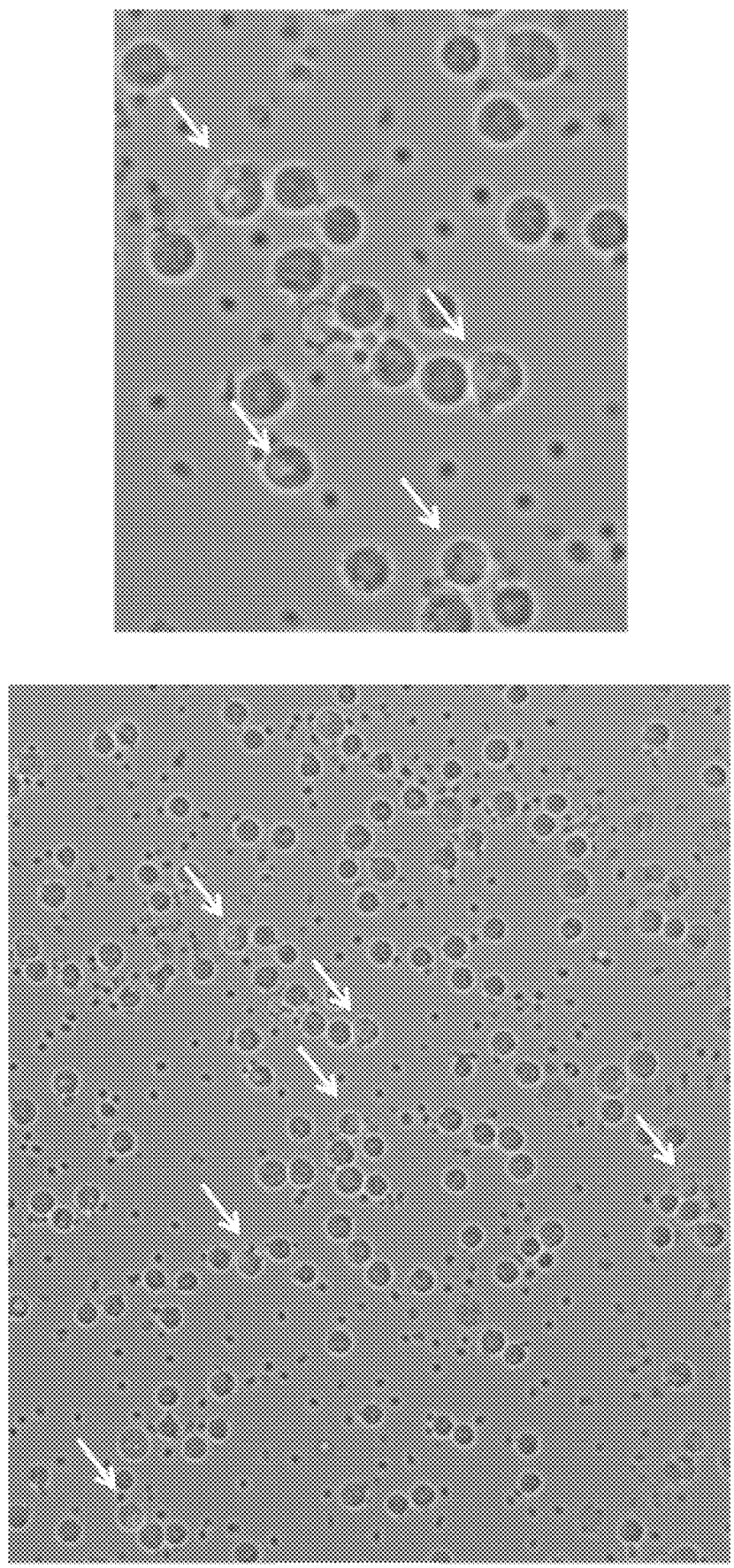

FIG. 114 shows fluorescent microscope images of in vitro phagocytosis by CER91+ Ba/F3 cells co-cultured with dexamethasone treated thymocytes. High magnification of an engulfment event is shown to the right. White arrows indicate phagocytosis events.

Figure 115:
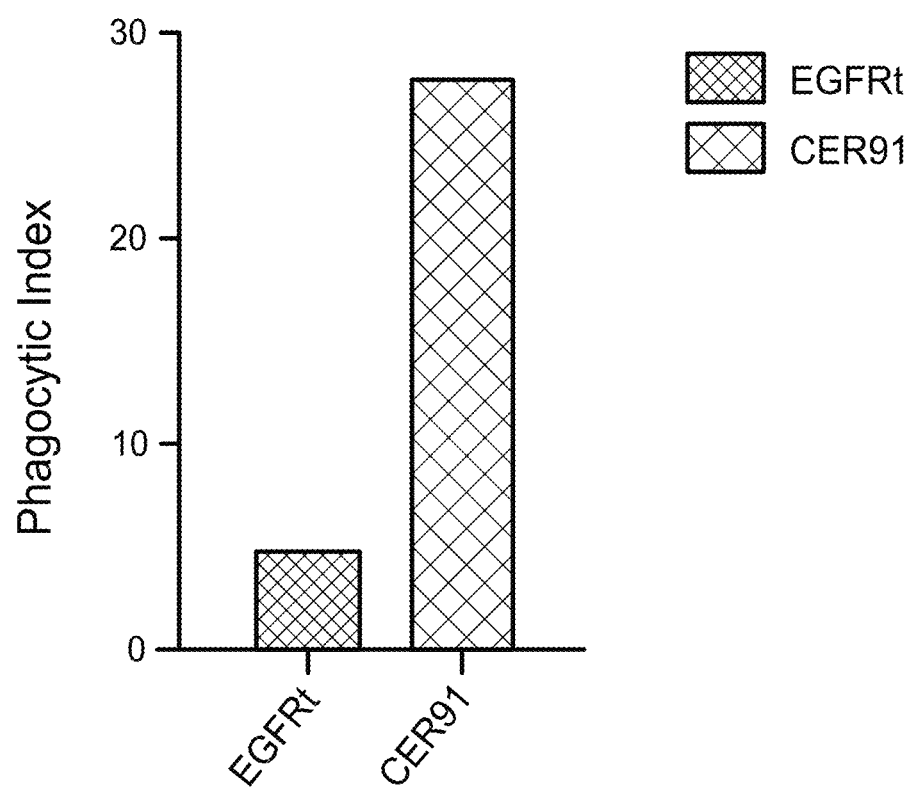

FIG. 115 shows a graph of phagocytic index of CER91+ Ba/F3 cells co-cultured with dexamethasone treated thymocytes compared to control Ba/F3 cells transduced with truncated EGFR.

Figure 116:
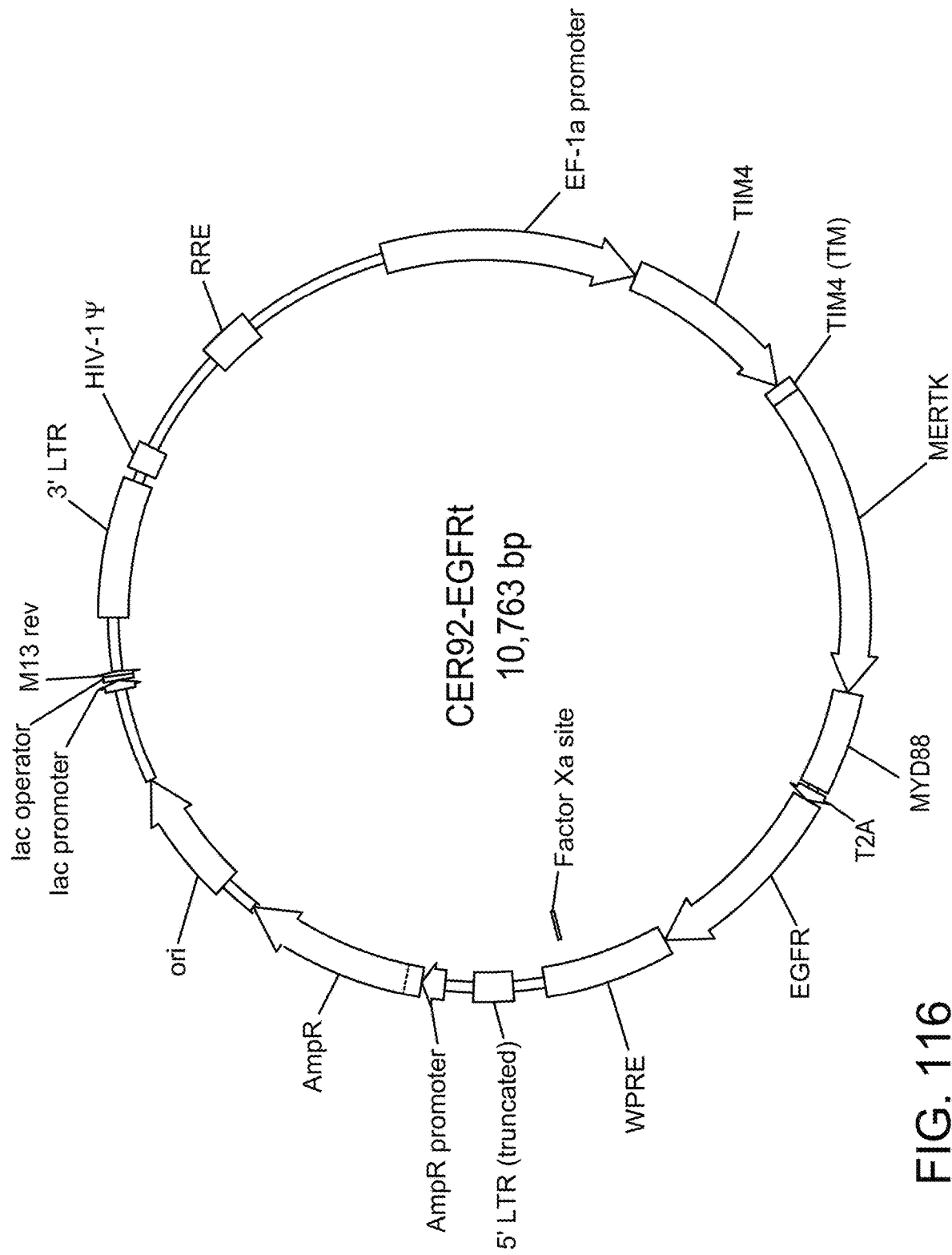

FIG. 116 shows a vector map for a lentiviral vector comprising "CER92" chimeric engulfment receptor having an amino acid sequence of SEQ ID NO:133. CER92 comprises a Tim4 binding domain, a Tim4 transmembrane domain, a primary engulfment signaling domain that is a MERTK signaling domain, and a secondary engulfment signaling domain that is a truncated MyD88 signaling domain. The lentiviral vector also comprises a sequence encoding truncated EGFR (SEQ ID NO:121), which is separated from the CER92 sequence by a viral T2A sequence.

Figure 117B:
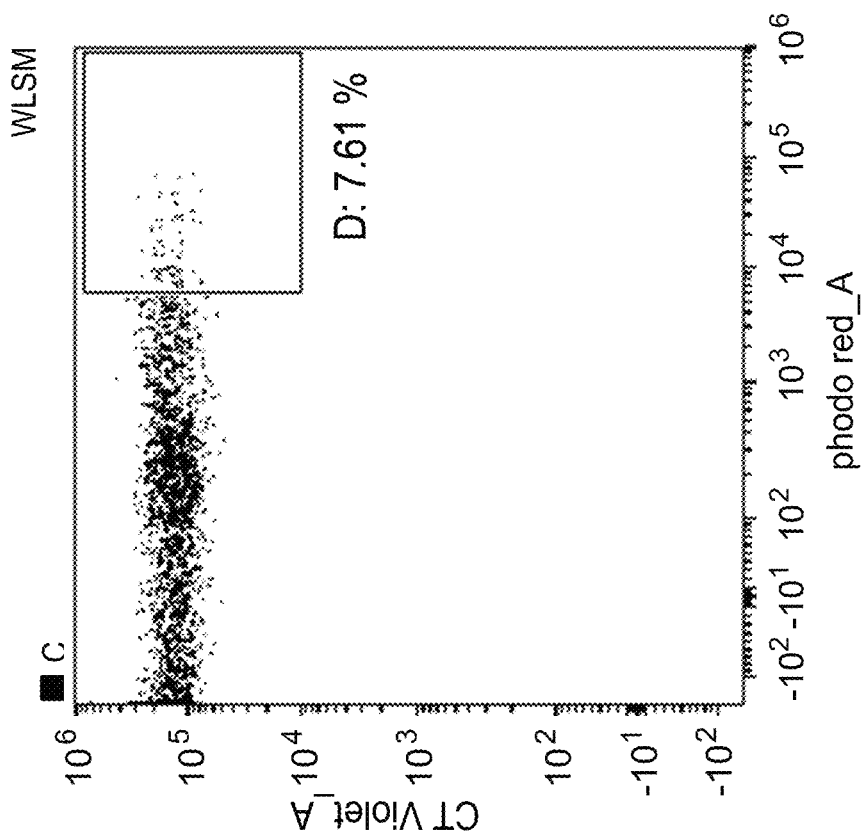
Figure 117A:
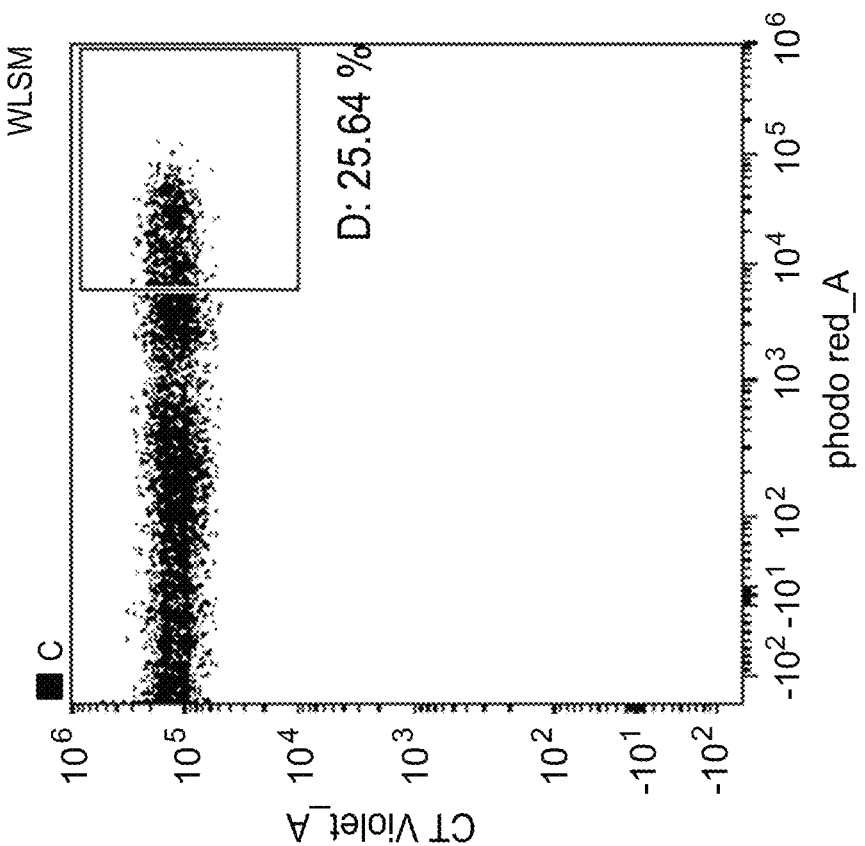

FIGS. 117A-117B show FACS quantification of engulfment of dexamethasone treated thymocytes by CER92+ Ba/F3 murine B cells by measuring the cell population that stained double positive for pHrodo Red and CELLTRACE Violet (FIG. 117A) compared to control Ba/F3 cells transduced with truncated EGFR (FIG. 117B).

FIG. 118 shows fluorescent microscope images of in vitro phagocytosis by CER92+ Ba/F3 cells co-cultured with dexamethasone treated thymocytes. High magnification of an engulfment event is shown to the right. White arrows indicate phagocytosis events.

Figure 119:
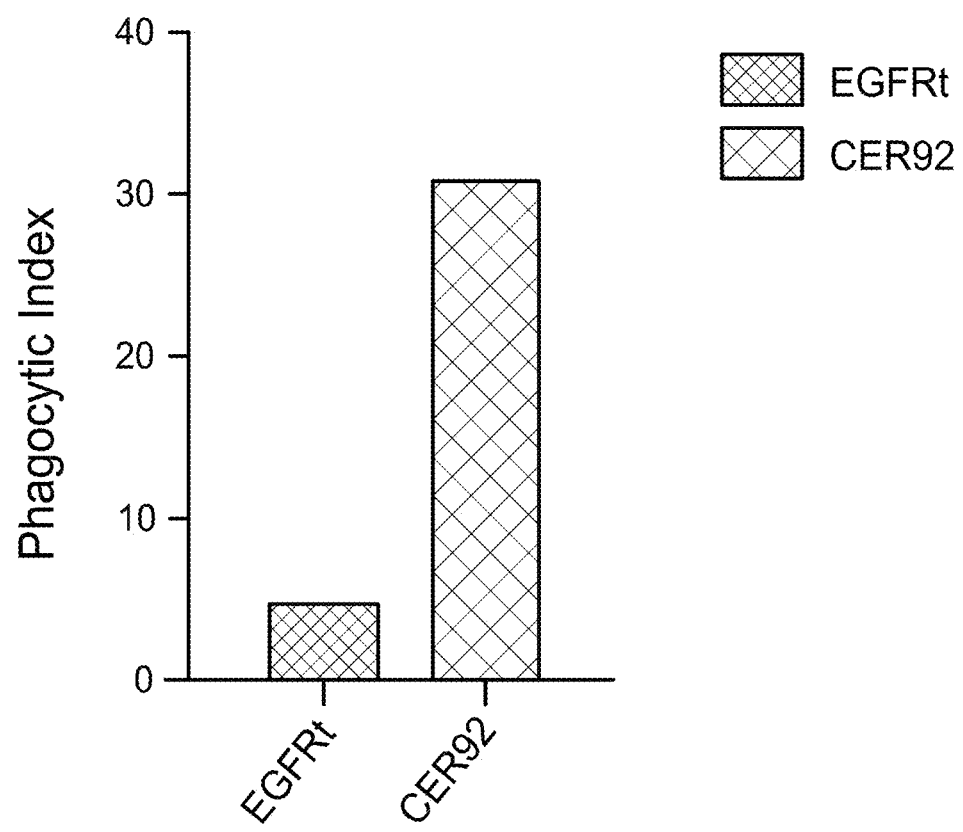

FIG. 119 shows a graph of phagocytic index of CER92+ Ba/F3 cells co-cultured with dexamethasone treated thymocytes compared to control Ba/F3 cells transduced with truncated EGFR.

Figure 120:
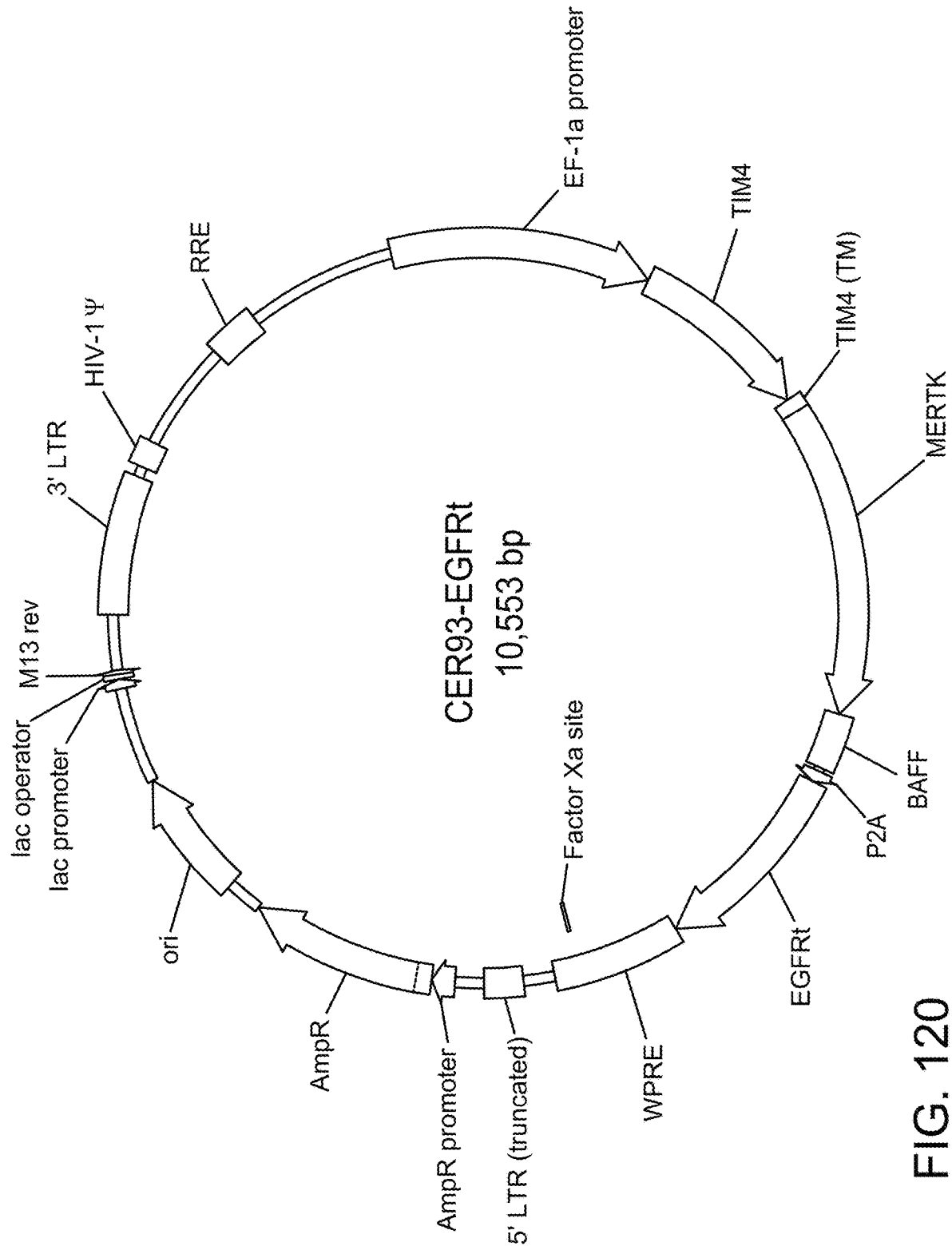

FIG. 120 shows a vector map for a lentiviral vector comprising "CER93" chimeric engulfment receptor having an amino acid sequence of SEQ ID NO:103. CER93 comprises a Tim4 binding domain, a Tim4 transmembrane domain, a primary engulfment signaling domain that is a MERTK signaling domain, and a secondary engulfment signaling domain that is a BAFFR signaling domain. The lentiviral vector also comprises a sequence encoding truncated EGFR (SEQ ID NO:121), which is separated from the CER93 sequence by a viral T2A sequence.

Figure 121B:
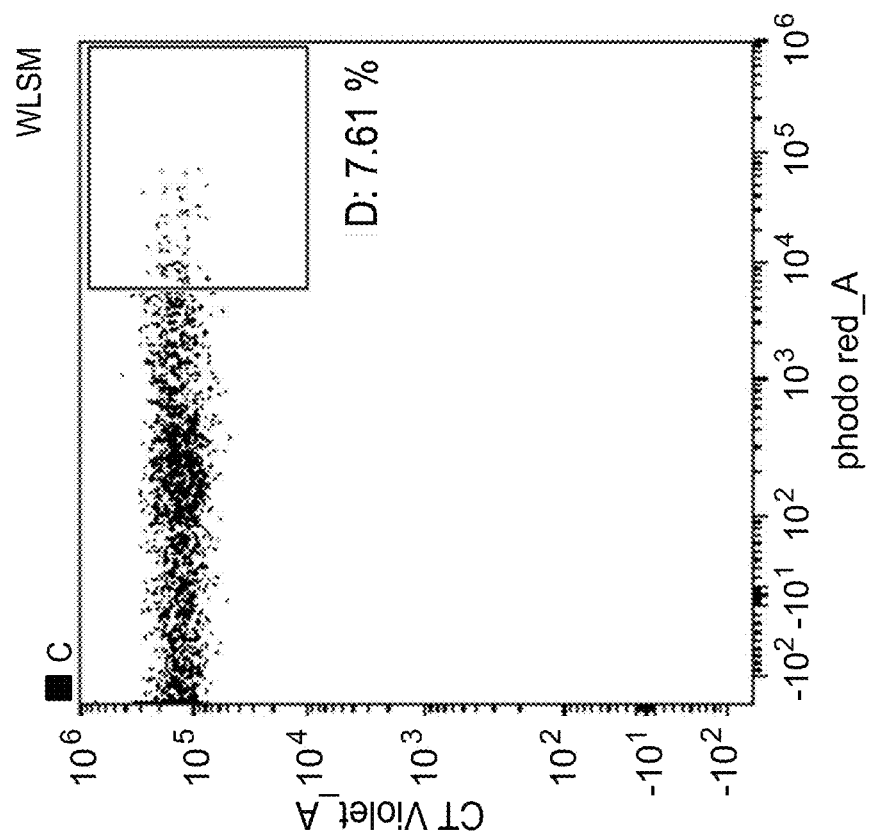
Figure 121A:
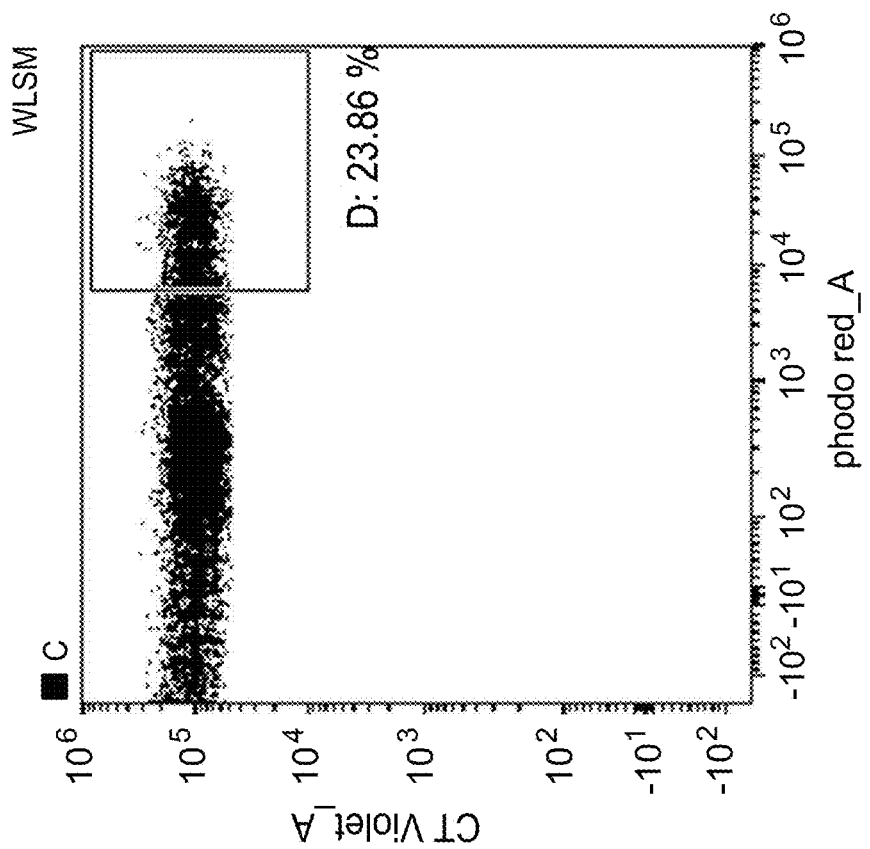

FIGS. 121A-121B show FACS quantification of engulfment of dexamethasone treated thymocytes by CER93+ Ba/F3 murine B cells by measuring the cell population that stained double positive for pHrodo Red and CELLTRACE Violet (FIG. 121A) compared to control Ba/F3 cells transduced with truncated EGFR (FIG. 121B).

FIG. 122 shows fluorescent microscope images of in vitro phagocytosis by CER93+ Ba/F3 cells co-cultured with dexamethasone treated thymocytes. High magnification of an engulfment event is shown to the right. White arrows indicate phagocytosis events.

Figure 123:
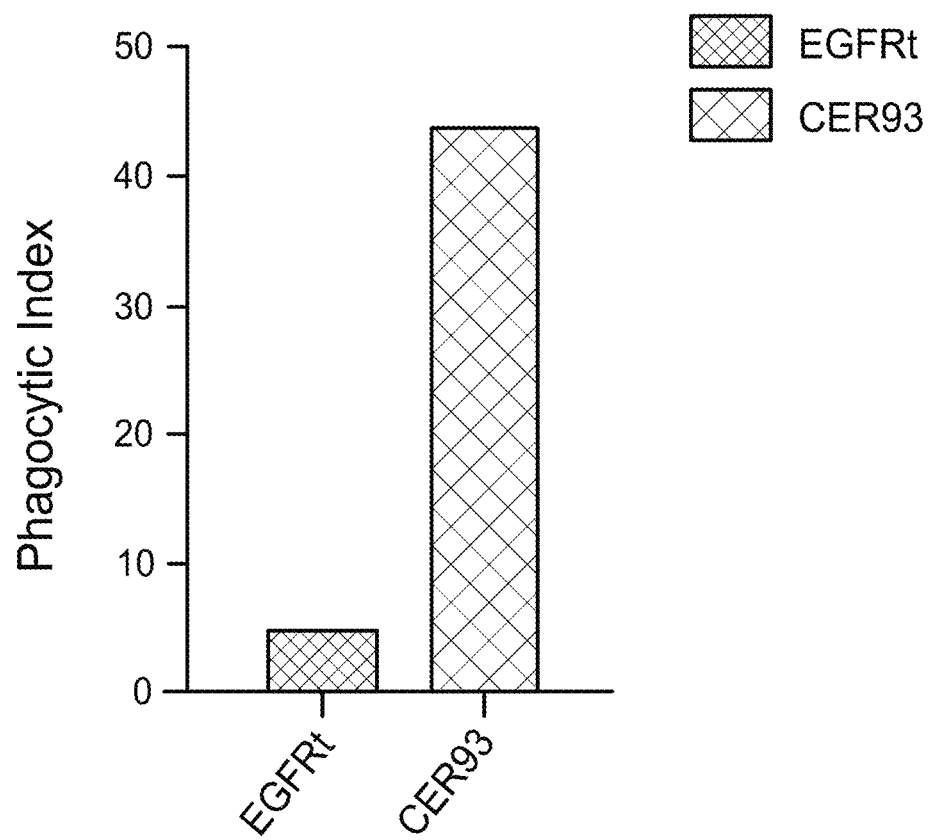

FIG. 123 shows a graph of phagocytic index of CER93+ Ba/F3 cells co-cultured with dexamethasone treated thymocytes compared to control Ba/F3 cells transduced with truncated EGFR.

Figure 124:
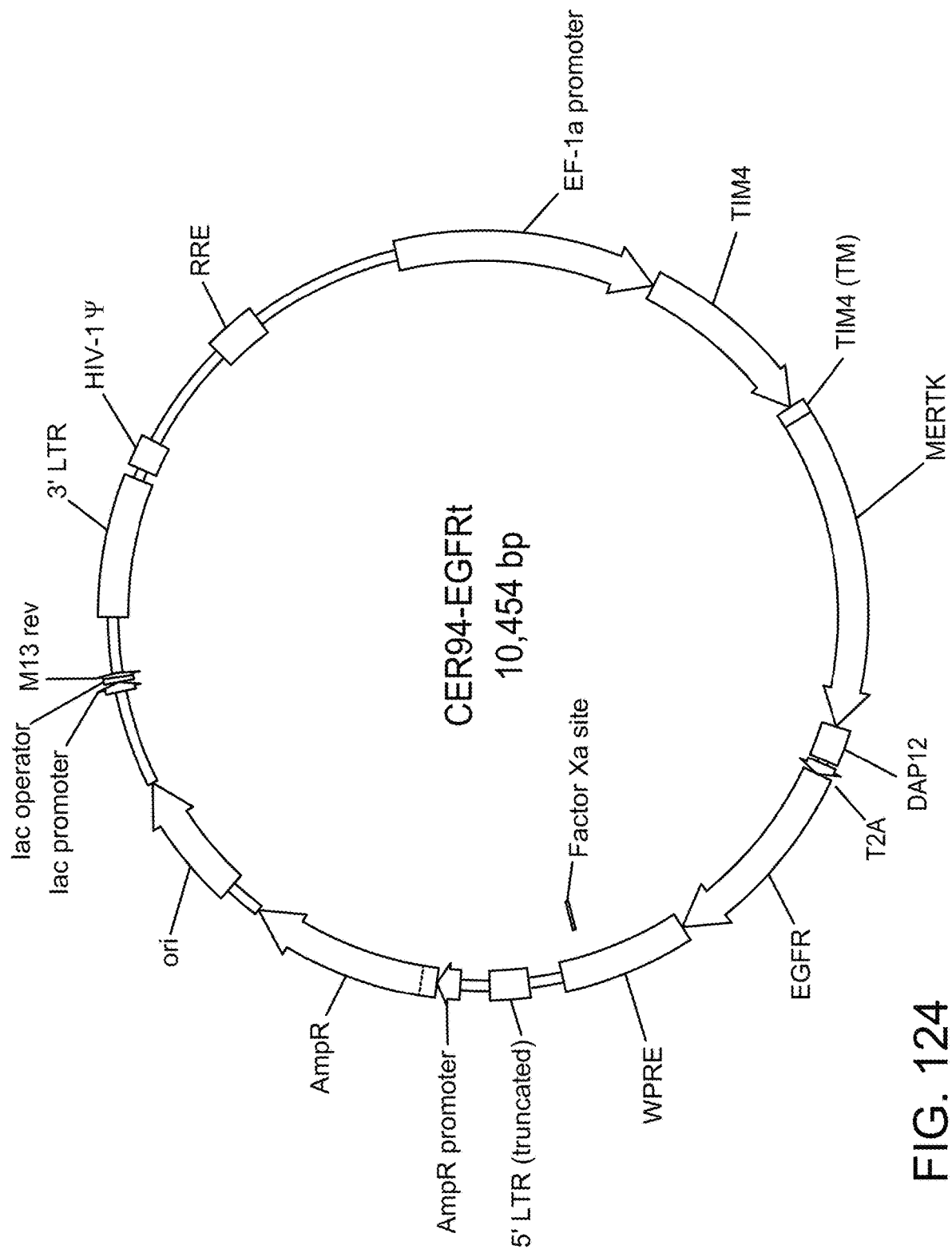

FIG. 124 shows a vector map for a lentiviral vector comprising "CER94" chimeric engulfment receptor having an amino acid sequence of SEQ ID NO:134. CER94 comprises a Tim4 binding domain, a Tim4 transmembrane domain, a primary engulfment signaling domain that is a MERTK signaling domain, and a secondary engulfment signaling domain that is a DAP12 signaling domain. The lentiviral vector also comprises a sequence encoding truncated EGFR (SEQ ID NO:121), which is separated from the CER94 sequence by a viral T2A sequence.

Figure 125:
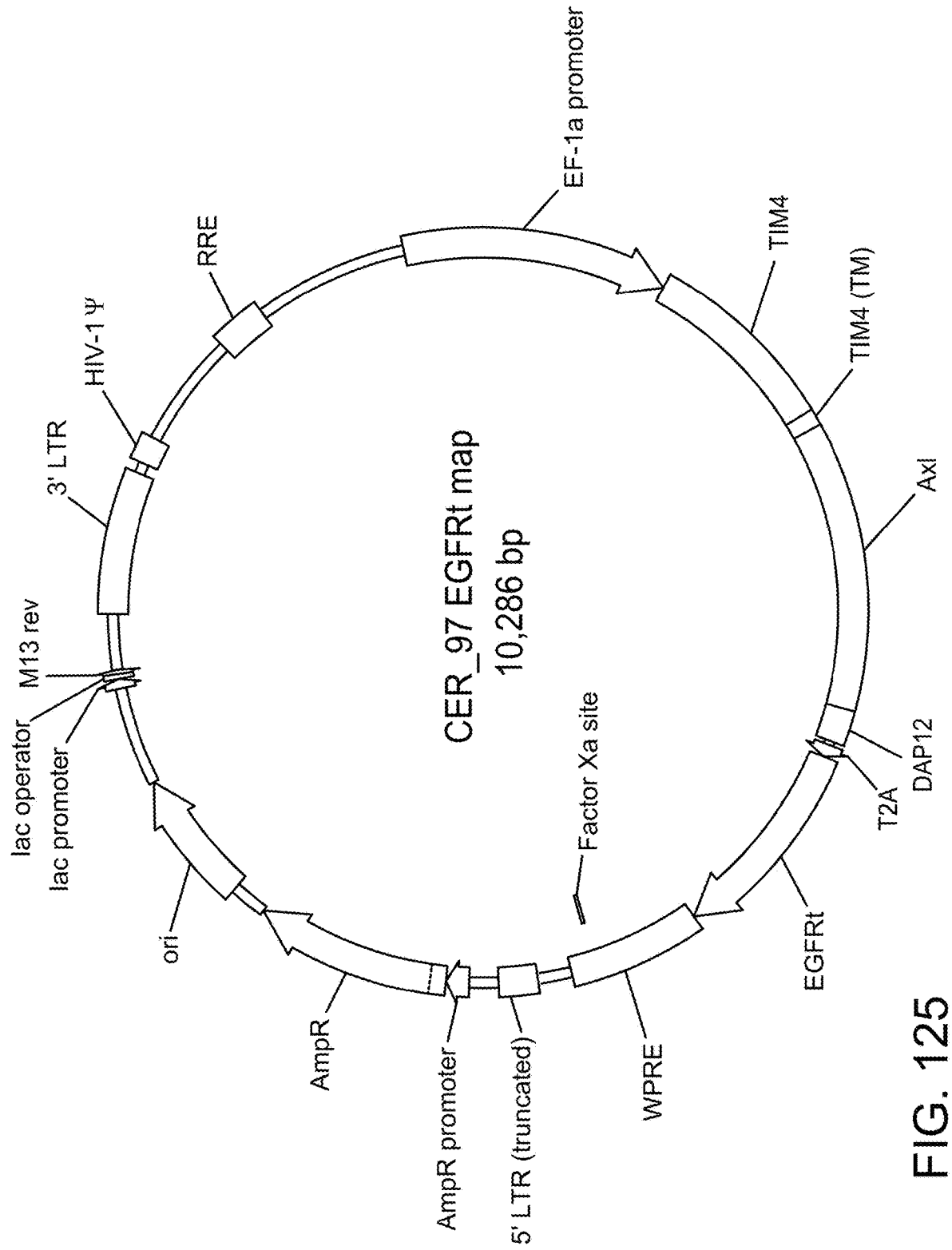

FIG. 125 shows a vector map for a lentiviral vector comprising "CER97" chimeric engulfment receptor having an amino acid sequence of SEQ ID NO:152. CER97 comprises a Tim4 binding domain, a Tim4 transmembrane domain, a primary engulfment signaling domain that is an Ax1 signaling domain, and a secondary engulfment signaling domain that is a DAP12 signaling domain. The lentiviral vector also comprises a sequence encoding truncated EGFR (SEQ ID NO:121), which is separated from the CER97 sequence by a viral T2A sequence.

Figure 126:
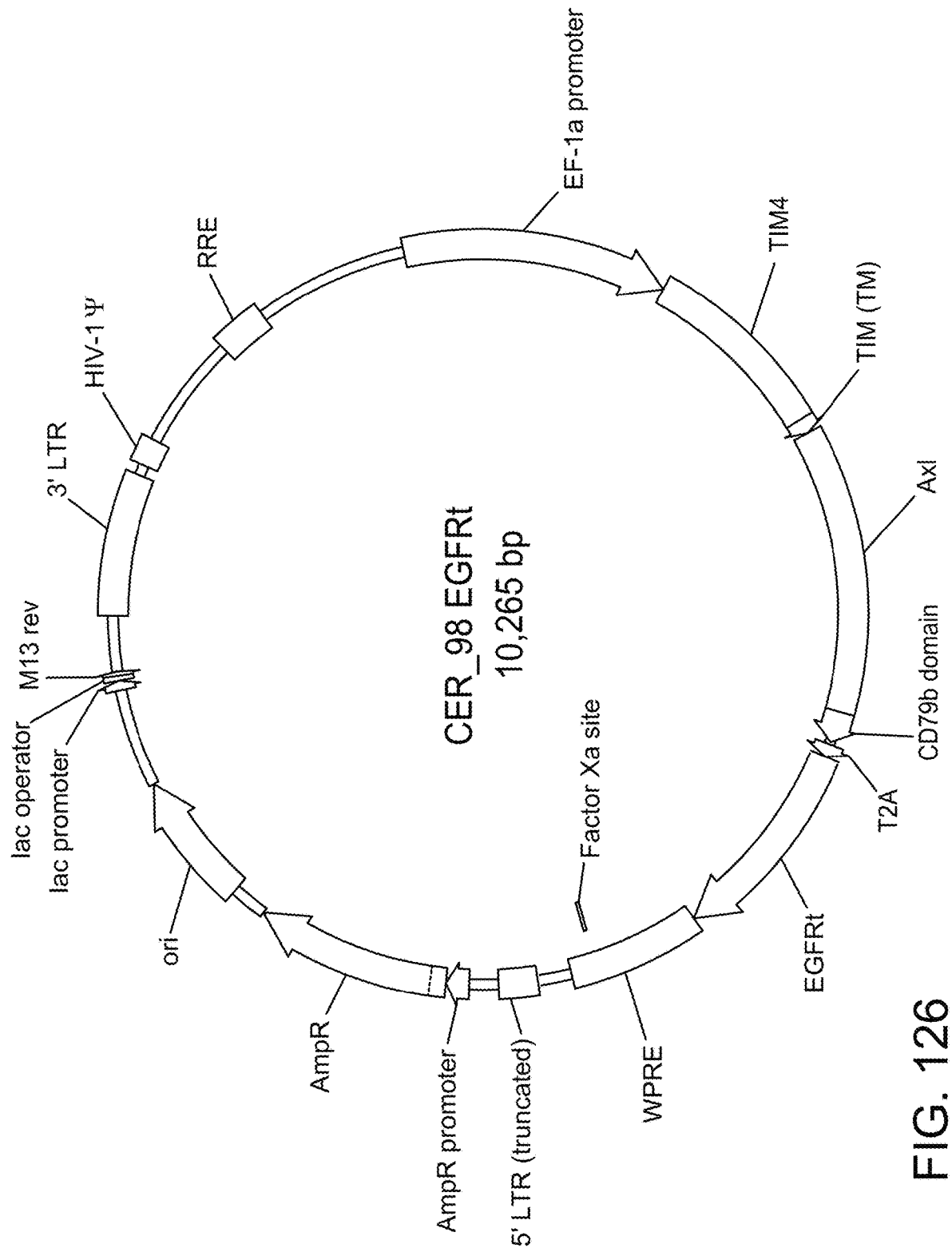

FIG. 126 shows a vector map for a lentiviral vector comprising "CER98" chimeric engulfment receptor having an amino acid sequence of SEQ ID NO:153. CER98 comprises a Tim4 binding domain, a Tim4 transmembrane domain, a primary engulfment signaling domain that is an Ax1 signaling domain, and a secondary engulfment signaling domain that is a CD79b signaling domain. The lentiviral vector also comprises a sequence encoding truncated EGFR (SEQ ID NO:121), which is separated from the CER98 sequence by a viral T2A sequence.

Figure 127:
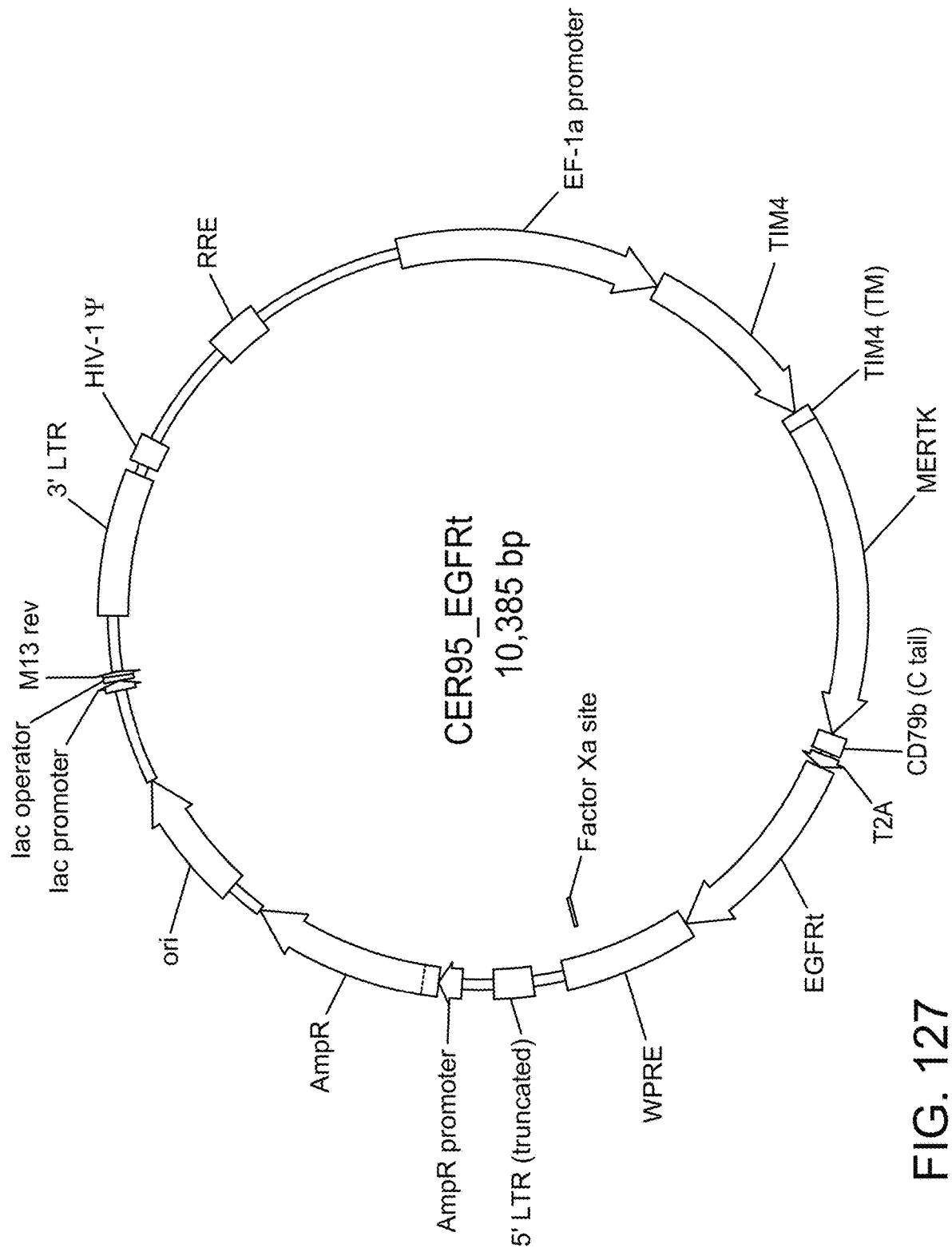

FIG. 127 shows a vector map for a lentiviral vector comprising "CER95" chimeric engulfment receptor having an amino acid sequence of SEQ ID NO:101. CER95 comprises a Tim4 binding domain, a Tim4 transmembrane domain, a primary engulfment signaling domain that is a MERTK signaling domain, and a secondary engulfment signaling domain that is a CD79b signaling domain. The lentiviral vector also comprises a sequence encoding truncated EGFR (SEQ ID NO:121), which is separated from the CER95 sequence by a viral T2A sequence.

Figure 128:
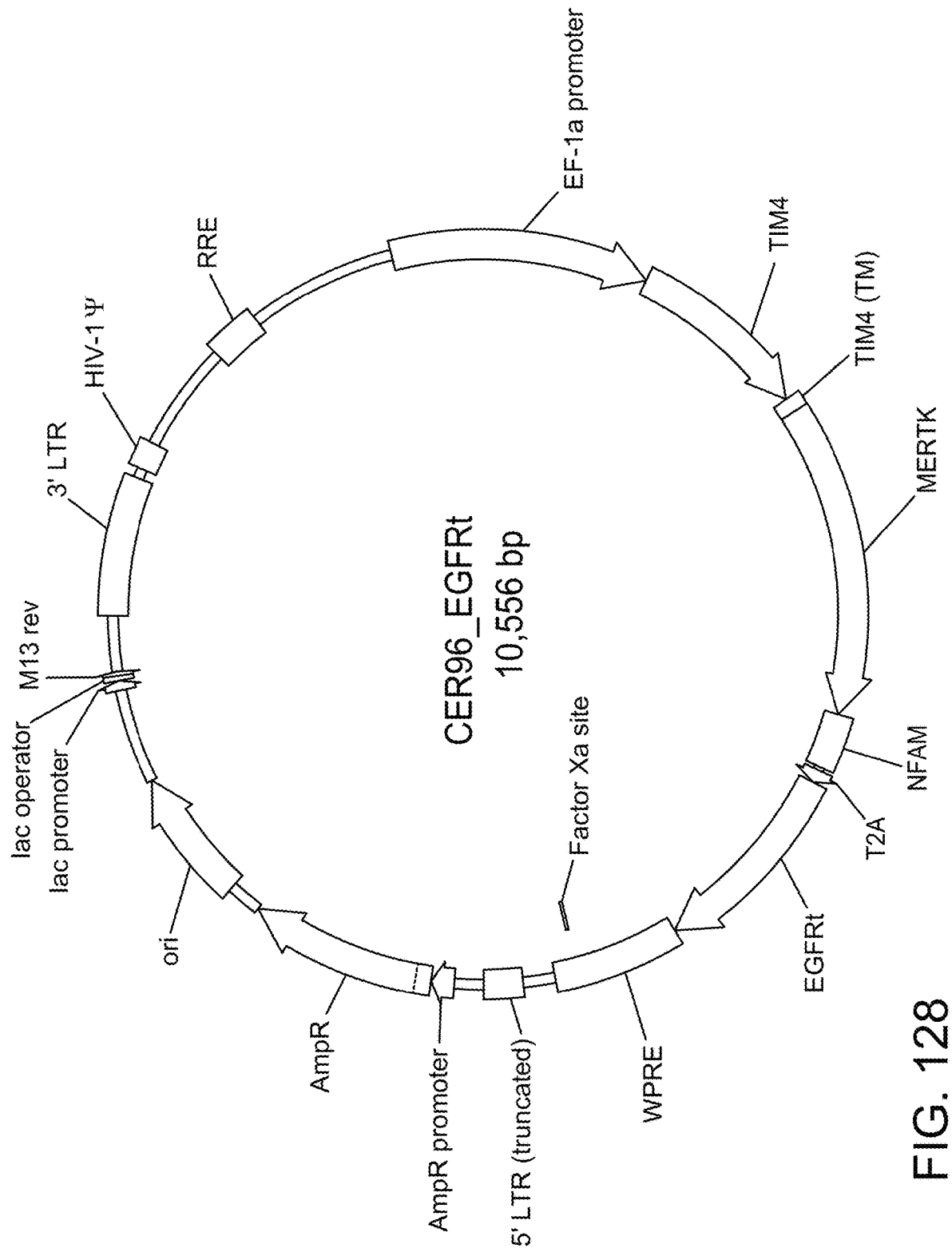

FIG. 128 shows a vector map for a lentiviral vector comprising "CER96" chimeric engulfment receptor having an amino acid sequence of SEQ ID NO:102. CER96 comprises a Tim4 binding domain, a Tim4 transmembrane domain, a primary engulfment signaling domain that is a MERTK signaling domain, and a secondary engulfment signaling domain that is a NFAM1 signaling domain. The lentiviral vector also comprises a sequence encoding truncated EGFR (SEQ ID NO:121), which is separated from the CER96 sequence by a viral T2A sequence.

Figure 129:

FIG. 129 shows phagocytic index of various CER+ Ba/F3 cells co-incubated with dexamethasone treated thymocytes as compared to control Ba/F3 cells transduced with truncated EGFRt.

Figure 130:
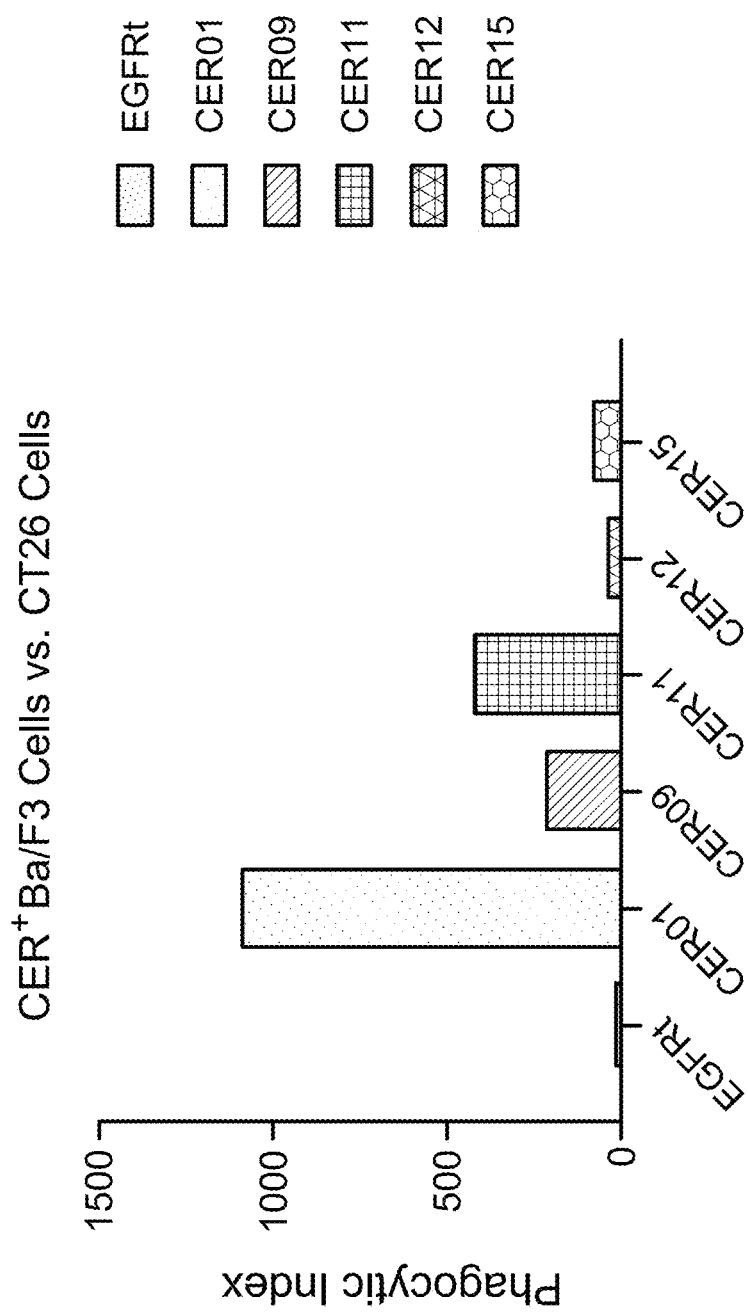

FIG. 130 shows phagocytic index of various CER+ Ba/F3 cells co-incubated with staurosporine treated CT26 colon carcinoma cells as compared to control Ba/F3 cells transduced with truncated EGFRt.

Figure 131:
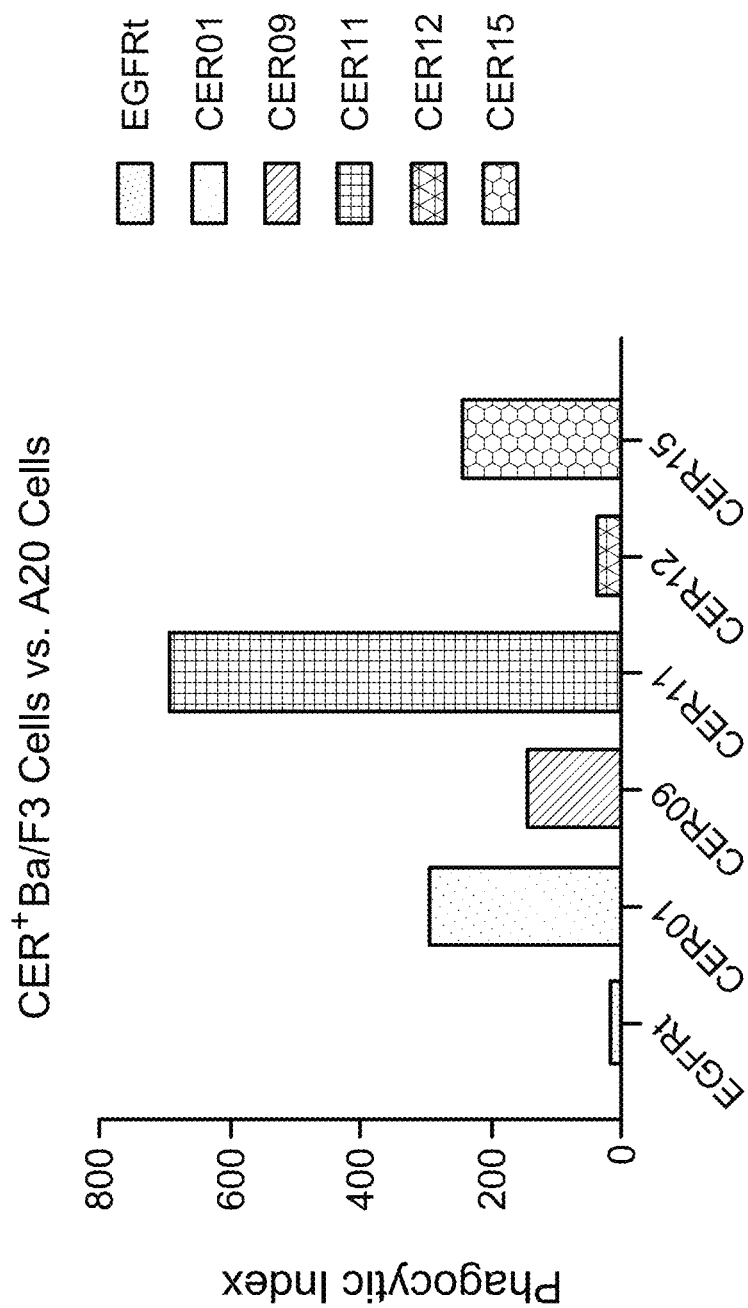

FIG. 131 shows phagocytic index of various CER+ Ba/F3 cells co-incubated with staurosporine treated A20 lymphoma cells as compared to control Ba/F3 cells transduced with truncated EGFRt.

Figure 132A:
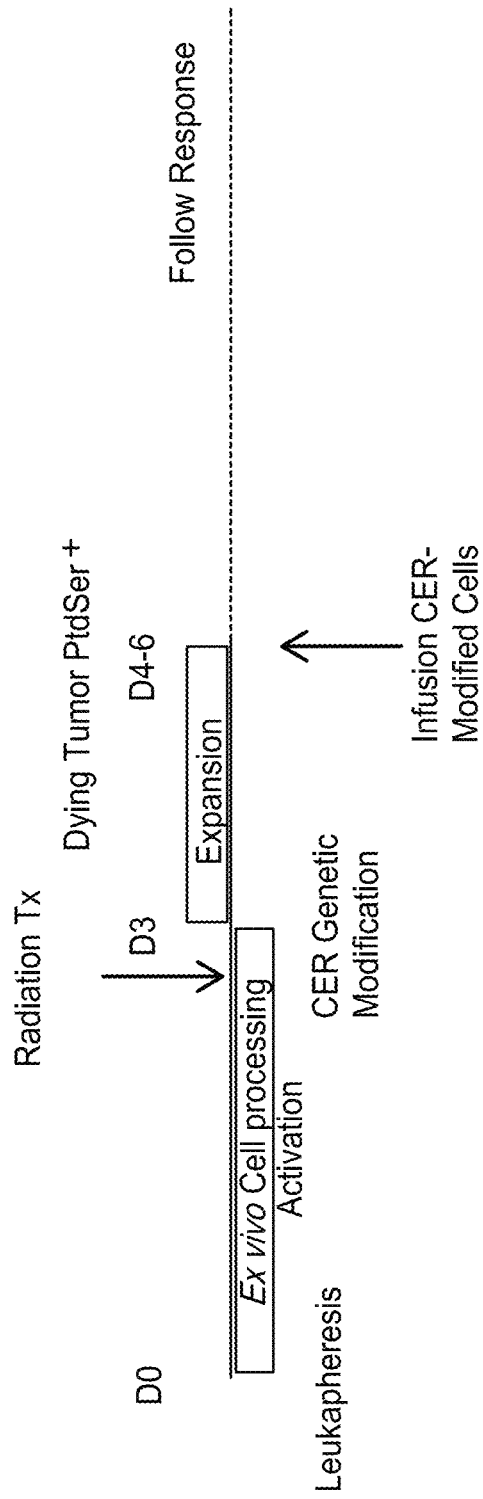
Figure 132B:
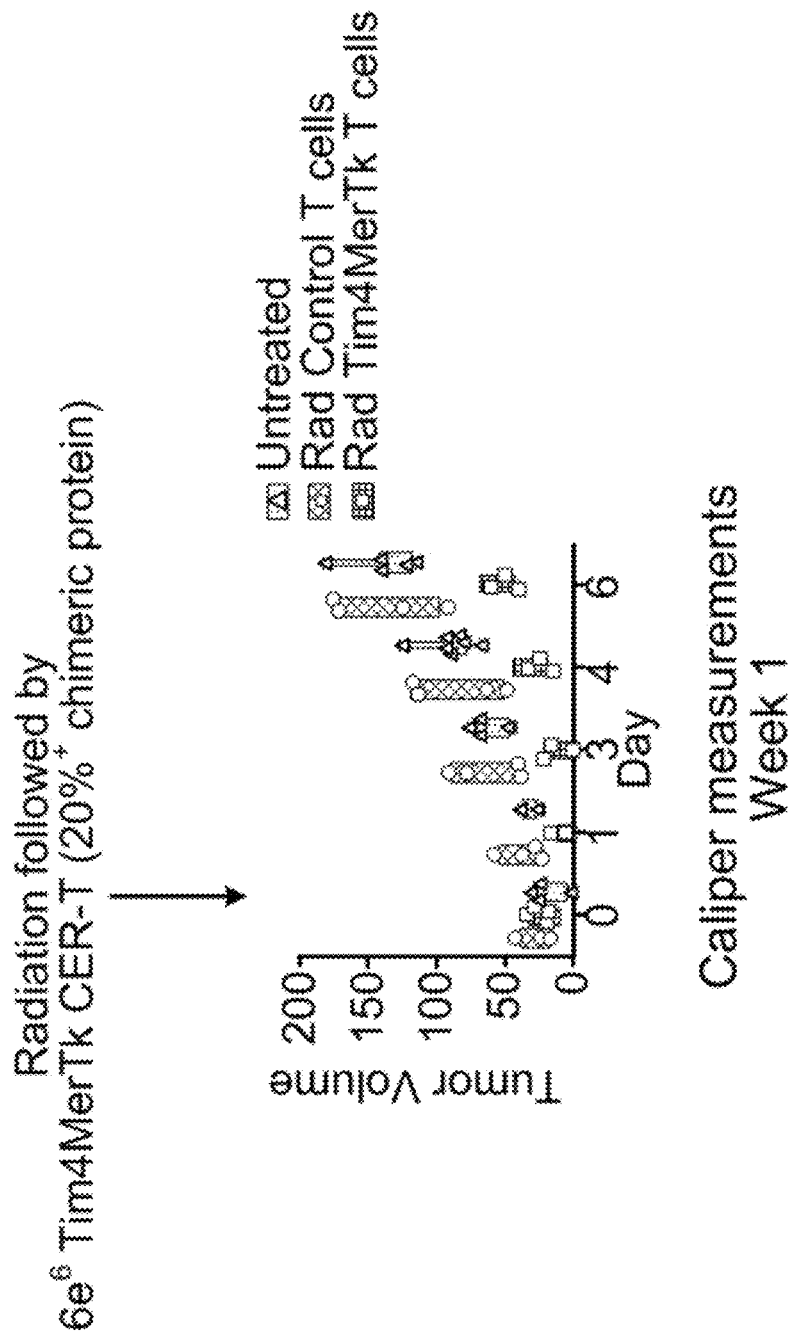

FIGS. 132A-132C show in vivo synergy of CERO (Tim4MerTk) 1 treatment with low dose radiation in a mouse model of lymphoma. FIG. 132A shows an exemplary timeline for a combination therapy regimen. FIG. 132B shows measurement of tumor size in untreated mice, mice receiving radiation+control T cells, or mice receiving radiation+CER01 modified T cells.

Figure 133A:
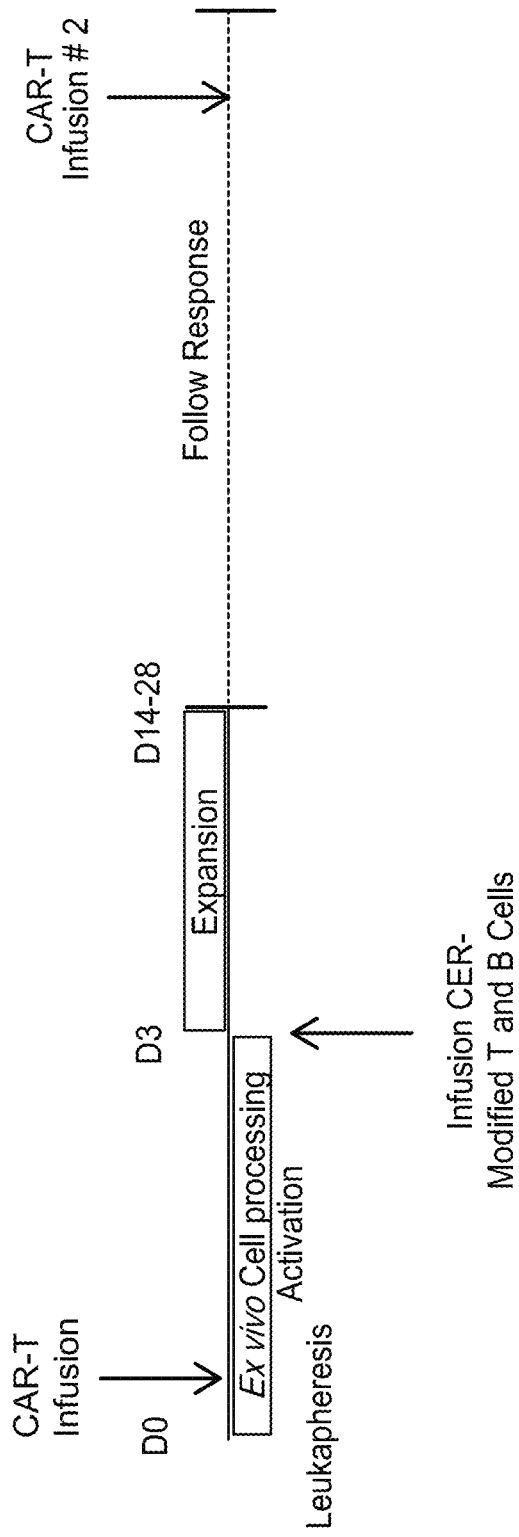

FIGS. 133A-133B show in vivo synergy of CER01 (Tim4MerTk) treatment with chimeric antigen receptor (CAR) T cell therapy in a mouse model of lymphoma. FIG. 133A shows an exemplary timeline for a combination therapy regimen. FIG. 133B shows lucerifase imaging of tumor size in mice receiving anti-CD19 CAR modified T cells and CER modified B cells (n=3) or T cells (n=2) at day 4 post CER infusion (right image) as compared to control mice receiving anti-CD19 CAR modified T cells and pMSCV empty retroviral vector modified T cells (left photo).

Figure 134:
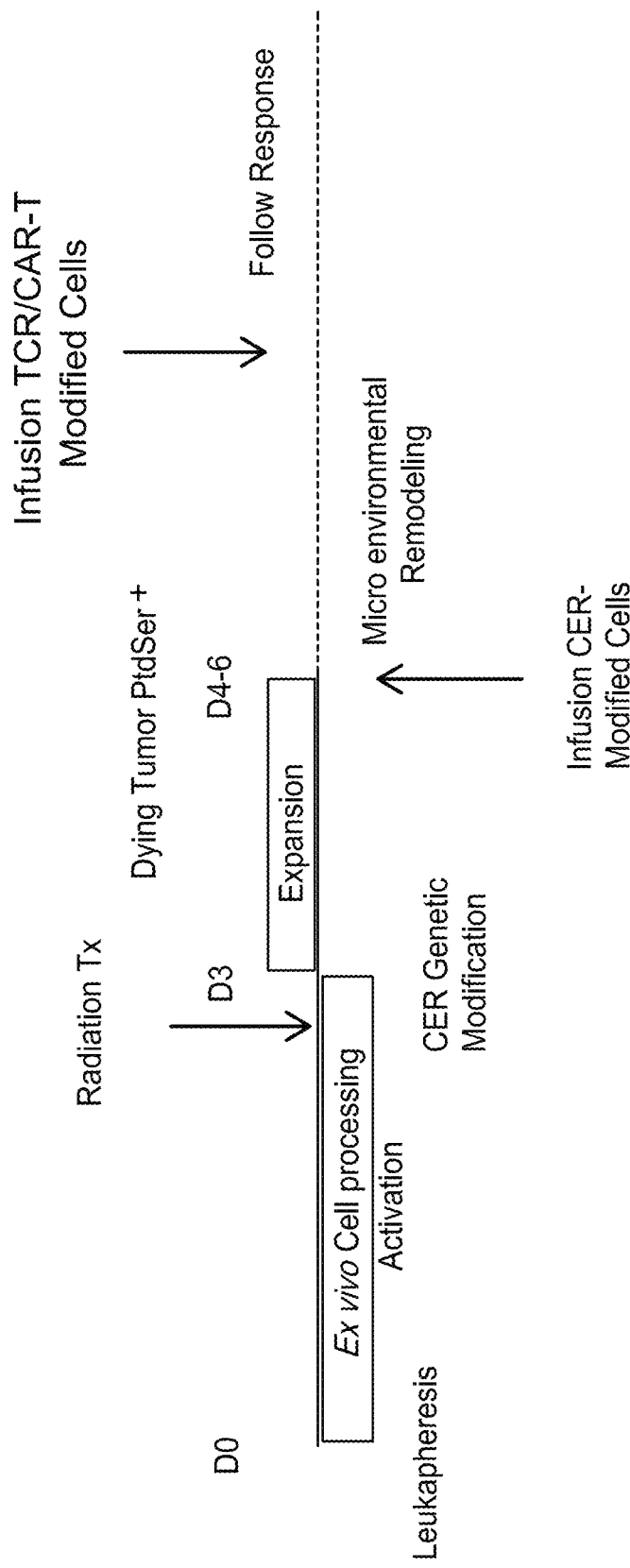

FIG. 134 shows an illustrative triple combination treatment timeline comprising radiation therapy, CER immunotherapy (e.g., targeting phosphatidylserine expressing cells), followed by TCR or CAR immunotherapy.

DETAILED DESCRIPTION

Chimeric proteins including (a) an extracellular domain comprising an extracellular binding domain and, optionally, an extracellular spacer domain, (b) a transmembrane domain, and (c) an engulfment signaling domain, and nucleic acid molecules encoding said chimeric proteins are described herein. Additionally, cells modified to express these chimeric proteins and methods and compositions for delivery of such modified cells to a subject in need thereof are provided. The chimeric proteins are referred to herein as a "chimeric engulfment receptor" or "chimeric engulfment receptors" ("CER" in the singular and "CERs" in the plural). Chimeric engulfment receptors described herein are capable of conferring an engulfment phenotype to a host cell that is genetically modified to express said chimeric engulfment receptor. In such certain embodiments, expression of a CER as described herein confers an engulfment phenotype to a host cell that does not naturally exhibit an engulfment phenotype. In other such embodiments, expression of a CER as described herein by a host cell confers an engulfment phenotype specific to a pro-engulfment marker or antigenic marker not naturally targeted by the host cell. In still other such embodiments, expression of a CER as described herein by a host cell confers an engulfment phenotype specific to a pro-engulfment marker or antigenic marker naturally targeted by the host cell and expression of the CER by the host cell enhances engulfment by the host cell of cells, microbes, or particles exhibiting the targeted pro-engulfment or antigenic marker.

In certain embodiments, the CER targets an engulfment marker associated with apoptotic, dead, dying, damaged, infected, or necrotic cells. In other embodiments, the CER targets an antibody bound cell associated with an infectious microbe or particle. In still other embodiments, the CER targets an antigenic marker displayed by aberrant cells or misfolded proteins associated with a disease, disorder, or other undesired condition.

One or more CERs according to the present description can be transduced into and expressed in cells, such as T cells, Natural Killer Cells, Natural Killer T cells, B cells, lymphoid precursor cells, dendritic cells, Langerhans cells, and myeloid cells. In certain embodiments, in addition to engineering the CER to bind to a specified target molecule (e.g., an engulfment marker or an antigenic marker), the engulfment signaling domain of the CER is selected to provide desired engulfment activity. In one such embodiment, the engulfment signaling domain is selected to induce homeostatic engulfment signaling. In another such embodiment, the engulfment signaling domain is selected to induce pro-inflammatory engulfment signaling. In yet another embodiment, the engulfment signaling domain comprises a primary engulfment signaling domain and a secondary engulfment signaling domain. The primary engulfment signaling domain and the secondary engulfment signaling domain may both be homeostatic engulfment signaling domains, both be pro-inflammatory engulfment signaling domains, or the primary engulfment signaling domain may be a homeostatic engulfment signaling domain and the secondary engulfment signaling domain may be a pro-inflammatory engulfment signaling domain (or vice versa).

Host cells that are genetically modified to express one or more CERs according to the present description can be used for specific engulfment of a target cell or particle expressing a target molecule to which the extracellular domain of the CER binds. In certain embodiments, the target cell or particle may be a tumor cell, a cancer cell, a microbe (e.g., bacteria, fungus, virus), a protozoan parasite, an aberrant cell, or a misfolded protein associated with an infection, disease, disorder, or other undesired condition. In further embodiments, host cells that are genetically modified to express one or more CERs according to the present description are used to treat cancer, an infectious disease (viral, bacterial, fungal, protozoan), an inflammatory disease, an immune disease (e.g., autoimmune disease), or a neurodegenerative disease (e.g., Alzheimer's disease) in a subject, either as a primary therapy or as an adjunct or combination therapy. The CER of the present disclosure can be designed to confer a specific engulfment phenotype (e.g., homeostatic (non-immunogenic) vs. pro-inflammatory (immunogenic)) via selection of a homeostatic engulfment signaling domain or pro-inflammatory engulfment signaling domain, depending upon on the target molecule and therapeutic indication. Without wishing to be bound by theory, a CER comprising a proinflammatory engulfment domain may be useful in improving the microenvironment of cancers and enhancing tumor regression.

Definitions

Prior to setting forth this disclosure in more detail, it may be helpful to an understanding thereof to provide definitions of certain terms to be used herein.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

Terms understood by those in the art of antibody technology are each given the meaning acquired in the art, unless expressly defined differently herein. The term "antibody" is used in the broadest sense and includes polyclonal and monoclonal antibodies. An "antibody" may refer to an intact antibody comprising at least two heavy (H) chains and two light (L) chains inter-connected by disulfide bonds, as well as an antigen-binding portion (or antigen-binding domain) of an intact antibody that has or retains the capacity to bind a target molecule. An antibody may be naturally occurring, recombinantly produced, genetically engineered, or modified forms of immunoglobulins, for example intrabodies, peptibodies, nanobodies, single domain antibodies, SMIPs, multispecific antibodies (e.g., bispecific antibodies, diabodies, triabodies, tetrabodies, tandem di-scFV, tandem tri-scFv, ADAPTIR). A monoclonal antibody or antigen-binding portion thereof may be non-human, chimeric, humanized, or human, preferably humanized or human. Immunoglobulin structure and function are reviewed, for example, in Harlow et al., Eds., Antibodies: A Laboratory Manual, Chapter 14 (Cold Spring Harbor Laboratory, Cold Spring Harbor, 1988). "Antigen-binding portion" or "antigen-binding domain" of an intact antibody is meant to encompass an "antibody fragment," which indicates a portion of an intact antibody and refers to the antigenic determining variable regions or complementary determining regions of an intact antibody. Examples of antibody fragments include, but are not limited to, Fab, Fab', F(ab')2, and Fv fragments, Fab'-SH, F(ab')$_2$, diabodies, linear antibodies, scFv antibodies, VH, and multispecific antibodies formed from antibody fragments. A "Fab" (fragment antigen binding) is a portion of an antibody that binds to antigens and includes the variable region and CH1 of the heavy chain linked to the light chain via an inter-chain disulfide bond. An antibody may be of any class or subclass, including IgG and subclasses thereof (IgG$_1$, IgG$_2$, IgG$_3$, IgG$_4$), IgM, IgE, IgA, and IgD.

The term "variable region" or "variable domain" refers to the domain of an antibody heavy or light chain that is involved in binding of the antibody to antigen. The variable domains of the heavy chain and light chain (VH and VL, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150: 880-887 (1993); Clarkson et al., Nature 352:624-628 (1991).

The terms "complementarity determining region" and "CDR," which are synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (HCDR1, HCDR2, HCDR3) and three CDRs in each light chain variable region (LCDR1, LCDR2, LCDR3).

The terms "antigen" and "Ag" refer to a molecule that provokes an immune response. The immune response provoked may involve antibody production, the activation of specific immunologically-competent cells, or both. Macromolecules, including proteins, glycoproteins, and glycolipids, can serve as an antigen. Antigens can be derived from recombinant or genomic DNA. As contemplated herein, an antigen need not be encoded (i) solely by a full length nucleotide sequence of a gene or (ii) by a "gene" at all. An antigen can be generated or synthesized, or an antigen can be derived from a biological sample. Such a biological sample can include, but is not limited, to a tissue sample, a tumor sample, a cell, or a biological fluid.

The term "epitope" or "antigenic epitope" includes any molecule, structure, amino acid sequence or protein determinant within an antigen that is specifically bound by a cognate immune binding molecule, such as an antibody or fragment thereof (e.g., scFv), T cell receptor (TCR), chimeric engulfment receptor, or other binding molecule, domain or protein. Epitopic determinants generally contain chemically active surface groupings of molecules, such as amino acids or sugar side chains, and can have specific three dimensional structural characteristics, as well as specific charge characteristics. An epitope may be a linear epitope or a conformational epitope.

The term "anti-tumor effect" refers to a biological effect which can be manifested by a decrease in tumor volume, a decrease in the number of tumor cells, a decrease in the number of metastases, an increase in life expectancy, or amelioration of various physiological symptoms associated with a cancerous condition. An "anti-tumor effect" can also be manifested by prevention of a hematological malignancy or tumor formation.

"Autoimmune disease" refers to a disorder that results from an autoimmune response. An autoimmune disease is the result of an inappropriately excessive response to a self-antigen. An autoimmune response may involve self-reactive B-cells that produce autoantibodies, self-reactive T-cells, or both. An "autoantibody" as used herein is an antibody produced by a subject that binds to a self-antigen also produced by the subject.

"Autologous" refers to any material derived from the same subject to which it is later to be re-introduced.

"Allogeneic" refers to a graft derived from a different subject of the same species.

As used herein, the terms "binding domain," "binding region," and "binding moiety" refer to a molecule, such as a peptide, oligopeptide, polypeptide, or protein that possesses the ability to specifically and non-covalently bind, associate, unite, recognize, or combine with a target molecule (e.g., PtdSer, an IgG antibody, an IgE antibody, an IgA antibody, CD138, CD38, CD33, CD123, CD79b, mesothelin, PSMA, BCMA, ROR1, MUC-16, L1CAM, CD22, CD19, EGFRviii, VEGFR-2, or GD2). A binding domain includes any naturally occurring, synthetic, semi-synthetic, or recombinantly produced binding partner for a biological molecule or other target of interest. In some embodiments, the binding domain is an antigen-binding domain, such as an antibody or functional binding domain or antigen-binding portion thereof. Exemplary binding domains include single chain antibody variable regions (e.g., domain antibodies, sFv, scFv, Fab), receptor ectodomains (e.g., TNF-α), ligands (e.g., cytokines, chemokines), or synthetic polypeptides selected for the specific ability to bind to a biological molecule.

A variety of assays are known for identifying binding domains of the present disclosure that specifically bind a particular target, as well as determining binding domain affinities, such as Western blot, ELISA, and BIACORE® analysis (see also, e.g., Scatchard et al., Ann. N.Y. Acad. Sci. 51:660, 1949; and U.S. Pat. Nos. 5,283,173, 5,468,614, or the equivalent). As used herein, "specifically binds" refers to an association or union of a binding domain, or a fusion protein thereof, to a target molecule with an affinity or $K_a$ (i.e., an equilibrium association constant of a particular binding interaction with units of 1/M) equal to or greater than $10^5$ $M^{-1}$, while not significantly associating or uniting with any other molecules or components in a sample.

The term "cancer" as used herein is defined as disease characterized by the rapid and uncontrolled growth of aberrant cells. The aberrant cells may form solid tumors or constitute a hematological malignancy. Cancer cells can spread locally or through the bloodstream and lymphatic system to other parts of the body. Examples of various cancers include, but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

A "disease" is a state of health of a subject wherein the subject cannot maintain homeostasis, and wherein, if the disease is not ameliorated, then the subject's health continues to deteriorate. In contrast, a "disorder" or "undesirable condition" in a subject is a state of health in which the subject is able to maintain homeostasis, but in which the subject's state of health is less favorable than it would be in the absence of the disorder or undesirable condition. Left untreated, a disorder or undesirable condition does not necessarily result in a further decrease in the subject's state of health.

A "microbe" or "microorganism" refers to any species of bacteria, virus, archaea, or fungi.

A "particle" refers to a fragment of a cell or a small object of at least 100 nm and up to 6 μm in diameter and that is derived from a living cell or organism. A particle can be a viral particle, small mineral particle, cellular debris, or a synthetic particle.

"Encoding" refers to the inherent property of specific polynucleotide sequences, such as DNA, cDNA, and mRNA sequences, to serve as templates for synthesis of other polymers and macromolecules in biological processes having either a defined sequence of nucleotides (i.e., rRNA, tRNA and mRNA) or a defined sequence of amino acids and the biological properties resulting therefrom.

Thus, a polynucleotide encodes a protein if transcription and translation of mRNA corresponding to that polynucleotide produces the protein in a cell or other biological system. Both a coding strand and a non-coding strand can be referred to as encoding a protein or other product of the polynucleotide.

Unless otherwise specified, a "nucleotide sequence encoding an amino acid sequence" includes all nucleotide sequences that are degenerate versions of each other and that encode the same amino acid sequence.

As used herein, the term "endogenous" or "native" refers to a gene, protein, compound, molecule or activity that is normally present in a host or host cell.

As used herein, the term "engulfment" refers to a receptor-mediated process wherein endogenous or exogenous cells or particles greater than 100 nm in diameter are internalized by a phagocyte or host cell of the present disclosure. Engulfment is typically composed of multiple steps: (1) tethering of the target cell or particle via binding of an engulfment receptor to a pro-engulfment marker or antigenic marker directly or indirectly (via a bridging molecule) on a target cell or particle; and (2) internalization or engulfment of the whole target cell or particle, or a portion thereof. In certain embodiments, internalization may occur via cytoskeletal rearrangement of a phagocyte or host cell to form a phagosome, a membrane-bound compartment containing the internalized target. Engulfment may further include maturation of the phagosome, wherein the phagosome becomes increasingly acidic and fuses with lysosomes (to form a phagolysosome), whereupon the engulfed target is degraded (e.g., "phagocytosis"). Alternatively, phagosome-lysosome fusion may not be observed in engulfment. In yet another embodiment, a phagosome may regurgitate or discharge its contents to the extracellular environment before complete degradation. In some embodiments, engulfment refers to phagocytosis. In some embodiments, engulfment includes tethering of the target cell or particle by the phagocyte of host cell of the present disclosure, but not internalization. In some embodiments, engulfment includes tethering of the target cell or particle by the phagocyte of host cell of the present disclosure and internalization of part of the target cell or particle.

As used herein, the term "phagocytosis" refers to an engulfment process of cells or large particles (≥0.5 µm) wherein tethering of a target cell or particle, engulfment of the target cell or particle, and degradation of the internalized target cell or particle occurs. In certain embodiments, phagocytosis comprises formation of a phagosome that encompasses the internalized target cell or particle and phagosome fusion with a lysosome to form a phagolysosome, wherein the contents therein are degraded. In certain embodiments, during phagocytosis, following binding of a CER expressed on a phagocyte or a host cell of the present disclosure to an engulfment marker expressed by a target cell or particle, a phagocytic synapse is formed; an actin-rich phagocytic cup is generated at the phagocytic synapse; phagocytic arms are extended around the target cell or particle through cytoskeletal rearrangements; and ultimately, the target cell or particle is pulled into the phagocyte or host cell through force generated by motor proteins. As used herein, "phagocytosis" includes the process of "efferocytosis", which specifically refers to the phagocytosis of apoptotic or necrotic cells in a non-inflammatory manner.

As used herein, the term "pro-engulfment marker" refers to a moiety (e.g., protein, lipid, or polysaccharide) that an apoptotic, necrotic, pyroptotic, or infected cell exhibits on its surface that distinguishes it from a non-apoptotic, non-necrotic, non-pyroptotic, oncotic, or uninfected cell, respectively. A pro-engulfment marker can be an intracellular moiety that is surface exposed on an apoptotic or necrotic cell, a moiety that has altered glycosylation or altered surface charge on an apoptotic or necrotic cell, or a serum moiety that is bound to an apoptotic, necrotic, pyroptotic, or oncotic cell. Examples of pro-engulfment markers for apoptotic cells include phosphatidylserine (PtdSer), ICAM-3, oxidized low density lipoprotein, calreticulin, annexin I, complement C1q, and thrombospondin. Necrotic, oncotic, and pyroptotic cells also expose PtdSer pro-engulfment markers on the cell surface. Engulfment receptors can detect (or bind) a pro-engulfment marker on a target cell (e.g., a damaged, infected, apoptotic, necrotic, pyroptotic, or oncotic cell) directly or indirectly using soluble bridging molecules as intermediaries that bind to the pro-engulfment marker.

An "engulfment signaling domain" refers to an intracellular effector domain, which, upon binding of the target molecule (e.g., pro-engulfment marker or antigenic marker) targeted by the extracellular domain of a CER expressed by a host cell, activates one or more signaling pathways in the host cell resulting in engulfment, including, in specific embodiments, cytoskeletal rearrangement of the host cell and internalization of the target cell, microbe, or particle associated with the marker or antigen. In certain embodiments, an engulfment signaling domain activates one or more signaling pathways resulting in phagocytosis of the target cell, microbe, or particle. In certain embodiments, the engulfment signaling domain includes a primary engulfment signaling domain. In certain other embodiments, the engulfment signaling domain includes a primary engulfment signaling domain and a secondary engulfment signaling domain. A primary engulfment may be a homeostatic engulfment signaling domain or a pro-inflammatory engulfment signaling domain. In embodiments where the engulfment signaling domain includes a primary engulfment signaling domain and a secondary engulfment signaling domain, the primary engulfment signaling domain can be a homeostatic engulfment signaling domain or a pro-inflammatory engulfment signaling domain. Similarly, the secondary engulfment signaling domain can be selected from a homeostatic engulfment signaling domain or a pro-inflammatory engulfment signaling domain. In certain embodiments, the CER includes a primary engulfment signaling domain and a secondary engulfment signaling domain that are both homeostatic engulfment signaling domains. In certain other embodiments, the CER includes a primary engulfment signaling domain and a secondary engulfment signaling domain that are both pro-inflammatory engulfment signaling domains. In still other embodiments, the CER includes a primary engulfment signaling domain that is a homeostatic engulfment signaling domain and a secondary engulfment signaling domain that is a pro-inflammatory engulfment signaling domain. In still other embodiments, the CER includes a primary engulfment signaling domain that is a pro-inflammatory engulfment signaling domain and a secondary engulfment signaling domain that is a homeostatic engulfment signaling domain.

The term "homeostatic engulfment signaling domain" refers to an effector domain that (i) stimulates engulfment of the targeted cell, microbe, or particle without (ii) is derived from an endogenous receptor or signaling molecule that typically stimulates an inflammatory or immunogenic response. In some embodiments, a homeostatic engulfment signaling domain stimulates host cell secretion of anti-inflammatory and/or immunosuppressive cytokines, such as, for example, TGF-β and IL-10. In certain embodiments, stimulation of homeostatic engulfment signaling dampens, attenuates, or resolves inflammation in the local tissue milieu. A homeostatic engulfment signaling domain can also be referred to as a "non-inflammatory" engulfment signaling domain or a "non-immunogenic" engulfment signaling domain.

A "pro-inflammatory engulfment signaling domain" refers to an effector domain that (i) stimulates engulfment of the targeted cell, microbe, or particle and (ii) is derived from an endogenous receptor or signaling molecule that typically stimulates one or more of (a) host cell secretion of inflammatory cytokines, such as, for example, TNFα, IL-1, IL-6, IL-12, and IL-23, (b) host cell secretion of inflammatory chemokines, such as, for example, CCL5 (RANTES), CXCL9, and CXCL10, (c) upregulation of cell surface co-stimulatory markers, such as, for example, CD80, CD86, HLA-DR, CD40, HVEM, and 4-1BBL, and (d) activation of one or more signaling cascades, such as NF-κB, that induce, potentiate, or complement chemotherapies, antibody-based immune therapies, or cellular therapies, such as, for example, T cell targeted therapies. In certain embodiments, stimulation of pro-inflammatory engulfment signaling promotes inflammation in the local tissue milieu. A pro-inflammatory engulfment signaling domain can also be referred to as an "immunogenic" engulfment signaling domain or an "inflammatory" engulfment signaling domain.

As used herein, an "effector domain" is an intracellular portion of a fusion protein or receptor that can directly or indirectly promote a biological or physiological response in a cell expressing the effector domain when receiving the appropriate signal. In certain embodiments, an effector domain is part of a protein or protein complex that receives a signal when bound, or it binds directly to a target molecule, which triggers a signal from the effector domain. For example, in response to binding of the CER to a target molecule, the effector domain may transduce a signal to the interior of the host cell, eliciting an effector function, e.g., engulfment, phagolysosome maturation, secretion of anti-inflammatory and/or immunosuppressive cytokines, secretion of inflammatory cytokines and/or chemokines. An effector domain may directly promote a cellular response when it contains one or more signaling domains or motifs. In other embodiments, an effector domain will indirectly promote a cellular response by associating with one or more other proteins that directly promote a cellular response.

As used herein, "heterologous" or "non-endogenous" or "exogenous" refers to any gene, protein, compound, molecule, or activity that is not native to a host cell or a subject, or is any gene, protein, compound, molecule, or activity native to a host or host cell but has been altered or mutated such that the structure, activity, or both is different as between the native and mutated molecules. In certain embodiments, heterologous, non-endogenous or exogenous molecules (e.g., receptors, ligands) may not be endogenous to a host cell or subject, but instead nucleic acids encoding such molecules may have been added to a host cell by conjugation, transformation, transfection, electroporation, or the like, wherein the added nucleic acid molecule may integrate into a host cell genome or can exist as extra-chromosomal genetic material (e.g., as a plasmid or other self-replicating vector). The term "homologous" or "homolog" refers to a molecule or activity found in or derived from a host cell, species or strain. For example, a heterologous or exogenous molecule or gene encoding the molecule may be homologous to a native host or host cell molecule or gene that encodes the molecule, respectively, but may have an altered structure, sequence, expression level, or combinations thereof. A non-endogenous molecule may be from the same species, a different species or a combination thereof.

"Junction amino acids" or "junction amino acid residues" refer to one or more (e.g., about 2-20) amino acid residues between two adjacent motifs, regions or domains of a polypeptide. Junction amino acids may result from the construct design of a chimeric protein (e.g., amino acid residues resulting from the use of a restriction enzyme site during the construction of a nucleic acid molecule encoding a fusion protein).

"Nucleic acid molecule" and "polynucleotide" can be in the form of RNA or DNA, which includes cDNA, genomic DNA, and synthetic DNA. A nucleic acid molecule may be double stranded or single stranded, and if single stranded, may be the coding strand or non-coding (anti-sense strand). A coding molecule may have a coding sequence identical to a coding sequence known in the art or may have a different coding sequence, which, as the result of the redundancy or degeneracy of the genetic code, or by splicing, can encode the same polypeptide.

The term "overexpressed" or "overexpression" of an antigen refers to an abnormally high level of antigen expression in a cell. Overexpressed antigen or overexpression of antigen is often associated with a disease state, such as in hematological malignancies and cells forming a solid tumor within a specific tissue or organ of a subject. Solid tumors or hematological malignancies characterized by overexpression of a tumor antigen can be determined by standard assays known in the art.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, the term "mature polypeptide" or "mature protein" refers to a protein or polypeptide that is secreted or localized in the cell membrane or inside certain cell organelles (e.g., the endoplasmic reticulum, golgi, or endosome) and does not include an N-terminal signal peptide.

A "signal peptide", also referred to as "signal sequence", "leader sequence", "leader peptide", "localization signal" or "localization sequence", is a short peptide (usually 15-30 amino acids in length) present at the N-terminus of newly synthesized proteins that are destined for the secretory pathway. A signal peptide typically comprises a short stretch of hydrophilic, positively charged amino acids at the N-terminus, a central hydrophobic domain of 5-15 residues, and a C-terminal region with a cleavage site for a signal peptidase. In eukaryotes, a signal peptide prompts translocation of the newly synthesized protein to the endoplasmic reticulum where it is cleaved by the signal peptidase, creating a mature protein that then proceeds to its appropriate destination.

The "percent identity" between two or more nucleic acid or amino acid sequences is a function of the number of identical positions shared by the sequences (i.e., % identity=number of identical positions/total number of positions×100), taking into account the number of gaps, and the length of each gap that needs to be introduced to optimize alignment of two or more sequences. The comparison of sequences and determination of percent identity between two or more sequences can be accomplished using a mathematical algorithm, such as BLAST and Gapped BLAST programs at their default parameters (e.g., Altschul et al., *J. Mol. Biol.* 215:403, 1990; see also BLASTN at www.ncbi.nlm.nih.gov/BLAST).

A "conservative substitution" is recognized in the art as a substitution of one amino acid for another amino acid that has similar properties. Exemplary conservative substitutions are well known in the art (see, e.g., WO 97/09433, page 10, published Mar. 13, 1997; Lehninger, Biochemistry, Second Edition; Worth Publishers, Inc. NY:NY (1975), pp. 71-'7'7; Lewin, Genes IV, Oxford University Press, NY and Cell Press, Cambridge, Mass. (1990), p. 8).

The term "chimeric" refers to any nucleic acid molecule or protein that is not endogenous and comprises sequences joined or linked together that are not normally found joined or linked together in nature. For example, a chimeric nucleic acid molecule may comprise regulatory sequences and coding sequences that are derived from different sources, or regulatory sequences and coding sequences that are derived from the same source but arranged in a manner different than that found in nature.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The term "subject," "patient" and "individual" are used interchangeably herein and are intended to include living organisms in which an immune response can be elicited (e.g., mammals). Examples of subjects include humans, primates, cows, horses, sheep, dogs, cats, mice, rats, rabbits, guinea pigs, pigs, and transgenic species thereof The term "T cells" refers to cells of T cell lineage. "Cells of T cell lineage" refers to cells that show at least one phenotypic characteristic of a T cell or a precursor or progenitor thereof that distinguishes the cells from other lymphoid cells, and cells of the erythroid or myeloid lineages. Such phenotypic characteristics can include expression of one or more proteins specific for T cells (e.g., CD3$^+$, CD4$^+$, CD8$^+$), or a physiological, morphological, functional, or immunological feature specific for a T cell. For example, cells of the T cell lineage may be progenitor or precursor cells committed to the T cell lineage; CD25$^+$ immature and inactivated T cells; cells that have undergone CD4 or CD8 linage commitment; thymocyte progenitor cells that are CD4$^+$CD8$^+$ double positive; single positive CD4$^+$ or CD8$^+$; TCRαβ or TCR γδ; or mature and functional or activated T cells. The term "T cells" encompasses naïve T cells (CD45 RA+, CCR7+, CD62L+, CD27+, CD45RO−), central memory T cells (CD45RO$^+$, CD62L$^+$, CD8$^+$), effector memory T cells (CD45RA+, CD45RO−, CCR7−, CD62L−, CD27−), mucosal-associated invariant T cells, natural killer T cells, and tissue resident T cells.

The term "B cells" refers to cells of the B cell lineage. "Cells of B cell lineage" refers to cells that show at least one phenotypic characteristic of a B cell or a precursor or progenitor thereof that distinguishes the cells from other lymphoid cells, and cells of the erythroid or myeloid lineages. Such phenotypic characteristics can include expression of one or more proteins specific for B cells (e.g., CD19$^+$, CD72+, CD24+, CD20$^+$), or a physiological, morphological, functional, or immunological feature specific for a B cell. For example, cells of the B cell lineage may be progenitor or precursor cells committed to the B cell lineage (e.g., pre-pro-B cells, pro-B cells, and pre-B cells); immature and inactivated B cells or mature and functional or activated B cells. Thus, "B cells" encompass naïve B cells, plasma cells, regulatory B cells, marginal zone B cells, follicular B cells, lymphoplasmacytoid cells, plasmablast cells, and memory B cells (e.g., CD27$^+$, IgD$^−$).

A "therapeutically effective amount" or "effective amount" of a chimeric protein or cell expressing a chimeric protein of this disclosure (e.g., a CER or a cell expressing a CER) refers to that amount of protein or cells sufficient to result in amelioration of one or more symptoms of the disease, disorder, or undesired condition being treated. When referring to an individual active ingredient or a cell expressing a single active ingredient, administered alone, a therapeutically effective dose refers to the effects of that ingredient or cell expressing that ingredient alone. When referring to a combination, a therapeutically effective dose refers to the combined amounts of active ingredients or combined adjunctive active ingredient with a cell expressing an active ingredient that results in a therapeutic effect, whether administered serially or simultaneously.

"Treat" or "treatment" or "ameliorate" refers to medical management of a disease, disorder, or undesired condition of a subject. In general, an appropriate dose or treatment regimen comprising a host cell expressing a CER of this disclosure is administered in an amount sufficient to elicit a therapeutic or prophylactic benefit. Therapeutic or prophylactic/preventive benefit includes improved clinical outcome; lessening or alleviation of symptoms associated with a disease, disorder, or undesired condition; decreased occurrence of symptoms; improved quality of life; longer disease-free status; diminishment of extent of disease, disorder, or undesired condition; stabilization of disease state; delay of disease progression; remission; survival; prolonged survival; or any combination thereof.

The phrase "under transcriptional control" or "operatively linked" as used herein means that a promoter is in the correct location and orientation in relation to a polynucleotide to control the initiation of transcription by RNA polymerase and expression of the polynucleotide.

A "vector" is a nucleic acid molecule that is capable of transporting another nucleic acid. Vectors may be, for example, plasmids, cosmids, viruses, or phage. The term should also be construed to include non-plasmid and non-viral compounds which facilitate transfer of nucleic acid into cells. An "expression vector" is a vector that is capable of directing the expression of a protein encoded by one or more genes carried by the vector when it is present in the appropriate environment.

In certain embodiments, the vector is a viral vector. Examples of viral vectors include, but are not limited to, adenovirus vectors, adeno-associated virus vectors, retrovirus vectors, gammaretrovirus vectors, and lentivirus vectors. "Retroviruses" are viruses having an RNA genome. "Gammaretrovirus" refers to a genus of the retroviridae family. Examples of gammaretroviruses include mouse stem cell virus, murine leukemia virus, feline leukemia virus, feline sarcoma virus, and avian reticuloendotheliosis viruses. "Lentivirus" refers to a genus of retroviruses that are capable of infecting dividing and non-dividing cells. Examples of lentiviruses include, but are not limited to HIV (human immunodeficiency virus, including HIV type 1 and HIV type 2, equine infectious anemia virus, feline immunodeficiency virus (FIV), bovine immune deficiency virus (BIV), and simian immunodeficiency virus (SIV).

In other embodiments, the vector is a non-viral vector. Examples of non-viral vectors include lipid-based DNA vectors, modified mRNA (modRNA), self-amplifying mRNA, closed-ended linear duplex (CELiD) DNA, and transposon-mediated gene transfer (PiggyBac, Sleeping Beauty). Where a non-viral delivery system is used, the delivery vehicle can be a liposome. Lipid formulations can be used to introduce nucleic acids into a host cell in vitro, ex vivo, or in vivo. The nucleic acid may be encapsulated in the interior of a liposome, interspersed within the lipid bilayer of a liposome, attached to a liposome via a linking molecule that is associated with both the liposome and the nucleic acid, contained or complexed with a micelle, or otherwise associated with a lipid.

Additional definitions are provided throughout the present disclosure.

Chimeric Engulfment Receptors (CERs)

Figure 1A:
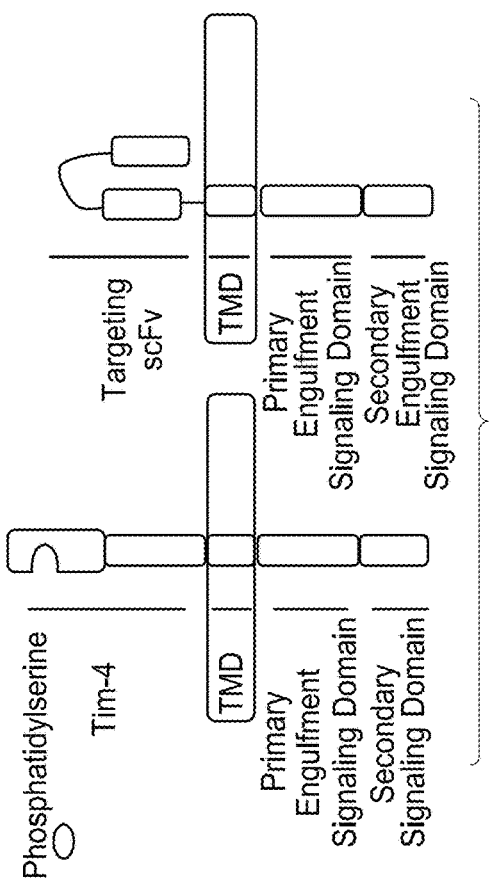
FIGS. 1A-1D show illustrative schematics of chimeric engulfment receptors (CERs).
Figure 1B:
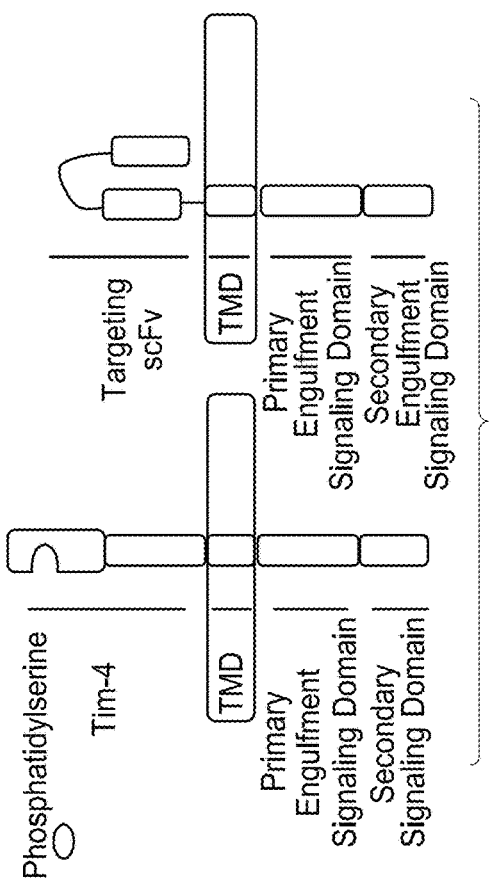
Figure 1C:
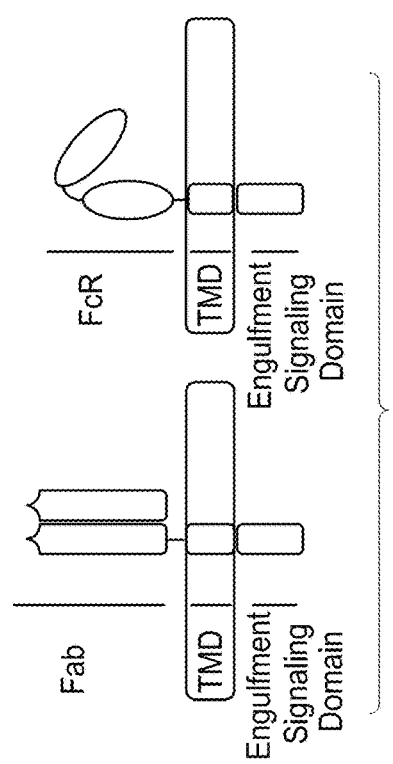
Figure 1D:
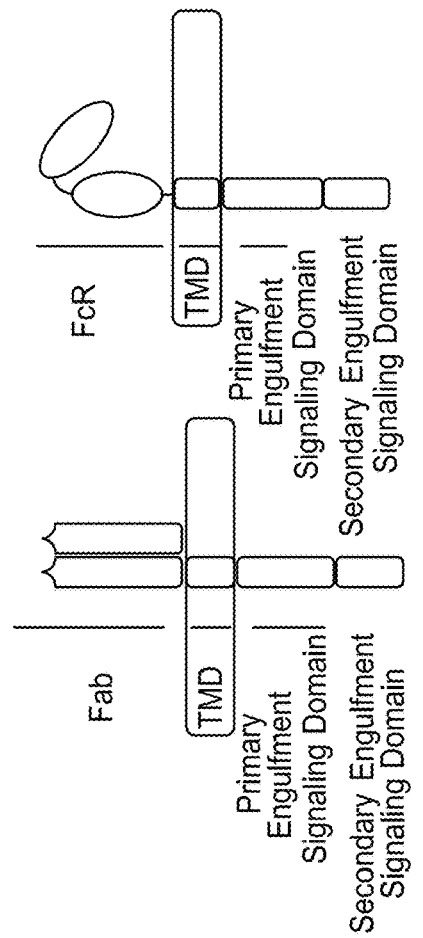

Chimeric engulfment receptors (CERs) are described herein. In particular embodiments, the CER is a chimeric, single chain protein, which comprises an extracellular domain and an engulfment signaling domain, which are connected by a transmembrane domain. The extracellular domain includes an extracellular binding domain and, optionally, an extracellular spacer domain. When expressed in a host cell, a CER confers an engulfment phenotype to the modified host cell (the host cell is "switched" to an engulfment phenotype) specific to a selected pro-engulfment marker or antigenic marker present on or expressed by target cells, microbes, particles, or other materials. In certain embodiments, a CER confers a phagocytic phenotype to the modified host cell specific to a selected pro-engulfment marker or antigenic marker present on or expressed by target cells, microbes, particles, or other materials. In particular CER embodiments, the chimeric protein comprises, from amino-terminus to carboxyl-terminus: an extracellular domain having a binding domain specific for a target molecule and an optional extracellular spacer domain; a transmembrane domain; and an engulfment signaling domain (see, e.g., FIGS. 1A and 1B).

The component parts of a CER as disclosed herein can be selected and arranged to provide a desired engulfment phenotype. For example, in certain embodiments, the extracellular domain can include a binding domain specific to: (i) a pro-engulfment marker associated with apoptotic, dead, dying, damaged, or necrotic cells; or (ii) an antigenic marker displayed by foreign (e.g., a microbe), infected, or aberrant cells associated with an infection, disease, disorder, or other undesired condition.

The engulfment signaling domain can include one or more effector (also referred to as "signaling") domains that drive engulfment of the targeted cell. Signaling by the engulfment signaling domain is triggered by binding of the extracellular domain to the targeted pro-engulfment or antigenic marker. In certain embodiments, the engulfment signaling domain comprises a primary engulfment signaling domain. In particular embodiments, the primary engulfment signaling domain is selected to initiate a homeostatic engulfment response. Alternatively, in other embodiments, the primary engulfment signaling domain is selected to initiate a pro-inflammatory engulfment response. In yet other embodiments, the engulfment signaling domain comprises a primary engulfment signaling domain and a secondary engulfment signaling domain, wherein the primary and secondary engulfment signaling domains are both homeostatic signaling domains, both pro-inflammatory signaling domains, or one of each (in any order). A CER according to the present disclosure can be engineered for application in a variety of therapeutic contexts (e.g., clearance of apoptotic, dead, dying, damaged, infected, or necrotic cells, clearance of microbes responsible for infectious disease, and clearance of aberrant cells associated with a disease, disorder or undesired condition), while providing engulfment signaling that complements the desired therapeutic outcome (e.g., homeostatic or pro-inflammatory engulfment signaling).

FIGS. 3A and 3B provide a functional comparison of a natural lymphocyte with a lymphocyte modified with an embodiment of a CER of the present disclosure. FIG. 3A shows an endogenous lymphocyte, and as is represented in the figure, the natural lymphocyte does not exhibit an engulfment phenotype. However, as is illustrated in FIG. 3B, a lymphocyte modified to express a CER as described herein exhibits an engulfment phenotype specific to the targeted cancer cell, leading to engulfment (e.g., phagocytosis) and elimination of the targeted cancer cell. Even further, as is illustrated in FIG. 3B, in certain embodiments the CER can be engineered to drive polarization of the engulfment process. In particular embodiments, the engulfment signaling domains included in CERs according to the present description can be selected to drive homeostatic engulfment signaling or pro-inflammatory engulfment signaling.

Component parts of the fusion proteins of the present disclosure are further described in detail herein.

Extracellular Domain

As described herein, a CER comprises an extracellular domain specific to a target molecule. In certain embodiments, the extracellular domain includes an extracellular binding domain that specifically binds a targeted pro-engulfment marker or antigen. Binding of a target molecule by the binding domain may block the interaction between the target molecule (e.g., a receptor or a ligand) and another molecule and, for example, interfere with, reduce or eliminate certain functions of the target molecule (e.g., signal transduction). In some embodiments, the binding of a target molecule may induce certain biological pathways or identify the target molecule or cell expressing the target molecule for elimination.

A binding domain may be any polypeptide or peptide that specifically binds a target molecule of interest. Sources of binding domains include receptor binding domains, ligand binding domains, and antibodies or antigen binding portions, such as antibody variable regions from various species (which can be in the form of antibodies, sFvs, scFvs, Fabs, scFv-based grababody, or soluble VH domain or domain antibodies), including human, rodent, avian, or ovine. Additional sources of binding domains include variable regions of antibodies from other species, such as camelid (from camels, dromedaries, or llamas; Ghahroudi et al., *FEBS Lett.* 414:521, 1997; Vincke et al., *J. Biol. Chem.* 284:3273, 2009; Hamers-Casterman et al., *Nature* 363:446, 1993 and Nguyen et al., *J. Mol. Biol.* 275:413, 1998), nurse sharks (Roux et al., *Proc. Nat'l. Acad. Sci.* (USA) 95:11804, 1998), spotted ratfish (Nguyen et al., *Immunogen.* 54:39, 2002), or lamprey (Herrin et al., *Proc. Nat'l. Acad. Sci.* (*USA*) 105:2040, 2008 and Alder et al. *Nat. Immunol.* 9:319, 2008). These antibodies can form antigen-binding regions using only a heavy chain variable region, i.e., these functional antibodies are homodimers of heavy chains only (referred to as "heavy chain antibodies") (Jespers et al., *Nat. Biotechnol.* 22:1161, 2004; Cortez-Retamozo et al., *Cancer Res.* 64:2853, 2004; Baral et al., *Nature Med.* 12:580, 2006; and Barthelemy et al., *J. Biol. Chem.* 283:3639, 2008).

In some embodiments, the extracellular domain binds to a pro-engulfment marker. In certain such embodiments, the pro-engulfment marker targeted by the extracellular domain is phosphatidylserine (PtdSer), ICAM-3, oxidized low density lipoprotein, calreticulin, annexin I, complement C1q, or thrombospondin. In further embodiments, the extracellular domain that binds to a pro-engulfment marker is derived from an endogenous engulfment receptor or a soluble bridging molecule for an engulfment receptor (e.g., GAS6, Protein S, MFG-E8). In some embodiments, the entire extracellular portion (for membrane spanning molecules), the entire bridging molecule, or a truncated portion of an engulfment receptor or bridging molecule is used, provided that the truncated portion retains sufficient binding activity to the pro-engulfment marker (i.e., is a functional variant). In further embodiments, the extracellular portion of an engulfment receptor or bridging molecule used for the extracellular domain is a variant of the entire extracellular portion (for membrane spanning molecules), the entire bridging molecule, or a truncated portion of the engulfment receptor or bridging molecule, provided that the variant retains sufficient binding activity to the pro-engulfment marker (i.e., is a functional variant).

In some embodiments, the extracellular domain includes a T-cell immunoglobulin and mucin domain 1 (Tim1), T-cell immunoglobulin and mucin domain 4 (Tim4), T-cell immunoglobulin and mucin domain 3 (Tim3), stabilin-2, RAGE, or Fc receptor (FcR) extracellular domain. In specific embodiments, an FcR extracellular domain can include a binding domain from FcγR1, FcγR2A, FcγR2B2, FcγR2C, FcγR3A, FcεR1, or FcαR1. In further embodiments, the extracellular domain can include a PtdSer binding domain from Tim1, Tim4, Tim3, stabilin-2, receptor for advanced glycation endproducts (RAGE), brain-specific angiogenesis inhibitor 1 (BAI1), Milk Fat Globule-EGF Factor 8 Protein (MFG-E8) (e.g., a FA58C2 domain that mediates high affinity binding to PtdSer), Growth Arrest Specific 6 (GAS6), protein S, protein C, Factor II, Factor VII, Factor IX, Factor X, Beta 2-glycoprotein I, α5β3 integrin and other integrins, CR3 complement receptor, CR4 complement receptor, CD14, CD93, annexin V, phosphatidylserine receptor (PSr), prothrombin, or scavenger receptors such as scavenger receptor B (SRB) (e.g., SRB1 (CD36)), scavenger receptor C (SRC) (e.g., LOX-1, SRCL), scavenger receptor D (SRD) (e.g., CD68, macrosialin), and PSOX.

In some embodiments, the extracellular domain comprises or is a sequence that is at least 90%, at least 91%, at least 92%, at least 93%, at least 94%, at least 95%, at least 96%, at least 97%, at least 98%, at least 99%, at least 99.5%, or 100% identical to a FcγRI binding domain comprising an amino acid sequence of SEQ ID NO:31 or amino acids 16-292 of SEQ ID NO:31, TIM1 binding domain comprising an amino acid sequence of SEQ ID NO:28 or amino acids 21-290 of SEQ ID NO:28, a TIM4 binding domain comprising an amino acid sequence of SEQ ID NO:29 or amino acids 25-314 of SEQ ID NO:29, a TIM3 binding domain comprising an amino acid sequence of SEQ ID NO: 34 or amino acids 22-202 of SEQ ID NO:34, a FA58C2 binding domain comprising an amino acid sequence of SEQ ID NO: 30, a GAS6 binding domain comprising an amino acid sequence of SEQ ID NO: 32 or amino acids 31-94 of SEQ ID NO:32, a BAH binding domain comprising an amino acid sequence of SEQ ID NO:117, or a protein S binding domain comprising an amino acid sequence of SEQ ID NO:33 or amino acids 25-87 of SEQ ID NO:33. In certain other embodiments, the extracellular domain is encoded by a polynucleotide sequence that comprises or is a sequence that is at least 90%, at least 91%, at least 92%, at least 93%, at least 94%, at least 95%, at least 96%, at least 97%, at least 98%, at least 99%, at least 99.5%, or 100% identical to a polynucleotide encoding FcγRI binding domain according to SEQ ID NO:4, a polynucleotide encoding a TIM1 binding domain according to SEQ ID NO:1, a polynucleotide encoding a TIM4 binding domain according to SEQ ID NO:2, a polynucleotide encoding a TIM3 binding domain according to SEQ ID NO:7, a polynucleotide encoding FA58C2 binding domain according to SEQ ID NO:3, a polynucleotide encoding a GAS6 binding domain according to SEQ ID NO:5, a polynucleotide encoding a BAH binding domain according to SEQ ID NO:135, or a polynucleotide sequence encoding a protein S binding domain according to SEQ ID NO:6.

In other embodiments, the extracellular domain is derived from least one of the following: CD14, which binds to ICAM3; a scavenger receptor extracellular domain, which binds to oxidized LDL; a lectin, which binds to altered sugars; CD36, which binds to thrombospondin; or LRP1/CD91 or a lectin moiety, which binds to calreticulin.

In still other embodiments, the extracellular domain includes an antibody or antigen binding fragment thereof, such as a single chain Fv fragment (scFv) that comprises VH and VL regions, specific for a target molecule of interest. In certain embodiments, the antibody is chimeric, human, or humanized. In further embodiments, the $V_H$ and $V_L$ regions are human or humanized. In particular embodiments, the extracellular domain is an antibody or antigen binding portion thereof that is specific for a pro-engulfment marker. Antibodies specific for phosphatidylserine are known in the art (see, U.S. Pat. No. 7,247,303; Khogeer et al., 2015, Lupus 24:186-90; Gerber et al., 2015, Am. J. Nucl. Med. Mol. Imaging, 5:493-503, each of which is incorporated by reference in its entirety). In particular embodiments, a target molecule of interest is a tumor antigen, for example CD138, CD38, CD33, CD123, CD72, CD79a, CD79b, mesothelin, PSMA, BCMA, ROR1, MUC-16, L1CAM, CD22, CD19, CD20, CD23, CD24, CD37, CD30, CA125, CD56, c-Met, EGFR, GD-3, HPV E6, HPV E7, MUC-1, HER2, folate receptor α, CD97, CD171, CD179a, CD44v6, WT1, VEGF-α, VEGFR1, IL-13Rα1, IL-13Rα2, IL-11Rα, PSA, FcRH5, NKG2D ligand, NY-ESO-1, TAG-72, CEA, ephrin A2, ephrin B2, Lewis A antigen, Lewis Y antigen, MAGE, MAGE-A1, RAGE-1, folate receptor β, EGFRviii, VEGFR-2, LGR5, SSX2, AKAP-4, FLT3, fucosyl GM1, GM3, o-acetyl-GD2, and GD2, and exemplary $V_H$ and $V_L$ regions include the segments of anti-CD138, -CD38, -CD33, -CD123, -CD72, -CD79a-CD79b, -mesothelin, -PSMA, -BCMA, -ROR1, -MUC-16, -L1CAM, -CD22, -CD19, -CD20, -CD23, -CD24, -CD37, -CD30, -CA125, -CD56, -c-Met, -EGFR, -GD-3, -HPV E6, -HPV E7, -MUC-1, -HER2, -folate receptor α, -CD97, -CD171, -CD179a, -CD44v6, -WT1, -VEGF-α, -VEGFR1, -IL-13Rα1, -IL-13Rα2, -IL-11Rα, -PSA, -FcRH5, -NKG2D ligand, -NY-ESO-1, -TAG-72, -CEA, -ephrin A2, -ephrin B2, -Lewis A antigen, -Lewis Y antigen, -MAGE, -MAGE-A1, -RAGE-1, -folate receptor β, -EGFRviii, -VEGFR-2, -LGR5, -SSX2, -AKAP-4, -FLT3, -fucosyl GM1, -GM3, -o-acetyl-GD2, and -GD2 specific monoclonal antibodies, respectively.

In further embodiments, the extracellular domain includes a Fab specific for a target of interest. In such embodiments, targets of interest include CD138, CD38, CD33, CD123, CD72, CD79a, CD79b, mesothelin, PSMA, BCMA, ROR1, MUC-16, L1CAM, CD22, CD19, CD20, CD23, CD24, CD37, CD30, CA125, CD56, c-Met, EGFR, GD-3, HPV E6, HPV E7, MUC-1, HER2, folate receptor α, CD97, CD171, CD179a, CD44v6, WT1, VEGF-α, VEGFR1, IL-13Rα1, IL-13Rα2, IL-11Rα, PSA, FcRH5, NKG2D ligand, NY-ESO-1, TAG-72, CEA, ephrin A2, ephrin B2, Lewis A antigen, Lewis Y antigen, MAGE, MAGE-A1, RAGE-1, folate receptor β, EGFRviii, VEGFR-2, LGR5, SSX2, AKAP-4, FLT3, fucosyl GM1, GM3, o-acetyl-GD2, and GD2, and Fab regions include portions of anti-CD138, -CD38, -CD33, -CD123, -CD72, -CD79a, -CD79b, -mesothelin, -PSMA, -BCMA, -ROR1, -MUC-16, -L1CAM, -CD22, -CD19, -CD20, -CD23, -CD24, -CD37, -CD30, -CA125, -CD56, -c-Met, -EGFR, -GD-3, -HPV E6, -HPV E7, -MUC-1, -HER2, -folate receptor α, -CD97, -CD171, -CD179a, -CD44v6, -WT1, -VEGF-α, -VEGFR1, -IL-13Rα1, -IL-13Rα2, -IL-11Rα, -PSA, -FcRH5, -NKG2D ligand, -NY-ESO-1, -TAG-72, -CEA, -ephrin A2, -ephrin B2, -Lewis A antigen, -Lewis Y antigen, -MAGE, MAGE-A1, -RAGE-1, -folate receptor β, -EGFRviii, -VEGFR-2, -LGR5, -SSX2, AKAP-4, -FLT3, -fucosyl GM1, -GM3, -o-acetyl-GD2, and -GD2 specific monoclonal antibodies, respectively.

A target molecule, which is specifically bound by an extracellular domain of a CER of the present disclosure, may be found on or in association with a cell of interest ("target cell"). Exemplary target cells include a cancer cell, a cell associated with an autoimmune disease or disorder or with an inflammatory disease or disorder, and an infectious microbe (e.g., bacteria, virus, or fungi), or infected cell (e.g., virus-infected cell). A cell of an infectious organism, such as a mammalian parasite, is also contemplated as a target cell.

In some embodiments, the extracellular domain optionally comprises an extracellular, non-signaling spacer or linker domain. Where included, such a spacer or linker domain may position the binding domain away from the host cell surface to further enable proper cell/cell contact, binding, and activation. An extracellular spacer domain is generally located between the extracellular binding domain and the transmembrane domain. The length of the extracellular spacer may be varied to optimize target molecule binding based on the selected target molecule, selected binding epitope, binding domain size and affinity (see, e.g., Guest et al., *J. Immunother.* 28:203-11, 2005; PCT Publication No. WO 2014/031687). In certain embodiments, an extracellular spacer domain is an immunoglobulin hinge region (e.g., IgG1, IgG2, IgG3, IgG4, IgA, IgD). An immunoglobulin hinge region may be a wild type immunoglobulin hinge region or an altered wild type immunoglobulin hinge region. An altered IgG$_4$ hinge region is described in PCT Publication No. WO 2014/031687, which hinge region is incorporated herein by reference in its entirety. In a particular embodiment, an extracellular spacer domain comprises a modified IgG$_4$ hinge region having an amino acid sequence of ESKYGPPCPPCP (SEQ ID NO:67). Other examples of hinge regions that may be used in the CERs described herein include the hinge region present in the extracellular regions of type 1 membrane proteins, such as CD8a, CD4, CD28 and CD7, which may be wild-type or variants thereof. In further embodiments, an extracellular spacer domain comprises all or a portion of an immunoglobulin Fc domain selected from: a CH1 domain, a CH2 domain, a CH3 domain, or combinations thereof (see, e.g., PCT Publication WO2014/031687, which spacers are incorporated herein by reference in their entirety). In yet further embodiments, an extracellular spacer domain may comprise a stalk region of a type II C-lectin (the extracellular domain located between the C-type lectin domain and the transmembrane domain). Type II C-lectins include CD23, CD69, CD72, CD94, NKG2A, and NKG2D. In yet further embodiments, an extracellular spacer domain may be derived from MERTK.

Engulfment Signaling Domain

The engulfment signaling domain of a CER is an intracellular effector domain and is capable of transmitting functional signals to a cell in response to binding of the extracellular domain of the CER to a target molecule. In certain embodiments, an engulfment signaling domain may include one or more homeostatic engulfment signaling domains, one or more pro-inflammatory signaling domains, or both a homeostatic signaling domain and a pro-inflammatory signaling domain.

In certain embodiments, an engulfment signaling domain is an intracellular signaling domain of an endogenous engulfment receptor. Examples of endogenous engulfment receptors from which engulfment signaling domains can be derived include Mer tyrosine kinase (MERTK), Tyro3 protein tyrosine kinase, Ax1 receptor tyrosine kinase, BAI1, mannose receptor C-type 1 (MRC1), and Fc receptor (FcR) (e.g., FcγR1, FcγR2A, FcγR2B2, FcγR2C, FcγR3A, FcεR1, or FcαR1). In other embodiments, an engulfment signaling domain is an intracellular signaling domain of an endogenous kinase or adaptor protein associated with a signaling pathway during phagocytosis. Examples of kinases associated with phagocytic signaling pathway include spleen associated tyrosine kinase (SYK), zeta chain of T cell receptor associated protein kinase 70 (Zap70), and phosphoinositide 3-kinase (PI3K).

The engulfment signaling domain may be any portion of an engulfment signaling molecule that retains sufficient signaling activity. In some embodiments, a full length or full length intracellular component of an engulfment signaling molecule is used. In some embodiments, a truncated portion of an engulfment signaling molecule or intracellular component of an engulfment signaling molecule is used, provided that the truncated portion retains sufficient signal transduction activity. In further embodiments, an engulfment signaling domain is a variant of an entire or truncated portion of an engulfment signaling molecule, provided that the variant retains sufficient signal transduction activity (i.e., is a functional variant).

In certain embodiments, the engulfment signaling domain includes a homeostatic engulfment signaling domain, for example an MRC1 signaling domain, an ItgB5 signaling domain, a MERTK signaling domain, a Tyro3 signaling domain, an Ax1 signaling domain, a BAH signaling domain, or an ELMO signaling domain. In more particular embodiments, the engulfment signaling domain comprises a homeostatic engulfment signaling domain that comprises or is a sequence that is at least 90%, at least 91%, at least 92%, at least 93%, at least 94%, at least 95%, at least 96%, at least 97%, at least 98%, at least 99%, at least 99.5%, or 100% identical to an MRC1 signaling domain comprising an amino acid sequence of SEQ ID NO:56, an ItgB5 signaling domain comprising an amino acid sequence of SEQ ID NO:114, a MERTK signaling domain comprising an amino acid sequence of SEQ ID NO:69, a Tyro3 signaling domain comprising an amino acid sequence of SEQ ID NO:45, an Ax1 signaling domain comprising an amino acid sequence of SEQ ID NO:44, a BAH signaling domain comprising an amino acid sequence of SEQ ID NO:136, or an ELMO signaling domain comprising an amino acid sequence of SEQ ID NO:120. In other embodiments, the engulfment signaling domain includes a homeostatic engulfment signaling domain and the homeostatic engulfment signaling domain is encoded by a polynucleotide sequence that comprises or is a sequence that is at least 90%, at least 91%, at least 92%, at least 93%, at least 94%, at least 95%, at least 96%, at least 97%, at least 98%, at least 99%, at least 99.5%, or 100% identical to a polynucleotide encoding a MRC1 signaling domain according to SEQ ID NO:55, a polynucleotide encoding a ItgB5 signaling domain according to SEQ ID NO:137, a polynucleotide encoding a MERTK signaling domain according to SEQ ID NO:138, a polynucleotide encoding a Tyro3 signaling domain according to SEQ ID NO:18, a polynucleotide encoding an Ax1 signaling domain according to SEQ ID NO:17, a polynucleotide encoding a BAI1 signaling domain according to SEQ ID NO:139, or polynucleotide encoding an ELMO signaling domain according to SEQ ID NO:140.

In certain embodiments, signaling by the homeostatic engulfment signaling domain results in expression of at least one of an anti-inflammatory cytokine and immunosuppressive cytokine. In particular embodiments, the at least one of anti-inflammatory cytokine and immunosuppressive cytokine is TGF-β, IL-10, or both.

In certain embodiments, the engulfment signaling domain includes a pro-inflammatory engulfment signaling domain, for example a Traf6 signaling domain, a Syk signaling domain, a MyD88 signaling domain, a truncated MyD88 signaling domain (e.g., comprising a death domain but lacking a Toll/interleukin-1 receptor (TIR) homology domain), a Zap70 signaling domain, a PI3K signaling domain, an FcR signaling domain (including an FcγR1 signaling domain, an FcγR2A signaling domain, an FcγR2C signaling domain, FcγR2B2 signaling domain, an FcγR3A signaling domain, FcγR2C signaling domain, FcγR3A signaling domain, FcεR1 signaling domain, and FcαR1 signaling domain), a B-cell activating factor receptor (BAFF-R) signaling domain, a DAP12 (also referred to as TYRO Protein Tyrosine Kinase Binding Protein (TYROBP)) signaling domain, an NFAT Activating Protein With ITAM Motif 1 (NFAM1) signaling domain, or a CD79b signaling domain.

In particular embodiments, the engulfment signaling domain includes a pro-inflammatory engulfment signaling domain that comprises or is a sequence that is at least 90%, at least 91%, at least 92%, at least 93%, at least 94%, at least 95%, at least 96%, at least 97%, at least 98%, at least 99%, at least 99.5%, or 100% identical to a Traf6 signaling domain comprising an amino acid sequence of SEQ ID NO:54, a Syk signaling domain comprising an amino acid sequence of SEQ ID NO:46, a MyD88 signaling domain comprising an amino acid sequence of SEQ ID NO:53, a truncated MyD88 signaling domain comprising an amino acid sequence of SEQ ID NO:78, a Zap70 signaling domain comprising an amino acid sequence of SEQ ID NO: 47, a FcεRIγ signaling domain comprising an amino acid sequence of SEQ ID NO:88, an FcγR1 signaling domain comprising an amino acid sequence of SEQ ID NO:48, an FcγR2A signaling domain comprising an amino acid sequence of SEQ ID NO:49, an FcγR2C signaling domain comprising an amino acid sequence of SEQ ID NO:50, an FcγR3A signaling domain comprising an amino acid sequence of SEQ ID NO:51, a BAFF-R signaling domain comprising an amino acid sequence of SEQ ID NO:94, a DAP12 signaling domain comprising an amino acid sequence of SEQ ID NO:82, a NFAM1 signaling domain comprising an amino acid sequence of SEQ ID NO:92, a truncated NFAM1 signaling domain comprising an amino acid sequence of SEQ ID NO:132, or a CD79b signaling domain comprising an amino acid sequence of SEQ ID NO:97.

In other embodiments, the engulfment signaling domain includes a pro-inflammatory engulfment signaling domain and the pro-inflammatory signaling domain is provided by a polynucleotide sequence that comprises or is a sequence that is at least 90%, at least 91%, at least 92%, at least 93%, at least 94%, at least 95%, at least 96%, at least 97%, at least 98%, at least 99%, at least 99.5%, or 100% identical to a polynucleotide encoding a Traf6 signaling domain according to SEQ ID NO:27, a polynucleotide encoding a Syk signaling domain according to SEQ ID NO:19, a polynucleotide encoding a MyD88 signaling domain according to SEQ ID NO:26, a polynucleotide encoding a truncated MyD88 signaling domain according to SEQ ID NO:99, a polynucleotide encoding a Zap70 according to SEQ ID NO:20, a polynucleotide encoding a FcεRIγ signaling domain according to SEQ ID NO:141, a polynucleotide encoding an FcγR1 signaling domain according to SEQ ID NO:21, a polynucleotide encoding an FcγR2A signaling domain according to SEQ ID NO:22, a polynucleotide encoding an FcγR2C signaling domain according to SEQ ID NO:23, a polynucleotide encoding an FcγR3A signaling domain according to SEQ ID NO:24, a polynucleotide encoding a BAFF-R signaling domain according to SEQ ID NO:126, a polynucleotide encoding a DAP12 signaling domain according to SEQ ID NO:127, a polynucleotide encoding a NFAM1 signaling domain according to SEQ ID NO:129, or a polynucleotide encoding a CD79b signaling domain according to SEQ ID NO:128.

In further embodiments, signaling by the pro-inflammatory engulfment signaling domain results in expression of at least one of an inflammatory cytokine, an inflammatory chemokine, or a co-stimulatory cell surface marker. In yet further embodiments, the inflammatory cytokine is TNFα, IL-1, IL-6, IL-12, or IL-23; the inflammatory chemokine is CCL5 (RANTES), CXCL9, or CXCL10; and the co-stimulatory cell surface marker is CD80, CD86, HLA-DR, CD40, HVEM, or 4-1BBL; or any combination thereof.

In yet further embodiments, the engulfment signaling domain of a CER can include more than one signaling domain. In certain such embodiments, the engulfment signaling domain includes a primary engulfment signaling domain and a secondary engulfment signaling domain. In embodiments where the engulfment signaling domain includes a primary engulfment signaling domain and a secondary engulfment signaling domain, the primary engulfment signaling domain can be a homeostatic engulfment signaling domain or a pro-inflammatory engulfment signaling domain. Similarly, the secondary engulfment signaling domain can be selected from a homeostatic engulfment signaling domain or a pro-inflammatory engulfment signaling domain. In certain embodiments, the CER includes a primary engulfment signaling domain and a secondary engulfment signaling domain that are both homeostatic engulfment signaling domains. In certain other embodiments, the CER includes a primary engulfment signaling domain and a secondary signaling domain that are both pro-inflammatory engulfment signaling domains. In still other embodiments, the CER includes a primary engulfment signaling domain that is a homeostatic engulfment signaling domain and a secondary engulfment signaling domain that is a pro-inflammatory engulfment signaling domain. In yet other embodiments, the CER includes a primary engulfment signaling domain that is a pro-inflammatory engulfment signaling domain and a secondary engulfment signaling domain that is a homeostatic engulfment signaling domain. In those embodiments where the primary engulfment signaling domain and the secondary engulfment signaling domain are both homeostatic engulfment signaling domains or both pro-inflammatory signaling domains, the primary and second engulfment signaling domains may be the same or different. In specific embodiments, the domains utilized as primary engulfment signaling domains and secondary engulfment signaling domains are selected from one or more of the specific signaling domains described herein, including MRC1, ItgB5, MERTK, ELMO, BAIL Tyro3, Ax1, Traf6, Syk, MyD88, Zap70, PI3K, FcγR1, FcγR2A, FcγR2B2, FcγR2C, FcγR3A, FcεR1, FcαR1, BAFF-R, DAP12, NFAM1, and CD79b.

In certain embodiments, the presence of a primary engulfment signaling domain and a secondary engulfment signaling domain enhances engulfment activity of the CER, persistence of the CER modified host cell, expansion of the CER modified host cell, or a combination thereof. In a particular embodiment, inclusion of a secondary engulfment signaling domain that is a pro-inflammatory signaling domain with a primary engulfment signaling domain that is a homeostatic engulfment signaling domain enhances engulfment activity of the CER, persistence of the CER modified host cell, expansion of the CER modified host cell, or a combination thereof.

Transmembrane Domain

The transmembrane domain connects and is positioned between the extracellular domain and the engulfment signaling domain. The transmembrane domain is a hydrophobic alpha helix that transverses the host cell membrane. The transmembrane domain may be directly fused to the binding domain or to the extracellular spacer domain if present. In certain embodiments, the transmembrane domain is derived from an integral membrane protein (e.g., receptor, cluster of differentiation (CD) molecule, enzyme, transporter, cell adhesion molecule, or the like). The transmembrane domain can be naturally associated with either the extracellular domain or the engulfment signaling domain included in the CER (e.g., a CER comprises a Tim4 binding domain and a Tim4 transmembrane domain). In certain embodiments, the transmembrane domain and the extracellular domain are derived from different molecules, the transmembrane domain and the engulfment signaling domain are derived from different molecules, or the transmembrane domain, extracellular domain, and engulfment signaling domain are all derived from different molecules.

In certain embodiments, the transmembrane domain is a Tim1 transmembrane domain, a Tim4 transmembrane domain, an FcR transmembrane domain (e.g., FcγR1, FcγR2A, FcγR2B2, FcγR2C, FcγR3A, FcεR1, or FcαR1 transmembrane domain), a CD8a transmembrane domain, a MERTK transmembrane domain, an Ax1 transmembrane domain, a Tyro3 transmembrane domain, a BAH transmembrane domain, a CD4 transmembrane domain, a CD28 transmembrane domain a MRC1 transmembrane domain, or a DAP12 transmembrane domain.

In specific embodiments, the transmembrane domain comprises or is a sequence that is at least 90%, at least 91%, at least 92%, at least 93%, at least 94%, at least 95%, at least 96%, at least 97%, at least 98%, at least 99%, at least 99.5%, or 100% identical to a Tim1 transmembrane domain comprising an amino acid sequence of SEQ ID NO:35, a Tim4 transmembrane domain comprising an amino acid sequence of SEQ ID NO:36, an FcγRI transmembrane domain comprising an amino acid sequence of SEQ ID NO:37, a FcεRIγ transmembrane domain comprising an amino acid sequence of SEQ ID NO:89, a CD8a transmembrane domain comprising an amino acid sequence of SEQ ID NO:38, a MERTK transmembrane domain comprising an amino acid sequence of SEQ ID NO:39, an Ax1 transmembrane domain comprising an amino acid sequence of SEQ ID NO:40, a Tyro3 transmembrane domain comprising an amino acid sequence of SEQ ID NO:41, a BAH transmembrane domain comprising an amino acid sequence of SEQ ID NO:142, a CD28 transmembrane domain as set forth in an amino acid sequence of SEQ ID NO:68, a CD4 transmembrane domain comprising an amino acid sequence of SEQ ID NO:42, a MRC1 transmembrane domain comprising an amino acid sequence of SEQ ID NO:118, or a DAP12 transmembrane domain comprising an amino acid sequence of SEQ ID NO:81. In other embodiments, the transmembrane domain is provided by a polynucleotide sequence that comprises or is a sequence that is at least 90%, at least 91%, at least 92%, at least 93%, at least 94%, at least 95%, at least 96%, at least 97%, at least 98%, at least 99%, at least 99.5%, or 100% identical to a polynucleotide sequence encoding a Tim1 transmembrane domain according to SEQ ID NO:8, a polynucleotide sequence encoding a Tim4 transmembrane domain according to SEQ ID NO:9, a polynucleotide sequence encoding a FcεRIγ transmembrane domain according to SEQ ID NO:85, a polynucleotide sequence encoding an FcγRI transmembrane domain according to SEQ ID NO:10, a polynucleotide sequence encoding a CD8a transmembrane domain according to SEQ ID NO:11, a polynucleotide sequence encoding MERTK transmembrane domain according to SEQ ID NO:12, a polynucleotide sequence encoding an Ax1 transmembrane domain according to SEQ ID NO:13, a polynucleotide sequence encoding a Tyro3 transmembrane domain according to SEQ ID NO:14, a polynucleotide sequence encoding a CD28 transmembrane domain according to SEQ ID NO:144, a polynucleotide sequence encoding a BAH transmembrane domain according to SEQ ID NO:143, a polynucleotide sequence encoding a CD4 transmembrane domain according to SEQ ID NO:15, or a polynucleotide sequence encoding a DAP12 transmembrane domain according to SEQ ID NO:145.

It is understood that direct fusion of one domain to another domain of a CER described herein does not preclude the presence of intervening junction amino acids. Junction amino acids may be natural or non-natural (e.g., resulting from the construct design of a chimeric protein).

Examples of CERs

The component parts of a CER as disclosed herein can be selected and arranged in various combinations to provide a desired engulfment phenotype to a host cell. In addition to inducing engulfment of a cell, microbe, or particle expressing or characterized by a molecule targeted by a CER-modified host cell, a CER as described herein may be designed to initiate a homeostatic engulfment response or pro-inflammatory engulfment response, depending upon the target cell or particle, disease state, and desired therapeutic outcome.

In one aspect, the present disclosure provides a chimeric engulfment receptor (CER) comprising a single chain chimeric protein, the single chain chimeric protein comprising: an extracellular domain comprising a binding domain that binds to phosphatidylserine (PtdSer); an engulfment signaling domain; and a transmembrane domain positioned between and connecting the extracellular domain and the engulfment signaling domain.

In certain embodiments, the extracellular domain further comprises an extracellular spacer domain positioned between the binding domain and the transmembrane domain.

In certain embodiments of a CER including an extracellular domain comprising a binding domain that binds to PtdSer, the engulfment signaling domain is a homeostatic engulfment signaling domain or a pro-inflammatory engulfment signaling domain. In certain such embodiments, the homeostatic engulfment signaling domain or the pro-inflammatory engulfment signaling domain can be selected from one or more of those described herein. In other embodiments of a CER including an extracellular domain comprising a binding domain that binds to PtdSer, the engulfment signaling domain comprises a primary engulfment signaling domain and a secondary engulfment signaling domain. The primary engulfment signaling domain and secondary engulfment signaling domain may both be homeostatic engulfment signaling domains, pro-inflammatory engulfment signaling domains, or both (in any order). In certain such embodiments, the homeostatic engulfment signaling domain or the pro-inflammatory engulfment signaling domain included in the primary signaling domain and the secondary signaling domain can be selected from one or more of the homeostatic engulfment signaling domains and the pro-inflammatory engulfment signaling domains described herein.

Figure 6B:
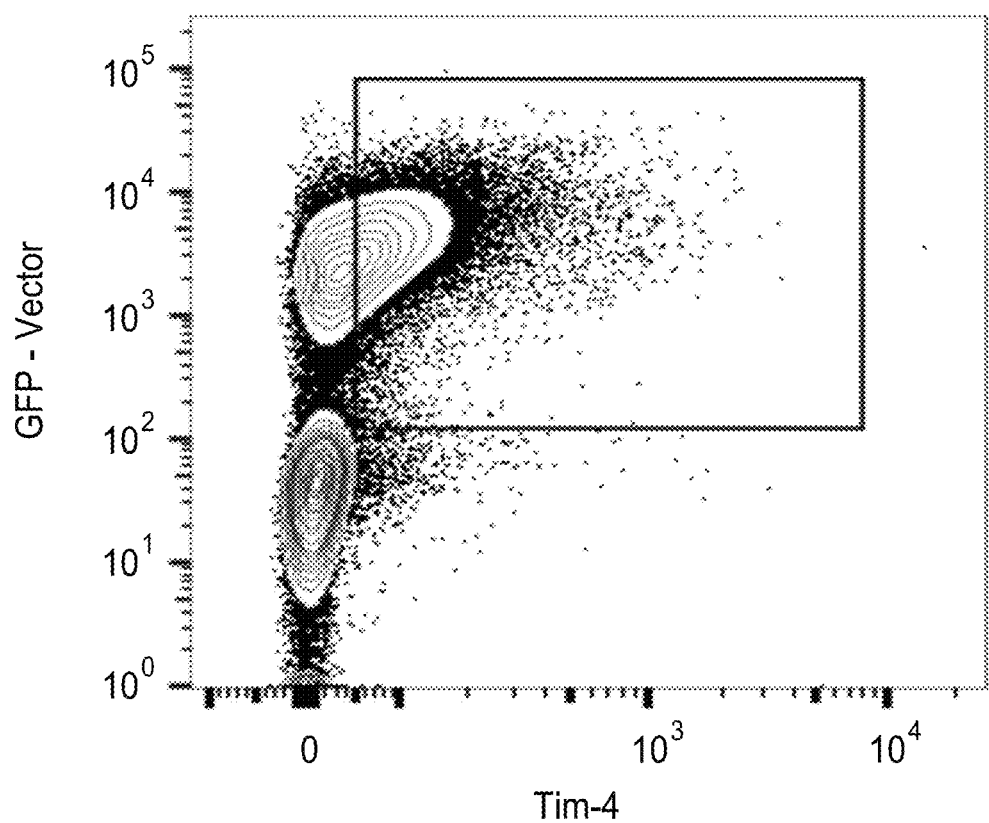

An embodiment of a CER including an extracellular domain comprising a binding domain that binds to PtdSer comprises an extracellular domain comprising a TIM4 PtdSer binding domain, a transmembrane domain comprising a TIM4 transmembrane domain, and an engulfment signaling domain comprising a MERTK signaling domain (also referred to herein as "CER01") (see, e.g., FIG. 6A). In certain embodiments, such a CER comprises an amino acid sequence of SEQ ID NO:71. In some embodiments, the CER mature polypeptide comprises an amino acid sequence of SEQ ID NO:71 without the signal peptide sequence (amino acids 1-22 of SEQ ID NO:71).

Figure 9A:
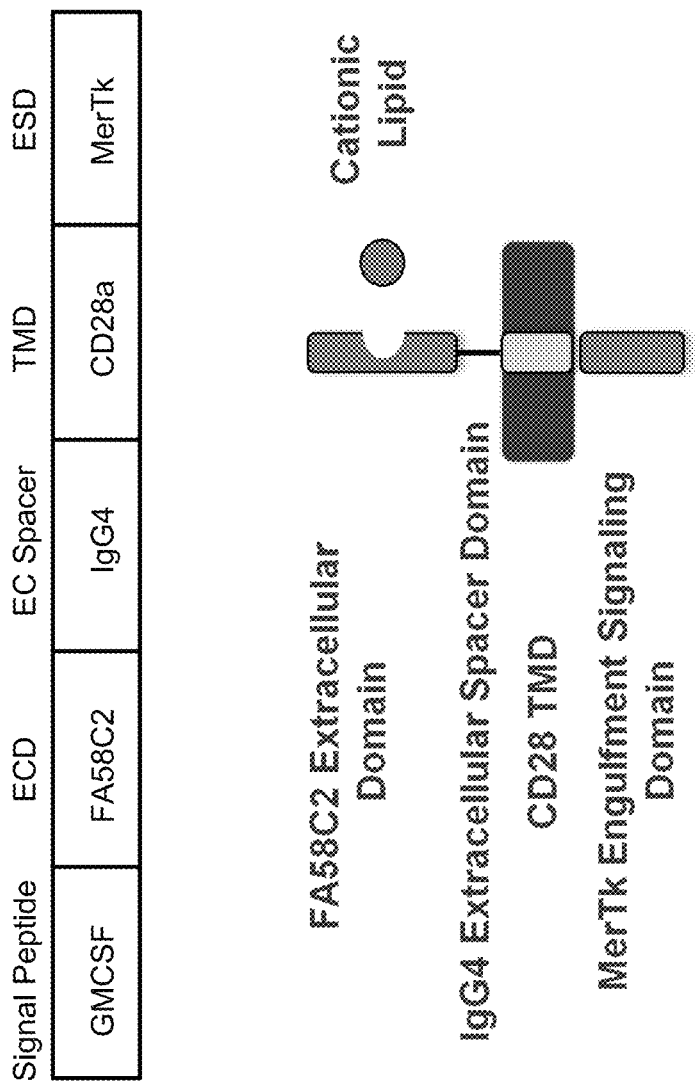
FIGS. 9A-9F show FA58C2-MERTK chimeric engulfment receptor (CER)-mediated in vitro engulfment of apoptotic target cells.

Another embodiment of a CER including an extracellular domain comprising a binding domain that binds to PtdSer comprises an extracellular domain comprising a FA58C2 PtdSer binding domain and an extracellular spacer domain comprising a modified IgG4 hinge region, a transmembrane domain comprising a CD28 transmembrane domain, and an engulfment signaling domain comprising a MERTK signaling domain (also referred to herein as "CER03") (see, e.g., FIG. 9A). In certain embodiments, such a CER comprises an amino acid sequence of SEQ ID NO:75. In some embodiments, the CER mature polypeptide comprises an amino acid sequence of SEQ ID NO:75 without the signal peptide sequence (amino acids 1-22 of SEQ ID NO:75).

Figure 11A:
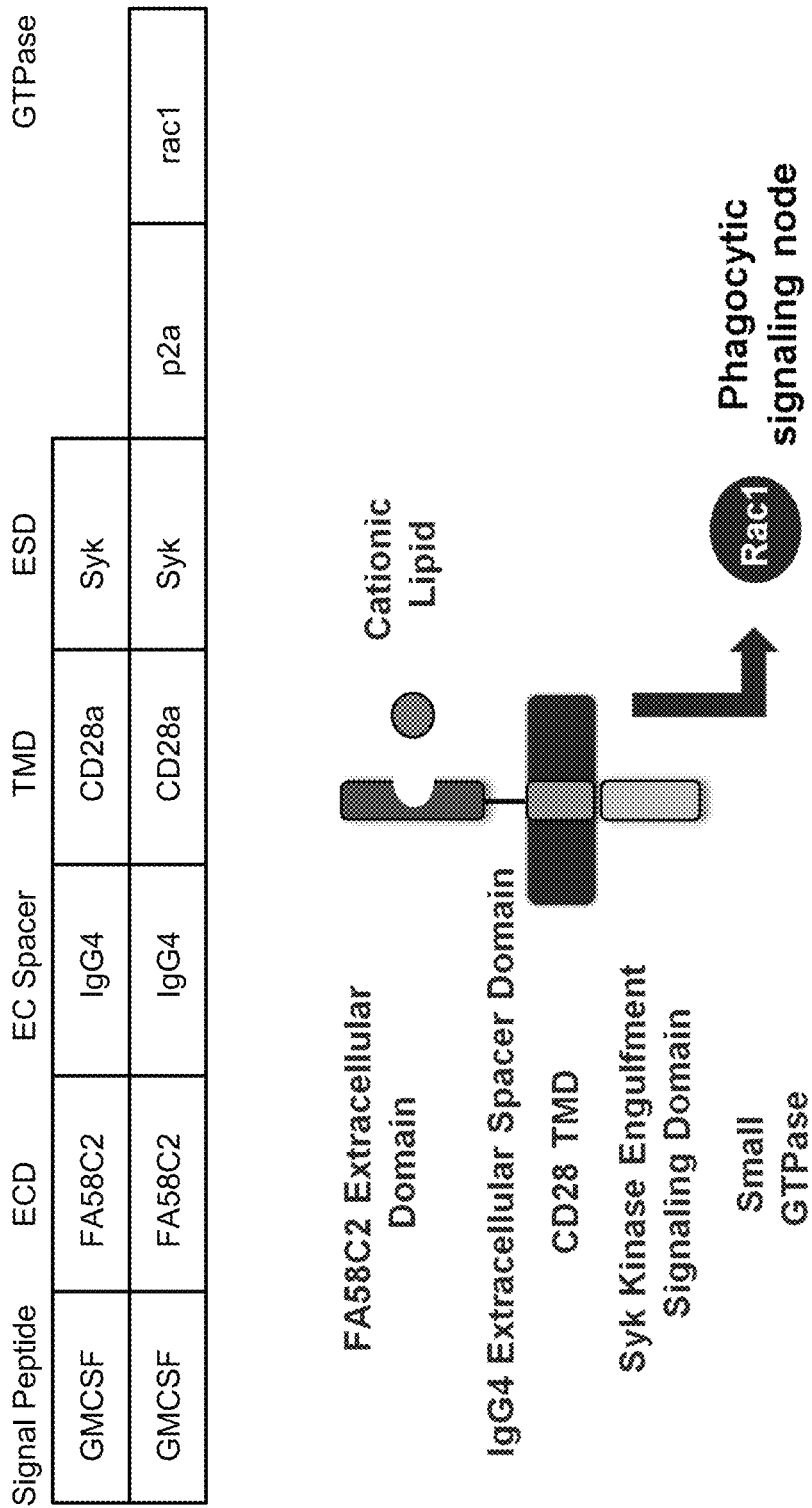
FIGS. 11A-11E show FA58C2-Syk CER-mediated in vitro engulfment of target apoptotic cells.

Yet another embodiment of a CER including an extracellular domain comprising a binding domain that binds to PtdSer comprises an extracellular domain comprising a FA58C2 PtdSer binding domain and extracellular spacer domain comprising a modified IgG$_4$ hinge region, a transmembrane domain comprising a CD28 transmembrane domain, and an engulfment signaling domain comprising a SYK signaling domain (also referred to as "CER04") (see, e.g., FIG. 11A). In certain embodiments, such a CER comprises an amino acid sequence of SEQ ID NO:70. In some embodiments, the CER mature polypeptide comprises an amino acid sequence of SEQ ID NO:70 without the signal peptide sequence (amino acids 1-22 of SEQ ID NO:70).

Another embodiment of a CER including an extracellular domain comprising a binding domain that binds to PtdSer comprises an extracellular domain comprising a TIM4 binding domain, a transmembrane domain comprising TIM4 transmembrane domain, and an engulfment signaling domain comprising a Tyro3 signaling domain (also referred to herein as "CER08"). In certain embodiments, such a CER comprises an amino acid sequence of SEQ ID NO:83. In some embodiments, the CER mature polypeptide comprises an amino acid sequence of SEQ ID NO:83 without the signal peptide sequence (amino acids 1-22 of SEQ ID NO:83).

Another embodiment of a CER including an extracellular domain comprising a binding domain that binds to PtdSer comprises an extracellular domain comprising a TIM4 binding domain, a transmembrane domain comprising TIM4 transmembrane domain, and an engulfment signaling domain comprising a DAP12 signaling domain (also referred to herein as "CER09"). In certain embodiments, such a CER comprises an amino acid sequence of SEQ ID NO:84. In some embodiments, the CER mature polypeptide comprises an amino acid sequence of SEQ ID NO:84 without the signal peptide sequence (amino acids 1-22 of SEQ ID NO:84).

Another embodiment of a CER including an extracellular domain comprising a binding domain that binds to PtdSer comprises an extracellular domain comprising a TIM4 binding domain, a transmembrane domain comprising DAP12 transmembrane domain, and an engulfment signaling domain comprising a DAP12 signaling domain (also referred to herein as "CER10"). In certain embodiments, such a CER comprises an amino acid sequence of SEQ ID NO:86. In some embodiments, the CER mature polypeptide comprises an amino acid sequence of SEQ ID NO:86 without the signal peptide sequence (amino acids 1-22 of SEQ ID NO:86).

Another embodiment of a CER including an extracellular domain comprising a binding domain that binds to PtdSer comprises an extracellular domain comprising a TIM4 binding domain, a transmembrane domain comprising TIM4 transmembrane domain, and an engulfment signaling domain comprising a Ax1 signaling domain (also referred to herein as "CER11"). In certain embodiments, such a CER comprises an amino acid sequence of SEQ ID NO:87. In some embodiments, the CER mature polypeptide sequence comprises an amino acid sequence of SEQ ID NO:87 without the signal peptide sequence (amino acids 1-22 of SEQ ID NO:87).

Another embodiment of a CER including an extracellular domain comprising a binding domain that binds to PtdSer comprises an extracellular domain comprising a TIM4 binding domain, a transmembrane domain comprising TIM4 transmembrane domain, and an engulfment signaling domain comprising a FcεRIγ signaling domain (also referred herein to as "CER12"). In certain embodiments, such a CER comprises an amino acid sequence of SEQ ID NO:90. In some embodiments, the CER mature polypeptide comprises an amino acid sequence of SEQ ID NO:90 without the signal peptide sequence (amino acids 1-22 of SEQ ID NO:90).

Another embodiment of a CER including an extracellular domain comprising a binding domain that binds to PtdSer comprises an extracellular domain comprising a TIM4 binding domain, a transmembrane domain comprising a FcεRIγ transmembrane domain, and an engulfment signaling domain comprising a FcεRIγ signaling domain (also referred to herein as "CER13"). In certain embodiments, such a CER comprises an amino acid sequence of SEQ ID NO:91. In some embodiments, the CER mature polypeptide comprises an amino acid sequence of SEQ ID NO:91 without the signal peptide sequence (amino acids 1-22 of SEQ ID NO:91).

Another embodiment of a CER including an extracellular domain comprising a binding domain that binds to PtdSer comprises an extracellular domain comprising a Tim4 binding domain, a transmembrane domain comprising a Tim4 transmembrane domain, and an engulfment signaling domain comprising a truncated MyD88 signaling domain comprising the death domain but lacking the TIR domain (also referred to herein as "CER15"). In certain embodiments, such a CER comprises an amino acid sequence of SEQ ID NO:79. In some embodiments, the CER mature polypeptide sequence comprises an amino acid sequence of SEQ ID NO:79 without the signal peptide sequence (amino acids 1-22 of SEQ ID NO:79).

Another embodiment of a CER including an extracellular domain comprising a binding domain that binds to PtdSer comprises an extracellular domain comprising a Tim4 binding domain, a transmembrane domain comprising a Tim4 transmembrane domain, and an engulfment signaling domain comprising a MyD88 signaling domain (also referred to herein as "CER16"). In certain embodiments, such a CER comprises an amino acid sequence of SEQ ID NO:80. In some embodiments, the CER mature polypeptide sequence comprises an amino acid sequence of SEQ ID NO:80 without the signal peptide sequence (amino acids 1-22 of SEQ ID NO:80).

Another embodiment of a CER including an extracellular domain comprising a binding domain that binds to PtdSer comprises an extracellular domain comprising a Tim4 binding domain, a transmembrane domain comprising a Tim4 transmembrane domain, and an engulfment signaling domain comprising a NFAM1 signaling domain (also referred to herein as "CER25"). In certain embodiments, such a CER comprises an amino acid sequence of SEQ ID NO:93. In some embodiments, the CER mature polypeptide sequence comprises an amino acid sequence of SEQ ID NO:93 without the signal peptide sequence (amino acids 1-22 of SEQ ID NO:93).

Another embodiment of a CER including an extracellular domain comprising a binding domain that binds to PtdSer comprises an extracellular domain comprising a Tim4 binding domain, a transmembrane domain comprising a Tim4 transmembrane domain, a primary engulfment signaling domain comprising a truncated MyD88 signaling domain, and a secondary engulfment signaling domain comprising a BAFF-R signaling domain (also referred to herein as "CER85"). In certain embodiments, such a CER comprises an amino acid sequence of SEQ ID NO:95. In some embodiments, the CER mature polypeptide sequence comprises an amino acid sequence of SEQ ID NO:95 without the signal peptide sequence (amino acids 1-22 of SEQ ID NO:95).

Another embodiment of a CER including an extracellular domain comprising a binding domain that binds to PtdSer comprises an extracellular domain comprising a Tim4 binding domain, a transmembrane domain comprising a Tim4 transmembrane domain, a primary engulfment signaling domain comprising a truncated MyD88 signaling domain, and a secondary engulfment signaling domain comprising a DAP12 signaling domain (also referred to herein as "CER86"). In certain embodiments, such a CER comprises an amino acid sequence of SEQ ID NO:96. In some embodiments, the CER mature polypeptide sequence comprises an amino acid sequence of SEQ ID NO:96 without the signal peptide sequence (amino acids 1-22 of SEQ ID NO:96).

Another embodiment of a CER including an extracellular domain comprising a binding domain that binds to PtdSer comprises an extracellular domain comprising a Tim4 binding domain, a transmembrane domain comprising Tim4 transmembrane domain, a primary engulfment signaling domain comprising a truncated MyD88 signaling domain, and a secondary engulfment signaling domain comprising a CD79b signaling domain (also referred to herein as "CER89"). In certain embodiments, such a CER comprises an amino acid sequence of SEQ ID NO:98. In some embodiments, the CER mature polypeptide sequence comprises an amino acid sequence of SEQ ID NO:98 without the signal peptide sequence (amino acids 1-22 of SEQ ID NO:98).

Another embodiment of a CER including an extracellular domain comprising a binding domain that binds to PtdSer comprises an extracellular domain comprising a Tim4 binding domain, a transmembrane domain comprising a Tim4 transmembrane domain, a primary engulfment signaling domain comprising a truncated MyD88 signaling domain, and a secondary engulfment signaling domain comprising a NFAM1 signaling domain (also referred to herein as "CER90"). In certain embodiments, such a CER comprises an amino acid sequence of SEQ ID NO:100. In some embodiments, the CER mature polypeptide sequence comprises an amino acid sequence of SEQ ID NO:100 without the signal peptide sequence (amino acids 1-22 of SEQ ID NO:100).

Another embodiment of a CER including an extracellular domain comprising a binding domain that binds to PtdSer comprises an extracellular domain comprising a Tim4 binding domain, a transmembrane domain comprising a Tim4 transmembrane domain, a primary engulfment signaling domain comprising a MERTK signaling domain, and a secondary engulfment signaling domain comprising a CD79b signaling domain (also referred to herein as "CER95"). In certain embodiments, such a CER comprises an amino acid sequence of SEQ ID NO:101. In some embodiments, the CER mature polypeptide sequence comprises an amino acid sequence of SEQ ID NO:101 without the signal peptide sequence (amino acids 1-22 of SEQ ID NO:101).

Another embodiment of a CER including an extracellular domain comprising a binding domain that binds to PtdSer comprises an extracellular domain comprising a Tim4 binding domain, a transmembrane domain comprising a Tim4 transmembrane domain, a primary engulfment signaling domain comprising a MERTK signaling domain, and a secondary engulfment signaling domain comprising a NFAM1 signaling domain (also referred to herein as "CER96"). In certain embodiments, such a CER comprises an amino acid sequence of SEQ ID NO:102. In some embodiments, the CER mature polypeptide sequence comprises an amino acid sequence of SEQ ID NO:102 without the signal peptide sequence (amino acids 1-22 of SEQ ID NO:102).

Another embodiment of a CER including an extracellular domain comprising a binding domain that binds to PtdSer comprises an extracellular domain comprising a Tim4 binding domain, a transmembrane domain comprising a Tim4 transmembrane domain, a primary engulfment signaling domain comprising a MERTK signaling domain, and a secondary engulfment signaling domain comprising a BAFF-R signaling domain (also referred to herein as "CER93"). In certain embodiments, such a CER comprises an amino acid sequence of SEQ ID NO:103. In some embodiments, the CER mature polypeptide sequence comprises an amino acid sequence of SEQ ID NO:103 without the signal peptide sequence (amino acids 1-22 of SEQ ID NO:103).

Another embodiment of a CER including an extracellular domain comprising a binding domain that binds to PtdSer comprises an extracellular domain comprising a Tim4 binding domain, a transmembrane domain comprising a Tim4 transmembrane domain, a primary engulfment signaling domain comprising a BAFF-R signaling domain, and a secondary engulfment signaling domain comprising a truncated MyD88 signaling domain (also referred to herein as "CER87"). In certain embodiments, such a CER comprises an amino acid sequence of SEQ ID NO:130. In some embodiments, the CER mature polypeptide sequence comprises an amino acid sequence of SEQ ID NO:130 without the signal peptide sequence (amino acids 1-22 of SEQ ID NO:130).

Another embodiment of a CER including an extracellular domain comprising a binding domain that binds to PtdSer comprises an extracellular domain comprising a Tim4 binding domain, a transmembrane domain comprising a Tim4 transmembrane domain, a primary engulfment signaling domain comprising a DAP12 signaling domain, and a secondary engulfment signaling domain comprising a truncated MyD88 signaling domain (also referred to herein as "CER88"). In certain embodiments, such a CER comprises an amino acid sequence of SEQ ID NO:131. In some embodiments, the CER mature polypeptide sequence comprises an amino acid sequence of SEQ ID NO:131 without the signal peptide sequence (amino acids 1-22 of SEQ ID NO:131).

Another embodiment of a CER including an extracellular domain comprising a binding domain that binds to PtdSer comprises an extracellular domain comprising a Tim4 binding domain, a transmembrane domain comprising a Tim4 transmembrane domain, a primary engulfment signaling domain comprising a MERTK signaling domain, and a secondary engulfment signaling domain comprising a truncated MyD88 signaling domain (also referred to herein as "CER92"). In certain embodiments, such a CER comprises an amino acid sequence of SEQ ID NO:133. In some embodiments, the CER mature polypeptide sequence comprises an amino acid sequence of SEQ ID NO:133 without the signal peptide sequence (amino acids 1-22 of SEQ ID NO:133).

Another embodiment of a CER including an extracellular domain comprising a binding domain that binds to PtdSer comprises an extracellular domain comprising a Tim4 binding domain, a transmembrane domain comprising a Tim4 transmembrane domain, a primary engulfment signaling domain comprising a MERTK signaling domain, and a secondary engulfment signaling domain comprising a DAP12 signaling domain (also referred to herein as "CER94"). In certain embodiments, such a CER comprises an amino acid sequence of SEQ ID NO:134. In some embodiments, the CER mature polypeptide sequence comprises an amino acid sequence of SEQ ID NO:134 without the signal peptide sequence (amino acids 1-22 of SEQ ID NO:134).

Another embodiment of a CER including an extracellular domain comprising a binding domain that binds to PtdSer comprises an extracellular domain comprising a Tim4 binding domain, a transmembrane domain comprising a Tim4 transmembrane domain, a primary engulfment signaling domain comprising a MERTK signaling domain, and a secondary engulfment signaling domain comprising a NFAM1 signaling domain (also referred to herein as "CER96"). In certain embodiments, such a CER comprises an amino acid sequence of SEQ ID NO:102. In some embodiments, the CER mature polypeptide comprises an amino acid sequence of SEQ ID NO:102 without the signal peptide sequence (amino acids 1-22 of SEQ ID NO:102).

Another embodiment of a CER including an extracellular domain comprising a binding domain that binds to PtdSer comprises an extracellular domain comprising a Tim4 binding domain, a transmembrane domain comprising a Tim4 transmembrane domain, a primary engulfment signaling domain comprising a MERTK signaling domain, and a secondary engulfment signaling domain comprising a truncated NFAM1 signaling domain (also referred to herein as "CER96 with truncated NFAM1"). In certain embodiments, such a CER comprises an amino acid sequence of SEQ ID NO:116. In some embodiments, the CER mature polypeptide comprises an amino acid sequence of SEQ ID NO:116 without the signal peptide sequence (amino acids 1-22 of SEQ ID NO:116).

Another embodiment of a CER including an extracellular domain comprising a binding domain that binds to PtdSer comprises an extracellular domain comprising a Tim4 binding domain, a transmembrane domain comprising a Tim4 transmembrane domain, a primary engulfment signaling domain comprising a BAFFR signaling domain, and a secondary engulfment signaling domain comprising a truncated MyD88 signaling domain (also referred to herein as "CER87"). In certain embodiments, such a CER comprises an amino acid sequence of SEQ ID NO:130. In some embodiments, the CER mature polypeptide sequence comprises an amino acid sequence of SEQ ID NO:130 without the signal peptide sequence (amino acids 1-22 of SEQ ID NO:130).

Another embodiment of a CER including an extracellular domain comprising a binding domain that binds to PtdSer comprises an extracellular domain comprising a Tim4 binding domain, a transmembrane domain comprising a Tim4 transmembrane domain, a primary engulfment signaling domain comprising an Ax1 signaling domain, and a secondary engulfment signaling domain comprising a DAP12 signaling domain (also referred to herein as "CER97"). In certain embodiments, such a CER comprises an amino acid sequence of SEQ ID NO:152. In some embodiments, the CER mature polypeptide sequence comprises an amino acid sequence of SEQ ID NO:152 without the signal peptide sequence (amino acids 1-22 of SEQ ID NO:152).

Another embodiment of a CER including an extracellular domain comprising a binding domain that binds to PtdSer comprises an extracellular domain comprising a Tim4 binding domain, a transmembrane domain comprising a Tim4 transmembrane domain, a primary engulfment signaling domain comprising an Ax1 signaling domain, and a secondary engulfment signaling domain comprising a CD79b signaling domain (also referred to herein as "CER98"). In certain embodiments, such a CER comprises an amino acid sequence of SEQ ID NO:153. In some embodiments, the CER mature polypeptide sequence comprises an amino acid sequence of SEQ ID NO:153 without the signal peptide sequence (amino acids 1-22 of SEQ ID NO:153).

In another aspect, the present disclosure provides a CER comprising a single chain chimeric protein, the single chain chimeric protein comprising: an extracellular domain comprising a binding domain that binds to a pro-engulfment marker or target antigen; a pro-inflammatory engulfment signaling domain; and a transmembrane domain positioned between and connecting the extracellular domain and the pro-inflammatory engulfment signaling domain. Such CERs are specifically "polarized" to provide an inflammatory or immunogenic engulfment phenotype upon binding a target molecule (e.g., pro-engulfment marker or target antigen).

In certain embodiments of a CER including a pro-inflammatory engulfment signaling domain, the extracellular domain further comprises an extracellular spacer domain positioned between the binding domain and the transmembrane domain.

In yet another aspect, the present disclosure provides a CER comprising a single chain chimeric protein, the single chain chimeric protein comprising: an extracellular domain comprising a binding domain that binds to a pro-engulfment marker or target antigen; an engulfment signaling domain comprising a primary engulfment signaling domain and a secondary engulfment signaling domain; and a transmembrane domain positioned between and connecting the extracellular domain and the pro-inflammatory engulfment signaling domain. The primary engulfment signaling domain and secondary engulfment signaling domain may both be homeostatic engulfment signaling domains, pro-inflammatory engulfment signaling domains, or both (in any order).

In certain embodiments of a CER including an engulfment signaling domain comprising a primary engulfment signaling domain and a secondary engulfment signaling domain, the extracellular domain further comprises an extracellular spacer domain positioned between the binding domain and the transmembrane domain.

In yet another aspect, the present disclosure provides a CER comprising a single chain chimeric protein, the single chain chimeric protein comprising: an extracellular domain comprising an scFv that binds to a pro-engulfment marker or target antigen; an engulfment signaling domain; and a transmembrane domain positioned between and connecting the extracellular domain and the engulfment signaling domain, wherein the transmembrane domain and engulfment signaling domain are each derived from a different molecule.

In certain embodiments of a CER that includes an extracellular domain comprising an scFv that binds to a pro-engulfment marker or target antigen, the extracellular domain further comprises an extracellular spacer domain positioned between the binding domain and the transmembrane domain.

Figure 13A:
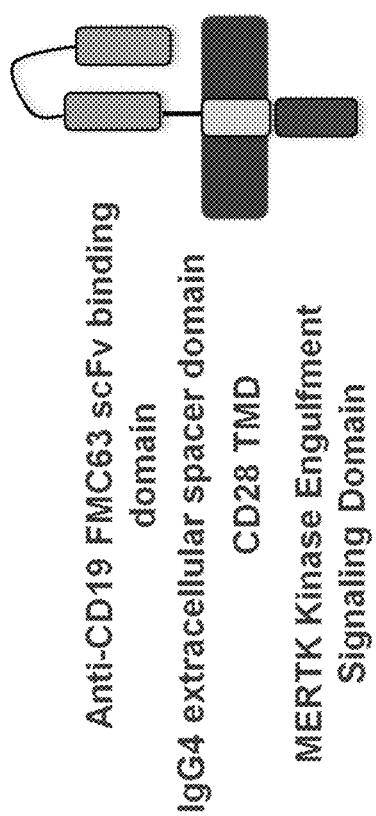
FIGS. 13A-13H show CD19-MERTK chimeric engulfment receptor (CER)-mediated in vitro engulfment of target B-cells.

An embodiment of a CER that includes an extracellular domain comprising an scFv that binds to a pro-engulfment marker or target antigen comprises an extracellular domain comprising a scFv binding domain specific for CD19 (e.g., FMC63 scFv (SEQ ID NO:66)) and an extracellular spacer domain comprising a modified IgG4 hinge region; an engulfment signaling domain comprising a MERTK signaling domain; and a transmembrane domain comprising a CD28 transmembrane domain positioned between and connecting the extracellular domain and the engulfment signaling domain; wherein the extracellular spacer domain is positioned between the binding domain and the transmembrane domain (also referred to as "CER40") (see, e.g., FIG. 13A). In certain embodiments, such a CER comprises an amino acid sequence of SEQ ID NO:64. In some embodiments, the CER mature polypeptide sequence comprises an amino acid sequence of SEQ ID NO:64 without the signal peptide sequence (amino acids 1-22 of SEQ ID NO:64).

Another of a CER that includes an extracellular domain comprising an scFv that binds to a pro-engulfment marker or target antigen comprises an extracellular domain comprising an scFv specific for mesothelin (e.g., M912 scFv, amino acids 23-264 of SEQ ID NO:106, signal peptide at amino acids 1-22 of SEQ ID NO:106) and an extracellular spacer domain comprising a modified IgG4 hinge region; an engulfment signaling domain comprising a truncated MyD88 signaling domain; and a transmembrane domain comprising a Tim4 transmembrane domain positioned between and connecting the extracellular domain and the engulfment signaling domain; wherein the extracellular spacer domain is positioned between the scFv and the transmembrane domain (also referred to herein as "CER50"). In certain embodiments, such a CER comprises an amino acid sequence of SEQ ID NO:107. In some embodiments, the CER mature polypeptide sequence comprises an amino acid sequence of SEQ ID NO:107 without the signal peptide sequence (amino acids 1-22 of SEQ ID NO:107).

In certain embodiments, following binding of a CER expressed on the surface of a host cell to its cognate target molecule, lateral clustering of CERs occurs on the host cell surface, increasing the local CER concentration. Clustering is driven by the presence of multivalent ligands on the target cell or particle surface.

In certain embodiments, following binding of a CER expressed on the surface of a host cell to its cognate target molecule, dimerization or multimerization of the CERs occurs, bringing together intracellular engulfment signaling domains, which then become targets of intracellular kinases.

In certain embodiments, a CER of the present disclosure when expressed on the surface of a host cell is capable of tethering, internalizing, and processing (degrading) a target molecule or particle (e.g., phagocytosing a target). In other embodiments, a CER of the present disclosure is capable of tethering and internalizing a target molecule or particle (e.g, engulfing a target). In some embodiments, the target cell or particle within the phagosome may be discharged before or during phagosome maturation. Moreover, internalizing may comprise internalizing the whole cell or particle that is bound by the extracellular domain of the CER, or may comprise internalization of a piece or portion of the cell or particle that is bound by the extracellular domain of the CER.

In certain embodiments, a CER of the present disclosure tethers a target molecule or particle without internalization. A host cell expressing a CER may engulf or be tethered to multiple target cells or particles. Without wishing to be bound by theory, even in the absence of internalization and degradation of the target cell or particle, tethering of a target cell or particle by a host cell expressing a CER may result in degradation of the target cell or particle or promote an inflammatory environment, which is desirable in certain therapeutic contexts (e.g., cancer).

Embodiments of CERs according to the present description are illustrated in FIGS. 6A, 9A, 10A, 11A, 12A, 13A, 13B, 14, 15, Sequence Listing, and the examples.

Host Cells and Nucleic Acids

In certain aspects, the present disclosure provides nucleic acid molecules that encode any one or more of the CERs described herein. The nucleic acid sequences encoding a desired CER can be obtained or produced using recombinant methods known in the art using standard techniques, such as by screening libraries from cells expressing the desired sequence or a portion thereof, by deriving the sequence from a vector known to include the same, or by isolating the sequence or a portion thereof directly from cells or tissues containing the same. Alternatively, the sequence of interest can be produced synthetically, rather than being cloned.

Polynucleotides encoding the CER compositions provided herein may be derived from any animal, such as humans, primates, cows, horses, sheep, dogs, cats, mice, rats, rabbits, guinea pigs, or pigs. In certain embodiments, a polynucleotide encoding the CER is from the same animal species as the host cell into which the polynucleotide is inserted.

Polynucleotides encoding the CER compositions provided herein may also include a sequence encoding a signal peptide (also referred to as leader peptide or signal sequence) at the amino terminal end of the CER for targeting of the precursor protein to the secretory pathway. The signal peptide is optionally cleaved from the N-terminus of the extracellular domain during cellular processing and localization of the CER to the cell membrane. A polypeptide from which a signal peptide sequence has been cleaved or removed may also be called a mature polypeptide. Examples of signal peptides that may be used in the CERs of the present disclosure include signal peptides derived from endogenous secreted proteins, including, e.g., GM-CSF (amino acid sequence of SEQ ID NO:65), Tim4 (amino acid sequence of SEQ ID NO:72). In certain embodiments, polynucleotide or polypeptide sequences of CERs of the present disclosure comprise sequences for mature polypeptides. It is understood by persons of skill in the art that for sequences disclosed herein that include a signal peptide sequence, the signal peptide sequence may be replaced with another signal peptide that is capable of trafficking the encoded protein to the extracellular membrane.

In certain embodiments, a nucleic acid molecule encoding a CER of the present disclosure is codon optimized for efficient expression in a target host cell.

Nucleic acid molecules encoding a desired CER can be inserted into an appropriate vector (e.g., viral vector, non-viral plasmid vector, and non-viral vectors, such as lipid-based DNA vectors, modified mRNA (modRNA), self-amplifying mRNA, CELiD, and transposon-mediated gene transfer (PiggyBac, Sleeping Beauty)) for introduction in a host cell of interest (e.g., a T cell, a natural killer cell, a B cell, a lymphocyte precursor cell, an antigen presenting cell, a Langerhans cell, or a myeloid cell). Nucleic acid molecules encoding a CER of the present disclosure can be cloned into any suitable vector, such as an expression vector, a replication vector, a probe generation vector, or a sequencing vector. In certain embodiments, a nucleic acid sequence encoding the extracellular domain, a nucleic acid sequence encoding the transmembrane domain, and a nucleic acid sequence encoding the engulfment signaling domain are joined together in a single polynucleotide and then inserted into a vector. In other embodiments, a nucleic acid sequence encoding the extracellular domain, a nucleic acid sequence encoding the transmembrane domain, and a nucleic acid sequence encoding the engulfment signaling domain may be inserted separately in a vector such that the resulting amino acid sequence produces a functional CER. A vector that encodes a CER is referred to herein as a "CER vector."

In certain embodiments, a vector comprises a nucleic acid molecule encoding one CER. In other embodiments, a vector comprises one or more nucleic acid molecules encoding two or more CERs. In one embodiment, two or more nucleic acid molecules each encoding a CER may be cloned sequentially into a vector at different multiple cloning sites, with each CER expressed under the regulation of different promoters. In another embodiment, a single nucleic acid molecule encoding multiple CERs is cloned into a cloning site and expressed from a single promoter, with each CER separated from each other by an IRES or viral 2A peptide sequence to allow for co-expression of multiple genes from a single open reading frame (e.g., a multicistronic vector). In certain embodiments, a viral 2A peptide is T2A (SEQ ID NO:147), P2A (SEQ ID NO:104), E2A (SEQ ID NO:148), or F2A (SEQ ID NO:149).

In some embodiments, vectors that allow long-term integration of a transgene and propagation to daughter cells are utilized. Examples include viral vectors such as, adenovirus, adeno-associated virus, vaccinia virus, herpes viruses, Cytomegalovirus, pox virus, or retroviral vectors, such as lentiviral vectors. Vectors derived from lentivirus can be used to achieve long-term gene transfer and have added advantages over vectors including the ability to transduce non-proliferating cells, such as hepatocytes, and low immunogenicity.

In certain embodiments, a CER vector can be constructed to optimize spatial and temporal control. For example, CER vector can include promoter elements to optimize spatial and temporal control. In some embodiments, a CER vector includes tissue specific promoters or enhancers that enable specific induction of a CER to an organ or a pathologic microenvironment, such as tumor or infected tissue. An "enhancer" is an additional promoter element that can function either cooperatively or independently to activate transcription. In other embodiments, a CER vector includes a constitutive promoter. In still other embodiments, a CER vector includes an inducible promoter.

In further embodiments, a CER vector can include a homing receptor, such as CCR4 or CXCR4, to improve homing and antitumor activity in vivo.

Where temporal control is desired, a CER vector may include an element that allows for inducible depletion of transduced cells. For example, such a vector may include an inducible suicide gene. A suicide gene may be an apoptotic gene or a gene that confers sensitivity to an agent (e.g., drug), such as chemically inducible caspase 9 (iCASP9), chemically inducible Fas, or HSV-TK (confers sensitivity to ganciclovir). In further embodiments, a CER vector can be designed to express a known cell surface antigen that, upon infusion of an associated antibody, enables depletion of transduced cells. Examples of cell surface antigens and their associated antibodies that may be used for depletion of transduced cells include CD20 and Rituximab, RQR8 (combined CD34 and CD20 epitopes, allowing CD34 selection and anti-CD20 deletion) and Rituximab, and EGFR and Cetuximab.

Inducible vector systems, such as the tetracycline (Tet)-On vector system which activates transgene expression with doxycycline (Heinz et al., Hum. Gene Ther. 2011, 22:166-76) may also be used for inducible CER expression. Inducible CER expression may be also accomplished via retention using a selective hook (RUSH) system based on streptavidin anchored to the membrane of the endoplasmic reticulum through a hook and a streptavidin binding protein introduced into the CER structure, where addition of biotin to the system leads to the release of the CER from the endoplasmic reticulum (Agaugue et al., 2015, Mol. Ther. 23(Suppl. 1):S88).

As used herein, the term "recombinant" or "non-natural" refers to an organism, microorganism, cell, nucleic acid molecule, or vector that includes at least one genetic alteration or has been modified by introduction of an exogenous nucleic acid molecule, wherein such alterations or modifications are introduced by genetic engineering. Genetic alterations include, for example, modifications introducing expressible nucleic acid molecules encoding proteins, chimeric proteins or enzymes, or other nucleic acid molecule additions, deletions, substitutions or other functional disruption of a cell's genetic material. Additional modifications include, for example, non-coding regulatory regions in which the modifications alter expression of a gene or operon. In certain embodiments, a cell, such as a T cell, obtained from a subject may be genetically modified into a non-natural or recombinant cell (e.g., a non-natural or recombinant T cell) by introducing a nucleic acid that encodes a CER as described herein and whereby the cell expresses a cell surface located CER.

A vector that encodes a core virus is referred to herein as a "viral vector." There are a large number of available viral vectors suitable for use with the compositions of the instant disclosure, including those identified for human gene therapy applications (see Pfeifer and Verma, *Ann. Rev.*

*Genomics Hum. Genet.* 2:177, 2001). Suitable viral vectors include vectors based on RNA viruses, such as retrovirus-derived vectors, e.g., Moloney murine leukemia virus (MLV)-derived vectors, and include more complex retrovirus-derived vectors, e.g., lentivirus-derived vectors. HIV-1-derived vectors belong to this category. Other examples include lentivirus vectors derived from HIV-2, FIV, equine infectious anemia virus, SIV, and Maedi-Visna virus (ovine lentivirus). Methods of using retroviral and lentiviral viral vectors and packaging cells for transducing mammalian host cells with viral particles containing chimeric receptor transgenes are known in the art and have been previous described, for example, in U.S. Pat. No. 8,119,772; Walchli et al., *PLoS One* 6:327930, 2011; Zhao et al., *J. Immunol.* 174:4415, 2005; Engels et al., *Hum. Gene Ther.* 14:1155, 2003; Frecha et al., *Mol. Ther.* 18:1748, 2010; Verhoeyen et al., *Methods Mol. Biol.* 506:97, 2009. Retroviral and lentiviral vector constructs and expression systems are also commercially available.

In certain embodiments, a viral vector is used to introduce a non-endogenous nucleic acid sequence encoding a CER specific for a target. A viral vector may be a retroviral vector or a lentiviral vector. A viral vector may also include nucleic acid sequences encoding a marker for transduction. Transduction markers for viral vectors are known in the art and include selection markers, which may confer drug resistance, or detectable markers, such as fluorescent markers or cell surface proteins that can be detected by methods such as flow cytometry. In particular embodiments, a viral vector further comprises a gene marker for transduction comprising fluorescent protein (e.g., green, yellow), an extracellular domain of human CD2, or a truncated human EGFR (encoding an amino acid sequence of SEQ ID NO:121) (huEGFRt; see Wang et al., *Blood* 118:1255, 2011). When a viral vector genome comprises a plurality of nucleic acid sequences to be expressed in a host cell as separate transcripts, the viral vector may also comprise additional sequences between the two (or more) transcripts allowing bicistronic or multicistronic expression. Examples of such sequences used in viral vectors include internal ribosome entry sites (IRES), furin cleavage sites, viral 2A peptides (e.g., T2A, P2A, E2A, F2A), or any combination thereof.

Figure 2A:
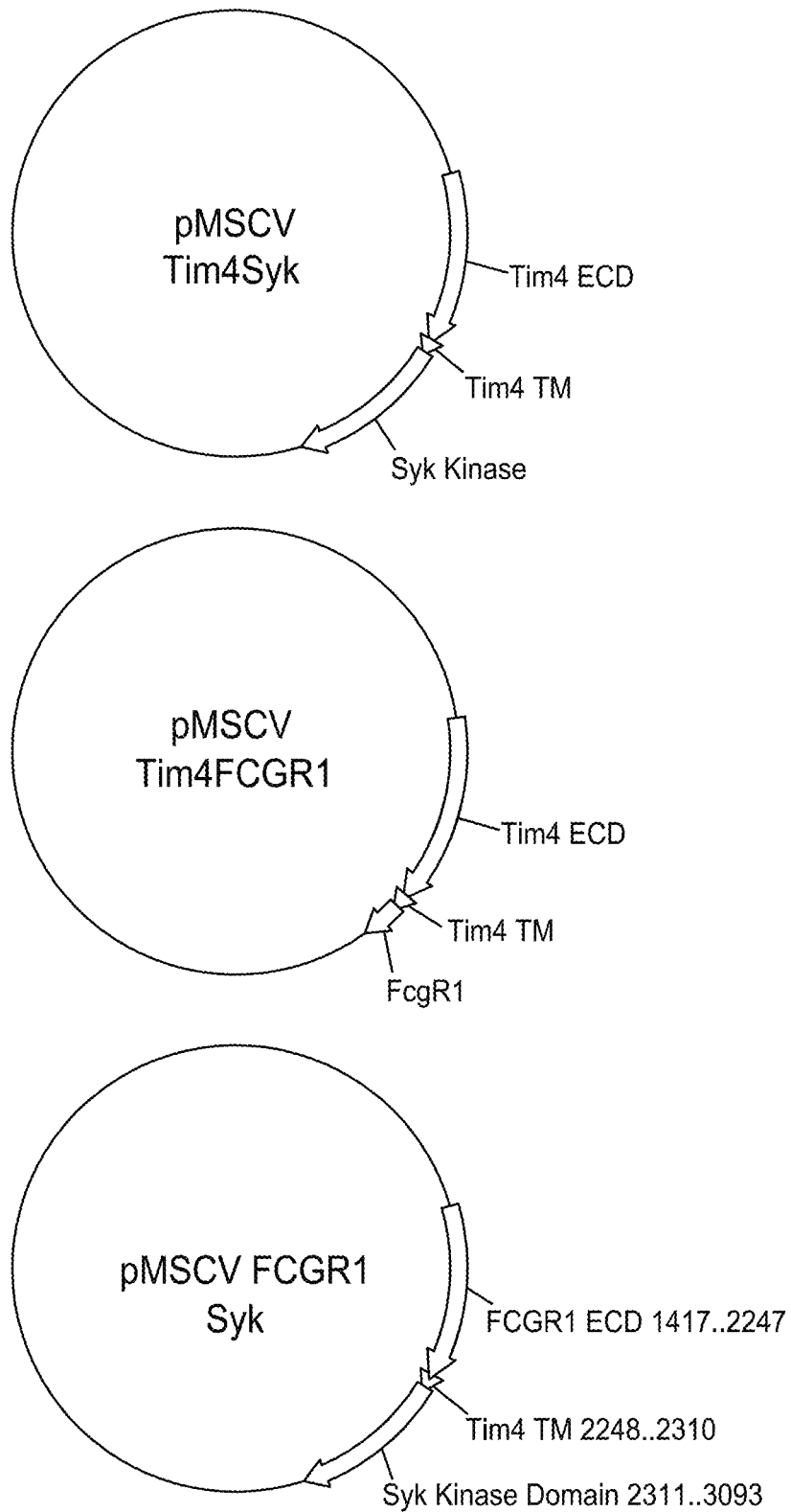
FIGS. 2A-2B show illustrative CER vectors. The CER vectors shown in FIG. 2A contain a single engulfment signaling domain. The CER vectors shown in FIG. 2B contain an engulfment signaling domain that includes a primary engulfment signaling domain and a secondary engulfment signaling domain. "ECD"=extracellular domain.
Figure 2B:
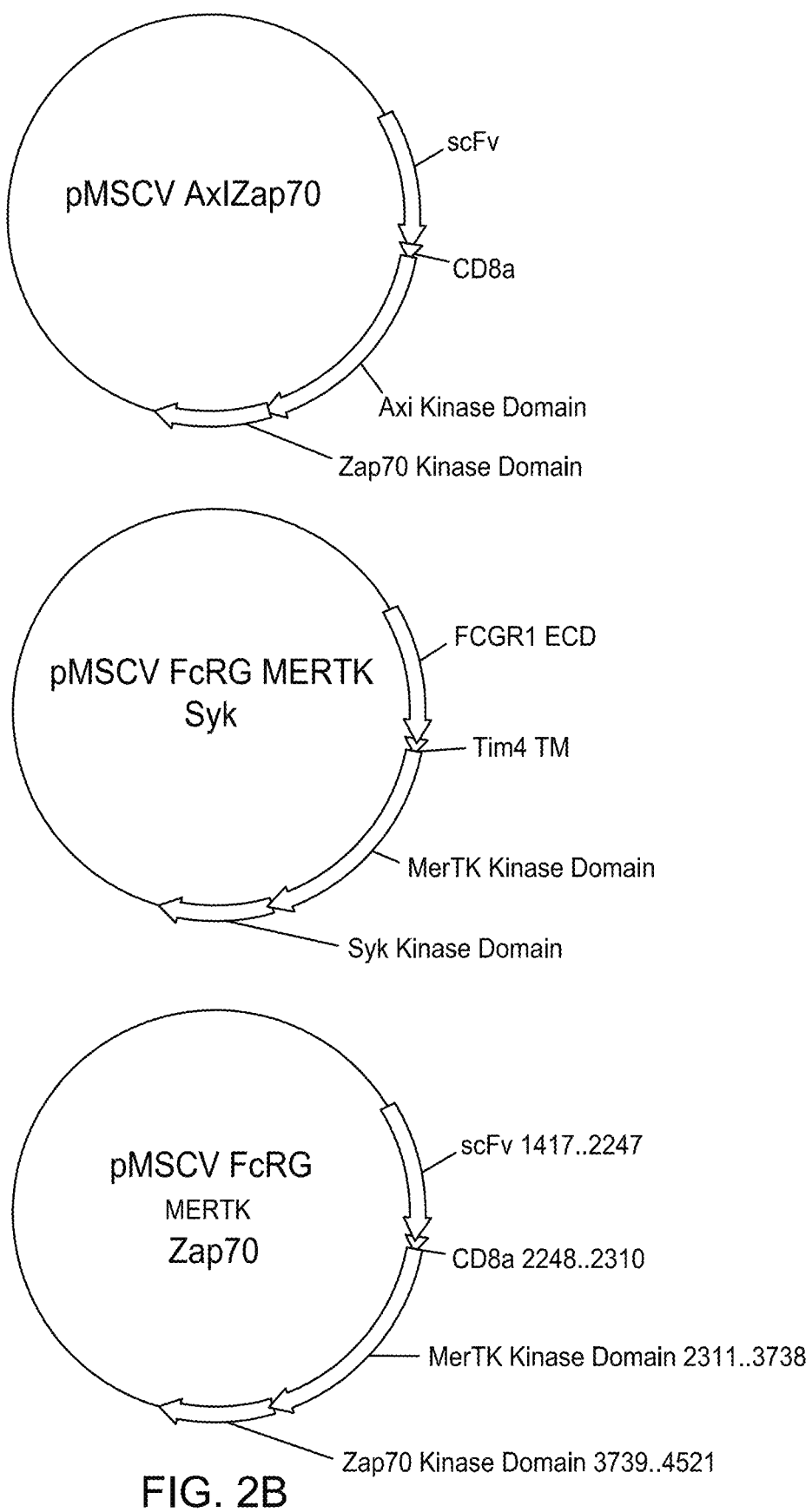
Figure 4:
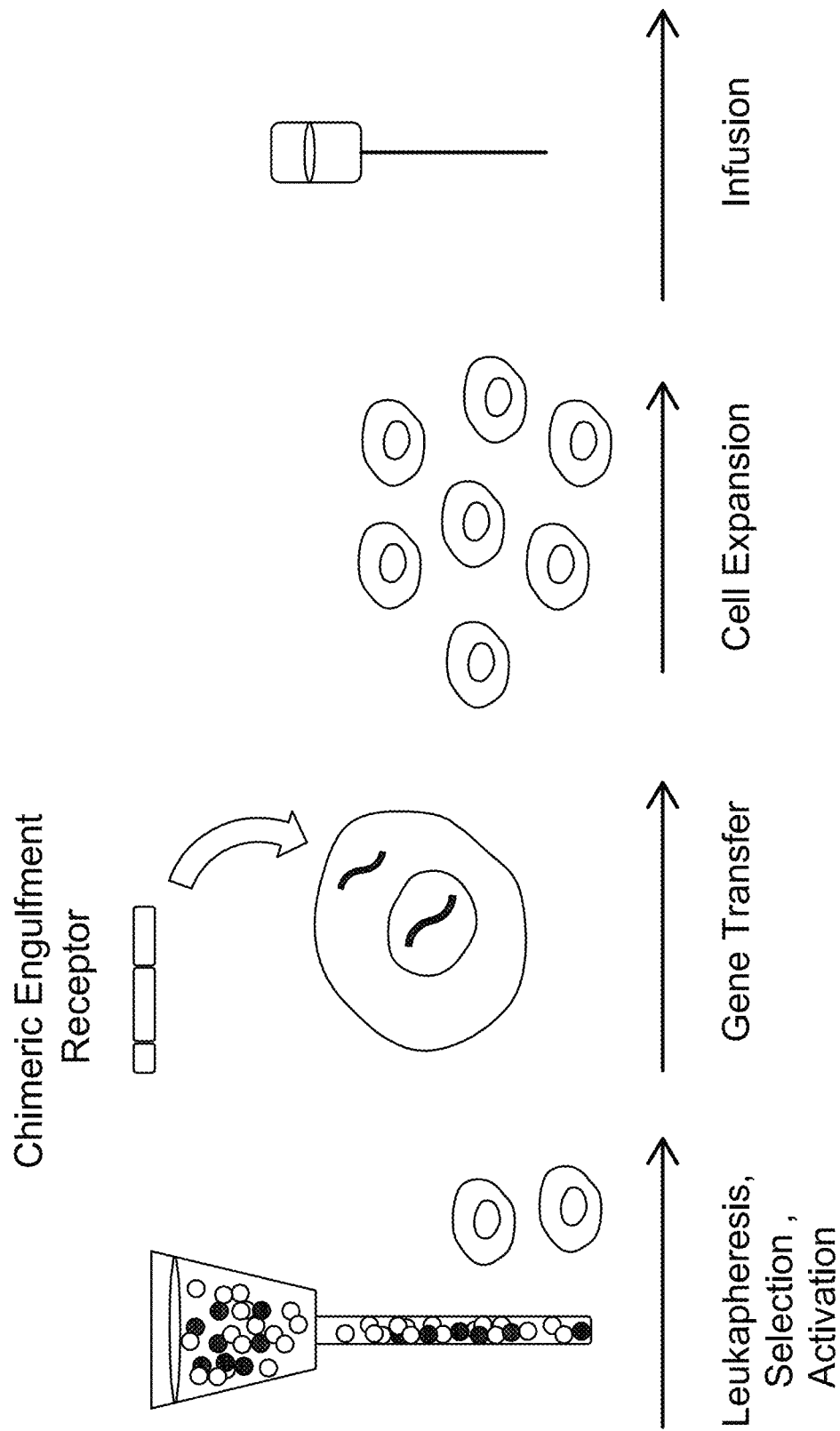
FIG. 4 shows an illustrative method of administration of the CERs of the present disclosure.

FIGS. 2A and 2B provide illustrative CER vectors. The CER vectors shown in FIG. 2A contain a single engulfment signaling domain. The CER vectors shown in FIG. 2B contain an engulfment signaling domain that includes a primary engulfment signaling domain and a secondary engulfment signaling domain.

Other viral vectors also can be used for polynucleotide delivery including DNA viral vectors, including, for example adenovirus-based vectors and adeno-associated virus (AAV)-based vectors; vectors derived from herpes simplex viruses (HSVs), including amplicon vectors, replication-defective HSV and attenuated HSV (Krisky et al., *Gene Ther.* 5: 1517, 1998).

Other viral vectors recently developed for gene therapy uses can also be used with the compositions and methods of this disclosure. Such vectors include those derived from baculoviruses and a-viruses. (Jolly, D J. 1999. Emerging Viral Vectors. pp 209-40 in Friedmann T. ed. The Development of Human Gene Therapy. New York: Cold Spring Harbor Lab), or plasmid vectors (such as sleeping beauty or other transposon vectors). In some embodiments, a viral or plasmid vector further comprises a gene marker for transduction (e.g., green fluorescent protein, huEGFRt (encoding an amino acid sequence of SEQ ID NO:121).

In certain embodiments, gene editing methods are used to modify the host cell genome to comprise a polynucleotide encoding a CER of the present disclosure. Gene editing, or genome editing, is a method of genetic engineering wherein DNA is inserted, replaced, or removed from a host cell's genome using genetically engineered endonucleases. The nucleases create specific double-stranded breaks at targeted loci in the genome. The host cell's endogenous DNA repair pathways then repair the induced break(s), e.g., by non-homologous ending joining (NHEJ) and homologous recombination. Exemplary endonucleases useful in gene editing include a zinc finger nuclease (ZFN), a transcription activator-like effector (TALE) nuclease, a clustered regularly interspaced short palindromic repeats (CRISPR)/Cas nuclease system (e.g., CRISPR-Cas9), a meganuclease, or combinations thereof. Methods of disrupting or knocking out genes or gene expression in immune cells including B cells and T cells, using gene editing endonucleases are known in the art and described, for example, in PCT Publication Nos. WO 2015/066262; WO 2013/074916; WO 2014/059173; Cheong et al., Nat. Comm. 2016 7:10934; Chu et al., Proc. Natl. Acad. Sci. USA 2016 113:12514-12519; methods from each of which are incorporated herein by reference in their entirety.

In certain embodiments, B cells, lymphoid precursor cells, including common lymphocyte precursor cells, antigen presenting cells, including dendritic cells, Langerhans cells, a myeloid precursor cell, or mature myeloid cells are modified to comprise a non-endogenous nucleic acid molecule that encodes a CER of this disclosure.

In some embodiments, B cells are genetically modified to express one or more CERs. B cells possess certain properties that may be advantageous as host cells, including: trafficking to sites of inflammation (e.g., lymph nodes, tumors), capable of internalizing and presenting antigen, capable of costimulating T cells, highly proliferative, and self-renewing (persist for life). In certain embodiments, CER modified B cells are capable of digesting an engulfed target cell or engulfed target particle into smaller peptides and presenting them to T cells via an MHC molecule. Antigen presentation by CER modified B cells may contribute to antigen spreading of the immune response to non-targeted antigens. B cells include progenitor or precursor cells committed to the B cell lineage (e.g., pre-pro-B cells, pro-B cells, and pre-B cells); immature and inactivated B cells or mature and functional or activated B cells. In certain embodiments, B cells may be naïve B cells, plasma cells, regulatory B cells, marginal zone B cells, follicular B cells, lymphoplasmacytoid cell, plasmablast cell, memory B cells, or any combination thereof. Memory B cells may be distinguished from naïve B cells by expression of CD27, which is absent on naïve B cells. In certain embodiments, the B cells can be primary cells or cell lines derived from human, mouse, rat, or other mammals. B cell lines are well known in the art. If obtained from a mammal, a B cell can be obtained from numerous sources, including blood, bone marrow, spleen, lymph node, or other tissues or fluids. In certain embodiments, a B cell is isolated from a tumor site (tumor infiltrating B cell). A B cell composition may be enriched or purified.

In certain embodiments, expression of an endogenous gene of the host B cell is inhibited, knocked down, or knocked out. Examples of endogenous genes that may be inhibited, knocked down, or knocked out in a B cell include a B cell receptor (BCR) gene (e.g., CD79b, IGH, IGκ, IGλ, or any combination thereof), an immune checkpoint molecule (e.g., PD-L1, PD-L2, CD80, CD86, B7-H3, B7-H4, HVEM, adenosine, GALS, VISTA, CEACAM-1, CEACAM-3, CEACAM-5, PVRL2, PD-1, CTLA-4, BTLA, KIR, LAG3, TIM3, A2aR, CD244/2B4, CD160, TIGIT, LAIR-1, PVRIG/CD112R, or any combination thereof), or any combination thereof. Expression of a BCR gene, an immune checkpoint molecule gene, or both may be inhibited, knocked down, or knocked out at the gene level, transcriptional level, or translational level, or a combination thereof. Methods of inhibiting, knocking down, or knocking out a BCR gene, immune checkpoint molecule gene, or both may be accomplished, for example, by RNA interference agents (e.g., siRNA, shRNA, miRNA, etc.) or engineered endonucleases (e.g., CRISPR/Cas nuclease system, a zinc finger nuclease (ZFN), a Transcription Activator Like Effector nuclease (TALEN), a meganuclease, or any combination thereof). In some embodiments, an endogenous gene (e.g., a BCR gene or an immune checkpoint molecule gene) is knocked out by insertion of a polynucleotide encoding a CER of the present disclosure into the locus of the endogenous B cell gene, such as via an engineered endonuclease.

In some embodiments, cells capable of expressing a CER of this disclosure on the cell surface are T cells, including CD4$^+$, CD8$^+$, naïve (CD45 RA+, CCR7+, CD62L+, CD27+, CD45RO−), central memory (CD45RO$^+$, CD62L$^+$, CD8$^+$), effector memory (CD45RA+, CD45RO−, CCR7−, CD62L−, CD27−), virus-specific, mucosal-associated invariant, γδ (gd), tissue resident T cells, and natural killer T cells. In certain embodiments, the T cells can be primary cells or cell lines derived from human, mouse, rat, or other mammals. If obtained from a mammal, a T cell can be obtained from numerous sources, including blood, bone marrow, lymph node, thymus, or other tissues or fluids. In certain embodiments, a T cell is isolated from a tumor site (tumor infiltrating T cell). A T cell composition may be enriched or purified. T cell lines are well known in the art, some of which are described in Sandberg et al., *Leukemia* 21:230, 2000. In certain embodiments, T cells that lack endogenous expression of TCRα and β chains are used. Such T cells may naturally lack endogenous expression of TCRα and β chains or may have been modified to block expression (e.g., T cells from a transgenic mouse that does not express TCR α and β chains or cells that have been manipulated to inhibit expression of TCR α and β chains) or to knockout TCRα chain, TCRβ chain, or both genes. In certain embodiments, cells capable of expressing a chimeric protein of this disclosure on the cell surface are not T cells or cells of a T cell lineage, but cells that are progenitor cells, stem cells or cells that have been modified to express cell surface anti-CD3.

In certain embodiments, a host T cell transfected to express a CER of this disclosure is a functional T cell, such as a virus-specific T cell, a tumor antigen specific cytotoxic T cell, a naïve T cell, a memory stem T cell, a central or effector memory T cell, or a CD4+ CD25+ regulatory T cell.

In certain embodiments, expression of an endogenous gene of the host T cell is inhibited, knocked down, or knocked out. Examples of endogenous genes that may be inhibited, knocked down, or knocked out in a T cell include a TCR gene (TRA, TRB, or both), HLA gene (HLA class I gene, HLA class II gene, or both), an immune checkpoint molecule (PD-L1, PD-L2, CD80, CD86, B7-H3, B7-H4, HVEM, adenosine, GALS, VISTA, CEACAM-1, CEACAM-3, CEACAM-5, PVRL2, PD-1, CTLA-4, BTLA, KIR, LAG3, TIM3, A2aR, CD244/2B4, CD160, TIGIT, LAIR-1, PVRIG/CD112R, or any combination thereof), or any combination thereof. Expression of a TCR gene, an HLA gene, an immune checkpoint molecule gene, or any combination thereof may be inhibited, knocked down, or knocked out at the gene level, transcriptional level, or translational level, or any combination thereof. Methods of inhibited, knocked down, or knocked out a TCR gene, an HLA gene, immune checkpoint molecule gene, or any combination thereof may be accomplished, for example, by RNA interference agents (e.g., siRNA, shRNA, miRNA, etc.) or engineered endonucleases (e.g., CRISPR/Cas nuclease system, a zinc finger nuclease (ZFN), a Transcription Activator Like Effector nuclease (TALEN), a meganuclease, or any combination thereof). In some embodiments, an endogenous gene (e.g., a TCR gene, an HLA gene, or an immune checkpoint molecule gene) is knocked out by insertion of a polynucleotide encoding a CER of the present disclosure into the locus of the endogenous T cell gene, such as via an engineered endonuclease.

In certain embodiments, a host cell may be genetically modified to express one type of CER. In other embodiments, a host cell may express at least two or more different CERs.

In certain embodiments, a population of host cells that are modified to express one or more CERs may be a population of B cells, a population of T cells, a population of natural killer cells, a population of lymphoid precursor cells, including common lymphocyte precursor cells, a population of antigen presenting cells, including dendritic cells, Langerhans cells, a population of myeloid precursor cells, a population of mature myeloid cells, or any combination thereof. In a particular embodiment, the population of host cells that are modified to express one or more CERs is a population of B cells, a population of T cells, or both.

In certain embodiments, each host cell within a population of host cells expresses the same CER or set of CERs. In other embodiments, a population of host cells comprises a mixture of two or more subpopulation of host cells, wherein each subpopulation expresses a different CER or set of CERs.

In certain embodiments, a host cell that is genetically modified to express a CER may also be modified to co-express one or more small GTPases. Rho GTPases, a family of small (~21 k Da) signaling G proteins and also a subfamily of the Ras superfamily, regulate actin cytoskeleton organization in various cell types and promote pseudopod extension and phagosome closure during phagocytosis (see, e.g., Castellano et al., 2000, J. Cell Sci. 113:2955-2961). Engulfment requires F-actin recruitment beneath tethered cells or particles, and F-actin rearrangement to allow membrane extension resulting in cell or particle internalization. RhoGTPases include RhoA, Rac1, Rac2, RhoG, and CDC42. Other small GTPases, such as Rap1, is involved in regulation of complement mediated phagocytosis. Co-expression of a small GTPase with the CER may promote target cell or particle internalization and/or phagosome formation by the host cell. In some embodiments, a recombinant nucleic acid molecule encoding a GTPase is encoded on a separate vector than the CER-containing vector. In other embodiments, a recombinant nucleic acid molecule encoding a GTPase is encoded on the same CER-containing vector as a multicistronic expression construct. The polynucleotide sequences encoding the CER and small GTPase(s) may be separated from each other by a viral 2A peptide sequence (e.g., T2A (SEQ ID NO:147), P2A (SEQ ID NO:104), E2A (SEQ ID NO:148), F2A (SEQ ID NO:149)) to allow multicistronic expression from a single open reading frame. Examples of GTPases that may be co-expressed with a CER include Rac1, Rac2, Rab5 (also referred to as Rab5a), Rab7, Rap1, RhoA, RhoG, CDC42, or any combination thereof. In specific embodiments, the GTPase comprises or is a sequence that is at least 90%, at least 91%, at least 92%, at least 93%, at least 94%, at least 95%, at least 96%, at least 97%, at least 98%, at least 99%, at least 99.5%, or 100% identical to a Rac1 amino acid sequence of SEQ ID NO:76, a Rab5 amino acid sequence of SEQ ID NO:77, a Rab7 amino acid sequence of SEQ ID NO:122, a Rap1 amino acid sequence of SEQ ID NO:123, a RhoA amino acid sequence of SEQ ID NO:124, a CDC42 amino acid sequence of SEQ ID NO:125, or any combination thereof. In a particular embodiment of a multicistronic expression construct, an expression construct encoding a Tim4-MyD88t CER and small GTPase Rab5a separated by a P2A sequence may comprise an amino acid sequence of SEQ ID NO:105 (CER91). In yet another particular embodiment, a CER mature polypeptide sequence comprises SEQ ID NO:105 without the signal peptide at amino acids 1-22.

In certain embodiments, when preparing host cells, e.g., B cells or T cells, that express a CER as described herein, one or more growth factor cytokines that promote proliferation of the host cells, e.g., B cells or T cells, may be added to the cell culture. The cytokines may be human or non-human. Exemplary growth factor cytokines that may be used to promote T cell proliferation include IL-2, IL-15, or the like. Exemplary growth factor cytokines that may be used to promote B cell proliferation include CD40L, IL-2, IL-4, IL-15, IL-21, BAFF, or the like.

In further embodiments, selective gene transfer is used to localize the CER vector to a specific region or organ. In some embodiments, selective gene transfer is used to localize the CER vector to the liver or the lungs of a subject.

Prior to genetic modification of the host cells with a CER vector, a source of host cells (e.g., T cells, B cells, natural killer cells, etc.) is obtained from a subject (e.g., whole blood, peripheral blood mononuclear cells, bone marrow, lymph node tissue, cord blood, thymus tissue, tissue from a site of infection, ascites, pleural effusion, spleen tissue), from which host cells are isolated using methods known in the art. Specific host cell subsets can be collected in accordance with known techniques and enriched or depleted by known techniques, such as affinity binding to antibodies, flow cytometry and/or immunomagnetic selection. After enrichment and/or depletion steps and introduction of a CER, in vitro expansion of the desired modified host cells can be carried out in accordance with known techniques, or variations thereof that will be apparent those skilled in the art.

In certain embodiments, a host cell, including a T cell, a natural killer cell, a B cell, a lymphoid precursor cell, an antigen presenting cell, dendritic cell, a Langerhans cell, a myeloid precursor cell, and a mature myeloid cell, comprising a CER according to any of the embodiments described herein has a phagocytic index of about 20 to about 1,500 for a target cell. A "phagocytic index" is a measure of phagocytic activity of the transduced host cell as determined by counting the number of target cells ingested per CER modified host cell during a set period of incubation of a suspension of target cells and CER modified host cells in media. Phagocytic index may be calculated by multiplying [total number of engulfed target cells/total number of counted CER modified cells (e.g., phagocytic frequency)]× [average area of target cell staining per CER+ Ba/F3 cell× 100 (e.g., hybrid capture)] or [total number of engulfed particles/total number of counted CER modified host cells]× [number of CER modified host cells containing engulfed particles/total number of counted CER cells]×100. In certain embodiments, a CER modified cell has a phagocytic index of about 30 to about 1,500; about 40 to about 1,500; about 50 to about 1,500; about 75 to about 1,500; about 100 to about 1,500; about 200 to about 1,500; about 300 to about 1,500; about 400 to about 1,500; about 500 to about 1,500; about 20 to about 1,400; about 30 to about 1,400; about 40 to about 1,400; about 50 to about 1,400; about 100 to about 1,400; about 200 to about 1,400; about 300 to about 1,400; about 400 to about 1,400; about 500 to about 1,400; about 20 to about 1,300; about 30 to about 1,300; about 40 to about 1,300; about 50 to about 1,300; about 100 to about 1,300; about 200 to about 1,300; about 300 to about 1,300; about 400 to about 1,300; about 500 to about 1,300; about 20 to about 1,200; about 30 to about 1,200; about 40 to about 1,200; about 50 to about 1,200; about 100 to about 1,200; about 200 to about 1,200; about 300 to about 1,200; about 400 to about 1,200; about 500 to about 1,200; about 20 to about 1,100; about 30 to about 1,100; about 40 to about 1,100; about 50 to about 1,100; about 100 to about 1,100; about 200 to about 1,100; about 300 to about 1,100; about 400 to about 1,100; or about 500 to about 1,100; about 20 to about 1,000; about 30 to about 1,000; about 40 to about 1,000; about 50 to about 1,000; about 100 to about 1,000; about 200 to about 1,000; about 300 to about 1,000; about 400 to about 1,000; or about 500 to about 1,000; about 20 to about 750; about 30 to about 750; about 40 to about 750; about 50 to about 750; about 100 to about 750; about 200 to about 750; about 300 to about 750; about 400 to about 750; or about 500 to about 750; about 20 to about 500; about 30 to about 500; about 40 to about 500; about 50 to about 500; about 100 to about 500; about 200 to about 500; or about 300 to about 500. In further embodiments, the incubation time is from about 2 hours to about 4 hours, about 2 hours, about 3 hours, or about 4 hours. In yet further embodiments, a CER modified cell exhibits phagocytic index that is statistically significantly higher than a cell transduced with truncated EGFR control. Phagocytic index may be calculated using methods known in the art and as further described in the Examples, including quantification by flow cytometry or fluorescence microscopy.

Host cells may be from an animal, such as a primate, cow, horse, sheep, dog, cat, mouse, rat, rabbit, guinea pig, or pig. In a preferred embodiment, the animal is a human. Host cells may be obtained from a healthy subject or a subject having a disease associated with expression of an antigen.

Uses of CERs and Cells Modified to Express CERs

The present disclosure provides methods for altering the engulfment phenotype of a host cell. In one aspect, the present disclosure provides methods for producing a population of cells exhibiting an engulfment phenotype comprising introducing into a population of host cells that do not naturally exhibit an engulfment phenotype a nucleic acid molecule encoding at least one CER or a vector comprising at least one CER according to any of the embodiments described herein; and expressing the at least one CER in the population of host cells. In certain embodiments, the engulfment phenotype is phagocytosis.

In another aspect, the present disclosure provides methods for altering the engulfment phenotype of a population of cells comprising introducing into a population of host cells a nucleic acid molecule encoding at least one CER or a vector comprising at least one CER according to any of the embodiments described herein; and expressing the at least one CER in the population of host cells, wherein the at least one CER confers an engulfment phenotype specific to a pro-engulfment marker or antigenic marker (target antigen) that is not naturally targeted by the host cells. In certain embodiments, the engulfment phenotype is phagocytosis.

In yet another aspect, the present disclosure provides methods for enhancing the engulfment phenotype of a population of cells comprising introducing into a population of host cells a nucleic acid molecule encoding at least one CER or a vector comprising at least one CER according to any of the embodiments described herein; and expressing the at least one CER in the population of host cells, wherein the at least one CER is specific to a pro-engulfment marker or antigenic marker (target antigen) that is naturally targeted by the host cells and expression of the at least one CER by the host cells enhances the engulfment by the host cells of cells, microbes, or particles exhibiting the targeted pro-engulfment or antigenic marker.

CERs, nucleic acid molecules encoding CERs, vectors comprising CERs, and host cells that express CERs according to any of the embodiments described herein may also be used in a method treating a subject suffering from a disease, disorder or undesired condition. Embodiments of these methods include administering to a subject a therapeutically effective amount of a pharmaceutical composition including one or more CERs, nucleic acid molecules encoding one or more CERs, vectors comprising one or more CERs, or a population of host cells genetically modified to express one or more CERs according to the present description.

Diseases that may be treated with cells expressing a CER as described in the present disclosure include cancer, infectious diseases (viral, bacterial, fungal, protozoan infections), inflammatory, or immune diseases (e.g., autoimmune diseases, inflammatory bowel diseases, multiple sclerosis), degenerative disease (e.g., joint and cartilage), and neurodegenerative diseases (e.g., Alzheimer's disease). Adoptive immune and gene therapies are promising treatments for various types of cancer (Morgan et al., *Science* 314:126, 2006; Schmitt et al., *Hum. Gene Ther.* 20:1240, 2009; June, *J. Clin. Invest.* 117:1466, 2007) and infectious disease (Kitchen et al., *PLoS One* 4:38208, 2009; Rossi et al., *Nat. Biotechnol.* 25:1444, 2007; Zhang et al., *PLoS Pathog.* 6:e1001018, 2010; Luo et al., *J. Mol. Med.* 89:903, 2011).

Subjects that can be treated by the compositions and methods of the present disclosure include animals, such as humans, primates, cows, horses, sheep, dogs, cats, mice, rats, rabbits, guinea pigs, or pigs. The subject may be male or female, and can be any suitable age, including infant, juvenile, adolescent, adult, and geriatric subjects.

A wide variety of cancers, including solid tumors and leukemias are amenable to the compositions and methods disclosed herein. Exemplary types of cancer that may be treated include adenocarcinoma of the breast, prostate, and colon; all forms of bronchogenic carcinoma of the lung; myeloid leukemia; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, Merkel cell, mucinous, non-small cell lung, oat cell, papillary, scirrhous, bronchiolar, bronchogenic, squamous cell, and transitional cell). Additional types of cancers that may be treated include histiocytic disorders; malignant histiocytosis; leukemia; Hodgkin's disease; immunoproliferative small; non-Hodgkin's lymphoma; plasmacytoma; multiple myeloma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor. Further, the following types of cancers are also contemplated as amenable to treatment: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. The types of cancers that may be treated also include angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

Exemplifying hyperproliferative disorders amenable to CER therapy are B-cell cancers, including B-cell lymphomas (such as various forms of Hodgkin's disease, non-Hodgkins lymphoma (NHL) or central nervous system lymphomas), leukemias (such as acute lymphoblastic leukemia (ALL), chronic lymphocytic leukemia (CLL), Hairy cell leukemia, B cell blast transformation of chronic myeloid leukemia) and myelomas (such as multiple myeloma). Additional B cell cancers include small lymphocytic lymphoma, B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, intravascular large B-cell lymphoma, primary effusion lymphoma, Burkitt's lymphoma/leukemia, B-cell proliferations of uncertain malignant potential, lymphomatoid granulomatosis, and post-transplant lymphoproliferative disorder.

Inflammatory and autoimmune diseases include arthritis, rheumatoid arthritis, juvenile rheumatoid arthritis, osteoarthritis, polychondritis, psoriatic arthritis, psoriasis, dermatitis, polymyositis/dermatomyositis, inclusion body myositis, inflammatory myositis, toxic epidermal necrolysis, systemic scleroderma and sclerosis, CREST syndrome, inflammatory bowel disease, Crohn's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), subacute cutaneous lupus erythematosus, discoid lupus, lupus myelitis, lupus cerebritis, juvenile onset diabetes, multiple sclerosis, allergic encephalomyelitis, neuromyelitis optica, rheumatic fever, Sydenham's chorea, immune responses associated with acute and delayed hypersensitivity mediated by cytokines and T-lymphocytes, tuberculosis, sarcoidosis, granulomatosis including Wegener's granulomatosis and Churg-Strauss disease, agranulocytosis, vasculitis (including hypersensitivity vasculitis/angiitis, ANCA and rheumatoid vasculitis), aplastic anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, Alzheimer's disease, multiple organ injury syndrome, myasthenia gravis, antigen-antibody complex mediated diseases, anti-glomerular basement membrane disease, anti-phospholipid antibody syndrome, allergic neuritis, Behcet disease, Castleman's syndrome, Goodpasture's syndrome, Lambert-Eaton Myasthenic Syndrome, Reynaud's syndrome, Sjorgen's syndrome, Stevens-Johnson syndrome, solid organ transplant rejection, graft versus host disease (GVHD), bullous pemphigoid, pemphigus, autoimmune polyendocrinopathies, seronegative spondyloarthropathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), Henoch-Schonlein purpura, autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, lymphoid interstitial pneumonitis (HIV), bronchiolitis obliterans (non-transplant), non-specific interstitial pneumonia (NSIP), Guillain-BarréSyndrome, large vessel vasculitis (including polymyalgia rheumatica and giant cell (Takayasu's) arteritis), medium vessel vasculitis (including Kawasaki's disease and polyarteritis nodosa), polyarteritis nodosa (PAN) ankylosing spondylitis, Berger's disease (IgA nephropathy), rapidly progressive glomerulonephritis, primary biliary cirrhosis, Celiac sprue (gluten enteropathy), cryoglobulinemia, cryoglobulinemia associated with hepatitis, amyotrophic lateral sclerosis (ALS), coronary artery disease, familial Mediterranean fever, microscopic polyangiitis, Cogan's syndrome, Whiskott-Aldrich syndrome and thromboangiitis obliterans. In certain embodiments, in the context of treating an inflammatory disease, it may be preferable to design a CER with a homeostatic (non-inflammatory) engulfment signaling domain.

Infectious diseases include those associated with infectious agents and include any of a variety of bacteria (e.g., pathogenic *E. coli, S. typhimurium, P. aeruginosa, B. anthracis, C. botulinum, C. difficile, C. perfringens, H. pylori, V. cholerae, Listeria* spp., *Rickettsia* spp., *Chlamydia* spp., and the like), mycobacteria, and parasites (including any known parasitic member of the Protozoa). Infectious viruses include eukaryotic viruses, such as adenovirus, bunyavirus, herpesvirus, papovavirus, papillomavirus (e.g., HPV), paramyxovirus, picornavirus, rhabdovirus (e.g., Rabies), orthomyxovirus (e.g., influenza), poxvirus (e.g., Vaccinia), reovirus, retrovirus, lentivirus (e.g., HIV), flavivirus (e.g., HCV, HBV) or the like. In certain embodiments, a composition comprising a CER according to the present disclosure is used for treating infection with a microbe capable of establishing a persistent infection in a subject.

Neurodegenerative diseases include Lewy body disease, postpoliomyelitis syndrome, Shy-Draeger syndrome, olivopontocerebellar atrophy, Parkinson's disease, multiple system atrophy, striatonigral degeneration, frontotemporal lobar degeneration with ubiquitinated inclusions (FLTD-U), tauopathies (including, but not limited to, Alzheimer disease and supranuclear palsy), prion diseases (also known as transmissible spongiform encephalopathies, including, but not limited to, bovine spongiform encephalopathy, scrapie, Creutz-feldt-Jakob syndrome, kuru, Gerstmann-Straussler-Scheinker disease, chronic wasting disease, and fatal familial insomnia), bulbar palsy, motor neuron disease (including Amyotrophic lateral sclerosis (Lou Gherig's disease)), and nervous system heterodegenerative disorders (including, but not limited to, Canavan disease, Huntington's disease, neuronal ceroid-lipofuscinosis, Alexander's disease, Tourette's syndrome, Menkes kinky hair syndrome, Cockayne syndrome, Halervorden-Spatz syndrome, lafora disease, Rett syndrome, hepatolenticular degeneration, Lesch-Nyhan syndrome, and Unverricht-Lundborg syndrome), dementia (including, but not limited to, Pick's disease, and spinocerebellar ataxia), cancer (e.g., of the CNS and/or brain, including brain metastases resulting from cancer elsewhere in the body). Many neurodegenerative diseases, including Alzheimer's disease, Parkinson's disease, Huntington's disease, Amyotrophic lateral sclerosis (Lou Gehrig's disease) and prion diseases, share a neuropathological signature, the aberrant accumulation of proteins, such as amyloid-β or tau in Alzheimer's disease; α-synuclein in Parkinson's disease (PD), dementia with Lewy bodies, multiple system atrophy, or Alzheimer's disease; huntingtin in Huntington's disease, SOD1 in Amyotrophic lateral sclerosis, proteins with polyglutamine (polyQ) repeats in Huntington's disease or Amyotrophic lateral sclerosis; TDP-43 in Amyotrophic lateral sclerosis or FLTD-U; or prion protein (e.g., $PrP^{Sc}$) in prion diseases. Thus, in certain embodiments, CER therapy may be designed to target the disease-associated protein in order to reduce or prevent aberrant protein accumulation, thereby slowing or preventing progression of the neurodegenerative disease.

A CER of this disclosure may be administered to a subject in cell-bound form (e.g., gene therapy of target cell population (mature T cells (e.g., $CD8^+$ or $CD4^+$ T cells) or other cells of T cell lineage)). Thus, for example, a CER of the present disclosure may be administered to a subject expressed on the surface of T cells, Natural Killer Cells, Natural Killer T cells, B cells, lymphoid precursor cells, antigen presenting cells, dendritic cells, Langerhans cells, myeloid precursor cells, mature myeloid cells, including subsets thereof, or any combination thereof. In certain embodiments, methods of treating a patient include administering an effective amount of CER modified cells (i.e., recombinant cells that express one or more CERs). In such embodiments, the CER modified cells are xenogeneic, syngeneic, allogeneic, or autologous cells of T cell lineage, Natural Killer cell lineage, Natural Killer T cell lineage, B cell lineage, lymphoid precursor cell lineage, dendritic cell lineage, Langerhans cell lineage, myeloid cell lineage, or any combination thereof.

Pharmaceutical compositions including a CER modified cells may be administered in a manner appropriate to the disease or condition to be treated (or prevented) as determined by persons skilled in the medical art. An appropriate dose, suitable duration, and frequency of administration of the compositions will be determined by such factors as the condition of the patient, size, weight, body surface area, age, sex, type and severity of the disease, particular therapy to be administered, particular form of the active ingredient, time and the method of administration, and other drugs being administered concurrently. The present disclosure provides pharmaceutical compositions comprising CER modified cells and a pharmaceutically acceptable carrier, diluent, or excipient. Suitable excipients include water, saline, dextrose, glycerol, or the like and combinations thereof. Other suitable infusion medium can be any isotonic medium formulation, including saline, Normosol R (Abbott), Plasma-Lyte A (Baxter), 5% dextrose in water, or Ringer's lactate.

A treatment effective amount of cells in a pharmaceutical composition is at least one cell (for example, one CER modified B cell) or is more typically greater than $10^2$ cells, for example, up to $10^6$, up to $10^7$, up to $10^8$ cells, up to $10^9$ cells, up to $10^{10}$ cells, or up to $10^{11}$ cells or more. In certain embodiments, the cells are administered in a range from about $10^6$ to about $10^{10}$ cells/m$^2$, preferably in a range of about $10^7$ to about $10^9$ cells/m$^2$. The number of cells will depend upon the ultimate use for which the composition is intended as well the type of cells included therein. For example, a composition comprising cells modified to contain a CER specific for a particular antigen will comprise a cell population containing from about 5% to about 95% or more of such cells. In certain embodiments, a composition comprising CER modified cells comprises a cell population comprising at least 5%, 10%, 15%, 20%, 25%, 30%, 35%, 40%, 45%, 50%, 55%, 60%, 65%, 70%, 75%, 80%, 85%, 90%, 95% or more of such cells. For uses provided herein, the cells are generally in a volume of a liter or less, 500 mls or less, 250 mls or less, or 100 mls or less. Hence the density of the desired cells is typically greater than $10^4$ cells/ml and generally is greater than $10^7$ cells/ml, generally $10^8$ cells/ml or greater. The cells may be administered as a single infusion or in multiple infusions over a range of time. Repeated infusions of CER modified cells may be separated by days, weeks, months, or even years if relapses of disease or disease activity are present. A clinically relevant number of immune cells can be apportioned into multiple infusions that cumulatively equal or exceed $10^6$, $10^7$, $10^8$, $10^9$, $10^{10}$, or $10^{11}$ cells. A preferred dose for administration of a host cell comprising a recombinant expression vector as described herein is about $10^7$ cells/m$^2$, about $5\times10^7$ cells/m$^2$, about $10^8$ cells/m$^2$, about $5\times10^8$ cells/m$^2$, about $10^9$ cells/m$^2$, about $5\times10^9$ cells/m$^2$, about $10^{10}$ cells/m$^2$, about $5\times10^{10}$ cells/m$^2$, or about $10^{11}$ cells/m$^2$. In certain embodiments, a composition of CER modified B cells and a composition of CER modified T cells are both administered, which administration may be simultaneous, concurrent or sequential.

In some embodiments, a composition as described herein is administered intravenously, intraperitoneally, intratumoraly, into the bone marrow, into the lymph node, and/or into cerebrospinal fluid. In some embodiments, chimeric engulfment receptor engineered compositions are delivered to the site of the tumor.

In some embodiments, CER modified cells are administered to a subject in conjunction or combination with one or more additional therapies. In such embodiments, the one or more additional therapies may be one or more of radiation therapy, genetically engineered cellular immunotherapy (e.g., T cell, dendritic cell, natural killer cell, macrophage, chimeric antigen receptor (CAR) therapy), antibody therapy, immune checkpoint molecule inhibitor therapy, or a pharmaceutical therapy, such as a chemotherapeutic, a therapeutic peptide, antibiotic, anti-viral agent, anti-fungal agent, anti-inflammatory agent, or a small molecule therapy. In such embodiments, the CER modified cells may clear apoptotic, dead, dying, damaged, infected, or necrotic cells displaying pro-apoptotic markers induced in the setting of the one or more additional therapies. In certain embodiments where CER modified cells are administered in combination with one or more additional therapies, the one or more additional therapies may be administered at a subtherapeutic dose due to an additive or synergistic effect of the combination with CER therapy. Combination therapy includes administration of a CER before an additional therapy (e.g., 1 day to 30 days or more before the additional therapy), concurrently with an additional therapy (on the same day), or after an additional therapy (e.g., 1 day-30 days or more after the additional therapy). In certain embodiments, the CER modified cells are administered after administration of the one or more additional therapies. In further embodiments, the CER modified cells are administered 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days after administration of the one or more additional therapies. In still further embodiments, the CER modified cells are administered within 4 weeks, within 3 weeks, within 2 weeks, or within 1 week after administration of the one or more additional therapies. Where the one or more additional therapies involves multiple doses, the CER modified cells may be administered after the initial dose of the one or more additional therapies, after the final dose of the one or more additional therapies, or in between multiple doses of the one or more additional therapies.

An example of a triple combination therapy (radiation+CER+CAR/or TCR) regimen is shown in FIG. 134. Following radiation therapy, tumor antigen specific, CER modified host cells (e.g., comprising a binding domain that binds to a tumor antigen) according to the present disclosure are administered to a subject to promote an anti-tumor immune response and recruit immune activating cells into the tumor microenvironment. In certain embodiments, CERs traffic to local, irradiated tumors and render the tumor tissue permissive for immune infiltration and destruction (e.g., via expression of inflammatory cytokines, activation of effector T cells, activation of dendritic cells, inhibition of regulatory T cells), thereby sensitizing the tumor microenvironment for subsequent adoptive T cell immunotherapy (e.g., CAR or TCR immunotherapy). In certain embodiments, the CER modified cells are administered 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days after administration of the radiation therapy. In further embodiments, the CER modified cells are administered within 4 weeks, within 3 weeks, within 2 weeks, or within 1 week after administration of the radiation therapy. In certain embodiments, the CAR or TCR immunotherapy is administered 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days after administration of the CER therapy or within 4 weeks, within 3 weeks, within 2 weeks, or within 1 week after administration of the CER therapy. In certain embodiments, the radiation therapy, the CAR or TCR immunotherapy, or both are administered at subtherapeutic levels.

Examples of radiation therapy that may be used in combination with CER therapy include external beam radiation therapy (e.g., conventional external beam radiation therapy, stereotactic radiation, 3-dimensional conformal radiation therapy, intensity-modulated radiation therapy, volumetric modulated arc therapy, particle therapy, proton therapy, and auger therapy), brachytherapy, systemic radioisotope therapy, intraoperative radiotherapy, or any combination thereof.

Examples of immune checkpoint molecules that may be targeted in combination with CER therapy include PD-L1, PD-L2, CD80, CD86, B7-H3, B7-H4, HVEM, adenosine, GALS, VISTA, CEACAM-1, CEACAM-3, CEACAM-5, PVRL2, PD-1, CTLA-4, BTLA, KIR, LAG3, TIM3, A2aR, CD244/2B4, CD160, TIGIT, LAIR-1, PVRIG/CD112R, or any combination thereof. In certain embodiments, an immune checkpoint molecule inhibitor is an antibody, a peptide, an RNAi agent, or a small molecule. An antibody specific for CTLA-4 may be ipilimumab or tremelimumab. An antibody specific for PD-1 may be pidilizumab, nivolumab, or pembrolizumab. An antibody specific for PD-L1 may be durvalumab, atezolizumab, or avelumab.

Exemplary chemotherapeutics include an alkylating agent, a platinum based agent, an angiogenesis inhibitor (e.g., a VEGF pathway inhibitor), a tyrosine kinase inhibitor (e.g., an EGF pathway inhibitor), a B-Raf inhibitor, a MEK inhibitor, an mTOR inhibitor, a cytotoxic agent, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor.

Examples of chemotherapeutic agents considered for use in combination therapies include vemurafenib, dabrafenib, trametinib, cobimetinib, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Exemplary alkylating agents include nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary platinum based agents include carboplatin, cisplatin, oxaliplatin, nedaplatin, picoplatin, satraplatin, phenanthriplatin, and triplatin tetranitrate.

Exemplary angiogenesis inhibitors include, without limitation A6 (Angstrom Pharmaceuticals), ABT-510 (Abbott Laboratories), ABT-627 (Atrasentan) (Abbott Laboratories/Xinlay), ABT-869 (Abbott Laboratories), Actimid (CC4047, Pomalidomide) (Celgene Corporation), AdGVPEDF.11D (GenVec), ADH-1 (Exherin) (Adherex Technologies), AEE788 (Novartis), AG-013736 (Axitinib) (Pfizer), AG3340 (Prinomastat) (Agouron Pharmaceuticals), AGX1053 (AngioGenex), AGX51 (AngioGenex), ALN-VSP (ALN-VSP 02) (Alnylam Pharmaceuticals), AMG 386 (Amgen), AMG706 (Amgen), Apatinib (YN968D1) (Jiangsu Hengrui Medicine), AP23573 (Ridaforolimus/MK8669) (Ariad Pharmaceuticals), AQ4N (Novavea), ARQ 197 (ArQule), ASA404 (Novartis/Antisoma), Atiprimod (Callisto Pharmaceuticals), ATN-161 (Attenuon), AV-412 (Aveo Pharmaceuticals), AV-951 (Aveo Pharmaceuticals), Avastin (Bevacizumab) (Genentech), AZD2171 (Cediranib/Recentin) (AstraZeneca), BAY 57-9352 (Telatinib) (Bayer), BEZ235 (Novartis), BIBF1120 (Boehringer Ingelheim Pharmaceuticals), BIBW 2992 (Boehringer Ingelheim Pharmaceuticals), BMS-275291 (Bristol-Myers Squibb), BMS-582664 (Brivanib) (Bristol-Myers Squibb), BMS-690514 (Bristol-Myers Squibb), Calcitriol, CCI-779 (Torisel) (Wyeth), CDP-791 (ImClone Systems), Ceflatonin (Homoharringtonine/HHT) (ChemGenex Therapeutics), Celebrex (Celecoxib) (Pfizer), CEP-7055 (Cephalon/Sanofi), CHIR-265 (Chiron Corporation), NGR-TNF, COL-3 (Metastat) (Collagenex Pharaceuticals), Combretastatin (Oxigene), CP-751,871(Figitumumab) (Pfizer), CP-547,632 (Pfizer), CS-7017 (Daiichi Sankyo Pharma), CT-322 (Angiocept) (Adnexus), Curcumin, Dalteparin (Fragmin) (Pfizer), Disulfiram (Antabuse), E7820 (Eisai Limited), E7080 (Eisai Limited), EMD 121974(Cilengitide) (EMD Pharmaceuticals), ENMD-1198 (EntreMed), ENMD-2076 (EntreMed), Endostar (Simcere), Erbitux (ImClone/Bristol-Myers Squibb), EZN-2208 (Enzon Pharmaceuticals), EZN-2968 (Enzon Pharmaceuticals), GC1008 (Genzyme), Genistein, GSK1363089(Foretinib) (GlaxoSmithKline), GW786034 (Pazopanib) (GlaxoSmithKline), GT-111 (Vascular Biogenics Ltd.), IMC-1121B (Ramucirumab) (ImClone Systems), IMC-18F1 (ImClone Systems), IMC-3G3 (ImClone LLC), INCB007839 (Incyte Corporation), INGN 241 (Introgen Therapeutics), Iressa (ZD1839/Gefitinib), LBH589 (Faridak/Panobinostst) (Novartis), Lucentis (Ranibizumab) (Genentech/Novartis), LY317615 (Enzastaurin) (Eli Lilly and Company), Macugen (Pegaptanib) (Pfizer), MEDI522 (Abegrin) (MedImmune), MLN518(Tandutinib) (Millennium), Neovastat (AE941/Benefin) (Aeterna Zentaris), Nexavar (Bayer/Onyx), NM-3 (Genzyme Corporation), Noscapine (Cougar Biotechnology), NPI-2358 (Nereus Pharmaceuticals), OSI-930 (OSI), Palomid 529 (Paloma Pharmaceuticals, Inc.), Panzem Capsules (2ME2) (EntreMed), Panzem NCD (2ME2) (EntreMed), PF-02341066 (Pfizer), PF-04554878 (Pfizer), PI-88 (Progen Industries/ Medigen Biotechnology), PKC412 (Novartis), Polyphenon E (Green Tea Extract) (Polypheno E International, Inc), PPI-2458 (Praecis Pharmaceuticals), PTC299 (PTC Therapeutics), PTK787 (Vatalanib) (Novartis), PXD101 (Belinostat) (CuraGen Corporation), RAD001 (Everolimus) (Novartis), RAF265 (Novartis), Regorafenib (BAY73-4506) (Bayer), Revlimid (Celgene), Retaane (Alcon Research), SN38 (Liposomal) (Neopharm), SNS-032 (BMS-387032) (Sunesis), SOM230(Pasireotide) (Novartis), Squalamine (Genaera), Suramin, Sutent (Pfizer), Tarceva (Genentech), TB-403 (Thrombogenics), Tempostatin (Collard Biopharmaceuticals), Tetrathiomolybdate (Sigma-Aldrich), TG100801 (TargeGen), Thalidomide (Celgene Corporation), Tinzaparin Sodium, TKI258 (Novartis), TRC093 (Tracon Pharmaceuticals Inc.), VEGF Trap (Aflibercept) (Regeneron Pharmaceuticals), VEGF Trap-Eye (Regeneron Pharmaceuticals), Veglin (VasGene Therapeutics), Bortezomib (Millennium), XL184 (Exelixis), XL647 (Exelixis), XL784 (Exelixis), XL820 (Exelixis), XL999 (Exelixis), ZD6474 (AstraZeneca), Vorinostat (Merck), and ZSTK474.

Exemplary Vascular Endothelial Growth Factor (VEGF) receptor inhibitors include, but are not limited to, Bevacizumab (Avastin®), axitinib (Inlyta®); Brivanib alaninate (BMS-582664, (S)—((R)-1-(4-(4-Fluoro-2-methyl-1H-indol-5-yloxy)-5-methylpyrrolo[2,1-f][1,2,4]triazin-6-yloxy) propan-2-yl)2-aminopropanoate); Sorafenib (Nexavar®); Pazopanib (Votrient®); Sunitinib malate (Sutent®); Cediranib (AZD2171, CAS 288383-20-1); Vargatef (BIBF1120, CAS 928326-83-4); Foretinib (GSK1363089); Telatinib (BAY57-9352, CAS 332012-40-5); Apatinib (YN968D1, CAS 811803-05-1); Imatinib (Gleevec®); Ponatinib (AP24534, CAS 943319-70-8); Tivozanib (AV951, CAS 475108-18-0); Regorafenib (BAY73-4506, CAS 755037-03-7); Vatalanib dihydrochloride (PTK787, CAS 212141-51-0); Brivanib (BMS-540215, CAS 649735-46-6); Vandetanib (Caprelsa® or AZD6474); Motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); Dovitinib dilactic acid (TKI258, CAS 852433-84-2); Linfanib (ABT869, CAS 796967-16-3); Cabozantinib (XL184, CAS 849217-68-1); Lestaurtinib (CAS 111358-88-4); N-[5-[[[5-(1,1-Dimethylethyl)-2-oxazolyl] methyl]thio]-2-thiazolyl]-4-piperidinecarboxamide (BMS38703, CAS 345627-80-7); (3R,4R)-4-Amino-1-((4-((3-methoxyphenyl)amino)pyrrolo[2,1-f][1,2,4]triazin-5-yl) methyl)piperidin-3-ol (BMS690514); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); 4-Methyl-3-[[1-methyl-6-(3-pyridinyl)-1H-pyrazolo[3,4-d]pyrimidin-4-yl]amino]-N-[3-(trifluoromethyl)phenyl]-benzamide (BHG712, CAS 940310-85-0); and Aflibercept (Eylea®).

Exemplary EGF pathway inhibitors include, without limitation tyrphostin 46, EKB-569, erlotinib (Tarceva®), gefitinib (Iressa®), erbitux, nimotuzumab, lapatinib (Tykerb®), cetuximab (anti-EGFR mAb), [188]Re-labeled nimotuzumab (anti-EGFR mAb), and those compounds that are generically and specifically disclosed in WO 97/02266, EP 0 564 409, WO 99/03854, EP 0 520 722, EP 0 566 226, EP 0 787 722, EP 0 837 063, U.S. Pat. No. 5,747,498, WO 98/10767, WO 97/30034, WO 97/49688, WO 97/38983 and WO 96/33980. Exemplary EGFR antibodies include, but are not limited to, Cetuximab (Erbitux®); Panitumumab (Vectibix®); Matuzumab (EMD-72000); Trastuzumab (Herceptin®); Nimotuzumab (hR3); Zalutumumab; TheraCIM h-R3; MDX0447 (CAS 339151-96-1); and ch806 (mAb-806, CAS 946414-09-1). Exemplary Epidermal growth factor receptor (EGFR) inhibitors include, but not limited to, Erlotinib hydrochloride (Tarceva®), Gefitnib (Iressa®); N-[4-[(3-Chloro-4-fluorophenyl)amino]-7-[[(3"S")-tetrahydro-3-furanyl]oxy]-6-quinazolinyl]-4(dimethylamino)-2-butenamide, Tovok®); Vandetanib (Caprelsa®); Lapatinib (Tykerb®); (3R,4R)-4-Amino-1-((4-((3-methoxyphenyl) amino)pyrrolo[2,1-f][1,2,4]triazin-5-yl)methyl)piperidin-3-ol (BMS690514); Canertinib dihydrochloride (CI-1033); 6-[4-[(4-Ethyl-1-piperazinyl)methyl]phenyl]-N-[(1R)-1-phenylethyl]-7H-Pyrrolo[2,3-d]pyrimidin-4-amine (AEE788, CAS 497839-62-0); Mubritinib (TAK165); Pelitinib (EKB569); Afatinib (BIBW2992); Neratinib (HKI-272); N-[4-[[1-[(3-Fluorophenyl)methyl]-1H-indazol-5-yl] amino]-5-methylpyrrolo[2,1-f][1,2,4]triazin-6-yl]-carbamic acid, (3S)-3-morpholinylmethyl ester (BMS599626); N-(3, 4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); and 4-[4-[[(1R)-1-Phenylethyl]amino]-7H-pyrrolo[2,3-d]pyrimidin-6-yl]-phenol (PKI166, CAS 187724-61-4).

Exemplary mTOR inhibitors include, without limitation, rapamycin (Rapamune®), and analogs and derivatives thereof; SDZ-RAD; Temsirolimus (Torisel®; also known as CCI-779); Ridaforolimus (formally known as deferolimus, (1R,2R,4S)-4-[(2R)-2[(1R,9S,12S,15R,16E,18R,19R,21R, 23 S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0$^{4,9}$]hexatriaconta-16,24,26,28-tetraen-12-yl]propyl]-2-methoxycyclohexyl dimethylphosphinate, also known as AP23573 and MK8669, and described in PCT Publication No. WO 03/064383); Everolimus (Afinitor® or RAD001); Rapamycin (AY22989, Sirolimus®); Simapimod (CAS 164301-51-3); (5-{2,4-Bis[(3S)-3-methylmorpholin-4-yl]pyrido[2,3-d] pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7 (8H)-one (PF04691502, CAS 1013101-36-4); and N$^2$-[1,4-dioxo-[[4-(4-oxo-8-phenyl-4H-1-benzopyran-2-yl) morpholinium-4-yl]methoxy]butyl]-L-arginylglycyl-L-α-aspartylL-serine-, inner salt (SF1126, CAS 936487-67-1).

Exemplary Phosphoinositide 3-kinase (PI3K) inhibitors include, but are not limited to, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730); 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806); 4-(trifluoromethyl)-5-(2,6-dimorpholinopyrimidin-4-yl)pyridin-2-amine (also known as BKM120 or NVP-BKM120, and described in PCT Publication No. WO2007/084786); Tozasertib (VX680 or MK-0457, CAS 639089-54-6); (5Z)-5-[[4-(4-Pyridinyl)-6-quinolinyl]methylene]-2,4-thiazolidinedione (GSK1059615, CAS 958852-01-2); (1E,4S,4aR,5R, 6aS,9aR)-5-(Acetyloxy)-1-[(di-2-propenylamino) methylene]-4,4a,5,6,6a,8,9,9a-octahydro-11-hydroxy-4-(methoxymethyl)-4a,6a-dimethyl-cyclopenta[5,6]naphtho [1,2-c]pyran-2,7,10(1H)-trione (PX866, CAS 502632-66-8); and 8-Phenyl-2-(morpholin-4-yl)-chromen-4-one (LY294002, CAS 154447-36-6). Exemplary Protein Kinase B (PKB) or AKT inhibitors include, but are not limited to 8-[4-(1-Aminocyclobutyl)phenyl]-9-phenyl-1,2,4-triazolo [3,4-f][1,6]naphthyridin-3(2H)-one (MK-2206, CAS 1032349-93-1); Perifosine (KRX0401); 4-Dodecyl-N-1,3,4-thiadiazol-2-yl-benzenesulfonamide (PHT-427, CAS 1191951-57-1); 4-[2-(4-Amino-1,2,5-oxadiazol-3-yl)-1-ethyl-7-[(3 S)-3-piperidinylmethoxy]-1H-imidazo[4,5-c] pyridin-4-yl]-2-methyl-3-butyn-2-ol (GSK690693, CAS 937174-76-0); 8-(1-Hydroxyethyl)-2-methoxy-3-[(4-methoxyphenyl)methoxy]-6H-dibenzo[b,d]pyran-6-one (palomid 529, P529, or SG-00529); Tricirbine (6-Amino-4-methyl-8-(β-D-ribofuranosyl)-4H,8H-pyrrolo[4,3,2-de]pyrimido[4,5-c]pyridazine); (αS)-α-[[[5-(3-Methyl-1H-indazol-5-yl)-3-pyridinyl]oxy]methyl]-benzeneethanamine (A674563, CAS 552325-73-2); 4-[(4-Chlorophenyl) methyl]-1-(7H-pyrrolo[2,3-d]pyrimidin-4-yl)-4-piperidinamine (CCT128930, CAS 885499-61-6); 4-(4-Chlorophenyl)-4-[4-(1H pyrazol-4-yl)phenyl]-piperidine (AT7867, CAS 857531-00-1); and Archexin (RX-0201, CAS 663232-27-7).

Figure 5A:
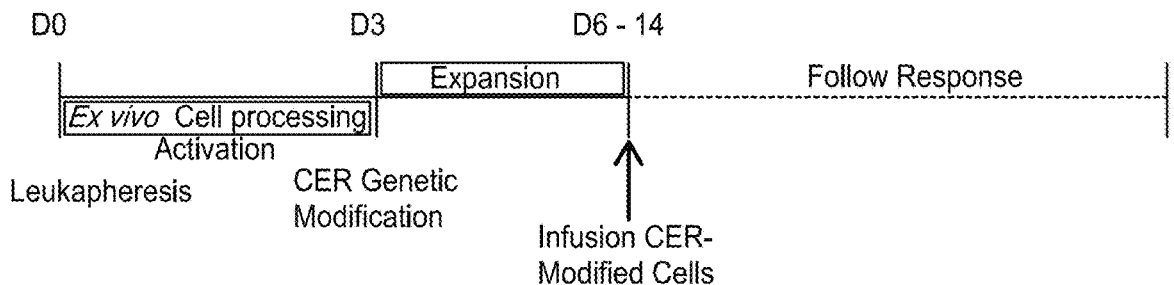
FIGS. 5A-5C show illustrative treatment timelines.
Figure 5B:
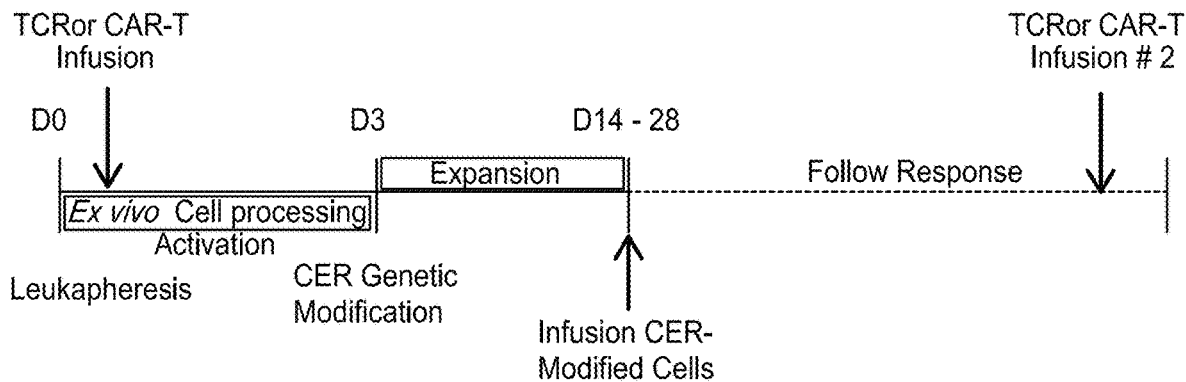
Figure 5C:
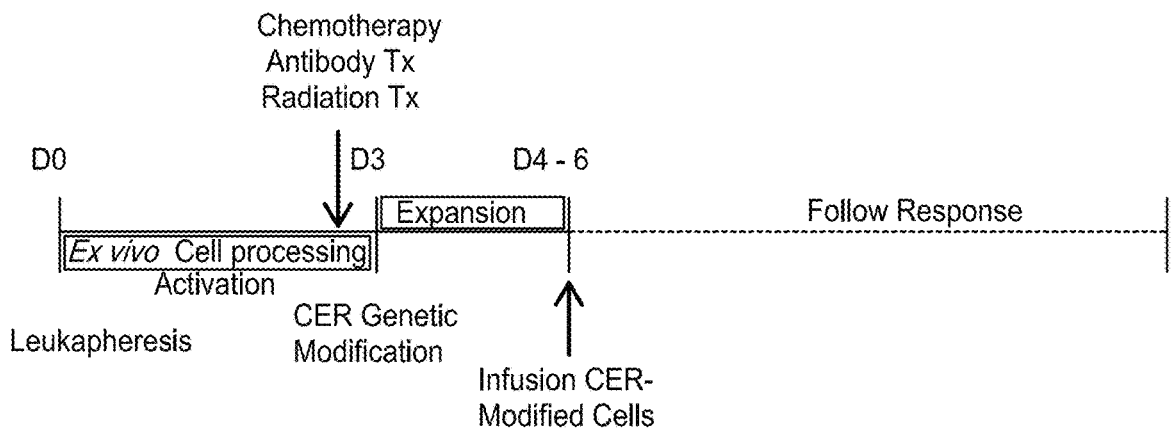

FIGS. 5A-5C, 93, and 94 illustrate embodiments of regimens that utilize CER modified cells. As shown in FIG. 5A, following leukapheresis, cells can be processed and activated ex vivo, undergoing genetic modification and expansion in preparation for infusion into a subject. FIG. 5B shows an illustrative treatment scheme for CER-modified cells used in combination with conventional T cell based therapies. An initial infusion of engineered T cells induces tumor cell apoptosis indicative of an anti-tumor effect. CER modified cells are then infused. The CER modified cells clear tumor cells displaying a pro-engulfment (e.g., PtdSer), which facilitates tumor regression while also bypassing the T cell suppressive tumor microenvironment. Alteration of the tumor microenvironment then re-sensitizes the tumor to T cell therapy, allowing a second infusion of T cells. Another embodiment of a therapeutic method is shown in FIG. 5C. The treatment scheme shown in FIG. 5C utilizes CER modified cells in combination with a monoclonal antibody therapy. Infusion of tumor-specific antibodies, such as Cetuximab targeting EGFR or Rituximab targeting CD20 may trigger cell death or induce a targeting moiety that is bound by CER modified cells. Subsequently, a subject receives CER modified cells that bind to and clear antibody bound cells. In such an embodiment, the CER extracellular domain may include an FcR binding domain, a PtdSer binding domain, or other antigen binding domain.

In another scenario, a CER modified cell can be combined with small molecule inhibitors such as a BTK inhibitor, a MEK inhibitor, an adenosine pathway inhibitor A2AR antagonist, an IDO1 inhibitor, IMiDs such as Lenalidomide, PI3Kδ inhibitors, a BRAF inhibitor, or a BCR-ABL inhibitor.

In certain embodiments, methods of the present disclosure include a depletion step. A depletion step to remove CERs from the subject may occur after a sufficient amount of time for therapeutic benefit in order to mitigate toxicity to a subject. In such embodiments, the CER vector includes an inducible suicide gene, such as iCASP9, inducible Fas, or HSV-TK. Similarly, a CER vector may be designed for expression of a known cell surface antigen such as CD20 or truncated EGFR (SEQ ID NO:121) that facilitates depletion of transduced cells through infusion of an associated monoclonal antibody (mAb), for example, Rituximab for CD20 or Cetuximab for EGFR. Alemtuzumab, which targets CD52 present on the surface of mature lymphocytes, may also be used to deplete transduced B cells, T cells, or natural killer cells.

In further embodiments, cells expressing CER of the instant disclosure may be used in diagnostic methods or imaging methods, including methods used in relation to the indications or conditions identified herein.

EXAMPLES

Example 1

Creation of CER Constructs

The expression of natural or synthetic nucleic acid molecules encoding CERs is achieved by operably linking a nucleic acid molecule encoding the CER protein or portions thereof to a promoter, and incorporating the construct into an expression vector suitable for replication and integration eukaryotes. The vector contains transcription and translation terminators, an initiation sequence, and a promoter useful for regulation of the expression of the desired nucleic acid sequence. In order to assess the expression of a CER protein or portions thereof, the expression vector to be introduced into a cell contains a selectable marker gene, such as an antibiotic resistance gene, or a reporter gene to facilitate identification and selection of expressing cells from the population of cells sought to be transfected or infected through viral vectors. The selectable marker is carried on a separate piece of DNA and used in a co-transfection procedure. The selectable marker or reporter gene is flanked with appropriate regulatory sequences to enable expression in the host cells. The expression vector is transferred into a host cell by way of a retroviral vector. In order to confirm the presence of the recombinant DNA sequence in the host cell, a variety of assays are performed including RT-PCR and ELISA.

Evaluation of CER Performance

To identify and characterize CERs, an in vitro system that reconstitutes phagocytic cell engulfment using retroviral-mediated transduction of candidate CER has been established. Murine and human lymphocyte cell lines, which normally lack the capacity to engulf cells, are transduced with CERs to assess for gain of function activity. If a CER is successfully expressed, engulfment occurs in heterologous cells. In addition to their engulfment activity, CERs are evaluated for their capacity to: (1) polarize cells to release inflammatory cytokines and chemokines; (2) activate downstream proliferative pathways and; (3) render target cells with a non-therapy-induced resistance pattern. In order to evaluate the candidate CERs, multi-dimensional flow cytometry, cytokine/chemokine arrays, and functional assays (below) are used.

Example 2

In Vitro Phagocytosis

The mouse pro-B cell line Ba/F3 or human Jurkat T cells lack intrinsic phagocytic capacity to phagocytose apoptotic or tumor cells in vitro and are used as an initial screening cell line to identify lead CER candidates. Following CER Retroviral transduction, Ba/F3 or Jurkat T cells are purified, labeled, and immuno-phenotypically characterized. Phagocytic activity is measured using in vitro co-culture experiments with defined target cells under various co-culture conditions and engulfment measured by FACs or light emission microscopy. Ba/F3 or Jurkat T cell-transduced CER cells with extracellular PtdSer targeting domains are co-cultured with pHrodo-labeled apoptotic cells. This assay permits evaluation of phagocytosis of apoptotic cells entering cytosolic lysosomes. In other cases, Ba/F3 or Jurkat T cell-transduced CER cells with Fc receptor extracellular domains are co-incubated with target cells pre-incubated with an antibody, such as a tumor specific antibody, to measure the capacity of these cells to phagocytose antibody-coated tumor cells. Finally, Ba/F3 or Jurkat T cell-transduced CERs that bind to tumor antigens through antibody binding moieties, such as a single-chain variable fragment, are co-cultured with tumor cells, and phagocytosis quantified. In some cases, target cells are pre-treated with conventional chemotherapy, radiation, or small molecule therapy, prior to co-culture experiments, to induce a 'pro-phagocytic' molecular state. Phagocytic activity is quantified as the percentage of Cell Tracker-positive cells in labeled Ba/F3 Jurkat transformants after a 90 minute co-culture experiment.

Cytokine/Chemokine Array Analysis from Conditioned Media

In parallel, conditioned media is collected from Ba/F3 or Jurkat T cell transformant co-culture experiments and analyzed for release of inflammatory cytokines/chemokines assays. Cytokines/chemokine changes before and after Ba/F3 Jurkat transduction and relative comparisons are quantified to evaluate for gain of functionality. CER candidates that polarize cells to an inflammatory state by both (i) down-regulating immunosuppressive cytokines, such as IL-10 and TGF-β, monocyte chemo attractants involved in recruitment of immature monocytes and myeloid-derived suppressive cells, and (ii) upregulating inflammatory cytokines TNF alpha, IL12p70, IFNα, and IFNγ are identified.

Multi-Dimensional Flow Cytometry

Ba/F3 and Jurkat transformants are analyzed in parallel using multi-dimensional cytometry to characterize activation and inhibitory receptor profiles. An activation profile may include CD137, CD69, HLA-DR, CD107a, CD123, CD11 c, TNF, IFNγ, IL-2, Granzyme, Perforin, CD25, CD40L, CD80, and CD86, while an inhibitory profile may include PD-1, Tim-3, Lag-3, ICOS, and CD172a. Bystander cells within culture are immunophenotypically evaluated for therapy-induced resistance patterns.

Proliferative Assays

Primary human T cells transduced with CER cassettes are analyzed for constitutive or non-constitutive growth patterns in the presence or absence of exogenous cytokines or feeder cells.

Downstream Pro-Inflammatory Signaling Pathways

To further test downstream pro-inflammatory responses, phospho-CYTOF are performed to measure downstream signaling pathways activated by candidate CERs such as, IkBtot, pSTAT1, p38, and JNK.

Example 3

In Vivo Analysis

To test CER modified cells in vivo, animal models and ex vivo experiments are used. Human primary tumor cell or xenograft specimens are engrafted into Nod/SCDγ mice. Expansion and persistence of modified CER cells can be quantified using primers specific to the CER cassette with a droplet PCR (ddPCR) machine from blood and tissue specimens. To analyze the functional capacity of CER cells ex vivo, tumor tissues and splenocytes are processed and analyzed by FACS and tissue staining for phenotyping and demonstration of in vivo phagocytosis after adoptive transfer of CER-modified cells. Tumor growth is monitored and quantified in vivo.

Example 4

Construction of Tim4-MERTK Chimeric Engulfment Receptor (CER) "CER01"

The extracellular domain of the phosphatidylserine binding protein Tim4 (amino acid sequence of SEQ ID NO:73), including the signal peptide (encoding amino acid sequence of SEQ ID NO:72) and transmembrane domain (encoding amino acid sequence of SEQ ID NO:74) (together having a polynucleotide sequence of SEQ ID NO: 57), were fused to the intracellular kinase domain of the tyrosine kinase MERTK (encoding SEQ ID NO: 58) to create a chimeric engulfment receptor "CER01" (Tim4-MERTK CER having an amino acid sequence of SEQ ID NO:71) (FIG. 6A). The MERTK receptor tyrosine kinase transduces a signal for engulfment, and Tim4 has recently been described as a phosphatidylserine binding receptor (Miyanishi et al., Nature, 2007, 450:435-9; Nishi et al., 2014, Mol. Cell Biol. 34:1512-20). The Tim-4-MERTK chimeric engulfment receptor nucleotide sequence was then inserted into the pMSCV (murine stem cell virus) retroviral vector. Early passage murine Ba/F3 B-cells were transduced with pMSCV Tim4-MERTK retrovirus expressing yellow fluorescent protein (GFP) as a transduction marker. Positive Ba/F3 cell transductants were sorted by GFP expression using flow cytometry (FACs), expanded in culture, and used for in vitro studies.

Phagocytic Activity Against Primary Apoptotic Thymocytes

Primary thymocytes were incubated with 10 µM dexamethasone for 24 hours to induce cell death. Thymocytes were then labeled with 1 µM of pHrodo Red dye in PBS for 15 minutes at room temperature, washed 2× with RPMI media containing 10% fetal bovine serum, and used as target cells for phagocytosis assays. 50 µl of pHrodo Red-labeled thymocytes ($10^6$/mL) were incubated with 50 µl of Tim4-MERTK chimeric engulfment receptor expressing sorted Ba/F3 cells ($10^5$/mL) (target cell to effector cell ratio of 10:1). Labeling target cells with pHrodo Red dye permits visualization of cells that are engulfed and transported into lysosomes due to their increased light emission in the acidic lysosomal environment (Miksa et al., 2009, Immunol. Methods 342:71-7). Co-culture experiments were carried out and Ba/F3 GFP+ cells were serially quantified for phagocytosis by fluorescence microscopy and FACs at 2 hr, 24 hr, 48 hr, and 72 hr post-incubation. Ba/F3 cells transduced with pMSCV vector expressing Tim4 and GFP (non-engulfment receptor) were used as a negative control.

Figure 6C:
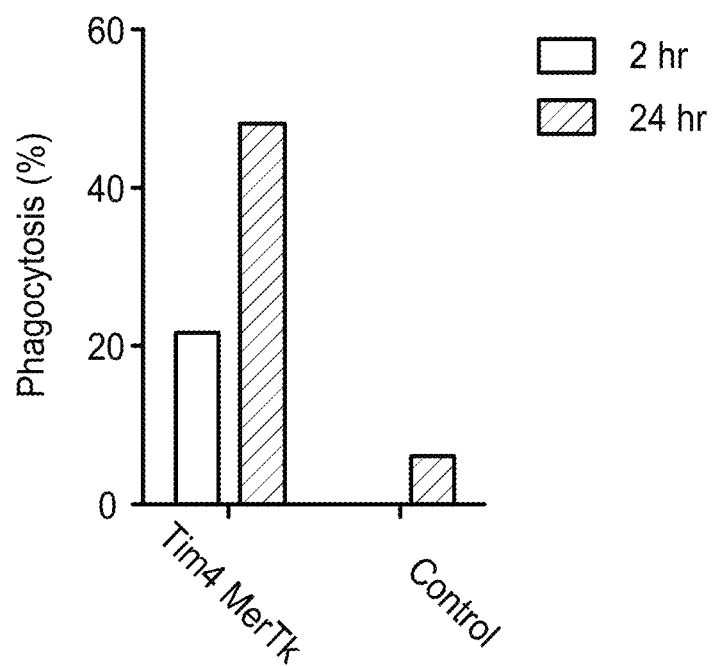
Figure 6D:
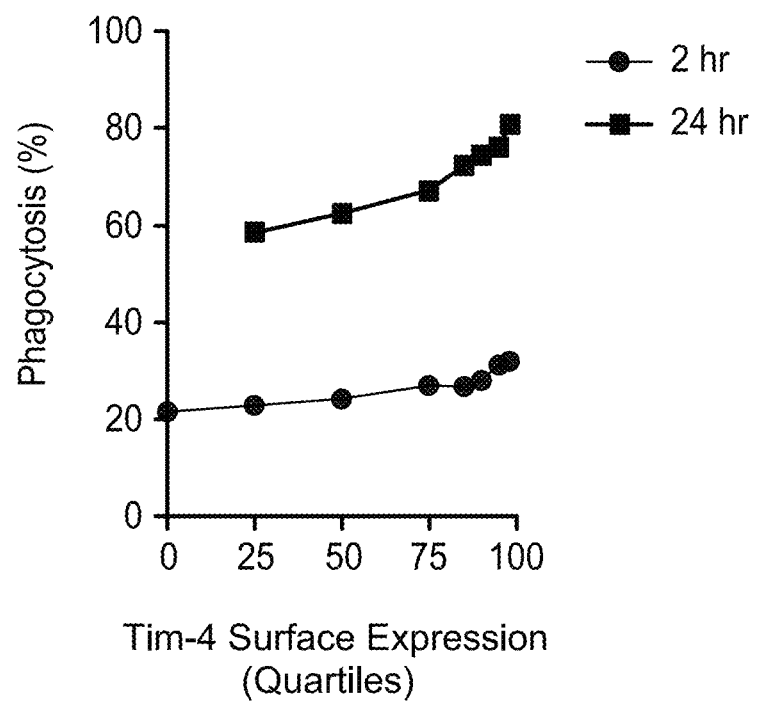

Under normal conditions, the Ba/F3 murine B-cell line lacks the capacity to engulf target cells and was therefore selected to establish an assay system for engulfment. Tim4-MERTK CER-mediated engulfment of apoptotic thymocytes were first examined (FIGS. 6A-F). Expression of Tim4-MERTK CER in the murine Ba/F3 B-cell line strongly enhanced phagocytic uptake of phosphatidylserine positive (PtdSer+) thymocytes (FIGS. 6C-6F). Observation by fluorescent microscopy and FACs show that the amount of phagocytosis correlates with incubation time with target cells, as well as, the quantity of Tim4-MERTK CER expression (FIGS. 6C-6D). Two hours following co-incubation, 21.6% of Tim4-MERTK CER transduced Ba/F3 cells had engulfed target apoptotic thymocytes, compared to 0% in control groups (FIG. 6C). The number of phagocytic Ba/F3 cells expressing Tim4-MERTK CER increased to 57.5% at 24 hours incubation time, and 75% at 72 hours incubation time (FIGS. 6C-6D). Furthermore, Ba/F3 cells that expressed the highest amount of Tim4-MERTK CERs exhibited the greatest amount of phagocytosis, approaching 80% within the top expression quartile (FIG. 6D), indicating a concentration dependent effect of the Tim4-MERTK CER.

Figure 6E:
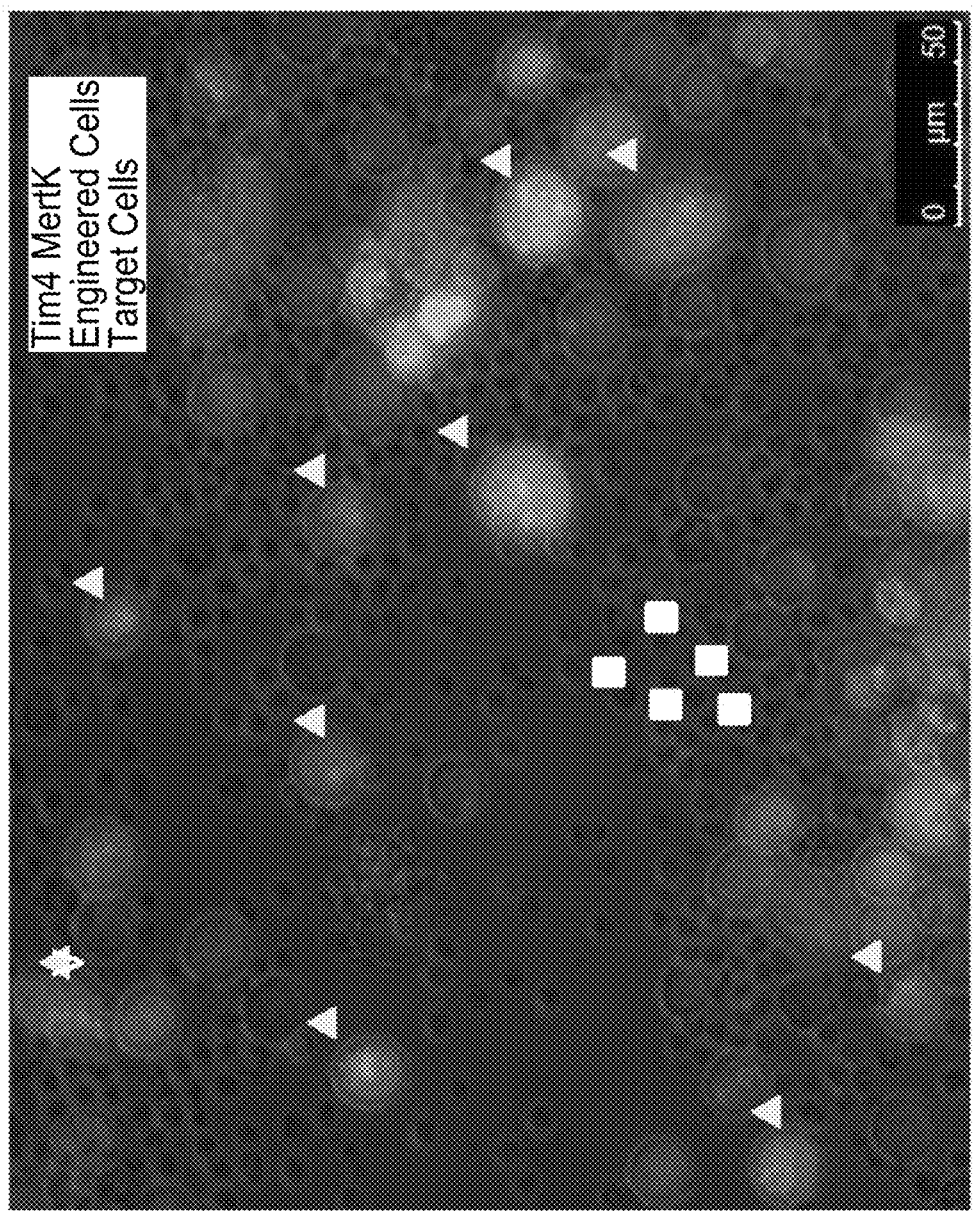
Figure 6F:
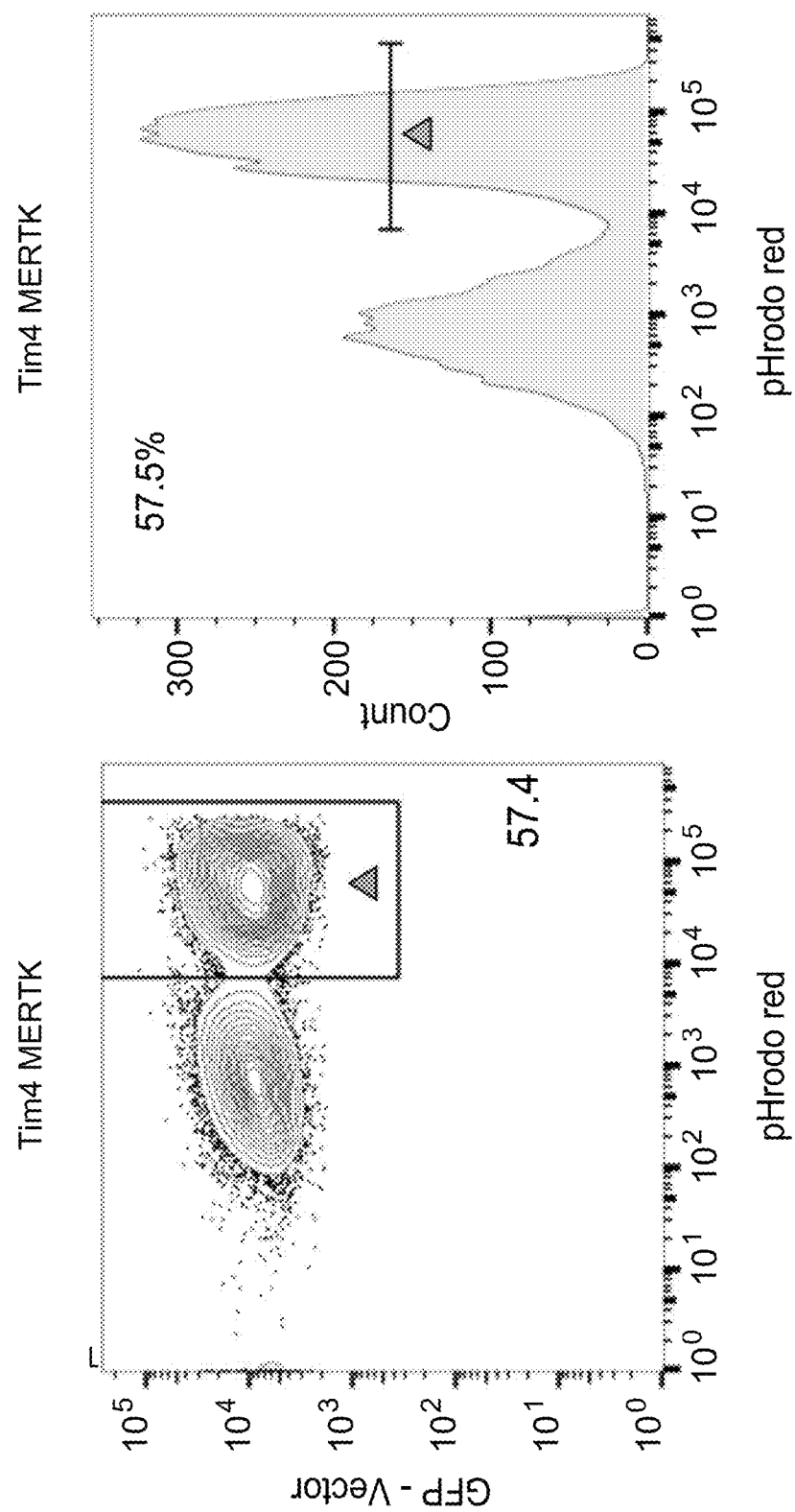
Figure 7A:
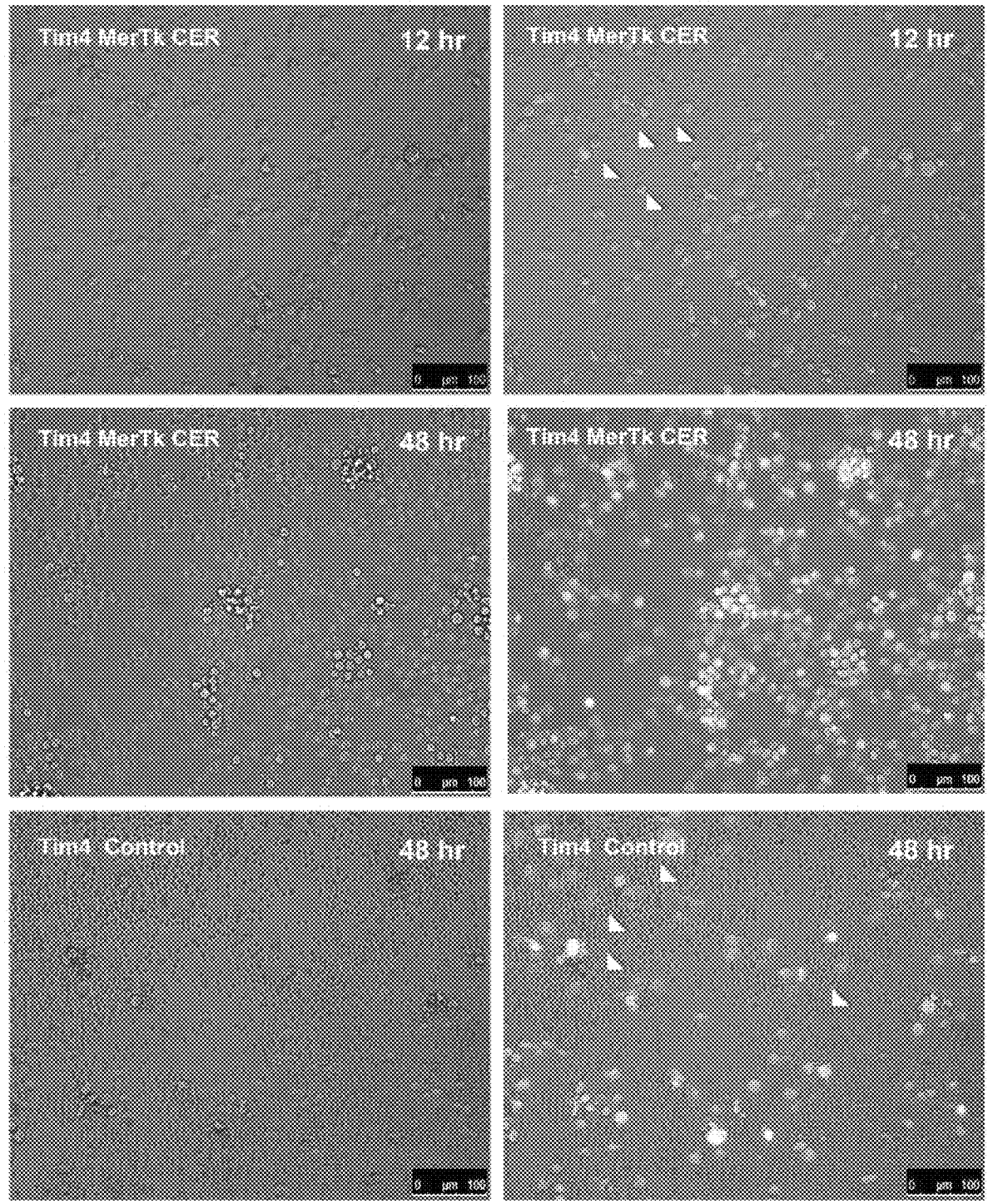
FIGS. 7A-7B show Tim4-MERTK chimeric engulfment receptor (CER)-mediated engulfment of apoptotic target cells.
Figure 7B:
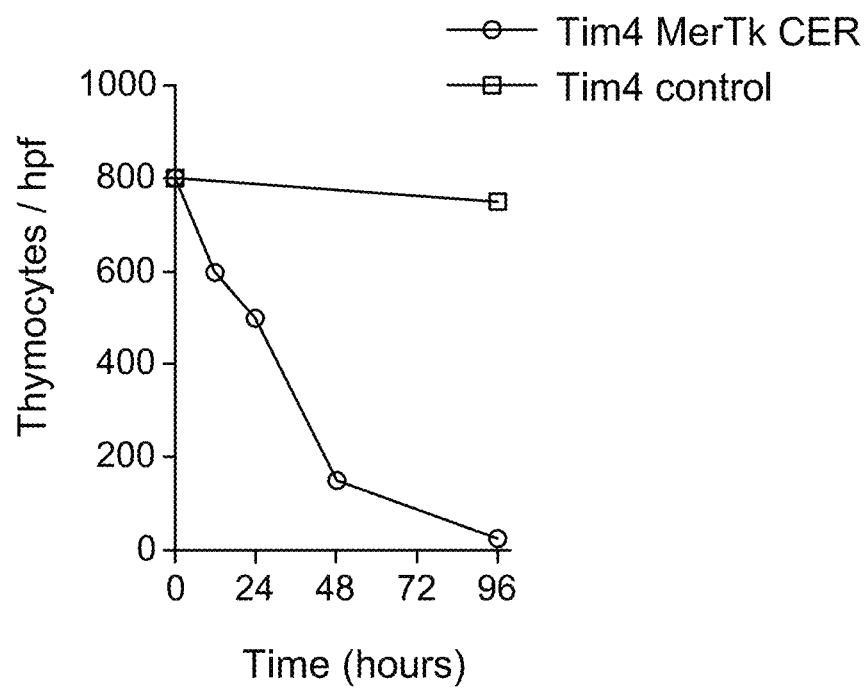

The ability of the Tim4-MERTK CER to facilitate transfer of ingested target cells into phagolysosomes was then examined. The lysosome, containing hydrolytic enzymes, digests ingested cells in a reduced pH internal environment (Arandjelovic et al., 2015, Nat. Immunol. 16:907-17). In this setting, pHrodo Red-labeled target thymocytes increase in fluorescent intensity. Observation by fluorescence microscopy showed several pHrodo Red-positive cells present inside most of Tim4-MERTK CER-expressing Ba/F3 cells (FIG. 6E). In full agreement with this observation, the entry of target cells into phagolysosomes of Tim4-MERTK CER–expressing Ba/F3 cells was associated with their clearance. By day 4, 97% of target cells had been eliminated through phagocytic uptake and lysosome degradation (FIGS. 7A-7B). These results indicate the addition of a Tim4-MERTK CER strongly enhances clearance of PtdSer cells.

Figure 8A:
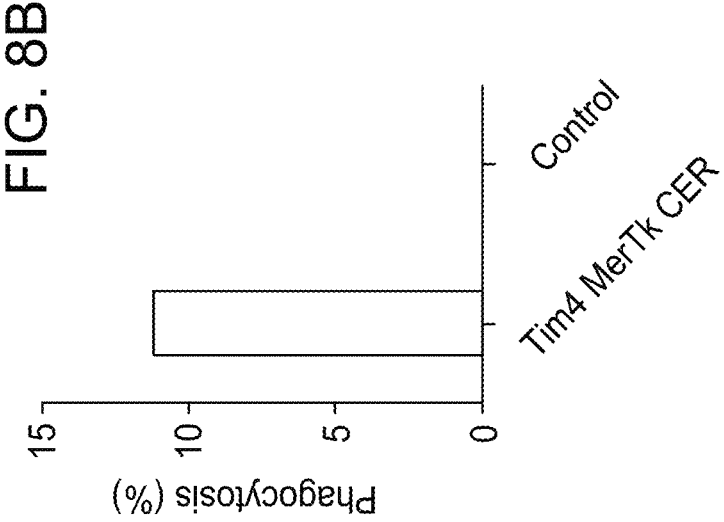
FIGS. 8A-8C show Tim4-MERTK chimeric engulfment receptor-mediated clearance of Raji Burkitt's lymphoma cells.
Figure 8B:
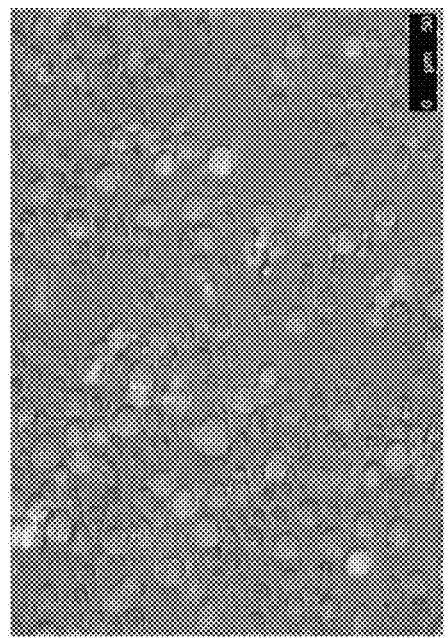
Figure 8C:
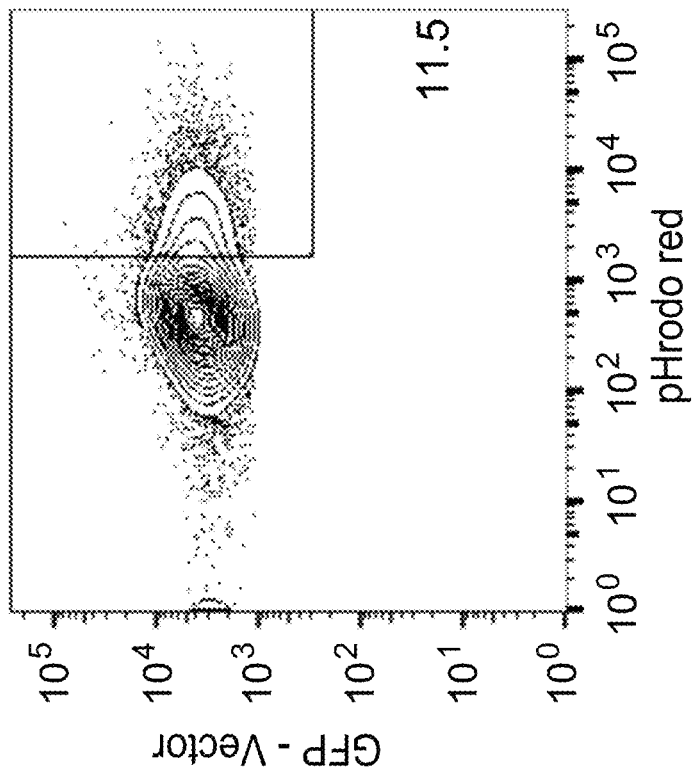

To examine the capacity to CER-expressing cells to clear tumor cells, Tim4-MERTK CER-mediated engulfment of the Raji human Burkitt B-cell lymphoma cell line was tested (FIGS. 8A-8B). Studies indicate B-cell receptors (BCRs) incorporate PtdSer into membrane microdomains in anti-IgM-activated B-cells and in the setting of aberrant signaling activity, such as exists in constitutively active Raji lymphoma cells (Dillon et al., 2000, J. Immunol. 164:1322-32). Expression of Tim4-MERTK CER in the murine Ba/F3 B-cell line enhanced phagocytic uptake of Raji cells (FIGS. 8A-8C), indicating Tim4-MERTK CER-mediated anti-tumor effects.

Example 5

Construction of FA58C2-MERTK CER "CER03"

The phosphatidylserine binding motif FA58C2 from the macrophage opsonin MFGE8 (amino acid sequence of SEQ ID NO:30) was fused to a modified IgG4 extracellular spacer domain (amino acid sequence of SEQ ID NO:67) and the transmembrane domain of costimulatory molecule CD28 (amino acid sequence of SEQ ID NO:68), and the cytoplasmic kinase domain of MERTK (amino acid sequence of SEQ ID NO:43) to create the chimeric engulfment receptor "CER03" (FA58C2-MERTK CER) (polynucleotide sequence of SEQ ID NO: 59, amino acid sequence of SEQ ID NO:75) FIG. 9A). The construct had a GM-CSF derived signal peptide (encoding amino acid sequence of SEQ ID NO:65). The MERTK receptor tyrosine kinase transduces a signal for engulfment, and the C-terminal domain of the second FA58C repeat (C2) of MFP-E8 (referred to herein as FA58C2) has been shown to be responsible for phosphatidylserine binding (Hanayama et al., 2002, Nature, 417:182-7; Nishi et al., supra). The FA58C2-MERTK CER nucleotide sequence was then inserted into the pMSCV (murine stem cell virus) retroviral vector. Early passage murine Ba/F3 B-cells were transduced with pMSCV FA58C2-MERTK CER retrovirus expressing yellow fluorescent protein (GFP). Positive Ba/F3 transductants were sorted by GFP expression using flow cytometry (FACs), expanded in culture, and used for in vitro studies.

Phagocytic Activity Against Primary Apoptotic Thymocytes

Primary thymocytes were incubated with 10 μM dexamethasone for 24 hours to induce cell death. Thymocytes were then labeled with 1 μM of pHrodo Red dye in PBS for 15 minutes at room temperature, washed 2× with RPMI media containing 10% FBS, and used as target cells for phagocytosis assays. 50 μl of pHrodo Red-labeled thymocytes ($10^6$/mL) were incubated with 50 μl of FA58C2-MERTK sorted Ba/F3 B-cells ($10^5$/mL) (target cell to effector cell ratio of 10:1). Labeling target cells with pHrodo Red permits visualization of cells that are engulfed and transported into lysosomes due to their increased light emission in the acidic lysosomal environment (Miksa et al., supra). Co-culture experiments were carried out and Ba/F3 GFP+ cells were serially quantified for phagocytosis by fluorescence microscopy and FACs at 2 hr, 24 hr, 48 hr, and 72 hr. Ba/F3 cells transduced with pMSCV vector expressing Tim4 and GFP (non-engulfment receptor) were used as a negative control.

Figures 9B, 9C:
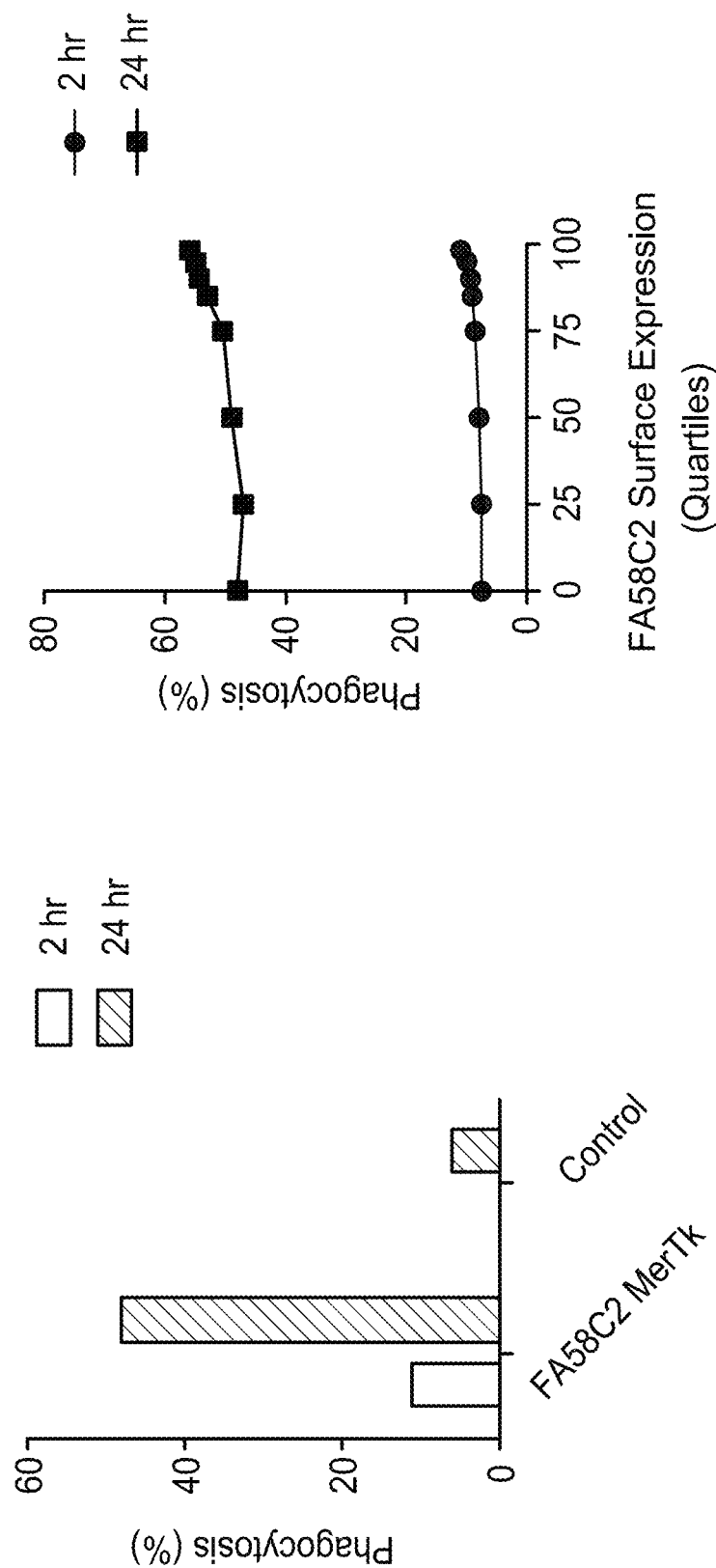
Figure 9D:
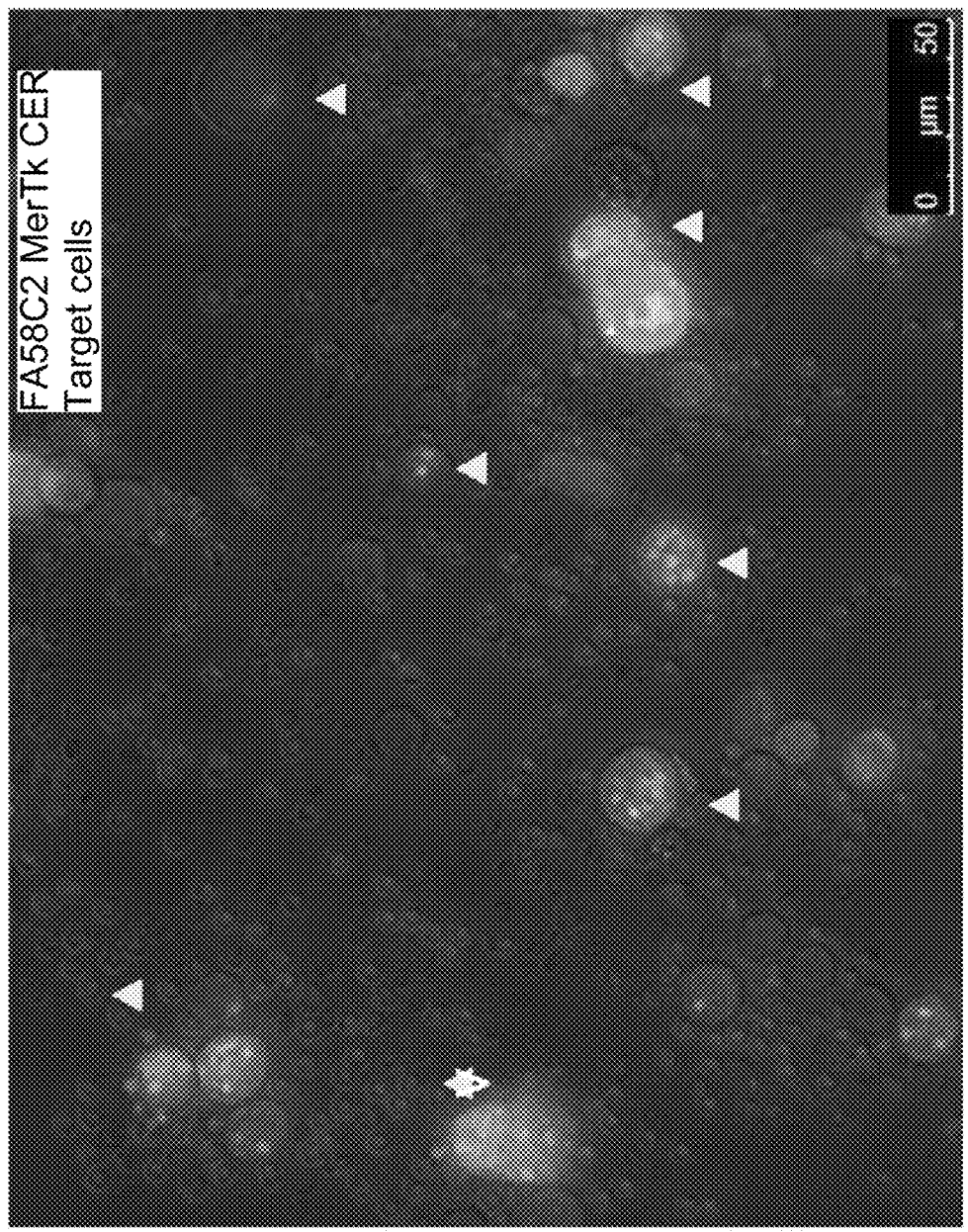
Figure 9F:
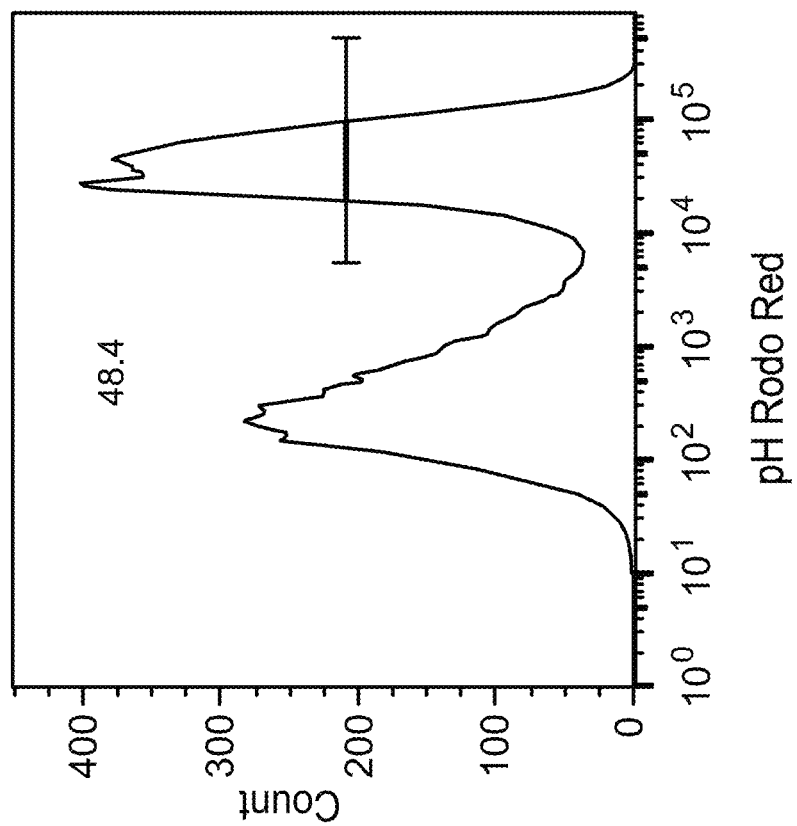
Figure 9E:
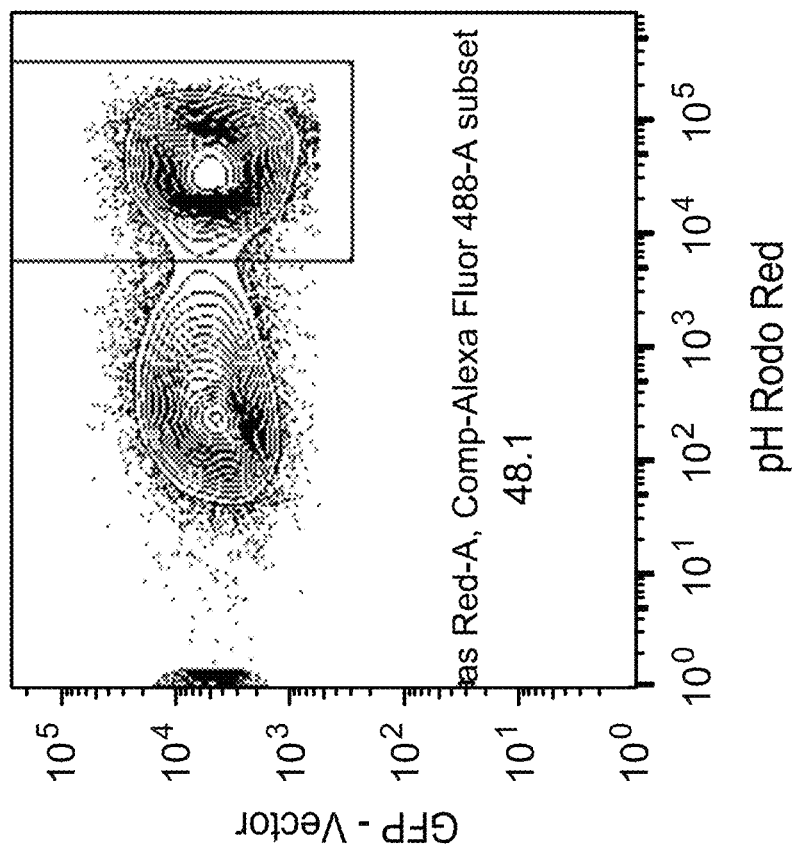

FA58C2-MERTK CER-mediated engulfment of apoptotic thymocytes was first examined (FIGS. 9B-9F). Expression of FA58C2-MERTK CER in murine Ba/F3 B-cells strongly enhanced phagocytic uptake of phosphatidylserine positive (PtdSer+) thymocytes (FIGS. 9B-9F). Observation by fluorescent microscopy and FACs show that the amount of phagocytosis correlates with incubation time with target cells, as well as the quantity of FA58C2-MERTK CER expression (FIGS. 9B-9C). Two hours following co-incubation, 11% of FA58C2-MERTK CER transduced Ba/F3 cells had engulfed, compared to 0% in control groups (FIG. 9B). The number of phagocytic Ba/F3 cells expressing FA58C2-MERTK CER increased to 48% at 24 hours incubation time (FIGS. 9B-9F). Furthermore, Ba/F3 cells that expressed the highest amount of FA58C2-MERTK CERs exhibited the greatest amount of phagocytosis (FIG. 9C), indicating a concentration dependent effect of the FA58C2-MERTK CER.

Effect of Small GTPASE on FA58C2-MERTK Engulfment

Figure 10A:
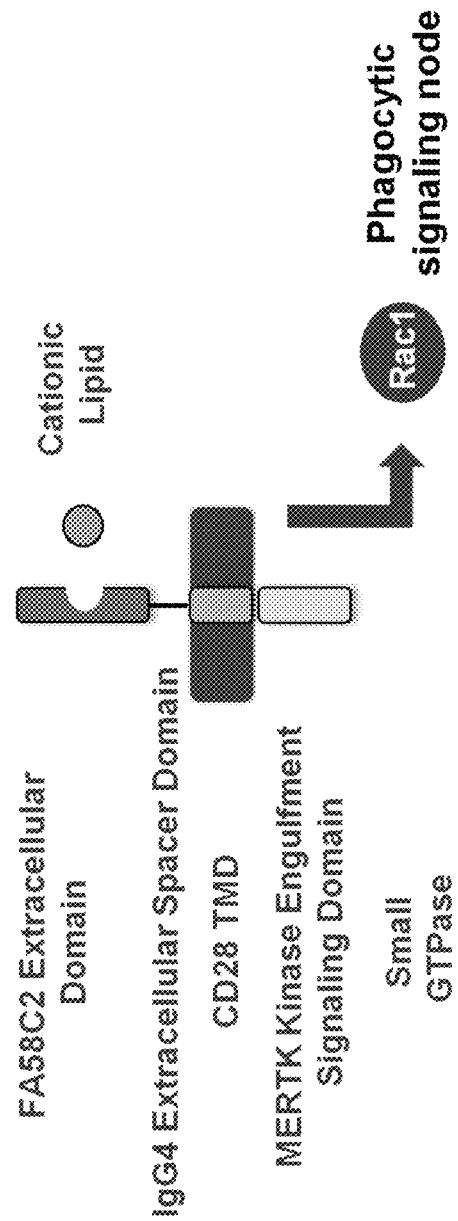
FIGS. 10A-10E show enhancement of CER-mediated phagocytosis by small GTPase Rac1.
Figure 10B:
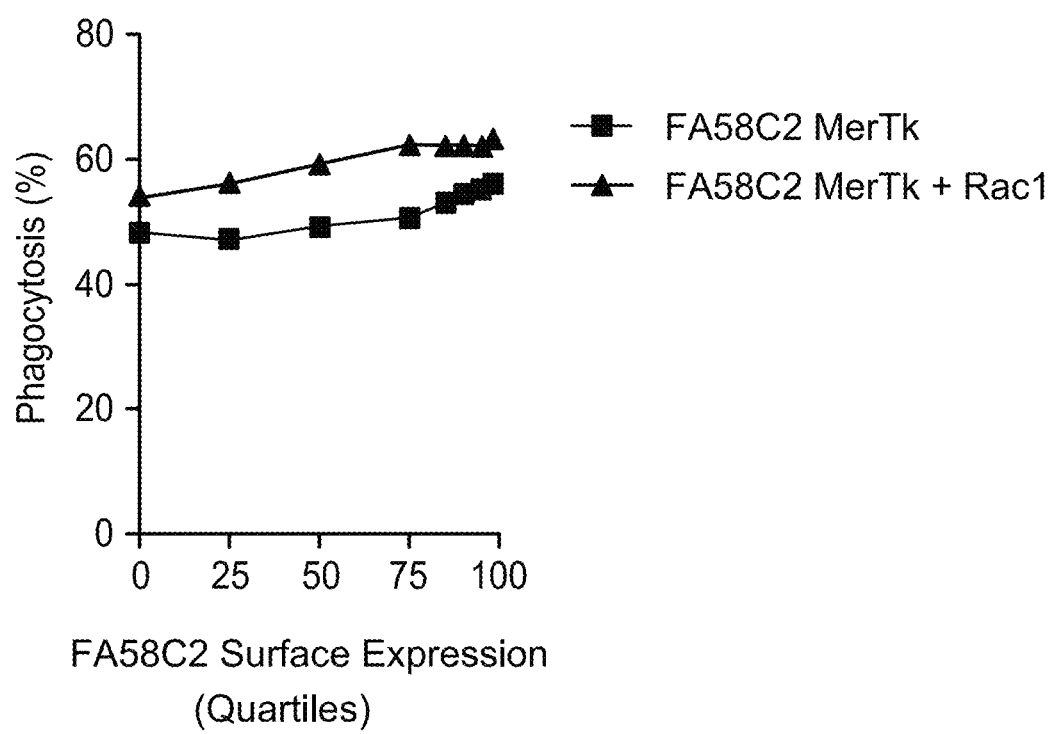
Figure 10C:
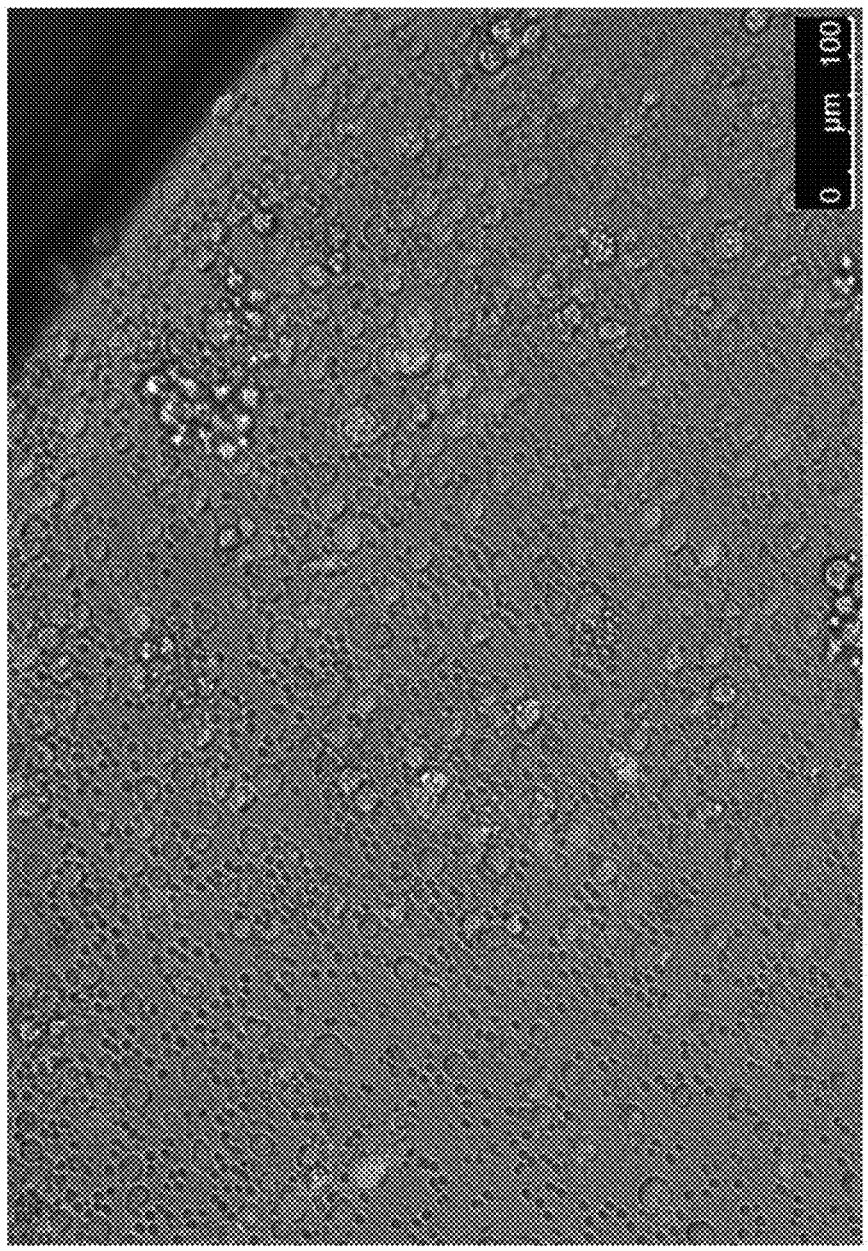
Figure 10E:
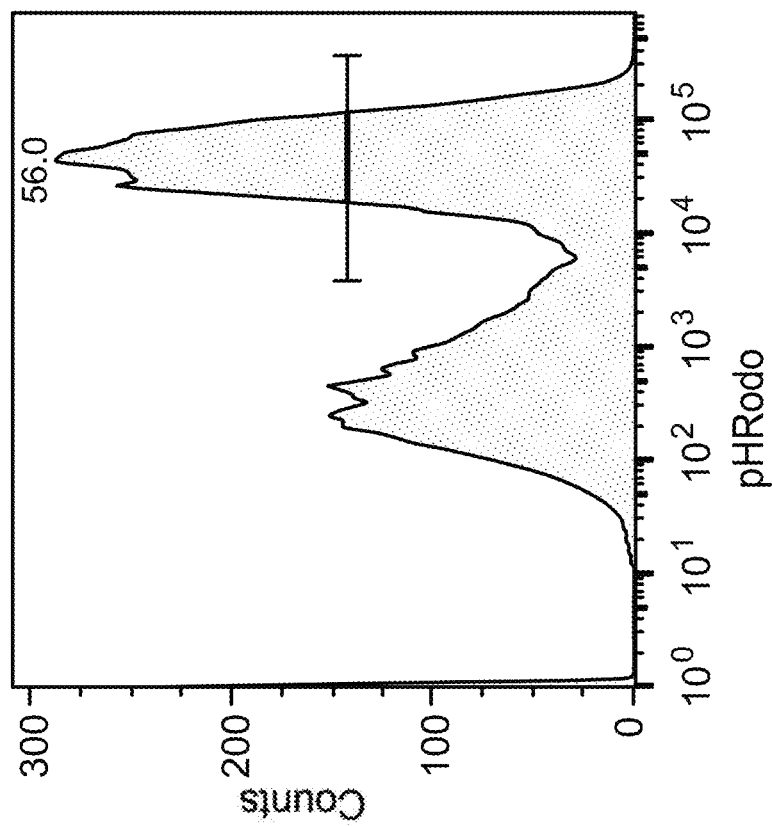
Figure 10D:
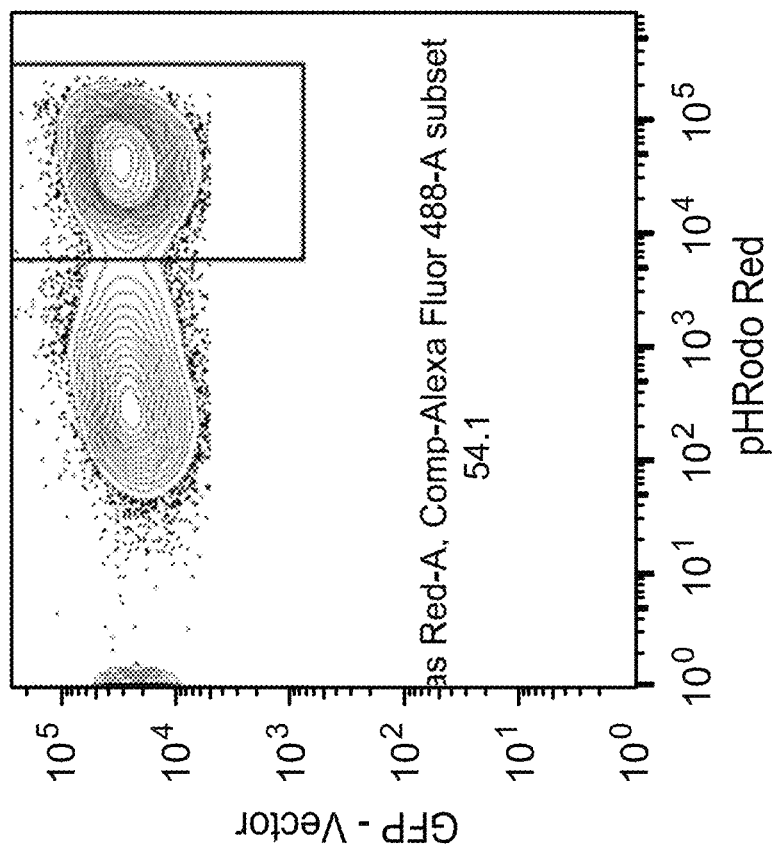

The effect of addition of small GTPase Rac1 and/or Rab5a on engulfment by CER– expressing Ba/F3 cells was tested. The Rho and Rab family GTPases regulate the engulfment of apoptotic cells by macrophages and immature dendritic cells. To form the phagocytic cup to engulf cells, integrin receptors expressed by macrophages activate Rac1 of the Rho family of GTPase to induce actin polymerization (Albert et al., 2000, Nat. Cell Biol. 2:899-905). Rab5, a member of the Rab family of GTPases, regulates the fusion of phagosomes with endosomes and may play a role in lysosome biogenesis (Duclos et al., 2000, J. Cell Sci. 113:3531-41). The cDNA sequence encoding Rac1 (SEQ ID NO: 60), Rab5 (SEQ ID NO: 61), or both (SEQ ID NO: 62) was co-expressed with FA58C2-MERTK using a bi-cistronic or tri-cistronic retroviral expression cassette (pMSCV FA58C2-MERTK-P2A-Rac1, pMSCV FA58C2-MERTK-P2A-Rab5a, or pMSCV FA58C2-MERTK-P2A-Rac1-T2A-Rab5a (FIG. 10A). As evident in FIGS. 10B-10E, the addition of Rac1 increased FA58C2-MERTK CER-mediated engulfment of target apoptotic thymocytes (56% vs. 48% as shown in FIG. 10E vs. FIG. 9F). Furthermore, transfer of ingested thymocytes into phagolysosomes was observed. Observation by fluorescence microscopy show several pHrodo Red-positive cells present inside most of FA58C2-MERTK CER/Rac1-expressing Ba/F3 B-cells (FIG. 10C).

Example 6

Construction of FA58C2-SYK CER "CER04"

The phosphatidylserine binding motif FA58C2 from the macrophage opsonin MFGE8 fused to a GM-CSF derived signal peptide was fused to a modified IgG4 extracellular spacer domain, the transmembrane domain of costimulatory molecule CD28, and the Syk kinase domain to create the chimeric engulfment receptor "CER04" (FA58C2-Syk CER) (polynucleotide sequence of SEQ ID NO:63, amino acid sequence of SEQ ID NO:70, FIG. 11A). Clustered Syk tyrosine kinase domains trigger phagocytosis in COS cells (Greenberg et al., 1996, Proc. Natl. Acad. Sci. USA 93:1103-7). The FA58C2-Syk CER nucleotide sequence was then inserted into the pMSCV (murine stem cell virus) retroviral vector. Early passage murine Ba/F3 B-cells were transduced with pMSCV FA58C2-Syk retrovirus expressing the GFP fluorescent protein. Positive Ba/F3 transductants were sorted by GFP expression using flow cytometry (FACs), expanded in culture, and used for in vitro studies.

Phagocytic Activity Against Primary Apoptotic Thymocytes

Primary thymocytes were induced into apoptosis and labeled with pHrodo Red dye as described in Example 4. Co-culture experiments were carried out and Ba/F3 GFP+ cells were serially quantified for phagocytosis by fluorescence microscopy and FACs as described in Example 4. Ba/F3 cells transduced with pMSCV vector expressing Tim4 and GFP (non-engulfment receptor) were used as a negative control.

Figures 11B, 11C:
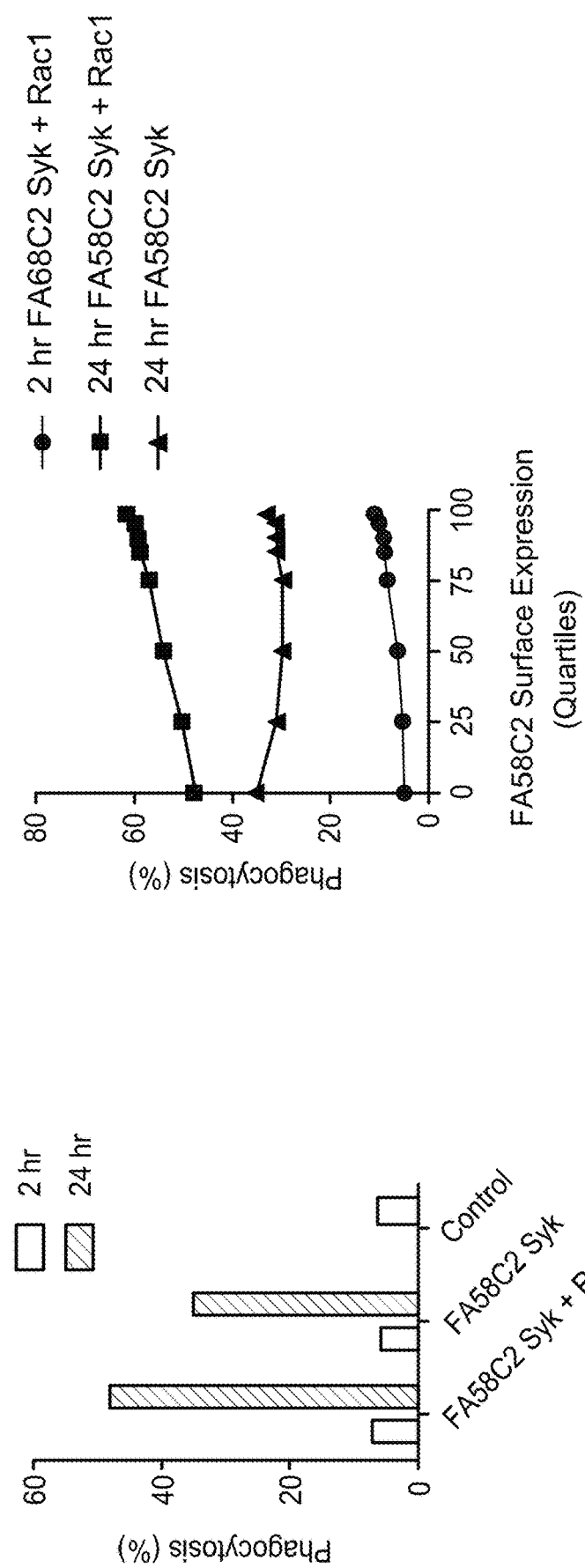
Figure 11D:
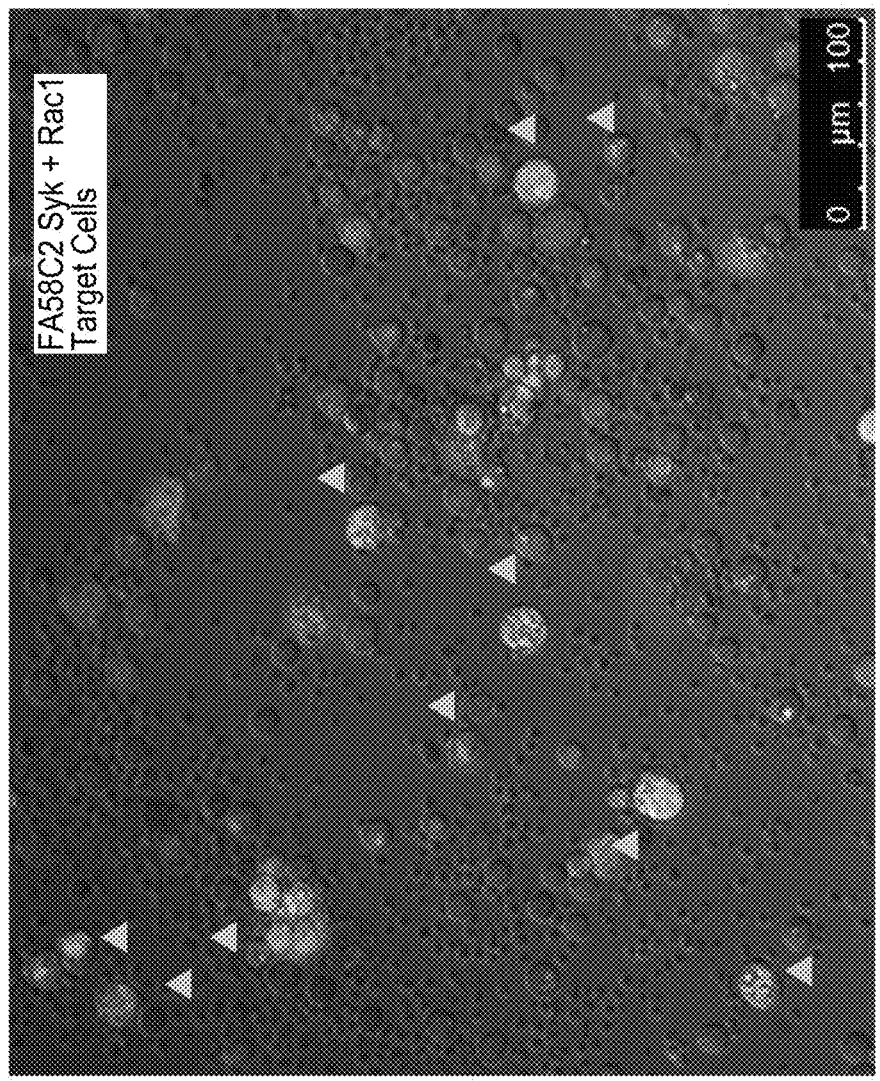
Figure 11E:
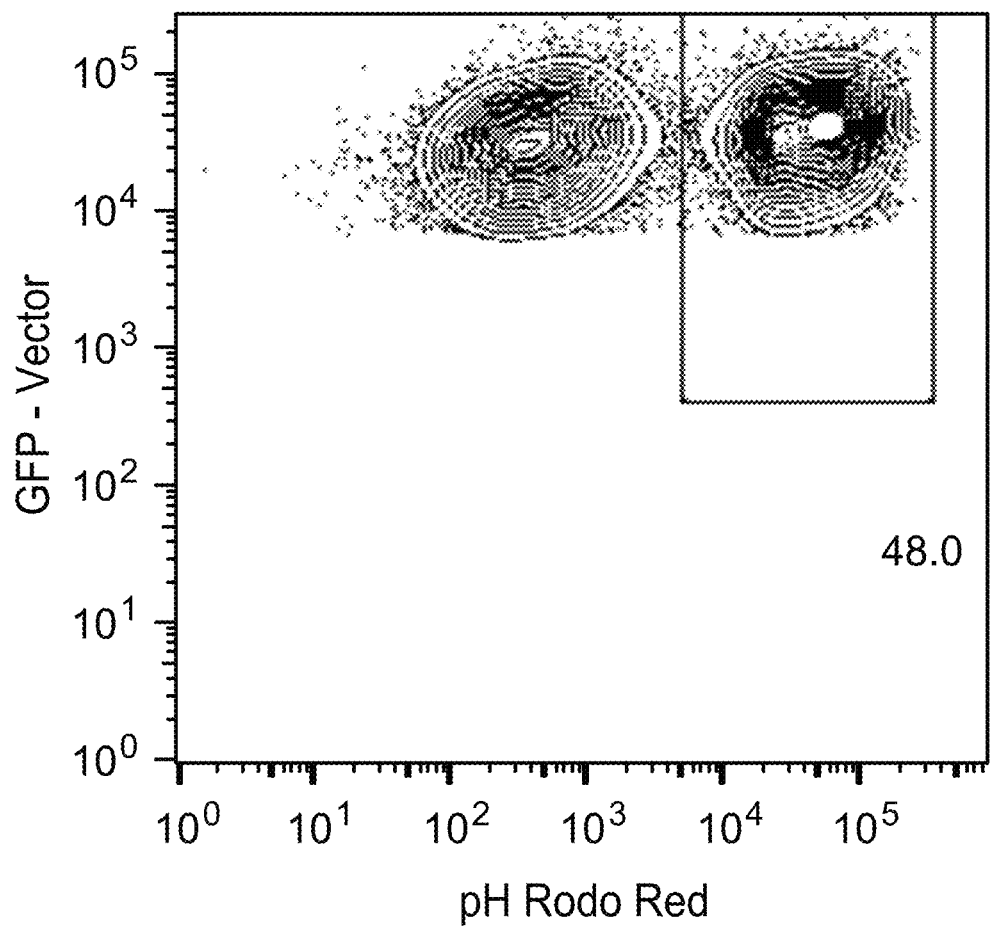

FA58C2-Syk CER-mediated engulfment of apoptotic thymocytes was examined (FIGS. 11A-11E). Expression of FA58C2-Syk CER in the murine Ba/F3 B-cell line strongly enhanced phagocytic uptake of phosphatidylserine positive (PtdSer$^+$) thymocytes (FIGS. 11B-11E). Observation by fluorescent microscopy and FACs show that the amount of phagocytosis correlates with time of target cell incubation, as well as the quantity of FA58C2-Syk CER expression. Two hours following co-incubation, 9.5% of FA58C2-Syk CER-transduced Ba/F3 cells had engulfed target apoptotic thymocytes, compared to 0% in control groups (FIG. 11B). The number of phagocytic Ba/F3 cells expressing FA58C2-Syk CER increased to 48% at 24 hours incubation (FIGS. 11B, 11C, and 11E). Furthermore, Ba/F3 cells that expressed the highest amount of FA58C2-Syk CERs exhibited the greatest amount of phagocytosis (FIG. 11C), indicating a concentration dependent effect of the FA58C2-Syk CER.

Effect of Small GTPASE RAB5 on FA58C2-SYK Engulfment

Figure 12A:
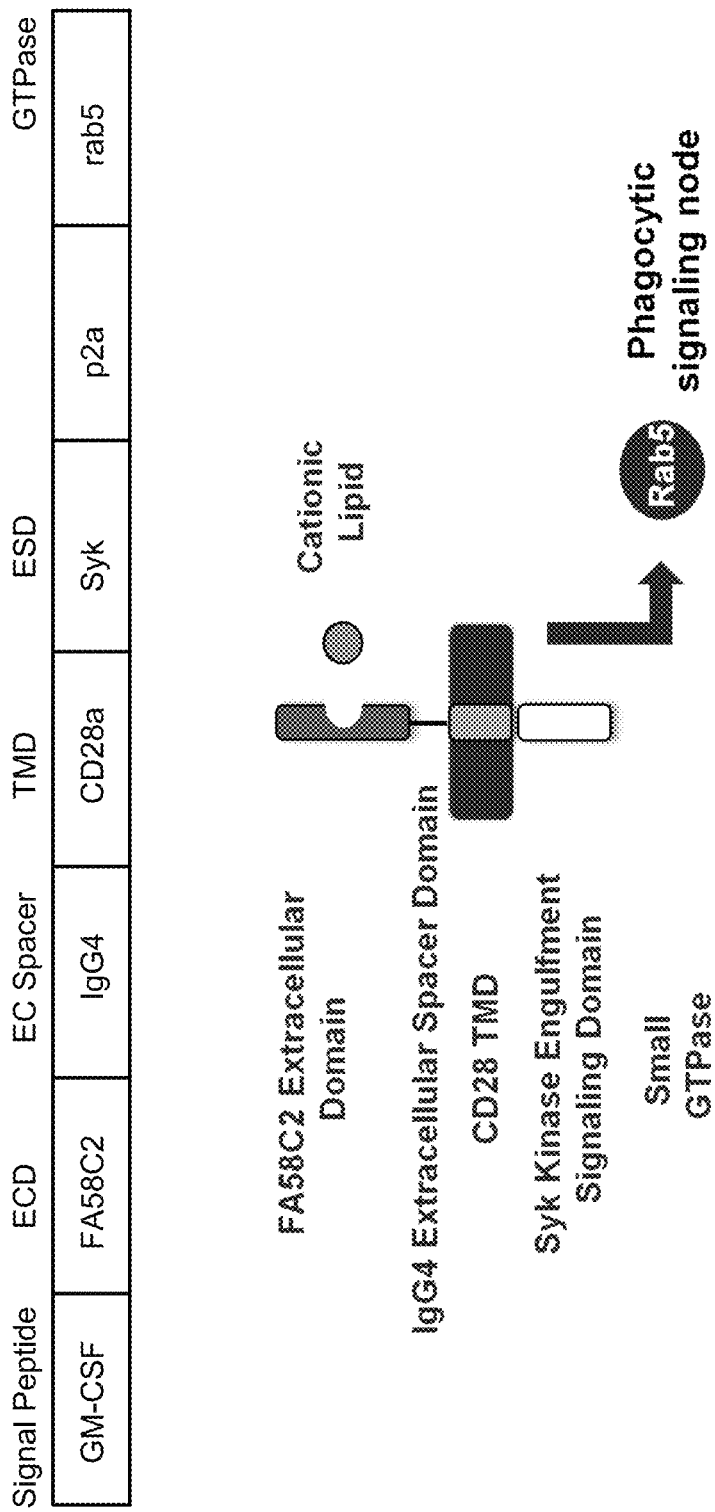
FIGS. 12A-12D show that co-expression of small GTPase Rab5 enhances CER-mediated phagocytosis.
Figure 12B:
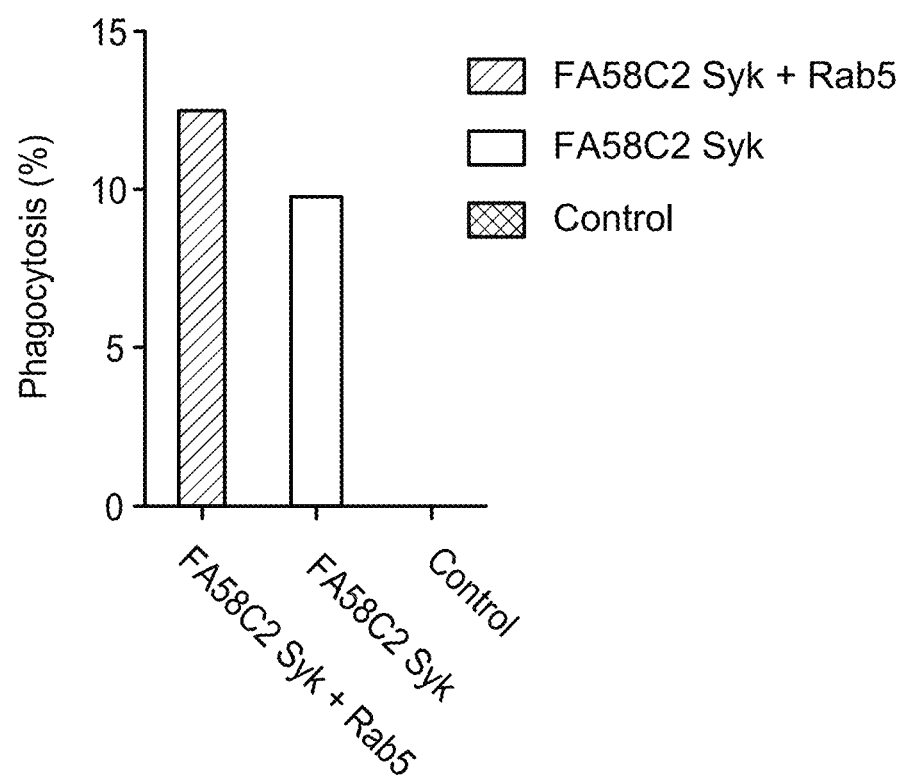
Figure 12C:
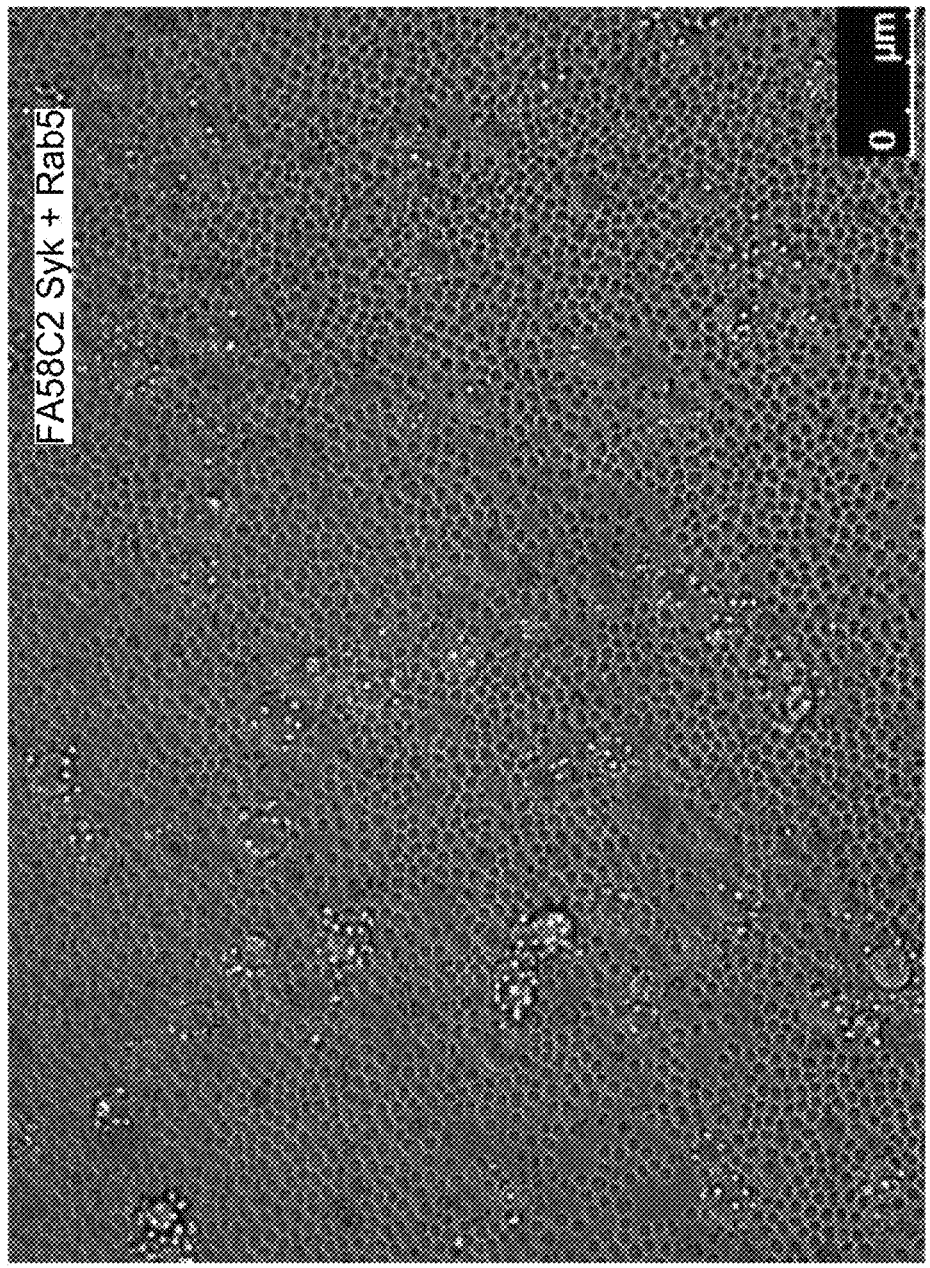
Figure 12D:
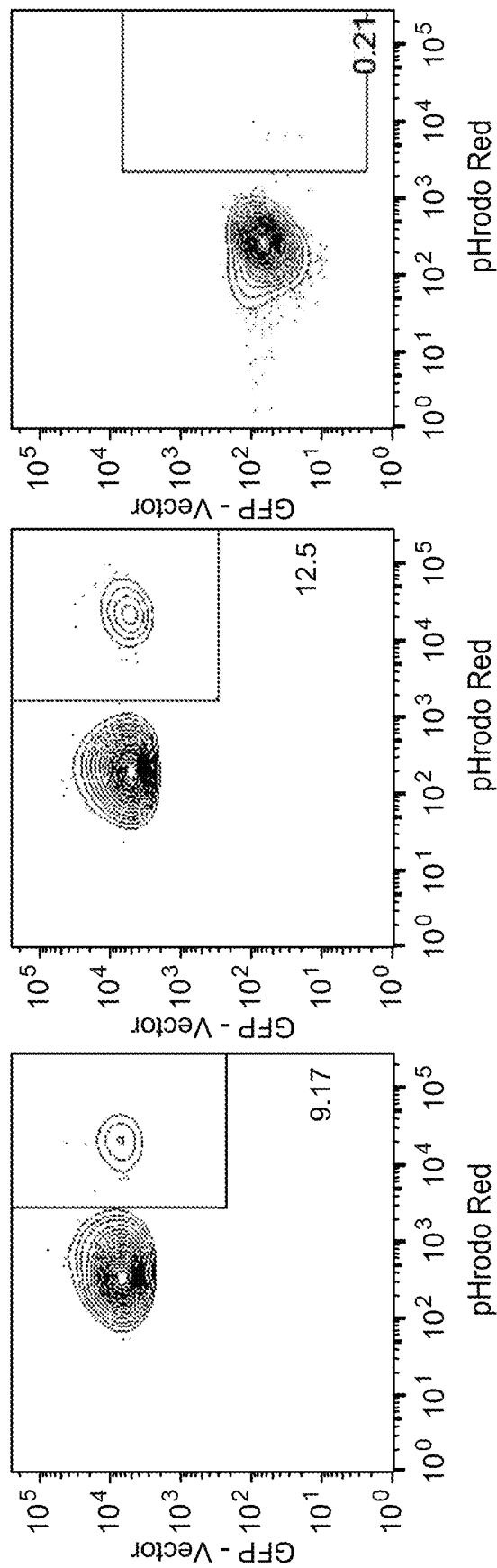

The effect of the addition of small GTPase Rac1 and/or Rab5a on engulfment by Ba/F3 cells was examined. The cDNA sequence encoding Rac1 (SEQ ID NO: 60) and/or Rab5 (SEQ ID NO: 61), or both (SEQ ID NO:62) was co-expressed with FA58C2-Syk CER using a bi-cistronic or tri-cistronic retroviral expression cassette (pMSCV FA58C2-Syk-P2A-Rac1, pMSCV FA58C2-Syk-P2A-Rab5a, and pMSCV FA58C2-Syk-P2A-Rac1-T2A-Rab5a constructs) (FIGS. 11A, 12A). As evident in FIGS. 11B and 11C, the addition of Rac1 increased FA58C2-Syk CER-mediated engulfment or target apoptotic thymocytes. Furthermore, the addition of Rab5 also increased phagocytosis (FIGS. 12B-12D).

Example 7

Construction of CD19-MERTK CER "CER40"

Figure 13B:
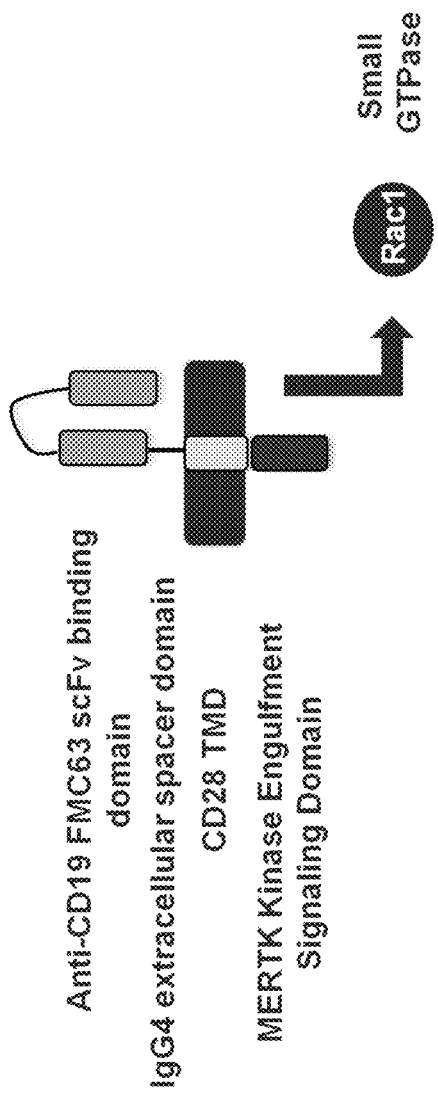
Figure 13D:
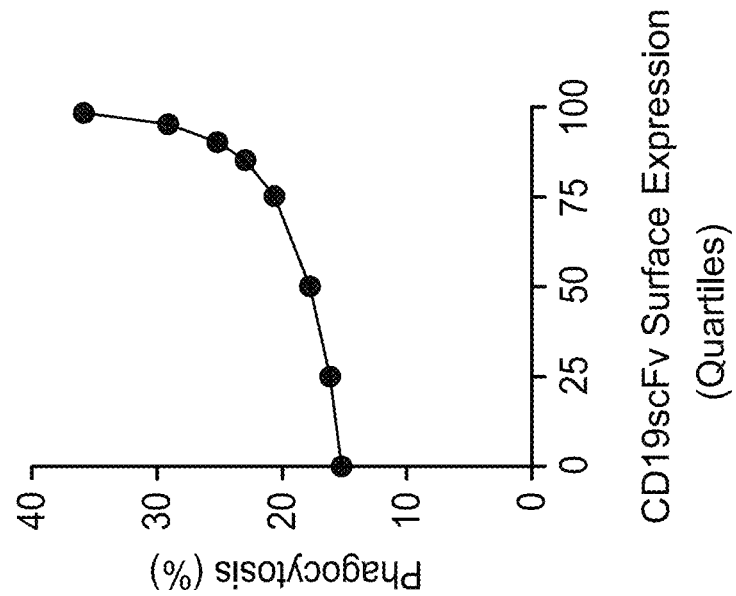

An anti-CD19 single chain fragment variable (scFv) (encoding amino acid sequence of SEQ ID NO:66) derived from the FMC63 mouse IgG2a mouse monoclonal antibody and fused to a GM-CSF derived signal peptide (encoding amino acid sequence of SEQ ID NO:65) was fused to a modified IgG4 extracellular spacer domain (encoding amino acid sequence of SEQ ID NO:67), transmembrane domain of costimulatory molecule CD28 (encoding amino acid sequence of SEQ ID NO:68), and the intracellular kinase domain of MERTK (amino acid sequence of SEQ ID NO:43) to create the chimeric engulfment receptor "CER40" (CD19-MERTK CER) (having amino acid sequence of SEQ ID NO:64) (FIG. 13A) (Kochenderfer et al., 2009, J. Immunother. 32:689-702). To enhance engulfment, a bi-cistronic retroviral expression construct comprising CD19-MERTK CER and Rac1 was constructed (FIG. 13B). The CD19-MERTK CER nucleotide sequence was then inserted into the pMSCV (murine stem cell virus) retroviral vector. Early passage murine Ba/F3 B-cells were transduced with pMSCV CD19-MERTK CER retrovirus expressing green fluorescent protein (GFP). Positive Ba/F3 transductants were sorted by GFP expression using flow cytometry (FACs), expanded in culture, and used for in vitro studies.

Phagocytic Activity Against Human Lymphoma Cell Line

Raji human Burkitt B-cell lymphoma cells, which are CD19$^+$, were labeled with 1 μM of pHrodo Red dye and used as target cells for phagocytosis assays as described in Example 4. Co-culture experiments were carried out and Ba/F3 GFP+ cells were serially quantified for phagocytosis by fluorescence microscopy and FACs as described in Example 4. Ba/F3 cells transduced with pMSCV vector expressing Tim4 and GFP (non-engulfment receptor) and non-transduced Ba/F3 cells were used as negative controls.

Figure 13C:
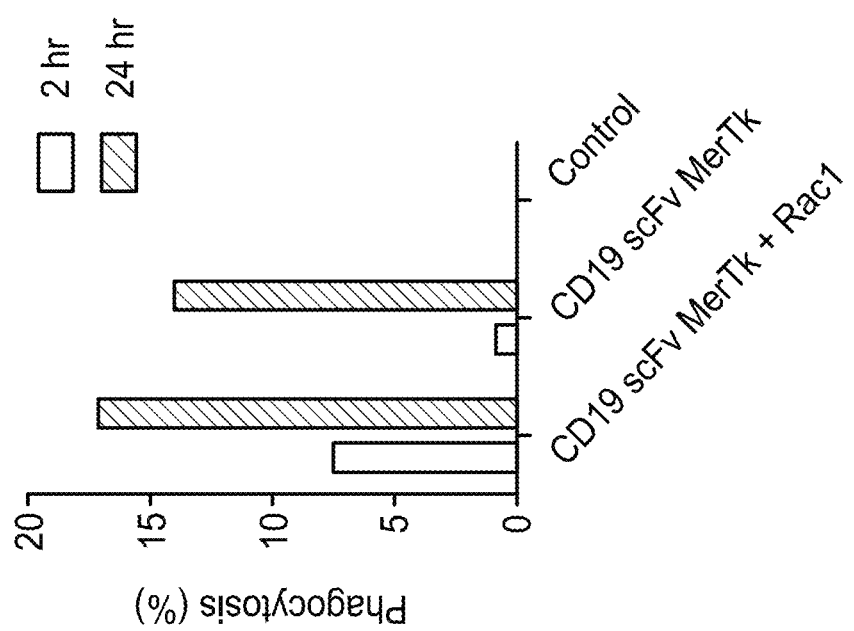
Figure 13E:
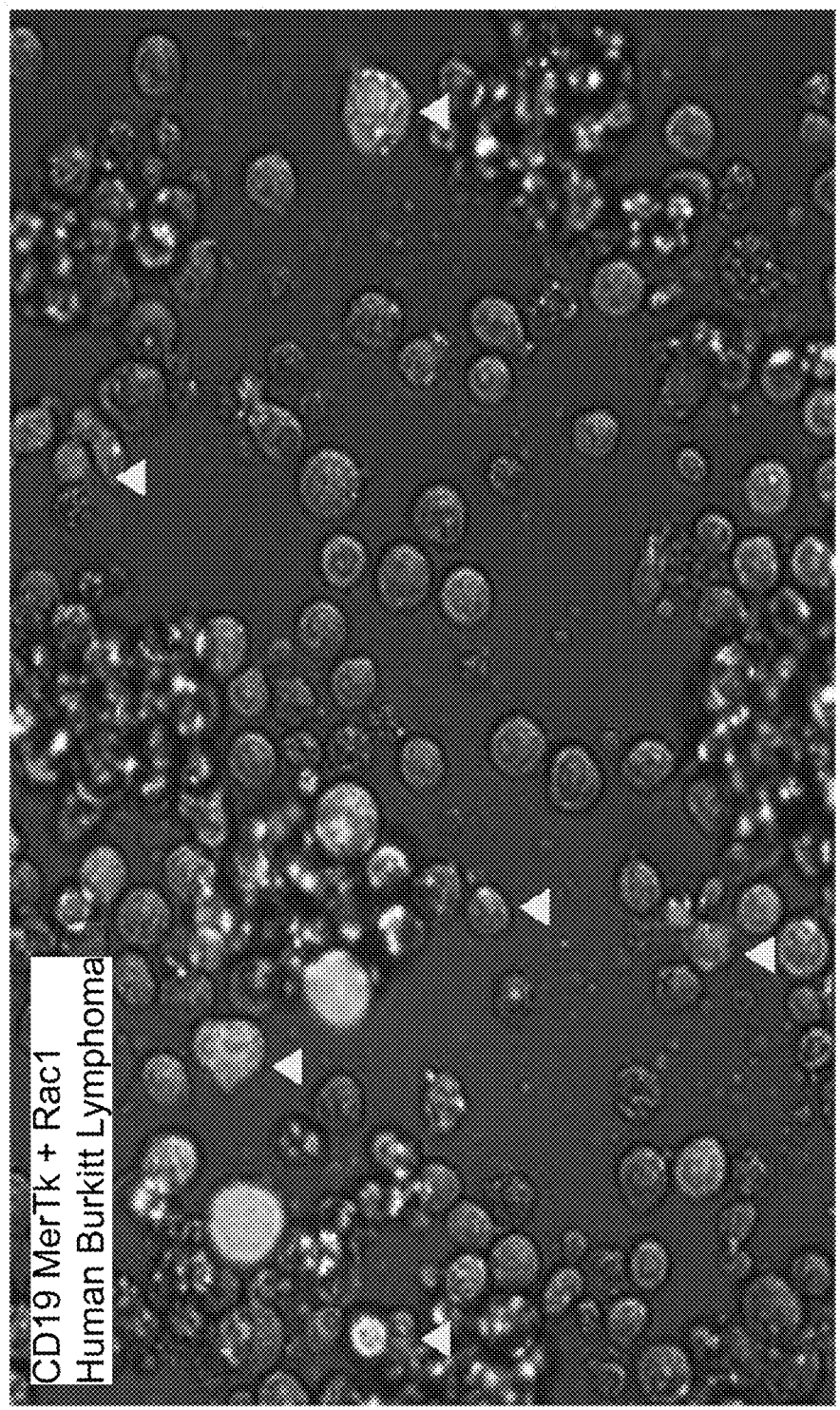
Figure 13G:
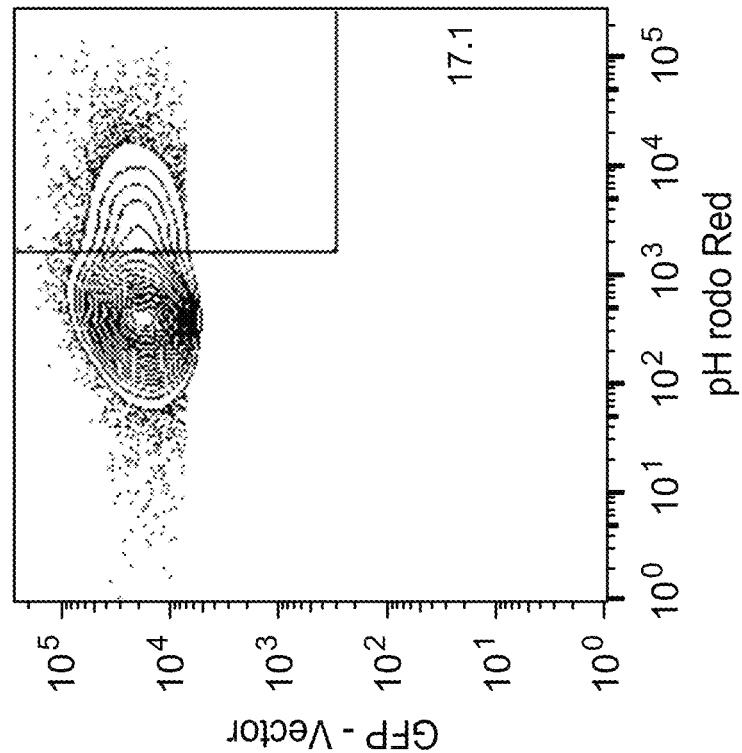
Figure 13F:
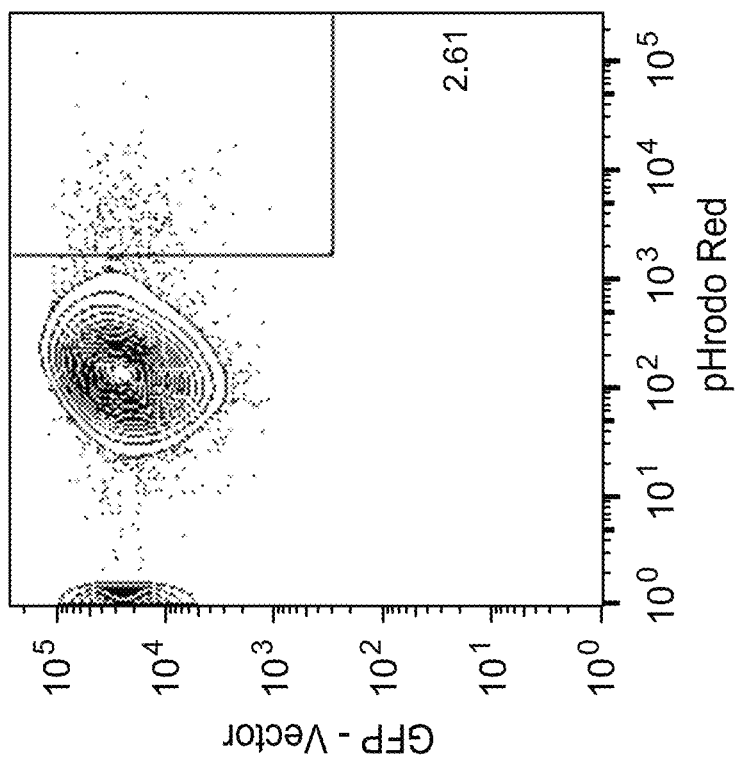

CD19-MERTK CER-mediated engulfment of Raji Burkitt B-cell lymphoma cells was first examined (FIGS. 13C-13F). Expression of CD19-MERTK CER in murine Ba/F3 B-cell line strongly enhanced phagocytic uptake of Raji lymphoma cells (FIGS. 13C-13G). Observation by fluorescent microscopy and FACs show that the amount of phagocytosis correlates with time of target cell incubation, as well as the quantity of CD19-MERTK CER expression. 24 hours following co-incubation, 17% of CD19-MERTK-P2A-Rac1 CER transduced Ba/F3 cells had engulfed Raji Burkitt B-cell lymphoma cells, compared to 0% in control groups (FIG. 13C, 13G). Ba/F3 cells that expressed the highest amount of CD19-MERTK CERs exhibited the greatest amount of phagocytosis (FIG. 13D), indicating a concentration dependent effect of the CD19-MERTK CER.

Figure 13H:
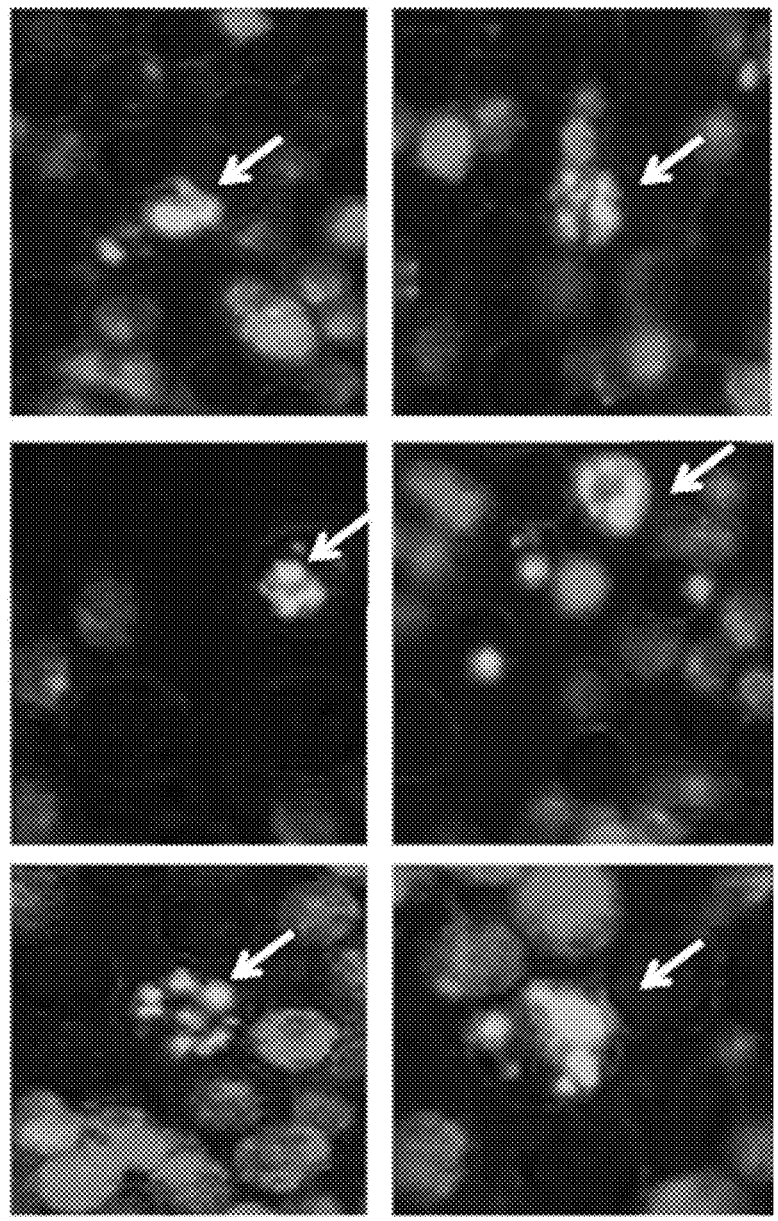

The ability of the CD19-MERTK CER to facilitate transfer of ingested Raji cells into phagolysosomes was examined. Fluorescence microscopy showed that pHrodo Red-positive whole Raji cells were present inside CD19-MERTK CER+Rac1-expressing Ba/F3 cells (FIG. 13E). FIG. 13H shows engulfment of Raji cells by CD19-MERTK CER expressing Ba/F3 cells (white arrows indicate phagocytosis). These results demonstrate the capacity for CD19-MerTk CER-expressing to eliminate targets in a CD19-specific manner.

Example 8

Construction of TIM4-MERTK CER "CER01"

Figure 16:
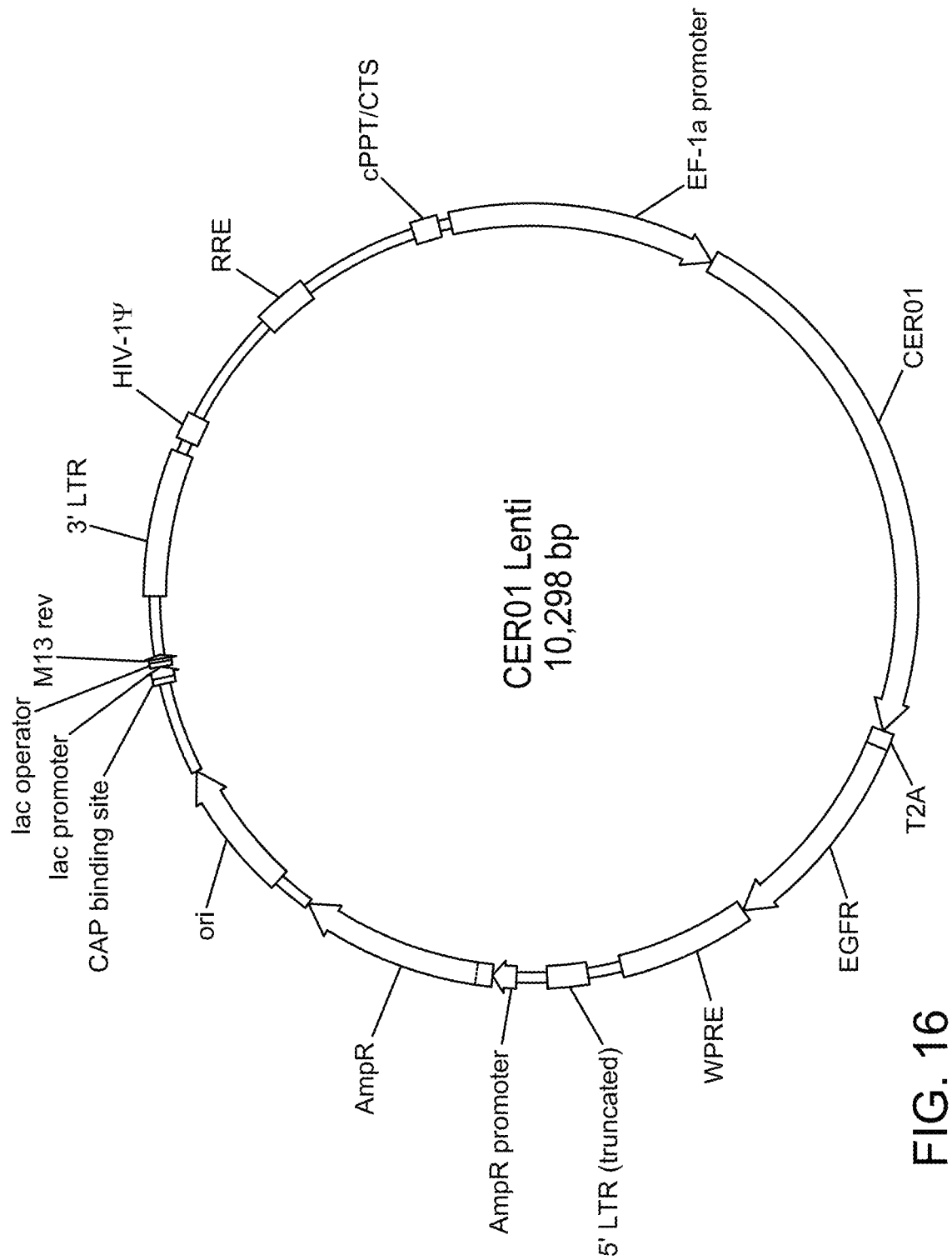
FIG. 16 shows a vector map for a lentiviral vector comprising "CER01" chimeric engulfment receptor having an amino acid sequence of SEQ ID NO:71. CER01 comprises a Tim4 binding domain, a Tim4 transmembrane domain, and a MERTK signaling domain. The lentiviral vector also comprises a sequence encoding truncated EGFR (SEQ ID NO:121), which is separated from the CER01 sequence by a viral T2A sequence.

A Tim-4-MERTK chimeric engulfment receptor nucleotide sequence encoding CER01 having an amino acid sequence of SEQ ID NO:71, as described in Example 4, was inserted into a pLenti lentiviral vector. Murine Ba/F3 B-cells were cultured in RMPI 1640 media supplemented with 10% fetal bovine serum, 1% penicillin-streptomycin, and 10 ng/mL murine IL-3 (Peprotech Catalog #213-13) in a 12 well plate at a density of 0.5 million cells/ml. To transduce Ba/F3 cells, 100 μl of pLenti lentivirus vector expressing Tim4-MERTK (CER01) and truncated EGFR (also referred to as tEGFR or EGFRt) as a transduction marker (see, FIG. 16) and 5 μl TRANSDUX™ transduction reagent were diluted in 0.5 ml Complete Cell Growth Media and added to the Ba/F3 cells. The Ba/F3 cells were then centrifuged at 270×g rpm for 1 hour in a 32° C. pre-warmed centrifuge. The Ba/F3 cells were incubated for 24 hours at 37° C. Ba/F3 cells were expanded for another 48 hours in Complete Cell Growth Media. Positive Ba/F3 cell transductants were sorted using fluorescence activated cell sorting (FACs) (Sony Sorter SH800) by either staining with a labeled Tim4 specific antibody (Katy-18, Abcam Catalog #176486) or a labeled EGFR-specific antibody (Cetixumab) (see, FIGS. 17A-17B). Post sorting, purified, transduced Ba/F3 cells comprising the Tim4-MERTK-T2A-truncated EGFR containing lentivirus (see, FIG. 17C) were rested for 48 hours prior to being utilized for phagocytic assays. Percentage of cells with positive staining is indicated in each histogram.

Phagocytic Activity Against Primary Apoptotic Thymocytes

One day prior to phagocytic assay, primary thymocytes were isolated from a C3H mouse (Charles River Laboratories International, Inc.). Thymocytes were cultured in complete RPMI 1640 growth media supplemented with 10% fetal bovine serum and 1% penicillin-streptomycin in a 6-well plate. To induce apoptosis and phosphatidylserine expression on the cell surface, thymocytes were treated with 1 µM dexamethansone for 24 hours. Untreated thymocytes were used as a negative control. Thymocytes were collected from the 6-well plates, washed once with sterile 1×PBS, and then stained with 1 ng/µl pH sensitive pHrodo™ Red dye (ThermoFisher Scientific, Catalog #P36600) in PBS at room temperature for 15 minutes. The cells were then supplemented with growth media and washed one more time to remove any excess pHrodo Red. pHrodo Red stained thymocytes were plated on a flat bottom 96 well plate at 250,000 cells/well in RMPI 1640 complete media.

Ba/F3 CER01$^+$ tEGFR$^+$ cells made as described above were washed once with 1×PBS and stained with 1 µM CELLTRACE™ Violet dye (ThermoFisher Scientific, Catalog #C34557) in PBS for 10 minutes at 37° C. Stained, transduced Ba/F3 cells were supplemented with growth media, washed once with 1×PBS to remove excess CELL-TRACE™ Violet, and plated on the same flat bottom 96 well plate at approximately 25,000 cells/well in RPMI 1640 complete media.

Figure 18A:
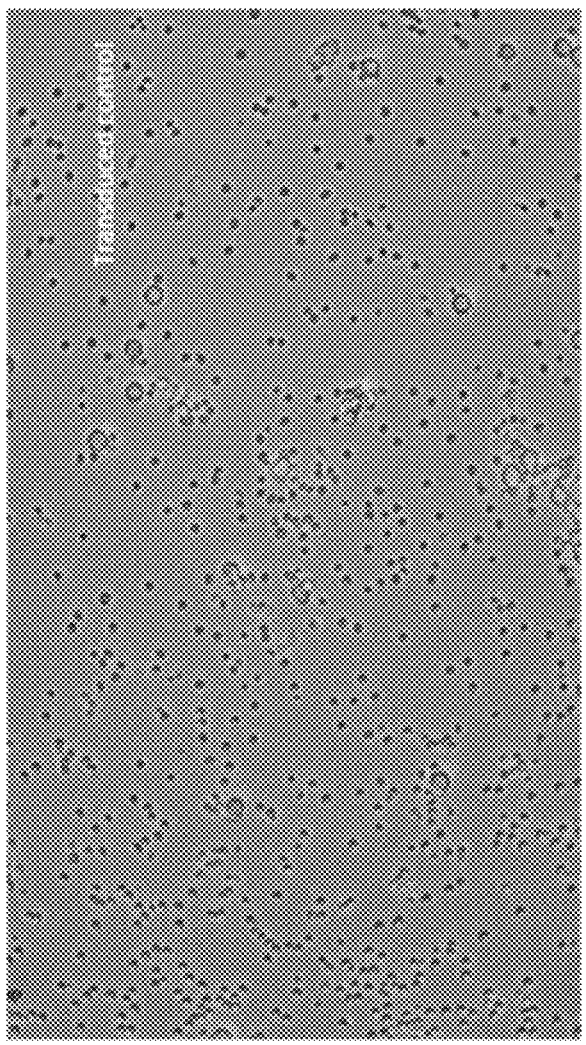
FIGS. 18A-18B show in vitro engulfment of dexamethasone-treated thymocytes by CER01+ Ba/F3 murine B cells.
Figure 18B:
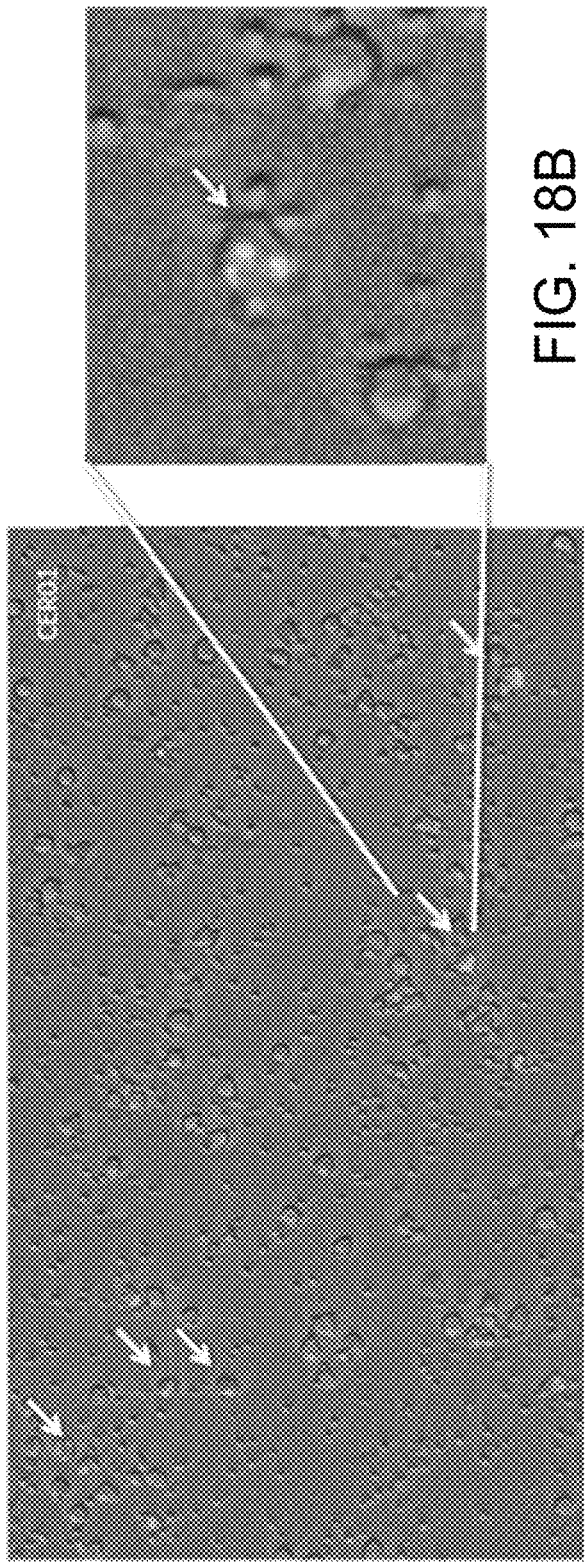

Target thymocytes were co-cultured with stained, Ba/F3 CER01$^+$ tEGFR$^+$ cells at a ratio of 10:1 (target cell:effector cell) for 3 hours or overnight (~14 hours) at 37° C. After incubation, the plate was centrifuged and the media replaced with PBS supplemented with 2% fetal bovine serum, pH 9. The 96 well plate was then viewed using KEYENCE BZ-X710 fluorescence microscope, 20× objective. A duplicate 96-well co-culture plate was also set up in parallel for analysis by flow cytometry. 7-aminoactinomycin D (7-AAD) dye was used as a cell viability dye along with pHrodo Red stained target thymocytes and CELLTRACE Violet stained effector cells. Ba/F3 cells transduced with pLenti vector expressing truncated EGFR were used as a negative control. Fluorescent microscopy showed that CER01$^+$ Ba/F3 cells engulf dexamethasone-treated thymocytes (white arrows indicate engulfment events) (see, FIG. 18B) as compared to truncated EGFR transduced Ba/F3 control cells (see, FIG. 18A). High magnification of an engulfment event is shown in the bottom right of FIG. 18B.

Figure 19B:
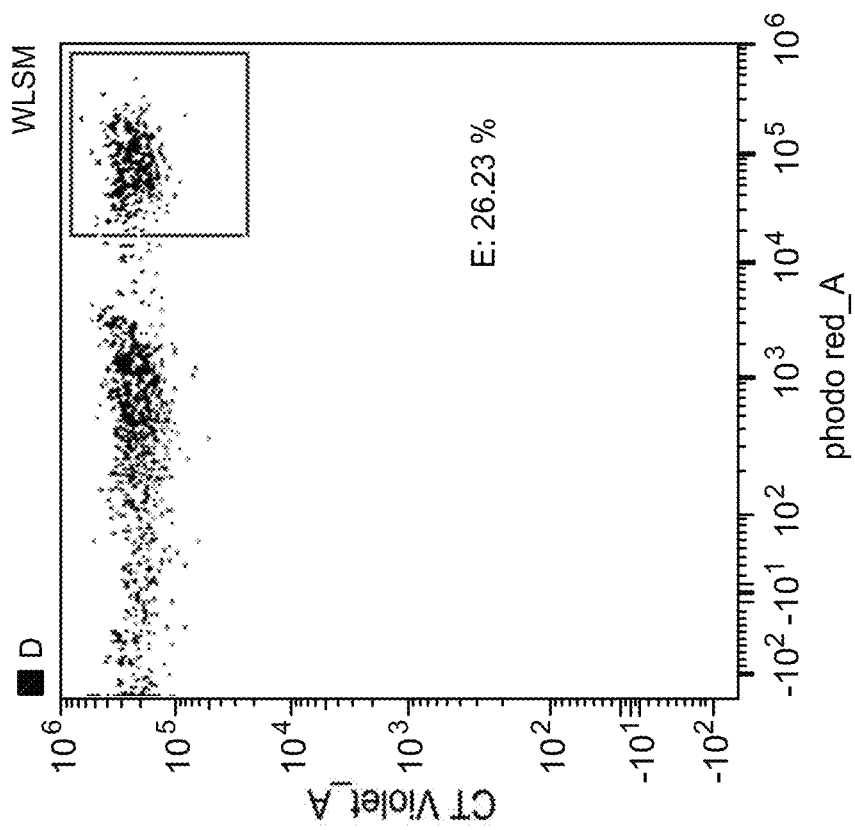
FIGS. 19A-19B show FACS analysis of CER01+ Ba/F3 effector cells (FIG. 19A) and quantification of engulfment of dexamethasone-treated thymocytes by CER01+ Ba/F3 murine B cells by measuring the cell population that stained double positive for pHrodo Red and CELLTRACE Violet (FIG. 19B).
Figure 19A:
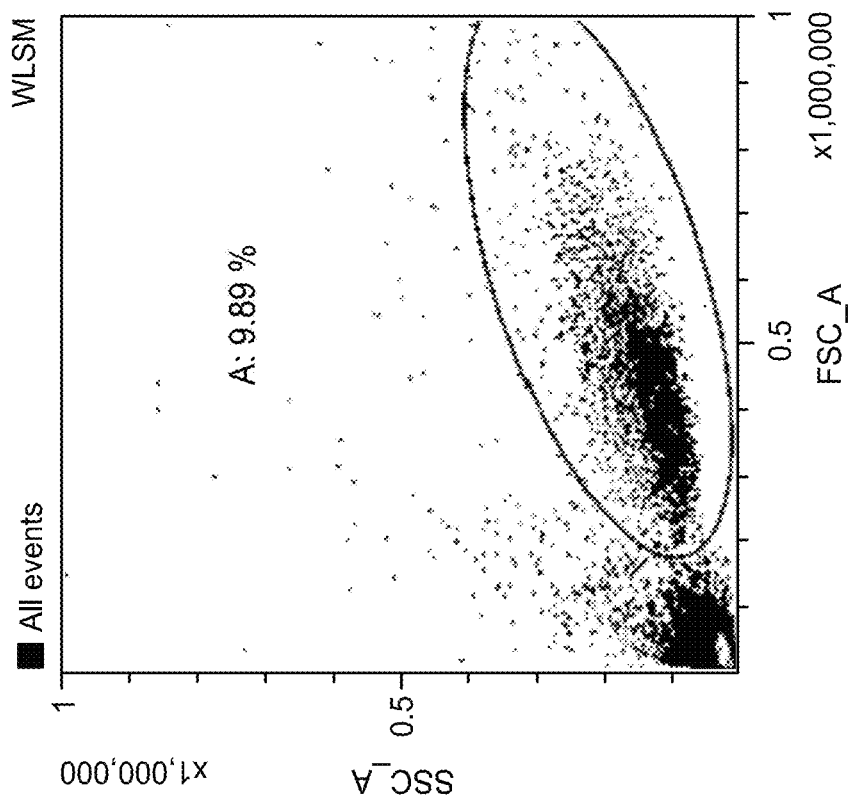

The amount of Ba/F3 effector cells as measured by FACS is depicted in FIG. 19A. Phagocytosis was quantified as the cell population staining double positive for pHrodo Red and CELLTRACE Violet as measured by FACS (see, FIG. 19B).

Figures 20A, 20B:
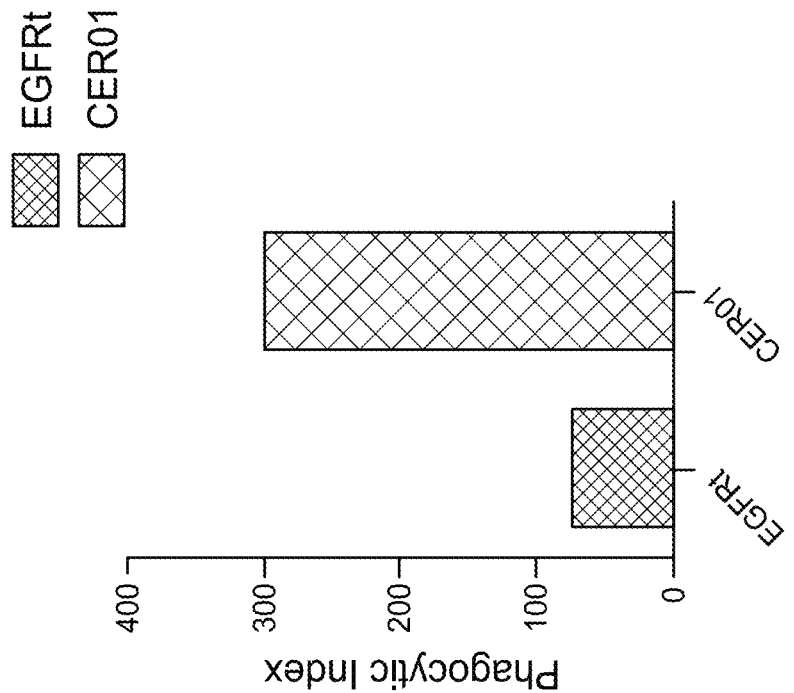
FIGS. 20A-20B depict phagocytic index for CER01+ cells or EGFRt+ control Ba/F3 cells.

A phagocytic index was calculated by multiplying [mean of total number of engulfed target cells/total number of counted CER modified cells (e.g., phagocytic frequency)] by [average area of target cell staining per CER+ Ba/F3 cell× 100 (e.g., hybrid capture)] as compared to EGFRt transduced Ba/F3control cells (see, FIGS. 20A-20B).

Phagocytic Activity Against Murine Cell Lines

One day prior to the phagocytosis assay, CT26 murine colon carcinoma cells were cultured in complete RPMI 1640 growth media supplemented with 10% fetal bovine serum and 1% penicillin-streptomycin in a 6-well plate and treated with 1 mM staurosporine (STS) for 12 hours to induce apoptosis. Untreated CT26 cells were used as a negative control.

On the day of the phagocytosis assay, CT26 cells were collected, washed twice with 1× PBS to remove excess staurosporine and then stained with 1 ng/µl pHrodo Red in PBS at room temperature for 15 minutes. The CT26 cells were supplemented with growth media, washed once to remove excess pHrodo Red, and plated onto a flat bottom, 96 well plate at 250,000 cells/well in RPMI 1640 complete media.

Ba/F3 CER01$^+$ EGFR$^+$ cells made as described above were washed once with 1×PBS and stained with 1 µM CELLTRACE™ Violet dye (ThermoFisher Scientific, Catalog #C34557) in PBS for 10 minutes at 37° C. Stained, transduced Ba/F3 cells were supplemented with growth media, washed once with 1×PBS to remove excess CELL-TRACE™ Violet, and plated on the same flat bottom 96 well plate at approximately 50,000 cells/well in RPMI 1640 complete media.

Figure 21:
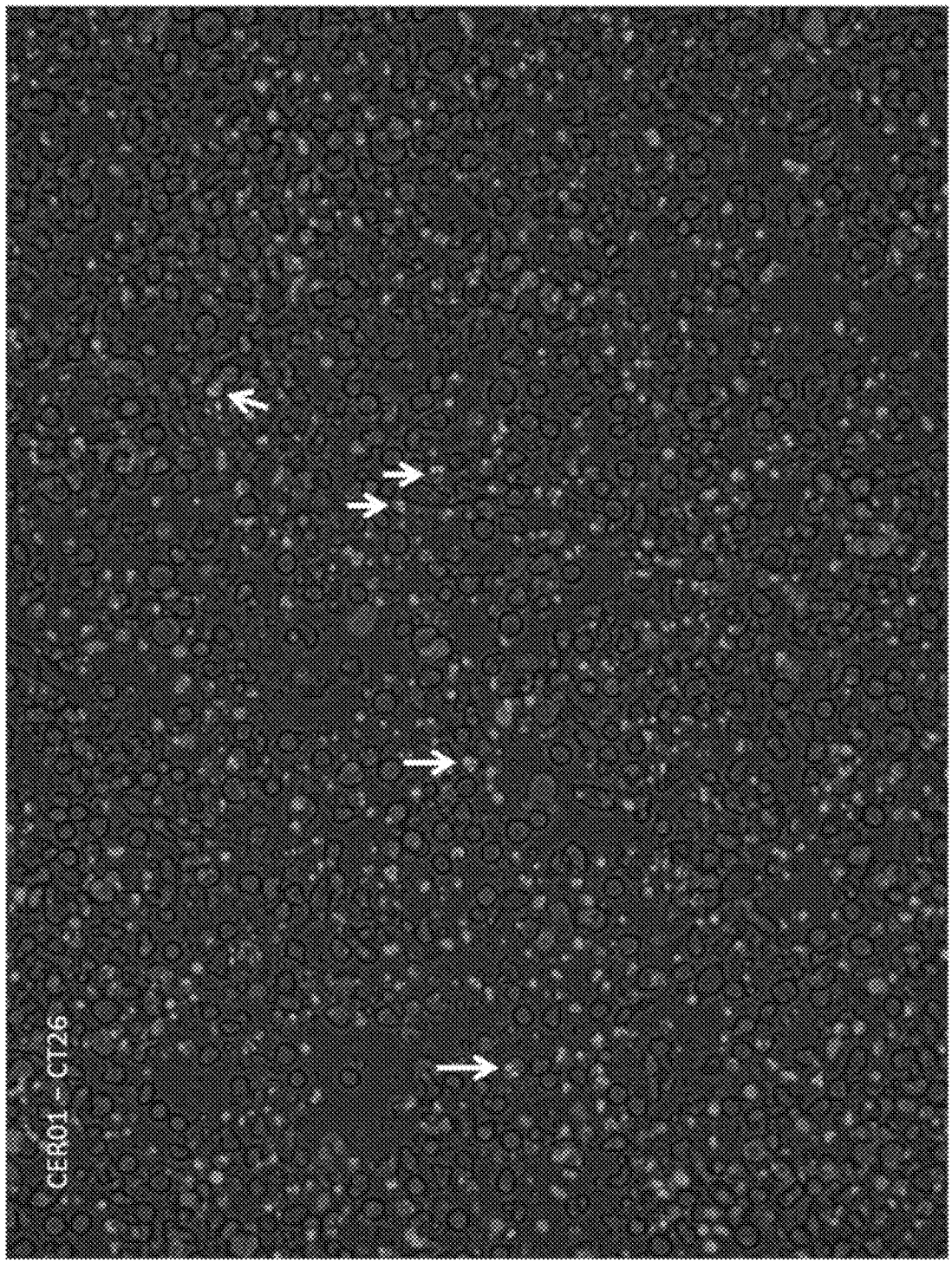
FIG. 21 shows a fluorescent microscope image of phagocytosis of CT26 colon carcinoma cells by CER01+ Ba/F3 cells. White arrows indicate phagocytosis events.

Target CT26 cells were co-cultured with stained, CER01$^+$ tEGFR$^+$ cells at a ratio of 5:1 (target cell:effector cell) for 3 hours at 37° C. After incubation, the plate was centrifuged and the media replaced with PBS supplemented with 2% fetal bovine serum, pH 9. The 96 well plate was then viewed using KEYENCE BZ-X710 fluorescence microscope, 20× objective. Ba/F3 cells transduced with pLenti vector expressing truncated EGFR were used as negative control. Fluorescent micrograph showing in vitro phagocytosis is shown in FIG. 21 (white arrows show phagocytosis events). CT26 cells labeled with pHrodo Red fluoresced inside the low pH compartments of lysosomes when engulfed (outlined in pink).

Figure 22A:
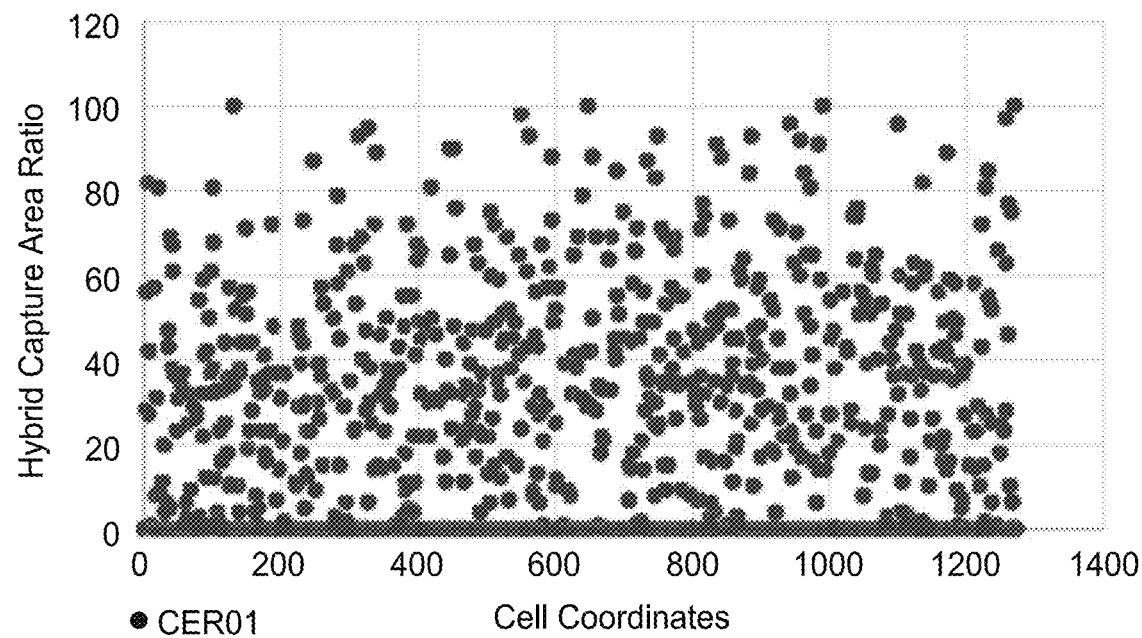
FIGS. 22A-22B—a hybrid capture algorithm was used to detect fluorescence of pHrodo Red stained target cells within CER01+ Ba/F3 cells CELLTRACE Violet stained area on fluorescent images of phagocytosis assay.
Figure 22B:
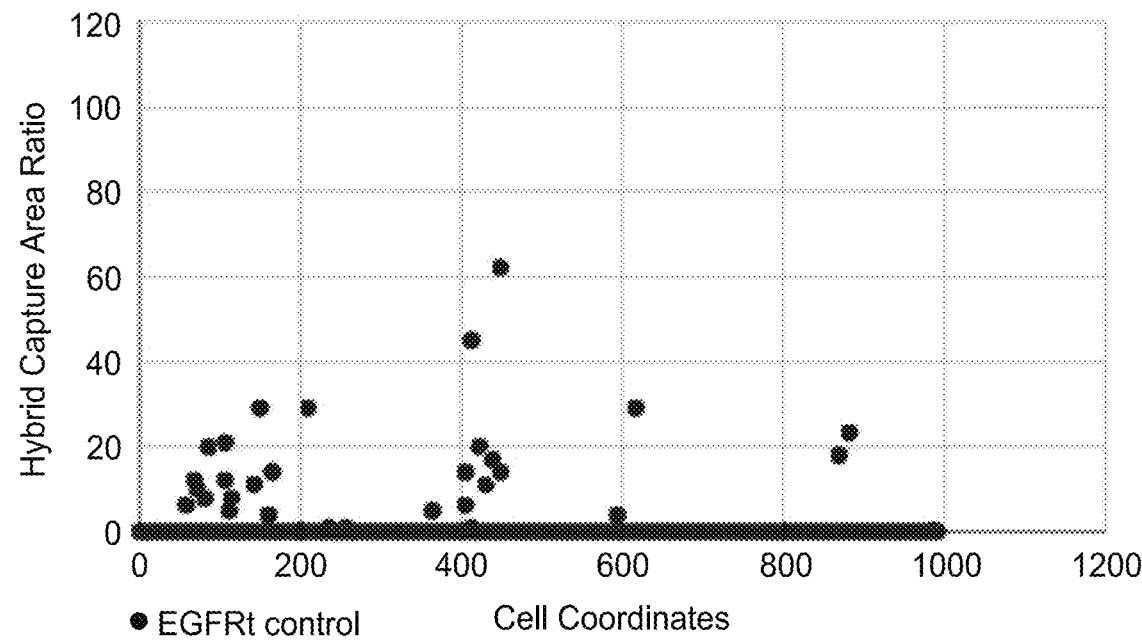
Figure 23:
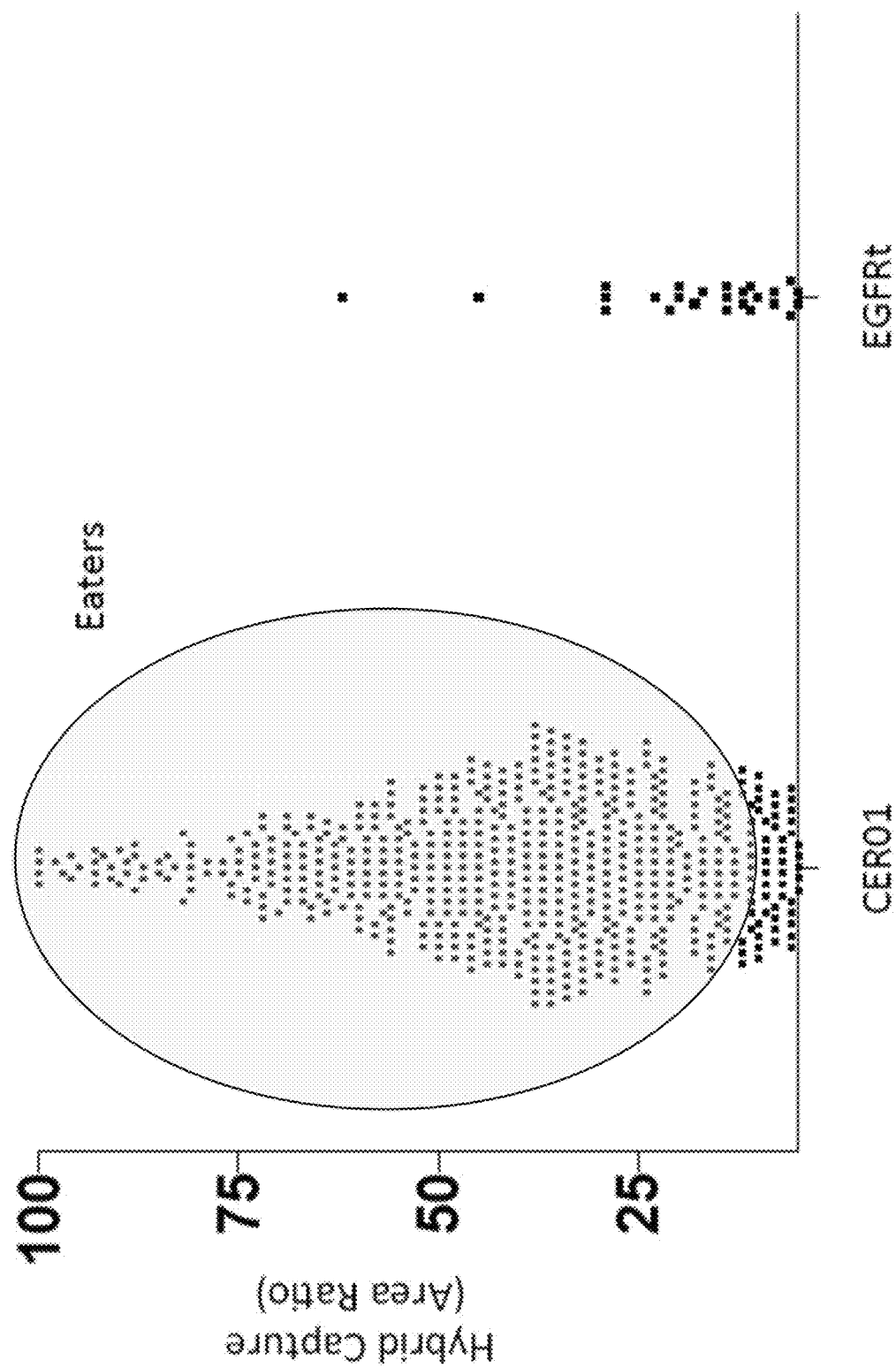
FIG. 23 shows a scatterplot of hybrid cell counts extracting CT26 target cell area from CER01+ Ba/F3 cells or EGFRt+ control Ba/F3 cells. The area ratio represents the overlay area of CT26 cells within Ba/F3 cells.
Figure 24A:
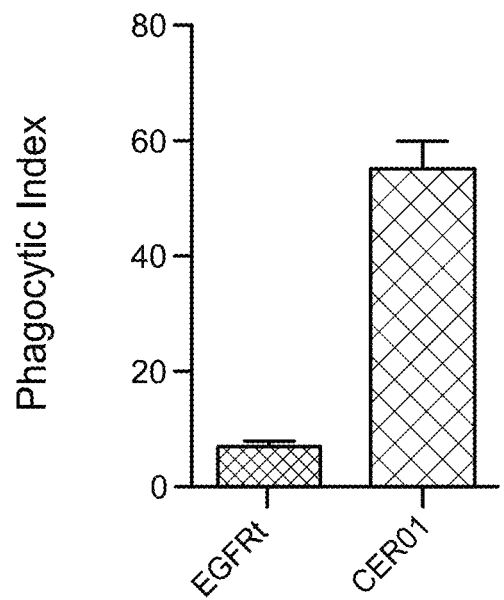
FIGS. 24A-24B show frequency of phagocytosis (A) and phagocytic index (B) of CER01+ Ba/F3 cells or EGFRt+ control Ba/F3 cells co-cultured with CT26 colon carcinoma cells.
Figure 24B:
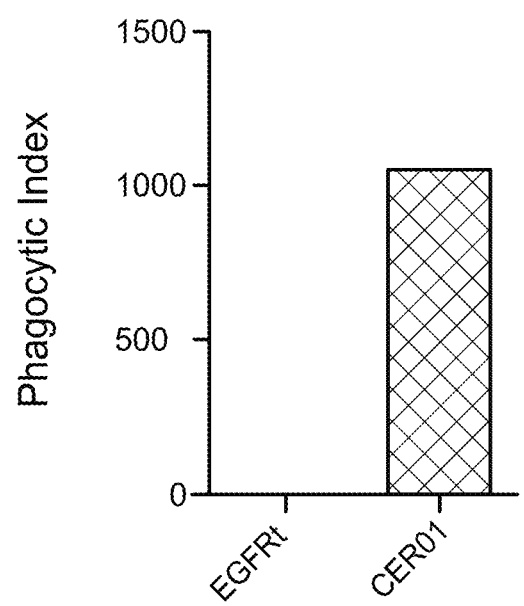

A hybrid capture algorithm that detects fluorescence of pHrodo Red within CELLTRACE Violet staining area was applied to fluorescent images to quantify the area of engulfed target cells/area of CER$^+$ B cells. FIG. 22 shows histogram plots of hybrid cell counts extracting CT26 target cell area within Ba/F3 cells transduced with CER01$^+$ EGFR$^+$ (FIG. 22A) or EGFR$^+$ control (FIG. 22B). FIG. 23 shows a scatterplot of hybrid cell counts extracting CT26 target cell area within Ba/F3 cells transduced with CER01$^+$ EGFR$^+$ or EGFR$^+$ control. The area ratio represents the co-localization area of CT26 cells within Ba/F3 cells. Frequency of phagocytosis of Ba/F3 cells transduced with CER01$^+$ EGFR$^+$ or EGFR$^+$ control is shown in FIG. 24A. A phagocytic index for CER01+ Ba/F3 cells as compared to EGFRt transduced Ba/F3 control cells is shown in FIG. 24B.

Ba/F3 CER01$^+$ EGFR$^+$ cells were transduced, purified, expanded, and labeled with CELLTRACE™ Violet dye as described above. A20 murine B cell lymphoma cells were treated with staurosporine, stained with pHrodo Red, co-cultured with stained CER01$^+$ tEGFR$^+$ cells at a ratio of 5:1 (target cell:effector cell) as described above for the phagocytosis assay with CT26 cells. Ba/F3 cells transduced with pLenti vector expressing truncated EGFR were used as negative control. Phagocytic events were quantified by fluorescent microscopy (KEYENCE BZ-X710 fluorescence microscope, 20× objective) using the hybrid capture algorithm described above for the assay with CT26 cells.

Figure 25:
FIG. 25 shows a fluorescent microscope image of phagocytosis of A20 lymphoma cells by CER01+ Ba/F3 cells. White arrows indicate phagocytosis events.
Figure 26A:
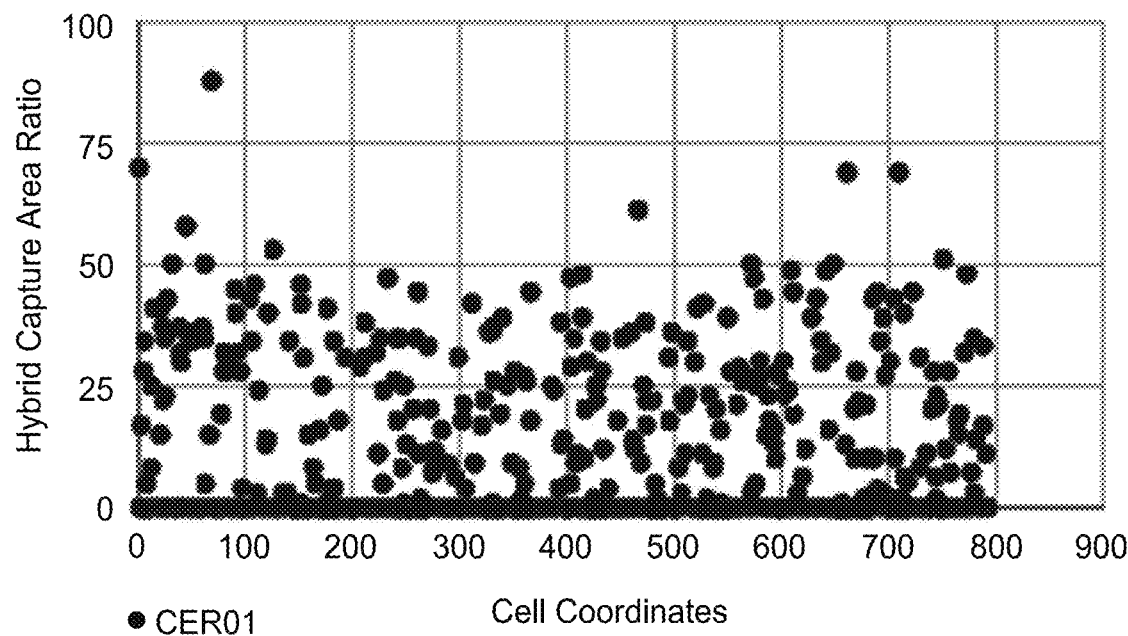
FIGS. 26A-26B—a hybrid capture algorithm was used to detect fluorescence of pHrodo Red stained target cells within CER01+ Ba/F3 cells CELLTRACE Violet stained area on fluorescent images of phagocytosis assay.
Figure 26B:
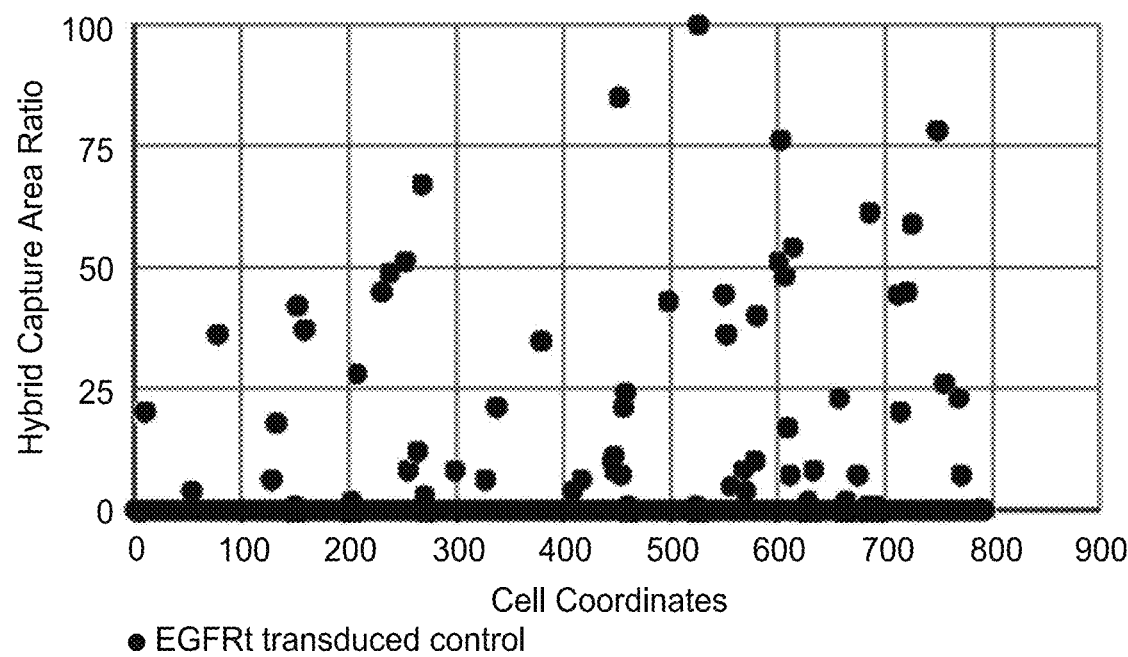
Figure 27:
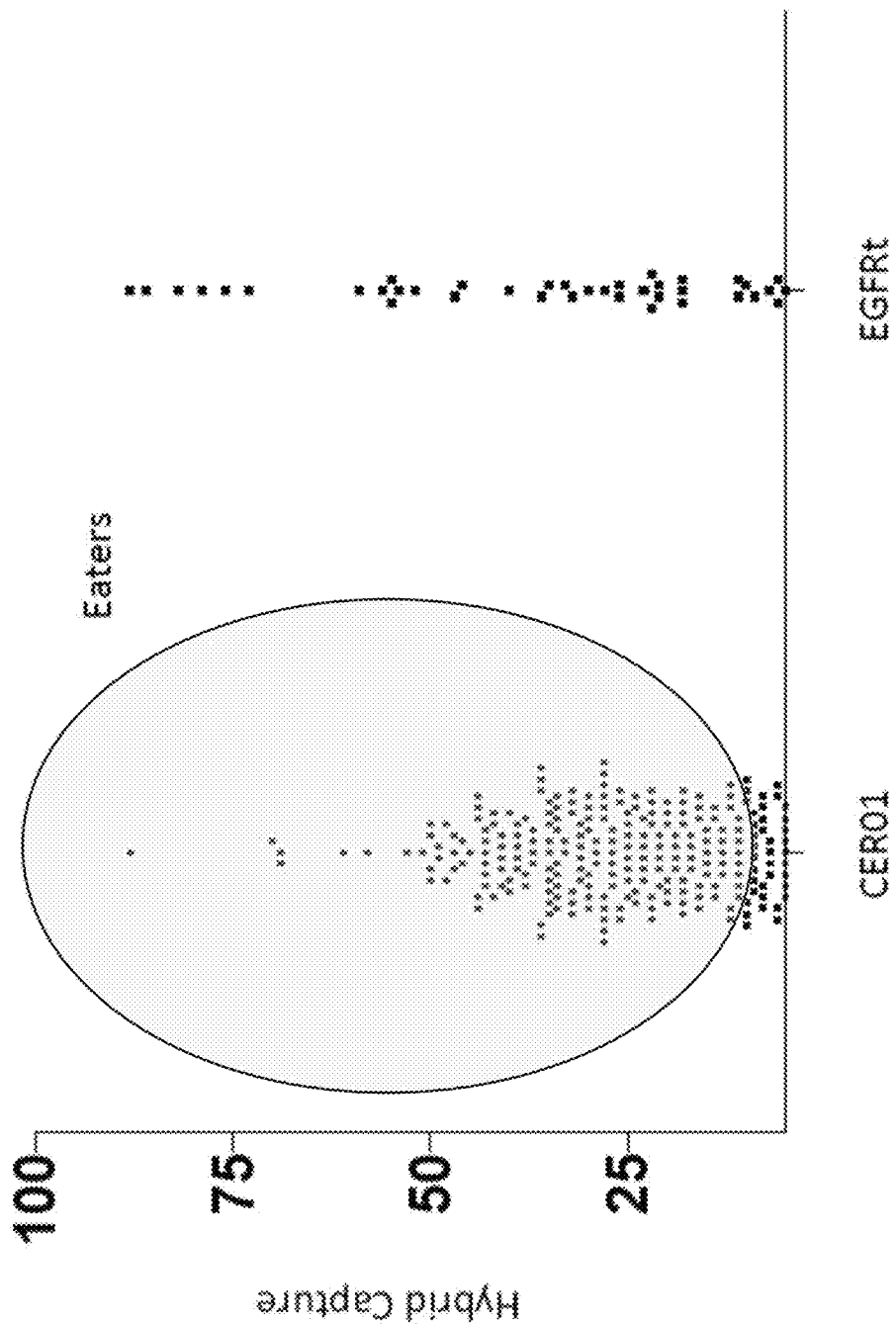
FIG. 27 shows a scatterplot of hybrid cell counts extracting A20 target cell area from CER01+ Ba/F3 cells or EGFRt+ control Ba/F3 cells. The area ratio represents the area of A20 cells within Ba/F3 cells.
Figure 28:
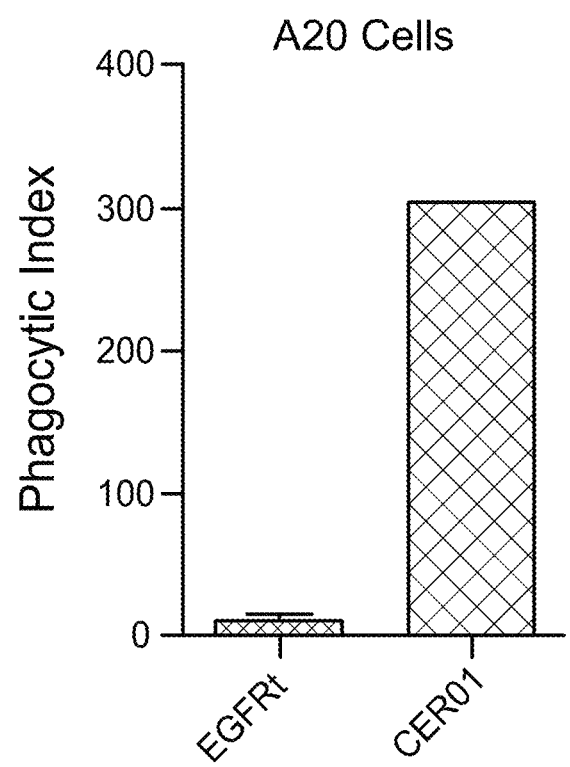
FIG. 28 show a graph of phagocytic index of CER01+ Ba/F3 cells or EGFRt+ control Ba/F3 cells co-cultured with A20 cells.

A fluorescent microscope image showing in vitro phagocytosis of target A20 cells is shown in FIG. 25 (white arrows showing phagocytosis events). FIG. 26 shows histogram plots of hybrid cell counts extracting A20 target cell area within Ba/F3 cells transduced with CER01+ EGFR+ (FIG. 26A) or EGFR+ control (FIG. 26B). FIG. 27 shows a scatterplot of hybrid cell counts extracting A20 target cell area within Ba/F3 cells transduced with CER01+ EGFR+ or EGFR+ control. The area ratio represents the co-localization area of A20 cells within Ba/F3 cells. A phagocytic index for CER01+ Ba/F3 cells as compared to EGFRt transduced Ba/F3 control cells is shown in FIG. 28.

Figure 29:
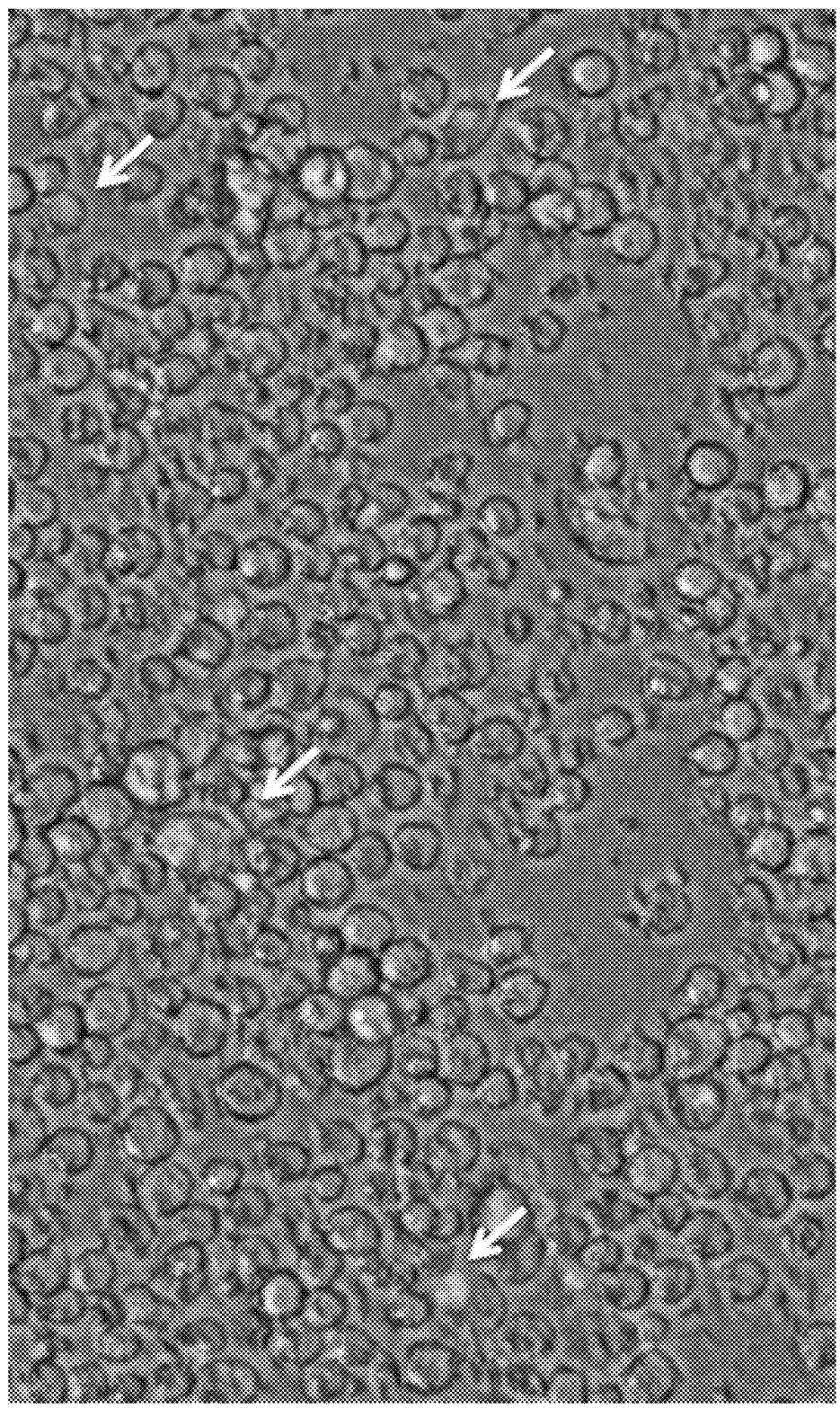
FIG. 29 shows a microscope image of phagocytosis of WR19L T cell lymphoma cells by CER01+ Ba/F3 cells. White arrows indicate phagocytosis events.
Figure 30:
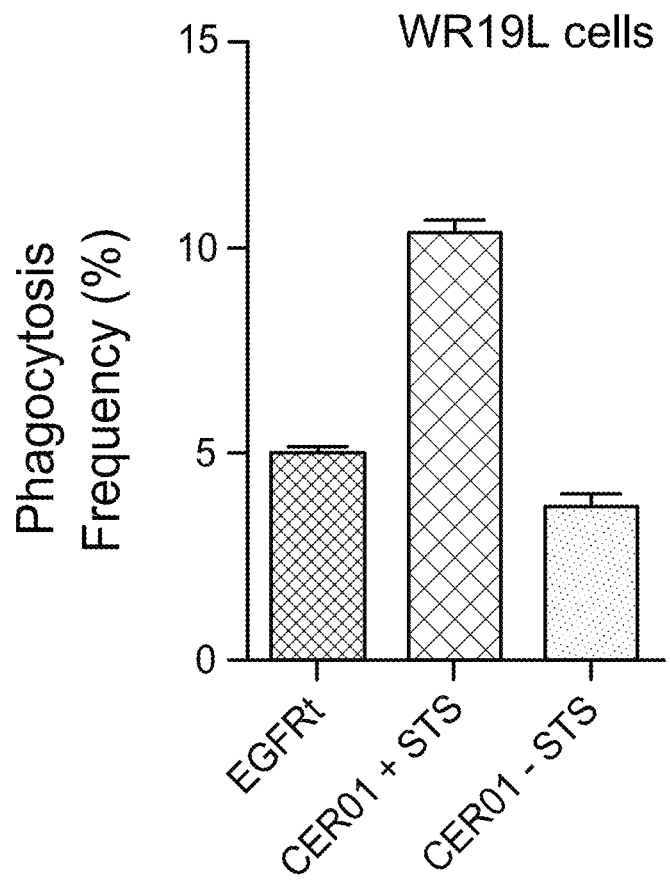
FIG. 30 shows a graph of frequency of phagocytosis of WR19L cells by CER01+ Ba/F3 cells.

Ba/F3 CER01+ EGFR+ cells were also co-cultured with staurosporine treated WR19L murine T cell lymphoma cells as described above in the assay for CT26 cells using a target cell to effector cell ratio of 5:1 and co-incubation time of 3 hours. Ba/F3 cells transduced with pLenti vector expressing truncated EGFR were used as negative control. Phagocytosis of WR19L cells by CER01+ Ba/F3 cells was quantified by fluorescence microscopy as described above. A fluorescent microscope image showing in vitro phagocytosis is shown in FIG. 29 (white arrows show phagocytosis events). FIG. 30 shows frequency of WR19L cell phagocytosis by Ba/F3 cells transduced with CER01+ EGFR+ (+ or − staurosporine (STS)) or EGFR+ control.

Phagocytic Activity of Human CER01+ B Cells Against Human Cell Line

Figure 31A:
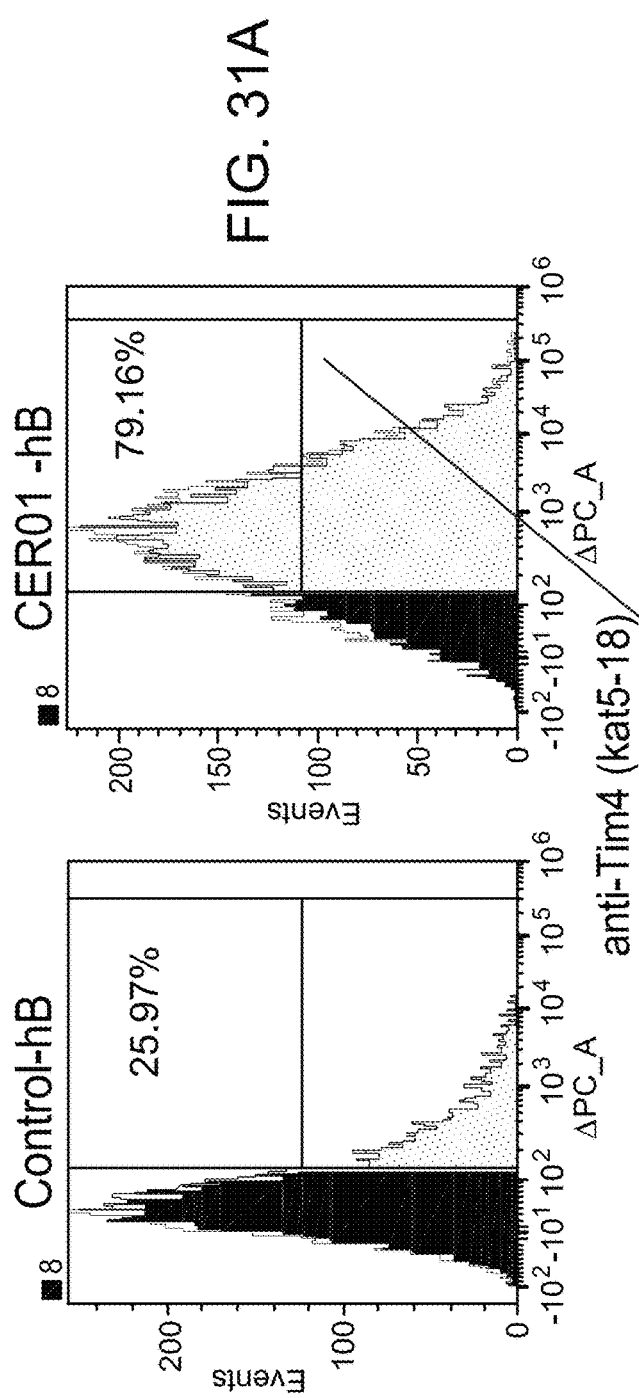
FIGS. 31A-31B show transduction and expansion of CER01+ human primary B cells.
Figure 31B:
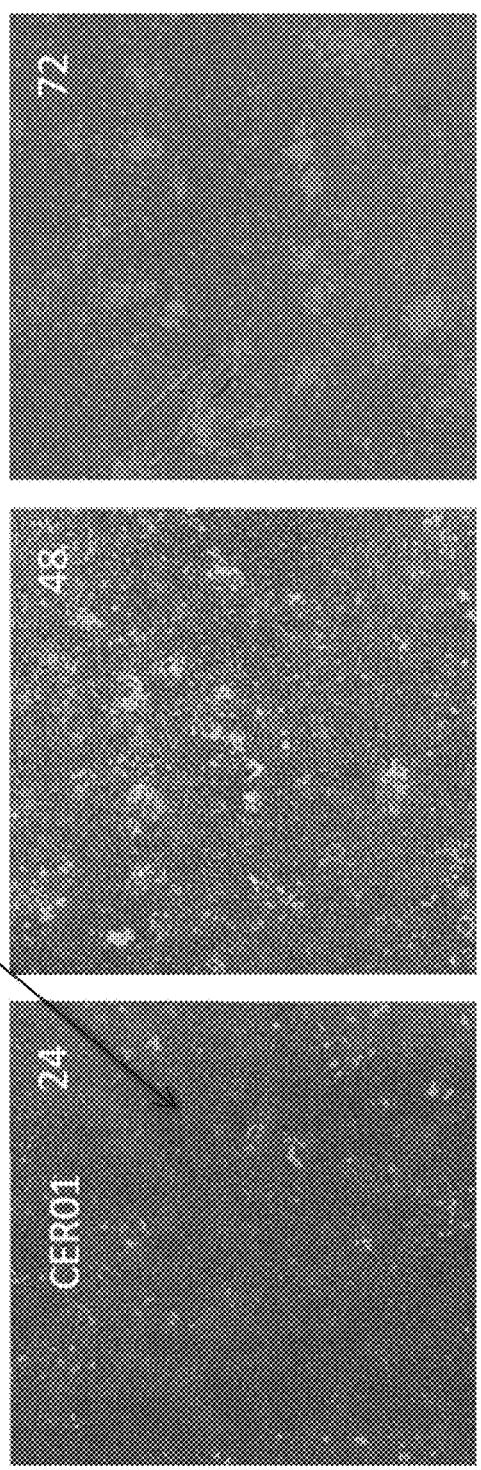

Human primary B cells were transduced with pLenti Tim4-MERTK (CER01) lentivirus expressing truncated EGFR as a transduction marker as described above for Ba/F3 cells, except transduced human B cells were sorted by FACS with a labeled anti-EGFR antibody (Cetuximab) and then stained with a Kat5-18 antibody (Tim4 specific) (Abcam Catalog #176486) (see, FIG. 31A where the % in the right FACS plot represents the % of cells expressing Tim4 binding domain (CER01)). Purified CER01+ B cells were expanded, and imaged at 24 hours, 48 hours, and 72 hours shown in FIG. 31B.

One day prior to setting up the phagocytosis assay, Jurkat human B lymphocytes were cultured in complete RPMI 1640 growth media supplemented with 10% fetal bovine serum and 1% penicillin-streptomycin in a 6 well plate and treated with 1 mM staurosporine for three hours to induce apoptosis. Jurkat cells were washed twice in 1×PBS to remove excess staurosporine and then stained with pHrodo Red (1 ng/µl in PBS) for 15 minutes at room temperature. The Jurkat cells were supplemented with growth media, washed once to remove excess pHrodo Red, and plated on flat bottom 96 well plates at approximately 250,000 cells/well in RPMI 1640 complete media.

Figure 32A:
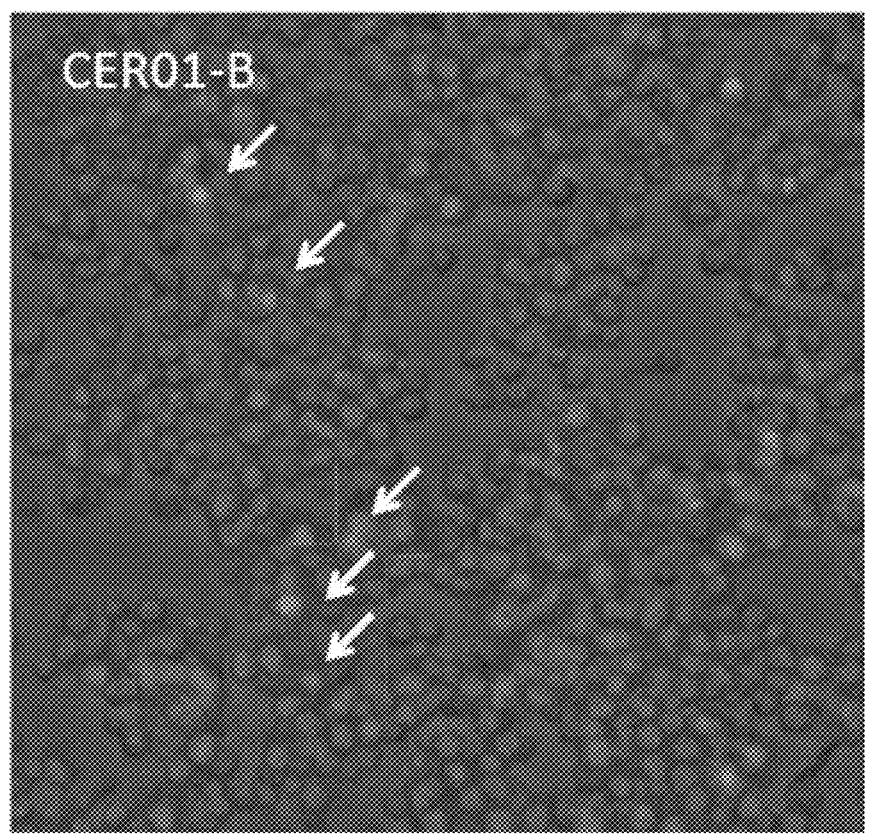
FIGS. 32A-32B shows fluorescent microscope images of in vitro phagocytosis of staurosporine treated Jurkat cells by CER01+ human primary B cells (FIG. 32A) compared to control human primary B cells transduced with truncated EGFR (FIG. 32B). White arrows indicate phagocytosis events.
Figure 32B:
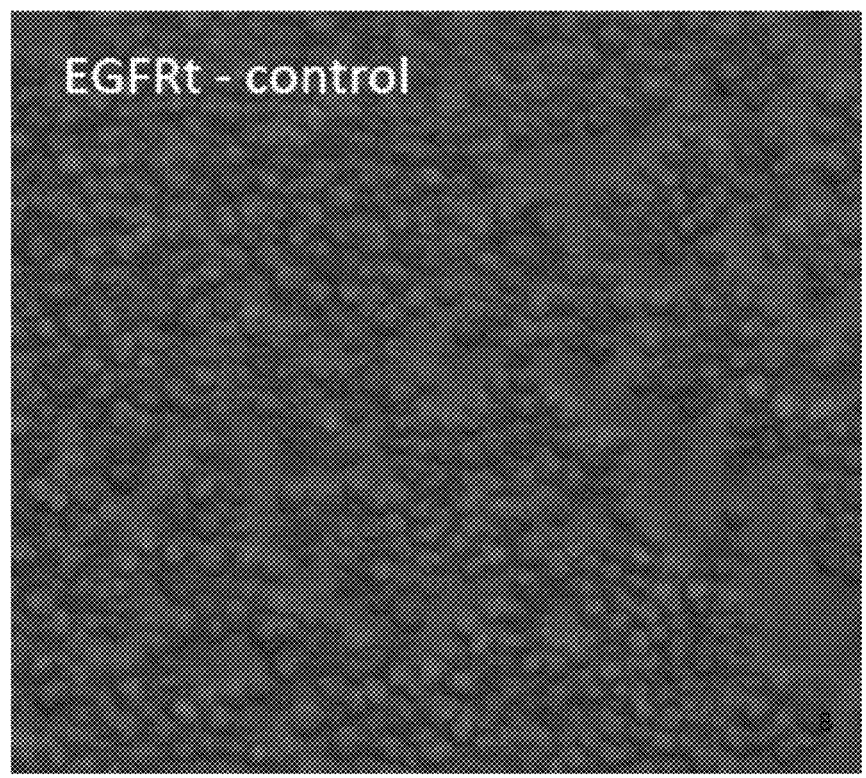

Transduced human primary B cells were washed once with 1×PBS and stained with 1 CELLTRACE Violet in PBS for 10 minutes at 37° C. The human primary B cells were supplemented with growth media, washed once with 1×PBS to remove excess CELLTRACE Violet, and plated onto 96 well plate at approximately 50,000 cells/well in RPMI 1640 complete media. Human primary B cells and Jurkat cells were co-cultured at a target cell to effector cell ratio of 5:1 at 37° C. for 3 hours. After incubation, the co-culture plate was then centrifuged, and the media replaced with PBS supplemented with 2% fetal bovine serum, pH 9. Phagocytic events were quantified by fluorescent microscopy (KEYENCE BZ-X710 fluorescence microscope, 20× objective). Fluorescent microscope image showing in vitro phagocytosis is shown in FIG. 32A for CER01+ B cells and in FIG. 32B for EGFR+ control (white arrows show phagocytosis events).

Figure 33:
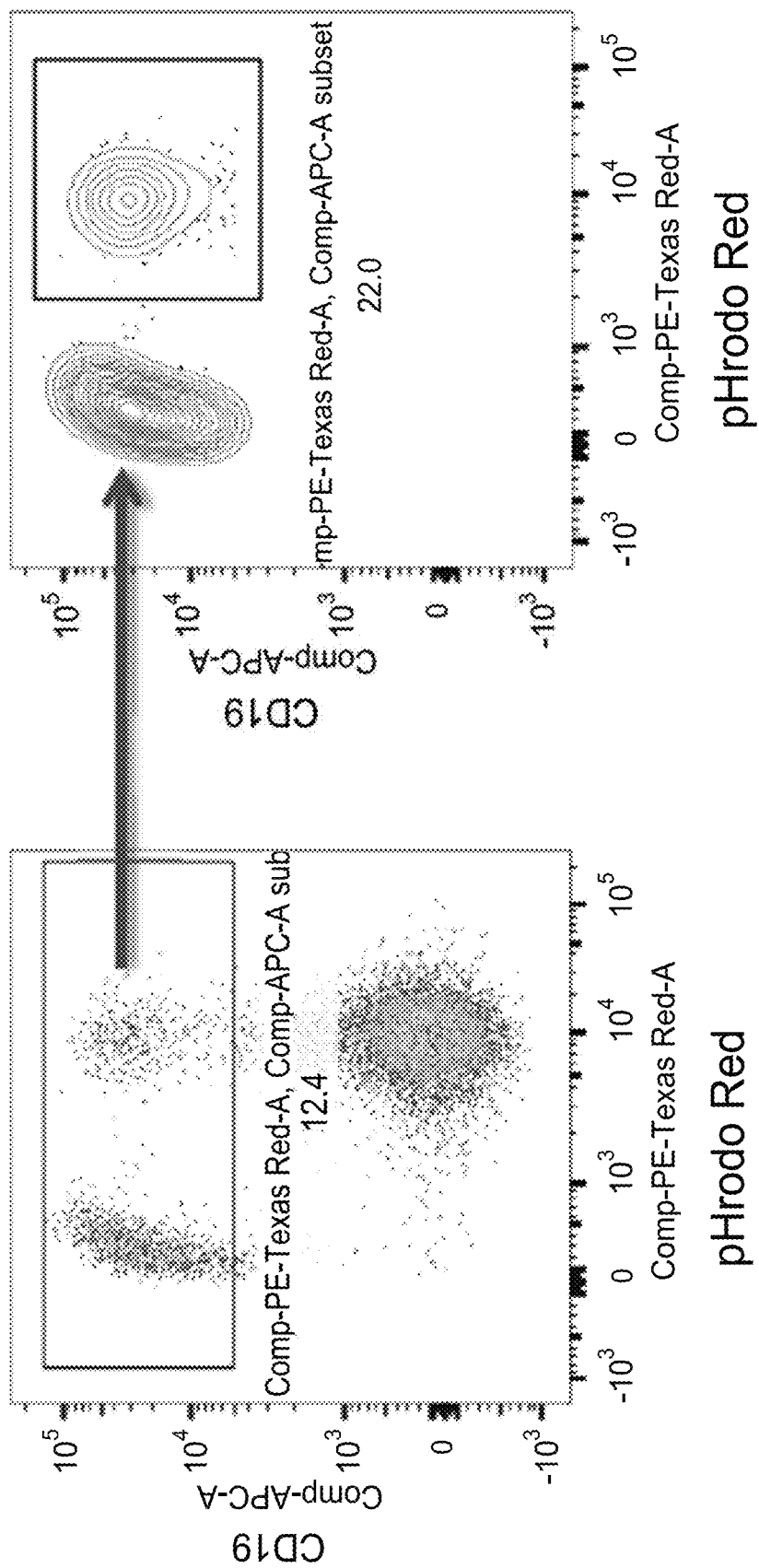
FIG. 33 shows phagocytosis of staurosporine treated, pHrodo Red stained Jurkat cells by CER01+ human primary B cells as analyzed by FACS. Gating was performed on viable CD19+, allophycocyanin (APC)-labeled cells (left plot) and frequency of double positive stained events (APC and pHrodo Red) was defined as phagocytosis events (right plot).
Figure 34:
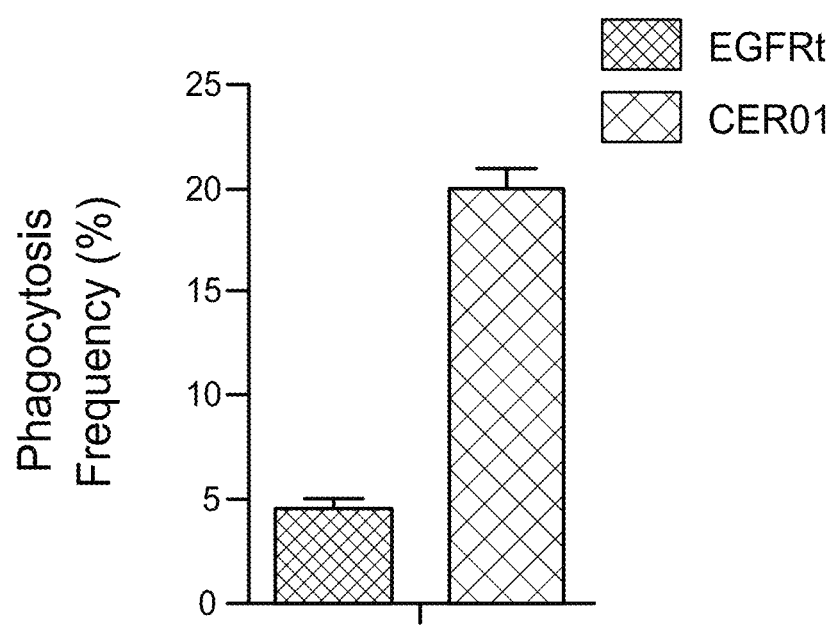
FIG. 34 shows a graph of frequency of phagocytosis of staurosporine treated Jurkat cells co-incubated with CER01+ human primary B cells.

A duplicate 96-well co-culture plate was also set up in parallel for analysis by flow cytometry using a 10:1 target cell to effector cell ratio (approximately 300,000 cells/well pHrodo Red labeled, staurosporine treated Jurkat cells co-cultured with approximately 30,000 cells/well CER01+ transduced human primary B cells). The co-culture plate was centrifuged at 1200 rpm for 5 minutes, media replaced with FACS buffer (PBS+2% fetal bovine serum) containing a 1:50 dilution of allophycocyanin (APC) labeled CD19 antibody to stain human primary B cells. The human primary B cells were incubated with APC labeled CD19 antibody for 30 minutes at 4° C., washed once, and the cell culture plates were supplemented with FACS buffer containing DAPI (4′,6-diamidino-2-phenylindole), which was used as a marker for cell viability. During FACS analysis, gating was performed on viable CD19-APC positive cells (see, FIG. 33 left FACS plot) and evaluated for frequency of CD19 positive-pHrodo Red positive events (double positive events), which were defined as phagocytosis events (see, FIG. 33 right FACS plot). FIG. 34 shows frequency of Jurkat cell phagocytosis by B cells transduced with CER01+ EGFR+ or EGFR+ control.

Figure 35:
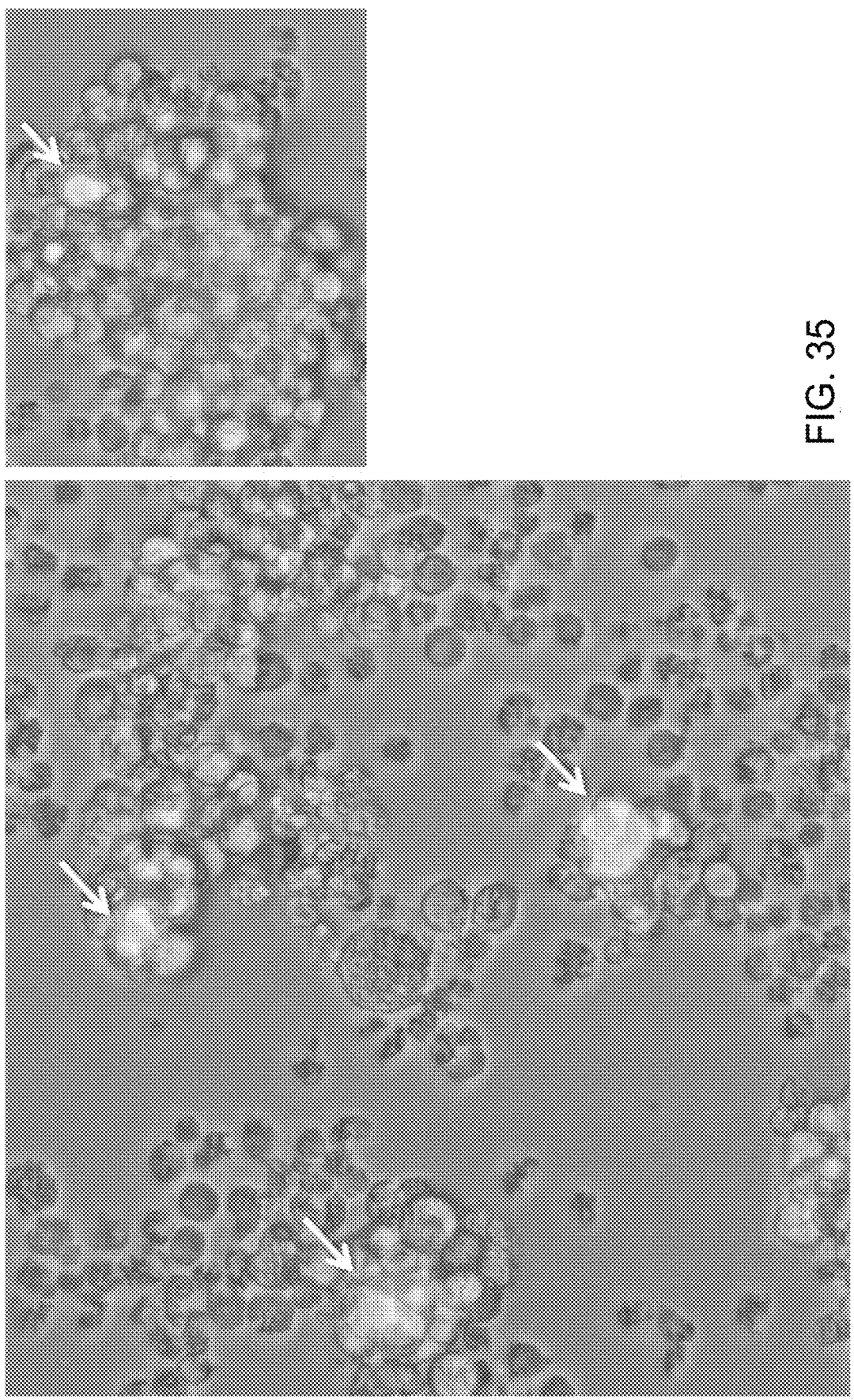
FIG. 35 shows fluorescent microscope images of in vitro phagocytosis of oxaliplatin and fluorouracil treated Jurkat cells by CER01+ human primary B cells. White arrows indicate phagocytosis events.

Phagocytic Activity of Human CER01+ B Cells Against Chemotherapy-Treated Human Cell Line Human primary B cells were transduced with pLenti Tim4-MERTK (CER01) lentivirus expressing truncated EGFR as a transduction marker as described above. One day prior to setting up the phagocytosis assay, Jurkat human B lymphocyte cells were cultured in complete RPMI 1640 growth media supplemented with 10% fetal bovine serum and 1% penicillin-streptomycin in a 6 well plate and treated with oxaliplatin (5 µM) and fluorouracil (5-FU) (10 µM). The following day, target Jurkat cells were collected, washed twice with 1×PBX, and stained with pHrodo Red (1 ng/mL in PBS) for 15 minutes at room temperature. The Jurkat cells were supplemented with growth media, washed once to remove excess pHrodo Red, and plated on flat bottom 96 well plates at approximately 200,000 cells/well in RPMI 1640 complete media. Transduced human primary B cells were washed once with 1×PBS and then stained with CELLTRACE Violet (1 mM in PBS) for 10 minutes at 37° C. The human primary B cells were supplemented with growth media, washed once with 1×PBS to remove excess CELLTRACE Violet, and plated onto a 96 well plate at approximately 50,000 cells in RPMI complete media. Human primary B cells and Jurkat cells were co-cultured at a target cell to effector cell ratio of 4:1 at 37° C. for 3 hours. The plate was then imaged using a 20× objective, Keyence BZ-X710 microscope. FIG. 35 shows fluorescent microscope images showing engulfment of chemotherapy treated Jurkat cells by CER01+ human primary B cells (right image shows enlargement of a phagocytosis event; white arrows indicate phagocytosis).

Example 9

Construction of TIM4-TYRO3 CER "CER08"

Figure 36:
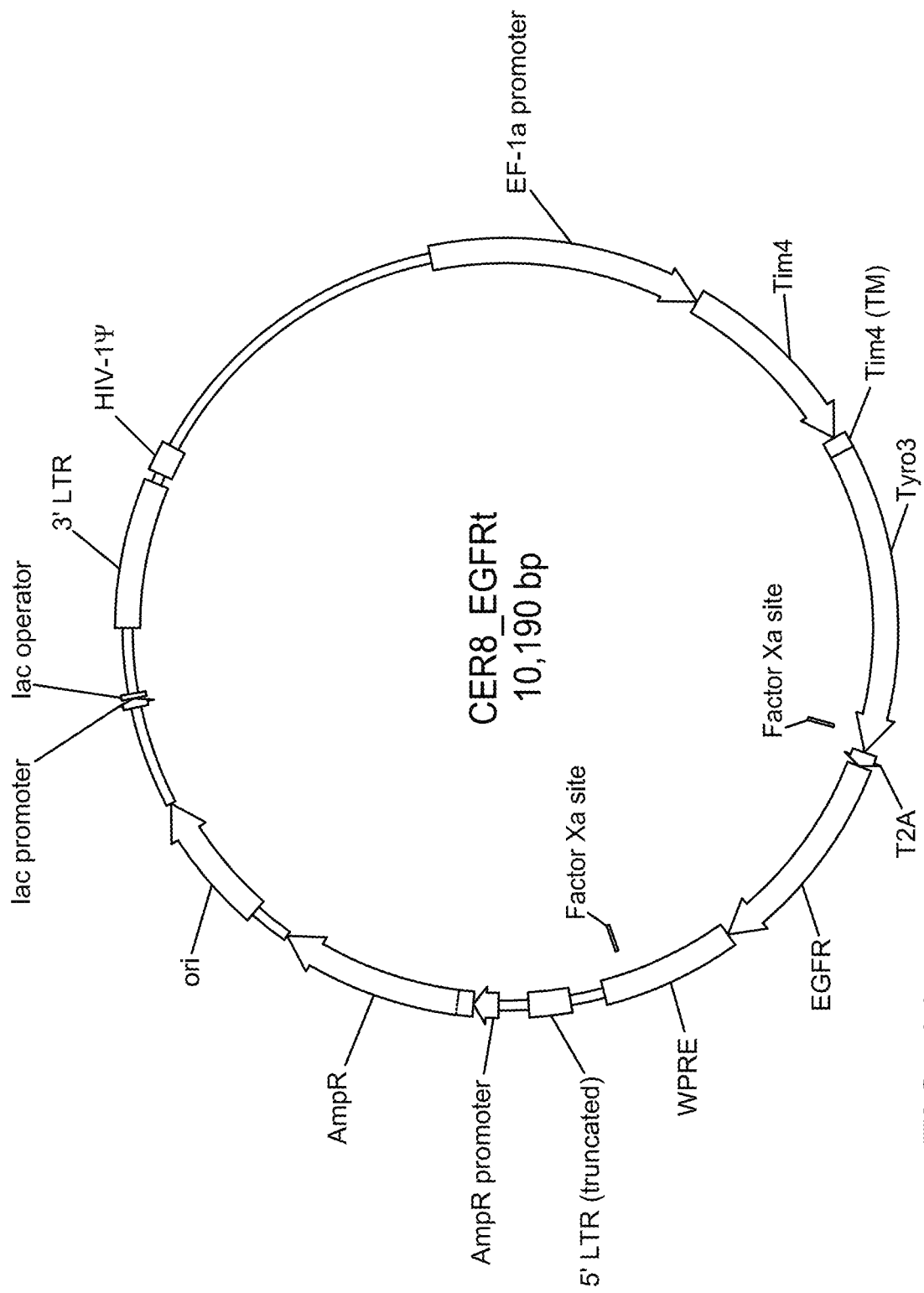
FIG. 36 shows a vector map for a lentiviral vector comprising "CER08" chimeric engulfment receptor having an amino acid sequence of SEQ ID NO:83. CER08 comprises a Tim4 binding domain, a Tim4 transmembrane domain, and a Tyro3 signaling domain. The lentiviral vector also comprises a sequence encoding truncated EGFR (SEQ ID NO:121), which is separated from the CER08 sequence by a viral T2A sequence.

The extracellular domain of the phosphatidylserine binding protein Tim4 (amino acid sequence of SEQ ID NO:73), including the signal peptide (amino acid sequence of SEQ ID NO:72) and transmembrane domain (amino acid sequence of SEQ ID NO:74) (together having a polynucleotide sequence of SEQ ID NO:57), were fused to the intracellular signaling domain of the Tyro3 (SEQ ID NO:45) to create a chimeric engulfment receptor "CER08" (Tim4-Tyro3 CER having an amino acid sequence of SEQ ID NO:83). The Tyro3 signaling domain transduces a signal for engulfment, and Tim4 is a phosphatidylserine binding receptor. The Tim4-Tyro3 (CER08) chimeric engulfment receptor nucleotide sequence was then inserted into the pLenti lentiviral vector along with truncated EGFR as a transduction marker, separated by T2A sequence (see, FIG. 36). Murine Ba/F3 B-cells were transduced with pLenti vector expressing Tim4-Tyro3 (CER08) and EGFRt, expanded, sorted by FACs, and used for in vitro studies as described in Example 8.

Phagocytic Activity Against Primary Apoptotic Thymocytes

Primary C3H mouse thymocytes were isolated, treated with dexamethasone, and stained with pHrodo Red as described in Example 8. Ba/F3 CER08$^+$ tEGFR$^+$ cells were labeled with CELLTRACE™ Violet dye as described in Example 8. Co-culture experiments were carried out at a 10:1 target cell to effector cell ratio, and Ba/F3 CER08'EGFR$^+$ cells were quantified for phagocytosis by fluorescence microscopy and FACs as described in Example 8. Ba/F3 cells transduced with pLenti vector expressing truncated EGFR were used as a negative control.

Figure 37B:
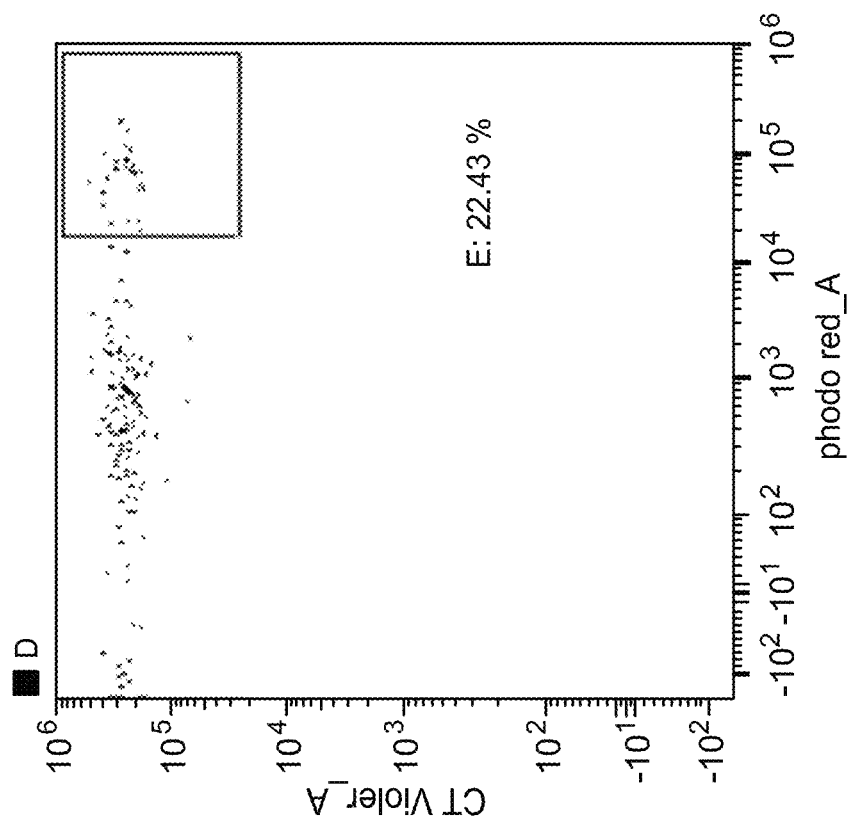
FIGS. 37A-37B show FACS plots of viable, CER08+ modified Ba/F3 cells (FIG. 37A) and cell populations staining double positive for pHrodo red and CELLTRACE Violet representing frequency of phagocytosis (FIG. 37B) in a co-culture of dexamethasone treated, pHrodo Red stained thymocytes with CELLTRACE Violet stained, CER08+ mouse Ba/F3 cells.
Figure 37A:
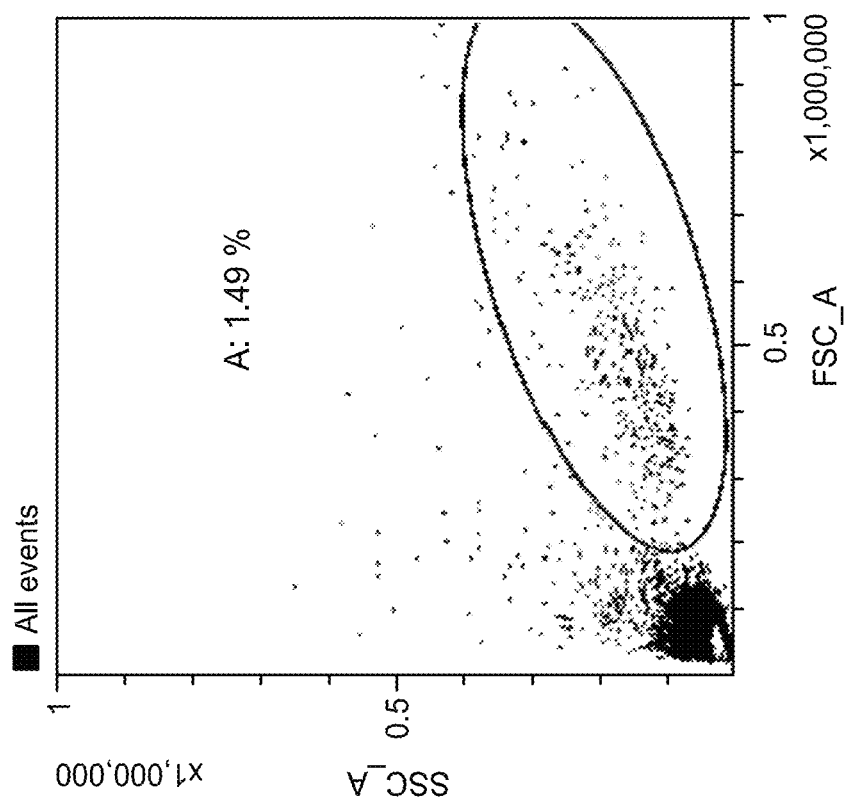

The quantity of viable, CER08+ transduced Ba/F3 cells as quantified by FACS is shown in FIG. 37A. The frequency of phagocytosis was quantified as the cell population staining double positive for pHrodo Red and CELLTRACE Violet as detected by FACS (see, FIG. 37B).

Fluorescent microscopy showed that CER08$^+$ Ba/F3 cells engulf dexamethasone-treated thymocytes as compared to tEGFR transduced Ba/F3 control cells (white arrows indicate engulfment events) (see, FIGS. 38A-38B). High magnification of an engulfment event is shown in the right of FIG. 38B.

Figures 39A, 39B:
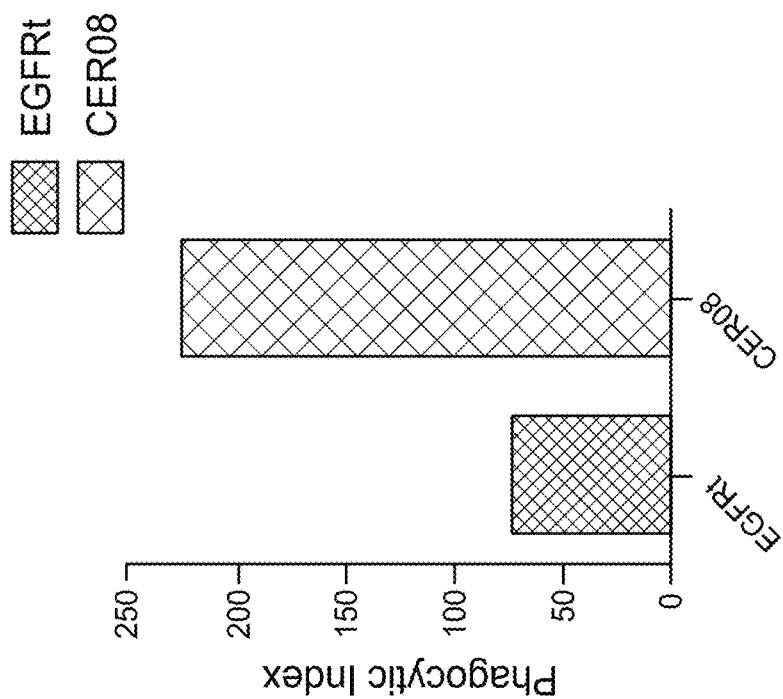
FIGS. 39A-39B show phagocytic index for CER08+ cells or EGFRt+ control Ba/F3 cells.

A phagocytic index was calculated by multiplying [mean of total number of engulfed target cells/total number of counted CER modified cells (e.g., phagocytic frequency)] by [average area of target cell staining per CER+ Ba/F3 cell× 100 (e.g., hybrid capture)] as compared to EGFRt transduced Ba/F3control cells (see, FIGS. 39A-39B).

Example 10

Construction of TIM4-DAP12 CER "CER09"

Figure 40:
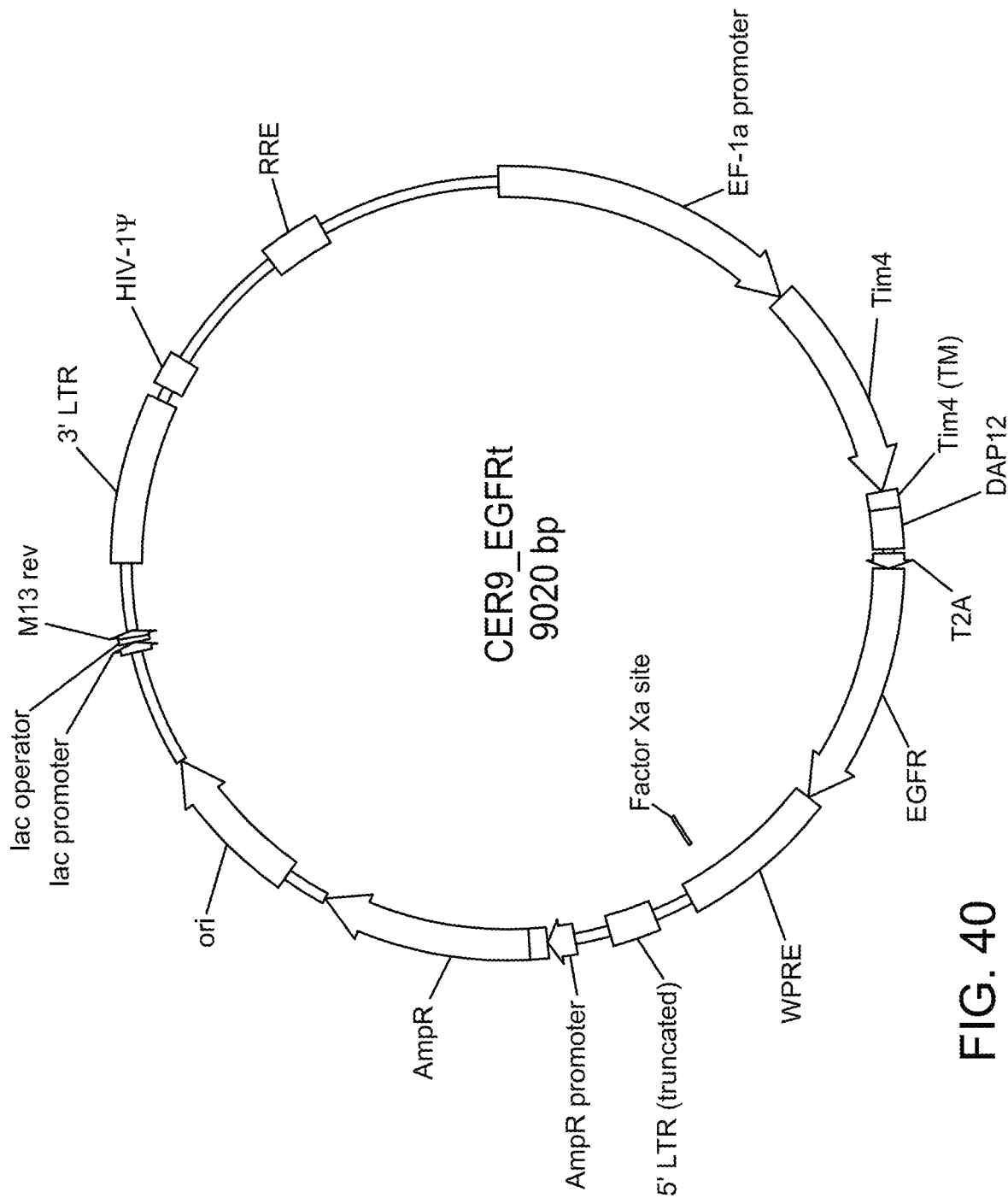
FIG. 40 shows a vector map for a lentiviral vector comprising "CER09" chimeric engulfment receptor having an amino acid sequence of SEQ ID NO:84. CER09 comprises a Tim4 binding domain, a Tim4 transmembrane domain, and a DAP12 signaling domain. The lentiviral vector also comprises a sequence encoding truncated EGFR (SEQ ID NO:121), which is separated from the CER09 sequence by a viral T2A sequence.

The extracellular domain of the phosphatidylserine binding protein Tim4 (amino acid sequence of SEQ ID NO:73), including the signal peptide (amino acid sequence of SEQ ID NO:72) and transmembrane domain (amino acid sequence of SEQ ID NO:74) (together having a polynucleotide sequence of SEQ ID NO: 57), were fused to the intracellular signaling domain of DAP12 (SEQ ID NO:82) to create a chimeric engulfment receptor "CER09" (Tim4-DAP12 CER having an amino acid sequence of SEQ ID NO:84). The DAP12 transduces a signal for engulfment, and Tim4 is a phosphatidylserine binding receptor. The Tim4-DAP12 (CER09) chimeric engulfment receptor nucleotide sequence was then inserted into the pLenti lentiviral vector along with truncated EGFR as a transduction marker, separated by T2A sequence (see, FIG. 40). Murine Ba/F3 B-cells were transduced with pLenti vector expressing Tim4-DAP12 (CER09) and EGFRt, expanded, sorted by FACs, and used for in vitro studies as described in Example 8.

Phagocytic Activity Against Primary Apoptotic Thymocytes

Primary C3H mouse thymocytes were isolated, treated with dexamethasone, and stained with pHrodo Red as described in Example 8. Ba/F3 CER09$^+$ tEGFR$^+$ cells were labeled with CELLTRACE™ Violet dye as described in Example 8. Co-culture experiments with Ba/F3 CER09$^+$ tEGFR$^+$ cells and primary thymocytes were carried out at a 10:1 target cell to effector cell ratio, and Ba/F3 CER09$^+$ EGFR$^+$ cells were quantified for phagocytosis by fluorescence microscopy and FACs as described in Example 8. Ba/F3 cells transduced with pLenti vector expressing truncated EGFR were used as a negative control.

Figure 41B:
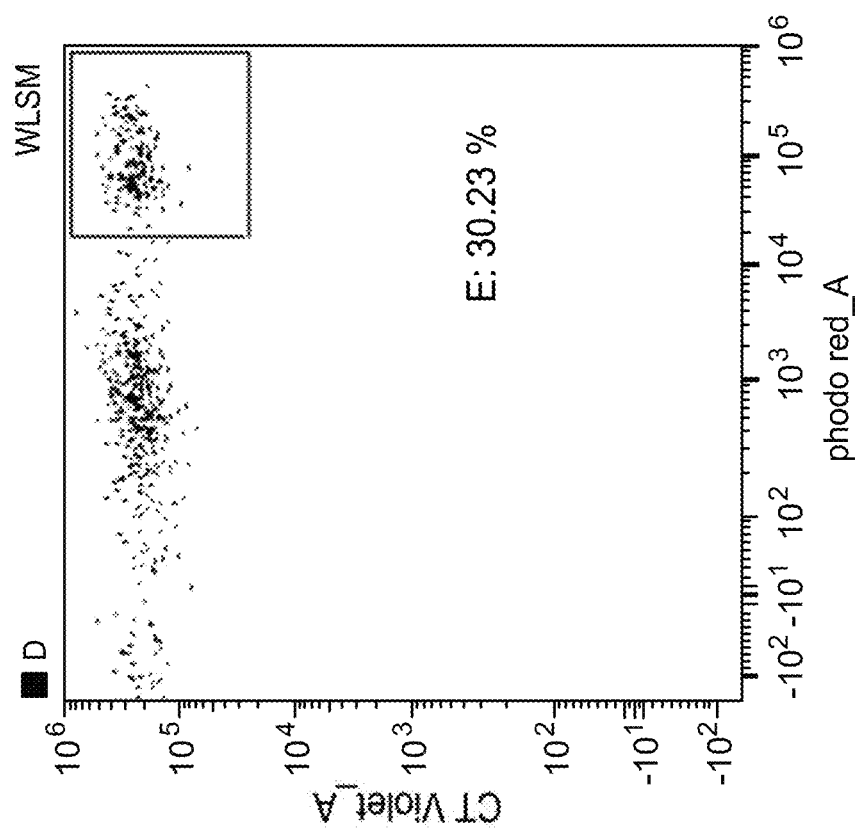
FIGS. 41A-41B show FACS plots of viable, CER09+ modified Ba/F3 cells (FIG. 41A) and cell populations staining double positive for pHrodo red and CELLTRACE Violet representing frequency of phagocytosis (FIG. 41B) in a co-culture of dexamethasone treated, pHrodo Red stained thymocytes with CELLTRACE Violet stained, CER09+ mouse Ba/F3 cells.
Figure 41A:
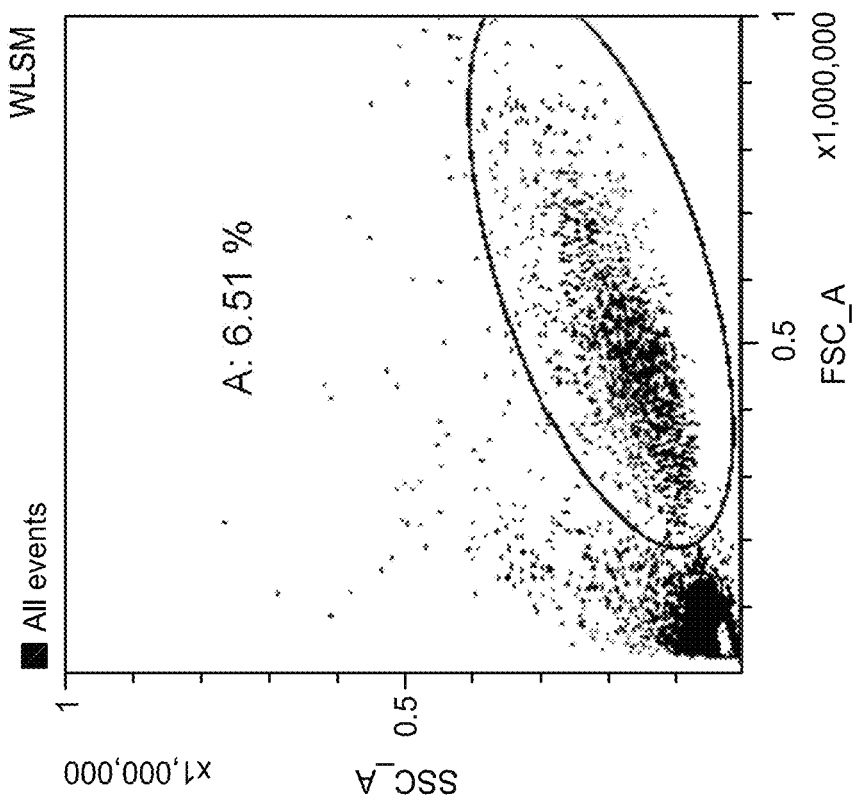

The quantity of viable, CER09+ transduced Ba/F3 cells as quantified by FACS is shown in FIG. 41A. The frequency of phagocytosis was quantified as the cell population staining double positive for pHrodo Red and CELLTRACE Violet as detected by FACS (see, FIG. 41B).

Fluorescent microscopy showed that CER09$^+$ Ba/F3 cells engulf dexamethasone-treated thymocytes as compared to tEGFR transduced Ba/F3 control cells (white arrows indicate engulfment events) (see, FIGS. 42A-42B). High magnification of an engulfment event is shown in the right of FIG. 42B.

Figures 43A, 43B:
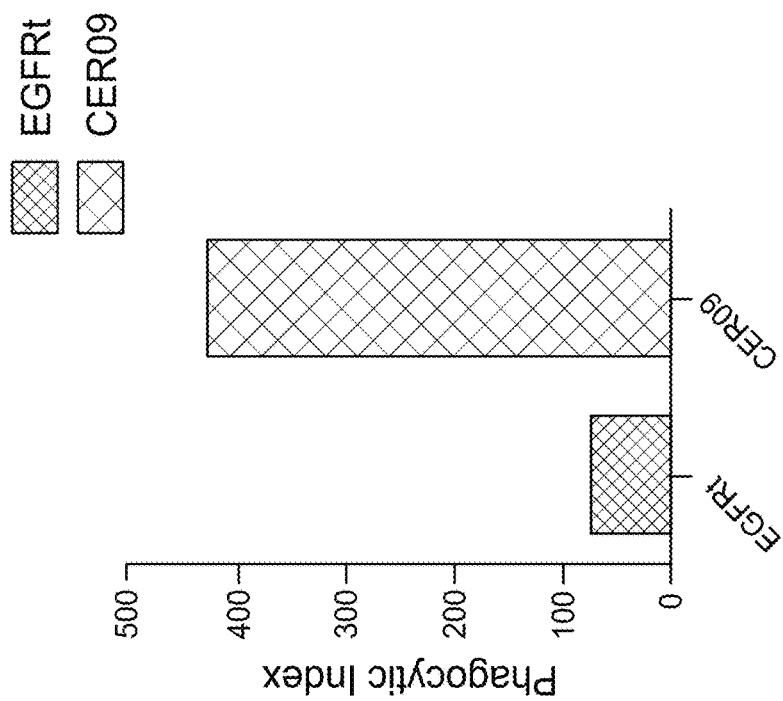
FIGS. 43A-43B show phagocytic index for CER09+ cells or EGFRt+ control Ba/F3 cells.

A phagocytic index was calculated by multiplying [mean of total number of engulfed target cells/total number of counted CER modified cells (e.g., phagocytic frequency)] by [average area of target cell staining per CER+ Ba/F3 cell× 100 (e.g., hybrid capture)] as compared to EGFRt transduced Ba/F3control cells (see, FIGS. 43A-43B).

Phagocytic Activity Against Murine Cell Lines

Figure 44B:
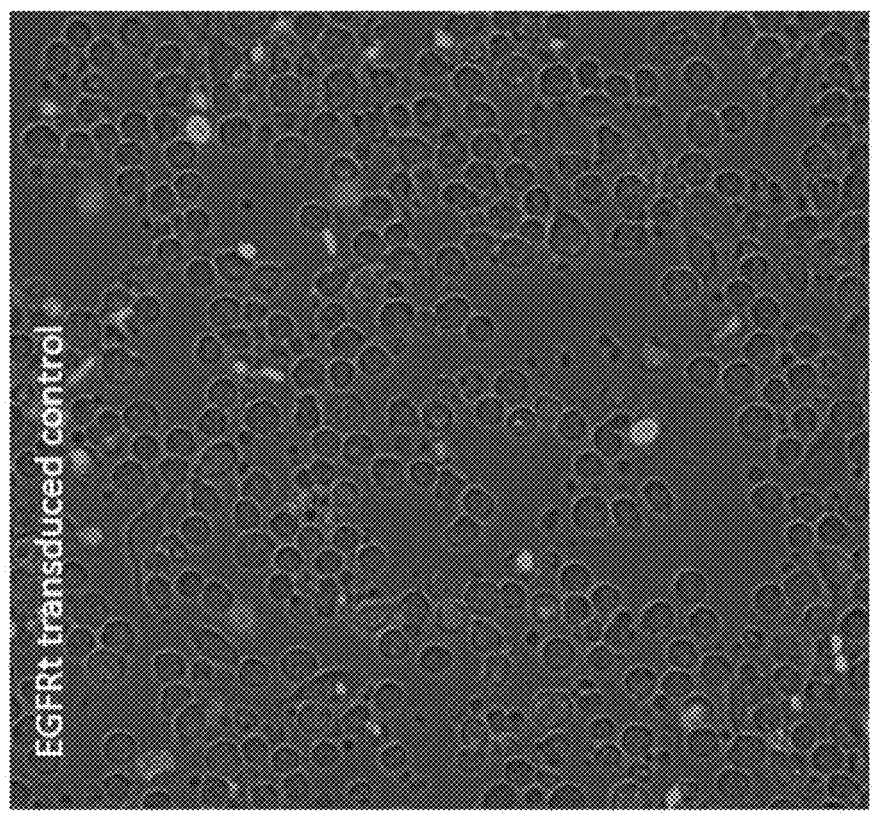
FIGS. 44A-44B show fluorescent microscope images of in vitro phagocytosis of staurosporine treated CT26 colon carcincoma cells by CER09+ Ba/F3 cells (FIG. 44A) and EGFRt+ control Ba/F3 cells. White arrows indicate phagocytosis events.
Figure 44A:
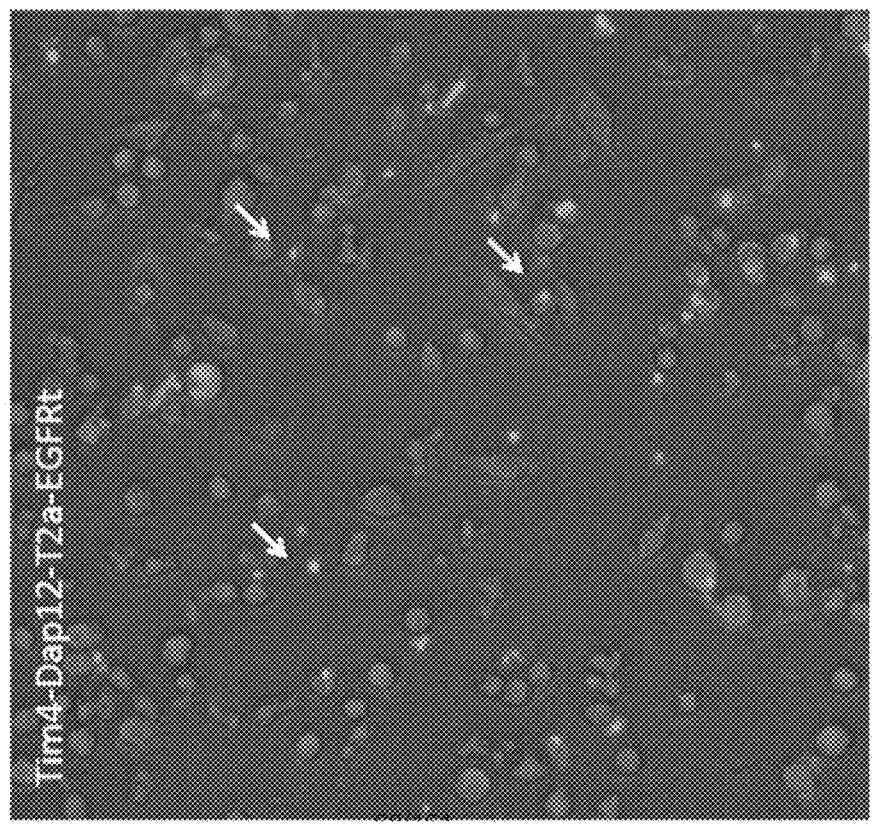

Ba/F3 CER09$^+$ tEGFR$^+$ cells were labeled with CELLTRACE™ Violet dye as described in Example 8. CT26 murine colon carcinoma cells were treated with staurosporine, labeled with pHrodo Red and co-cultured with Ba/F3 CER09$^+$ tEGFR$^+$ cells at a target cell to effector cell ratio of 5:1 for 3 hours as described in Example 8. Phagocytosis of CT26 cells by CER09$^+$ Ba/F3 cells was quantified by fluorescence microscopy and FACs as described in Example 8. Ba/F3 cells transduced with pLenti vector expressing truncated EGFR were used as a negative control. Fluorescent microscope images showing in vitro phagocytosis by CER09+ Ba/F3 cells and EGFRt control cells are shown in FIGS. 44A-44B (white arrows show phagocytosis events). CT26 cells labeled with pHrodo Red fluoresce inside the low pH compartments of lysosomes when engulfed (outlined in pink).

Figure 45:
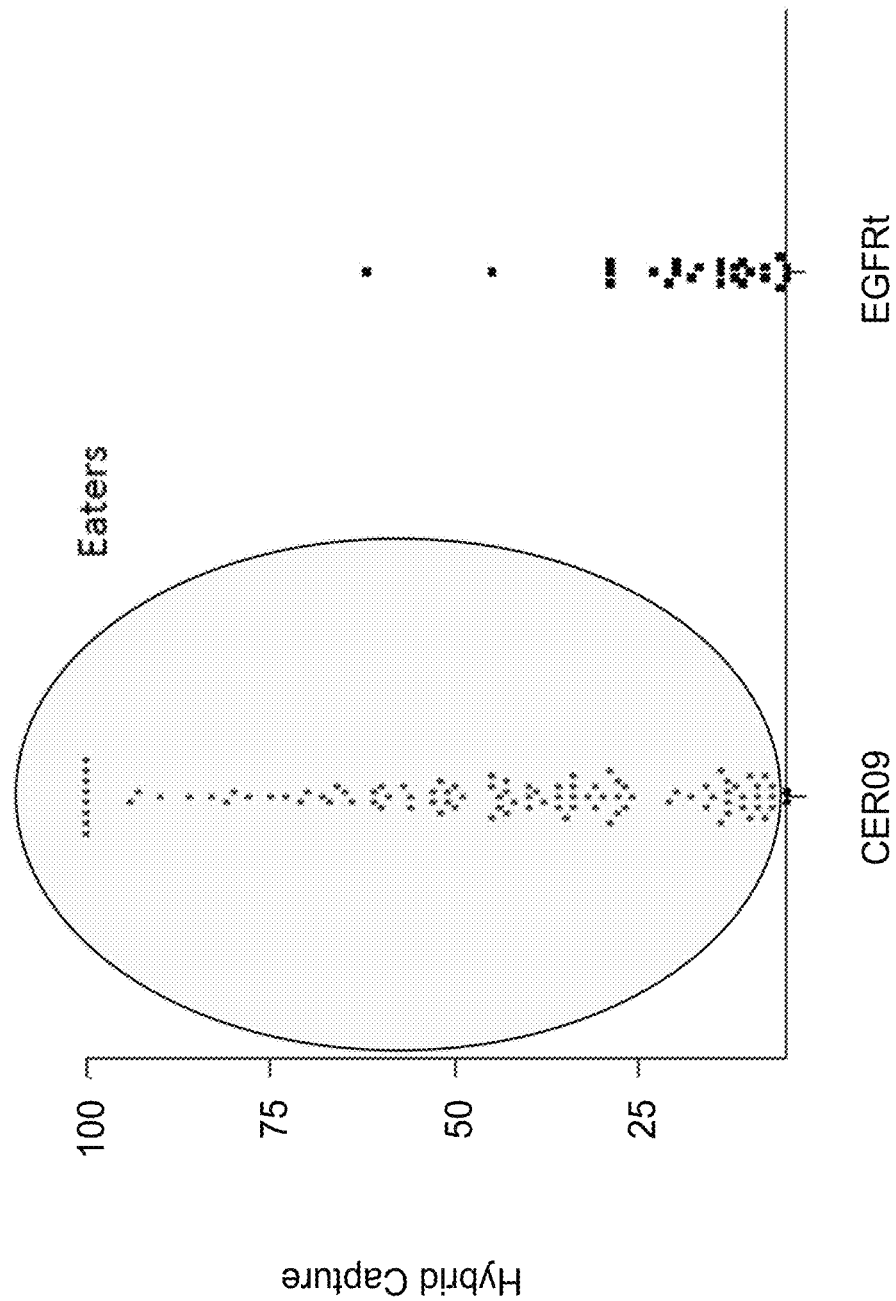
FIG. 45 shows a scatterplot of hybrid cell counts extracting CT26 target cell area from CER09+ Ba/F3 cells or EGFRt+ control Ba/F3 cells. The area ratio represents the area of CT26 cells within Ba/F3 cells.
Figure 46:
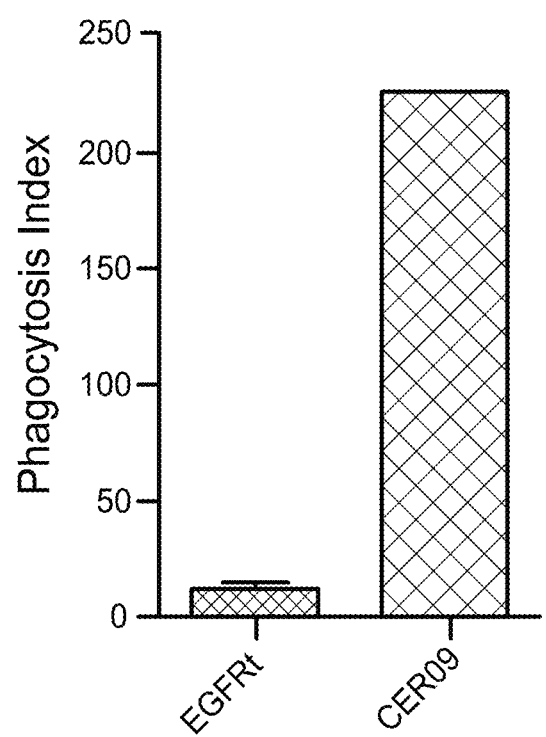
FIG. 46 shows phagocytic index for CER09+ cells or EGFRt+ control Ba/F3 cells co-incubated with staurosporine treated CT26 cells.

A hybrid capture algorithm that detects fluorescence of pHrodo Red within CELLTRACE Violet staining area was applied to fluorescent images to quantify the area of engulfed target cells/area of CER$^+$ B cells. FIG. 45 shows a scatterplot of hybrid cell counts extracting CT26 target cell area within Ba/F3 cells transduced with CER09$^+$ tEGFR$^+$ or tEGFR$^+$ control. The area ratio represents the co-localization area of CT26 cells within Ba/F3 cells. A phagocytic index for CER09+ Ba/F3 cells as compared to EGFRt transduced Ba/F3 control cells is shown in FIG. 46.

Figure 47:
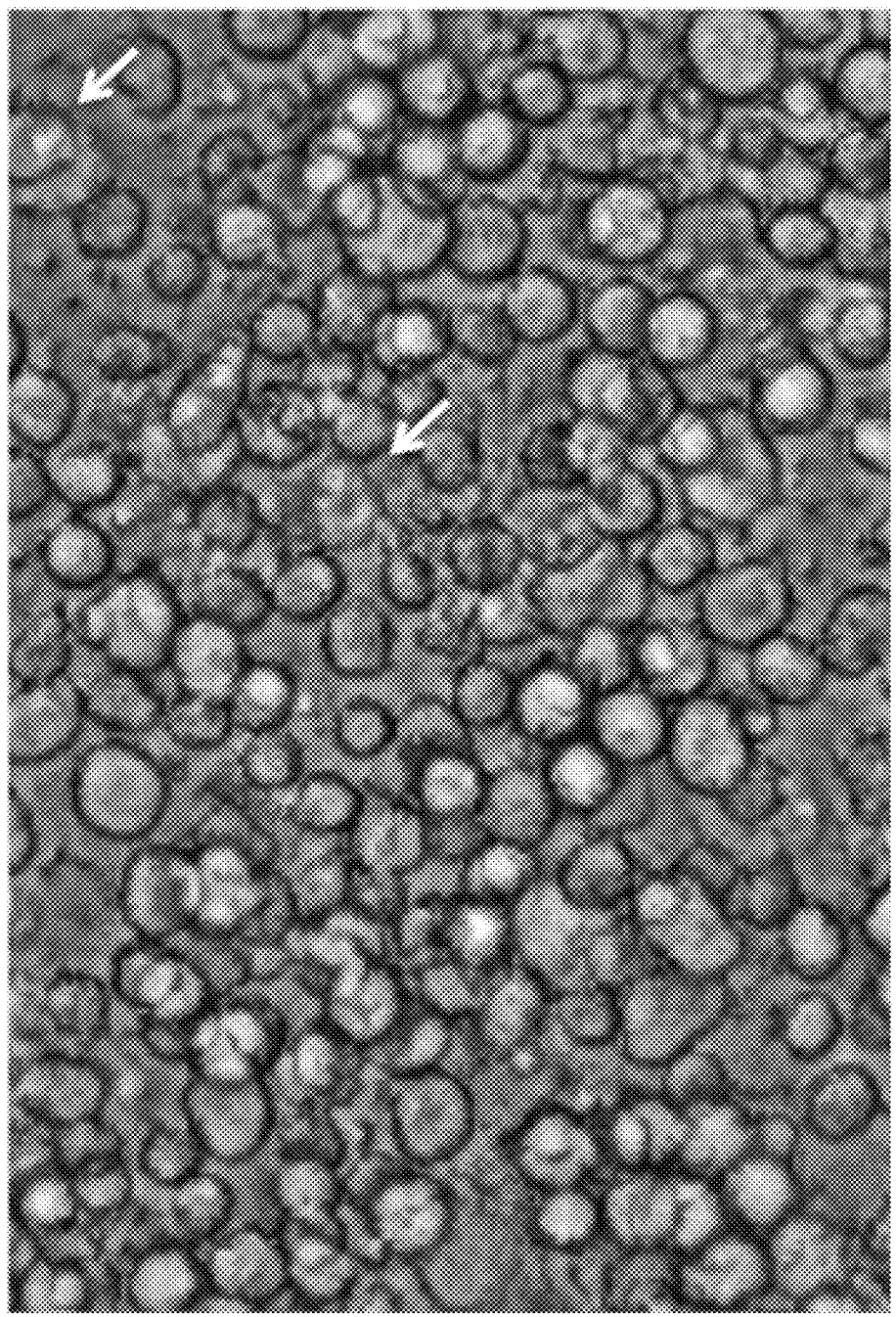
FIG. 47 shows a fluorescent microscope image of in vitro phagocytosis of staurosporine treated WR19L lymphoma cells by CER09+ Ba/F3 cells. White arrows indicate phagocytosis events.

WR19L murine lymphoma cells were treated with staurosporine, labeled with pHrodo Red and co-cultured with CELLTRACE Violet labeled Ba/F3 CER09$^+$ EGFR$^+$ cells at a target cell to effector cell ratio of 5:1 for 3 hours as described in Example 8. Phagocytosis of WR19L cells by CER09$^+$ Ba/F3 cells was quantified by fluorescence microscopy as described in Example 8. Ba/F3 cells transduced with pLenti vector expressing truncated EGFR were used as a negative control. Fluorescent microscope imaging showed in vitro phagocytosis of WR19L cells by CER09+ Ba/F3 cells is shown in FIG. 47 (white arrows show phagocytosis events).

Figure 48:
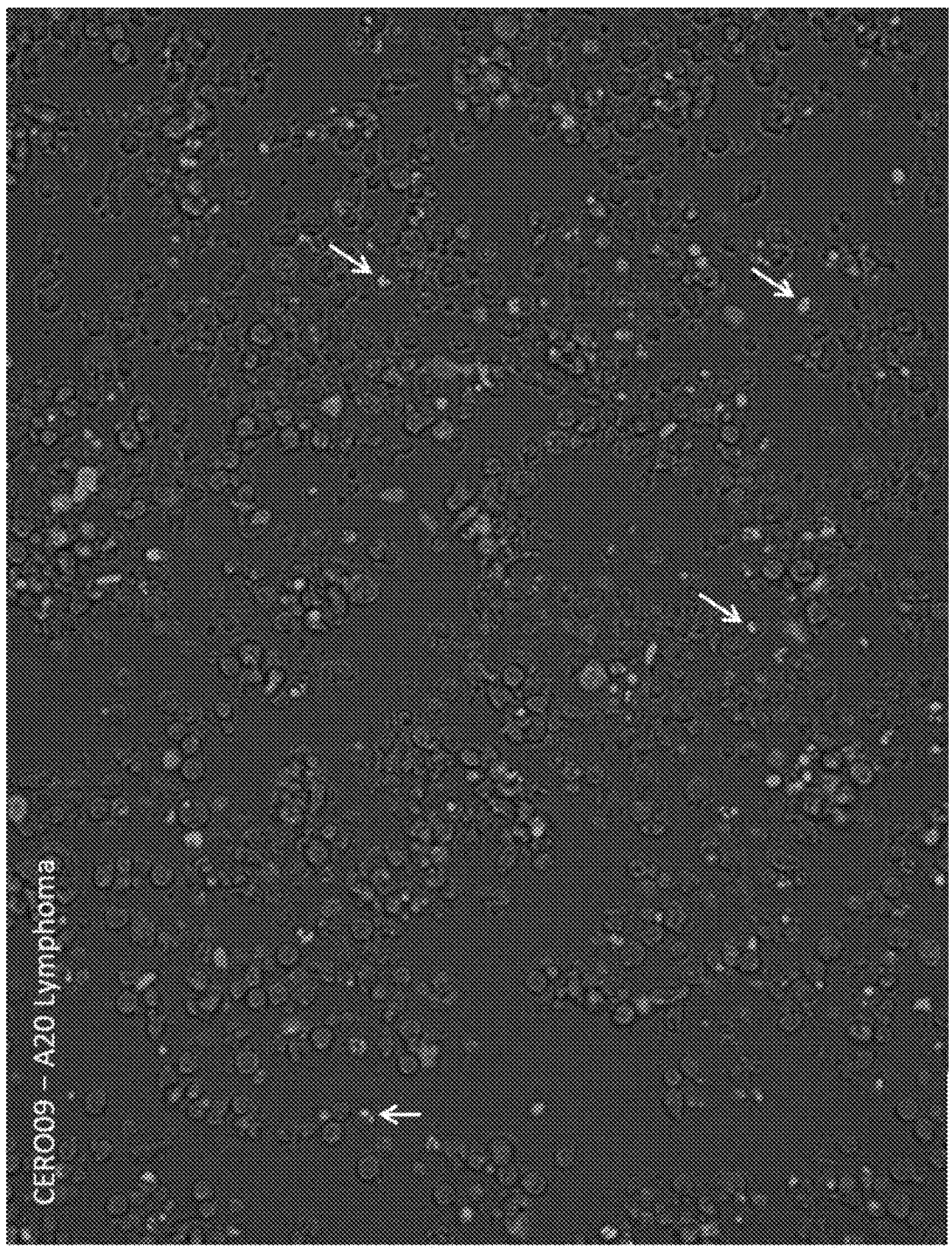
FIG. 48 shows a fluorescent microscope image of in vitro phagocytosis of staurosporine treated A20 lymphoma cells by CER09+ Ba/F3 cells. White arrows indicate phagocytosis events.

A20 murine lymphoma cells were treated with staurosporine, labeled with pHrodo Red and co-cultured with CELLTRACE Violet labeled Ba/F3 CER09$^+$ EGFR$^+$ cells at a target cell to effector cell ratio of 5:1 for 3 hours as described in Example 8. Phagocytosis of A20 cells by CER09$^+$ Ba/F3 cells was quantified by fluorescence microscopy and FACs as described in Example 8. Ba/F3 cells transduced with pLenti vector expressing truncated EGFR were used as a negative control. Fluorescent microscope image showing in vitro phagocytosis of A20 cells by CER09+ Ba/F3 cells is shown in FIG. 48 (white arrows show phagocytosis events).

Phagocytic Activity of Human CER09+ B Cells Against Human Cell Line

Human primary B cells were transduced with pLenti Tim4-DAP12 (CER09) lentivirus expressing truncated EGFR as a transduction marker as described in Example 8. Transduced human B cells were sorted by FACS with a labeled anti-EGFR antibody (Cetuximab) and then stained with a Kat5-18 antibody (Tim4 specific) (Abcam Catalog #176486) (see, FIG. 49A where the % in the right FACS plot represents the % of cells expressing Tim4 binding domain (CER09)). Purified CER09$^+$ B cells were expanded, and imaged at 24 hours, 48 hours, and 72 hours shown in FIG. 49B.

Figure 50:
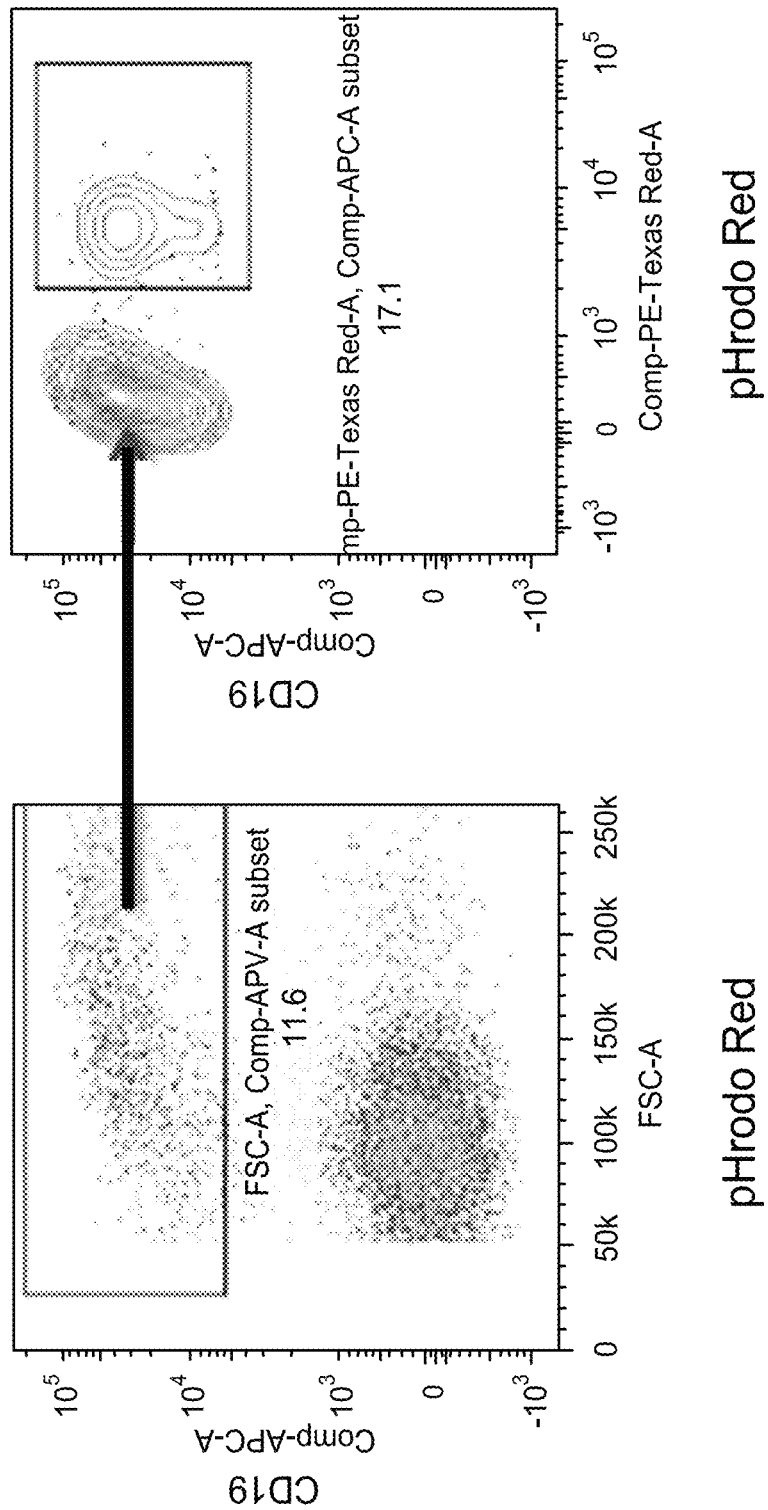
FIG. 50 shows phagocytosis of staurosporine treated, pHrodo Red stained Jurkat cells by CER09+ human primary B cells as analyzed by FACS. Gating was performed on viable CD19+, allophycocyanin (APC)-labeled cells (left plot) and frequency of double positive stained events (APC and pHrodo Red) was defined as phagocytosis events (right plot).
Figure 51:
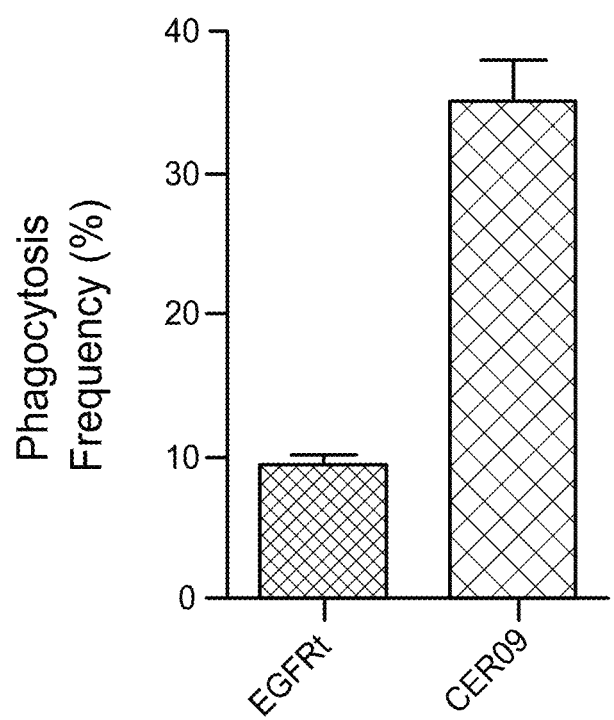
FIG. 51 shows a graph of frequency of phagocytosis of staurosporine treated Jurkat cells by CER09+ human primary B cells or control EGFRt+ human primary B cells.

Jurkat human T lymphocytes were treated with staurosporine, labeled with pHrodo Red, and co-cultured with CER09+ primary B cells in a phagocytosis assay as described in Example 8 using a target cell to effector cell ratio of 5:1 and co-incubation time of 3 hours. Phagocytosis of Jurkat cells by CER09$^+$ human B cells was quantified by fluorescence microscopy and FACs as described in Example 8. The frequency of viable CD19 positive human primary B cells and frequency of CD19 positive-pHrodo Red positive events (double positive events) are shown in FIG. 50 (left and right plots, respectively). FIG. 51 shows frequency of phagocytosis of B cells transduced with CER09+ tEGFR+ or EGFR+ control.

Figure 52:
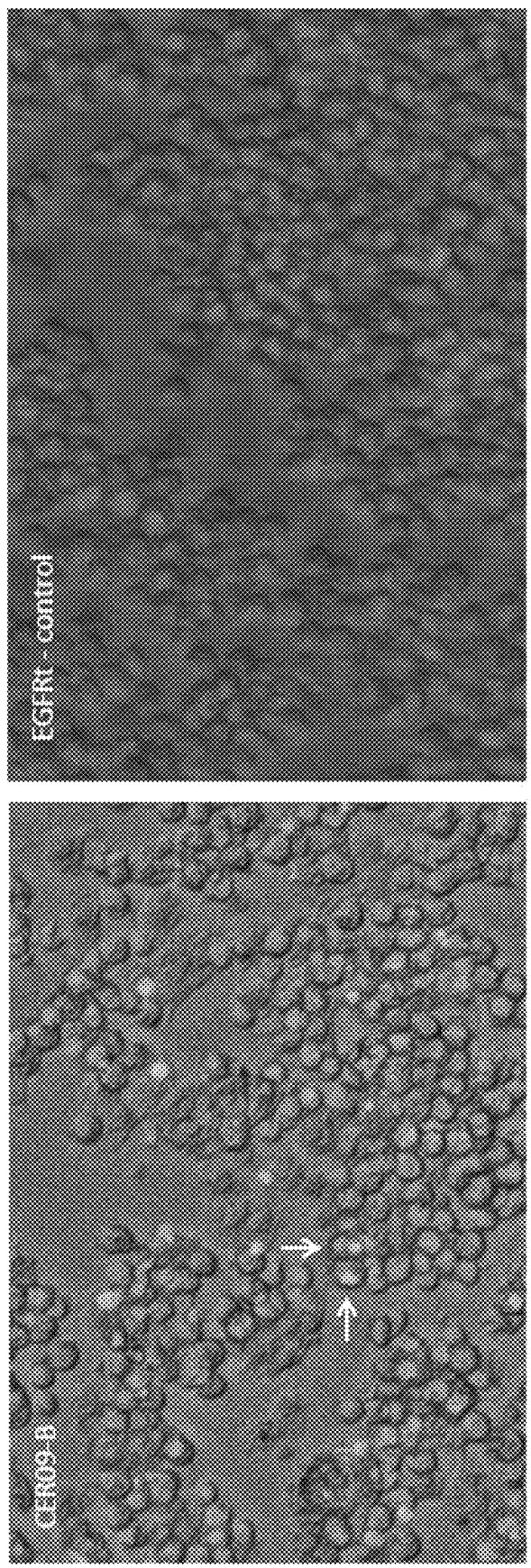
FIG. 52 shows fluorescent microscope images of in vitro phagocytosis of staurosporine treated Jurkat cells by CER09+ human primary B cells (left photo) or EGFRt+ human primary B cells (right photo). White arrows indicate phagocytosis events.

A fluorescent microscope image showing in vitro phagocytosis of Jurkat cells by CER09$^+$ human primary B cells is shown in FIG. 52 (left photo), and phagocytosis of Jurkat cells by tEGFR+ human primary B cells control is shown in FIG. 52 (right photo) (white arrows show phagocytosis events).

Example 11

Construction of TIM4-DAP12-DAP12 CER "CER10"

Figure 53:
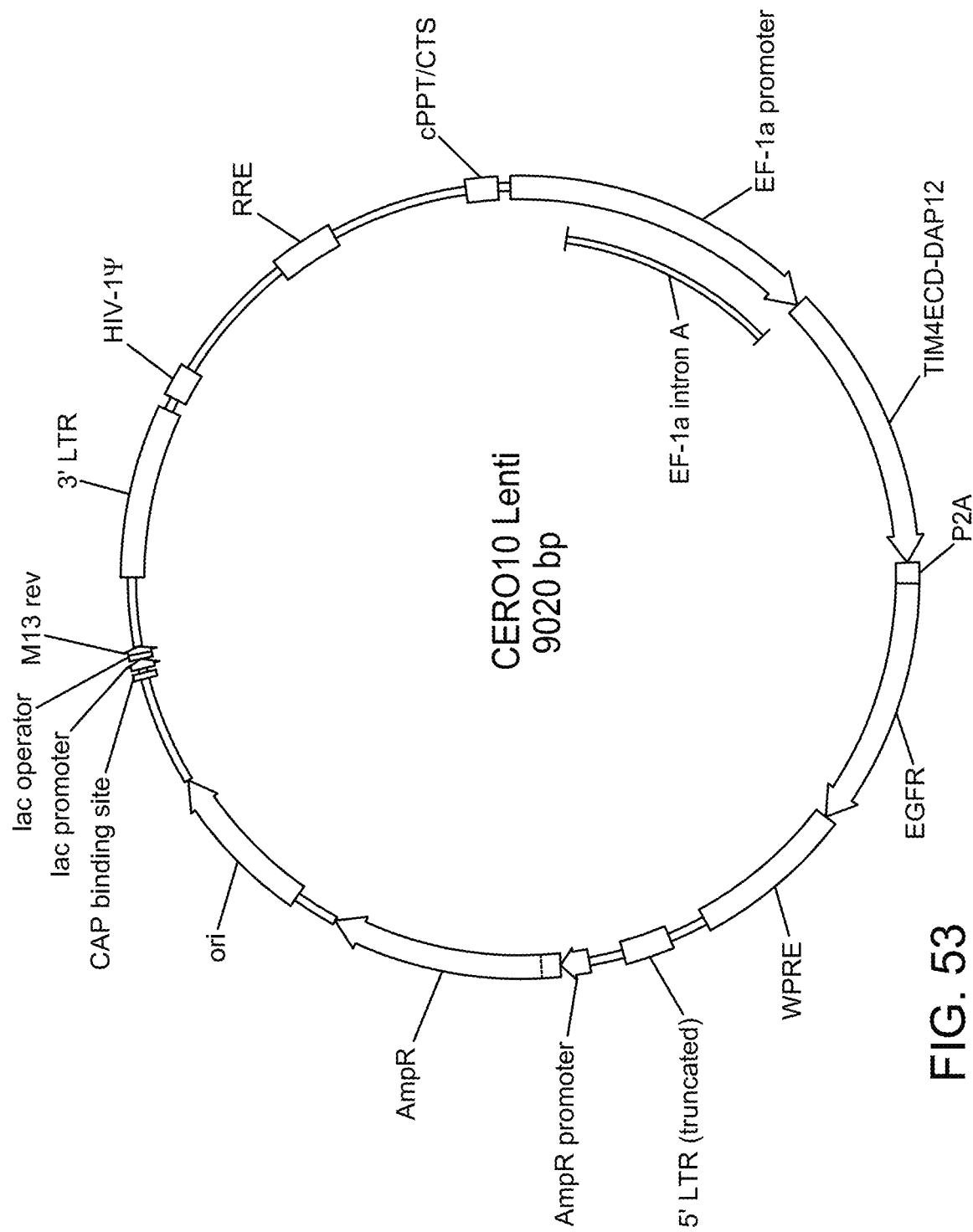
FIG. 53 shows a vector map for a lentiviral vector comprising "CER10" chimeric engulfment receptor having an amino acid sequence of SEQ ID NO:86. CER10 comprises a Tim4 binding domain, a Dap12 transmembrane domain, and a DAP12 signaling domain. The lentiviral vector also comprises a sequence encoding truncated EGFR (SEQ ID NO:121), which is separated from the CER10 sequence by a viral P2A sequence.

The extracellular domain of the phosphatidylserine binding protein Tim4 (amino acid sequence of SEQ ID NO:73), including the signal peptide (amino acid sequence of SEQ ID NO:72) were fused to the DAP12 transmembrane (SEQ ID NO:81) and intracellular signaling (SEQ ID NO:82) to create a chimeric engulfment receptor "CER10" (Tim4-DAP12-DAP12 CER having an amino acid sequence of SEQ ID NO:86). The DAP12 signaling domain transduces a signal for engulfment, and Tim4 is a phosphatidylserine binding receptor. The Tim4-DAP12-DAP12 (CER10) chimeric engulfment receptor nucleotide sequence was then inserted into the pLenti lentiviral vector along with truncated EGFR as a transduction marker, separated by P2A sequence (SEQ ID NO:104) (see, FIG. 53). Murine Ba/F3 B-cells were transduced with pLenti vector expressing Tim4-DAP12-DAP12 (CER10) and EGFRt, expanded, sorted by FACs, and used for in vitro studies as described in Example 8.

Phagocytic Activity Against Primary Apoptotic Thymocytes

Primary C3H mouse thymocytes were isolated, treated with dexamethasone, and stained with pHrodo Red as described in Example 8. Ba/F3 CER10$^+$ tEGFR$^+$ cells were labeled with CELLTRACE™ Violet dye as described in Example 8. Co-culture experiments with Ba/F3 CER10$^+$ tEGFR$^+$ cells and primary thymocytes were carried out at a 10:1 target cell to effector cell ratio, and Ba/F3 CER10$^+$ EGFR$^+$ cells were quantified for phagocytosis of target thymocytes by fluorescence microscopy and FACs as described in Example 8. Ba/F3 cells transduced with pLenti vector expressing truncated EGFR were used as a negative control.

Figure 54B:
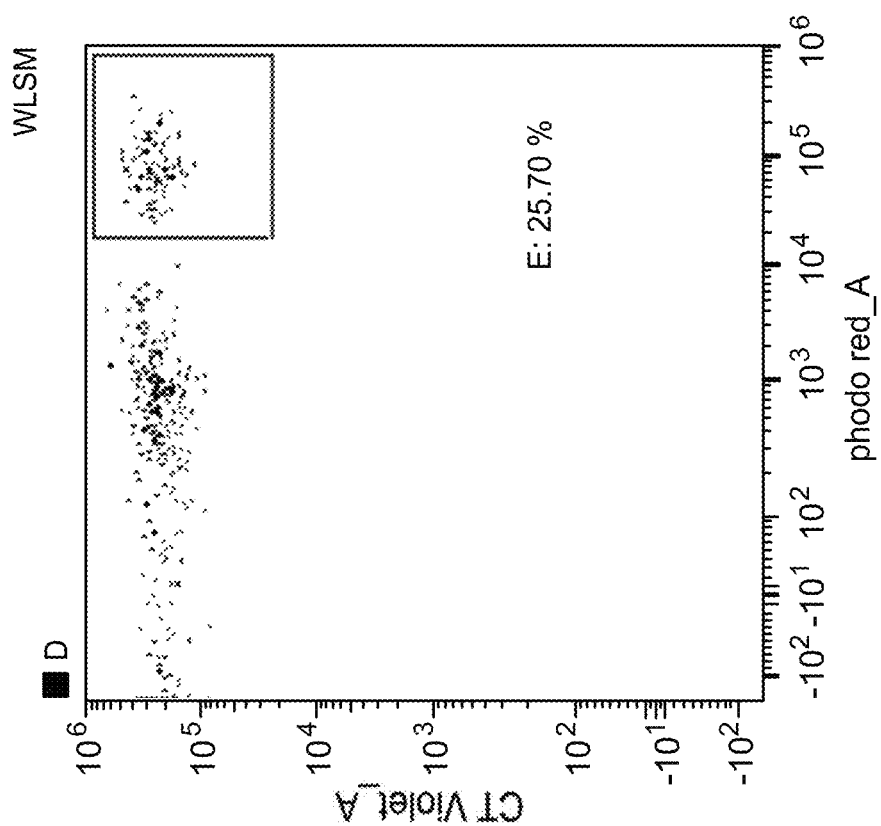
FIGS. 54A-54B show FACS analysis of viable, CER10+ Ba/F3 effector cells (FIG. 54A) and quantification of engulfment of dexamethasone-treated thymocytes by CER10+ Ba/F3 murine B cells by measuring the cell population that stained double positive for pHrodo Red and CELLTRACE Violet (FIG. 54B).
Figure 54A:
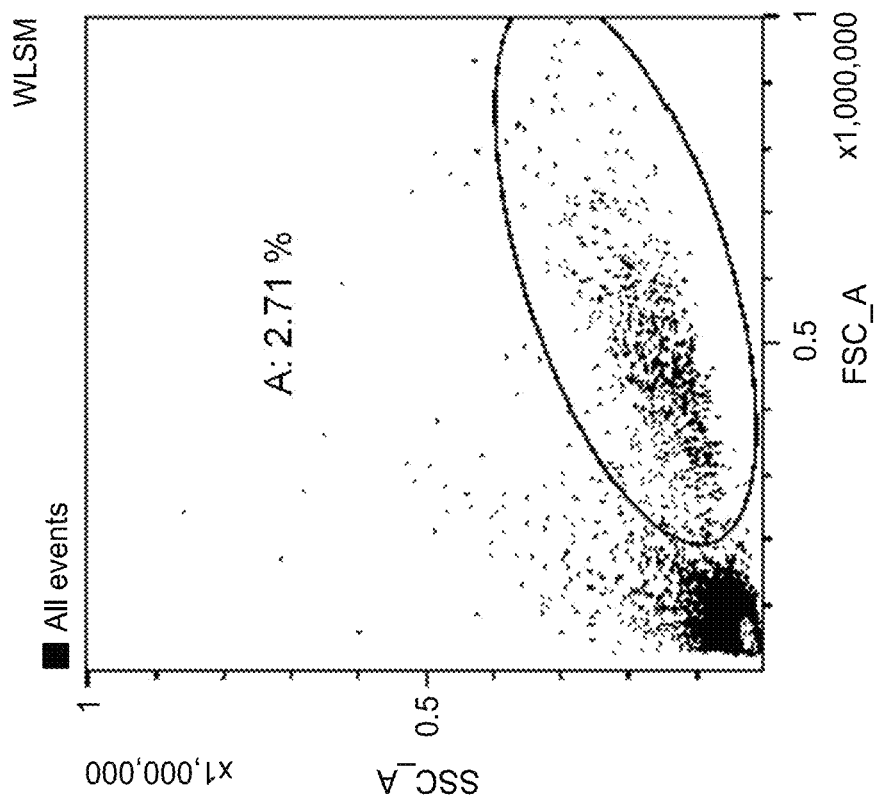

The quantity of viable, CER10+ transduced Ba/F3 cells as quantified by FACS is shown in FIG. 54A. The frequency of phagocytosis was quantified as the cell population staining double positive for pHrodo Red and CELLTRACE Violet as detected by FACS (see, FIG. 54B).

Figure 55A:
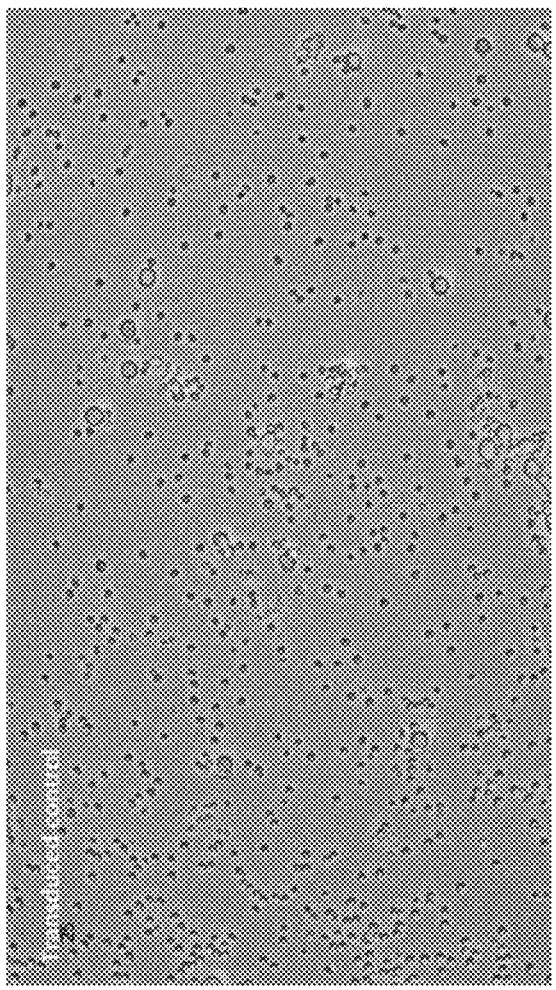
FIGS. 55A-55B show fluorescent microscope images of in vitro phagocytosis of dexamethasone treated thymocytes by CER10+ Ba/F3 cells (FIG. 55B) or control EGFRt+ Ba/F3 cells (FIG. 55A). White arrows indicate phagocytosis events. High magnification of an engulfment event is shown on the right.
Figure 55B:
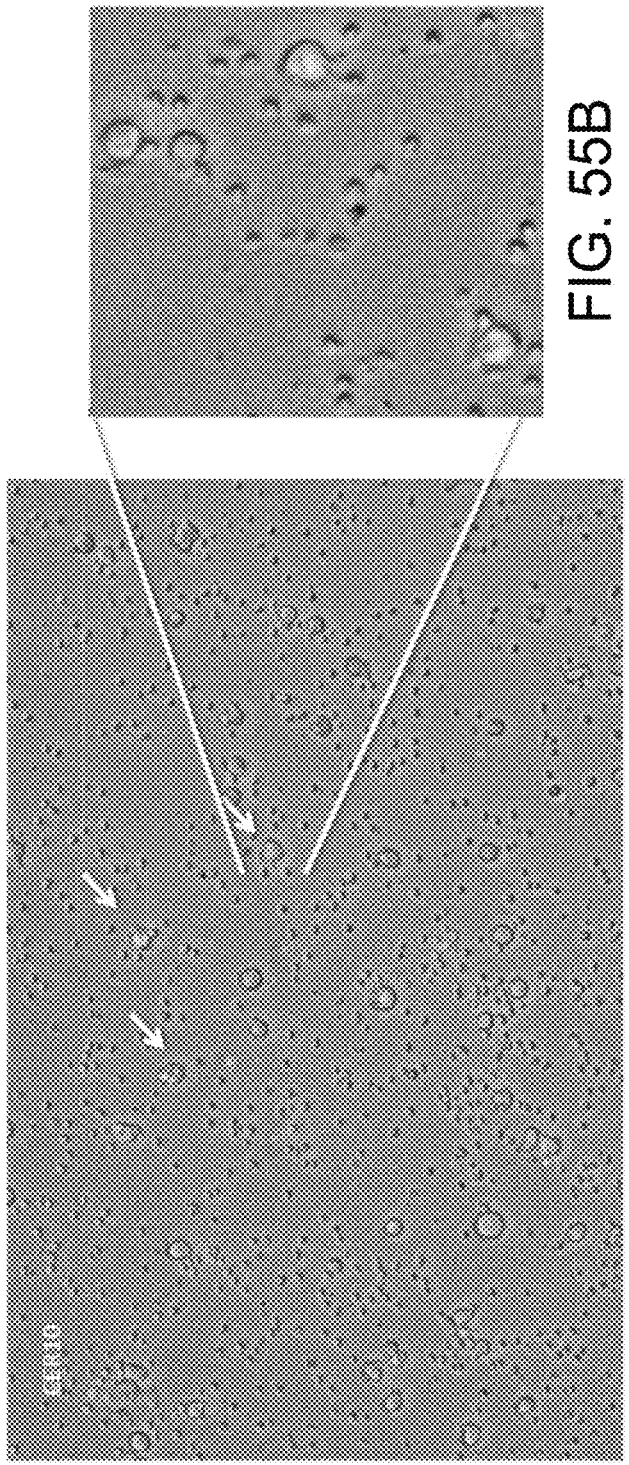

Fluorescent microscopy showed that CER10$^+$ Ba/F3 cells engulf dexamethasone-treated thymocytes (white arrows indicate engulfment events) as compared to tEGFR transduced Ba/F3 control cells (see, FIGS. 55A-B). High magnification of an engulfment event is shown in the bottom right of FIG. 55B.

Figures 56A, 56B:
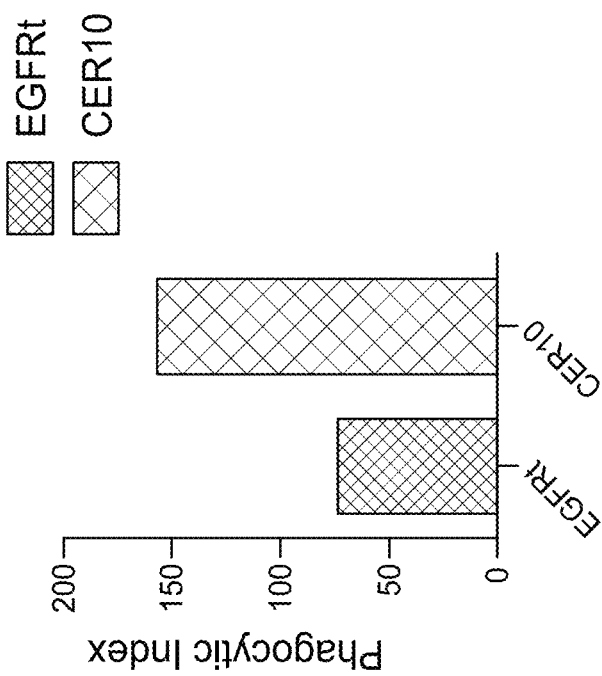
FIGS. 56A-56B show phagocytic index for CER10+ cells or EGFRt+ control Ba/F3 cells.
Figure 57:
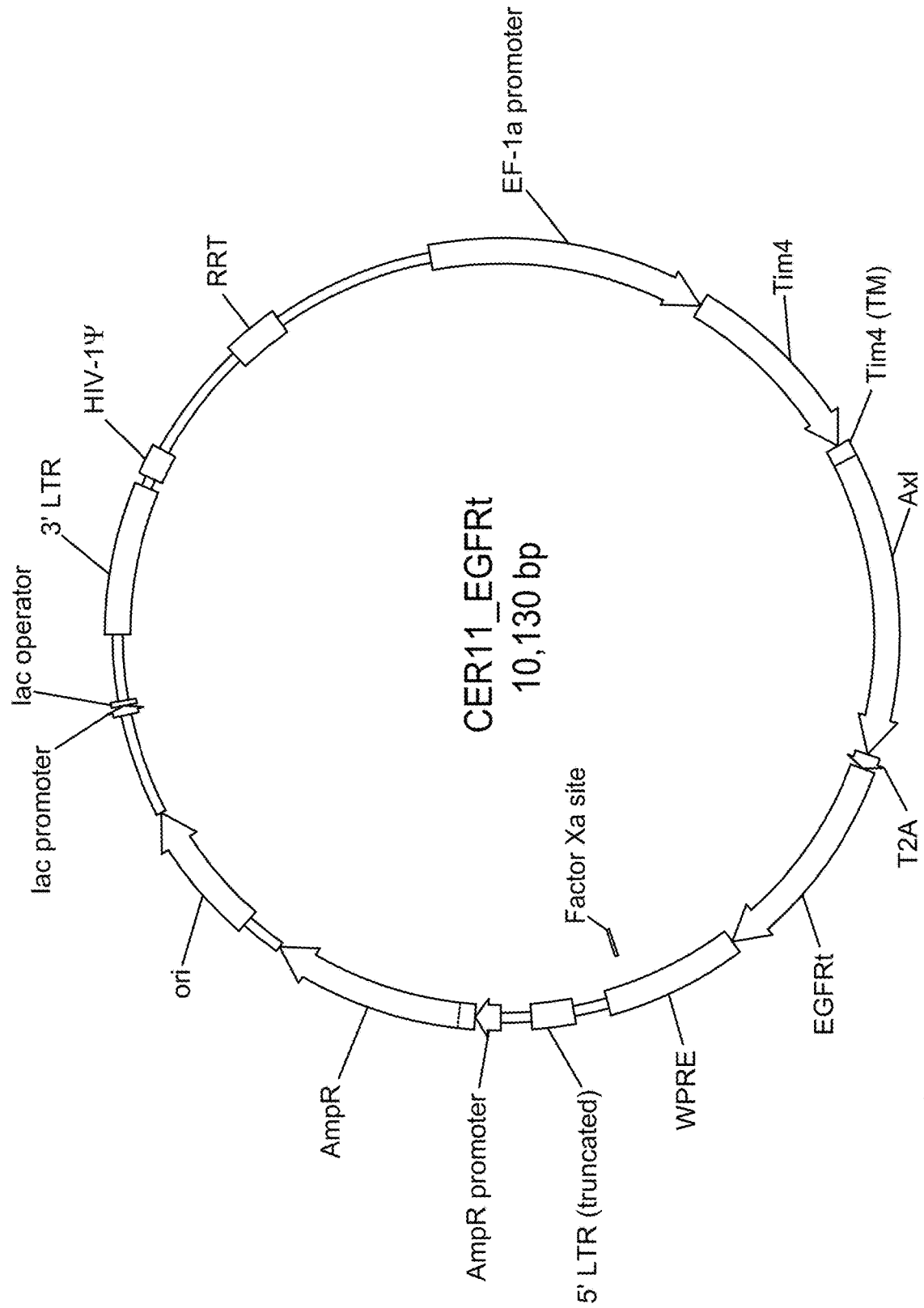
FIG. 57 shows a vector map for a lentiviral vector comprising "CER11" chimeric engulfment receptor having an amino acid sequence of SEQ ID NO:87. CER11 comprises a Tim4 binding domain, a Tim4 transmembrane domain, and an Ax1 signaling domain. The lentiviral vector also comprises a sequence encoding truncated EGFR (SEQ ID NO:121), which is separated from the CER11 sequence by a viral T2A sequence.

A phagocytic index was calculated by multiplying [mean of total number of engulfed target cells/total number of counted CER modified cells (e.g., phagocytic frequency)] by [average area of target cell staining per CER+ Ba/F3 cell× 100 (e.g., hybrid capture)] as compared to EGFRt transduced Ba/F3control cells (see, FIGS. 56A-B).

Example 12

Construction of TIM4-Ax1 CER "CER11"

The extracellular domain of the phosphatidylserine binding protein Tim4 (amino acid sequence of SEQ ID NO:73), including the signal peptide (amino acid sequence of SEQ ID NO:72) and transmembrane domain (amino acid sequence of SEQ ID NO:74) were fused to the Ax1 intracellular signaling (SEQ ID NO:44) to create a chimeric engulfment receptor "CER11" (Tim4-Ax1 CER having an amino acid sequence of SEQ ID NO:87). The Ax1 signaling domain transduces a signal for engulfment, and Tim4 is a phosphatidylserine binding receptor. The Tim4-Ax1 (CER11) chimeric engulfment receptor nucleotide sequence was then inserted into the pLenti lentiviral vector along with truncated EGFR as a transduction marker, separated by T2A sequence (see, FIG. 49). Murine Ba/F3 B-cells were transduced with pLenti vector expressing Tim4-Ax1 (CER11) and EGFRt, expanded, sorted by FACs, and used for in vitro studies as described in Example 8.

Phagocytic Activity Against Primary Apoptotic Thymocytes

Primary C3H mouse thymocytes were isolated, treated with dexamethasone, and stained with pHrodo Red as described in Example 8. Ba/F3 CER11$^+$ tEGFR$^+$ cells were labeled with CELLTRACE™ Violet dye as described in Example 8. Co-culture experiments with Ba/F3 CER11$^+$ tEGFR$^+$ cells and primary thymocytes were carried out at a 10:1 target cell to effector cell ratio, and Ba/F3 CER11$^+$ EGFR$^+$ cells were quantified for phagocytosis of target thymocytes by fluorescence microscopy and FACs as described in Example 8. Ba/F3 cells transduced with pLenti vector expressing truncated EGFR were used as a negative control.

Figure 58B:
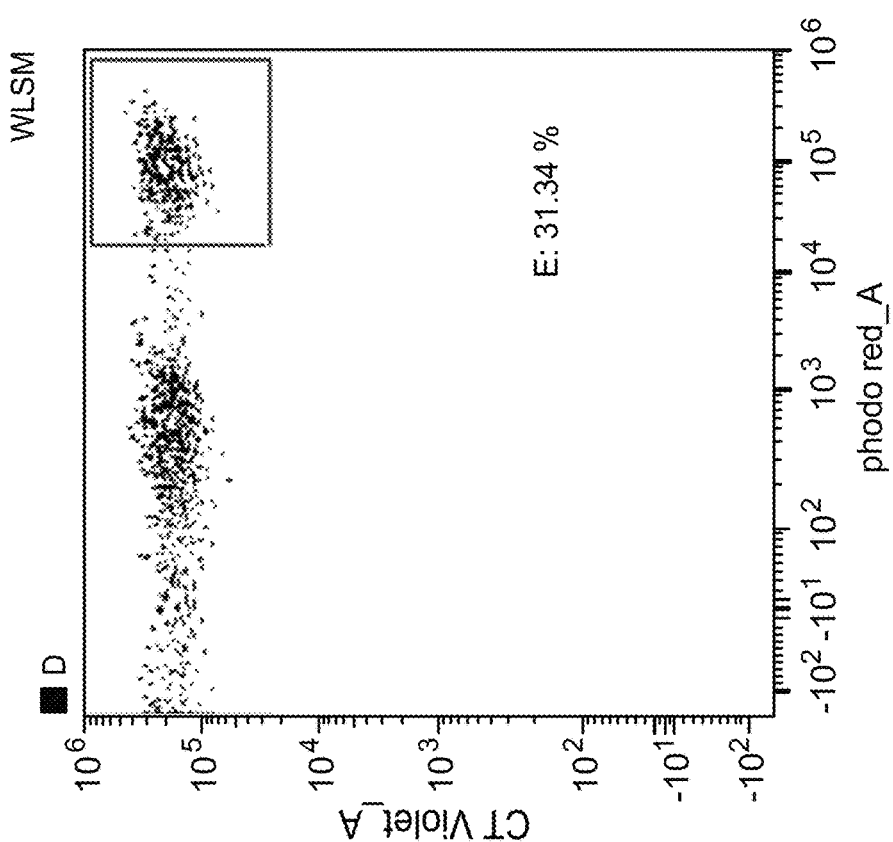
FIGS. 58A-58B show FACS analysis of CER11+ Ba/F3 effector cells (FIG. 58A) and quantification of engulfment of dexamethasone-treated thymocytes by CER11+ Ba/F3 murine B cells by measuring the cell population that stained double positive for pHrodo Red and CELLTRACE Violet (FIG. 58B).
Figure 58A:
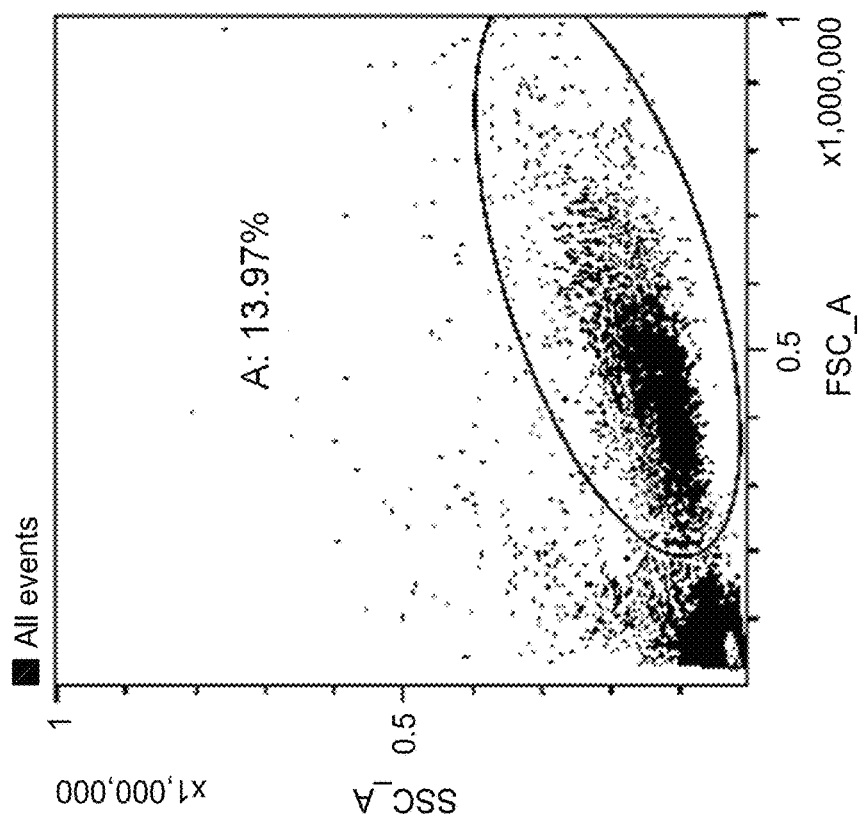

The quantity of viable, CER11+ transduced Ba/F3 cells as quantified by FACS is shown in FIG. 58A. The frequency of phagocytosis was quantified as the cell population staining double positive for pHrodo Red and CELLTRACE Violet as detected by FACS (see, FIG. 58B).

Fluorescent microscopy showed that CER11$^+$ Ba/F3 cells engulf dexamethasone-treated thymocytes (white arrows indicate engulfment events) as compared to tEGFR transduced Ba/F3 control cells (see, FIGS. 59A-59B). High magnification of an engulfment event is shown in the right of FIG. 59B.

Figures 60A, 60B:
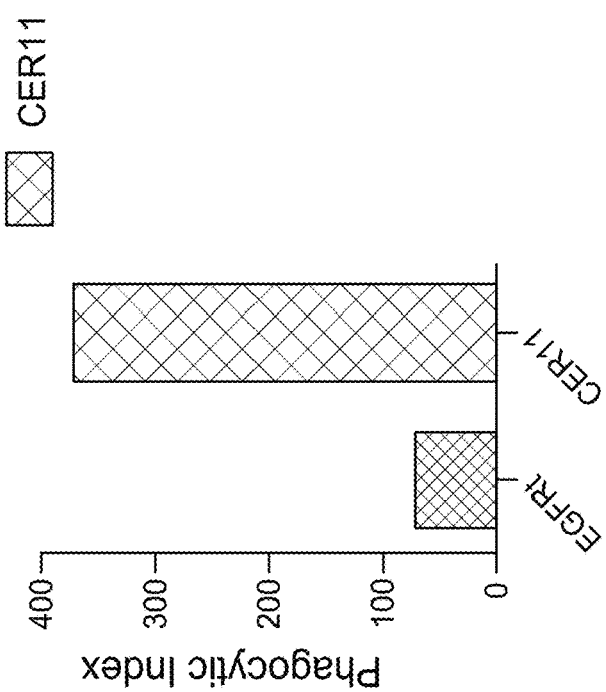
FIGS. 60A-60B show phagocytic index for CER11+ cells or EGFRt+ control Ba/F3 cells.

A phagocytic index was calculated by multiplying [mean of total number of engulfed target cells/total number of counted CER modified cells (e.g., phagocytic frequency)] by [average area of target cell staining per CER+ Ba/F3 cell× 100 (e.g., hybrid capture)] as compared to EGFRt transduced Ba/F3control cells (see, FIGS. 60A-60B).

Phagocytic Activity Against Murine Cell Lines

Ba/F3 CER11+ tEGFR+ cells were labeled with CELL-TRACE™ Violet dye as described in Example 8. CT26 murine colon carcinoma cells were treated with staurosporine, labeled with pHrodo Red and co-cultured with Ba/F3 CER11+ tEGFR+ cells at a target cell to effector cell ratio of 5:1 for 3 hours as described in Example 8. Phagocytosis of CT26 cells by CER11+ Ba/F3 cells was quantified by fluorescence microscopy and FACs as described in Example 8. Ba/F3 cells transduced with pLenti vector expressing truncated EGFR were used as a negative control. Fluorescent microscope images showing in vitro phagocytosis by CER11+ Ba/F3 cells and EGFRt+ control Ba/F3 cells are shown in FIGS. 61A-61B (white arrows show phagocytosis events). CT26 cells labeled with pHrodo Red fluoresce inside the low pH compartments of lysosomes when engulfed (outlined in pink).

Figure 62:
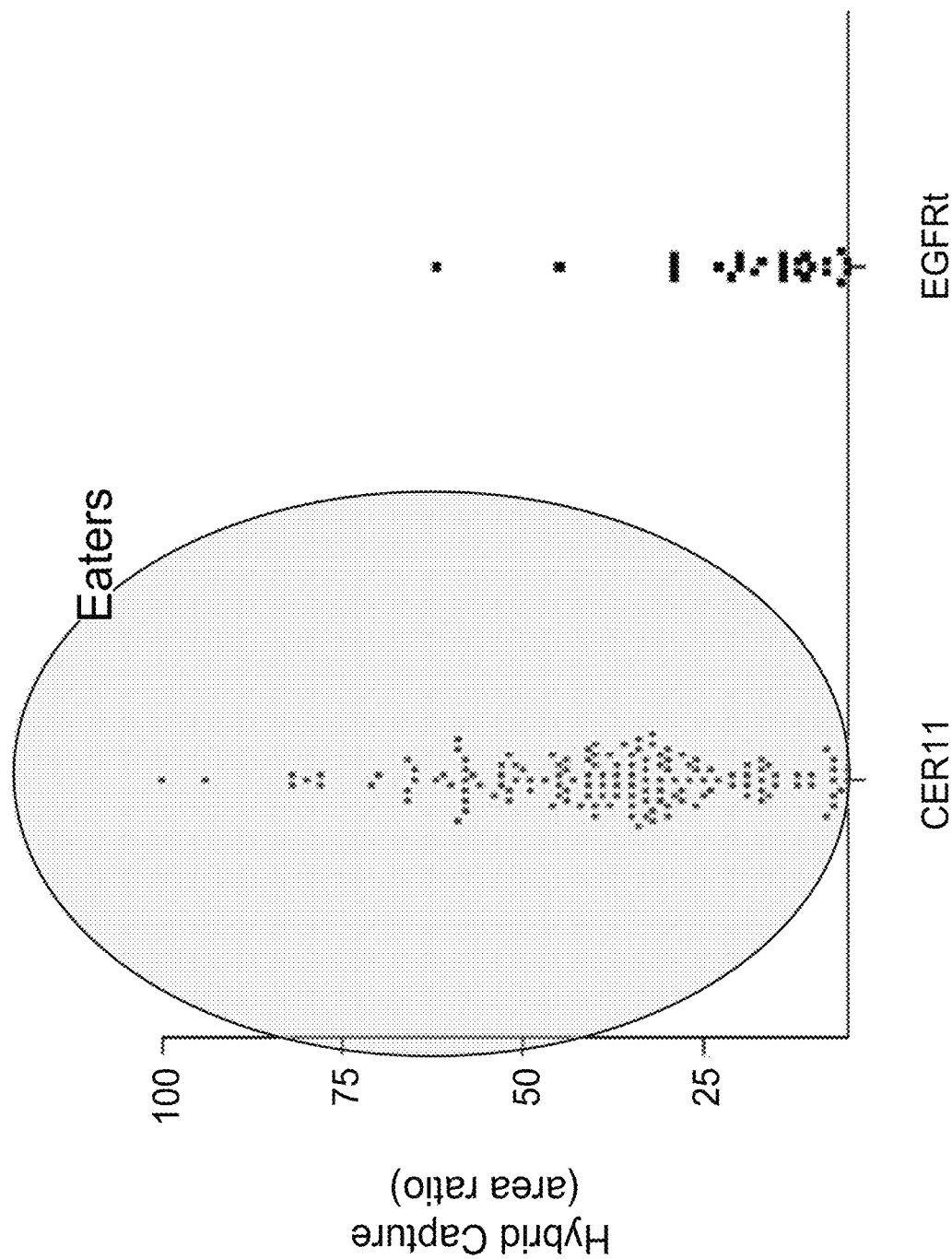
FIG. 62 shows a scatterplot of hybrid cell counts extracting CT26 target cell area from CER11+ Ba/F3 cells or EGFRt+ control Ba/F3 cells. The area ratio represents the area of CT26 cells within Ba/F3 cells.

A hybrid capture algorithm that detects fluorescence of pHrodo Red within CELLTRACE Violet staining area was applied to fluorescent images to quantify the area of engulfed target cells/area of CER+ B cells. FIG. 62 shows a scatterplot of hybrid cell counts extracting CT26 target cell area within Ba/F3 cells transduced with CER11+ tEGFR+ or tEGFR+ control. The area ratio represents the co-localization area of CT26 cells within Ba/F3 cells.

Figure 63:
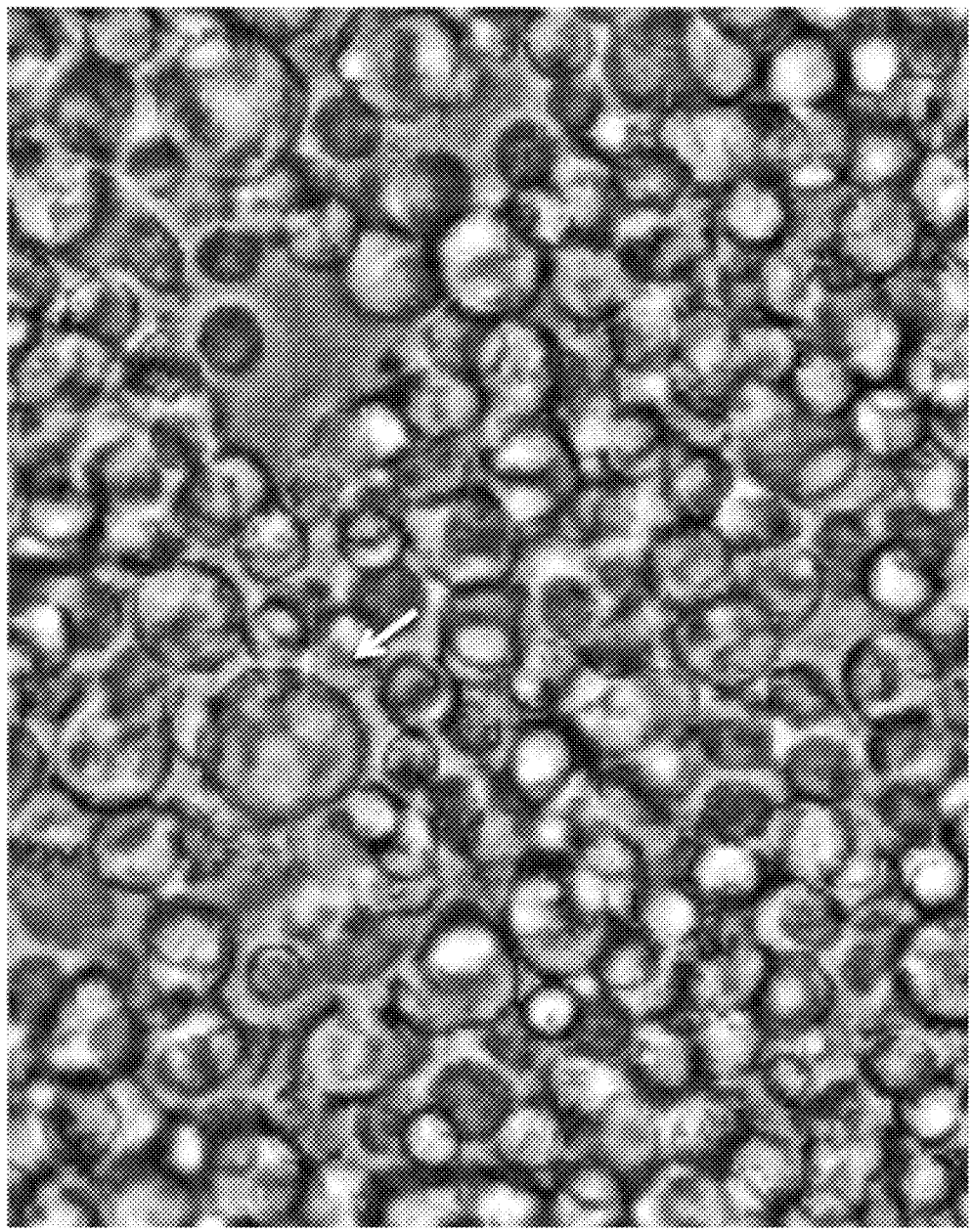
FIG. 63 shows fluorescent microscope image showing in vitro phagocytosis of WR19L cells by CER11+ Ba/F3. White arrow shows phagocytosis event.

WR19L murine lymphoma cells were treated with staurosporine, labeled with pHrodo Red and co-cultured with CELLTRACE Violet labeled Ba/F3 CER11+ tEGFR+ cells at a target cell to effector cell ratio of 5:1 for 3 hours as described in Example 8. Phagocytosis of WR19L cells by CER11+ Ba/F3 cells was quantified by fluorescence microscopy and FACs as described in Example 8. Ba/F3 cells transduced with pLenti vector expressing truncated EGFR were used as a negative control. Fluorescent microscope image showing in vitro phagocytosis of WR19L cells by CER11+ Ba/F3 cells is shown in FIG. 63 (white arrow shows phagocytosis events). The quantity of viable, CER11+ transduced Ba/F3 cells as quantified by FACS is shown in FIG. 64A. The frequency of phagocytosis was quantified as the cell population staining double positive for pHrodo Red and CELLTRACE Violet as detected by FACS (see, FIG. 64B).

Figures 65A, 65B:
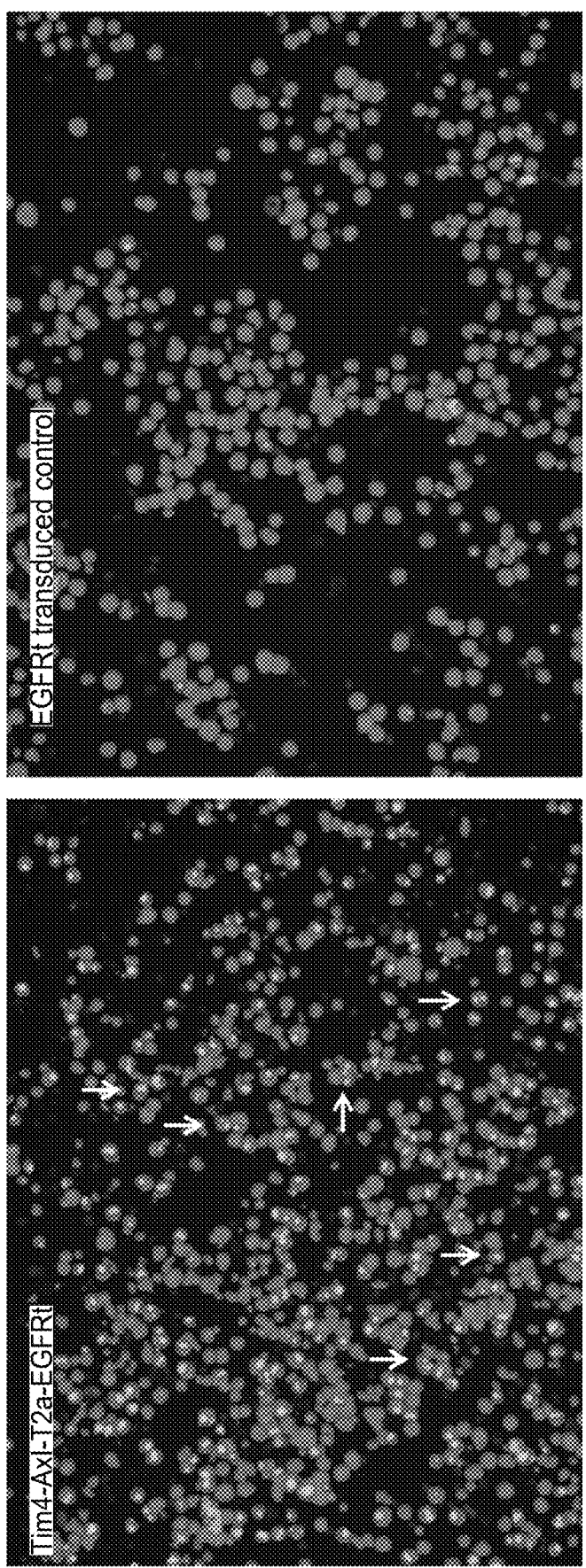
FIGS. 65A-65B show fluorescent microscope images of in vitro phagocytosis of staurosporine treated A20 lymphoma cells by CER11+ Ba/F3 cells (left photo) or control EGFRt+ Ba/F3 cells (right photo). White arrows indicate phagocytosis events.
Figure 66:
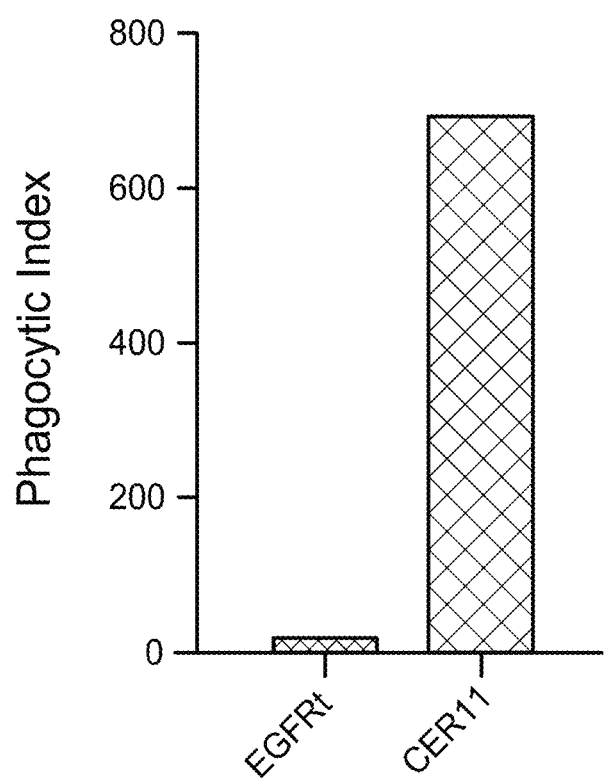
FIG. 66 shows phagocytic index for CER11+ cells or EGFRt+ control Ba/F3 cells co-incubated with staurosporine treated A20 cells.

A20 murine cell lymphoma cells were treated with staurosporine, labeled with pHrodo Red and co-cultured with CELLTRACE Violet labeled Ba/F3 CER11+ tEGFR+ cells at a target cell to effector cell ratio of 5:1 for 3 hours as described in Example 8. Phagocytosis of A20 cells by CER11+ Ba/F3 cells was quantified by fluorescence microscopy and FACs as described in Example 8. Ba/F3 cells transduced with pLenti vector expressing truncated EGFR were used as a negative control. Fluorescent microscope image showing in vitro phagocytosis of A20 cells by CER11+ Ba/F3 cells is shown in FIG. 65A (white arrow show phagocytosis events) as compared to EGFRt transduced Ba/F3 control (FIG. 65B). Phagocytic index was calculated or CER11+ Ba/F3 cells as compared to EGFRt+ control cells and is shown in FIG. 66.

Figure 67:
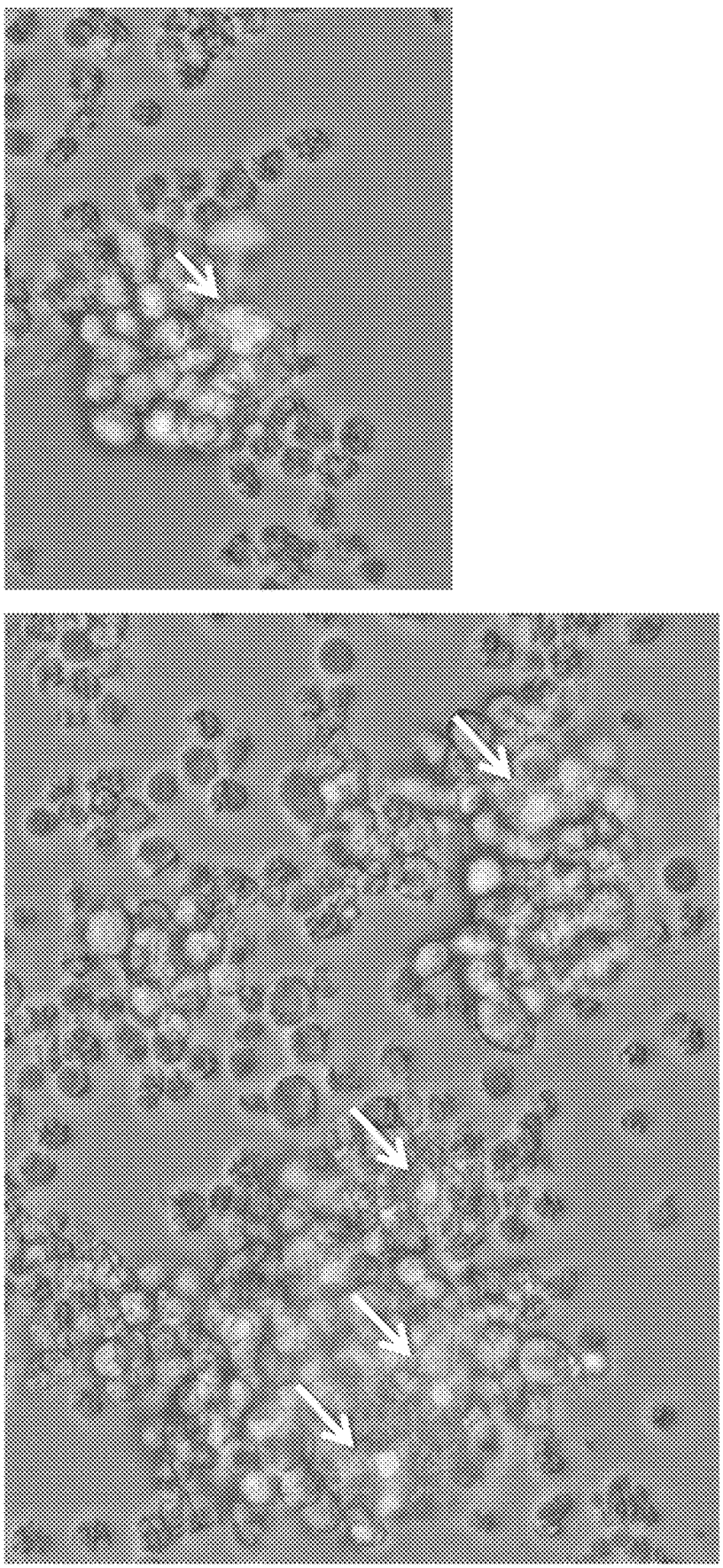
FIG. 67 shows fluorescent microscope images of in vitro phagocytosis of oxaliplatin and fluorouracil treated Jurkat cells by CER11+ human primary B cells (left photo) or control EGFRt+ human primary B cells (right photo). White arrows indicate phagocytosis events.

Phagocytic Activity of Human Cer11+ B Cells Against Chemotherapy-Treated Human Cell Line Human primary B cells were transduced with pLenti Tim4-Ax1 (CER11) lentivirus expressing truncated EGFR as a transduction marker as described in Example 8. One day prior to setting up the phagocytosis assay, Jurkat human B lymphocyte cells were cultured in complete RPMI 1640 growth media supplemented with 10% fetal bovine serum and 1% penicillin-streptomycin in a 6 well plate and treated with oxaliplatin (5 µM) and fluorouracil (5-FU) (10 The following day, target Jurkat cells were collected, washed twice with 1×PBX, and stained with pHrodo Red (1 ng/mL in PBS) for 15 minutes at room temperature. The Jurkat cells were supplemented with growth media, washed once to remove excess pHrodo Red, and plated on flat bottom 96 well plates at approximately 200,000 cells/well in RPMI 1640 complete media. Transduced human primary B cells were washed once with 1×PBS and then stained with CELL-TRACE Violet (1 mM in PBS) for 10 minutes at 37° C. The human primary B cells were supplemented with growth media, washed once with 1×PBS to remove excess CELL-TRACE Violet, and plated onto a 96 well plate at approximately 50,000 cells in RPMI complete media. Human primary B cells and Jurkat cells were co-cultured at a target cell to effector cell ratio of 4:1 at 37° C. for 3 hours. The plate was then imaged using a 20× objective, Keyence BZ-X710 microscope. FIG. 67 shows fluorescent microscope images showing engulfment of chemotherapy treated Jurkat cells by CER11+ human primary B cells (right image shows an enlargement of a phagocytosis event; white arrows indicate phagocytosis).

Figure 68:
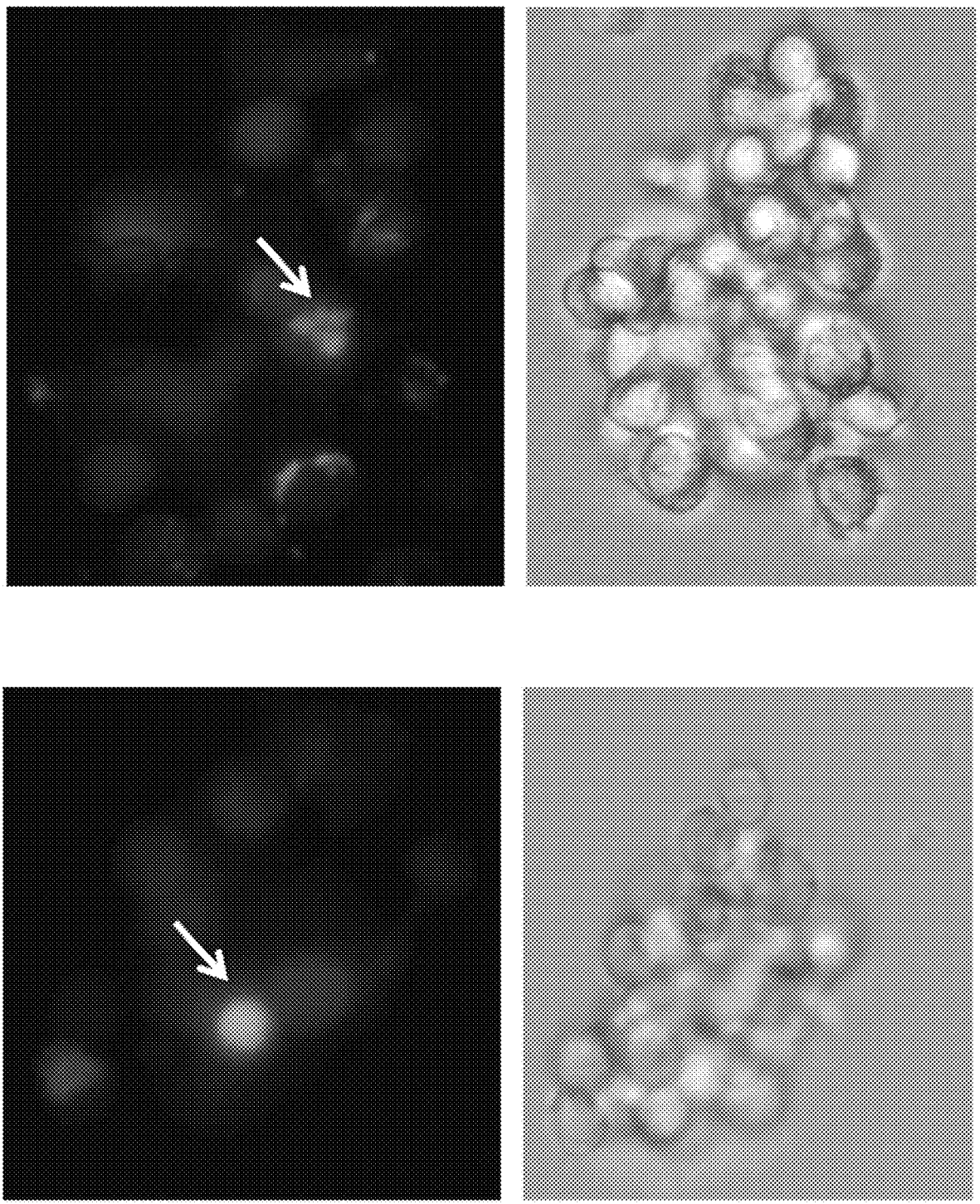
FIG. 68 shows fluorescent microscope images of in vitro phagocytosis of gemcitabine treated COLO320HSR colon cancer cells by CER11+ human primary B cells. White arrows indicate phagocytosis events.

Human primary B cells were transduced with pLenti Tim4-Ax1 (CER11) lentivirus expressing truncated EGFR as a transduction marker as described in Example 8. One day prior to setting up the phagocytosis assay, Colo320 HSR colon cancer cells were incubated with phosphatidylserine inducing chemotherapy Gemcitabine (10 µM) in serum-free media for 24 hours. Floating and adherent target cells after the treatment were collected, centrifuged, incubated with pHrodo red (1 ng/µL) for 15 minutes at room temperature in PBS, washed and then plated in a non-adherent 96 well plate. Human CER11+ expressing B cells and Colo320HSR cells were co-cultured at a target cell to effector cell ratio of 4:1 at 37° C. for 3 hours. The plate was then imaged using a 20× objective, Keyence BZ-X710 microscope (see, FIG. 68; white arrows shows phagocytic events).

Figure 70:
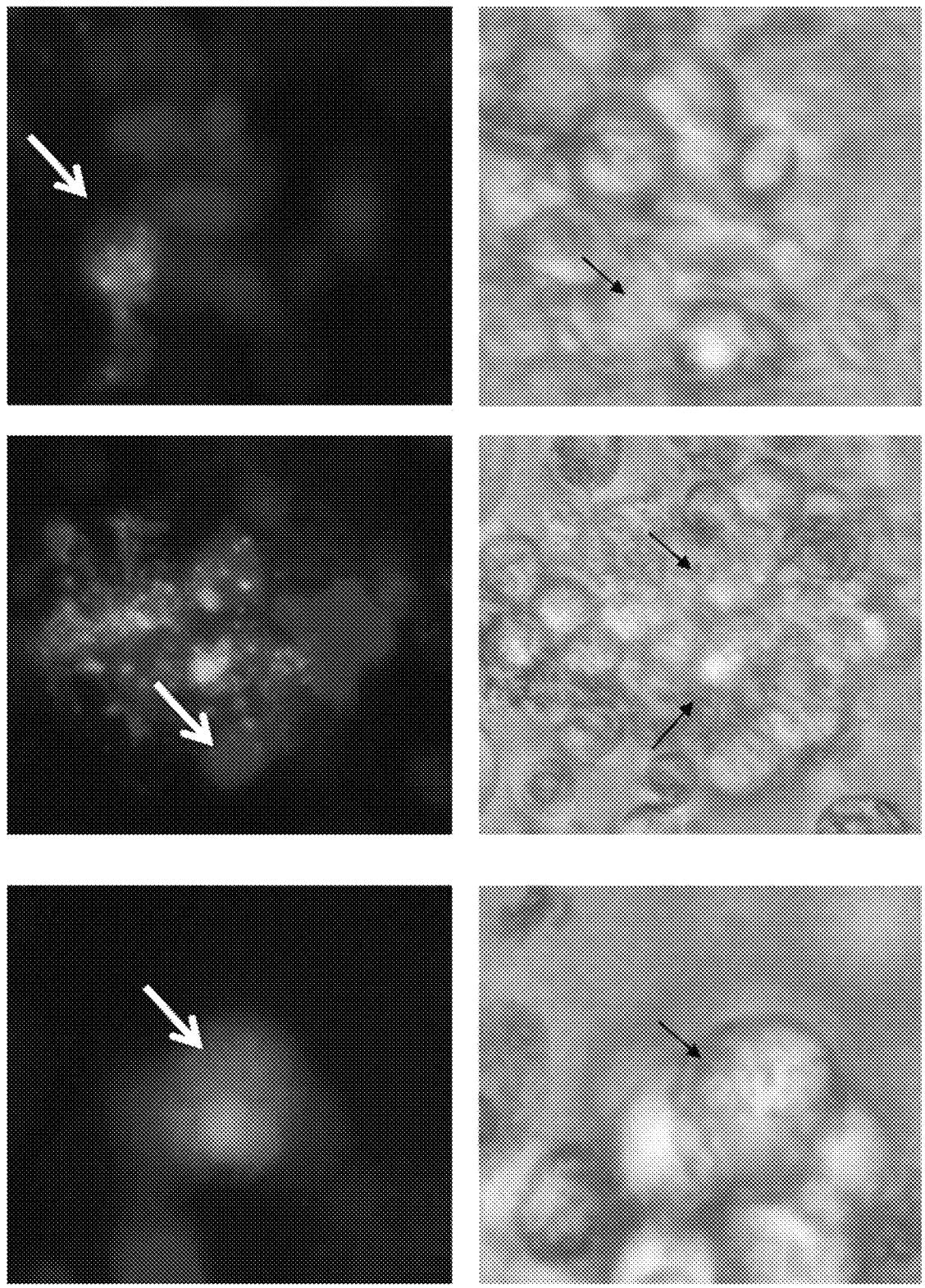
FIG. 70 shows fluorescent microscope images of in vitro phagocytosis of paclitaxel or paclitaxel+gemcitabine treated H1703 non small cell lung cancer cells by CER11+ human primary B cells. Arrows indicate phagocytosis events.

Human primary B cells were transduced with pLenti Tim4-Ax1 (CER11) lentivirus expressing truncated EGFR as a transduction marker as described in Example 8. One day prior to setting up the phagocytosis assay, A204 rhabdomyosarcoma cells were incubated in phosphatidylserine inducing chemotherapy Paclitaxel, and H1703 non-small cell lung cancer (NSCLC) adenocarcinoma cancer cells were incubated with phosphatidylserine inducing chemotherapy Paclitaxel (30 µM)+ Gemcitabine (10 µM) in serum-free media for 24 hours. Floating and adherent target cells after the treatment were collected, centrifuged, incubated with pHrodo red (1 ng/µL) for 15 minutes at room temperature in PBS, washed and then plated in a non-adherent 96 well plate. Human CER11+ expressing B cells and A204 or H1703 cells were co-cultured at a target cell to effector cell ratio of 4:1 at 37° C. for 3 hours. The plate was then imaged using a 20× objective, Keyence BZ-X710 microscope (see, FIG. 69 for A204 cells and FIG. 70 for H1703 cells; arrows show phagocytic events).

Example 13

Construction of TIM4-FcεR1γ CER "CER12"

Figure 71:
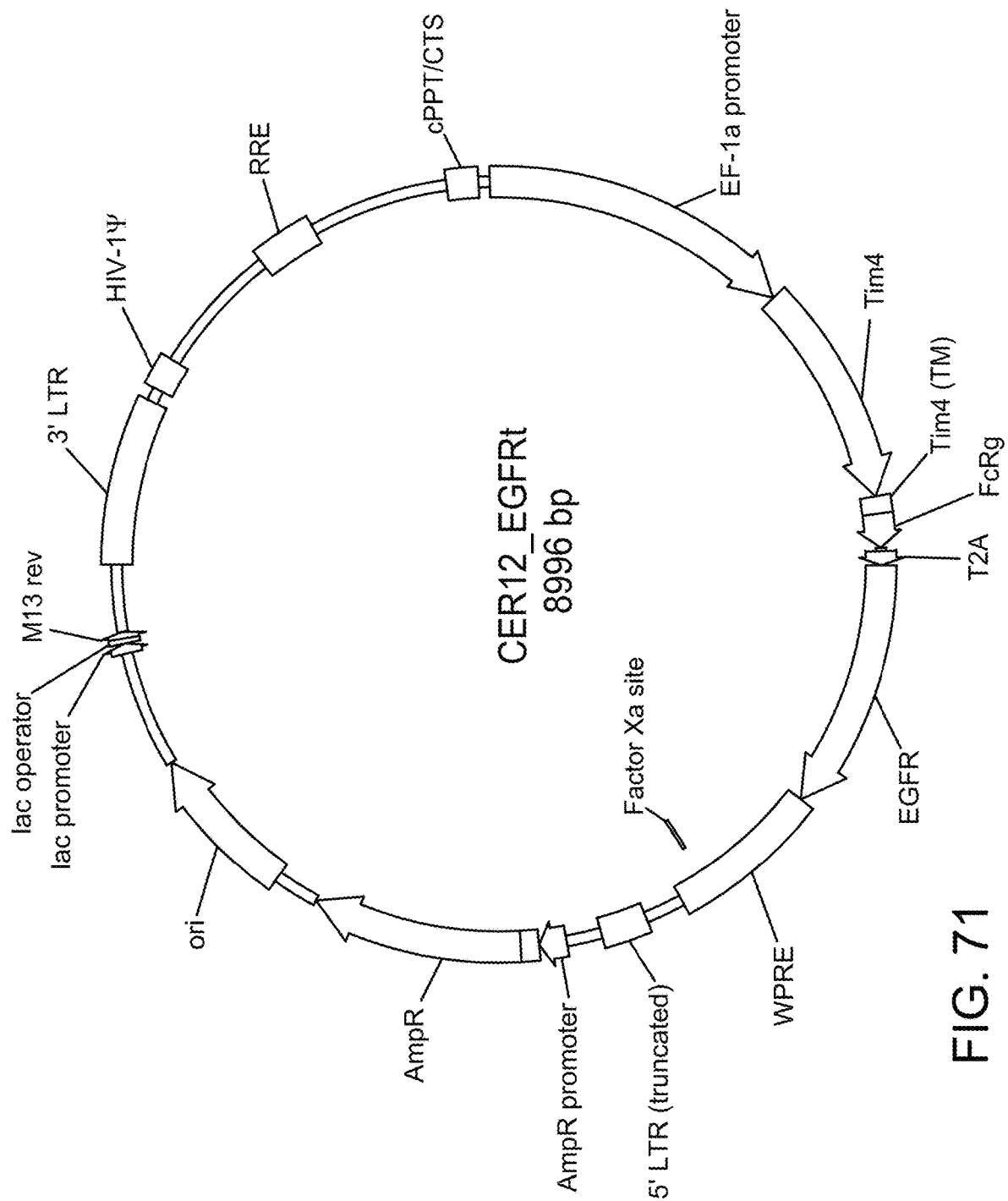
FIG. 71 shows a vector map for a lentiviral vector comprising "CER12" chimeric engulfment receptor having an amino acid sequence of SEQ ID NO:90. CER12 comprises a Tim4 binding domain, a Tim4 transmembrane domain, and an FcεRIγ signaling domain. The lentiviral vector also comprises a sequence encoding truncated EGFR (SEQ ID NO:121), which is separated from the CER12 sequence by a viral T2A sequence.

The extracellular domain of the phosphatidylserine binding protein Tim4 (amino acid sequence of SEQ ID NO:73), including the signal peptide (amino acid sequence of SEQ ID NO:72) and transmembrane domain (amino acid sequence of SEQ ID NO:74) were fused to the FcεR1γ intracellular signaling (SEQ ID NO:88) to create a chimeric engulfment receptor "CER12" (Tim4-FcεR1γ CER having an amino acid sequence of SEQ ID NO:90). The FcεR1γ signaling domain transduces a signal for engulfment, and Tim4 is a phosphatidylserine binding receptor. The Tim4-FcεR1γ (CER12) chimeric engulfment receptor nucleotide sequence was then inserted into the pLenti lentiviral vector along with truncated EGFR as a transduction marker, separated by T2A sequence (see, FIG. 71). Murine Ba/F3 B-cells were transduced with pLenti vector expressing Tim4-FcεR1γ (CER12) and EGFRt, expanded, sorted by FACs, and used for in vitro studies as described in Example 8.

Phagocytic Activity Against Primary Apoptotic Thymocytes

Primary C3H mouse thymocytes were isolated, treated with dexamethasone, and stained with pHrodo Red as described in Example 8. Ba/F3 CER12$^+$ tEGFR$^+$ cells were labeled with CELLTRACE™ Violet dye as described in Example 8. Co-culture experiments with Ba/F3 CER12$^+$ tEGFR$^+$ cells and primary thymocytes were carried out at a 10:1 target cell to effector cell ratio, and Ba/F3 CER12$^+$ EGFR$^+$ cells were quantified for phagocytosis of target thymocytes by fluorescence microscopy and FACs as described in Example 8. Ba/F3 cells transduced with pLenti vector expressing truncated EGFR were used as a negative control.

Figure 72B:
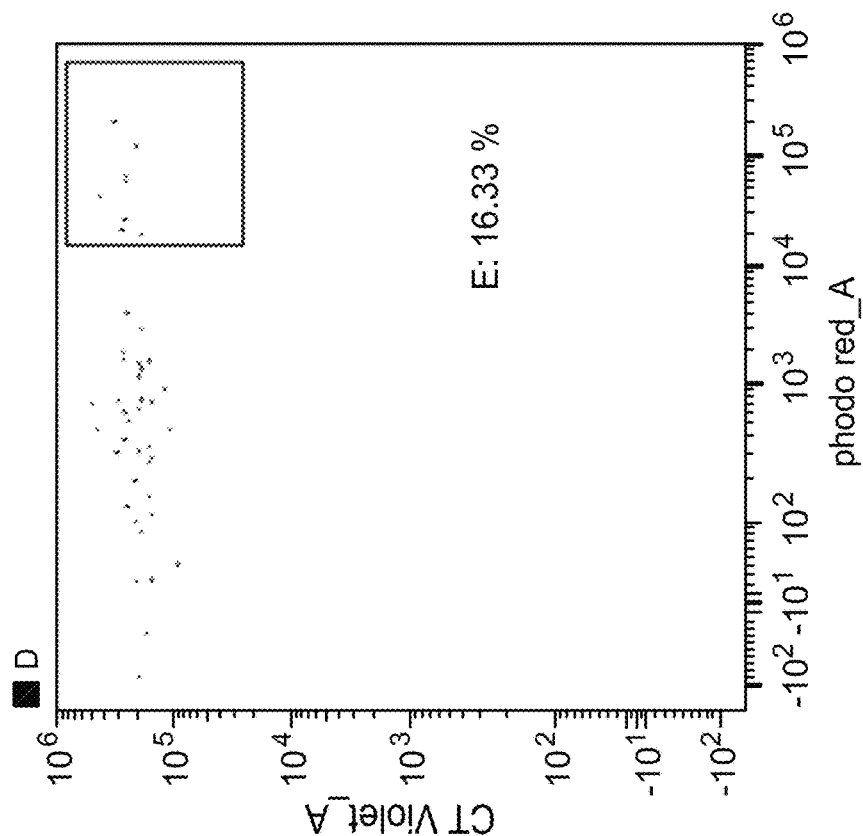
FIGS. 72A-72B show FACS analysis of CER12+ Ba/F3 effector cells (FIG. 72A) and quantification of engulfment of thymocytes by CER12+ Ba/F3 murine B cells by measuring the cell population that stained double positive for pHrodo Red and CELLTRACE Violet (FIG. 72B).
Figure 72A:
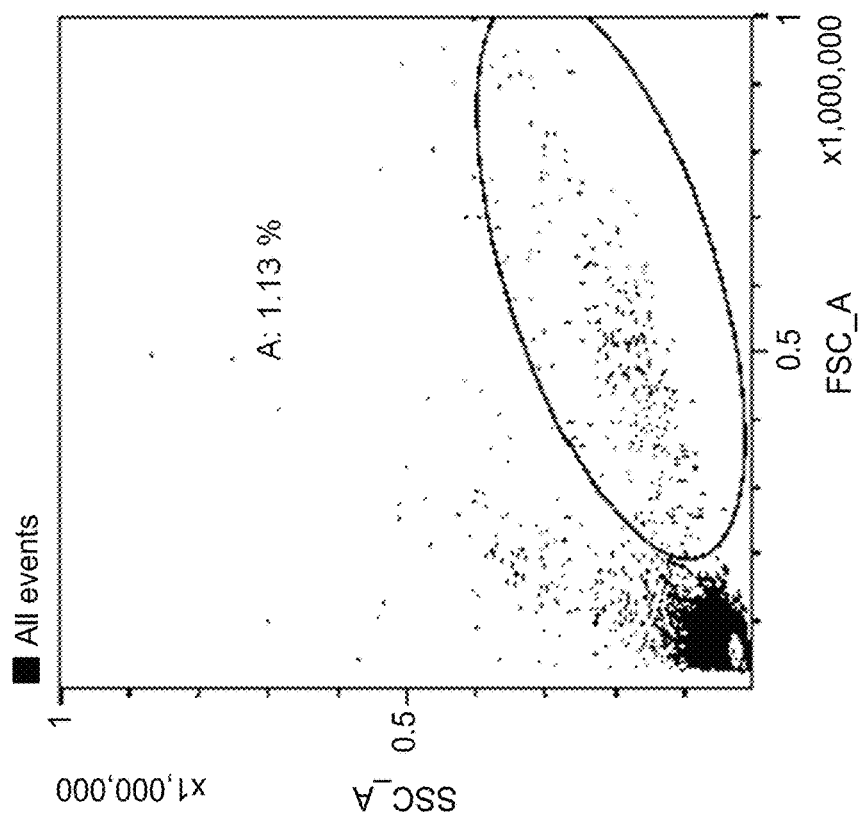

The quantity of viable, CER12+ transduced Ba/F3 cells as quantified by FACS is shown in FIG. 72A. The frequency of phagocytosis was quantified as the cell population staining double positive for pHrodo Red and CELLTRACE Violet as detected by FACS (see, FIG. 72B).

Fluorescent microscopy showed that CER12$^+$ Ba/F3 cells engulf dexamethasone-treated thymocytes (white arrows indicate engulfment events) as compared to tEGFR transduced Ba/F3 control cells (see, FIGS. 73A-73B). High magnification of an engulfment event is shown in the right of FIG. 73B.

Figures 74A, 74B:
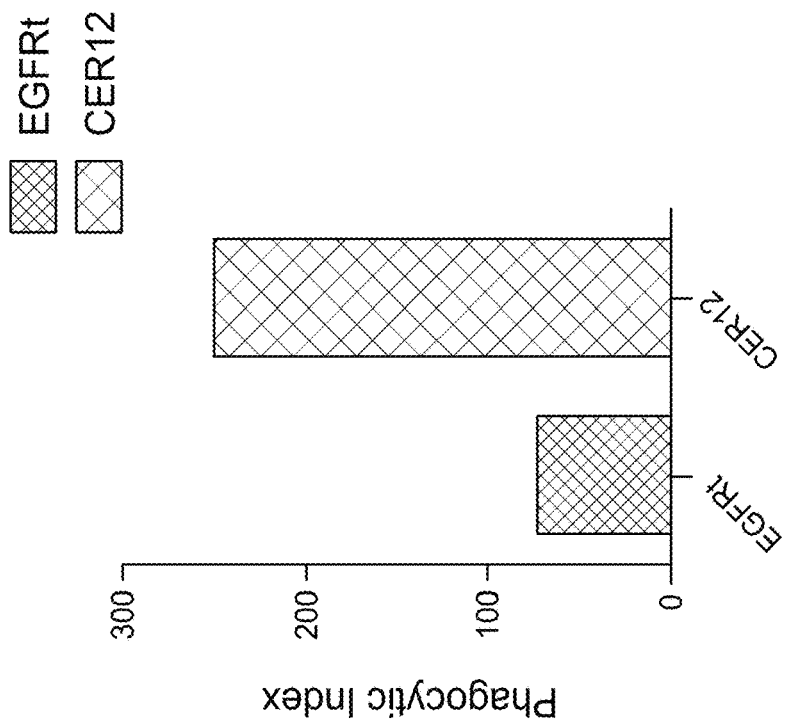
FIGS. 74A-74B show phagocytic index for CER12+ cells or EGFRt+ control Ba/F3 cells.

A phagocytic index was calculated by multiplying [mean of total number of engulfed target cells/total number of counted CER modified cells (e.g., phagocytic frequency)] by [average area of target cell staining per CER+ Ba/F3 cell× 100 (e.g., hybrid capture)] as compared to EGFRt transduced Ba/F3control cells (see, FIGS. 74A-74B).

Phagocytic Activity Against Murine Cell Lines

Figure 75:
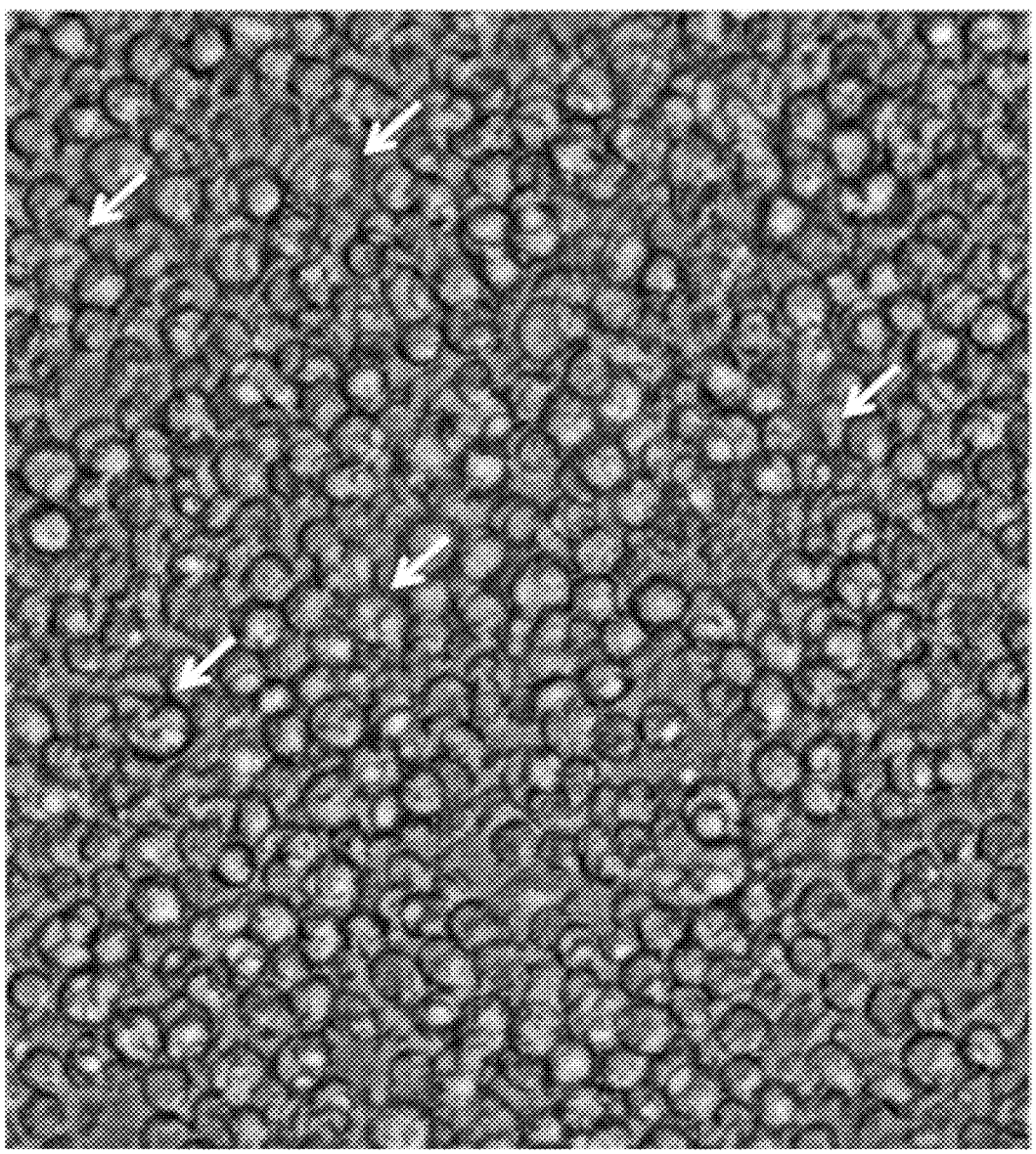
FIG. 75 shows a fluorescent microscope image of in vitro phagocytosis of staurosporine treated WR19L lymphoma cells by CER12+ Ba/F3 cells. White arrows indicate phagocytosis events.

WR19L murine lymphoma cells were treated with staurosporine, labeled with pHrodo Red and co-cultured with CELLTRACE Violet labeled Ba/F3 CER12$^+$ tEGFR$^+$ cells at a target cell to effector cell ratio of 5:1 for 3 hours as described in Example 8. Phagocytosis of WR19L cells by CER12$^+$ Ba/F3 cells was quantified by fluorescence microscopy and FACs as described in Example 8. Ba/F3 cells transduced with pLenti vector expressing truncated EGFR were used as a negative control. Fluorescent microscope image showing in vitro phagocytosis of WR19L cells by CER12+ Ba/F3 cells is shown in FIG. 75 (white arrow show phagocytosis events).

Figure 76:
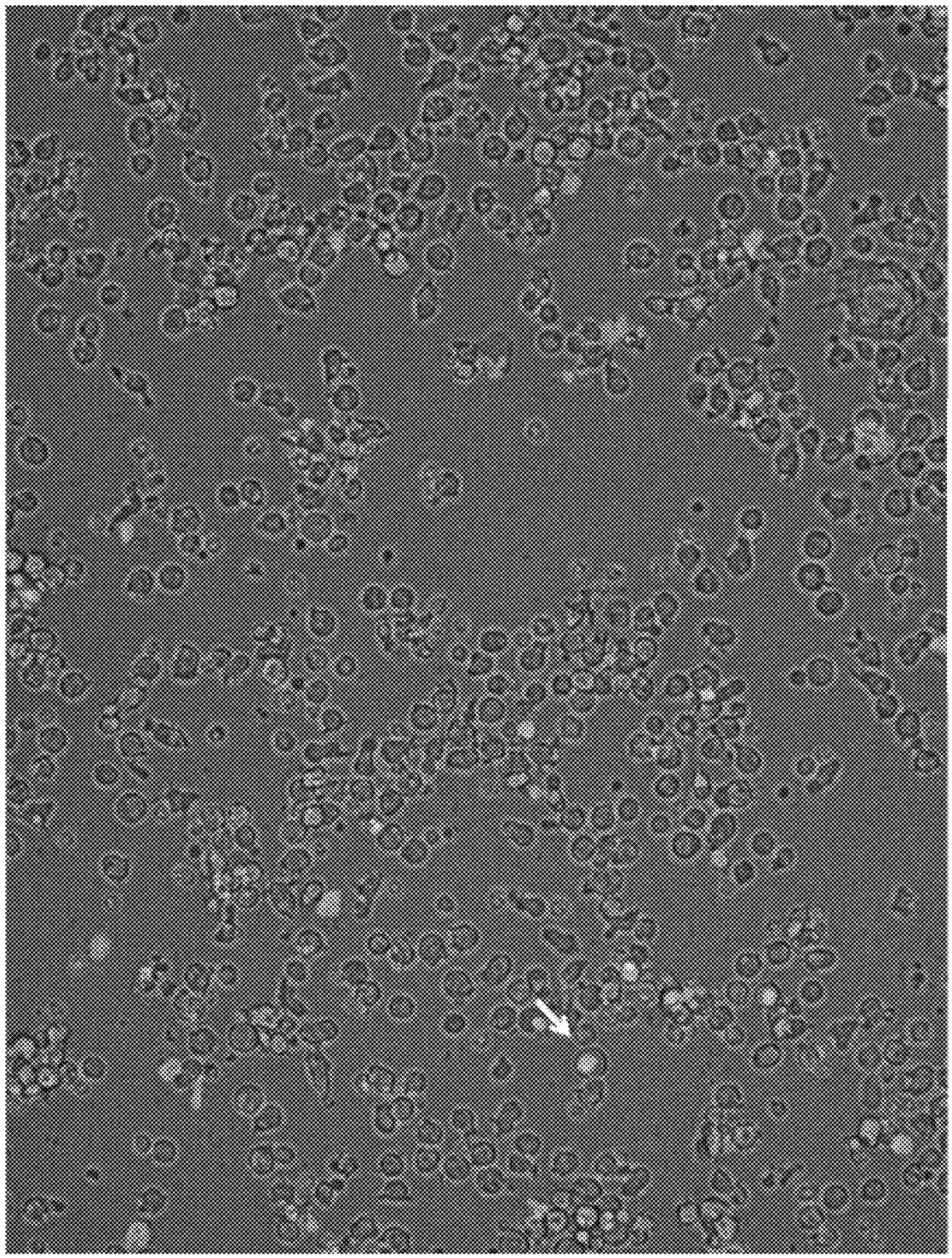
FIG. 76 shows a fluorescent microscope image of in vitro phagocytosis of staurosporine treated A20 lymphoma cells by CER12+ Ba/F3 cells. The white arrow indicates a phagocytosis event.
Figure 77:
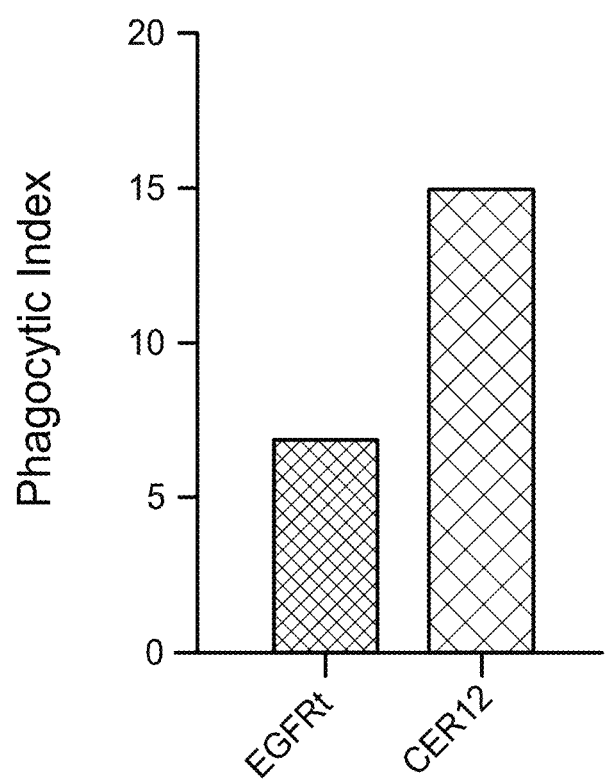
FIG. 77 shows phagocytic index for CER12+ cells or EGFRt+ control Ba/F3 cells co-incubated with staurosporine treated A20 cells.

A20 murine B cell lymphoma cells were treated with staurosporine, labeled with pHrodo Red and co-cultured with CELLTRACE Violet labeled Ba/F3 CER12$^+$ tEGFR$^+$ cells at a target cell to effector cell ratio of 5:1 for 3 hours as described in Example 8. Phagocytosis of A20 cells by CER12$^+$ Ba/F3 cells was quantified by fluorescence microscopy and FACs as described in Example 8. Ba/F3 cells transduced with pLenti vector expressing truncated EGFR were used as a negative control. Fluorescent microscope image showing in vitro phagocytosis of A20 cells by CER12+ Ba/F3 cells is shown in FIG. 76 (white arrow shows phagocytosis event). Phagocytic index was calculated for CER12+ Ba/F3 cells as compared to EGFRt transduced Ba/F3control cells and is shown in FIG. 77.

Example 14

Construction of TIM4-FcεR1γ-FcεR1γ CER "CER13"

Figure 78:
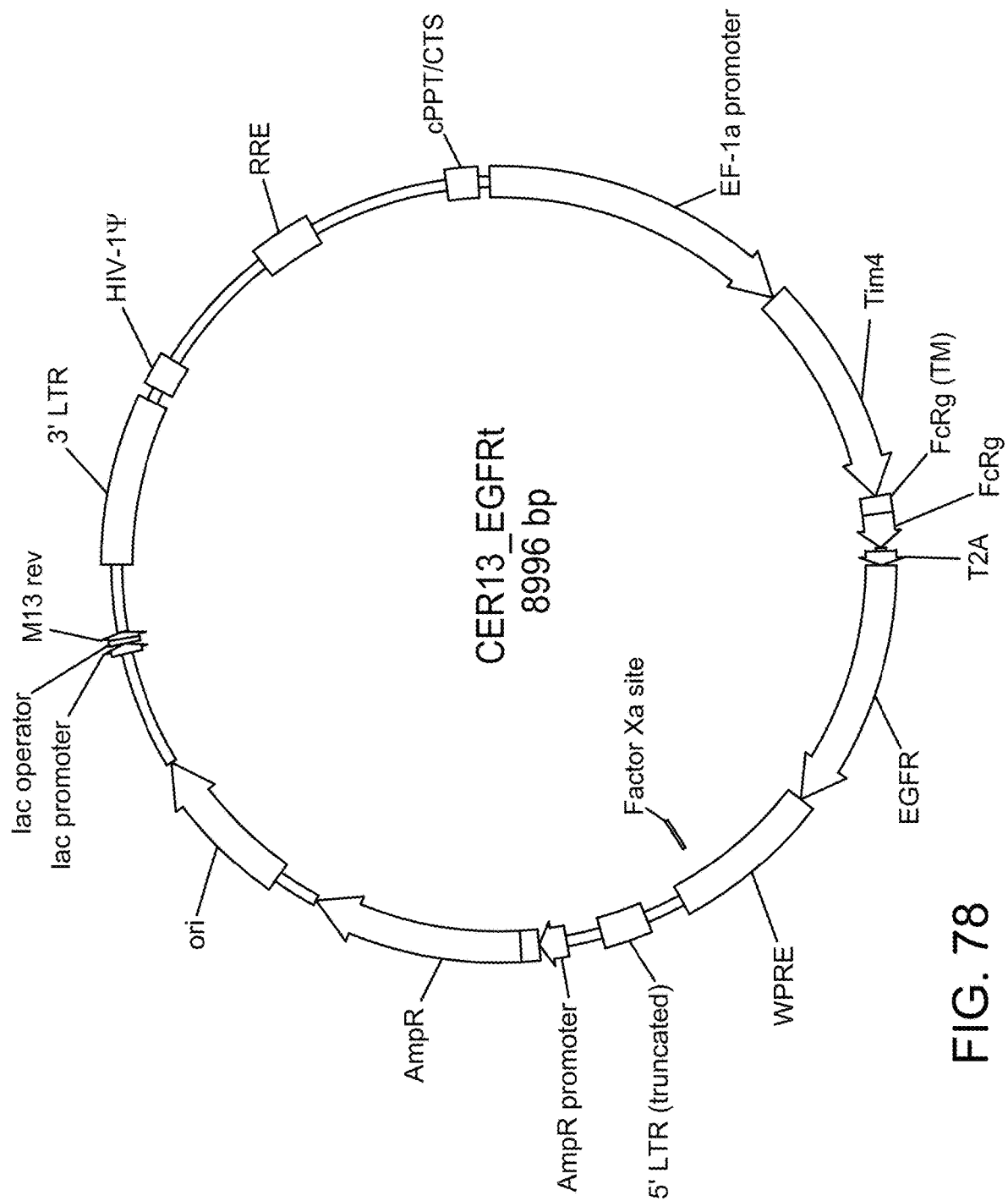
FIG. 78 shows a vector map for a lentiviral vector comprising "CER13" chimeric engulfment receptor having an amino acid sequence of SEQ ID NO:91. CER13 comprises a Tim4 binding domain, an FcεRIγ transmembrane domain, and an FcεRIγ signaling domain. The lentiviral vector also comprises a sequence encoding truncated EGFR (SEQ ID NO:121), which is separated from the CER13 sequence by a viral T2A sequence.
Figure 79B:
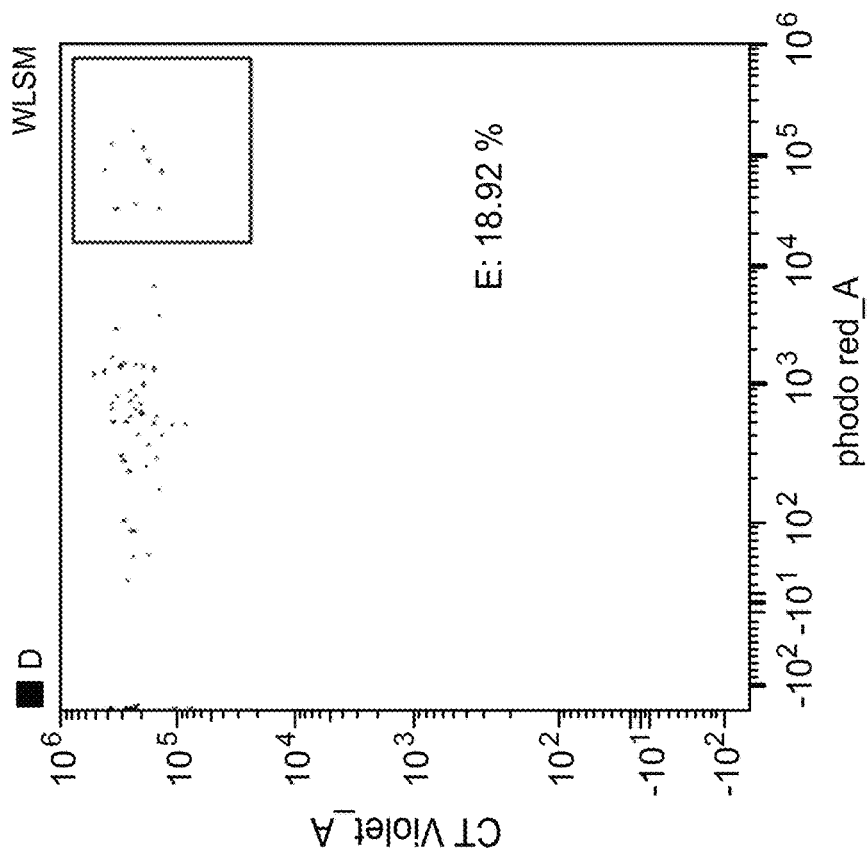
FIGS. 79A-79B show FACS analysis of CER13+ Ba/F3 effector cells (FIG. 79A) and quantification of engulfment of thymocytes by CER13+ Ba/F3 murine B cells by measuring the cell population that stained double positive for pHrodo Red and CELLTRACE Violet (FIG. 79B).
Figure 79A:
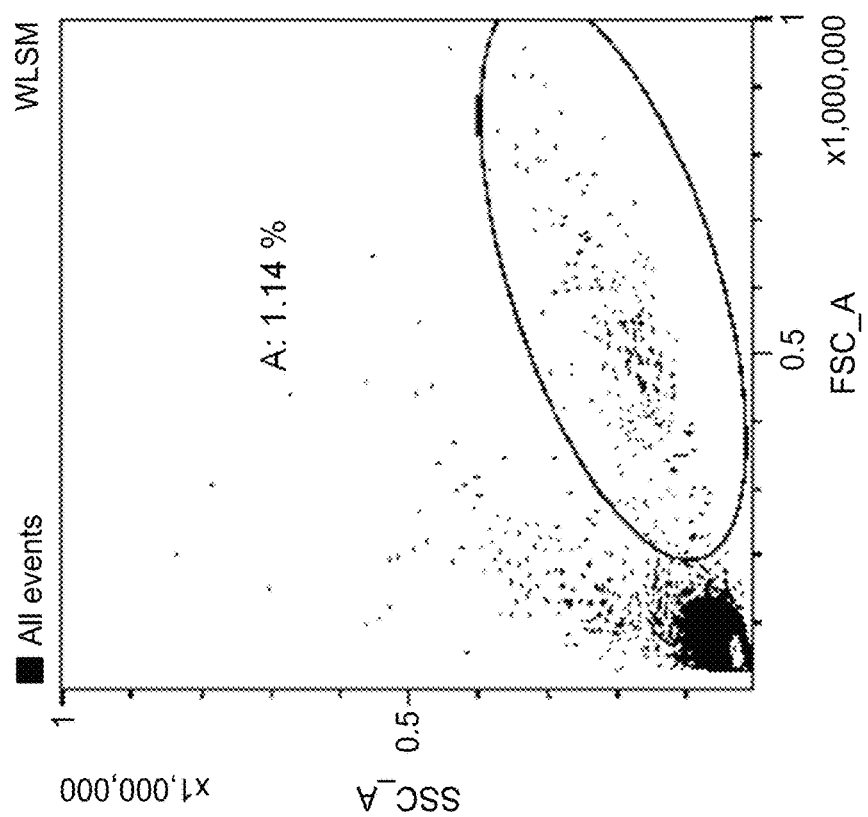

The extracellular domain of the phosphatidylserine binding protein Tim4 (amino acid sequence of SEQ ID NO:73), including the signal peptide (amino acid sequence of SEQ ID NO:72) and were fused to the FcεR1γ transmembrane domain (amino acid sequence of SEQ ID NO:89) and intracellular signaling (SEQ ID NO:88) to create a chimeric engulfment receptor "CER13" (Tim4-FcεR1γ-FcεR1γ CER having an amino acid sequence of SEQ ID NO:91). The FcεR1γ signaling domain transduces a signal for engulfment, and Tim4 is a phosphatidylserine binding receptor. The Tim4-FcεR1γ-FcεR1γ (CER13) chimeric engulfment receptor nucleotide sequence was then inserted into the pLenti lentiviral vector along with truncated EGFR as a transduction marker, separated by T2A sequence (see, FIG. 78). Murine Ba/F3 B-cells were transduced with pLenti vector expressing Tim4-FcεR1γ-FcεR1γ (CER13) and EGFRt, expanded, sorted by FACs, and used for in vitro studies as described in Example 8.

Phagocytic Activity Against Primary Apoptotic Thymocytes

Primary C3H mouse thymocytes were isolated, treated with dexamethasone, and stained with pHrodo Red as described in Example 8. Ba/F3 CER13$^+$ tEGFR$^+$ cells were labeled with CELLTRACE™ Violet dye as described in Example 8. Co-culture experiments with Ba/F3 CER13$^+$ tEGFR$^+$ cells and primary thymocytes were carried out at a 10:1 target cell to effector cell ratio, and Ba/F3 CER13$^+$ EGFR$^+$ cells were quantified for phagocytosis of target thymocytes by fluorescence microscopy and FACs as described in Example 8. Ba/F3 cells transduced with pLenti vector expressing truncated EGFR were used as a negative control.

The quantity of viable, CER13+ transduced Ba/F3 cells as quantified by FACS is shown in FIG. 64A. The frequency of phagocytosis was quantified as the cell population staining double positive for pHrodo Red and CELLTRACE Violet as detected by FACS (see, FIG. 64B).

Figure 80:
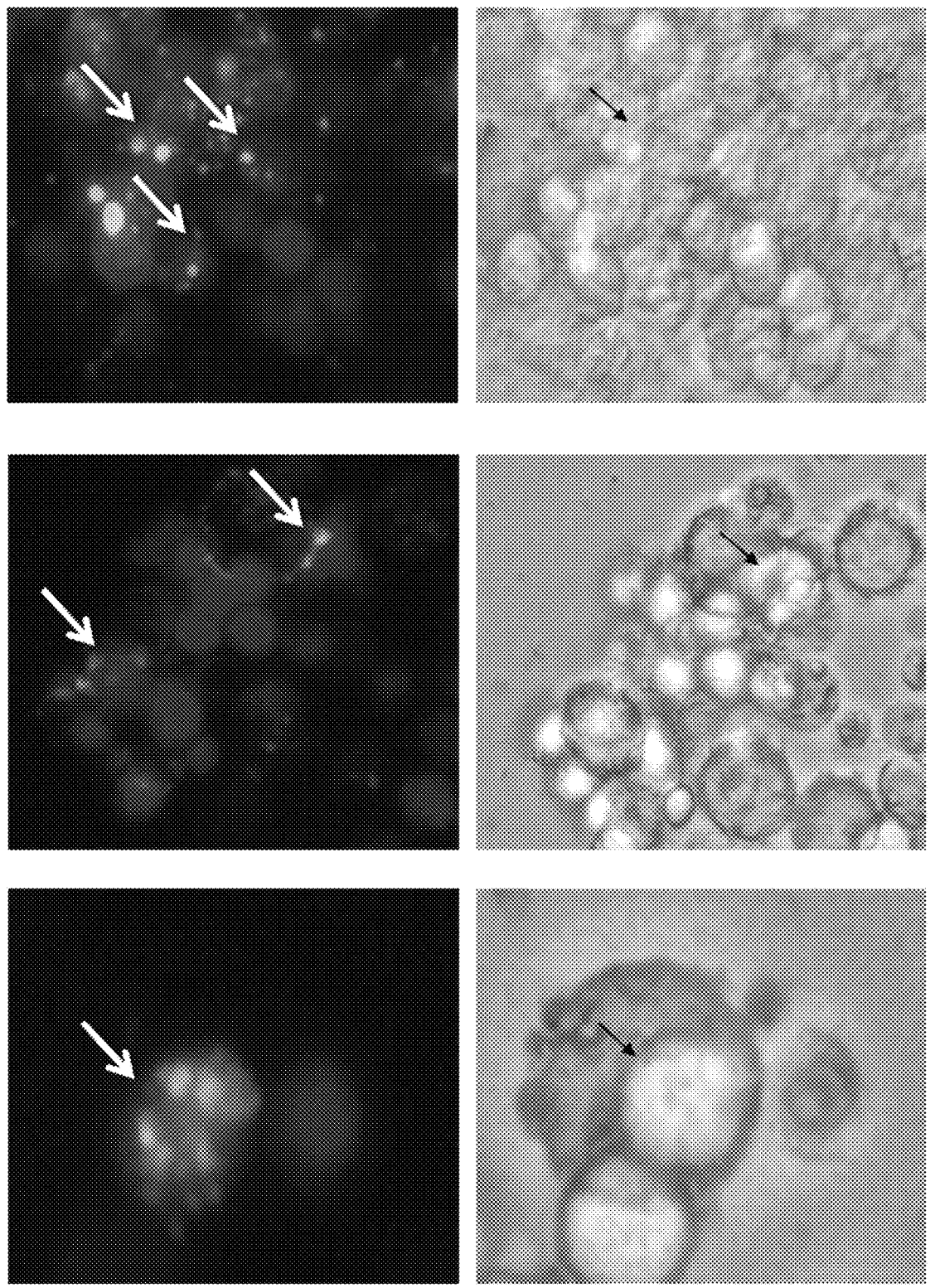
FIG. 80 shows fluorescent microscope images of in vitro phagocytosis of paclitaxel and gemcitabine treated Colo320 HSR colon cancer cells by CER13+ human primary B cells. Arrows indicate phagocytosis events.

Phagocytic Activity of Human CER13$^+$ B Cells Against Chemotherapy-Treated Human Cell Line Human primary B cells were transduced with pLenti Tim4-FcεR1γ-FcεR1γ (CER13) lentivirus expressing truncated EGFR as a transduction marker as described in Example 11. One day prior to setting up the phagocytosis assay, Colo320 HSR colon cancer cells were incubated with phosphatidylserine inducing chemotherapy Gemcitabine (10 μM) and Paclitaxel (30 μM) in serum-free media for 24 hours. Floating and adherent target cells after the treatment were collected, centrifuged, incubated with pHrodo red (1 ng/μL) for 15 minutes at room temperature in PBS, washed and then plated in a non-adherent 96 well plate. Human CER13+ expressing B cells and Colo320HSR cells were co-cultured at a target cell to effector cell ratio of 4:1 at 37° C. for 3 hours. The plate was then imaged using a 20× objective, Keyence BZ-X710 microscope (FIG. 80, arrows show phagocytic events).

Human primary B cells were transduced with pLenti Tim4-FcεR1γ-FcεR1γ (CER13) lentivirus expressing truncated EGFR as a transduction marker as described in Example 11. One day prior to setting up the phagocytosis assay, A204 rhabdomyosarcoma cells were incubated with phosphatidylserine inducing Paclitaxel (30 μM) chemotherapy and H1703 Non Small Cell Lung Cancer (NSCLC) adenocarcinoma cancer cells were incubated with phosphatidylserine inducing Paclitaxel (30 μM)+ Gemcitabine (10 μM) chemotherapy in serum-free media for 24 hours. Floating and adherent target cells after the treatment were collected, centrifuged, incubated with pHrodo red (1 ng/μL) for 15 minutes at room temperature in PBS, washed and then plated in a non-adherent 96 well plate. Human CER13+ expressing B cells and A204 or H1703 cells were co-cultured at a target cell to effector cell ratio of 4:1 at 37° C. for 3 hours. The plate was then imaged using a 20× objective, Keyence BZ-X710 microscope (see, FIG. 81 for A204 cells and FIG. 82 for H1703 cells; arrows indicate phagocytic events).

Example 15

Construction of TIM4-MyD88t CER "CER15"

Figure 83:
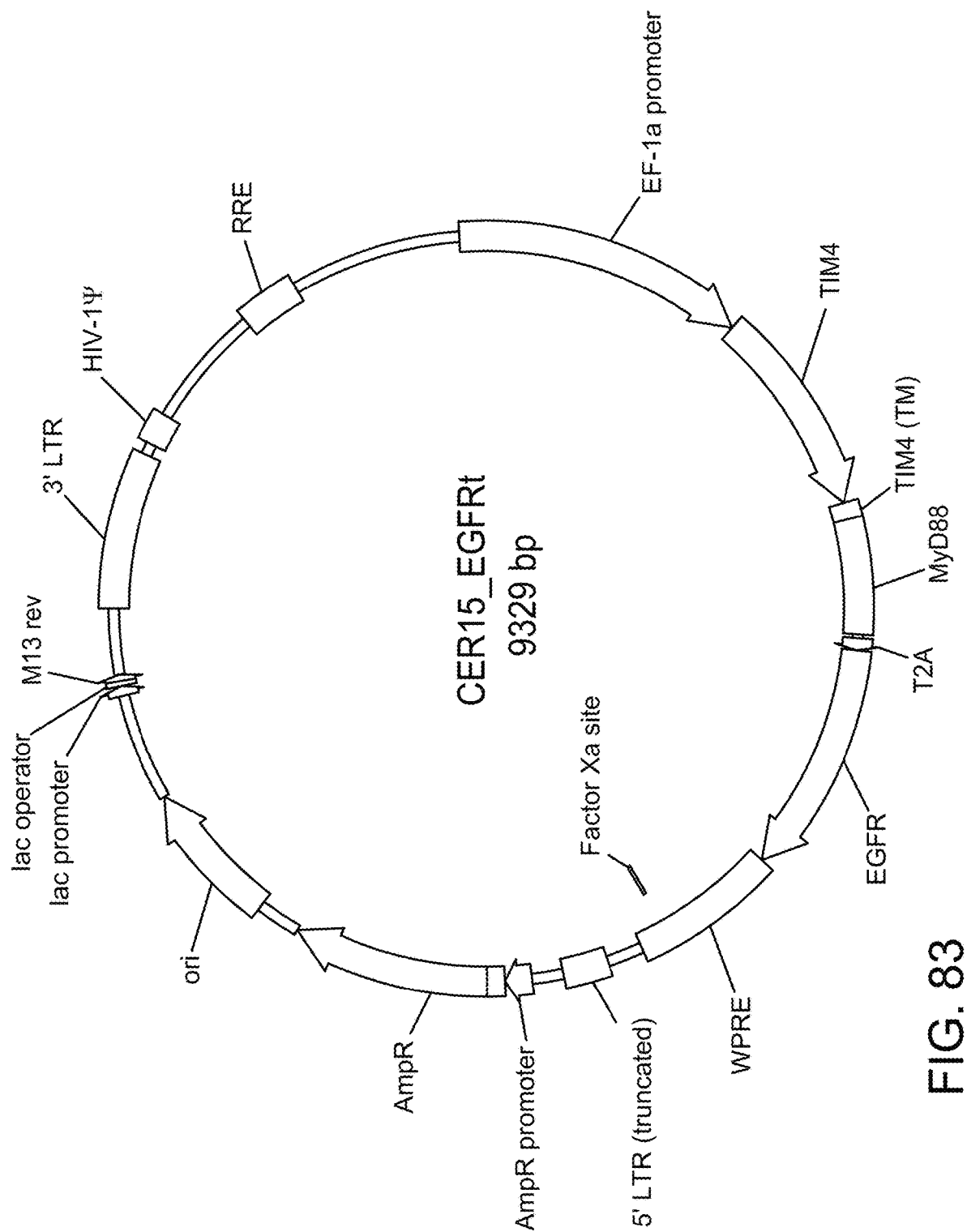
FIG. 83 shows a vector map for a lentiviral vector comprising "CER15" chimeric engulfment receptor having an amino acid sequence of SEQ ID NO:79. CER15 comprises a Tim4 binding domain, a Tim4 transmembrane domain, and truncated MyD88 signaling domain. The lentiviral vector also comprises a sequence encoding truncated EGFR (SEQ ID NO:121), which is separated from the CER15 sequence by a viral T2A sequence.

The extracellular domain of the phosphatidylserine binding protein Tim4 (amino acid sequence of SEQ ID NO:73), including the signal peptide (amino acid sequence of SEQ ID NO:72) and transmembrane domain (amino acid sequence of SEQ ID NO:74) were fused to a truncated MyD88 (MyD88t) comprising a death domain but lacking the TIR domain (SEQ ID NO:78) to create a chimeric engulfment receptor "CER15" (Tim4-MyD88t CER having an amino acid sequence of SEQ ID NO:79). The truncated MyD88 transduces a signal for engulfment, and Tim4 is a phosphatidylserine binding receptor. The Tim4-MyD88t (CER15) chimeric engulfment receptor nucleotide sequence was then inserted into the pLenti lentiviral vector along with truncated EGFR as a transduction marker, separated by T2A sequence (see, FIG. 83). Murine Ba/F3 B-cells were transduced with pLenti vector expressing Tim4-MyD88t (CER15) and EGFRt, expanded, sorted by FACs, and used for in vitro studies as described in Example 8.

Phagocytic Activity Against Primary Apoptotic Thymocytes

Primary C3H mouse thymocytes were isolated, treated with dexamethasone, and stained with pHrodo Red as described in Example 8. Ba/F3 CER15+ tEGFR+ cells were labeled with CELLTRACE™ Violet dye as described in Example 8. Co-culture experiments with Ba/F3 CER15+ tEGFR+ cells and primary thymocytes were carried out at a 10:1 target cell to effector cell ratio, and Ba/F3 CER15+ EGFR+ cells were quantified for phagocytosis of target thymocytes by fluorescence microscopy and FACs as described in Example 8. Ba/F3 cells transduced with pLenti vector expressing truncated EGFR were used as a negative control.

Figure 84B:
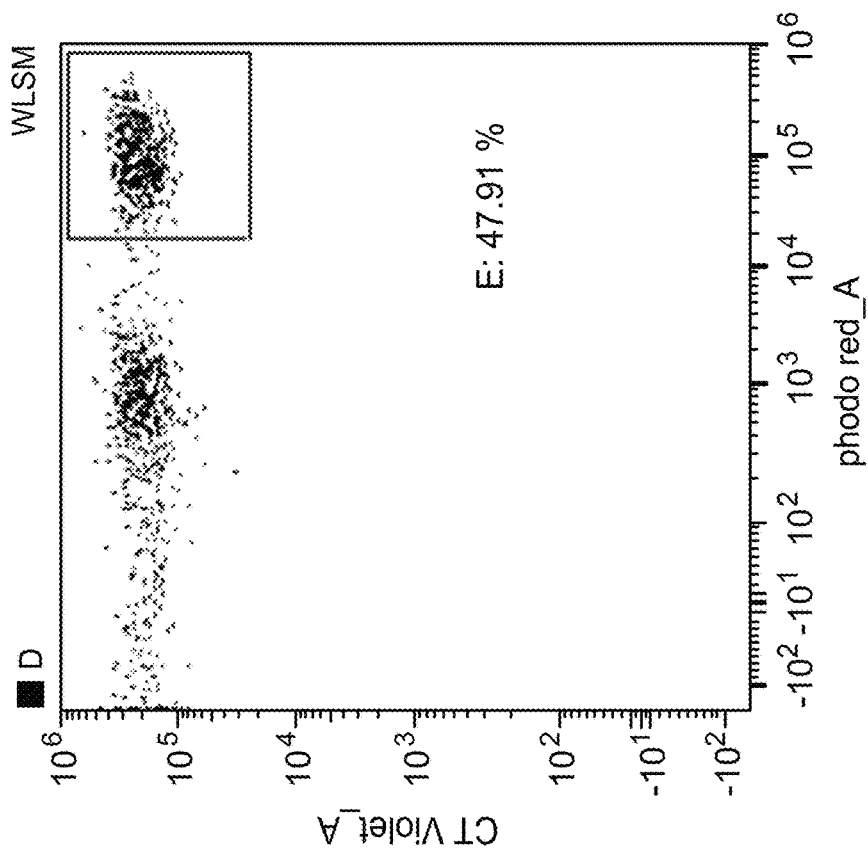
FIGS. 84A-84B show FACS analysis of CER15+ Ba/F3 effector cells (FIG. 84A) and quantification of engulfment of thymocytes by CER15+ Ba/F3 murine B cells by measuring the cell population that stained double positive for pHrodo Red and CELLTRACE Violet (FIG. 84B).
Figure 84A:
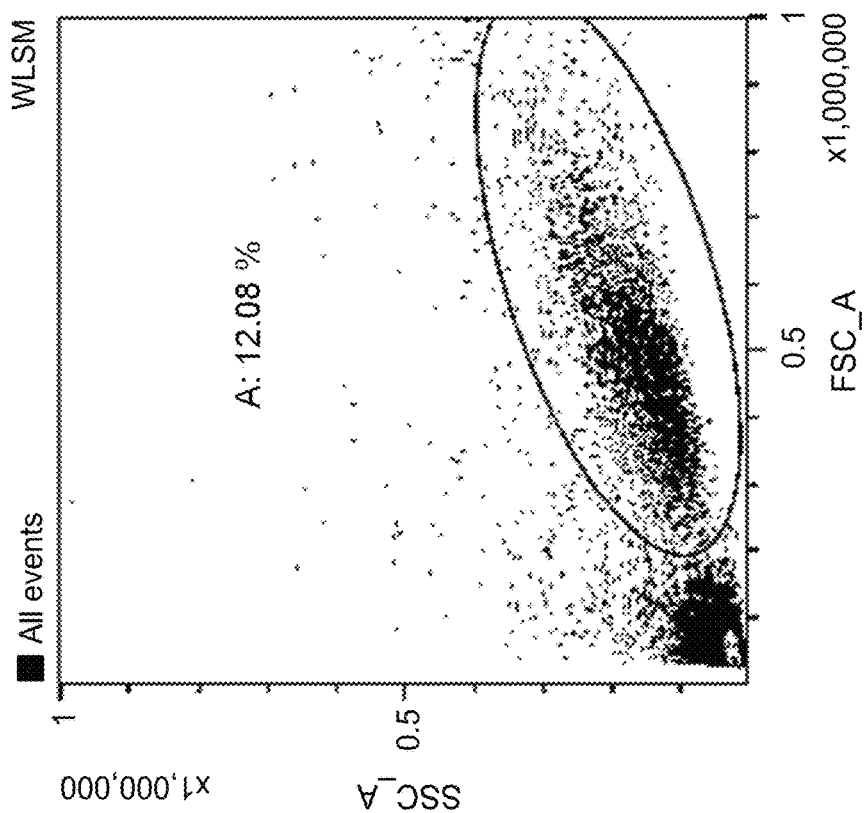

The quantity of viable, CER15+ transduced Ba/F3 cells as quantified by FACS is shown in FIG. 84A. The frequency of phagocytosis was quantified as the cell population staining double positive for pHrodo Red and CELLTRACE Violet as detected by FACS (see, FIG. 84B).

Fluorescent microscopy showed that CER15+ Ba/F3 cells engulf dexamethasone-treated thymocytes (white arrows indicate engulfment events) as compared to tEGFR transduced Ba/F3 control cells (see, FIGS. 85A-85B). High magnification of an engulfment event is shown in the right of FIG. 85B.

Figures 86A, 86B:
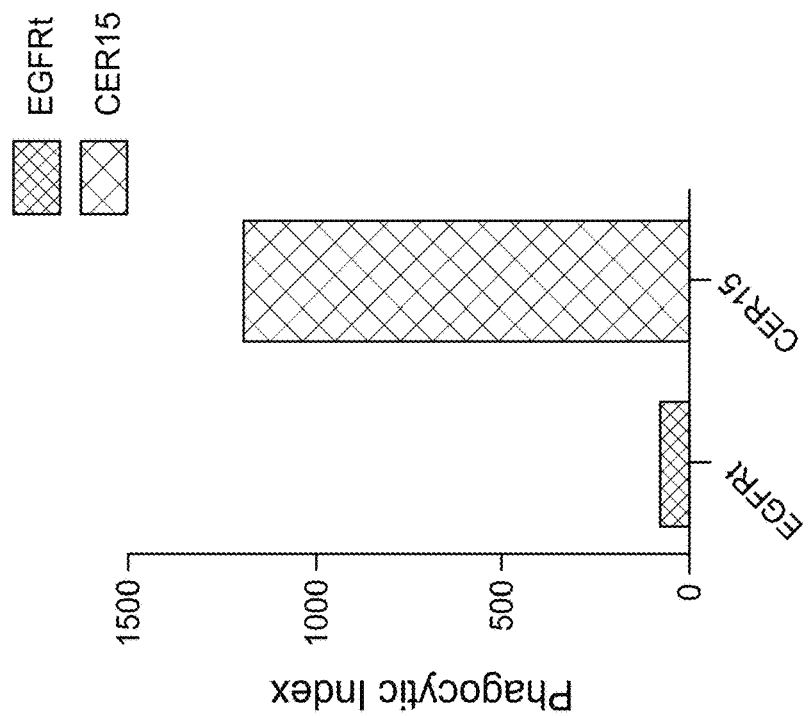
FIGS. 86A-86B show phagocytic index for CER15+ cells or EGFRt+ control Ba/F3 cells.

A phagocytic index was calculated by multiplying [mean of total number of engulfed target cells/total number of counted CER modified cells (e.g., phagocytic frequency)] by [average area of target cell staining per CER+ Ba/F3 cell× 100 (e.g., hybrid capture)] as compared to EGFRt transduced Ba/F3control cells (see, FIGS. 86A-86B).

Phagocytic Activity Against Murine Cell Lines

Figure 87:
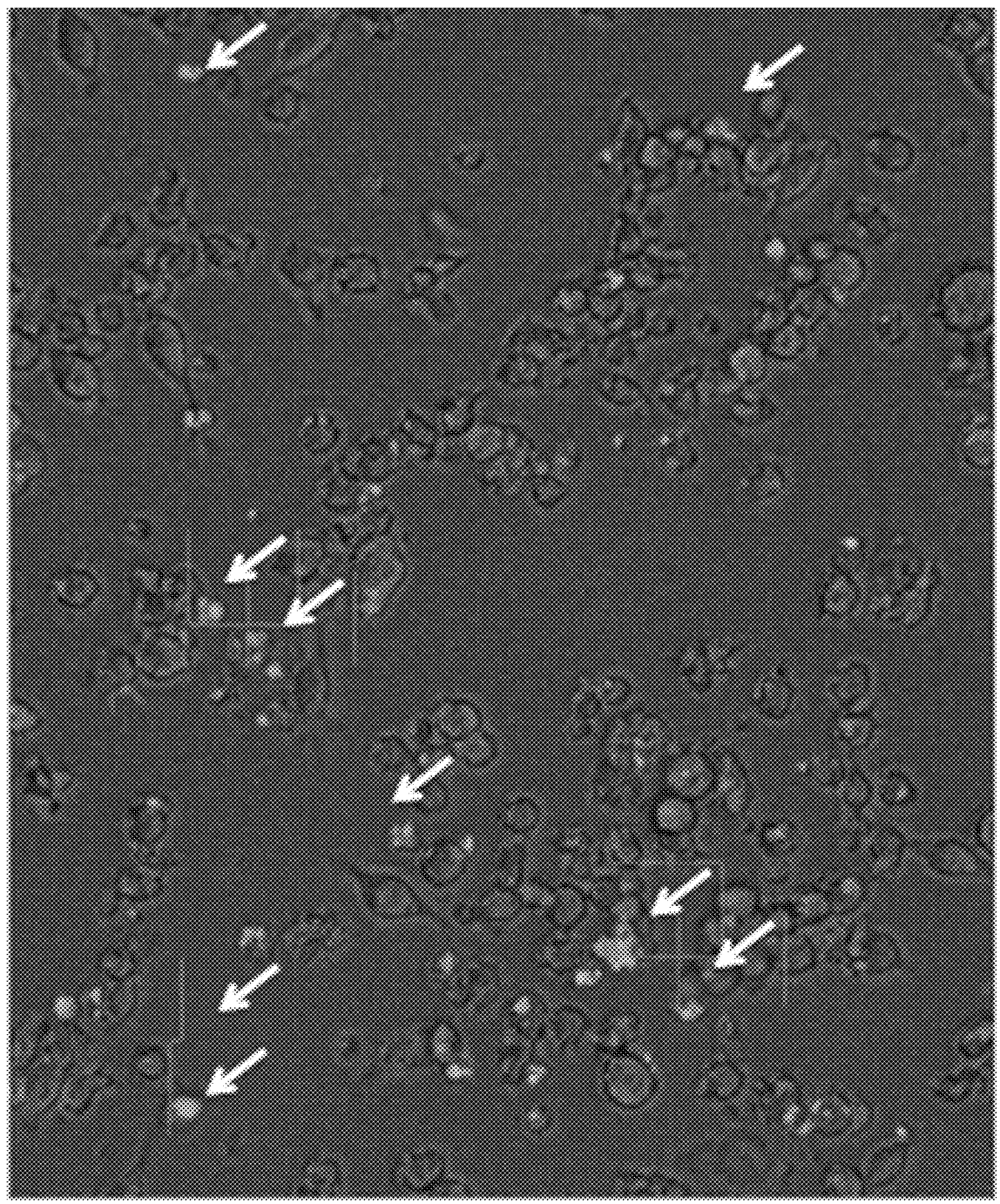
FIG. 87 shows a fluorescent microscope image of in vitro phagocytosis of staurosporine treated CT26 colon carcinoma cells by CER15+ Ba/F3 cells. White arrows indicate phagocytosis events.

Ba/F3 CER15+ tEGFR+ cells were labeled with CELLTRACE™ Violet dye as described in Example 8. CT26 murine colon carcinoma cells were treated with staurosporine, labeled with pHrodo Red and co-cultured with Ba/F3 CER15+ tEGFR+ cells at a target cell to effector cell ratio of 5:1 for 3 hours as described in Example 8. Phagocytosis of CT26 cells by CER15+ Ba/F3 cells was quantified by fluorescence microscopy and FACs as described in Example 8. Ba/F3 cells transduced with pLenti vector expressing truncated EGFR were used as a negative control. Fluorescent microscope image showing in vitro phagocytosis of CT26 cells by CER15+ Ba/F3 cells is shown in FIG. 87 (white arrows show phagocytosis events). CT26 cells labeled with pHrodo Red fluoresce inside the low pH compartments of lysosomes when engulfed (outlined in pink).

Figure 88:
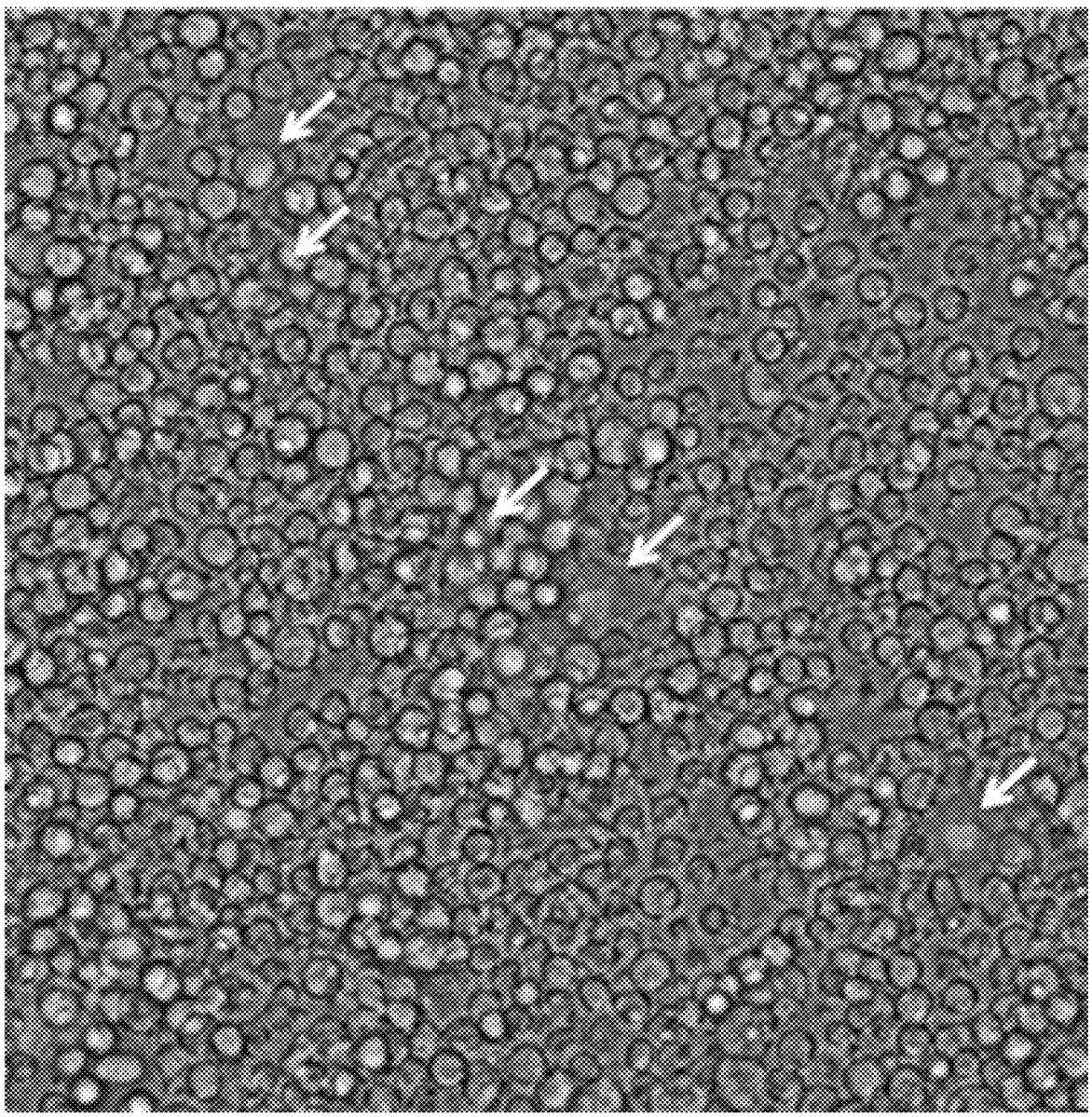
FIG. 88 shows a fluorescent microscope image of in vitro phagocytosis of staurosporine treated WR19L lymphoma cells by CER15+ Ba/F3 cells. White arrows indicate phagocytosis events.

WR19L murine lymphoma cells were treated with staurosporine, labeled with pHrodo Red and co-cultured with CELLTRACE Violet labeled Ba/F3 CER15+ tEGFR+ cells at a target cell to effector cell ratio of 5:1 for 3 hours as described in Example 8. Phagocytosis of WR19L cells by CER15+ Ba/F3 cells was quantified by fluorescence microscopy and FACs as described in Example 8. Ba/F3 cells transduced with pLenti vector expressing truncated EGFR were used as a negative control. Fluorescent microscope image showing in vitro phagocytosis of WR19L cells by CER15+ Ba/F3 cells is shown in FIG. 88 (white arrow show phagocytosis events).

Figure 89:
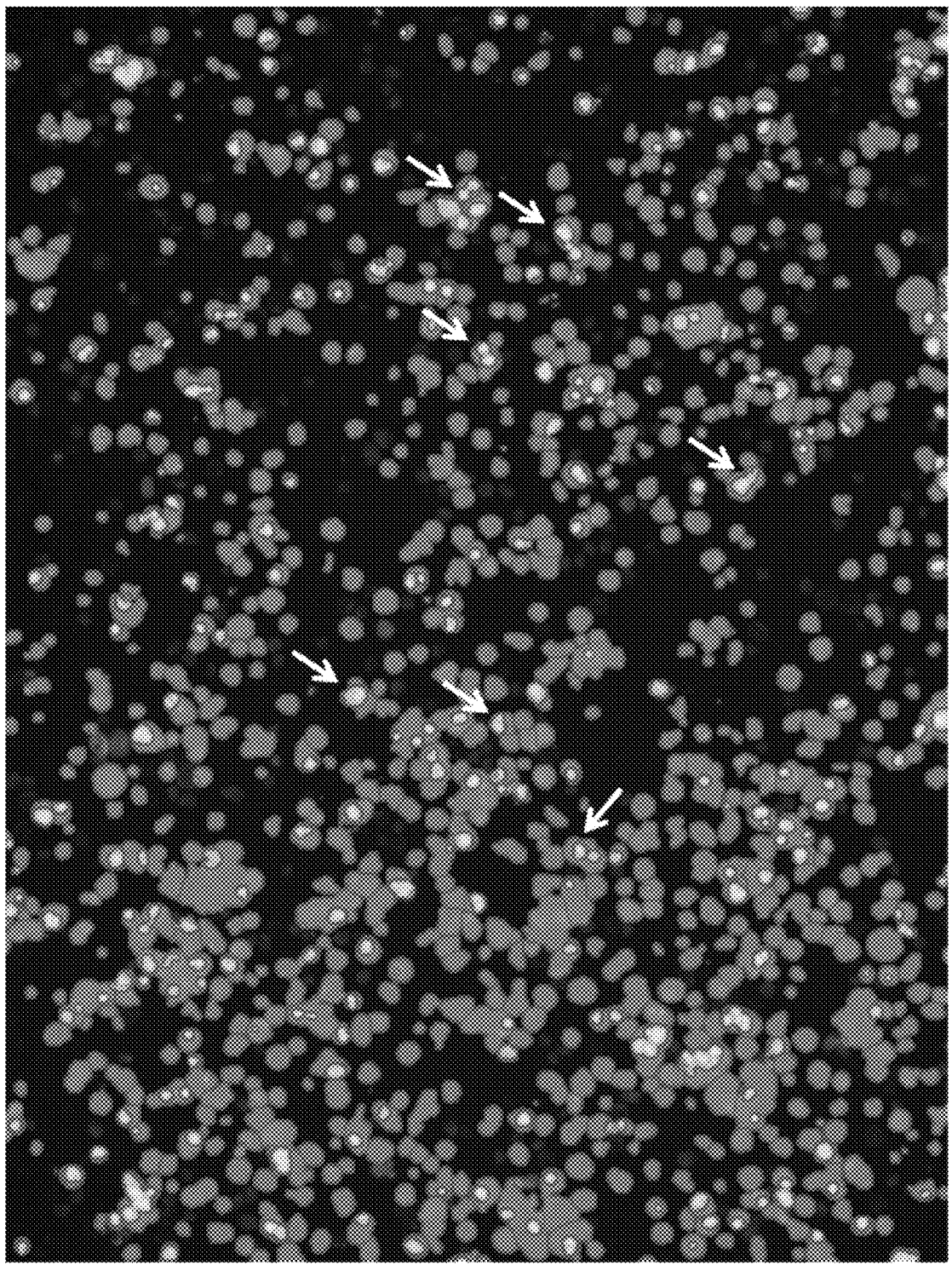
FIG. 89 shows a fluorescent microscope image of in vitro phagocytosis of staurosporine treated A20 lymphoma cells by CER15+ Ba/F3 cells. White arrows indicate phagocytosis events.

A20 murine lymphoma cells were treated with staurosporine, labeled with pHrodo Red and co-cultured with CELLTRACE Violet labeled Ba/F3 CER15+ tEGFR+ cells at a target cell to effector cell ratio of 5:1 for 3 hours as described in Example 8. Phagocytosis of A20 cells by CER15+ Ba/F3 cells was quantified by fluorescence microscopy and FACs as described in Example 8. Ba/F3 cells transduced with pLenti vector expressing truncated EGFR were used as a negative control. Fluorescent microscope image showing in vitro phagocytosis of A20 cells by CER15+ Ba/F3 cells is shown in FIG. 89 (white arrow show phagocytosis events).

Phagocytic Activity of Human CER15+ B Cells Against Human Cell Line

Human primary B cells were transduced with pLenti Tim4-MyD88t (CER15) lentivirus expressing truncated EGFR as a transduction marker as described in Example 8. Transduced human B cells were sorted by FACS with a labeled anti-EGFR antibody (Cetuximab) and then stained with a Kat5-18 antibody (Tim4 specific) (Abcam Catalog #176486) (see, FIG. 90A where the % in the right FACS plot represents the % of cells expressing Tim4 binding domain (CER15)). Purified CER15+ B cells were expanded, and imaged at 24 hours, 48 hours, and 72 hours shown in FIG. 90B.

Figure 91:
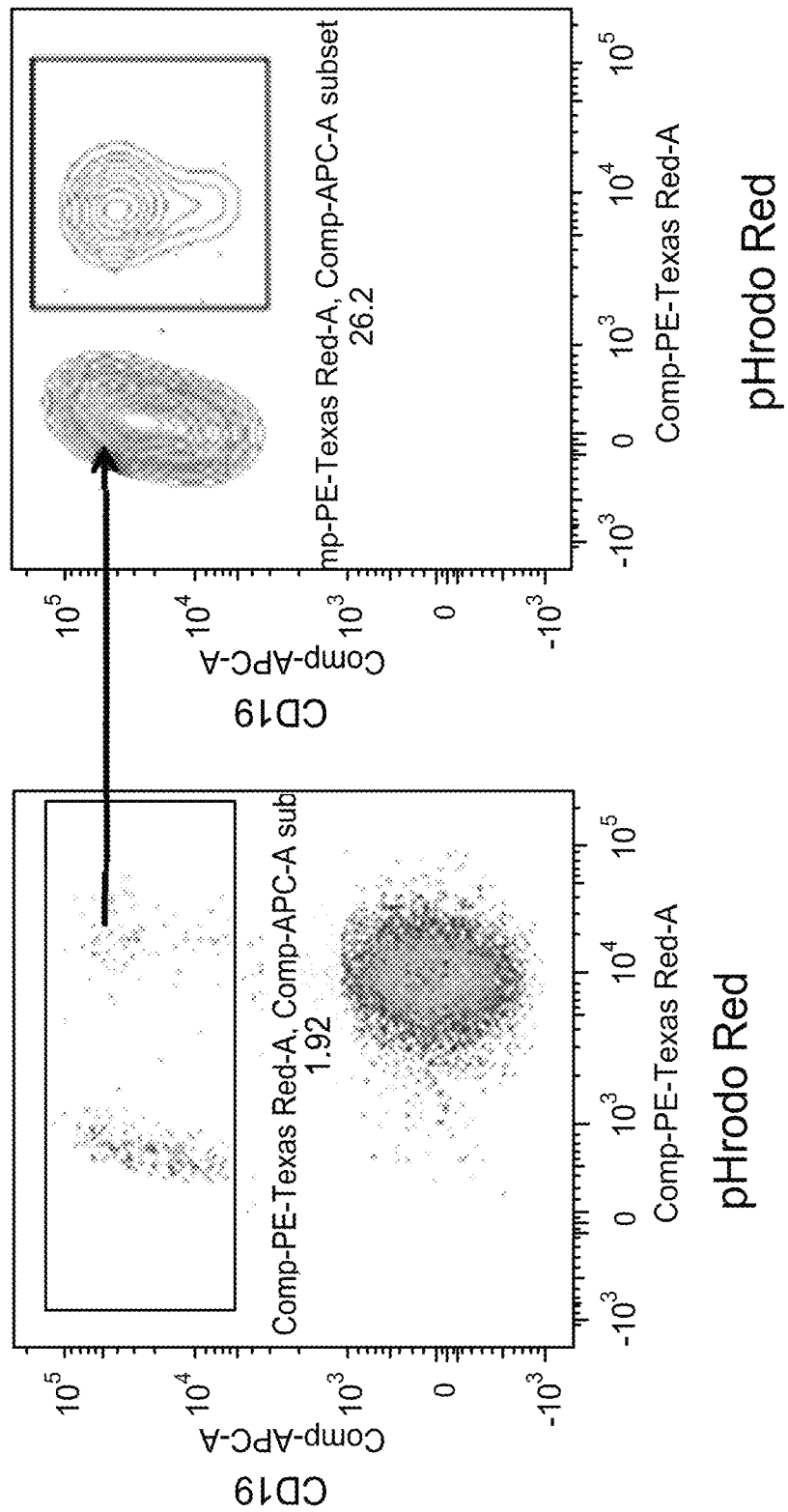
FIG. 91 shows phagocytosis of staurosporine treated, pHrodo Red stained Jurkat cells by CER15+ human primary B cells as analyzed by FACS. Gating was performed on viable CD19+, allophycocyanin (APC)-labeled cells (left plot) and frequency of double positive stained events (APC and pHrodo Red) was defined as phagocytosis events (right plot).
Figure 92:
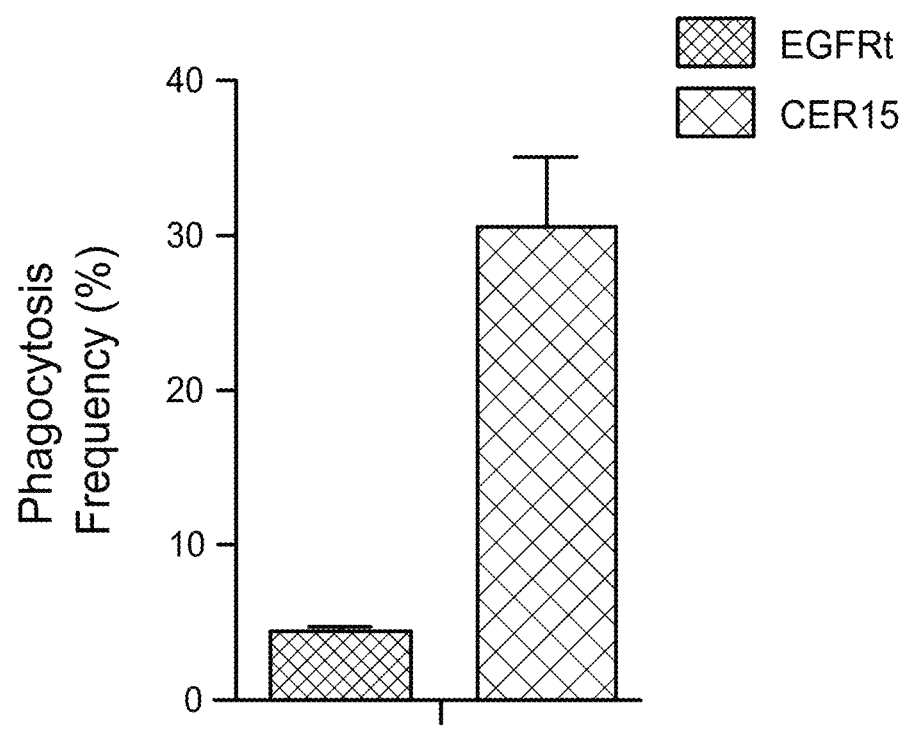
FIG. 92 shows a graph of frequency of phagocytosis by CER15+ human primary B cells co-incubated with staurosporine treated Jurkat cells compared to control human primary B cells transduced with truncated EGFR.
Figure 94:
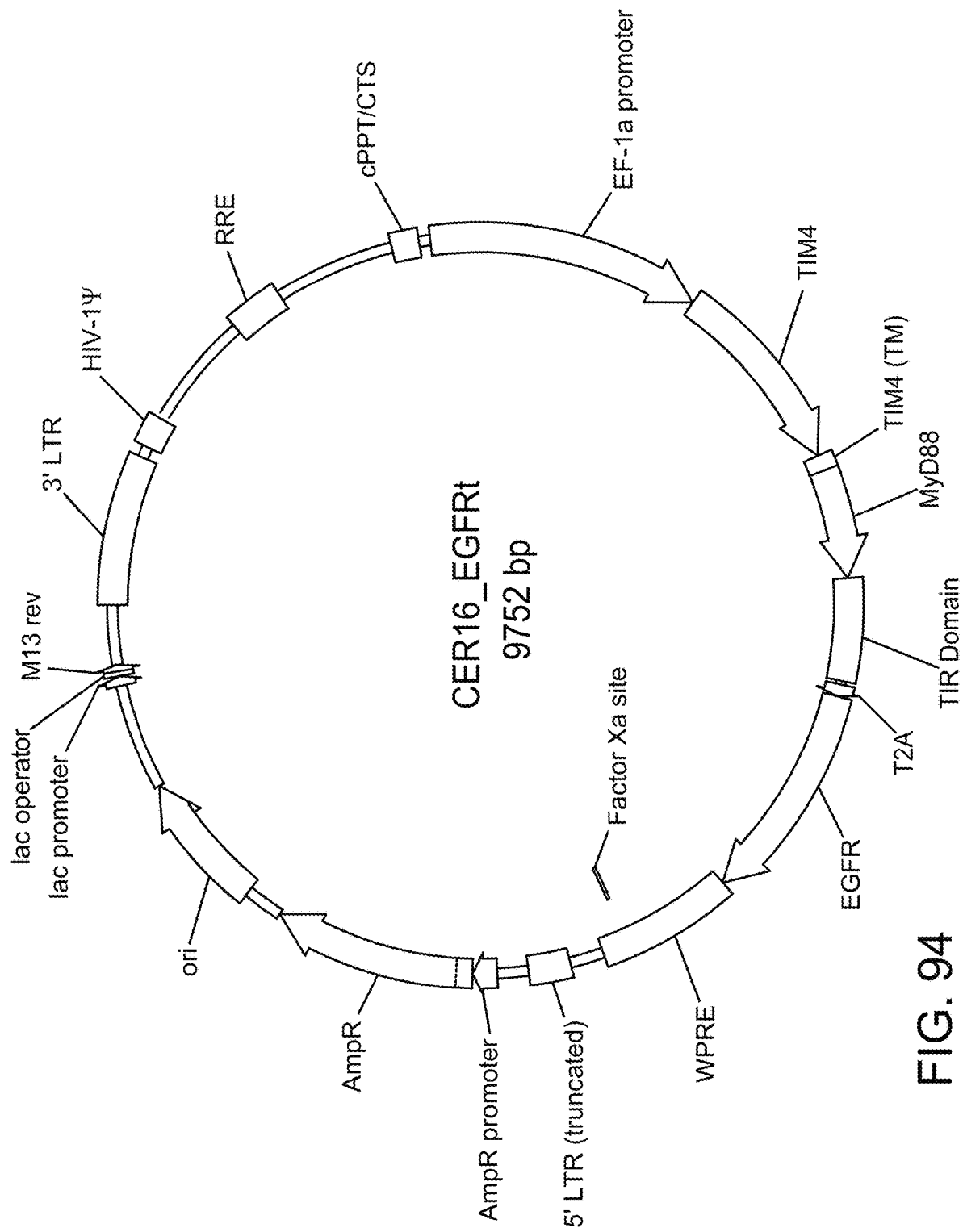
FIG. 94 shows a vector map for a lentiviral vector comprising "CER16" chimeric engulfment receptor having an amino acid sequence of SEQ ID NO:80. CER16 comprises a Tim4 binding domain, a Tim4 transmembrane domain, and a MyD88 signaling domain. The lentiviral vector also comprises a sequence encoding truncated EGFR (SEQ ID NO:121), which is separated from the CER16 sequence by a viral T2A sequence.

Jurkat human T lymphocytes were treated with staurosporine, labeled with pHrodo Red, and co-cultured with CER15+ primary B cells in a phagocytosis assay as described in Example 8 using a target cell to effector cell ratio of 5:1 and co-incubation time of 3 hours. Phagocytosis of Jurkat cells by CER15+ human B cells was quantified by fluorescence microscopy and FACs as described in Example 8. The frequency of viable CD19 positive human primary B cells and frequency of CD19 positive-pHrodo Red positive events (double positive events) are shown in FIG. 91 (left and right plots, respectively). FIG. 92 shows frequency of phagocytosis of Jurkat cells by primary human B cells transduced with CER15+ tEGFR+ or EGFR+ control.

A fluorescent microscope image showing in vitro phagocytosis of Jurkat cells by CER15+ human primary B cells is shown in FIG. 93A, and phagocytosis of Jurkat cells by tEGFR+ human primary B cells control is shown in FIG. 93B (white arrows show phagocytosis events).

Example 16

Construction of TIM4-MyD88 CER "CER16"

The extracellular domain of the phosphatidylserine binding protein Tim4 (amino acid sequence of SEQ ID NO:73), including the signal peptide (amino acid sequence of SEQ ID NO:72) and transmembrane domain (amino acid sequence of SEQ ID NO:74) were fused to MyD88 signaling domain comprising the death domain and TIR domain (SEQ ID NO:53) to create a chimeric engulfment receptor "CER16" (Tim4-MyD88 CER having an amino acid sequence of SEQ ID NO:80). The MyD88 transduces a signal for engulfment, and Tim4 is a phosphatidylserine binding receptor. The Tim4-MyD88 (CER16) chimeric engulfment receptor nucleotide sequence was then inserted into the pLenti lentiviral vector along with truncated EGFR as a transduction marker, separated by T2A sequence (see, FIG. 94). Murine Ba/F3 B-cells were transduced with pLenti vector expressing Tim4-MyD88 (CER16) and EGFRt, expanded, sorted by FACs, and used for in vitro studies as described in Example 8.

Phagocytic Activity of Human CER16+ B Cells Against Chemotherapy-Treated Human Cell Line Human primary B cells were transduced with pLenti Tim4-MyD88 (CER16) lentivirus expressing truncated EGFR as a transduction marker as described in Example 8. One day prior to setting up the phagocytosis assay, Jurkat human B lymphocyte cells were cultured in complete RPMI 1640 growth media supplemented with 10% fetal bovine serum and 1% penicillin-streptomycin in a 6 well plate and treated with oxaliplatin (5 µM) and fluorouracil (5-FU) (10

Figure 95:
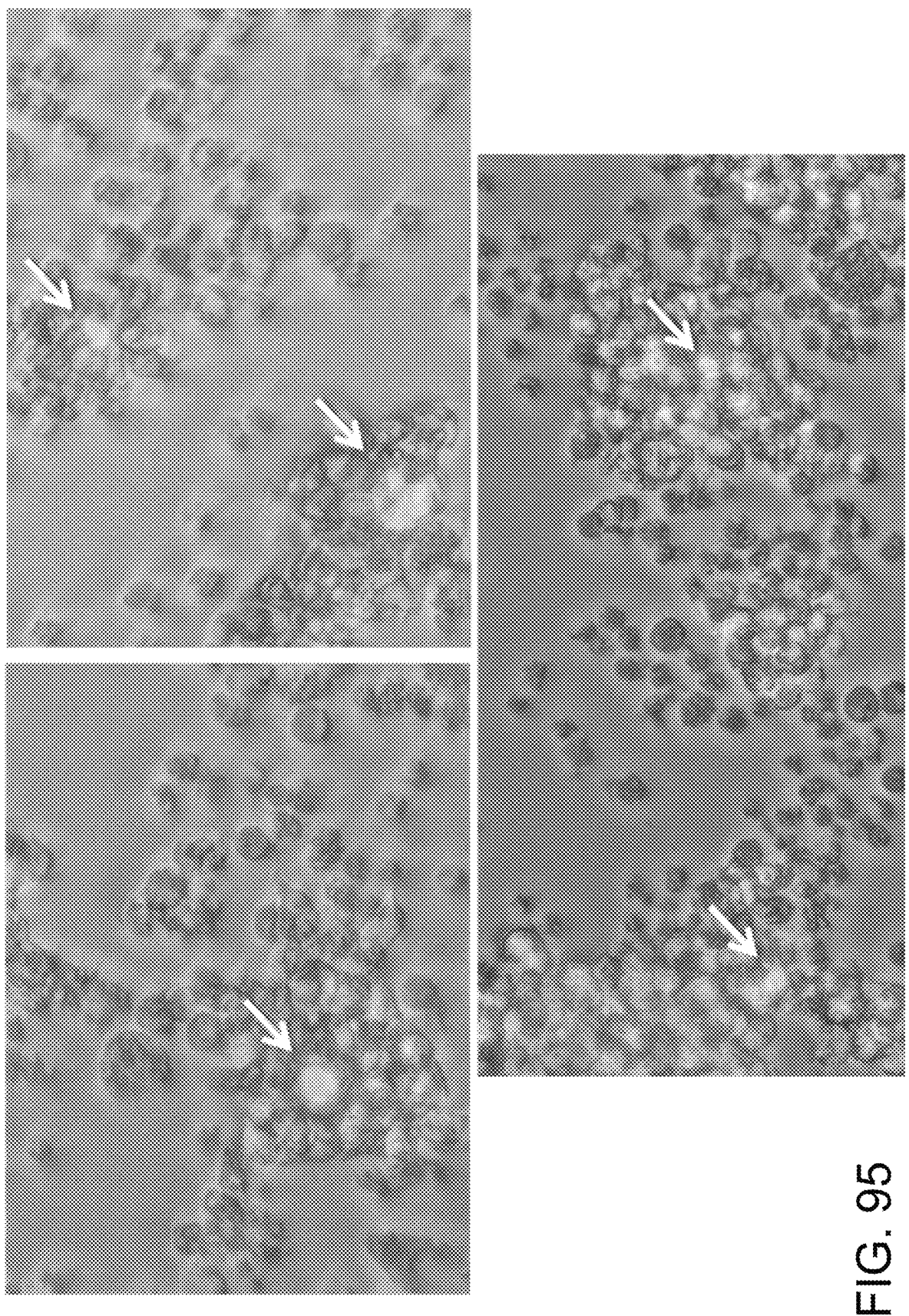
FIG. 95 shows fluorescent microscope images of in vitro phagocytosis of Jurkat cells treated with oxaliplatin and fluorouracil by CER16+ human primary B cells. White arrows indicate phagocytosis events.

The following day, target Jurkat cells were collected, washed twice with 1×PBX, and stained with pHrodo Red (1 ng/mL in PBS) for 15 minutes at room temperature. The Jurkat cells were supplemented with growth media, washed once to remove excess pHrodo Red, and plated on flat bottom 96 well plates at approximately 200,000 cells/well in RPMI 1640 complete media. Transduced primary B cells were washed once with 1×PBS and then stained with CELLTRACE Violet (1 mM in PBS) for 10 minutes at 37° C. The human primary B cells were supplemented with growth media, washed once with 1×PBS to remove excess CELLTRACE Violet, and plated onto a 96 well plate at approximately 50,000 cells in RPMI complete media. Human primary B cells and Jurkat cells were co-cultured at a target cell to effector cell ratio of 4:1 at 37° C. for 3 hours. The plate was then imaged using a 20× objective, Keyence BZ-X710 microscope. FIG. 95 shows fluorescent microscope images showing engulfment of chemotherapy treated Jurkat cells by CER16+ human primary B cells (white arrows indicate phagocytosis).

Example 17

Construction of TIM4-NFAM1 CER "CER25"

Figure 96:
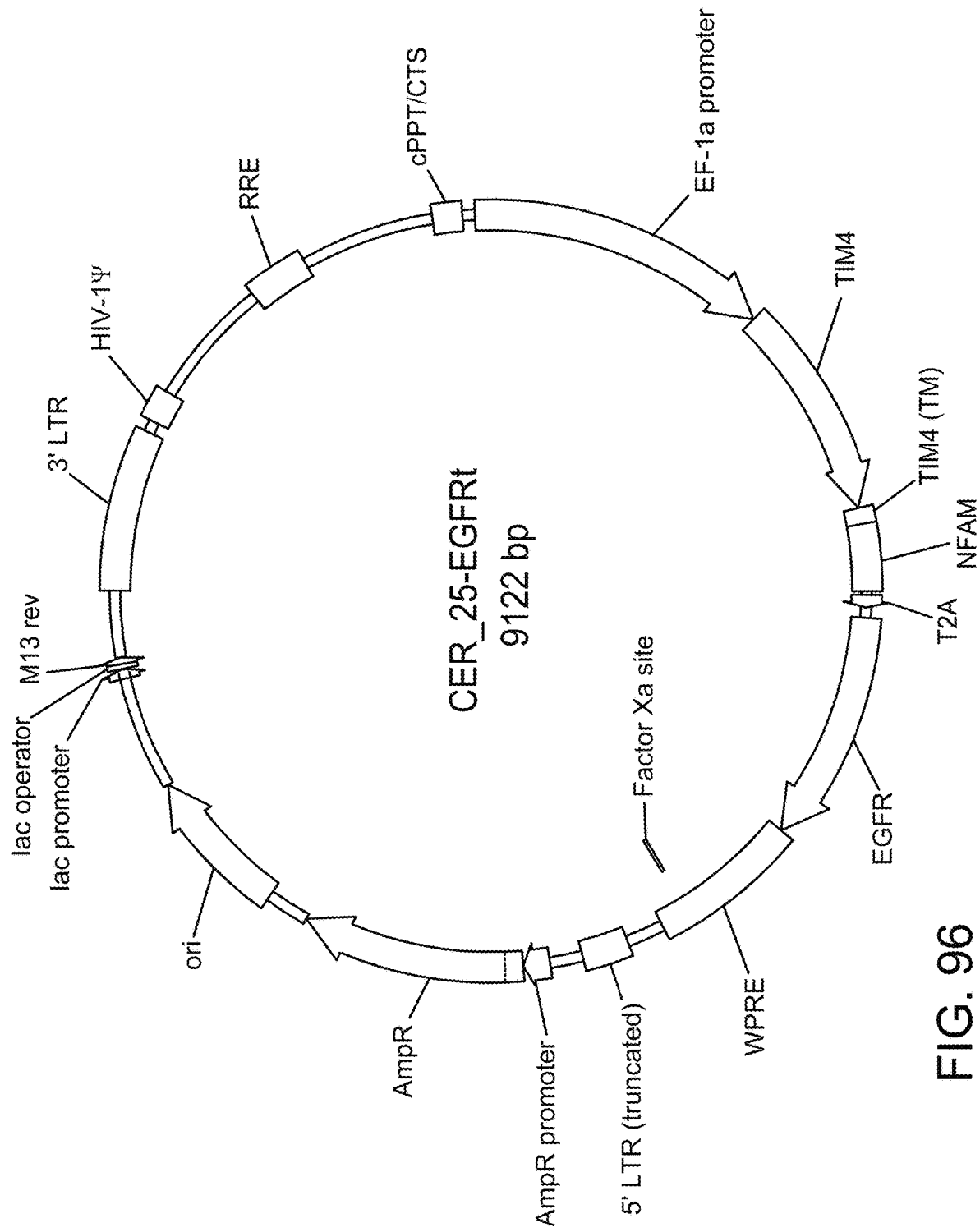
FIG. 96 shows a vector map for a lentiviral vector comprising "CER25" chimeric engulfment receptor having an amino acid sequence of SEQ ID NO:93. CER25 comprises a Tim4 binding domain, a Tim4 transmembrane domain, and a NFAM1 signaling domain. The lentiviral vector also comprises a sequence encoding truncated EGFR (SEQ ID NO:121), which is separated from the CER25 sequence by a viral T2A sequence.

The extracellular domain of the phosphatidylserine binding protein Tim4 (amino acid sequence of SEQ ID NO:73), including the signal peptide (amino acid sequence of SEQ ID NO:72) and transmembrane domain (amino acid sequence of SEQ ID NO:74) were fused to NFAM1 signaling domain (SEQ ID NO:92) to create a chimeric engulfment receptor "CER25" (Tim4-NFAM1 CER having an amino acid sequence of SEQ ID NO:93). The NFAM1 signaling domain transduces a signal for engulfment, and Tim4 is a phosphatidylserine binding receptor. The Tim4-NFAM1 (CER25) chimeric engulfment receptor nucleotide sequence was then inserted into the pLenti lentiviral vector along with truncated EGFR as a transduction marker, separated by T2A sequence (see, FIG. 96). Murine Ba/F3 B-cells were transduced with pLenti vector expressing Tim4-NFAM1 (CER25) and EGFRt, expanded, sorted by FACs, and used for in vitro studies as described in Example 8.

Phagocytic Activity Against Primary Apoptotic Thymocytes

Primary C3H mouse thymocytes were isolated, treated with dexamethasone, and stained with pHrodo Red as described in Example 8. Ba/F3 CER25+ tEGFR+ cells were labeled with CELLTRACE™ Violet dye as described in Example 8. Co-culture experiments with Ba/F3 CER25+ tEGFR+ cells and primary thymocytes were carried out at a 10:1 target cell to effector cell ratio, and Ba/F3 CER25+ EGFR+ cells were quantified for phagocytosis of target thymocytes by fluorescence microscopy and FACs as described in Example 8. Ba/F3 cells transduced with pLenti vector expressing truncated EGFR were used as a negative control.

Figure 97:
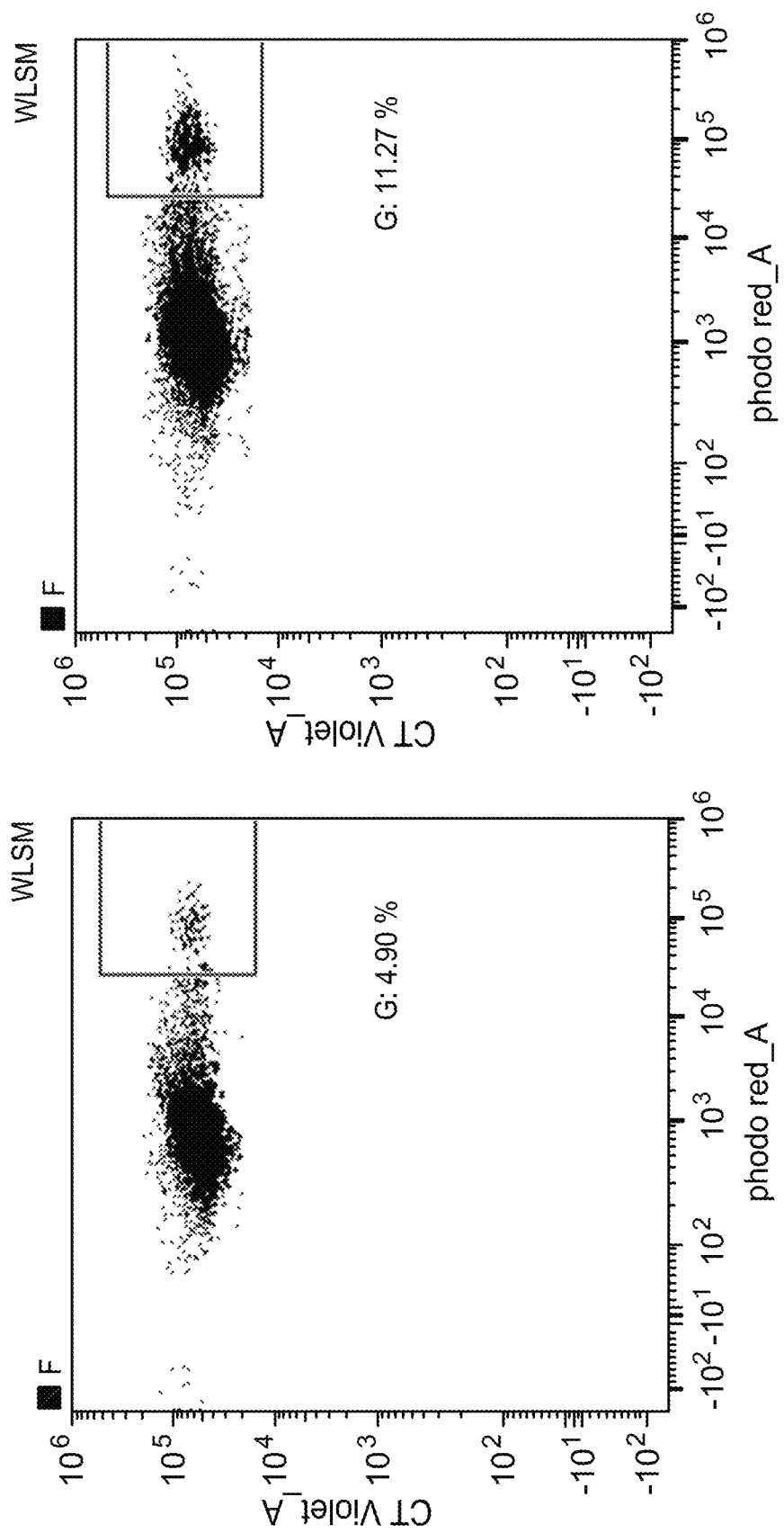
FIGS. 97A-97B show FACS quantification of engulfment of dexamethasone treated thymocytes by CER25+ Ba/F3 murine B cells by measuring the cell population that stained double positive for pHrodo Red and CELLTRACE Violet (FIG. 97B) compared to control Ba/F3 cells transduced with truncated EGFR (FIG. 97A).

Viable, CER25+ transduced Ba/F3 cells as quantified by FACS is shown in FIG. 97. The frequency of phagocytosis by CER25+ Ba/F3 cells co-cultured with dexamethasone treated thymocytes was quantified as the cell population staining double positive for pHrodo Red and CELLTRACE Violet as detected by FACS (see, FIG. 97B). Frequency of double positive staining cells for control Ba/F3 cells transduced with truncated EGFR and co-cultured with dexamethasone treated thymocytes is shown in FIG. 97A.

Fluorescent microscopy showed that CER25+ Ba/F3 cells engulf dexamethasone-treated thymocytes (white arrows indicate engulfment events) as compared to tEGFR transduced Ba/F3 control cells (see, FIG. 98 High magnification of an engulfment event is shown in the right of FIG. 98).

Figure 99:
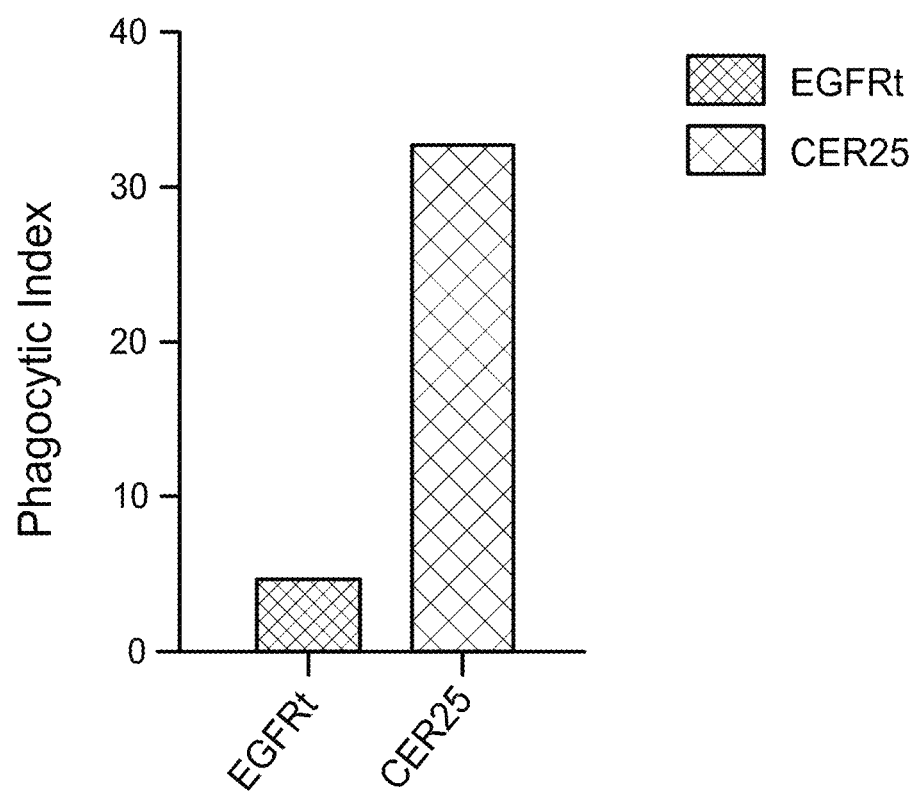
FIG. 99 shows a graph of phagocytic index of CER25+ Ba/F3 cells co-cultured with dexamethasone treated thymocytes compared to Ba/F3 cells transduced with truncated EGFR.

A phagocytic index was calculated by multiplying [mean of total number of engulfed target cells/total number of counted CER modified cells (e.g., phagocytic frequency)] by [average area of target cell staining per CER+ Ba/F3 cell× 100 (e.g., hybrid capture)] as compared to EGFRt transduced Ba/F3control cells (see, FIG. 99).

Example 18

Construction of TIM4-MyD88t-BAFFR CER "CER85"

Figure 100:
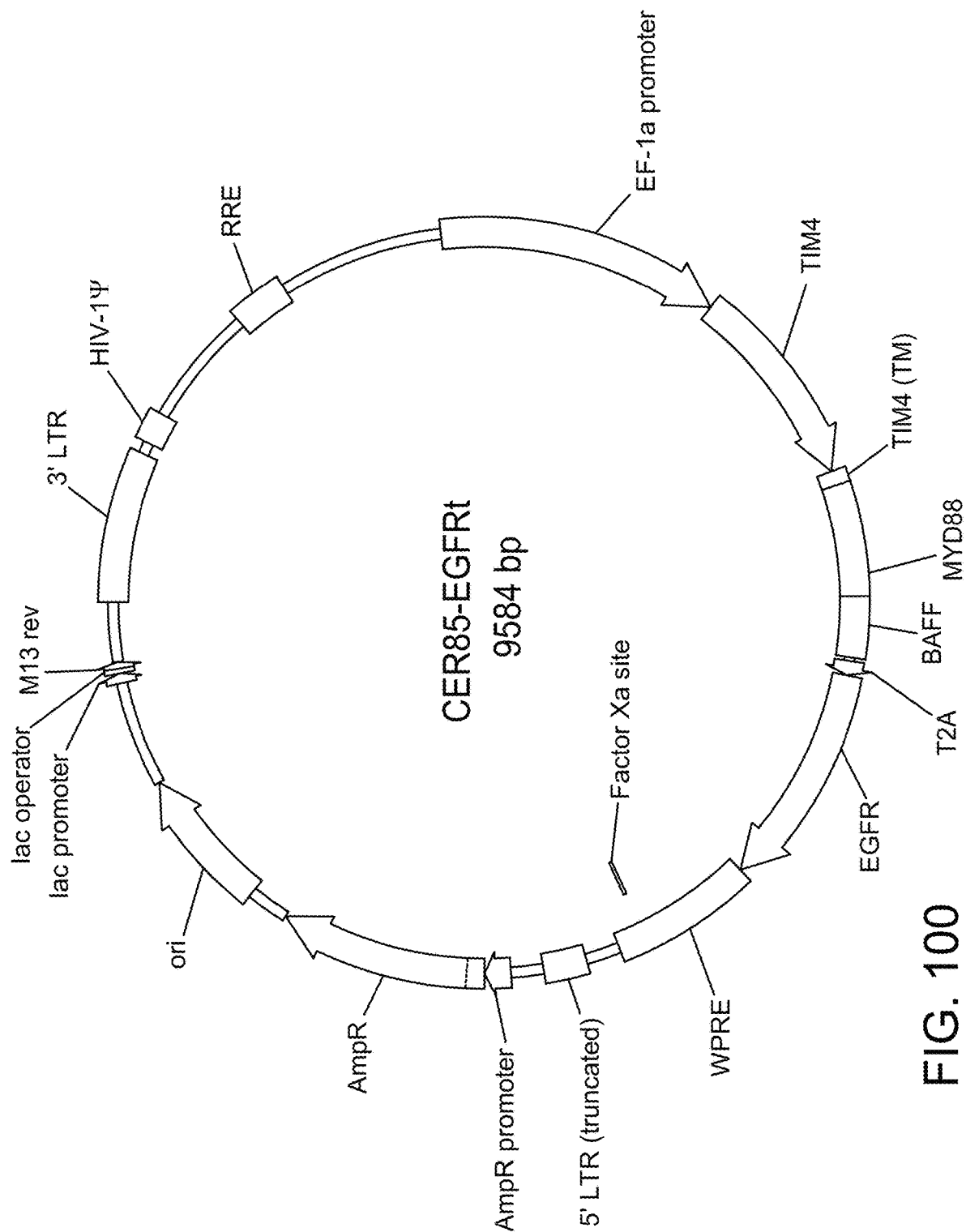
FIG. 100 shows a vector map for a lentiviral vector comprising "CER85" chimeric engulfment receptor having an amino acid sequence of SEQ ID NO:95. CER85 comprises a Tim4 binding domain, a Tim4 transmembrane domain, a primary engulfment signaling domain that is a truncated MyD88 signaling domain, and a secondary engulfment signaling domain that is a BAFFR signaling domain. The lentiviral vector also comprises a sequence encoding truncated EGFR (SEQ ID NO:121), which is separated from the CER85 sequence by a viral T2A sequence.

The extracellular domain of the phosphatidylserine binding protein Tim4 (amino acid sequence of SEQ ID NO:73), including the signal peptide (amino acid sequence of SEQ ID NO:72) and transmembrane domain (amino acid sequence of SEQ ID NO:74) were fused to primary signaling domain comprising a truncated MyD88 (SEQ ID NO:78) and a secondary signaling domain comprising a BAFF-R signaling domain (SEQ ID NO:94) to create a chimeric engulfment receptor "CER85" (Tim4-MyD88t-BAFFR CER having an amino acid sequence of SEQ ID NO:95). The MyD88t or BAFF-R signaling domain transduces a signal for engulfment, and Tim4 is a phosphatidylserine binding receptor. The Tim4-MyD88t-BAFF4 (CER85) chimeric engulfment receptor nucleotide sequence was then inserted into the pLenti lentiviral vector along with truncated EGFR as a transduction marker, separated by T2A sequence (see, FIG. 100). Murine Ba/F3 B-cells were transduced with pLenti vector expressing Tim4-MyD88t-BAFFR (CER85) and EGFRt, expanded, sorted by FACs, and used for in vitro studies as described in Example 8.

Phagocytic Activity Against Primary Apoptotic Thymocytes

Primary C3H mouse thymocytes were isolated, treated with dexamethasone, and stained with pHrodo Red as described in Example 8. Ba/F3 CER85⁺ tEGFR⁺ cells were labeled with CELLTRACE™ Violet dye as described in Example 8. Co-culture experiments with Ba/F3 CER85⁺ tEGFR⁺ cells and primary thymocytes were carried out at a 10:1 target cell to effector cell ratio, and Ba/F3 CER85⁺ EGFR⁺ cells were quantified for phagocytosis of target thymocytes by fluorescence microscopy and FACs as described in Example 8. Ba/F3 cells transduced with pLenti vector expressing truncated EGFR were used as a negative control.

Figure 101B:
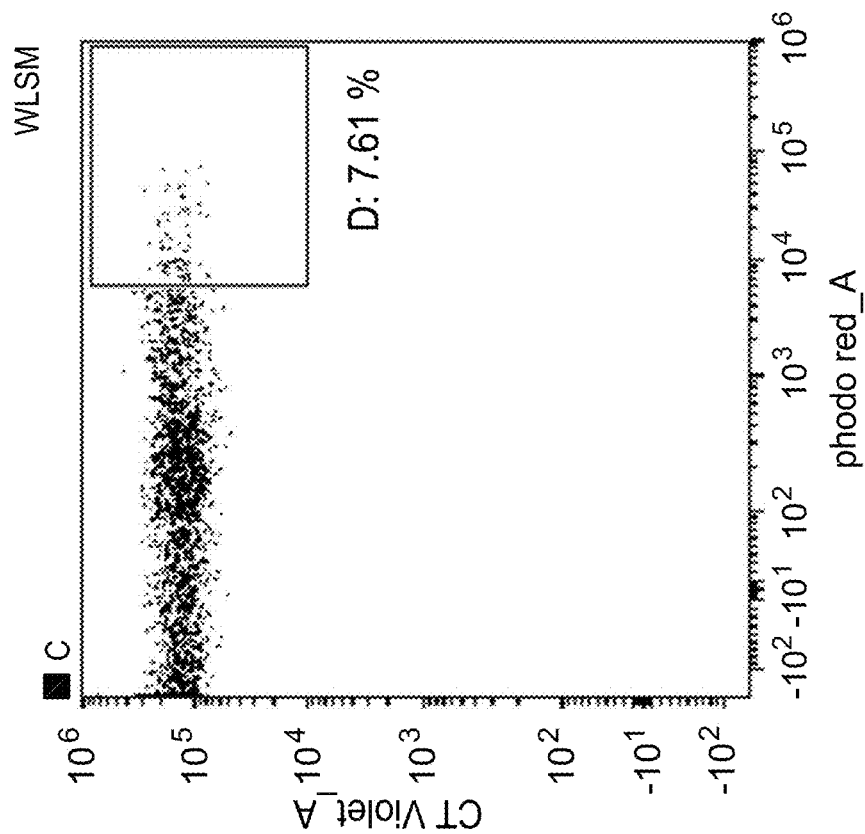
FIGS. 101A-101B show FACS quantification of engulfment of dexamethasone treated thymocytes by CER85+ Ba/F3 murine B cells by measuring the cell population that stained double positive for pHrodo Red and CELLTRACE Violet (FIG. 101A) compared to control Ba/F3 cells transduced with truncated EGFR (FIG. 101B).
Figure 101A:
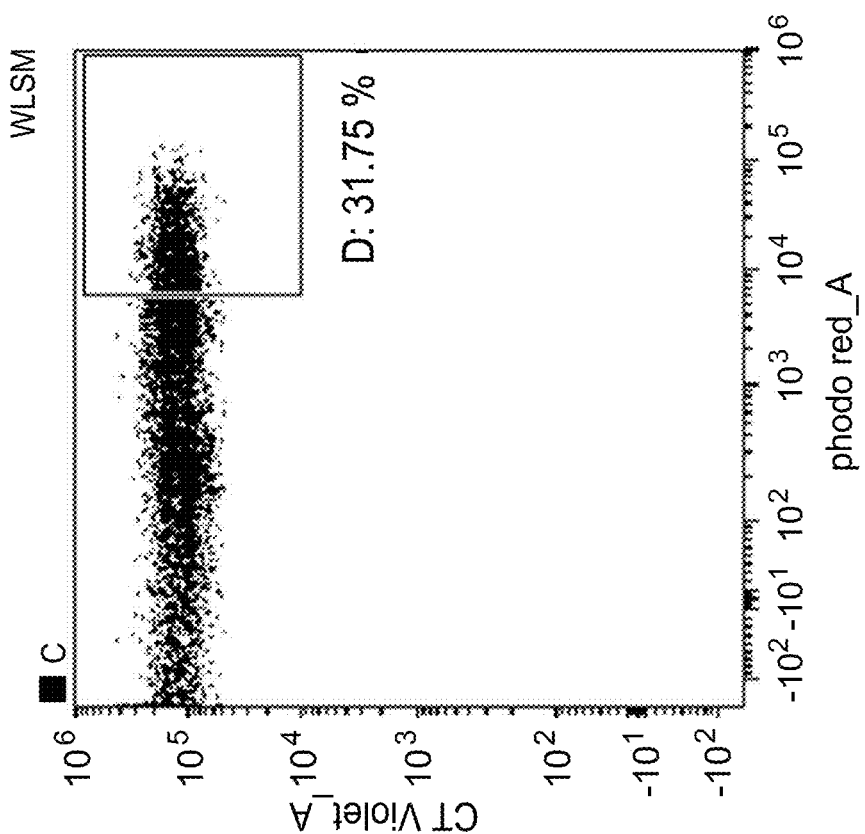

The quantity of viable, CER85+ transduced Ba/F3 cells as quantified by FACS is shown in FIG. 101. The frequency of phagocytosis by CER+85 Ba/F3 cells co-cultured with dexamethasone treated thymocytes was quantified as the cell population staining double positive for pHrodo Red and CELLTRACE Violet as detected by FACS (see, FIG. 101A). Frequency of double positive staining cells for control Ba/F3 cells transduced with truncated EGFR and co-cultured with dexamethasone treated thymocytes is shown in FIG. 101B.

Figure 102:
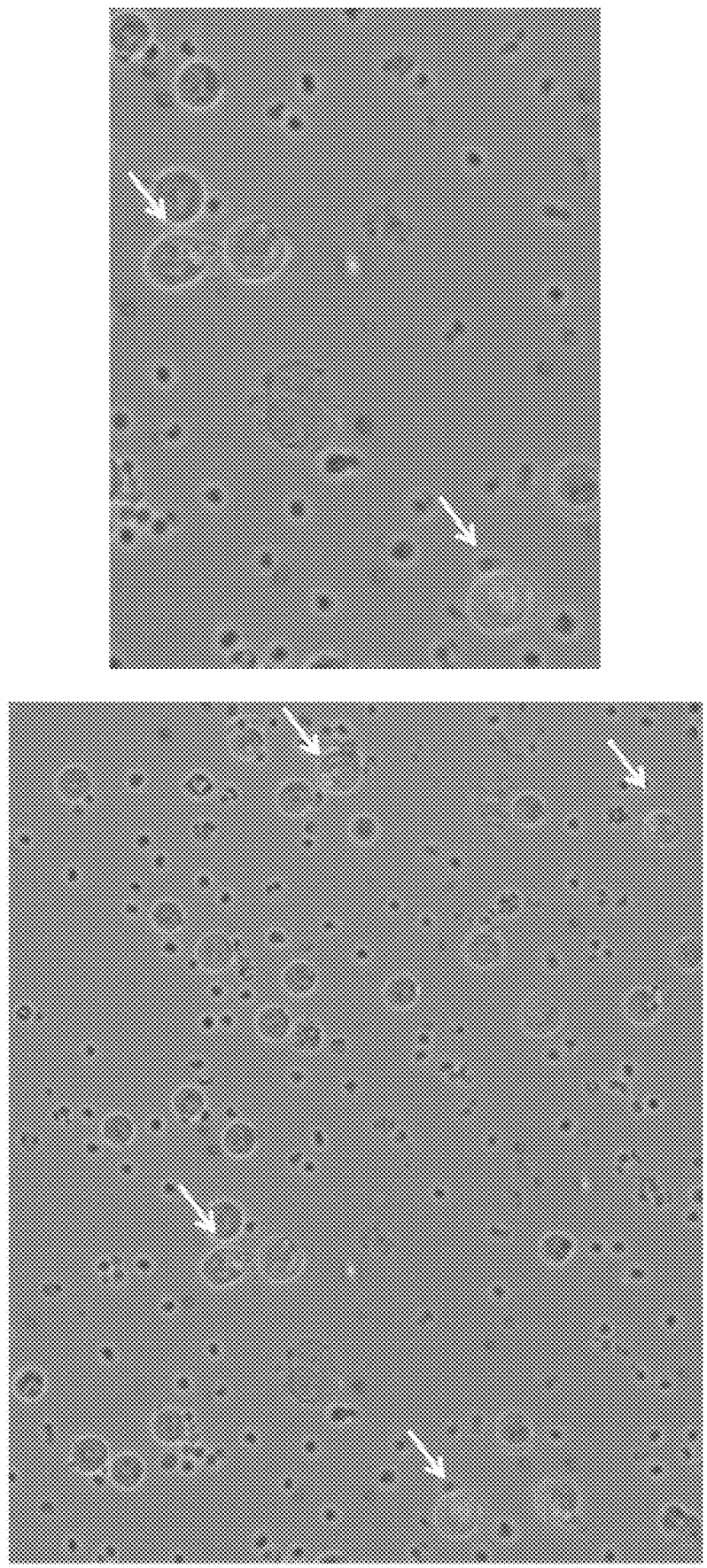
FIG. 102 shows fluorescent microscope images of in vitro phagocytosis by CER85+Ba/F3 cells co-cultured with dexamethasone treated thymocytes. High magnification of an engulfment event is shown to the right. White arrows indicate phagocytosis events.

Fluorescent microscopy showed that CER85⁺ Ba/F3 cells engulf dexamethasone-treated thymocytes (white arrows indicate engulfment events) as compared to tEGFR transduced Ba/F3 control cells (see, FIG. 102, high magnification of an engulfment event is shown in the right of FIG. 102).

Figure 103:
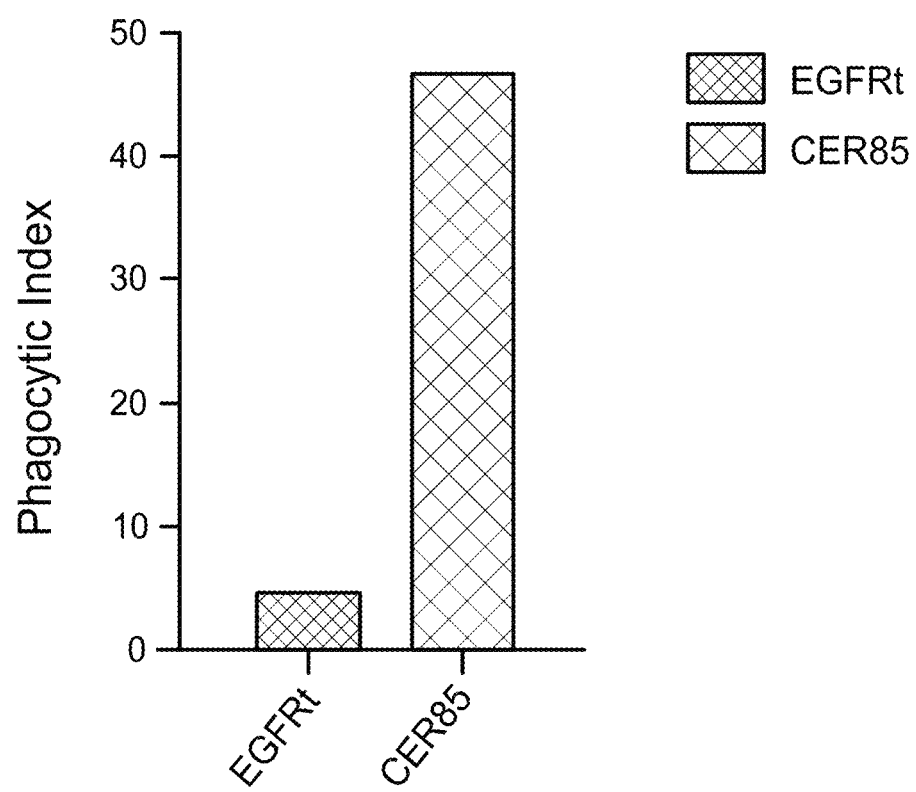
FIG. 103 shows a graph of phagocytic index of CER85+ Ba/F3 cells co-cultured with dexamethasone treated thymocytes compared to control Ba/F3 cells transduced with truncated EGFR.

A phagocytic index was calculated by multiplying [mean of total number of engulfed target cells/total number of counted CER modified cells (e.g., phagocytic frequency)] by [average area of target cell staining per CER+ Ba/F3 cell× 100 (e.g., hybrid capture)] as compared to EGFRt transduced Ba/F3control cells (see, FIG. 103).

Example 19

Construction of TIM4-MyD88t-DAP12 CER "CER86"

Figure 104:
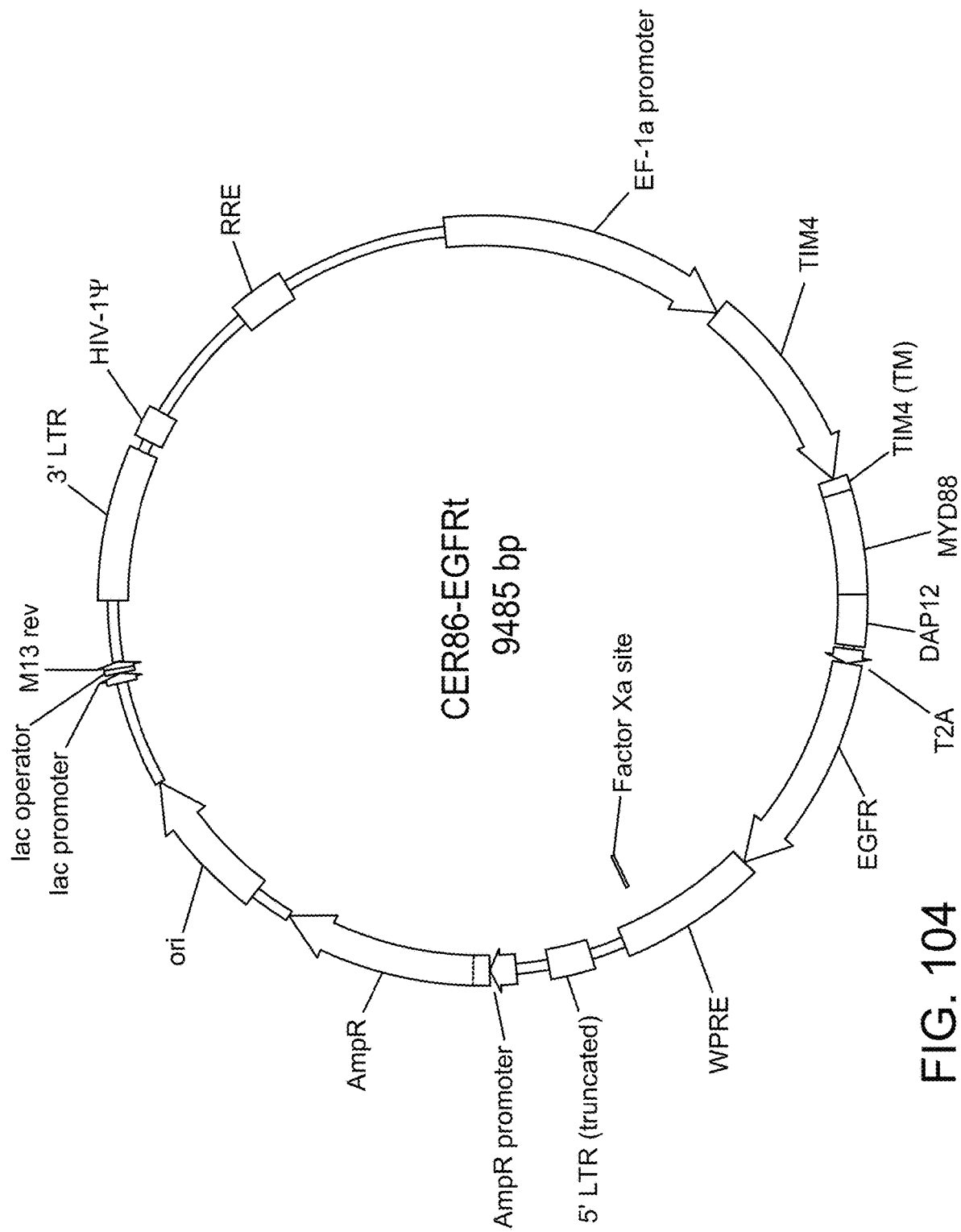
FIG. 104 shows a vector map for a lentiviral vector comprising "CER86" chimeric engulfment receptor having an amino acid sequence of SEQ ID NO:96. CER86 comprises a Tim4 binding domain, a Tim4 transmembrane domain, a primary engulfment signaling domain that is a truncated MyD88 signaling domain, and a secondary engulfment signaling domain that is a DAP12 signaling domain.

The extracellular domain of the phosphatidylserine binding protein Tim4 (amino acid sequence of SEQ ID NO:73), including the signal peptide (amino acid sequence of SEQ ID NO:72) and transmembrane domain (amino acid sequence of SEQ ID NO:74) were fused to primary signaling domain comprising a truncated MyD88 (SEQ ID NO:78) and a secondary signaling domain comprising a DAP12 signaling domain (SEQ ID NO:82) to create a chimeric engulfment receptor "CER86" (Tim4-MyD88t-DAP12 CER having an amino acid sequence of SEQ ID NO:96). The MyD88t or DAP12 signaling domain transduces a signal for engulfment, and Tim4 is a phosphatidylserine binding receptor. The Tim4-MyD88t-DAP (CER86) chimeric engulfment receptor nucleotide sequence was then inserted into the pLenti lentiviral vector along with truncated EGFR as a transduction marker, separated by T2A sequence (see, FIG. 104). Murine Ba/F3 B-cells were transduced with pLenti vector expressing Tim4-MyD88t-DAP12 (CER86) and EGFRt, expanded, sorted by FACs, and used for in vitro studies as described in Example 8.

Example 20

Construction of TIM4-BAFFR-MyD88 Cer "Cer87"

The extracellular domain of the phosphatidylserine binding protein Tim4 (amino acid sequence of SEQ ID NO:73), including the signal peptide (amino acid sequence of SEQ ID NO:72) and transmembrane domain (amino acid sequence of SEQ ID NO:74) were fused to primary signaling domain comprising a BAFF-R signaling domain (SEQ ID NO:94) and a secondary signaling domain comprising a truncated MyD88 signaling domain (SEQ ID NO:78) to create a chimeric engulfment receptor "CER87" (Tim4-BAFFR-MyD88 CER having an amino acid sequence of SEQ ID NO:130). The BAFF-R or truncated MyD88 signaling domain transduces a signal for engulfment, and Tim4 is a phosphatidylserine binding receptor. The Tim4-BAFFR-MyD88 (CER87) chimeric engulfment receptor nucleotide sequence was then inserted into the pLenti lentiviral vector along with truncated EGFR as a transduction marker, separated by T2A sequence (see, FIG. 105). Murine Ba/F3 B-cells were transduced with pLenti vector expressing Tim4-BAFFR-MyD88 (CER87) and EGFRt, expanded, sorted by FACs, and used for in vitro studies as described in Example 8.

Phagocytic Activity Against Primary Apoptotic Thymocytes

Primary C3H mouse thymocytes were isolated, treated with dexamethasone, and stained with pHrodo Red as described in Example 8. Ba/F3 CER87⁺ tEGFR⁺ cells were labeled with CELLTRACE™ Violet dye as described in Example 8. Co-culture experiments with Ba/F3 CER87⁺ tEGFR⁺ cells and primary thymocytes were carried out at a 10:1 target cell to effector cell ratio, and Ba/F3 CER87⁺ EGFR⁺ cells were quantified for phagocytosis of target thymocytes by fluorescence microscopy and FACs as described in Example 8. Ba/F3 cells transduced with pLenti vector expressing truncated EGFR were used as a negative control.

The quantity of viable, CER87+ transduced Ba/F3 cells as quantified by FACS is shown in FIG. 106. The frequency of phagocytosis by CER87+ Ba/Fe cells co-cultured with dexamethasone treated thymocytes was quantified as the cell population staining double positive for pHrodo Red and CELLTRACE Violet as detected by FACS (see, FIG. 106B). Frequency of double positive staining cells for control Ba/F3 cells transduced with truncated EGFR and co-cultured with dexamethasone treated thymocytes is shown in FIG. 106A.

Fluorescent microscopy showed that CER87⁺ Ba/F3 cells engulf dexamethasone-treated thymocytes (white arrows indicate engulfment events) as compared to tEGFR transduced Ba/F3 control cells (see, FIG. 107). High magnification of an engulfment event is shown in the right of FIG. 107.

A phagocytic index was calculated by multiplying [mean of total number of engulfed target cells/total number of counted CER modified cells (e.g., phagocytic frequency)] by [average area of target cell staining per CER+ Ba/F3 cell× 100 (e.g., hybrid capture)] as compared to EGFRt transduced Ba/F3control cells (see, FIG. 108).

Example 21

Construction of TIM4-DAP12-MyD88 CER "CER88"

The extracellular domain of the phosphatidylserine binding protein Tim4 (amino acid sequence of SEQ ID NO:73), including the signal peptide (amino acid sequence of SEQ ID NO:72) and transmembrane domain (amino acid sequence of SEQ ID NO:74) were fused to primary signaling domain comprising a DAP12 signaling domain (SEQ ID NO:82) and a secondary signaling domain comprising a truncated MyD88 signaling domain (SEQ ID NO:78) to create a chimeric engulfment receptor "CER88" (Tim4-DAP12-tMyD88 CER having an amino acid sequence of SEQ ID NO:131). The DAP12 or truncated MyD88 signaling domain transduces a signal for engulfment, and Tim4 is a phosphatidylserine binding receptor. The Tim4-DAP12-MyD88 (CER88) chimeric engulfment receptor nucleotide sequence was then inserted into the pLenti lentiviral vector along with truncated EGFR as a transduction marker, separated by T2A sequence (see, FIG. 109). Murine Ba/F3 B-cells were transduced with pLenti vector expressing Tim4-DAP12-MyD88 (CER88) and EGFRt, expanded, sorted by FACs, and used for in vitro studies as described in Example 8.

Example 22

Construction of TIM4-MyD88t-CD79b CER "CER89"

The extracellular domain of the phosphatidylserine binding protein Tim4 (amino acid sequence of SEQ ID NO:73), including the signal peptide (amino acid sequence of SEQ ID NO:72) and transmembrane domain (amino acid sequence of SEQ ID NO:74) were fused to primary signaling domain comprising a truncated MyD88 signaling domain (SEQ ID NO:78) and a secondary signaling domain comprising a CD79b signaling domain (SEQ ID NO:97) to create a chimeric engulfment receptor "CER89" (Tim4-MyD88t-CD79b CER having an amino acid sequence of SEQ ID NO:98). The MyD88t or CD79b signaling domain transduces a signal for engulfment, and Tim4 is a phosphatidylserine binding receptor. The Tim4-MyD88t-CD79b (CER89) chimeric engulfment receptor nucleotide sequence was then inserted into the pLenti lentiviral vector along with truncated EGFR as a transduction marker, separated by T2A sequence (see, FIG. 110). Murine Ba/F3 B-cells were transduced with pLenti vector expressing Tim4-MyD88t-CD79b (CER89) and EGFRt, expanded, sorted by FACs, and used for in vitro studies as described in Example 8.

Example 23

Construction of TIM4-MyD88t-NFAM1 CER "CER90"

The extracellular domain of the phosphatidylserine binding protein Tim4 (amino acid sequence of SEQ ID NO:73), including the signal peptide (amino acid sequence of SEQ ID NO:72) and transmembrane domain (amino acid sequence of SEQ ID NO:74) were fused to primary signaling domain comprising a truncated MyD88 signaling domain (SEQ ID NO:78) and a secondary signaling domain comprising a NFAM1 signaling domain (SEQ ID NO:92) to create a chimeric engulfment receptor "CER90" (Tim4-MyD88t-NFAM1 CER having an amino acid sequence of SEQ ID NO:100). The MyD88t or NFAM1 signaling domain transduces a signal for engulfment, and Tim4 is a phosphatidylserine binding receptor. The Tim4-MyD88t-NFAM1 (CER90) chimeric engulfment receptor nucleotide sequence was then inserted into the pLenti lentiviral vector along with truncated EGFR as a transduction marker, separated by T2A sequence (see, FIG. 111). Murine Ba/F3 B-cells were transduced with pLenti vector expressing Tim4-MyD88t-NFAM1 (CER90) and EGFRt, expanded, sorted by FACs, and used for in vitro studies as described in Example 8.

Example 24

Construction of TIM4-MyD88t-P2A-RAB5A CER "CER91"

The extracellular domain of the phosphatidylserine binding protein Tim4 (amino acid sequence of SEQ ID NO:73), including the signal peptide (amino acid sequence of SEQ ID NO:72) and transmembrane domain (amino acid sequence of SEQ ID NO:74) were fused to a truncated MyD88 signaling domain (SEQ ID NO:78) to create a chimeric engulfment receptor "CER15". The MyD88t signaling domain transduces a signal for engulfment, and Tim4 is a phosphatidylserine binding receptor. The Tim4-MyD88t (CER15) chimeric engulfment receptor nucleotide sequence was then inserted into the pLenti lentiviral vector along with Rab5a and truncated EGFR as a transduction marker, separated by P2A sequence and T2A sequence, respectively (see, FIG. 112). Murine Ba/F3 B-cells were transduced with pLenti vector expressing Tim4-MyD88t-Rab5a (CER91, SEQ ID NO:105) and EGFRt, expanded, sorted by FACs, and used for in vitro studies as described in Example 8.

Phagocytic Activity Against Primary Apoptotic Thymocytes

Primary C3H mouse thymocytes were isolated, treated with dexamethasone, and stained with pHrodo Red as described in Example 8. Ba/F3 CER91$^+$ tEGFR$^+$ cells were labeled with CELLTRACE™ Violet dye as described in Example 8. Co-culture experiments with Ba/F3 CER91$^+$ tEGFR$^+$ cells and primary thymocytes were carried out at a 10:1 target cell to effector cell ratio, and Ba/F3 CER91$^+$ EGFR$^+$ cells were quantified for phagocytosis of target thymocytes by fluorescence microscopy and FACs as described in Example 8. Ba/F3 cells transduced with pLenti vector expressing truncated EGFR were used as a negative control.

The quantity of viable, CER91+ transduced Ba/F3 cells as quantified by FACS is shown in FIG. 113. The frequency of phagocytosis by CER91+ Ba/F3 cells co-cultured with dexamethasone treated thymocytes was quantified as the cell population staining double positive for pHrodo Red and CELLTRACE Violet as detected by FACS (see, FIG. 113A). Frequency of double positive staining cells for control Ba/F3 cells transduced with truncated EGFR and co-cultured with dexamethasone treated thymocytes is shown in FIG. 113B.

Fluorescent microscopy showed that CER91$^+$ Ba/F3 cells engulf dexamethasone-treated thymocytes (white arrows indicate engulfment events) as compared to tEGFR transduced Ba/F3 control cells (see, FIG. 114). High magnification of an engulfment event is shown in the right of FIG. 114.

A phagocytic index was calculated by multiplying [mean of total number of engulfed target cells/total number of counted CER modified cells (e.g., phagocytic frequency)] by [average area of target cell staining per CER+ Ba/F3 cell× 100 (e.g., hybrid capture)] as compared to EGFRt transduced Ba/F3control cells (see, FIG. 115).

Example 25

Construction of TIM4-MERTK-MyD88 CER "CER92"

The extracellular domain of the phosphatidylserine binding protein Tim4 (amino acid sequence of SEQ ID NO:73), including the signal peptide (amino acid sequence of SEQ ID NO:72) and transmembrane domain (amino acid sequence of SEQ ID NO:74) were fused to primary signaling domain comprising a MERTK signaling domain (SEQ ID NO:69) and a secondary signaling domain comprising a truncated MyD88 signaling domain (SEQ ID NO:78) to create a chimeric engulfment receptor "CER92" (Tim4-MERTK-tMyD88 CER having an amino acid sequence of SEQ ID NO:133). The MERTK or truncated MyD88 signaling domain transduces a signal for engulfment, and Tim4 is a phosphatidylserine binding receptor. The Tim4-MERTK-tMyD88 (CER92) chimeric engulfment receptor nucleotide sequence was then inserted into the pLenti lentiviral vector along with truncated EGFR as a transduction marker, separated by T2A sequence (see, FIG. 116). Murine Ba/F3 B-cells were transduced with pLenti vector expressing Tim4-MERTK-tMyD88 (CER92) and EGFRt, expanded, sorted by FACs, and used for in vitro studies as described in Example 8.

Phagocytic Activity Against Primary Apoptotic Thymocytes

Primary C3H mouse thymocytes were isolated, treated with dexamethasone, and stained with pHrodo Red as described in Example 8. Ba/F3 CER92+ tEGFR+ cells were labeled with CELLTRACE™ Violet dye as described in Example 8. Co-culture experiments with Ba/F3 CER92+ tEGFR+ cells and primary thymocytes were carried out at a 10:1 target cell to effector cell ratio, and Ba/F3 CER92+ EGFR+ cells were quantified for phagocytosis of target thymocytes by fluorescence microscopy and FACs as described in Example 8. Ba/F3 cells transduced with pLenti vector expressing truncated EGFR were used as a negative control.

The quantity of viable, CER92+ transduced Ba/F3 cells as quantified by FACS is shown in FIG. 117. The frequency of phagocytosis by CER92+ Ba/F3 cells was quantified as the cell population staining double positive for pHrodo Red and CELLTRACE Violet as detected by FACS (see, FIG. 117A). Frequency of double positive staining cells for control Ba/F3 cells transduced with truncated EGFR and co-cultured with dexamethasone treated thymocytes is shown in FIG. 117B.

Fluorescent microscopy showed that CER92+ Ba/F3 cells engulf dexamethasone-treated thymocytes (white arrows indicate engulfment events) as compared to tEGFR transduced Ba/F3 control cells (see, FIG. 118). High magnification of an engulfment event is shown in the right of FIG. 118.

A phagocytic index was calculated by multiplying [mean of total number of engulfed target cells/total number of counted CER modified cells (e.g., phagocytic frequency)] by [average area of target cell staining per CER+ Ba/F3 cell× 100 (e.g., hybrid capture)] as compared to EGFRt transduced Ba/F3control cells (see, FIG. 119).

Example 26

Construction of TIM4-MERTK-BAFFR CER "CER93"

The extracellular domain of the phosphatidylserine binding protein Tim4 (amino acid sequence of SEQ ID NO:73), including the signal peptide (amino acid sequence of SEQ ID NO:72) and transmembrane domain (amino acid sequence of SEQ ID NO:74) were fused to primary signaling domain comprising a MERTK signaling domain (amino acid sequence of SEQ ID NO:43) and a secondary signaling domain comprising a BAFF-R (amino acid sequence of SEQ ID NO:94) to create a chimeric engulfment receptor "CER93" (Tim4-MERTK-BAFFR CER having an amino acid sequence of SEQ ID NO:103). The MERTK or BAFF-R signaling domain transduces a signal for engulfment, and Tim4 is a phosphatidylserine binding receptor. The Tim4-MERTK-BAFFR (CER93) chimeric engulfment receptor nucleotide sequence was then inserted into the pLenti lentiviral vector along with truncated EGFR as a transduction marker, separated by T2A sequence (see, FIG. 120). Murine Ba/F3 B-cells were transduced with pLenti vector expressing Tim4-MERTK-BAFFR (CER93) and EGFRt, expanded, sorted by FACs, and used for in vitro studies as described in Example 8.

Phagocytic Activity Against Primary Apoptotic Thymocytes

Primary C3H mouse thymocytes were isolated, treated with dexamethasone, and stained with pHrodo Red as described in Example 8. Ba/F3 CER93+ tEGFR+ cells were labeled with CELLTRACE™ Violet dye as described in Example 8. Co-culture experiments with Ba/F3 CER93+ tEGFR+ cells and primary thymocytes were carried out at a 10:1 target cell to effector cell ratio, and Ba/F3 CER92+ EGFR+ cells were quantified for phagocytosis of target thymocytes by fluorescence microscopy and FACs as described in Example 8. Ba/F3 cells transduced with pLenti vector expressing truncated EGFR were used as a negative control.

The quantity of viable, CER93+ transduced Ba/F3 cells as quantified by FACS is shown in FIG. 121. The frequency of phagocytosis by CER93+ Ba/F3 cells co-cultured with dexamethasone treated thymocytes was quantified as the cell population staining double positive for pHrodo Red and CELLTRACE Violet as detected by FACS (see, FIG. 121A). Frequency of double positive staining cells for control Ba/F3 cells transduced with truncated EGFR and co-cultured with dexamethasone treated thymocytes is shown in FIG. 121B.

Fluorescent microscopy showed that CER93+ Ba/F3 cells engulf dexamethasone-treated thymocytes (white arrows indicate engulfment events) as compared to tEGFR transduced Ba/F3 control cells (see, FIG. 122). High magnification of an engulfment event is shown in the right of FIG. 122.

A phagocytic index was calculated by multiplying [mean of total number of engulfed target cells/total number of counted CER modified cells (e.g., phagocytic frequency)] by [average area of target cell staining per CER+ Ba/F3 cell× 100 (e.g., hybrid capture)] as compared to EGFRt transduced Ba/F3control cells (see, FIG. 123).

Example 27

Construction of TIM4-MERTK-DAP12 CER "CER94"

The extracellular domain of the phosphatidylserine binding protein Tim4 (amino acid sequence of SEQ ID NO:73), including the signal peptide (amino acid sequence of SEQ ID NO:72) and transmembrane domain (amino acid sequence of SEQ ID NO:74) were fused to primary signaling domain comprising a MERTK signaling domain (amino acid sequence of SEQ ID NO:43) and a secondary signaling domain comprising a DAP12 signaling domain (amino acid sequence of SEQ ID NO:82) to create a chimeric engulfment receptor "CER94" (Tim4-MERTK-DAP12 CER having an amino acid sequence of SEQ ID NO:134). The MERTK or DAP12 signaling domain transduces a signal for engulfment, and Tim4 is a phosphatidylserine binding receptor. The Tim4-MERTK-DAP12 (CER94) chimeric engulfment receptor nucleotide sequence was then inserted into the pLenti lentiviral vector along with truncated EGFR as a transduction marker, separated by T2A sequence (see, FIG. 124). Murine Ba/F3 B-cells were transduced with pLenti vector expressing Tim4-MERTK-DAP12 (CER94) and EGFRt, expanded, sorted by FACs, and used for in vitro studies as described in Example 8.

Example 28

Construction of TIM4-Ax1-DAP12 CER "CER97"

The extracellular domain of the phosphatidylserine binding protein Tim4 (amino acid sequence of SEQ ID NO:73), including the signal peptide (amino acid sequence of SEQ ID NO:72) and transmembrane domain (amino acid sequence of SEQ ID NO:74) were fused to primary signaling domain comprising an Ax1 signaling domain (SEQ ID NO:44) and a secondary signaling domain comprising a DAP12 signaling domain (SEQ ID NO:82) to create a chimeric engulfment receptor "CER97" (Tim4-AXL- DAP12 CER having an amino acid sequence of SEQ ID NO:152). The AXL or DAP12 signaling domain transduces a signal for engulfment, and Tim4 is a phosphatidylserine binding receptor. The Tim4-AXL-DAP12 (CER97) chimeric engulfment receptor nucleotide sequence was then inserted into the pLenti lentiviral vector along with truncated EGFR as a transduction marker, separated by T2A sequence (see, FIG. 125). Murine Ba/F3 B-cells were transduced with pLenti vector expressing Tim4-AXL-DAP12 (CER97) and EGFRt, expanded, sorted by FACs, and used for in vitro studies as described in Example 8.

Example 29

Construction of TIM4-Ax1-CD79b CER "CER98"

The extracellular domain of the phosphatidylserine binding protein Tim4 (amino acid sequence of SEQ ID NO:73), including the signal peptide (amino acid sequence of SEQ ID NO:72) and transmembrane domain (amino acid sequence of SEQ ID NO:74) were fused to primary signaling domain comprising an Ax1 signaling domain (amino acid sequence of SEQ ID NO:44) and a secondary signaling domain comprising a CD79b signaling domain (amino acid sequence of SEQ ID NO:97) to create a chimeric engulfment receptor "CER98" (Tim4-AXL-CD79b CER having an amino acid sequence of SEQ ID NO:153. The Ax1 or CD79b signaling domain transduces a signal for engulfment, and Tim4 is a phosphatidylserine binding receptor. The Tim4-AXL-CD79B (CER98) chimeric engulfment receptor nucleotide sequence was then inserted into the pLenti lentiviral vector along with truncated EGFR as a transduction marker, separated by T2A sequence (see, FIG. 126). Murine Ba/F3 B-cells were transduced with pLenti vector expressing Tim4-AXL-CD79b (CER98) and EGFRt, expanded, sorted by FACs, and used for in vitro studies as described in Example 8.

Example 30

Construction of TIM4-MERTK-CD79b CER "CER95"

The extracellular domain of the phosphatidylserine binding protein Tim4 (amino acid sequence of SEQ ID NO:73), including the signal peptide (amino acid sequence of SEQ ID NO:72) and transmembrane domain (amino acid sequence of SEQ ID NO:74) were fused to primary signaling domain comprising a MERTK signaling domain (amino acid sequence of SEQ ID NO:43) and a secondary signaling domain comprising a CD79b signaling domain (amino acid sequence of SEQ ID NO:97) to create a chimeric engulfment receptor "CER95" (Tim4-MERTK-CD79b CER having an amino acid sequence of SEQ ID NO:101). The MERTK or CD79b signaling domain transduces a signal for engulfment, and Tim4 is a phosphatidylserine binding receptor. The Tim4-MERTK-CD79b (CER95) chimeric engulfment receptor nucleotide sequence was then inserted into the pLenti lentiviral vector along with truncated EGFR as a transduction marker, separated by T2A sequence (see, FIG. 127). Murine Ba/F3 B-cells were transduced with pLenti vector expressing Tim4-MERTK-CD79b (CER95) and EGFRt, expanded, sorted by FACs, and used for in vitro studies as described in Example 8.

Example 31

Construction of TIM4-MERTK-NFAM1 CER "CER96"

The extracellular domain of the phosphatidylserine binding protein Tim4 (amino acid sequence of SEQ ID NO:73), including the signal peptide (amino acid sequence of SEQ ID NO:72) and transmembrane domain (amino acid sequence of SEQ ID NO:74) were fused to primary signaling domain comprising a MERTK signaling domain (SEQ ID NO:43) and a secondary signaling domain comprising a NFAM1 signaling domain (SEQ ID NO:99) to create a chimeric engulfment receptor "CER96" (Tim4-MERTK-NFAM1 CER having an amino acid sequence of SEQ ID NO:102. The MERTK or NFAM1 signaling domain transduces a signal for engulfment, and Tim4 is a phosphatidylserine binding receptor. The Tim4-MERTK-NFAM1 (CER96) chimeric engulfment receptor nucleotide sequence was then inserted into the pLenti lentiviral vector along with truncated EGFR as a transduction marker, separated by T2A sequence (see, FIG. 128). Murine Ba/F3 B-cells were transduced with pLenti vector expressing Tim4-MERTK-NFAM1 (CER96) and EGFRt, expanded, sorted by FACs, and used for in vitro studies as described in Example 8.

A variant of CER96 was also constructed, having an extracellular domain of the phosphatidylserine binding protein Tim4, including the signal peptide and transmembrane domain were fused to primary signaling domain comprising a MERTK signaling domain and a secondary signaling domain comprising a truncated NFAM1 signaling domain to create a chimeric engulfment receptor CER96t having an amino acid sequence of SEQ ID NO:116.

Example 32

Construction of M912scFv-IgG4-Tim4-MyD88t CER "CER50"

The extracellular domain comprising an scFv derived from mesothelin specific human monoclonal antibody M912 (Feng et al., 2009, Mol. Cancer Ther. 8:1113-1118) (amino acid sequence of SEQ ID NO:106), including the signal peptide (amino acid sequence of SEQ ID NO:85) was fused to a modified IgG4 hinge region extracellular spacer domain (SEQ ID NO:67), a Tim4 transmembrane domain (amino acid sequence of SEQ ID NO:74) and a truncated MyD88 signaling domain (SEQ ID NO:69) to create a chimeric engulfment receptor "CER50" (M912scFv-IgG4-Tim4-MyD88t CER having an amino acid sequence of SEQ ID NO:107. The MyD88t signaling domain transduces a signal for engulfment, and M912scFv binds to cell surface associated mesothelin. The M912scFv-IgG4-Tim4-MyD88t CER (CER50) chimeric engulfment receptor nucleotide sequence was then inserted into the pLenti lentiviral vector along with truncated EGFR as a transduction marker, separated by T2A sequence. Murine Ba/F3 B-cells were transduced with pLenti vector expressing M912scFv-IgG4-Tim4-MyD88t and EGFRt, expanded, sorted by FACs, and used for in vitro studies as described in Example 8.

Example 33

Compilation of In Vitro Phagocytosis Data

Phagocytosis data for CER+ modified Ba/F3 cells for various cell types performed as previously described were compiled. FIG. 129 shows phagocytic index for Ba/F3 cells modified with CER01, CER08, CER09, CER10, CER11, CER12, CER15, or EGFRt control co-cultured with dexamethasone treated primary thymocytes. FIG. 130 shows phagocytic index of Ba/F3 cells transduced with CER01, CER09, CER11, CER12, CER15, or EGFRt control co-cultured with staurosporine treated CT26 colon carcinoma cells. FIG. 131 shows phagocytic index of Ba/F3 cells transduced with CER01, CER09, CER11, CER12, CER15, or EGFRt control co-cultured with staurosporine treated A20 lymphoma cells.

Example 34

Phagocytic Activity of CER01 in Mouse Model of Lymphoma

A Tim4-MERTK CER nucleotide sequence encoding CER01 having an amino acid sequence of SEQ ID NO:71 (see also, FIG. 6A) was inserted into a pMSCV retroviral vector with a nucleotide sequence encoding green fluorescent protein (GFP).

A timeline of a combination therapy regimen for radiation therapy and CER immunotherapy in a mouse model of lymphoma is shown in FIG. 132A.

$0.5 \times 10^6$ 38c13 mouse B-cell lymphoma cells were engrafted into NOD scid gamma (NSG) immunodeficient mice. Four days following engraftment, mice received 5 Gy of focal irradiation to the tumor site followed by intravenous injection of $6 \times 10^6$ CER01+ transduced murine T cells (derived from C3H/HeN-MTV-negative mice). Tumor size was measured in two dimensions using precision calipers, and luciferase imaging was performed on day 4 following infusion of CER01+ transduced T cells. pMSCV empty retroviral vector transduced T cells were used as controls. As shown in the graph in FIG. 132B, CER modified T cells targeting phosphatidylserine synergized with low dose radiotherapy. In the photos shown in FIG. 132C, tumor growth was decreased in mice receiving combination therapy of CER modified T cells targeting phosphatidylserine and low dose radiation.

A timeline of an alternative combination therapy regimen for chimeric antigen receptor (CAR) immunotherapy and CER immunotherapy in a mouse model of lymphoma is shown in FIG. 133A. $0.5 \times 10^6$ 38 c13 lymphoma cells were engrafted into NSG immunodeficient mice. Four days following engraftment, mice received an infusion of $5 \times 10^6$ murine CD19-targeted CAR-T cells ("1D3 19z28" CAR having an anti-CD19 1D3 scFv, CD3-$\zeta$ cytoplasmic domain and CD28 cytoplasmic domain). Three days post-infusion of CAR modified T cells, $6 \times 10^6$ CER01+ transduced T cells were infused in the mice. Tumor size was measured in two dimensions using precision calipers, and luciferase imaging performed on day 4 following infusion of CER01+ transduced T cells or CER01+ transduced B cells (see photos shown in bottom of FIG. 133B). pMSCV empty retroviral vector transduced T cells were used as controls. As shown in FIG. 133B, CER+ T cells or CER+ B cells targeting PtdSer$^+$ synergized with low dose CAR modified T cell therapy.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet including U.S. Patent Application No. 62/400,578 filed on Sep. 27, 2016, and U.S. Patent Application No. 62/445,235, filed on Jan. 11, 2017, are incorporated herein by reference, in their entireties. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

---

The invention claimed is:

1. A chimeric engulfment receptor (CER) comprising a single chain chimeric protein, the single chain chimeric protein comprising:
   an extracellular domain comprising a Tim4 binding domain that binds to phosphatidylserine (PtdSer);
   an engulfment signaling domain, wherein the engulfment signaling domain comprises an ItgB5, MERTK, Tyro3, Ax1, BAI1, ELMO, MRC1, PI3K, Traf6, Syk, MyD88, Zap70, FcγR1, FcγR2A, FcγR2B2, FcγR2C, FcγR3A, FcεR1, FcαR1, BAFF-R, DAP12, NFAM1, or CD79b engulfment signaling domain; and
   a transmembrane domain positioned between and connecting the extracellular domain and the engulfment signaling domain.

2. The CER of claim 1, wherein the binding domain comprises a TIM4 domain comprising the amino acid sequence of SEQ ID NO:29 or amino acids 25-314 of SEQ ID NO:29.

3. The CER of claim 1, wherein the extracellular domain further comprises an extracellular spacer domain positioned between the binding domain and transmembrane domain.

4. The CER of claim 3, wherein the extracellular spacer domain comprises an immunoglobulin hinge region, a hinge region of a type 1 membrane protein, a stalk region of a type II C-lectin, or an immunoglobulin constant domain.

5. The CER of claim 4, wherein the extracellular spacer domain comprises:
   (a) an immunoglobulin hinge region selected from an IgG1, IgG2, IgG3, IgG4, IgA, and IgD hinge region;
   (b) a hinge region of a type 1 membrane protein selected from CD8a, CD4, CD28, and CD7;
   (c) a stalk region of a type II C-lectin selected from CD23, CD69, CD72, CD94, NKG2A, and NKG2D; or
   (d) an immunoglobulin constant region domain selected from a CH1 domain, a CH2 domain, a CH3 domain, or any combination thereof.

6. The CER of claim 5, wherein, the extracellular domain comprises a modified IgG4 hinge region comprising the amino acid sequence of SEQ ID NO: 67.

7. The CER of claim 1, wherein the transmembrane domain comprises a Tim1, Tim4, Tim3, FcγR1, FcγR2A, FcγR2B2, FcγR2C, FcγR3A, FcεR1, FcαR1, CD8a, CD28, MERTK, Ax1, Tyro3, BAIL CD4, DAP12, or MRC1 transmembrane domain.

8. The CER of claim 7, wherein the transmembrane domain comprises a Tim1 transmembrane domain comprising the amino acid sequence of SEQ ID NO:35, a Tim4 transmembrane domain comprising the amino acid sequence of SEQ ID NO:36, an FcγRI transmembrane domain comprising the amino acid sequence of SEQ ID NO:37, a CD8a transmembrane domain comprising the amino acid sequence of SEQ ID NO:38, a MERTK transmembrane domain comprising the amino acid sequence of SEQ ID NO:39, an Ax1 transmembrane domain comprising the amino acid sequence of SEQ ID NO:40, a Tyro3 transmembrane domain comprising the amino acid sequence of SEQ ID NO:41, a CD28 transmembrane domain of SEQ ID NO:68, a BAI1 transmembrane domain of SEQ ID NO:142, a CD4 transmembrane domain comprising the amino acid sequence of SEQ ID NO:42, a FcεRIγ transmembrane domain comprising the amino acid sequence of SEQ ID NO:89, a MRC1 transmembrane domain comprising the amino acid sequence of SEQ ID NO:118, or a DAP12 transmembrane domain comprising the amino acid sequence of SEQ ID NO:81.

9. The CER of claim 1, wherein the engulfment signaling domain comprises a MERTK signaling domain comprising the amino acid sequence of SEQ ID NO:69, a Tyro3 signaling domain comprising the amino acid sequence of SEQ ID NO:45, an ItgB5 signaling domain comprising the amino acid sequence of SEQ ID NO:114, an MRC1 signaling domain comprising the amino acid sequence of SEQ ID NO:119, a BAH signaling domain comprising the amino acid sequence of SEQ ID NO:136, an ELMO signaling domain comprising the amino acid sequence of SEQ ID NO:120, an Ax1 signaling domain comprising the amino acid sequence of SEQ ID NO:44, a Traf6 signaling domain comprising the amino acid sequence of SEQ ID NO:54, Syk signaling domain comprising the amino acid sequence of SEQ ID NO:46, a MyD88 signaling domain comprising the amino acid sequence of SEQ ID NO:53, a truncated MyD88 signaling domain comprising the amino acid sequence of SEQ ID NO:78, a Zap70 signaling domain comprising the amino acid sequence of SEQ ID NO:47, a FcγR1 signaling domain comprising the amino acid sequence of SEQ ID NO:48, an FcγR2A signaling domain comprising the amino acid sequence of SEQ ID NO:49, an FcγR2C signaling domain comprising the amino acid sequence of SEQ ID NO:50, an FcγR3A signaling domain comprising the amino acid sequence of SEQ ID NO:51, a FcεRIγ signaling domain comprising the amino acid sequence of SEQ ID NO:88, a BAFF-R signaling domain comprising the amino acid sequence of SEQ ID NO:94, a DAP12 signaling domain comprising the amino acid sequence of SEQ ID NO:82, a NFAM1 signaling domain comprising the amino acid sequence of SEQ ID NO:92, or a CD79b signaling domain comprising the amino acid sequence of SEQ ID NO:97.

10. The CER of claim 1, wherein the engulfment signaling domain comprises a primary engulfment signaling domain and a secondary engulfment signaling domain, wherein the primary engulfment signaling domain and secondary engulfment signaling domain are independently selected from an ItgB5, MERTK, Tyro3, Ax1, BAI1, ELMO, MRC1, PI3K, Traf6, Syk, MyD88, Zap70, FcγR1, FcγR2A, FcγR2B2, FcγR2C, FcγR3A, FcεR1, FcαR1, BAFF-R, DAP12, NFAM1, and CD79b signaling domain.

11. The CER of claim 10, wherein, the primary engulfment signaling domain is a MERTK signaling domain comprising the amino acid sequence of SEQ ID NO:69, a Tyro3 signaling domain comprising the amino acid sequence of SEQ ID NO:45, an ItgB5 signaling domain comprising the amino acid sequence of SEQ ID NO:114, an MRC1 signaling domain comprising the amino acid sequence of SEQ ID NO:119, a BAH signaling domain comprising the amino acid sequence of SEQ ID NO:136, an ELMO signaling domain comprising the amino acid sequence of SEQ ID NO:120, an Ax1 signaling domain comprising the amino acid sequence of SEQ ID NO:44, a Traf6 signaling domain comprising the amino acid sequence of SEQ ID NO:54, Syk signaling domain comprising the amino acid sequence of SEQ ID NO:46, a MyD88 signaling domain comprising the amino acid sequence of SEQ ID NO:53, a truncated MyD88 signaling domain comprising the amino acid sequence of SEQ ID NO:78, a Zap70 signaling domain comprising the amino acid sequence of SEQ ID NO:47, a FcγR1 signaling domain comprising the amino acid sequence of SEQ ID NO:48, an FcγR2A signaling domain comprising the amino acid sequence of SEQ ID NO:49, an FcγR2C signaling domain comprising the amino acid sequence of SEQ ID NO:50, an FcγR3A signaling domain comprising the amino acid sequence of SEQ ID NO:51, a FcεRIγ signaling domain comprising the amino acid sequence of SEQ ID NO:88, a BAFF-R signaling domain comprising the amino acid sequence of SEQ ID NO:94, a DAP12 signaling domain comprising the amino acid sequence of SEQ ID NO:82, a NFAM1 signaling domain comprising the amino acid sequence of SEQ ID NO:92, or a CD79b signaling domain comprising the amino acid sequence of SEQ ID NO:97.

12. The CER of claim 10, wherein the secondary engulfment signaling domain is a MERTK signaling domain comprising the amino acid sequence of SEQ ID NO:69, a Tyro3 signaling domain comprising the amino acid sequence of SEQ ID NO:45, an ItgB5 signaling domain comprising the amino acid sequence of SEQ ID NO:114, an MRC1 signaling domain comprising the amino acid sequence of SEQ ID NO:119, a BAH signaling domain comprising the amino acid sequence of SEQ ID NO:136, an ELMO signaling domain comprising the amino acid sequence of SEQ ID NO:120, an Ax1 signaling domain comprising the amino acid sequence of SEQ ID NO:44, a Traf6 signaling domain comprising the amino acid sequence of SEQ ID NO:54, Syk signaling domain comprising the amino acid sequence of SEQ ID NO:46, a MyD88 signaling domain comprising the amino acid sequence of SEQ ID NO:53, a truncated MyD88 signaling domain comprising the amino acid sequence of SEQ ID NO:78, a Zap70 signaling domain comprising the amino acid sequence of SEQ ID NO:47, a FcγR1 signaling domain comprising the amino acid sequence of SEQ ID NO:48, an FcγR2A signaling domain comprising the amino acid sequence of SEQ ID NO:49, an FcγR2C signaling domain comprising the amino acid sequence of SEQ ID NO:50, an FcγR3A signaling domain comprising the amino acid sequence of SEQ ID NO:51, a FcεRIγ signaling domain comprising the amino acid sequence of SEQ ID NO:88, a BAFF-R signaling domain comprising the amino acid sequence of SEQ ID NO:94, a DAP12 signaling domain comprising the amino acid sequence of SEQ ID NO:82, a NFAM1 signaling domain comprising the amino acid sequence of SEQ ID NO:92, or a CD79b signaling domain comprising the amino acid sequence of SEQ ID NO:97.

* * * * *